(12) United States Patent
Bui et al.

(10) Patent No.: US 12,018,261 B2
(45) Date of Patent: Jun. 25, 2024

(54) COMPOUNDS AND METHODS FOR MODULATING FACTOR XII

(71) Applicant: Ionis Pharmaceuticals, Inc., Carlsbad, CA (US)

(72) Inventors: Huynh-Hoa Bui, San Diego, CA (US); Chenguang Zhao, San Diego, CA (US); Jeffrey R. Crosby, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/554,920

(22) Filed: Dec. 17, 2021

(65) Prior Publication Data

US 2023/0002771 A1   Jan. 5, 2023

Related U.S. Application Data

(60) Provisional application No. 63/127,616, filed on Dec. 18, 2020.

(51) Int. Cl.
*C12N 15/113* (2010.01)

(52) U.S. Cl.
CPC ...... *C12N 15/1137* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/3341* (2013.01); *C12N 2310/341* (2013.01); *C12N 2310/346* (2013.01)

(58) Field of Classification Search
CPC ............ C12N 15/1137; C12N 2310/11; C12N 2310/14; C12N 2310/31; C12N 2310/315; C12N 2310/322; C12N 2310/341; C12N 2310/346; C12N 2310/3341; A61K 31/7088

See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |

(Continued)

FOREIGN PATENT DOCUMENTS

| | | |
|---|---|---|
| WO | WO 1999/014226 | 3/1999 |
| WO | WO 2003/004602 | 1/2003 |

(Continued)

OTHER PUBLICATIONS

Adams et al., "Thrombin and Factor XII Drive Prostate Tumor Growth in vivo" Presentation for 57th ASH Annual Meeting and Exposition (Dec. 5-8, 2015) Orlando, FL.

Adams et al., "Thrombin and Factor XII Drive Prostate Tumor Growth in vivo" Abstract for 57th ASH Annual Meeting and Exposition (Dec. 5-8, 2015) Orlando, FL.

Adcock et al., "A laboratory approach to the evaluation of hereditary hypercoagulability" Am. J. Clin. Pathol. (1997) 108(4):434-449.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Terra C Gibbs
(74) *Attorney, Agent, or Firm* — Knobbe, Martens, Olson & Bear, LLP

(57) ABSTRACT

Provided are compounds, methods, and pharmaceutical compositions for reducing the amount or activity of FXII RNA in a cell or subject, and in certain instances reducing the amount of FXII protein in a cell or subject. Such compounds, methods, and pharmaceutical compositions are useful to prevent, treat, or ameliorate at least one symptom of a thromboembolic condition. Such thromboembolic conditions include deep vein thrombosis, venous or arterial thrombosis, pulmonary embolism, myocardial infarction, and stroke. Such symptoms include pain, shortness of breath, heart burn, cold sweat, fatigue, lightheadedness, dizziness, swelling, cramping, and death. Such compounds, methods, and pharmaceutical compositions are useful to prevent, treat, or ameliorate at least one symptom of hereditary angioedema.

58 Claims, No Drawings

Specification includes a Sequence Listing.

(56) References Cited

U.S. PATENT DOCUMENTS

| | | |
|---|---|---|
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,150,864 B2 | 10/2015 | Monia et al. |
| 9,187,749 B2 | 11/2015 | Bhattacharjee et al. |
| 9,290,760 B2 | 3/2016 | Rajeev et al. |
| 10,011,836 B2 | 7/2018 | Khvorova et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |

(56) References Cited

U.S. PATENT DOCUMENTS

| | | |
|---|---|---|
| 2008/0039618 A1 | 2/2008 | Allerson et al. |
| 2008/0254039 A1 | 10/2008 | Nieswandt et al. |
| 2009/0012281 A1 | 1/2009 | Swayze et al. |
| 2009/0064350 A1 | 3/2009 | Dewald |
| 2010/0137414 A1 | 6/2010 | Freier et al. |
| 2010/0190837 A1 | 7/2010 | Migawa et al. |
| 2010/0197762 A1 | 8/2010 | Swayze et al. |
| 2010/0324114 A1 | 12/2010 | Dewald |
| 2011/0067124 A1 | 3/2011 | Dewald |
| 2012/0309035 A1 | 12/2012 | Lindahl et al. |
| 2013/0130378 A1 | 5/2013 | Manoharan et al. |
| 2013/0331434 A1 | 12/2013 | Monia et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2019/0382763 A1 | 12/2019 | Li et al. |

FOREIGN PATENT DOCUMENTS

| | | |
|---|---|---|
| WO | WO 2004/106356 | 12/2004 |
| WO | WO 2005/021570 | 3/2005 |
| WO | WO 2005/111233 | 11/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/053050 | 4/2009 |
| WO | WO 2009/115478 | 9/2009 |
| WO | WO 2010/094732 | 8/2010 |
| WO | WO 2010/111702 | 9/2010 |
| WO | WO 2012/064758 | 5/2012 |
| WO | WO 2012/170947 | 12/2012 |
| WO | WO 2013/173637 | 11/2013 |
| WO | WO 2015/103339 | 7/2015 |
| WO | WO 2016/149331 | 9/2016 |
| WO | WO 2016/179342 | 11/2016 |
| WO | WO 2017/120397 | 7/2017 |
| WO | WO 2017/214112 | 12/2017 |
| WO | WO 2018/140920 | 8/2018 |
| WO | WO 2019/010342 | 1/2019 |
| WO | WO 2019/211585 | 11/2019 |
| WO | WO 2022/133278 | 6/2022 |

OTHER PUBLICATIONS

Altmann et al., "Second-generation antisense oligonucleoties: structure-activity relationships and the design of improved signal-transduction inhibitors" Biochem. Soc. Trans. (1996) 24: 630-637.

Altmann et al., "Second Generation of Antisense Oligonucleotides: From Nuclease Resistance to Biological Efficacy in Animals" Chimia (1996) 50: 168-176.

Altmann et al., "Second Generation Antisense Oligonucleotides—Inhibition of PKC-a and c-RAF Kinase Expression by Chimeric Oligonucleotides Incorporating 5'-Substituted Carbocyclic Nucleosides and 2'-O-Ethylene Glycol Substituted Ribonucleosides" Nucleosides Nucleotides (1997) 16(7-9): 917-926.

Altschul et al., "Basic Local Alignment Search Tool" J. Mol. Biol. (1990) 215: 403-410.

Anderson et al., "Towards next generation antisense oligonucleotides: mesylphosphoramidate modification improves therapeutic index and duration of effect of gapmer antisense oligonucleotides" Nucl Ac Res (2021) 49: 1-16.

Anderson et al., "Towards next generation antisense oligonucleotides-mesylphosphoramidate modification improves therapeutic index and duration of effect of gapmer antisense oligonucleotides" Presentation for 17th Annual Meeting of the Oligonucleotide Therapeutics Society OTS (Sep. 26-29, 2021).

Aulak et al., "Chymotrypsin inhibitory activity of normal C1-inhibitor and a P1 Arg to His mutant: evidence for the presence of overlapping reactive centers." Protein Sci. (1993) 2(5): 727-732.

Bennett et al., "Efficiency of Antisense Oligonucleotide Drug Discovery" Antisense & Nucleic Acid Drug Development (2002) 12: 215-224.

Bertina et al., "Mutation in blood coagulation factor V associated with resistance to activated protein C." Nature (1994) 369(6475):64-67.

Bhattacharjee et al., "Inhibition of Vascular Permeability by Antisense-Mediated Inhibition of Plasma Kallikrein and Coagulation Factor 12" Nucl Ac Res (2013) 23: 175-187.

Bhattacharjee et al., "Reversal of Vascular Permeability by Targeted Inhibition of Plasma Kallikrein and Factor XII" Presentation for FASEB Summer Research Conferences: Proteasesin Hemostasis and Vascular Biology (Jun. 12-17, 2011) Carefree, Arizona.

Bhattacharjee et al., "Reversal of Vascular Permeability by Targeted Inhibition of Plasma Kallikrein and Factor XII" Abstract for FASEB Summer Research Conferences: Proteasesin Hemostasis and Vascular Biology (Jun. 12-17, 2011) Carefree, Arizona.

Bjork et al., "Mechanism of the anticoagulant action of heparin." Mol Cell Biochem. (1982) 48(3): 161-182.

Bouillet et al. "Disease expression in women with hereditary angioedema" Am. J. Obstet. Gynecol. (2008) 199: 484.e1-484.e4.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chan et al., "The inhibition of activated factor XII (hageman factor) by antithrombin III: The effect of other plasma proteinase inhibitors" Biochem. Biophys. Res. Comm. (1977) 74(1): 150-158.

Chen et al., "Depletion of coagulation factor XII ameliorates brain pathology and cognitive impairment in Alzheimer disease mice" Thrombosis and Hemostasis (2017) 129: 2547-2556.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Cichon et al., "Increased activity of coagulation factor XII (Hageman factor) causes hereditary angioedema type III." Am. J. Hum. Genet. (2006) 79: 1098-1104.

Citarella et al., "The Second Exon-Encoded Factor XII Region Is Involved in the Interaction of Factor XII With Factor XI and Does Not Contribute to the Binding Site for Negatively Charged Surfaces" Blood (1998) 92: 4198-4206.

Citarella et al., "Identification of a putative binding site for negatively charged surfaces in the fibronectin type II domain of human factor XII—an immunochemical and homology modeling approach." Thromb. Haemost. (2000) 84(6): 1057-1065.

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Crosby et al., "FXII Antisense Oligonucleotide Mediated Depletion Results in Effective Anticoagulation Without Bleeding Risk" Abstract for 52nd Annual Meeting and Exposition ASH—American Society of Hematology (Dec. 4-7, 2010) Orange County Conve.

Crosby et al., "FXII Antisense Oligonucleotide Mediated Depletion Results in Effective Anticoagulation Without Bleeding Risk" Presentation for 52nd Annual Meeting and Exposition ASH—American Society of Hematology (Dec. 4-7, 2010) Orange County Convention Center, Orlando FL.

Crosby et al., "Antisense Oligonucleotide Mediated Depletion of Factor XII Results in Effective Anticoagulation Without Bleeding" Abstract for 59th ASH Annual Meeting & Exposition (Dec. 9-12, 2017) Atlanta, GA.

Crosby et al., "Systematic Evaluation of Coagulation Factors as Targets for Anti-Thrombotic therapy using Antisense Technology" Abstract for 51st Annual Meeting American Society of Hematology (Dec. 5-8, 2009) New Orleans, Louisiana.

Crosby et al., "Antisense Oligonucletide Mediated Depletion of Plasma Kallikrein and Factor XII Results in Effective Anticoagulation without Bleeding Risk" Abstract for ATVB—Arteriosclerosis, Thrombosis and Vascular Biology 2011 Scientific Sessions (Apr. 28-30, 2011) Chicago, IL.

(56) References Cited

OTHER PUBLICATIONS

Cugno et al., "C1-inhibitor deficiency and angioedema: molecular mechanisms and clinical progress" Trends. Mol. Med. (2009) 15(2): 69-78.
Drake et al., "Selective cellular expression of tissue factor in human tissues. Implications for disorders of hemostasis and thrombosis." Am J Pathol (1989) 134(5):1087-1097.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Applications of PNA and LNA oligomers to chemotherapy" Curr. Opinion Invest. Drugs (2001) 2:558-561.
Esnouf et al., "A monoclonal antibody raised against human beta-factor XIIa which also recognizes alpha-factor XIIa but not factor XII or complexes of factor XIIa with C1 esterase inhibitor." Thromb. Haemost. (2000) 83(6): 874-881.
Farsetti et al., "Orphan receptor hepatocyte nuclear factor-4 antagonizes estrogen receptor alpha-mediated induction of human coagulation factor XII gene." Endocrinology (1998) 139(11): 4581-4589.
Foster et al., "Inhibition of the activation of Hageman factor (factor XII) and of platelet aggregation by extracts of Brugia malayi microfilariae." J. Lab. Clin. Med. (1991) 117(5): 344-352.
Foster et al., "Inhibition of the activation of Hageman factor (factor XII) by extracts of Schistosoma mansoni." J. Lab. Clin. Med. (1992) 120(5): 735-739.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.
Gigli et al., "Interaction of plasma kallikrein with the C1 inhibitor." J. Immunol. (1970) 104:574-581.
Han et al., "Increased vascular permeability in C1 inhibitor-deficient mice mediated by the bradykinin type 2 receptor." J. Clin. Invest. (2002) 109: 1057-1063.
Hazegh-Azam et al., "The Corn Inhibitor of Activated Hageman Factor: Purification and Properties of Two Recombinant Forms of the Protein" Protein Expr. Purif. (1998) 13(2): 143-149.
Hisada et al., "The Intrinsic Pathway does not Contribute to Activation of Coagulation in Mice Bearing Human Pancreatic Tumors Expressing Tissue Factor" Thromb Haemost (2021) 121: 967-970.
Hojima et al., "Pumpkin seed inhibitor of human factor XIIa (activated Hageman factor) and bovine trypsin" Biochemistry (1982) 21(16): 3741-3746.
Isawa et al., "Identification and characterization of plasma kallikrein-kinin system inhibitors from salivary glands of the blood-sucking insect Triatoma infestans." FEBS J. (2007) 274(16): 4271-4286.
Ivanov et al., "A mechanism for hereditary angioedema with normal C1 inhibitor: an inhibitory regulatory role for the factor XII heavy chain" Thrombosis and Hemostasis (2019) 133: 1152-1163.
Kaplan et al., "Pathways for bradykinin formation and inflammatory disease." J. Allergy Clin. Immunol. (2002) 109(2): 195-209.
Kato et al., "Identification and characterization of the plasma kallikrein-kinin system inhibitor, haemaphysalin, from hard tick, *Haemaphysalis longicornis*" Thromb. Haemost. (2005) 93: 359-67.
Kleinschnitz et al., "Targeting coagulation factor XII provides protection from pathological thrombosis in cerebral ischemia without interfering with hemostasis" J. Exper. Med. (2006) 203:513-518.
Kohler et al., "The contact system proteases play disparate roles in streptococcal sepsis" Haematologica (2020) 105: 1424-1435.
Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Leumann, "DNA Analogues: From Supramolecular Principles to Biological Properties" Bioorganic & Medicinal Chemistry (2002) 10:841-854.
Mackenzie et al., "Plasma prekallikrein levels are positively associated with circulating lipid levels and the metabolic syndrome in children." Appl. Physiol. Nutr. Metab. (2010) 35: 518-525.
Mahdi et al., "Factor XII interacts with the multiprotein assembly of urokinase plasminogen activator receptor, gC1qR, and cytokeratin 1 on endothelial cell membranes" Blood (2002) 99(10): 3585-3596.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Malik et al., "Ployphosphate-induced thrombosis in mice is factor XII dependent and is attenuated by histidine-rich glycoprotein" Blood Advances (2021) 5: 3540-3551.
Martin, "Ein neuer Zugang zu 2'-O-Alkylribonucleosiden und Eigenschaften eren Oligonucleotide" Helv. Chim. Acta (1995) 78: 486-504.
New England Biolabs 1998/99 Catalog (cover page and pp. 121 and 284).
Nielsen, "Corn trypsin inhibitor decreases tissue-type plasminogen activator-mediated fibrinolysis of human plasma." Blood Coagul. Fibronolysis. (2009) 20(3): 191-196.
Nishikawa et al., "Effect of neurotropin® on the activation of the plasma kallikrein-kinin system" Biochem. Pharmacol. (1992) 43(6): 1361-1369.
Niwano et al., "Inhibitory action of amyloid precursor protein against human Hageman factor (factor XII)." J. Lab. Clin. Med. (1995) 125(2): 251-256.
Orum et al., "Locked nucleic acids: A promising molecular family for gene-function analysis and antisense drug development" Curr. Opinion Mol. Ther. (2001) 3(3):239-243.
Pollack et al., "Mechanism Driven Early Stage Identification and Avoidance of Antisense Oligonucleotides Causing TRL9 Mediated Inflammatory Responses in Bjab cells" bioRxiv preprint (2021) https://doi.org/10.1101/2021.12.12.472280 : 1-25.
Rajapakse et al., "A novel anticoagulant purified from fish protein hydrolysate inhibits factor XIIa and platelet aggregation." Life Sci. (2005) 76(22): 2607-2619.
Ratnoff et al., "Inhibition of the activation of hageman factor (factor XII) by eosinophils and eosinophilic constituents" Am. J. Hematol. (1993) 42(1): 138-145.
Revenko et al., "Selective deletion of plasma prekallikrein or coagulation factor XII inhibits thrombosis in mice without increasing risk of bleeding" Thrombosis & Hemostatsis (2011) 118: 5302-5311.
Reynolds et al., "Rational siRNA design for RNA interference" Nature Biotechnology (2004) 22(3):326-330.
Ryder et al., "The effect of chemical modification of basic amino acid residues on the activation and amidolytic activity of Hageman factor (factor XII)." J. Lab. Clin. Med. (1993) 122(6): 697-702.
Sampaio et al., "Plant serine proteinase inhibitors. Structure and biochemical applications on plasma kallikrein and related enzymes." Immunopharmacology (1996) 32(1-3): 62-66.
Sanghvi et al., "Heterocyclic Base Modifications in Nucleic Acids and Their Applications in Antisense Oligonucleotides" Antisense Research and Applications (1993) pp. 273-288.
Schousboe et al., "Synchronized inhibition of the phospholipid mediated autoactivation of factor XII in plasma by beta 2-glycoprotein I and anti-beta 2-glycoprotein I." Thromb. Haemost (1995) 73(5): 798-804.
Schwartz et al., "Tissue factor pathway inhibitor endocytosis." Trends Cardiovasc Med. (1997) 7(7):234-239.
Scott et al., "Alpha-1-antitrypsin—Pittsburgh. A potent inhibitor of human plasma factor XIa, kallikrein, and factor XIIf." J. Clin. Invest. (1986) 77(2): 631-634.

(56) References Cited

OTHER PUBLICATIONS

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Slingsby et al., "Sequence-specific 2'-O-methoxyethyl antisense oligonucleotides activate human platelets through glycoprotein VI, triggering formation of platelet-leukocyte aggregates" Haematologica (2022) 107: 519-531.

Srivastava et al., "Five- and Six-Membered Conformationally Locked 2',4'-Carbocyclic ribo-Thymidines: Synthesis, Structure, and Biochemical Studies" J. Am. Che,. Soc. (2007) 129:8362-8379.

Stroo et al., "Inhibition of the extrinsic or intrinsic coagulation pathway during pneumonia-derived sepsis" Am J Physiol Lung Cell Mol Physiol (2018) 315: L799-L809.

Tanabe et al., "Isolation and Characterization of Streptoverticillium Anticoagulant (SAC), a Novel Protein Inhibitor of Blood Coagulation Produced by *Streptoverticillium cinnamoneum* subsp. *Cinnamoneum*" J. Biochem. (1994) 115(4): 743-751.

Vu et al., "Arterial thrombosis is accelerated in mice deficient in histidine-rich glycoprotein" Thrombosis and Hemostasis (2015) 125: 2712-2719.

Wahlestedt et al., "Potent and nontoxic antisense oligonucleoties containing locked nucleic acids" PNAS (2000) 97(10):5633-5638.

Woolf et al., "Specificity of antisense oligonucleotides in vivo" PNAS (1992) 89:7305-7309.

Yau et al., "Selective depletion of factor XI or factor XII with antisense oligonucleotides attenuates catheter thrombosis in rabbits" Blood (2014) 123(13):2102-2107.

Zhang e al., "PowerBLAST: A New Network BLAST Application for Interactive or Automate Sequence Analysis and Annoation", Genome Res. (1997) 7: 649-656.

Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.

Zuraw, "Hereditary Angioedema" N. Engl. J. Med. (2008) 359: 1027-36.

International Search Report for application PCT/US11/59804 dated May 14, 2012.

International Search Report for application PCT/US2012/041747 dated Dec. 10, 2012.

International Search Report for application PCT/US2021/064145 dated Jun. 8, 2022.

COMPOUNDS AND METHODS FOR MODULATING FACTOR XII

SEQUENCE LISTING

The present application is being filed along with a Sequence Listing in electronic format. The Sequence Listing is provided as a file entitled BIOL0369USEQ_ST25.txt, created on Dec. 8, 2021, which is 1 MB in size. The information in the electronic format of the sequence listing is incorporated herein by reference in its entirety.

FIELD

Provided herein are compounds, methods, and pharmaceutical compositions for reducing an amount of Factor XII (FXII) RNA in a cell or a subject, and in certain instances reducing the amount of FXII protein in a cell or a subject. Such compounds, methods, and pharmaceutical compositions are useful to treat or prevent a thromboembolic condition. Such thromboembolic conditions include myocardial infarction (MI), stroke, limb ischemia and necrosis, and venous thromboembolism (VTE), including deep vein thrombosis (DVT) and pulmonary embolism (PE).

BACKGROUND

The human F12 gene encodes FXII protein, a zymogen that circulates in the blood stream. The zymogen is converted to an active enzyme (FXIIa) by plasma kallikrein (PK) or by its unique ability to auto-activate following binding to artificial or biologic surfaces. In vivo, FXIIa triggers the kallikrein-kinin system leading to release of bradykinin (BK) which induces microvascular permeability, nitric oxide-mediated vasodilation, hypotension, and inflammatory reactions such as swelling, hyperperfusion, and pain. FXIIa also initiates coagulation via the intrinsic pathway and promotes inflammation via the kallikrein-kinin system comprising, high molecular weight kininogen (HK) and PK.

FXII may contribute to a variety of inflammatory, life-threatening disease conditions, including hereditary angioedema (HAE) and thrombosis. HAE is a rare life-threatening inherited disorder characterized by recurrent episodes of acute swelling in multiple organs because of increased vascular permeability. An excess of FXII activity may trigger excessive BK formation or signaling, thereby contributing to the vascular permeability of hereditary angioedema. Thrombosis is a maladaptive process of vascular occlusion and remains a primary cause of vascular morbidity and mortality associated with myocardial infarction (MI), stroke, limb ischemia and necrosis, and venous thromboembolism (VTE), including deep vein thrombosis (DVT) and pulmonary embolism (PE). VTE is the third leading cause of vascular-related death, after MI and stroke, and is one of the leading causes of death in patients with cancer. While many thromboembolic conditions are due to acquired extrinsic issues, (e.g. surgery, cancer, immobility), other thromboembolic conditions are due to a genetic mutation, (e.g., antiphospholipid syndrome, Factor V Leiden thrombophilia). The most commonly used treatments for thromboembolic conditions (e.g., warfarin, heparin) and newer direct oral anticoagulants all possess significant drawbacks, such as an increased risk of bleeding. It is therefore an object herein to provide compounds, methods, and pharmaceutical compositions for the treatment and prevention of such thromboembolic conditions.

SUMMARY OF THE INVENTION

Provided herein are compounds, methods and pharmaceutical compositions for reducing an amount of FXII RNA, and in certain embodiments reducing the amount or activity of FXII protein in a cell or a subject. In certain embodiments, compounds, methods and pharmaceutical compositions disclosed herein reduce FXII RNA, FXII protein, FXII activity, or a combination thereof, in the blood of a subject. In certain embodiments, the subject has or is at risk for a thromboembolic condition. In certain embodiments, the thromboembolic condition is deep vein thrombosis, venous thrombosis, arterial thrombosis, pulmonary embolism, myocardial infarction, or stroke. In certain embodiments, compounds useful for reducing the amount of FXII RNA, the amount of FXII protein, or FXII activity are oligomeric compounds. In certain embodiments, oligomeric compounds comprise modified oligonucleotides.

Also provided are herein are methods useful for preventing a thromboembolic condition and methods useful for ameliorating a symptom of a thromboembolic condition. Exemplary symptoms of a thromboembolic condition include, but are not limited to, pain, shortness of breath, heart burn, cold sweat, fatigue, lightheadedness, dizziness, swelling, cramping, and death.

Also provided are herein are methods useful for treating hereditary angioedema and methods useful for ameliorating a symptom of hereditary angioedema. Exemplary symptoms of hereditary angioedema include, but are not limited to, swelling, nausea, vomiting, itching, headache, fatigue, abdominal pain, shortness of breath, rhinitis, anaphylaxis, and bronchoconstriction.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety. In certain embodiments, a 2'-deoxynucleoside is a 2'-β-D-deoxynucleoside and comprises a 2'-β-D-deoxyribosyl sugar moiety, which has the β-D configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" or "2'-MOE sugar moiety" means a 2'-OCH$_2$CH$_2$OCH$_3$ group in place of the 2'-OH group of a ribosyl sugar moiety. "MOE" means methoxyethyl. Unless otherwise indicated, a 2'-MOE has the β-D stereochemical configuration.

As used herein, "2'-MOE nucleoside" means a nucleoside comprising a 2'-MOE sugar moiety.

As used herein, "2'-OMe" or "2'-O-methyl sugar moiety" means a 2'-OCH$_3$ group in place of the 2'-OH group of a ribosyl sugar moiety. Unless otherwise indicated, a 2'-OMe has the β-D stereochemical configuration.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "administering" means providing a pharmaceutical agent to a subject.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound capable of achieving at least one antisense activity.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms of the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cell-targeting moiety" means a conjugate moiety that interacts with a cell or a portion thereof. In certain embodiments, the cell-targeting moiety binds a receptor on a surface of a cell.

As used herein, "cEt nucleoside" means a nucleoside comprising a cEt modified sugar moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "cleavable moiety" means a bond or group of atoms that is cleaved under physiological conditions, for example, inside a cell, a subject, or a human.

As used herein, "complementary" in reference to an oligonucleotide means that at least 70% of the nucleobases of the oligonucleotide or one or more portions thereof and the nucleobases of a target nucleic acid or one or more portions thereof are capable of hydrogen bonding with one another when the nucleobase sequence of the oligonucleotide and the other nucleic acid are aligned in opposing directions. As used herein, complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, "conjugate group" means a group of atoms that is directly or indirectly attached to an oligonucleotide. Conjugate groups include a conjugate moiety and a conjugate linker that attaches the conjugate moiety to the oligonucleotide. In certain embodiments, the conjugate moiety comprises a cell-targeting moiety.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "constrained ethyl" or "cEt" or "cEt modified sugar moiety" means a β-D ribosyl bicyclic sugar moiety wherein the second ring of the bicyclic sugar is formed via a bridge connecting the 4'-carbon and the 2'-carbon of the β-D ribosyl sugar moiety, wherein the bridge has the formula 4'-CH(CH$_3$)—O-2', and wherein the methyl group of the bridge is in the S configuration.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "FXII RNA" is the RNA expression product of a human F12 gene.

As used herein, "FXII protein" is the protein expression product of a FXII RNA, including zymogen and activated forms FXII protein.

As used herein, "gapmer" means an oligonucleotide having a central region positioned between a 5'-region and a 3'-region. Each nucleoside of the 5'-region and the 3'-region comprises a modified sugar moiety. The 3'- and 5'-most nucleosides of the central region are 2'-deoxynucleosides. The "central region" may be referred to as a "gap", and the "5'-region" and "3'-region" may also be referred to as a "wing." The hybridization of a gapmer to a target nucleic acid results in RNase H mediated cleavage of the target nucleic acid.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "identifying a subject at risk for developing a thromboembolic condition" means identifying a subject having been diagnosed with a thromboembolic condition or identifying a subject that has a risk factor for developing a thromboembolic condition.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "non-bicyclic modified sugar moiety" means a modified sugar moiety that comprises a modification, such as a substituent, that does not form a bridge between two atoms of the sugar to form a second ring.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, or sterile buffer solution. In certain embodiments, a pharmaceutically acceptable carrier or diluent is phosphate buffered saline.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prevent" or "preventing" refers to delaying or forestalling the onset or development of a thromboembolic condition for a period of time or indefinitely.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing the amount or activity," or "inhibiting the amount or activity," in connection with a gene transcript (RNA) refers to a reduction or blockade of the transcriptional expression or activity relative to the transcriptional expression or activity in an untreated or control sample and does not necessarily indicate a total elimination of transcriptional expression or activity.

As used herein, "reducing the amount or activity," or "inhibiting the amount or activity," in connection with a protein refers to a reduction or blockade of the protein's expression or activity relative to the protein expression or activity in an untreated or control sample and does not necessarily indicate a total elimination of protein expression or activity.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human subject.

As used herein, "sugar moiety" means an unmodified sugar moiety or a modified sugar moiety. As used herein, "unmodified sugar moiety" means a 2'-OH(H) β-D-ribosyl moiety, as found in RNA (an "unmodified RNA sugar moiety"), or a 2'-H(H) β-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom" means any physical feature or test result that indicates the existence or extent of a disease or disorder. In certain embodiments, a symptom is apparent to a subject or to a medical professional examining or testing said subject.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom of a disease.

As used herein, "thromboembolic condition" means any disease or condition involving a thrombosis or an embolism. A thrombosis is a pathological development of a blood clot, and an embolism occurs when the blood clot migrates to another part of the body and interferes with organ function. Conditions in which a thrombosis and/or an embolism occur are collectively referred to as a thromboembolic condition. Depending on where the blood clot occurs or settles, it may result in a variety of thromboembolic conditions, e.g., deep vein thrombosis (DVT), myocardial infarction (MI), pulmonary embolism (PE), and stroke. In certain embodiments, the thromboembolic condition comprises deep vein thrombosis, venous thrombosis, arterial thrombosis, pulmonary embolism, myocardial infarction, or stroke. Thromboembolic conditions may also be referred to as thromboembolic events or thrombotic events.

Certain Embodiments

The present disclosure provides the following non-limiting numbered embodiments:

Embodiment 1. An oligomeric compound comprising a modified oligonucleotide consisting of 12 to 50 linked nucleosides wherein the nucleobase sequence of the modified oligonucleotide is at least 90% complementary to an equal length portion of a FXII RNA, and wherein the modified oligonucleotide comprises at least one modification selected from a modified sugar moiety and a modified internucleoside linkage.

Embodiment 2. An oligomeric compound comprising a modified oligonucleotide consisting of 12 to 50 linked nucleosides and having a nucleobase sequence comprising at least 12, 13, 14, 15, 16, 17, 18, 19, or 20 contiguous nucleobases of any of SEQ ID NOs: 20-5042.

Embodiment 3. An oligomeric compound comprising a modified oligonucleotide consisting of 12 to 50 linked nucleosides and having a nucleobase sequence comprising at least 12, 13, 14, 15, 16, 17, or 18 contiguous nucleobases of any of SEQ ID NOs: 3379 and 5006.

Embodiment 4. An oligomeric compound comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, at least 18, at least 19, or at least 20 contiguous nucleobases complementary to: an equal length portion of nucleobases 1,899-1,979 of SEQ ID NO: 1; or an equal length portion of nucleobases 2,004-2,045 of SEQ ID NO: 1.

Embodiment 5. An oligomeric compound comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, or at least 18 contiguous nucleobases of a sequence selected from: SEQ ID NOs: 92, 156, 270, 271, 345, 346, 420, 421, 496, 497, 571, 572, 653, 654, 728, 729, 802, 803, 877, 951, 1028, 1103, 1179, 1253, 1330, 1407, 1484, 1560, 1636, 1710, 1711, 1784, 1859, 1860, 1934, 1935, 2008, 2009, 2084, 2085, 2158, 2232, 2233, 2307, 2308, 2393, 2394, 2395, 2396, 2397, 2398, 2461, 2537, 2538, 2614, 2615, 2691, 2692, 2768, 2769, 2845, 2846, 2921, 2922, 2997, 2998, 3073, 3074, 3144, 3145, 3226, 3227, 3303, 3304, 3379, 3380, 3455, 3456, 3531, 3607, 3683, 3759, 3835, 3911, 4948, 4949, 4954, 4955, 4956, 4957, 4961, 4965, 4966, 4967, 4971, 4972, 4976, 4994, 4995, 4996, 4997, 4998, 4999, 5024, 5025, 5026, 5027, 5028, and 5029; or SEQ ID NOs: 95, 159, 162, 163, 164, 165, 347, 422, 498, 573, 953, 1030, 1105, 1255, 1332, 1409, 1486, 1562, 2309, 2463, 2540, 2617, 2694, 2771, 2848, 2924, 3000, 3076, 3147, 3229, 3306, 3382, 3457, 3533, 3609, 3685, 3761, 3837, 3913, 5000, 5001, 5002, 5003, 5004, 5005, 5006, 5031, 5032, 5033, 5034, 5035, 5036, and 5037.

Embodiment 6. The oligomeric compound of any of embodiments 1-5, wherein the modified oligonucleotide has a nucleobase sequence that is at least 80%, 85%, 90%, 95%, or 100% complementary to the nucleobase sequence of any one of SEQ ID NOS: 1-4 when measured across the entire nucleobase sequence of the modified oligonucleotide.

Embodiment 7. The oligomeric compound of any of embodiments 1-6, wherein the modified oligonucleotide comprises at least one modified nucleoside.

Embodiment 8. The oligomeric compound of embodiment 7, wherein the modified oligonucleotide comprises at least one modified nucleoside comprising a modified sugar moiety.

Embodiment 9. The oligomeric compound of embodiment 8, wherein the modified oligonucleotide comprises at least one modified nucleoside comprising a bicyclic sugar moiety.

Embodiment 10. The oligomeric compound of embodiment 9, wherein the modified oligonucleotide comprises at least one modified nucleoside comprising a bicyclic sugar moiety having a 2'-4' bridge, wherein the 2'-4' bridge is selected from —O—CH$_2$—; and —O—CH(CH$_3$)—.

Embodiment 11. The oligomeric compound of any of embodiments 8-10, wherein the modified oligonucleotide comprises at least one modified nucleoside comprising a non-bicyclic modified sugar moiety.

Embodiment 12. The oligomeric compound of embodiment 11, wherein the non-bicyclic modified sugar moiety is a 2'-MOE sugar moiety or 2'-OMe sugar moiety.

Embodiment 13. The oligomeric compound of any of embodiments 7-8, wherein the modified oligonucleotide comprises at least one modified nucleoside comprising a sugar surrogate.

Embodiment 14. The oligomeric compound of any of embodiments 1-13, wherein the modified oligonucleotide is a gapmer.

Embodiment 15. The oligomeric compound of any of embodiments 1-14, wherein the modified oligonucleotide has a sugar motif comprising: a 5'-region consisting of 1-6 linked 5'-region nucleosides; a central region consisting of 6-10 linked central region nucleosides; and a 3'-region consisting of 1-6 linked 3'-region nucleosides, wherein each of the 5'-region nucleosides and each of the 3'-region nucleosides comprises a modified sugar moiety and each of the central region nucleosides comprises a 2'-β-D-deoxyribosyl sugar moiety.

Embodiment 16. The oligomeric compound of embodiment 15, wherein the 5'-region consists of 3 linked 5'-region nucleosides; the central region consists of 10 linked central region nucleosides; and the 3'-region consists of 3 linked 3'-region nucleosides, and wherein each of the 5'-region nucleosides and each of the 3'-region nucleosides comprises a cEt modified sugar moiety.

Embodiment 17. The oligomeric compound of any of embodiments 1-16, wherein the modified oligonucleotide comprises at least one modified internucleoside linkage.

Embodiment 18. The oligomeric compound of embodiment 17, wherein each internucleoside linkage of the modified oligonucleotide is a modified internucleoside linkage.

Embodiment 19. The oligomeric compound of embodiment 17 or 18, wherein each internucleoside linkage is a phosphorothioate internucleoside linkage.

Embodiment 20. The oligomeric compound of embodiment 17 or 18, wherein the modified oligonucleotide comprises at least one phosphodiester internucleoside linkage.

Embodiment 21. The oligomeric compound of embodiment 17, wherein each internucleoside linkage is independently selected from a phosphodiester internucleoside linkage and a phosphorothioate internucleoside linkage.

Embodiment 22. The oligomeric compound of any of embodiments 1-21, wherein the modified oligonucleotide comprises a modified nucleobase.

Embodiment 23. The oligomeric compound of embodiment 22, wherein the modified nucleobase is a 5-methyl cytosine.

Embodiment 24. The oligomeric compound of any of embodiments 1-23, wherein the modified oligonucleotide consists of 12-30, 12-22, 12-20, 14-18, 14-20, 15-17, 15-25, 16-20, 18-22 or 18-20 linked nucleosides.

Embodiment 25. The oligomeric compound of any of embodiments 1-23, wherein the modified oligonucleotide consists of 16 linked nucleosides.

Embodiment 26. The oligomeric compound of any of embodiments 1-25, consisting of the modified oligonucleotide.

Embodiment 27. The oligomeric compound of any of embodiments 1-25, comprising a conjugate group comprising a conjugate moiety and a conjugate linker.

Embodiment 28. The oligomeric compound of embodiment 27, wherein the conjugate linker consists of a single bond.

Embodiment 29. The oligomeric compound of embodiment 27, wherein the conjugate linker is cleavable.

Embodiment 30. The oligomeric compound of embodiment 27, wherein the conjugate linker comprises 1-3 linker-nucleosides.

Embodiment 31. The oligomeric compound of 27, wherein the oligomeric compound does not comprise a linker-nucleoside.

Embodiment 32. The oligomeric compound of any of embodiments 28-31, wherein the conjugate group is attached to the modified oligonucleotide at the 5'-end of the modified oligonucleotide.

Embodiment 33. The oligomeric compound of any of embodiments 28-31, wherein the conjugate group is attached to the modified oligonucleotide at the 3'-end of the modified oligonucleotide.

Embodiment 34. The oligomeric compound of any of embodiments 1-33, comprising a terminal group.

Embodiment 35. The oligomeric compound of any one of embodiments 1-34, wherein the conjugate group comprises a GalNAc moiety.

Embodiment 36. The oligomeric compound of anyone of embodiments 1-35, wherein the conjugate group comprises a cell-targeting moiety, a conjugate linker and a cleavable moiety, and wherein the cell-targeting moiety and the conjugate linker together have the following chemical structure:

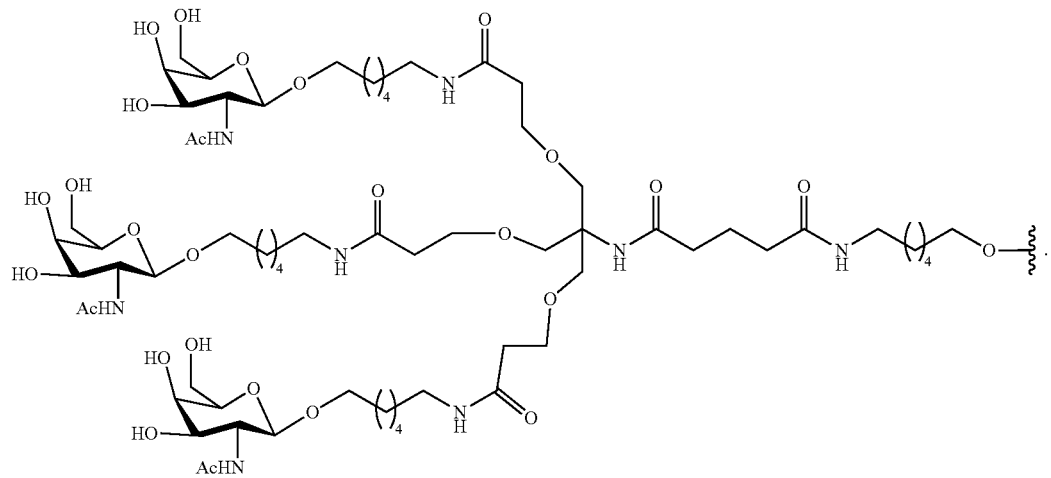

Embodiment 37. The oligomeric compound of any of embodiments 1-36, wherein the modified oligonucleotide is a single-stranded modified oligonucleotide.
Embodiment 38. An oligomeric compound according to the following chemical structure:
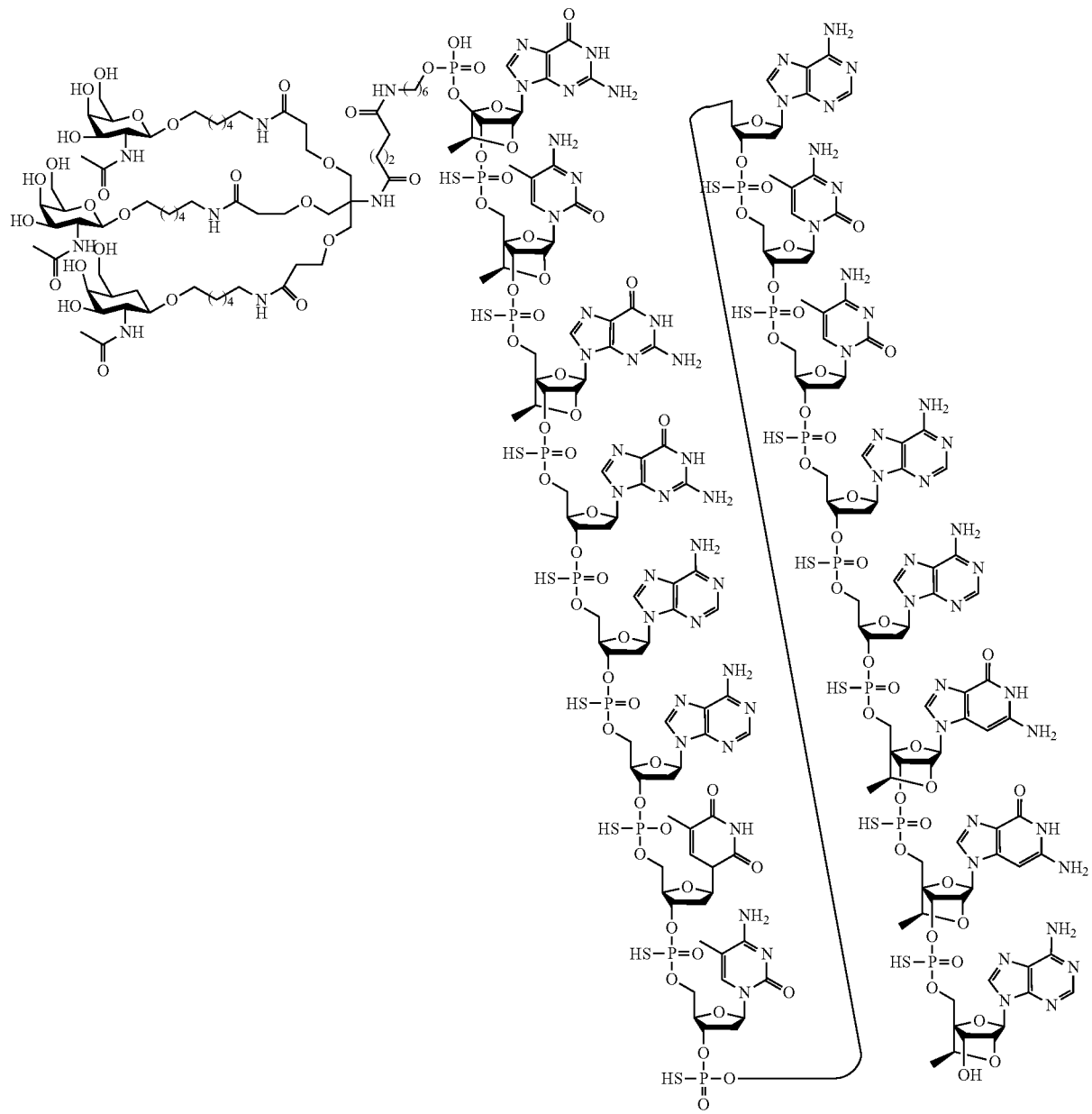
(SEQ ID NO: 3379), or a salt thereof.
Embodiment 39. The oligomeric compound of embodiment 38, which is the sodium salt or the potassium salt.

Embodiment 40. An oligomeric compound according to the following chemical structure:
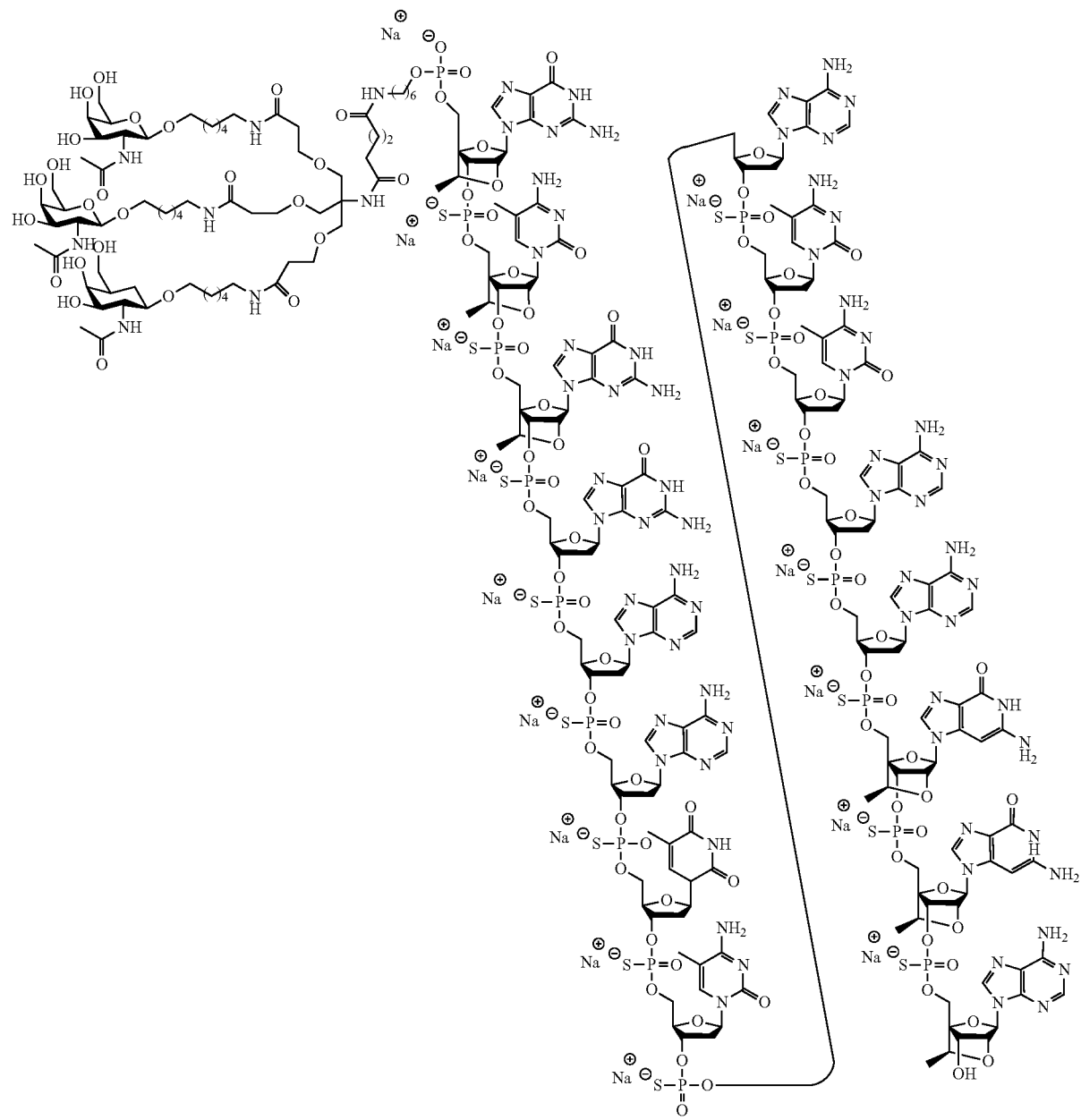
(SEQ ID NO: 3379).
Embodiment 41. An oligomeric compound according to the following chemical structure:

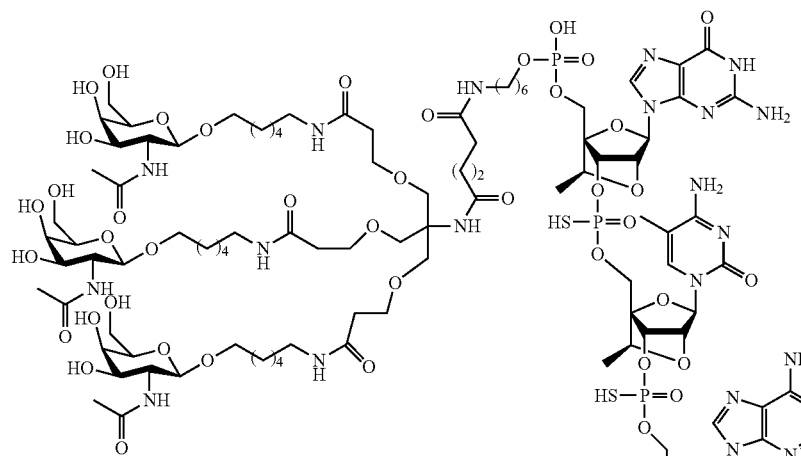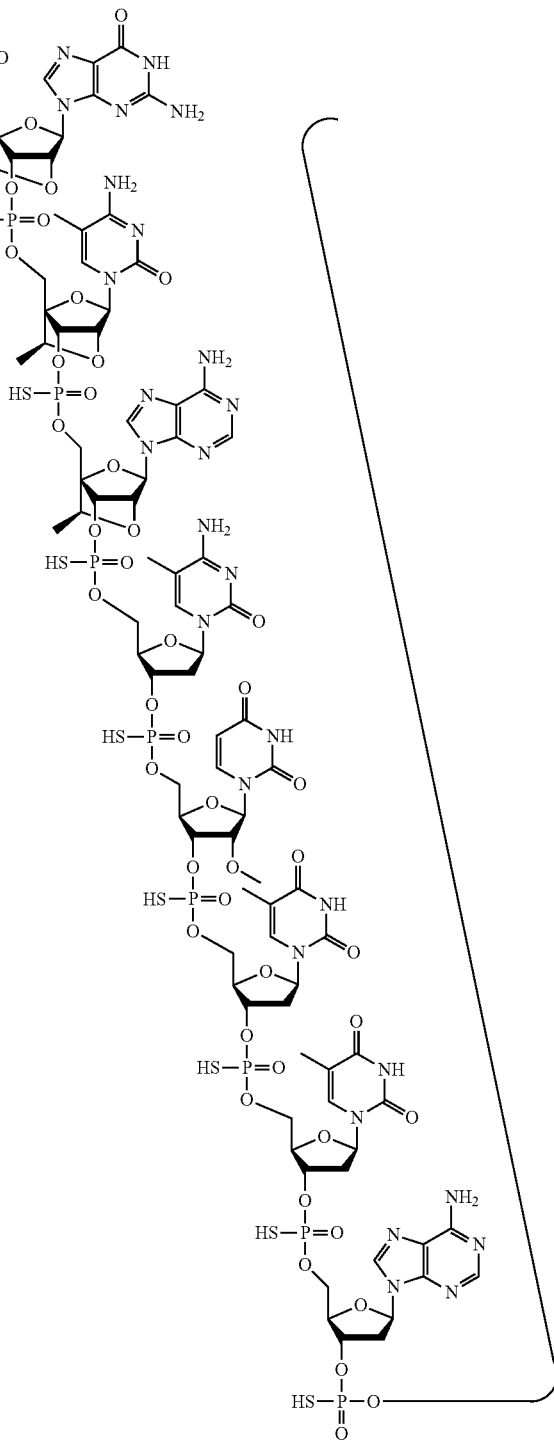

-continued
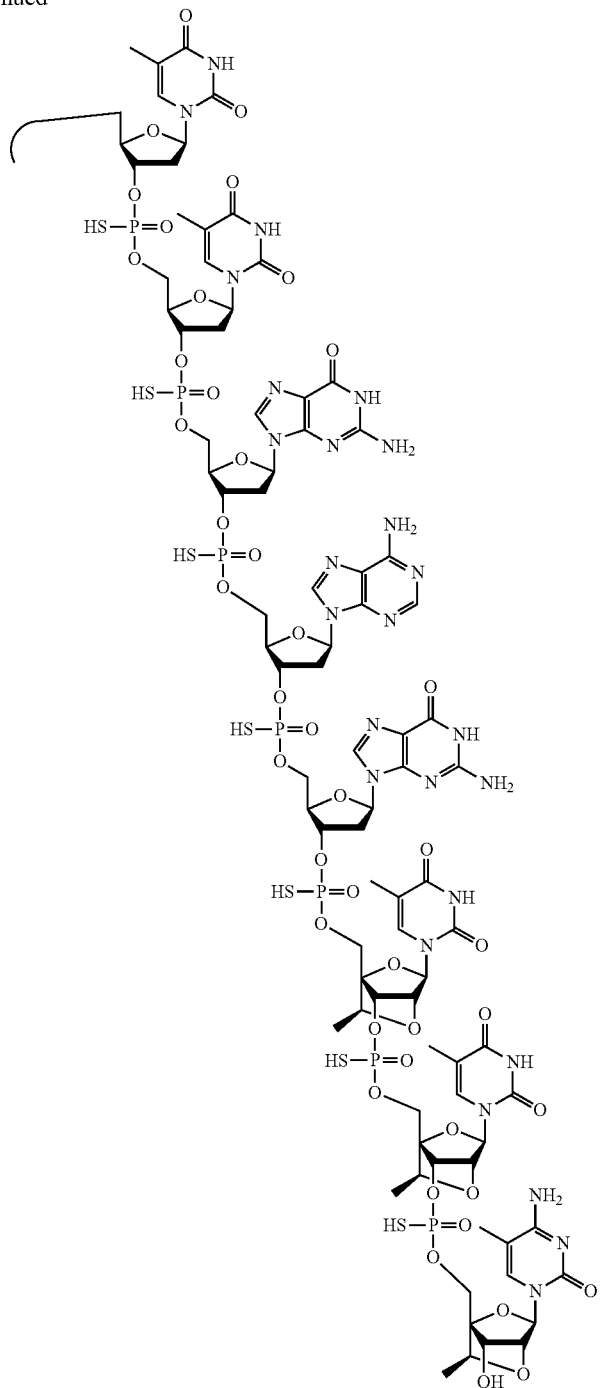
(SEQ ID NO: 5006), or a salt thereof.
Embodiment 42. The oligomeric compound of embodiment 41, which is the sodium salt or the potassium salt.

Embodiment 43. An oligomeric compound according to the following chemical structure:
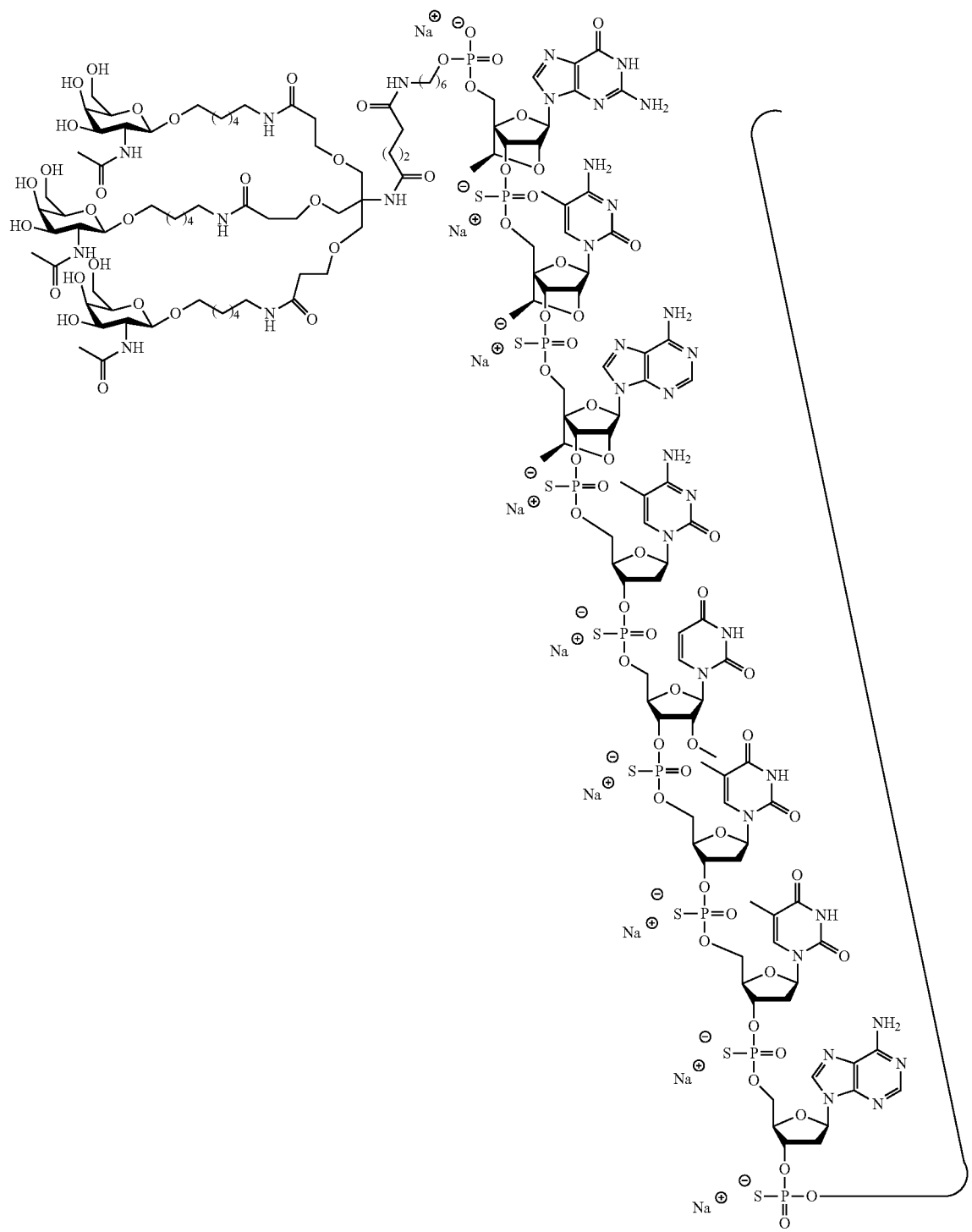

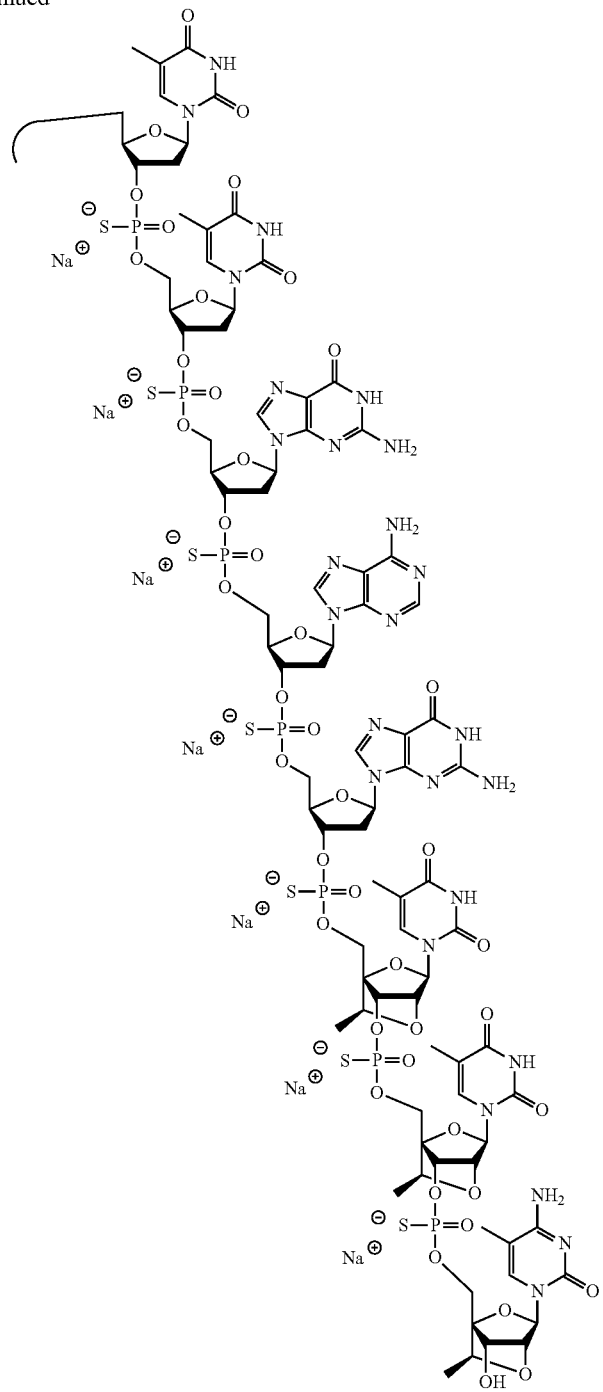

(SEQ ID NO: 5006).

Embodiment 44. An oligomeric compound comprising a modified oligonucleotide according to the following chemical notation: (THA-GalNAc₃)o Gks $^m$Cks Gks Gds Ads Ads Tds $^m$Cds Ads $^m$Cds $^m$Cds Ads Ads Gks Gks Ak (SEQ ID NO: 3379), wherein:
- A=an adenine nucleobase,
- mC=a 5-methyl cytosine nucleobase,
- G=a guanine nucleobase,
- T=a thymine nucleobase,
- k=a cEt modified sugar moiety,
- d=a 2'-β-D-deoxyribosyl sugar moiety,
- o=a phosphodiester linkage, and
- s=a phosphorothioate internucleoside linkage.

Embodiment 45. An oligomeric compound comprising a modified oligonucleotide according to the following chemical notation: (THA-GalNAc₃)o Gks $^m$Cks Aks $^m$Cds Ums Tds Tds Ads Tds Tds Gds Ads Gds Tks Tks mCk (SEQ ID NO: 5006), wherein: A=an adenine nucleobase, mC=a 5-methyl cytosine nucleobase, G=a guanine nucleobase, T=a thymine nucleobase, U=a uracil nucleobase, k=a cEt modified sugar moiety, d=a 2'-β-D-deoxyribosyl sugar moiety, o=a phosphodiester linkage, and s=a phosphorothioate internucleoside linkage.

Embodiment 46. An oligomeric duplex comprising the oligomeric compound of any of embodiments 1-36.

Embodiment 47. An antisense compound comprising or consisting of an oligomeric compound of any of embodiments 1-45 or an oligomeric duplex of embodiment 46.

Embodiment 48. A pharmaceutical composition comprising an oligomeric compound of any of embodiments 1-45, an oligomeric duplex of embodiment 46, or an antisense compound of embodiment 47; and a pharmaceutically acceptable carrier or diluent.

Embodiment 49. The pharmaceutical composition of embodiment 48, wherein the pharmaceutically acceptable diluent is phosphate buffered saline.

Embodiment 50. The pharmaceutical composition of embodiment 49, wherein the pharmaceutical composition consists essentially of the modified oligonucleotide and phosphate buffered saline.

Embodiment 50. A method comprising administering to a subject a pharmaceutical composition of any of embodiments 48-50.

Embodiment 51. A method of ameliorating or preventing a thromboembolic condition, comprising administering to a subject in need thereof a therapeutically effective amount of a pharmaceutical composition according to any of embodiments 48-50.

Embodiment 51. The method of embodiment 52, wherein the thromboembolic condition is selected from myocardial infarction (MI), stroke, limb ischemia and necrosis, venous thromboembolism (VTE), deep vein thrombosis (DVT), and pulmonary embolism (PE).

Embodiment 53. The method of any of embodiments 51-53, wherein at least one symptom of the thromboembolic condition is ameliorated.

Embodiment 54. The method of embodiment 54, wherein the symptom is pain, shortness of breath, heart burn, cold sweat, fatigue, lightheadedness, dizziness, swelling, cramping, and death.

Embodiment 55. The method of any one of embodiments 51-55, comprising identifying the subject as having the thromboembolic condition or as having a risk factor for having the thromboembolic condition.

Embodiment 56. The method of embodiment 56, wherein the risk factor is surgery, malignancy, pregnancy, aging, use of oral contraceptives, immobility, sepsis, a mechanical heart valve, valvular heart disease, atrial fibrillation, atherosclerosis, antiphospholipid syndrome, an inherited clotting disorder, or an acquired prothrombotic clotting disorder.

Embodiment 57. A method of ameliorating or preventing hereditary angioedema, comprising administering to a subject in need thereof a therapeutically effective amount of a pharmaceutical composition according to any of embodiments 48-50.

Embodiment 58. A chirally enriched population of oligomeric compounds of any of embodiments 1-45, wherein the population is enriched for oligomeric compounds comprising at least one particular phosphorothioate internucleoside linkage having a particular stereochemical configuration.

Embodiment 59. The chirally enriched population of embodiment 59, wherein the population is enriched for oligomeric compounds comprising at least one particular phosphorothioate internucleoside linkage having the (Sp) configuration.

Embodiment 60. The chirally enriched population of embodiment 59, wherein the population is enriched for oligomeric compounds comprising at least one particular phosphorothioate internucleoside linkage having the (Rp) configuration.

Embodiment 61. The chirally enriched population of embodiment 59, wherein the population is enriched for oligomeric compounds having a particular, independently selected stereochemical configuration at each phosphorothioate internucleoside linkage.

Embodiment 62. The chirally enriched population of embodiment 62, wherein the population is enriched for oligomeric compounds having the (Sp) configuration at each phosphorothioate internucleoside linkage.

Embodiment 63. The chirally enriched population of embodiment 62, wherein the population is enriched for oligomeric compounds having the (Rp) configuration at each phosphorothioate internucleoside linkage.

Embodiment 64. The chirally enriched population of embodiment 62, wherein the population is enriched for oligomeric compounds having the (Rp) configuration at one particular phosphorothioate internucleoside linkage and the (Sp) configuration at each of the remaining phosphorothioate internucleoside linkages.

Embodiment 65. The chirally enriched population of embodiment 59 or embodiment 62, wherein the population is enriched for oligomeric compounds having at least 3 contiguous phosphorothioate internucleoside linkages in the Sp, Sp, and Rp configurations, in the 5' to 3' direction.

Embodiment 66. A chirally enriched population of oligomeric compounds of any of embodiments 1-45, wherein all of the phosphorothioate internucleoside linkages of the oligomeric compounds are stereorandom.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$S$CH_3$, O($CH_2$)$_2$ON($R_m$)($R_n$) or O$CH_2$C(=O)—N($R_m$)($R_n$), where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, $NH_2$, $N_3$, O$CF_3$, O$CH_3$, O($CH_2$)$_3$$NH_2$, $CH_2$CH=$CH_2$, O$CH_2$CH=$CH_2$, O$CH_2$$CH_2$O$CH_3$, O($CH_2$)$_2$S$CH_3$, O($CH_2$)$_2$ ON($R_m$)($R_n$), O($CH_2$)$_2$O($CH_2$)$_2$N($CH_3$)$_2$, and N-substituted acetamide (O$CH_2$C(=O)—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside non-bicyclic modified nucleoside comprises a sugar moiety comprising a non-bridging 2'-substituent group selected from: F, O$CF_3$, O$CH_3$, O$CH_2$$CH_2$O$CH_3$, O($CH_2$)$_2$S$CH_3$, O($CH_2$)$_2$ON($CH_3$)$_2$, O($CH_2$)$_2$O($CH_2$)$_2$N($CH_3$)$_2$, and O$CH_2$C(=O)—N(H)$CH_3$ ("NMA").

In certain embodiments, a 2'-substituted non-bicyclic modified nucleoside comprises a sugar moiety comprising a non-bridging 2'-substituent group selected from: F, O$CH_3$, and O$CH_2$$CH_2$O$CH_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-($CH_2$)$_2$-2', 4'-($CH_2$)$_3$-2', 4'-$CH_2$—O-2' ("LNA"), 4'-$CH_2$—S-2', 4'-($CH_2$)$_2$—O-2' ("ENA"), 4'-CH($CH_3$)—O-2' (referred to as "constrained ethyl" or "cEt"), 4'-$CH_2$—O—$CH_2$-2', 4'-$CH_2$—N(R)-2', 4'-CH($CH_2$O$CH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N(O$CH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., J. Org. Chem., 2009, 74, 118-134), 4'-$CH_2$—C(=$CH_2$)-2' and analogs thereof (see e.g., Seth et al., U.S. Pat. No. 8,278,426), 4'-C($R_a$$R_b$)—N(R)—O-2', 4'-C($R_a$$R_b$)—O—N(R)-2', 4'-$CH_2$—O—N(R)-2', and 4'-$CH_2$—N(R)—O- 2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_a$)($R_b$)]$_n$—O—, —C($R_a$)=C($R_b$)—, —C($R_a$)=N—, —C(=N$R_a$)—, —C(=O)—, —C(=S)—, —O—, —Si($R_a$)$_2$—, —S(=O)$_x$—, and —N($R_a$)—;

wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, O$J_1$, N$J_1$$J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

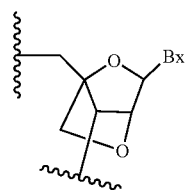

LNA (β-D-configuration)
bridge = 4'-CH$_2$—O-2'

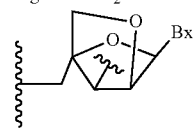

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

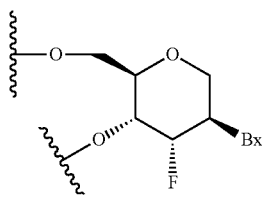

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

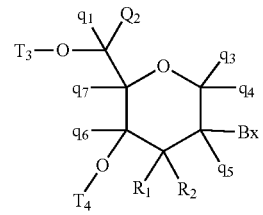

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

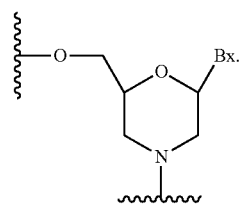

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.,* 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleosides comprising a modified nucleobase. In certain embodiments, modified oligonucleotides comprise one or more nucleosides that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("P(O$_2$)═O") (also referred to as unmodified or naturally occurring linkages), phosphotriesters, methylphosphonates, phosphoramidates, and phosphorothioates, and phosphorodithioates. Representative non-phosphorus containing internucleoside linking groups include but are not limited to methylenemethylimino (—CH$_2$—N(CH$_3$)—O—CH$_2$—), thiodiester, thionocarbamate (—O—C(═O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

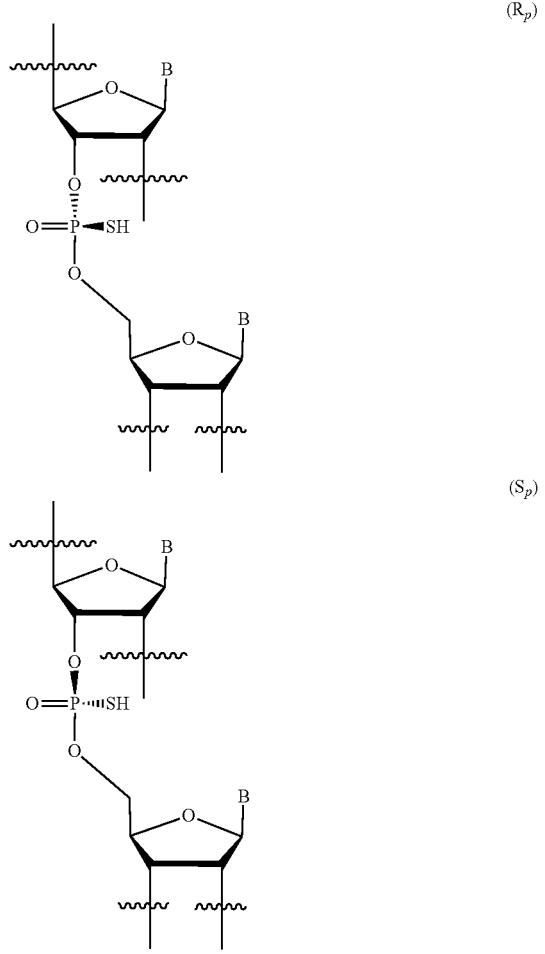

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-$CH_2$—$N(CH_3)$—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl (MOP), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research;* Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety.

In certain embodiments, the gapmer is a deoxy gapmer. In certain embodiments, the nucleosides on the gap side of each wing/gap junction comprise 2'-β-D-deoxyribosyl sugar moieties and the nucleosides on the wing sides of each wing/gap junction comprise modified sugar moieties. In certain embodiments, each nucleoside of the gap comprises a 2'-β-D-deoxyribosyl sugar moiety. In certain embodiments, each nucleoside of each wing of a gapmer comprises a modified sugar moiety. In certain embodiments, exactly one nucleoside of the gap comprises a modified sugar moiety and each remaining nucleoside of the gap comprises a 2'-β-D-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification in each sugar moiety of each wing and the gap nucleosides comprise 2'-β-D-deoxyribosyl sugar moieties. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked 2'-β-D-deoxynucleosides in the gap, and 5 linked nucleosides comprising a modified sugar moiety in the 3'-wing. A 5-8-5 mixed gapmer has at least two different modified sugar moieties in the 5'- and/or the 3'-wing.

In certain embodiments, modified oligonucleotides are 5-10-5 MOE gapmers. In certain embodiments, modified oligonucleotides are 4-10-6 MOE gapmers. In certain embodiments, modified oligonucleotides are 6-10-4 MOE gapmers. In certain embodiments, modified oligonucleotides are 5-8-5 MOE gapmers. In certain embodiments, modified oligonucleotides are 6-8-4 MOE gapmers. In certain embodiments, modified oligonucleotides are 4-8-6 MOE gapmers. In certain embodiments, modified oligonucleotides are X-Y-Z MOE gapmers, wherein X and Z are independently selected from 1, 2, 3, 4, 5, or 6 and Y is 7, 8, 9, 10, or 11.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-β-D-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or portion thereof in a defined pattern or motif. In certain embodiments, each internucleoside linking group is a phosphodiester internucleoside linkage ($P(O_2)$=O). In certain embodiments, each internucleoside linking group of a modified oligonucleotide is a phosphorothioate internucleoside linkage ($P(O_2)$=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, modified nucleotides have an internucleoside linkage motif of sooooosssssssssssooss, wherein each "s" represents a phosphorothioate internucleoside linkage and each "o" represents a phosphodiester internucleoside linkage. In certain embodiments, modified nucleotides have an internucleoside linkage motif of sooooosssssssssssoss, wherein each "s" represents a phosphorothioate internucleoside linkage and each "o" represents a phosphodiester internucleoside linkage. In certain embodiments, modified nucleotides have an internucleoside linkage motif of sooooosssssssssssoss, wherein each "s" represents a phosphorothioate internucleoside linkage and each "o" represents a phosphodiester internucleoside linkage. In certain embodiments, modified nucleotides have an internucleoside linkage motif of soooossssssssssooss, wherein each "s" represents a phosphorothioate internucleoside linkage and each "o" represents a phosphodiester internucleoside linkage. In certain embodiments, modified nucleotides have an internucleoside linkage motif of sooosssssssssssooss, wherein each "s" represents a phosphorothioate internucleoside linkage and each "o" represents a phosphodiester internucleoside linkage. In certain embodiments, modified nucleotides have an internucleoside linkage motif of soosssssssssooss, wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for R-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among an amide, an ester, an ether, one or both esters of a phosphodiester, a phosphate ester, a carbamate, and a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

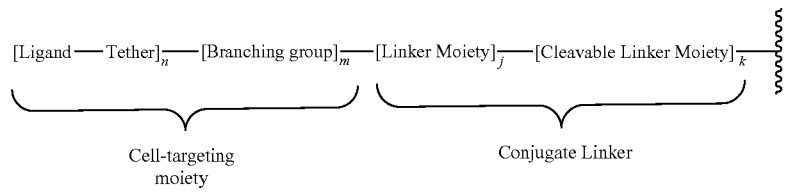

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactosamine (GalNAc), mannose, glucose, glucosamine and fucose. In certain embodiments, each ligand is N-acetyl galactosamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry*, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

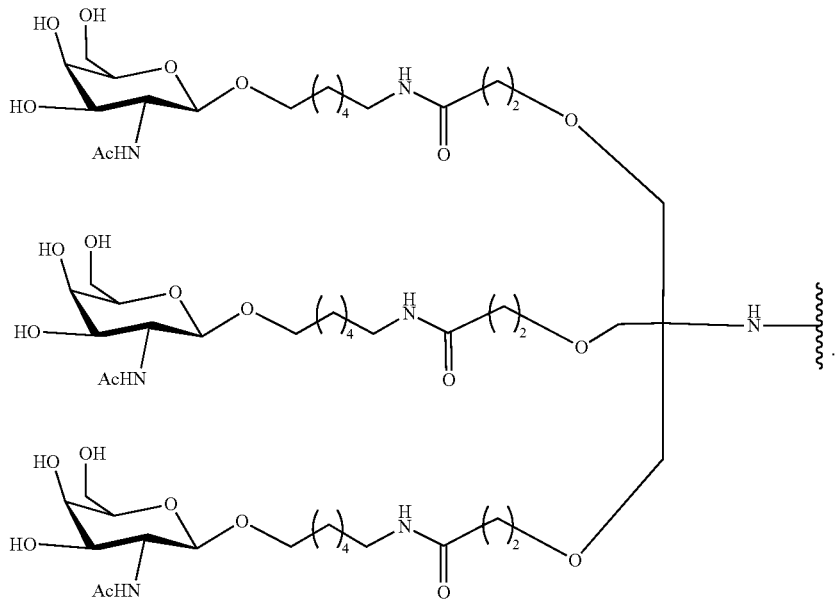

In certain embodiments, conjugate groups comprise a cell-targeting moiety having the formula:

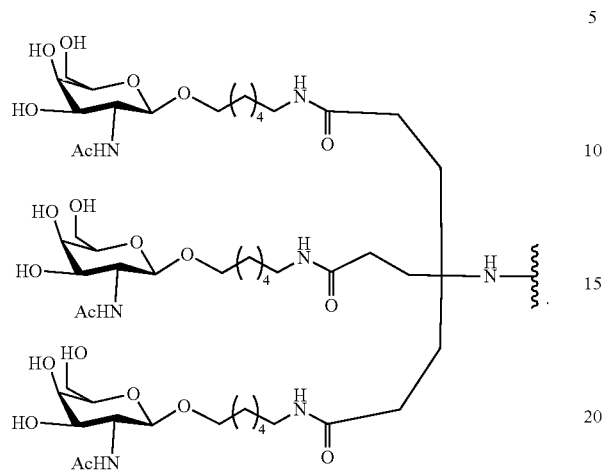

In certain embodiments, conjugate groups comprise a cell-targeting moiety having the formula:

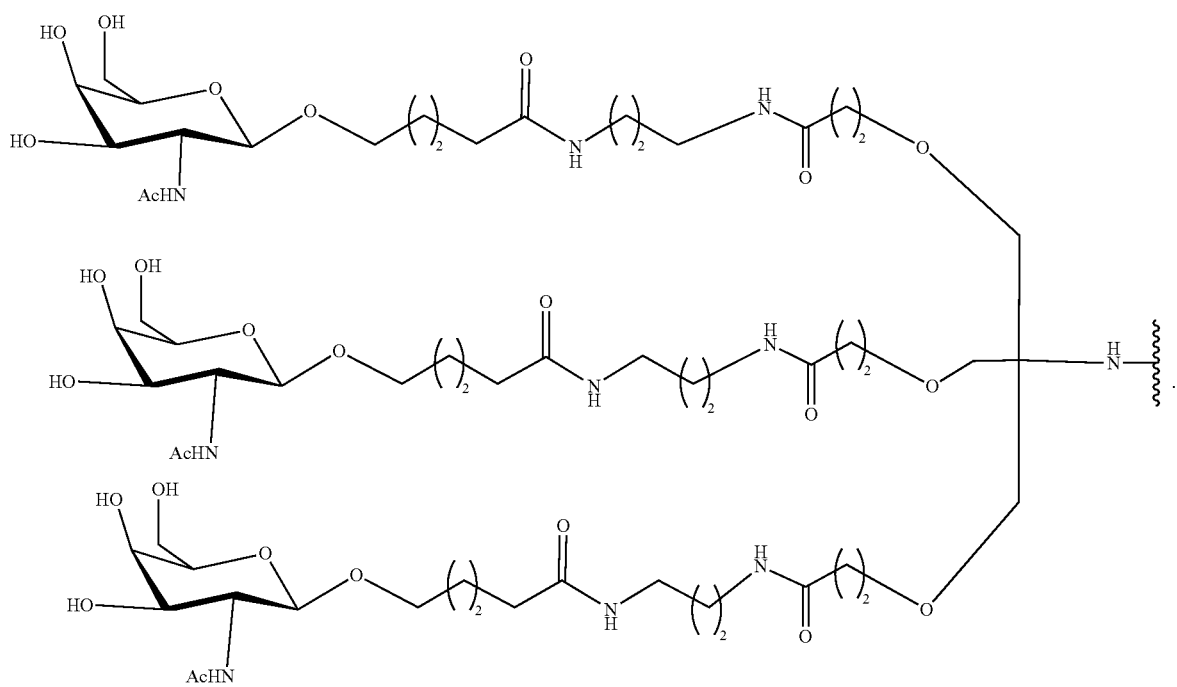

In certain embodiments, compounds described herein comprise a conjugate group described herein as "THA-GalNAac₃". THA-GalNAc₃ is shown below without the optional cleavable moiety at the end of the linker region:

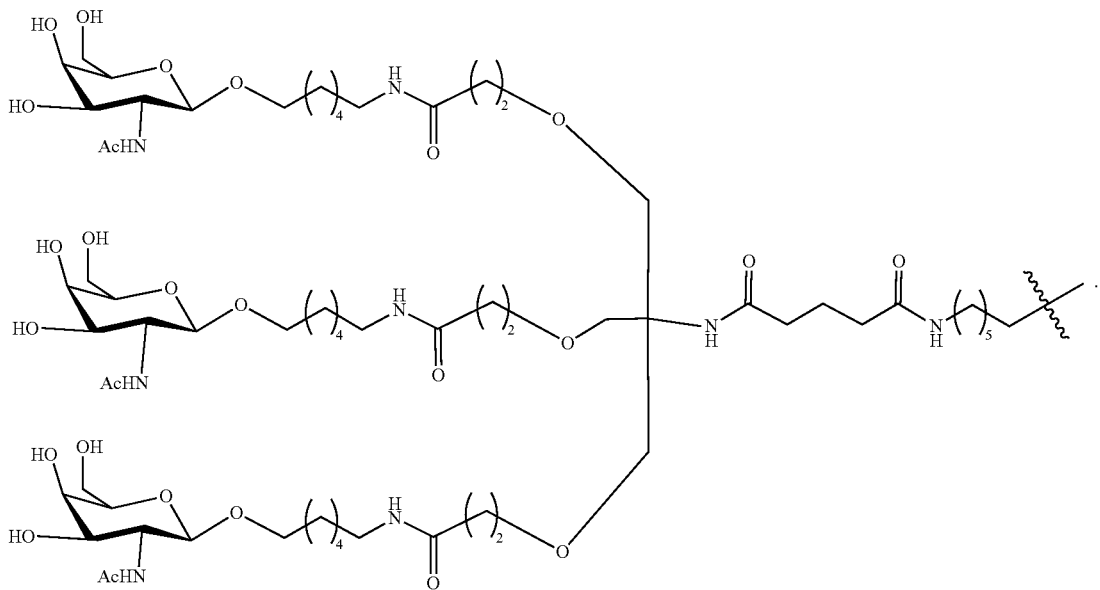

In certain embodiments, compounds described herein comprise THA-GalNAc$_3$-phosphate, also represented as (THA-GalNAc$_3$)o, having the formula:

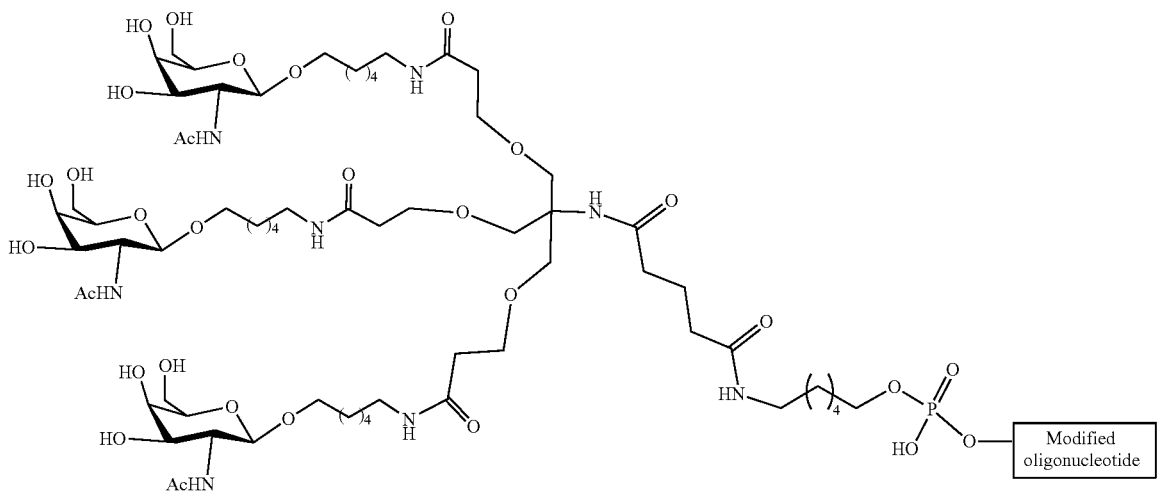

wherein modified oligonucleotide represents a modified oligonucleotide.

In certain embodiments, compounds described herein comprise a 3'-THA-C6-GalNAc hydroxyproline phosphate, ("HPPO-GalNAc"). 3'-HPPO-GalNAc is represented by the structure below wherein the phosphate group is attached to the 3'-oxygen atom of the 3' nucleoside:

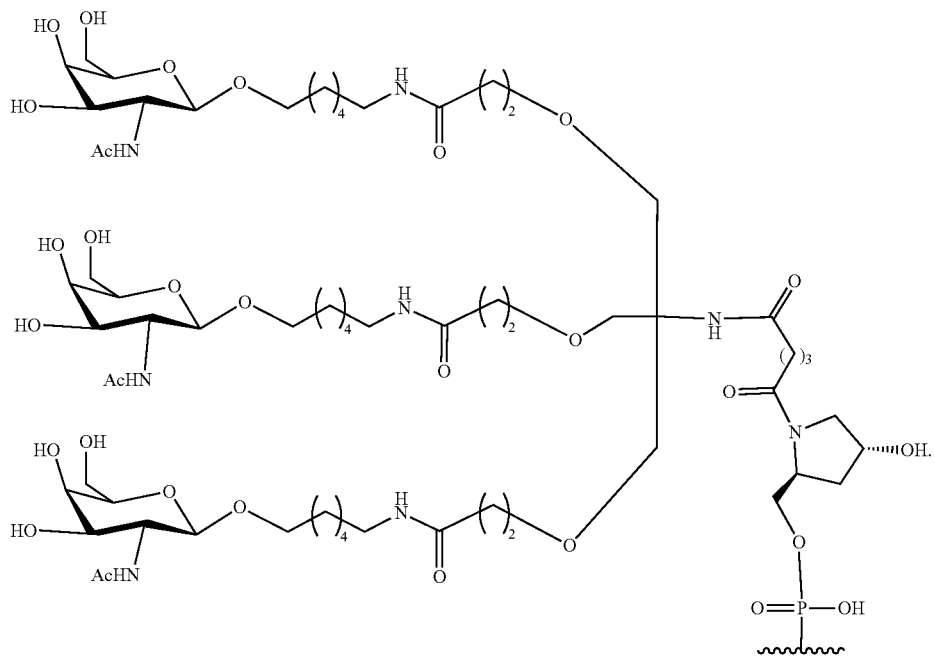

Representative publications that teach the preparation of certain of the above noted conjugate groups and compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, 9,127,276, US 2006/0148740, US 2011/0123520, WO 2013/033230 and WO 2012/037254, Biessen et al., *J. Med. Chem.* 1995, 38, 1846-1852, Lee et al., *Bioorganic & Medicinal Chemistry* 2011, 19, 2494-2500, Rensen et al., *J. Biol. Chem.* 2001, 276, 37577-37584, Rensen et al., *J. Med. Chem.* 2004, 47, 5798-5808, Sliedregt et al., *J. Med. Chem.* 1999, 42, 609-618, and Valentijn et al., *Tetrahedron*, 1997, 53, 759-770, each of which is incorporated by reference herein in its entirety.

In certain embodiments, compounds described herein comprise modified oligonucleotides comprising a gapmer or fully modified motif and a conjugate group comprising at least one, two, or three GalNAc ligands. In certain embodiments compounds described herein comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *Bioorg Med Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *Bioorg Med Chem*, 2011, 19, 2494-2500; Kornilova et al., Analyt Biochem, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther,* 2004, 11, 457-464; Sato et al., *J Am Chem Soc*, 2004, 126, 14013-14022; Lee et al., *J Org Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, *Antisense Nucleic Acid Drug Dev,* 2002, 12, 103-128; Merwin et al., *Bioconjug Chem*, 1994, 5, 612-620; Tomiya et al., *Bioorg Med Chem*, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/

0178512; US2013/0236968; US2011/0123520; US2003/0077829; US2008/0108801; and US2009/0203132; each of which is incorporated by reference in its entirety.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphinates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA, and a pre-mRNA, including intronic, exonic and untranslated regions. In certain embodiments, the target RNA is an antisense transcript. In certain embodiments, the target RNA is a mature mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. FXII

In certain embodiments, oligomeric compounds comprise or consist of an oligonucleotide, or portion thereof, that is complementary to a target nucleic acid, wherein the target nucleic acid is a FXII nucleic acid. In certain embodiments, the FXII nucleic acid has the human FXII mRNA sequence designated herein as SEQ ID NO: 1 (ENSEMBL ID ENST00000253496.3 from ENSEMBL version 99: January 2020). In certain embodiments, the FXII nucleic acid has the human F12 genomic sequence, designated herein as SEQ ID NO: 2 (ENSEMBL ID ENSG00000131187.9 from ENSEML version 99: January 2020, human reference assembly version GRCh38.p13 located on the reverse strand of chromosome 5 from positions 177,402,140 to 177,409,576). In certain embodiments, the FXII nucleic acid has the human F12 genomic sequence, designated herein as SEQ ID NO. 3 (the complement of GENBANK Accession No. NC_000005.10 truncated from truncated from nucleotides 177399001 to 177413000). In certain embodiments, the FXII nucleic acid has the human FXII mRNA sequence designated herein as SEQ ID NO: 4 (GENBANK Accession No. NM_000505.3).

In certain embodiments, an oligomeric compound complementary to any one of SEQ ID NOS: 1-4 is capable of reducing FXII RNA in a cell. In certain embodiments, an oligomeric compound complementary to any one of SEQ ID NOS: 1-4 is capable of reducing FXII protein in a cell. In certain embodiments, the cell is in vitro. In certain embodiments, the cell is in a subject. In certain embodiments, an oligomeric compound complementary to any one of SEQ ID NOS: 1-4 is capable of ameliorating one or more symptoms of a thromboembolic condition when administered to a subject. In certain embodiments, the thromboembolic condition is deep vein thrombosis, venous thrombosis, arterial thrombosis, pulmonary embolism, myocardial infarction, or stroke. In certain embodiments, the symptoms are selected from pain, shortness of breath, heart burn, cold sweat, fatigue, lightheadedness, dizziness, swelling, cramping, and death.

In certain embodiments, an oligomeric compound complementary to any one of SEQ ID NOS: 1-4 is capable of reducing the detectable amount of FXII RNA in vitro by at least 10%, at least 20%, at least 30%, at least 40%, at least 50%, at least 60%, at least 70%, at least 80%, or at least 90%. In certain embodiments, an oligomeric compound complementary to any one of SEQ ID NOS: 1-4 is capable of reducing the detectable amount of FXII protein in vitro by at least 10%, at least 20%, at least 30%, at least 40%, at least 50%, at least 60%, at least 70%, at least 80%, or at least 90%. In certain embodiments, an oligomeric compound complementary to any one of SEQ ID NOS: 1-4 is capable of reducing the detectable amount of FXII RNA in a biological sample of a subject by at least 10%, at least 20%, at least 30%, at least 40%, at least 50%, at least 60%, at least 70%, at least 80%, or at least 90%. In certain embodiments, an oligomeric compound complementary to any one of SEQ ID NOS: 1-4 is capable of reducing the detectable amount of FXII protein in a biological sample of a subject by at least 10%, at least 20%, at least 30%, at least 40%, at least 50%, at least 60%, at least 70%, at least 80%, or at least 90%. In certain embodiments, the biological sample comprises blood, plasma/serum, or a cell of the subject.

VI. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or a salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

VII. Certain Compositions

1. Compound No. 1194357

In certain embodiments, Compound No. 1194357 is characterized as an oligomeric compound consisting of a conjugate group and a modified oligonucleotide, wherein the conjugate group is a THA-GalNAc$_3$ that is directly attached to the 5' end of the modified oligonucleotide through a phosphodiester linkage, (THA-GalNAc$_3$)o; wherein (THA-GalNAc$_3$)o is represented by the following structure:

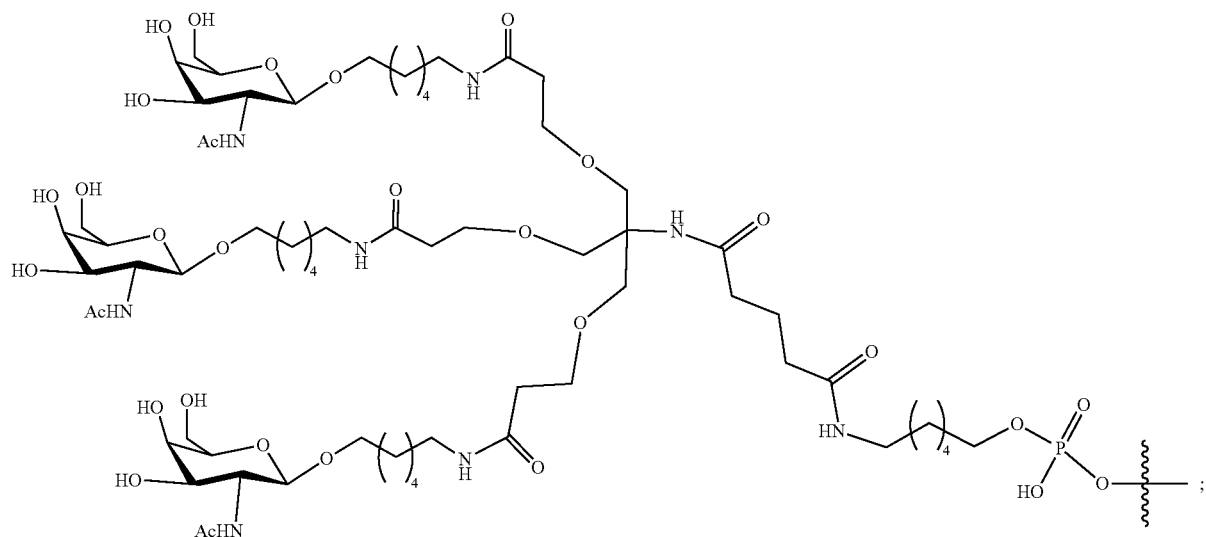

wherein the modified oligonucleotide is a 3-10-3 cEt gapmer, having a sequence of (from 5' to 3') GCGGAATCAC-CAAGGA (incorporated herein as SEQ ID NO: 3379); wherein each of nucleosides 1-3 and 14-16 (from 5' to 3') comprise a cEt modified sugar moiety and each of nucleosides 4-13 are 2'-β-D-deoxynucleosides; wherein each internucleoside linkage is a phosphorothioate internucleoside linkage; and wherein each cytosine is a 5-methyl cytosine.

In certain embodiments, Compound No. 1194357 is represented by the following chemical notation: (THA-GalNAc₃)o Gks $^m$Cks Gks Gds Ads Ads Tds $^m$Cds Ads $^m$Cds $^m$Cds Ads Ads Gks Gks Ak, wherein:
  A=an adenine nucleobase,
  $^m$C=a 5-methyl cytosine nucleobase,
  G=a guanine nucleobase,
  T=a thymine nucleobase,
  k=a cEt modified sugar moiety,
  d=a 2'-β-D-deoxyribosyl sugar moiety, and
  s=a phosphorothioate internucleoside linkage.

In certain embodiments, provided is an oligomeric compound comprising a modified oligonucleotide and a conjugate group according to the following chemical notation: (THA-GalNAc₃)o Gks $^m$Cks Gks Gds Ads Ads Tds $^m$Cds Ads $^m$Cds $^m$Cds Ads Ads Gks Gks Ak, wherein:
  A=an adenine nucleobase,
  $^m$C=a 5-methyl cytosine nucleobase,
  G=a guanine nucleobase,
  T=a thymine nucleobase,
  k=a cEt modified sugar moiety,
  d=a 2'-β-D-deoxyribosyl sugar moiety, and
  s=a phosphorothioate internucleoside linkage;
and wherein (THA-GalNAc₃)o=

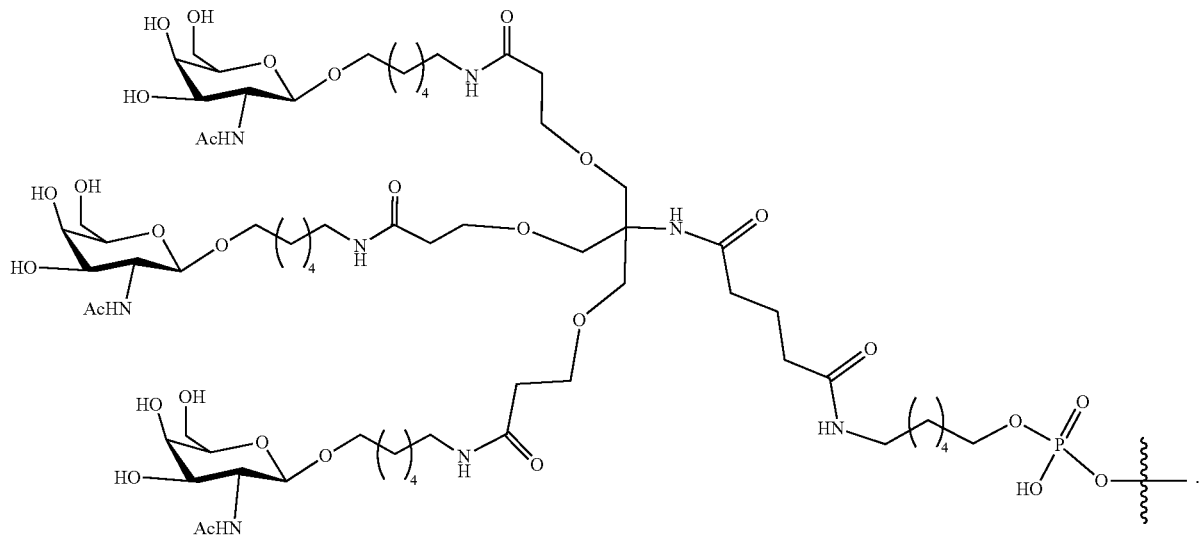

In certain embodiments, Compound No. 1194357 is represented by the following chemical structure:
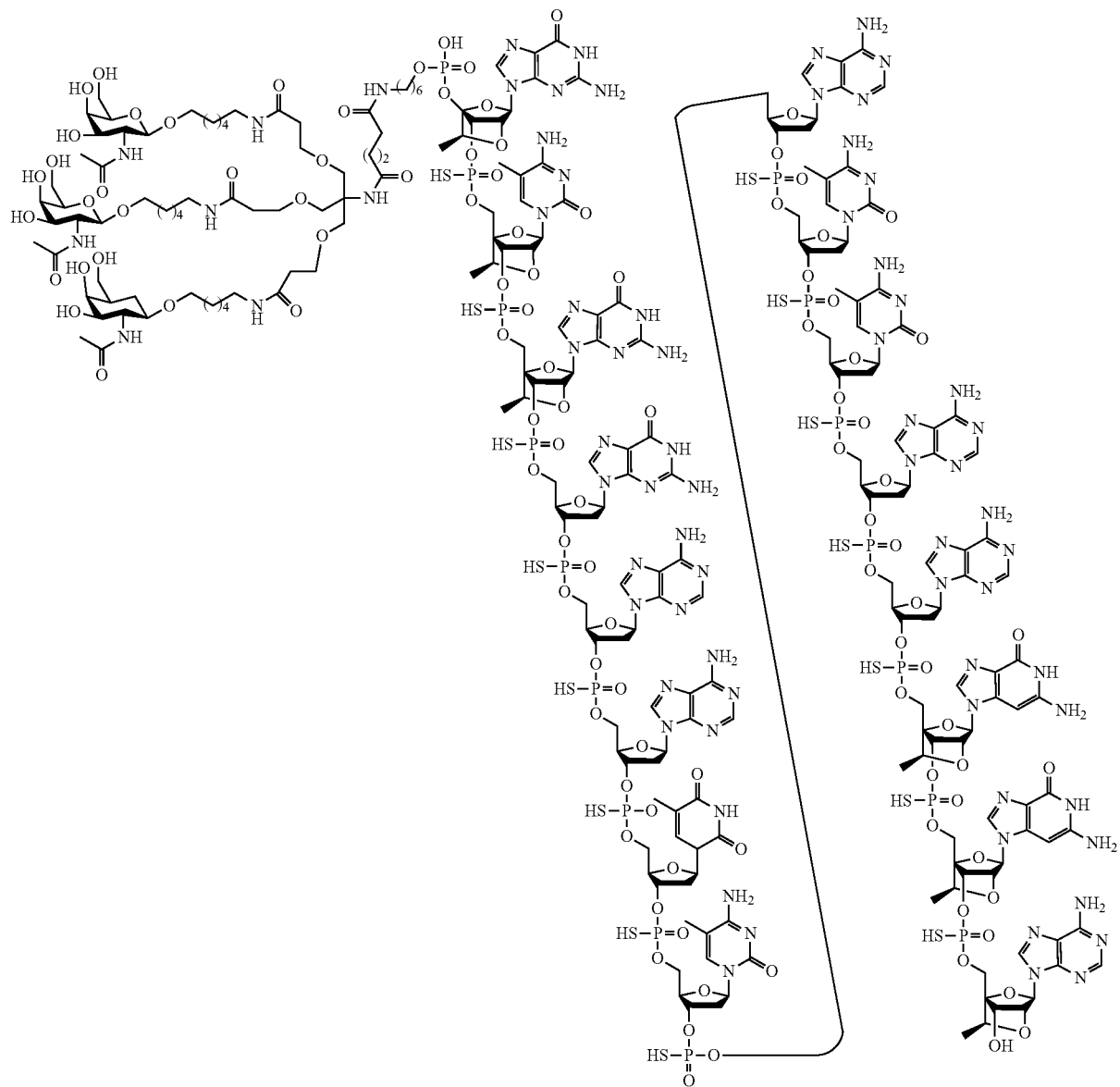
(SEQ ID NO: 3379). Structure 1. Compound No. 1194357
In certain embodiments, the sodium salt of Compound No. 1194357 is represented by the following chemical structure:

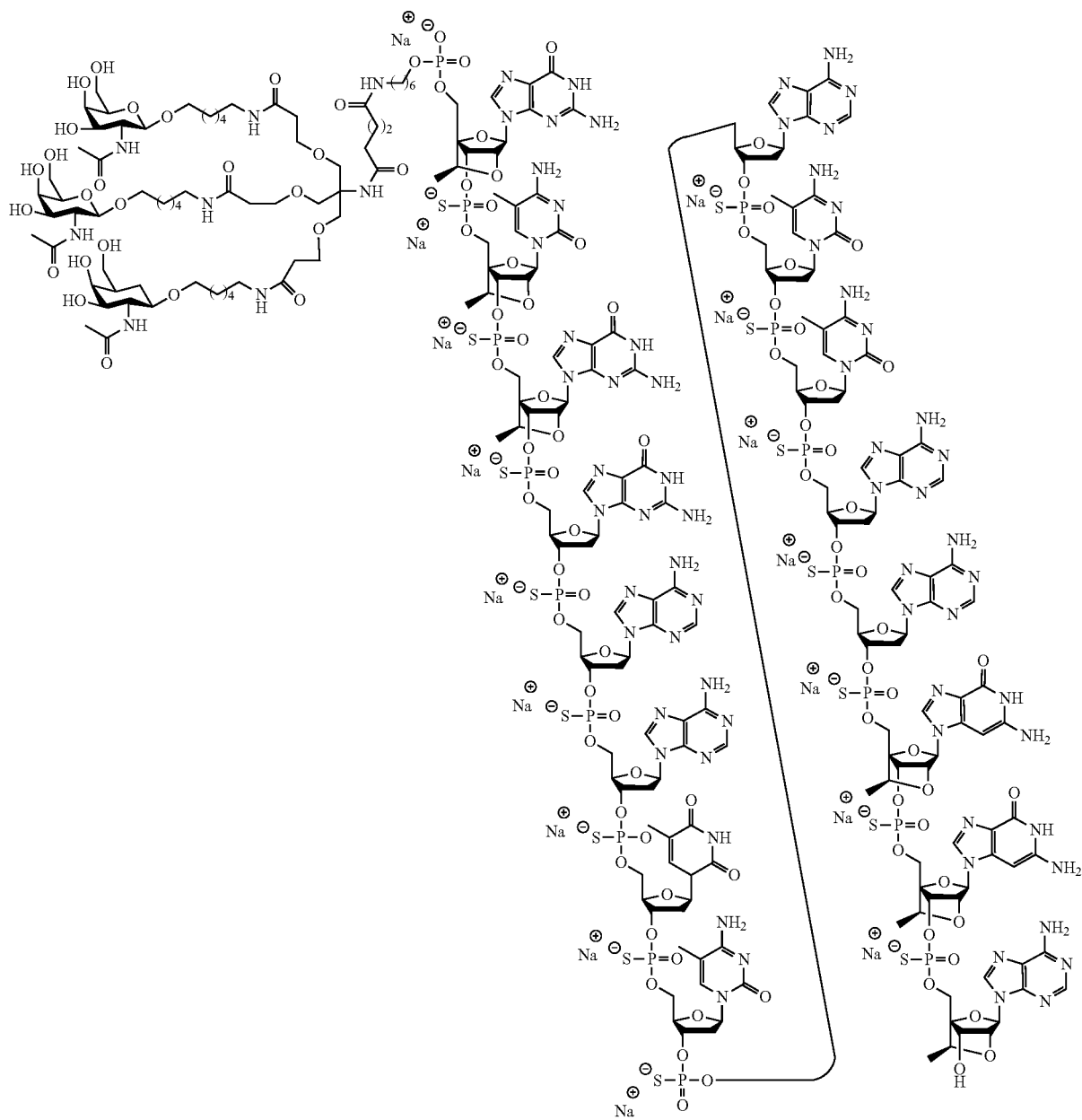

(SEQ ID NO: 3379). Structure 2. The sodium salt of Compound No. 1194357

2. Compound No. 1270705

In certain embodiments, Compound No. 1270705 is characterized as an oligomeric compound consisting of a conjugate group and a modified oligonucleotide; wherein the conjugate group is a THA-GalNAc$_3$ that is directly attached to the 5' end of the modified oligonucleotide through a phosphodiester linkage, (THA-GalNAc$_3$)o; wherein (THA-GalNAc$_3$)o is represented by the following structure:

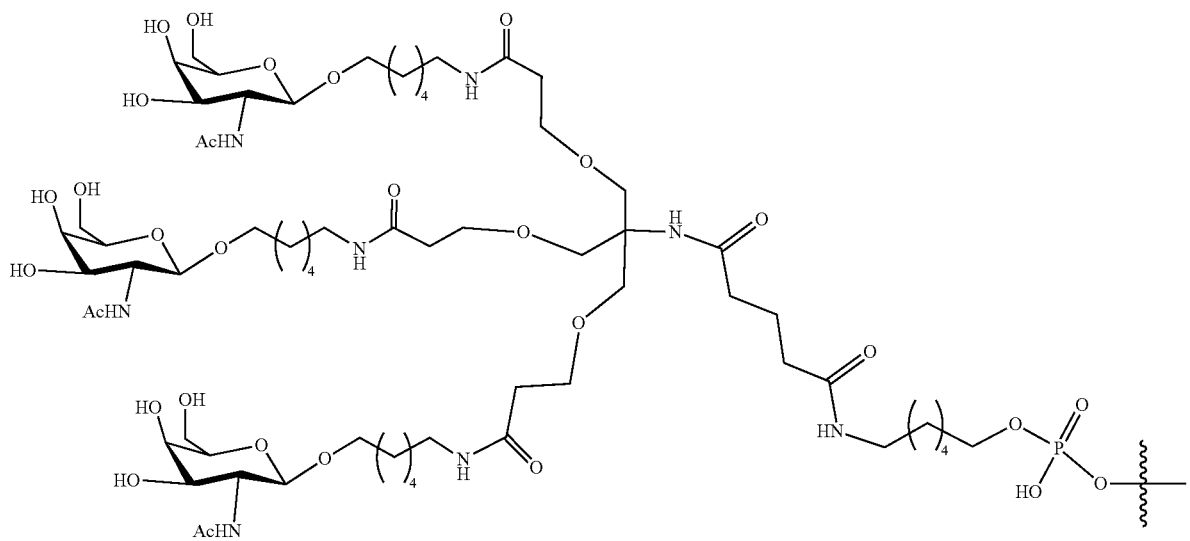

wherein the modified oligonucleotide is gapmer, having a sequence of (from 5' to 3') GCACUTTATTGAGTTC (incorporated herein as SEQ ID NO: 5006); wherein each of nucleosides 1-3 and 14-16 (from 5' to 3') comprise a cEt modified sugar moiety, each of nucleosides 4 and 6-13 are 2'-β-D-deoxynucleosides, and nucleoside 5 comprises a 2'-O-methyl sugar moiety; wherein each internucleoside linkage is a phosphorothioate internucleoside linkage, and wherein each cytosine is a 5-methyl cytosine.

In certain embodiments, Compound No. 1270705 is represented by the following chemical notation: (THA-GalNAc$_3$)o Gks $^m$Cks Aks $^m$Cds Uys Tds Tds Ads Tds Tds Gds Ads Gds Tks Tks $^m$Ck, wherein:
- A=an adenine nucleobase,
- $^m$C=a 5-methyl cytosine nucleobase,
- G=a guanine nucleobase,
- T=a thymine nucleobase,
- U=a uracil nucleobase,
- k=a cEt modified sugar moiety,
- y=a 2'-O-methyl modified ribosyl sugar moiety,
- d=a 2'-β-D-deoxyribosyl sugar moiety, and
- s=a phosphorothioate internucleoside linkage.

In certain embodiments, provided is an oligomeric compound comprising a modified oligonucleotide and a conjugate group according to the following chemical notation: (THA-GalNAc$_3$)o Gks $^m$Cks Aks $^m$Cds Uys Tds Tds Ads Tds Tds Gds Ads Gds Tks Tks $^m$Ck, wherein:
- A=an adenine nucleobase,
- $^m$C=a 5-methyl cytosine nucleobase,
- G=a guanine nucleobase,
- T=a thymine nucleobase,
- U=a uracil nucleobase,
- k=a cEt modified sugar moiety,
- y=a 2'-O-methyl modified ribosyl sugar moiety,
- d=a 2'-β-D-deoxyribosyl sugar moiety, and
- s=a phosphorothioate internucleoside linkage;

and wherein (THA-GalNAc$_3$)o=

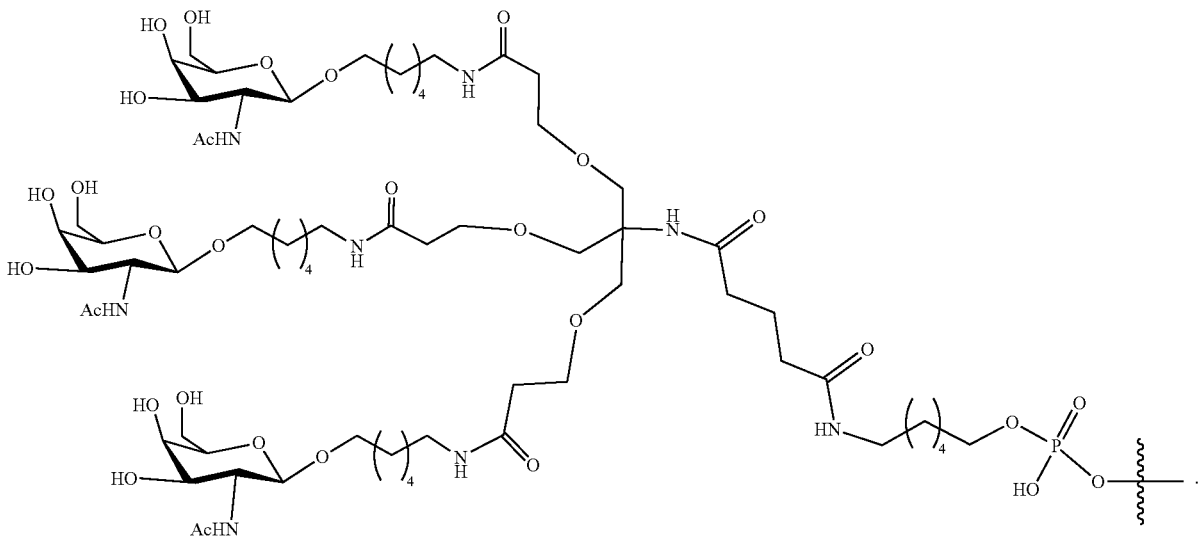

In certain embodiments, Compound No. 1270705 is represented by the following chemical structure:
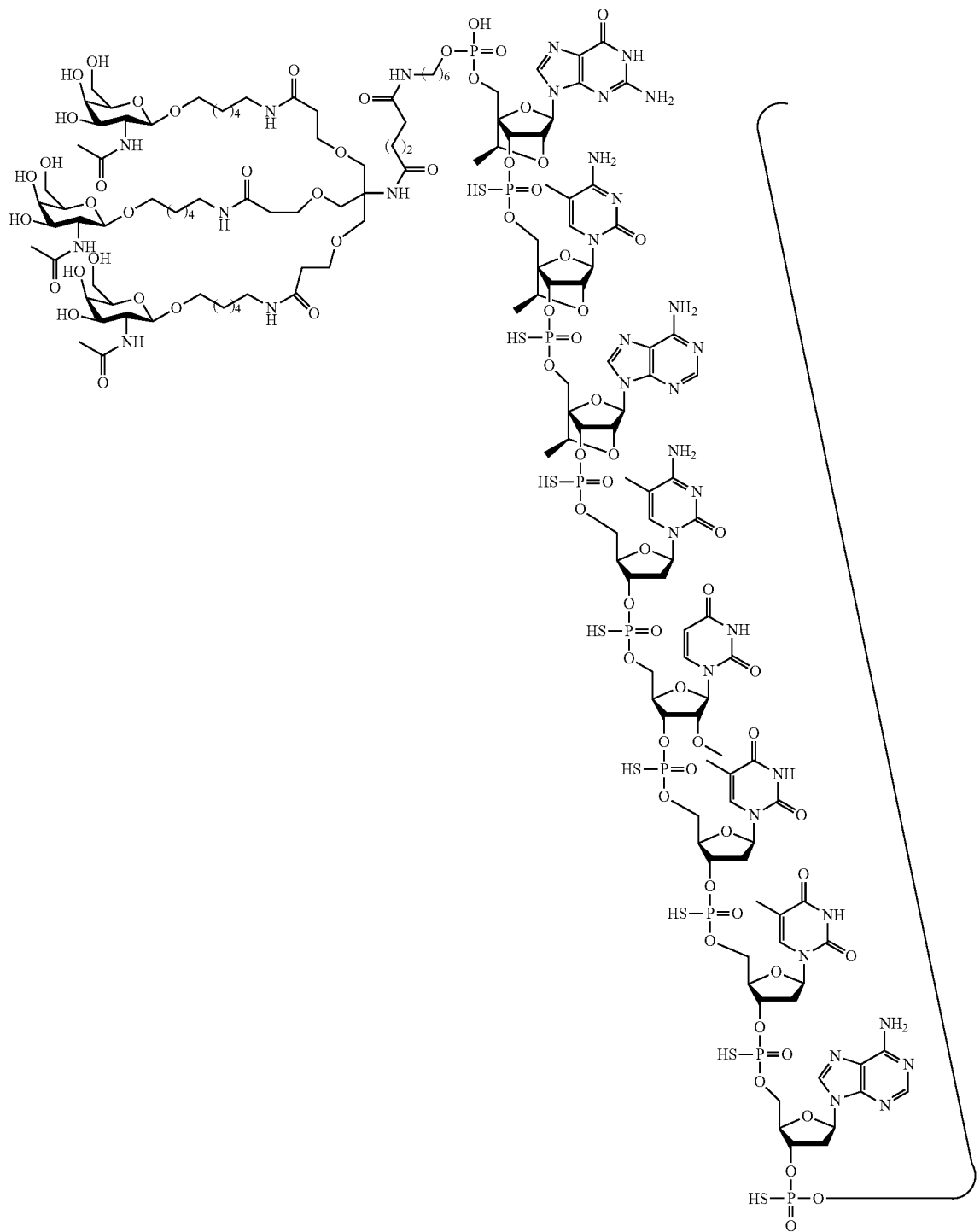

-continued
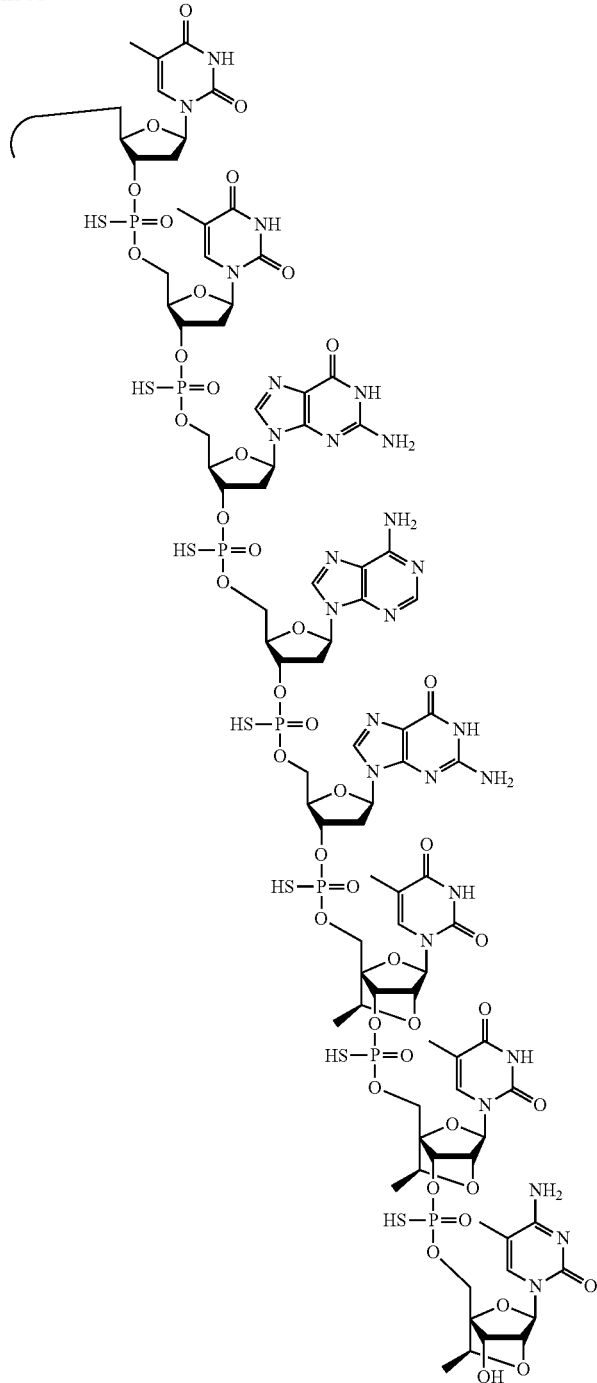 [SMILES: CC[C@H]1O[C@@H](n2cc(C)c(=O)[nH]c2=O)C[C@H]1OP(=O)(S)OC[C@H]1O[C@@H](n2cc(C)c(=O)[nH]c2=O)C[C@H]1OP(=O)(S)OC[C@H]1O[C@@H](n2cnc3c(=O)[nH]c(N)nc32)C[C@H]1OP(=O)(S)OC[C@H]1O[C@@H](n2cnc3c(N)ncnc32)C[C@H]1OP(=O)(S)OC[C@H]1O[C@@H](n2cnc3c(=O)[nH]c(N)nc32)C[C@H]1OP(=O)(S)OC[C@]12O[C@@H](n3cc(C)c(=O)[nH]c3=O)C(O[C@H]1C)[C@H]2OP(=O)(S)OC[C@]12O[C@@H](n3cc(C)c(=O)[nH]c3=O)C(O[C@H]1C)[C@H]2OP(=O)(S)OC[C@]12O[C@@H](n3cc(C)c(N)nc3=O)C(O[C@H]1C)[C@H]2O]
(SEQ ID NO: 5006).
Structure 3. Compound No. 1270705
In certain embodiments, the sodium salt of Compound No. 1270705 is represented by the following chemical structure:

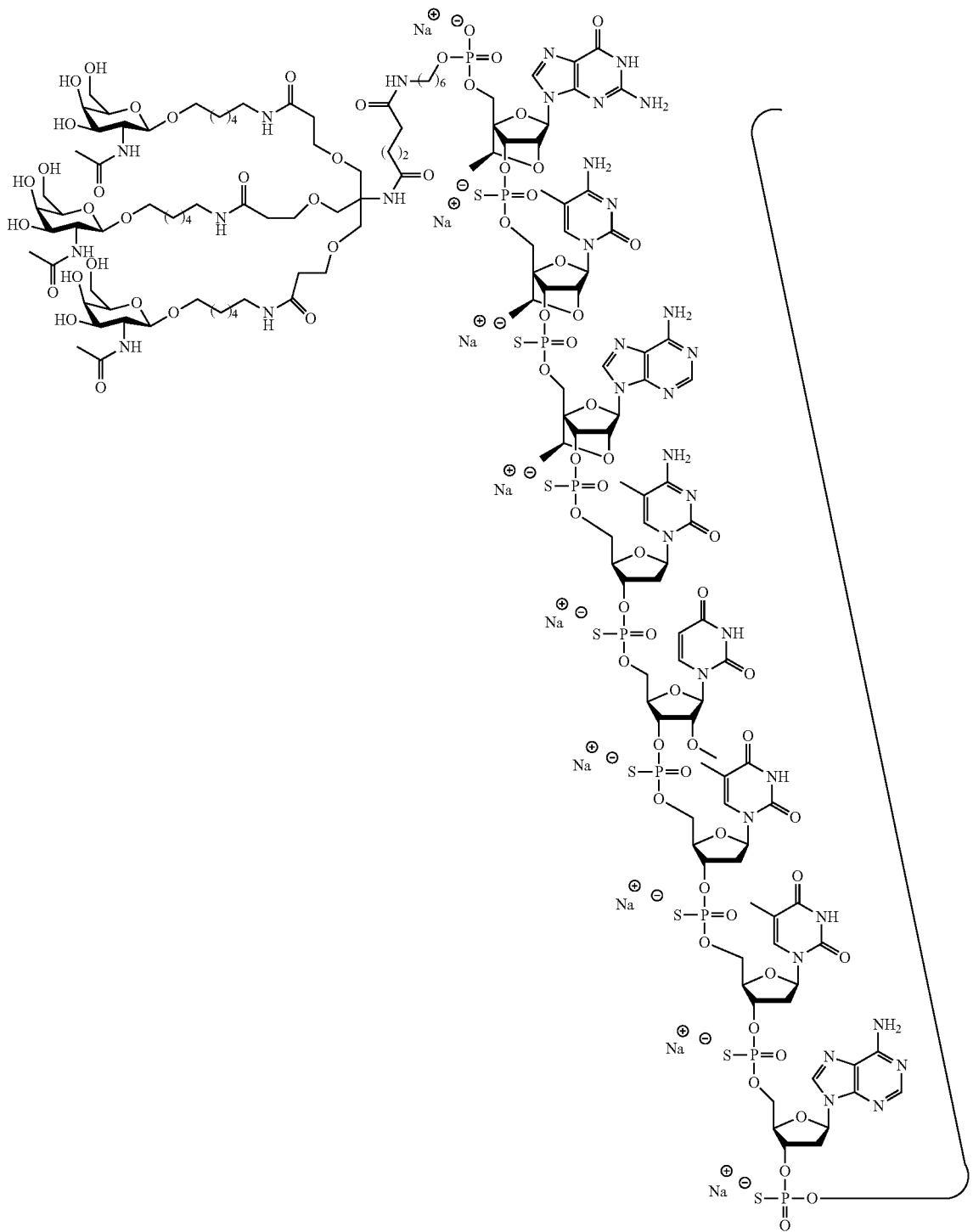

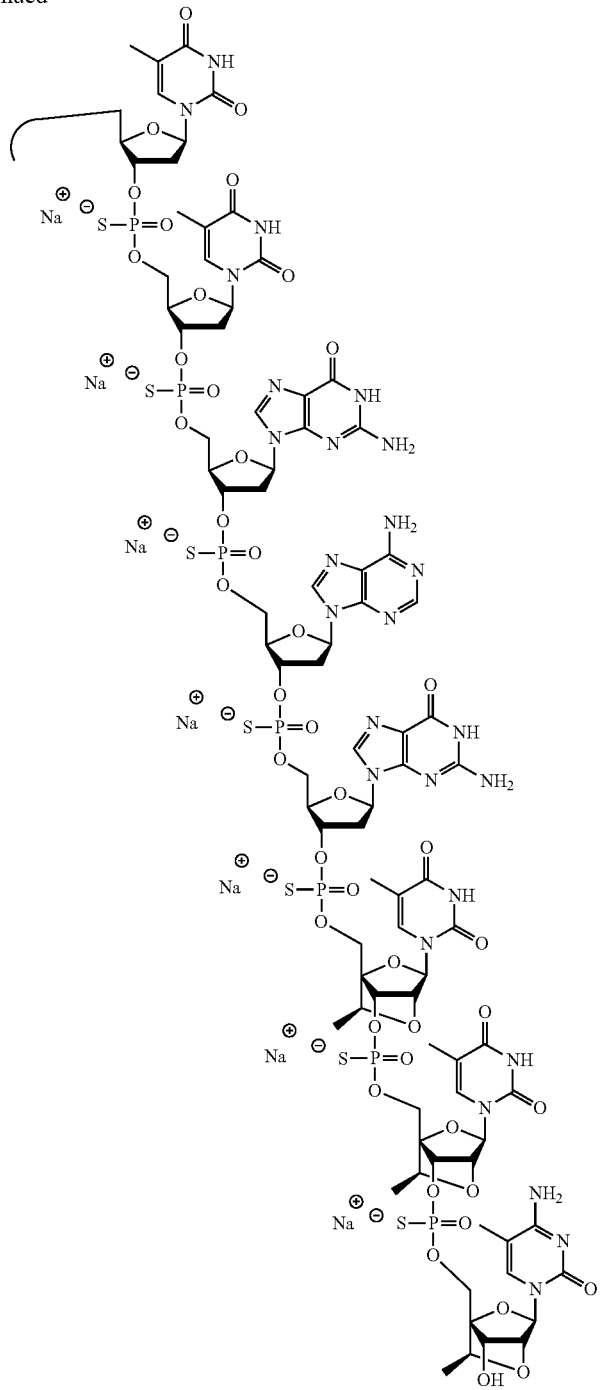

(SEQ ID NO: 5006).
Structure 4. The sodium salt of Compound No. 1270705
VIII. Certain Comparator Compounds Comparator Compound Nos. 1213029, 1213030, 1213034, and 1358035 (relating to Compound Nos. A-145667, A-145668, A-145676, and A-145669, respectively) were selected as comparator compounds from Example 1 of WO2017/120397 (incorporated herein by reference).

In certain embodiments, Compound No. 1213029, a surrogate of which (Compound A-145667) is provided in WO2017/120397, was used as a comparator compound, see Example 14. Compound No. 1213029 is a gapmer having a sugar motif of (from 5' to 3') yyyyydddddddddddyyyyy, wherein each "y" represents a 2'-O-methyl sugar moiety and each "d" represents a 2'-β-D-deoxyribosyl sugar moiety; having a sequence of (from 5' to 3') GAAUAC-CAAGGAGGGAAAG (SEQ ID NO: 5042), wherein each "C" of the gap is a 5-methyl cytosine; and wherein each internucleoside linkage is a phosphorothioate internucleoside linkage.

In certain embodiments, Compound No. 1213030, a surrogate of which (Compound A-145668) is provided in WO2017/120397, was used as a comparator compound, see Example 14. Compound No. 1213030 is a gapmer having a sugar motif of (from 5' to 3') yyyyyddddddddddyyyyy, wherein each "y" represents a 2'-O-methyl sugar moiety and each "d" represents a 2'-β-D-deoxyribosyl sugar moiety; having a sequence of (from 5' to 3') UCUCACTGCGGAAT-CACCAA (SEQ ID NO: 5041), wherein each "C" of the gap is a 5-methyl cytosine; and wherein each internucleoside linkage is a phosphorothioate internucleoside linkage.

In certain embodiments, Compound No. 1213034, a surrogate of which (Compound A-145676) is provided in WO2017/120397, was used as a comparator compound, see Example 14. Compound No. 1213034 is a gapmer having a sugar motif of (from 5' to 3') yyyyyddddddddddyyyyy, wherein each "y" represents a 2'-O-methyl sugar moiety and each "d" represents a 2'-β-D-deoxyribosyl sugar moiety; having a sequence of (from 5' to 3') CACUUTATT-GAGTTCCUGCG (SEQ ID NO: 5039), wherein each "C" of the gap is a 5-methyl cytosine; and wherein each internucleoside linkage is a phosphorothioate internucleoside linkage.

In certain embodiments, Compound No. 1358035, a surrogate of which (Compound A-145669) is provided in WO2017/120397, was used as a comparator compound, see Example 14. Compound No. 1358035 is a gapmer having a sugar motif of (from 5' to 3') yyyyyddddddddddyyyyy, wherein each "y" represents a 2'-O-methyl sugar moiety and each "d" represents a 2'-β-D-deoxyribosyl sugar moiety; having a sequence of (from 5' to 3') CCCCAGC-CACTCTCTCACUG (SEQ ID NO: 5040), wherein each "C" of the gap is a 5-methyl cytosine; and wherein each internucleoside linkage is a phosphorothioate internucleoside linkage.

In certain embodiments, compounds described herein are superior relative to comparator compounds described in WO2017/120397 because they demonstrate one or more improved properties, such as in vitro activity.

For example, as described herein, certain compounds, including Compound No. 1129485 and Compound No. 1213144, achieved IC50 values of 0.34 and 0.28, respectively, whereas each of comparator compounds Compound No. 1213029, Compound No. 1213030, Compound No. 1213034, and Compound No. 1358035 achieved IC50 values of >10, 8.15, >10, and 8.59, respectively, (see Table 154 in Example 14 for IC50 values). Therefore, certain compounds described herein are more potent than comparator compounds Compound No. 1213029, Compound No. 1213030, Compound No. 1213034, and Compound No. 1358035 in a multiple dose assay.

Compound No. 1194357 is identical to Compound No. 1129485, with the exception that Compound No. 1194357 comprises a conjugate group, and Compound No. 1270705 is identical to Compound No. 1213144, with the exception that Compound No. 1270705 comprises a conjugate group. Therefore, unconjugated versions of Compound No. 1129485 and Compound No. 1270705 are more active than comparator compounds Compound No. 1213029, Compound No. 1213030, Compound No. 1213034, and Compound No. 1358035 in a multiple dose assay.

IX. Certain Hotspot Regions

In certain embodiments, nucleobases in the ranges specified below comprise a hotspot region of FXII nucleic acid. In certain embodiments, modified oligonucleotides that are complementary to a hotspot region of a FXII nucleic acid achieve an average of more than 50% reduction of FXII RNA in vitro in a standard cell assay.

1. Nucleobases 1,899-1,979 of SEQ ID NO: 1

In certain embodiments, nucleobases 1,899-1,979 of SEQ ID NO: 1 comprise a hotspot region. In certain embodiments, modified oligonucleotides are complementary to a portion of nucleobases 1,899-1,979 of SEQ ID NO: 1. In certain embodiments, modified oligonucleotides are 20 nucleobases in length. In certain embodiments, modified oligonucleotides are 16 nucleobases in length. In certain embodiments, modified oligonucleotides are gapmers. In certain embodiments, the gapmers are MOE gapmers. In certain embodiments, the gapmers are cEt gapmers. In certain embodiments, the internucleoside linkages of the modified oligonucleotides are phosphorothioate internucleoside linkages and phosphodiester internucleoside linkages. In certain embodiments, each internucleoside linkage is a phosphorothioate internucleoside linkage.

The nucleobase sequences of SEQ ID NOs: 92, 156, 270, 271, 345, 346, 420, 421, 496, 497, 571, 572, 653, 654, 728, 729, 802, 803, 877, 951, 1028, 1103, 1179, 1253, 1330, 1407, 1484, 1560, 1636, 1710, 1711, 1784, 1859, 1860, 1934, 1935, 2008, 2009, 2084, 2085, 2158, 2232, 2233, 2307, 2308, 2393, 2394, 2395, 2396, 2397, 2398, 2461, 2537, 2538, 2614, 2615, 2691, 2692, 2768, 2769, 2845, 2846, 2921, 2922, 2997, 2998, 3073, 3074, 3144, 3145, 3226, 3227, 3303, 3304, 3379, 3380, 3455, 3456, 3531, 3607, 3683, 3759, 3835, 3911, 4948, 4949, 4954, 4955, 4956, 4957, 4961, 4965, 4966, 4967, 4971, 4972, 4976, 4994, 4995, 4996, 4997, 4998, 4999, 5024, 5025, 5026, 5027, 5028, and 5029 are complementary to nucleobases 1,899-1,979 of SEQ ID NO: 1.

The nucleobase sequences of Compound Nos: 1125047, 1125048, 1125049, 1125050, 1125051, 1125074, 1125075, 1125076, 1125077, 1125078, 1129474, 1129475, 1129476, 1129477, 1129478, 1129479, 1129480, 1129481, 1129482, 1129483, 1129484, 1129485, 1129486, 1129487, 1129488, 1129489, 1129490, 1129491, 1129492, 1129493, 1129494, 1129495, 1129496, 1129497, 1129498, 1129499, 1129500, 1129501, 1129502, 1129503, 1129504, 1129505, 1129506, 1131681, 1131682, 1131683, 1131684, 1131685, 1131686, 1131687, 1131688, 1131689, 1131690, 1131691, 1131692, 1131693, 1131694, 1131695, 1131696, 1131697, 1131698, 1131699, 1131700, 1131701, 1131702, 1131703, 1131704, 1131705, 1131706, 1131707, 1131708, 1131709, 1131710, 1131711, 1131712, 1131713, 1131714, 1131715, 1131716, 1131717, 1131718, 1131719, 1131720, 1131721, 1131722, 1131723, 1131724, 1131725, 1206454, 1206455, 1206456, 1206457, 1206458, 1206459, 1206485, 1206486, 1206487, 1206488, 1206489, 1206490, 1206491, 1206492, 1206505, 1206506, 1206507, 1206508, 1206509, 1206957, 1206958, 1206959, 1206960, 1206961, 1206962, 1206963, 1206964, 1206965, 1206966, 1206967, 1206968, 1206969, 1206970, 1206971, 1206972, 1206973, 1206974, 1206975, 1206976, 1206977, 1206978, 1206979, 1206980, 1206981, 1206982, 1206983, 1206985, 1206986, 1206987, 1206988, 1207098, 1207099, 1207100, 1207101, 1207102, 1207103, 1207104, 1207105, 1207106, 1207107, 1207108, 1207109, 1207110, 1207111, 1207112, 1207113, 1207114, 1207115, 1207116, 1207117, 1207118, 1207120, 1207123, 1207125, 1207127, 1207129, 1207131, 1207133, 1207135, 1207137, 1207139, 1207141, 1207228, 1207229, 1207230, 1207231, 1207232, 1207233, 1207234, 1207235, 1207236, 1207237, 1207238, 1207239, 1207240, 1207241, 1207242, 1207243, 1207244, 1207245, 1207246, 1207247, 1207248, 1207249, 1207250, 1207251, 1207252, 1207253, 1207254, 1207256, 1207257, 1207258, 1207259, 1207345, 1207346, 1207347, 1207348, 1207349, 1207350, 1207351, 1207352, 1207353, 1207354, 1207355, 1207356, 1207357, 1207358, 1207359, 1207360, 1207361, 1207362, 1207363, 1207364, 1207365, 1207366, 1207367, 1207368, 1207369, 1207370, 1207371, 1207372, 1207373, 1207374, 1207375, 1207376, 1207462, 1207463, 1207464, 1207465, 1207466, 1207467, 1207468, 1207469, 1207470, 1207471, 1207472, 1207473, 1207474, 1207475, 1207476, 1207477, 1207478, 1207479, 1207480, 1207481, 1207482, 1207483, 1207484, 1207485, 1207486, 1207487, 1207488, 1207489, 1207490, 1207491, 1207492, 1207493, 1213094, 1213095, 1213096, 1213097, 1213098, 1213099, 1213100, 1213101, 1213102, 1213103, 1213104, 1213105, 1213106, 1213107, 1213108, 1213109, 1213110, 1213111, 1213112, 1213113, 1213114, 1213115, 1213116, 1213117, 1213118, 1213119, 1213120, 1213121, 1213122, 1213123, 1213124, 1213125, 1213211, 1213212, 1213213, 1213214, 1213215, 1213216, 1213217, 1213218, 1213219, 1213220, 1213221, 1213222, 1213223, 1213224, 1213225, 1213226, 1213227, 1213228, 1213229, 1213230, 1213231, 1213232, 1213233, 1213234, 1213235, 1213236, 1213237, 1213238, 1213239, 1213240, 1213241, and 1213242 are complementary to nucleobases 1,899-1,979 of SEQ ID NO: 1.

In certain embodiments, modified oligonucleotides complementary to nucleobases 1,899-1,979 of SEQ ID NO: 1 achieve an average of 78% reduction of F12 mRNA in vitro in the standard cell assay.

2. Nucleobases 2,004-2,045 of SEO ID NO: 1

In certain embodiments, nucleobases 2,004-2,045 of SEQ ID NO: 1 comprise a hotspot region. In certain embodiments, modified oligonucleotides are complementary to nucleobases 2,004-2,045 of SEQ ID NO: 1.

The nucleobase sequences of SEQ ID NOs: 95, 159, 162, 163, 164, 165, 347, 422, 498, 573, 953, 1030, 1105, 1255, 1332, 1409, 1486, 1562, 2309, 2463, 2540, 2617, 2694, 2771, 2848, 2924, 3000, 3076, 3147, 3229, 3306, 3382, 3457, 3533, 3609, 3685, 3761, 3837, 3913, 5000, 5001, 5002, 5003, 5004, 5005, 5006, 5031, 5032, 5033, 5034, 5035, 5036, and 5037 are complementary to nucleobases 2,004-2,045 of SEQ ID NO: 1.

The modified oligonucleotides of Compound Nos: 462192, 1125101, 1125102, 1125103, 1125104, 1129526, 1129527, 1129528, 1129529, 1129530, 1129531, 1129532, 1129533, 1129534, 1129535, 1129536, 1129537, 1129538, 1129539, 1129540, 1129541, 1129542, 1129543, 1129544, 1129545, 1131745, 1131746, 1131747, 1131748, 1131749, 1131750, 1131751, 1131752, 1131753, 1131754, 1131755, 1131756, 1131757, 1131758, 1131759, 1131760, 1131761, 1131762, 1131763, 1206993, 1206994, 1206995, 1206996, 1206997, 1206998, 1206999, 1207000, 1207001, 1207002, 1207003, 1207004, 1207005, 1207006, 1207007, 1207008, 1207010, 1207011, 1207012, 1207147, 1207148, 1207149, 1207150, 1207151, 1207152, 1207153, 1207154, 1207155, 1207156, 1207157, 1207158, 1207159, 1207160, 1207161, 1207162, 1207163, 1207164, 1207165, 1207166, 1207264, 1207265, 1207266, 1207267, 1207268, 1207269, 1207270, 1207271, 1207272, 1207273, 1207274, 1207275, 1207276, 1207277, 1207278, 1207279, 1207280, 1207281, 1207282, 1207283, 1207381, 1207382, 1207383, 1207384, 1207385, 1207386, 1207387, 1207388, 1207389, 1207390, 1207391, 1207392, 1207393, 1207394, 1207395, 1207396, 1207397, 1207398, 1207399, 1207400, 1207498, 1207499, 1207500, 1207501, 1207502, 1207503, 1207504, 1207505, 1207506, 1207507, 1207508, 1207509, 1207511, 1207512, 1207513, 1207514, 1207515, 1207516, 1207517, 1213130, 1213131, 1213132, 1213133, 1213134, 1213135, 1213136, 1213137, 1213138, 1213139, 1213140, 1213141, 1213142, 1213143, 1213144, 1213145, 1213146, 1213147, 1213148, 1213149, 1213247, 1213248, 1213249, 1213250, 1213251, 1213252, 1213253, 1213254, 1213255, 1213256, 1213257, 1213258, 1213259, 1213260, 1213261, 1213262, 1213263, 1213264, 1213265, and 1213266 are complementary to nucleobases 2,004-2,045 of SEQ ID NO: 1.

In certain embodiments, modified oligonucleotides complementary to nucleobases 2,004-2,045 of SEQ ID NO: 1 achieve an average of 80% reduction of F12 mRNA in vitro in the standard cell assay.

X. Certain Indications

In certain embodiments, methods comprise administering a pharmaceutical composition described herein to a subject with a thromboembolic condition. Thromboembolic conditions include, but are not limited to, myocardial infarction (MI), stroke, limb ischemia and necrosis, and venous thromboembolism (VTE), including deep vein thrombosis (DVT) and pulmonary embolism (PE).

In certain embodiments, methods comprise administering a pharmaceutical composition described herein to a subject having a risk factor for developing a thromboembolic condition. In certain embodiments, the risk factor is genetic, health-associated, or environmental, or a combination thereof. In certain embodiments, the risk factor is surgery, malignancy, pregnancy, aging, use of oral contraceptives, immobility (including travel-related immobility), sepsis, having a mechanical heart valve, valvular heart disease, atrial fibrillation, atherosclerosis, antiphospholipid syndrome, an inherited clotting disorder (e.g., Factor V Leiden), or an acquired prothrombotic clotting disorder. Identifying a subject with a risk factor for developing a thromboembolic condition may be accomplished by evaluating a subject's medical history and/or by conducting standard clinical tests or assessments.

In certain embodiments, methods comprise administering a pharmaceutical composition described herein to a subject who has been identified as in need of anticoagulation therapy. Non-limiting examples of such subjects include a subject undergoing major orthopedic surgery (e.g., hip/knee replacement or hip fracture surgery) and a subject with atrial fibrillation.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or R such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1: Effects of 5-10-5 MOE Gapmers on Human FXII RNA In Vitro, Single Dose Modified oligonucleotides complementary to an FXII nucleic acid were synthesized and tested for their effect on FXII RNA levels in vitro. The modified oligonucleotides were tested in a series of experiments using culture conditions as indicated. The results for each separate experiment are presented in separate tables below.

The modified oligonucleotides in the tables below are 5-10-5 MOE gapmers (i.e., they have a central region of ten 2'-deoxynucleosides flanked on each side by wings, each comprising five 2'-MOE nucleosides). The motif for the gapmers is (from 5' to 3'): eeeeedddddddddddeeeee; wherein "d" represents a 2'-β-D-deoxyribosyl sugar moiety, and 'e' represents a 2'-MOE sugar moiety. The internucleoside linkages throughout each modified oligonucleotide are phosphorothioate linkages. All cytosine nucleobases throughout each modified oligonucleotide are 5-methylcytosines.

"Start site" indicates the 5'-most nucleoside of the target sequence to which the modified oligonucleotide is complementary. "Stop site" indicates the 3'-most nucleoside of the target sequence to which the modified oligonucleotide is complementary. As shown in the tables below, the modified oligonucleotides are 100% complementary to one or more human FXII target sequences, including the human FXII mRNA sequence designated herein as SEQ ID NO: 1 (ENSEMBL ID ENST00000253496.3 from ENSEMBL version 99: January 2020), the human FXII genomic sequence, designated herein as SEQ ID NO: 2 (ENSEMBL ID ENSG00000131187.9 from ENSEML version 99: January 2020), the human FXII genomic sequence, designated herein as SEQ ID NO: 3 (the complement of GENBANK Accession No. NC_000005.10 truncated from truncated from nucleotides 177399001 to 177413000), and the human FXII mRNA sequence designated herein as SEQ ID NO: 4 (GENBANK Accession No. NM_000505.3). 'N/A' indicates that the modified oligonucleotide is not complementary to that particular target sequence with 100% complementarity.

Cultured Huh7 cells were transfected either with lipofectin, oligofectamine, or by electroporation, as indicated in the tables below. In some cases, Huh7 cells, at a density of 8,000 cells per well, were transfected using lipofectin with 120 nM modified oligonucleotide. In other cases, Huh7 cells, at a density of 5,000 cells per well, were transfected using oligofectamine with 200 nM modified oligonucleotide. In other cases, Huh7 cells, at a density of 20,000 cells per well, were transfected using electroporation with 5000 nM modified oligonucleotide. After a treatment period of approximately 24 hours, RNA was isolated from the cells and FXII RNA levels were measured by quantitative real-time RTPCR. Either human primer probe set RTS2992 (forward sequence GTCAACACTTTCGATTCCACCTT, designated herein as SEQ ID NO: 5; reverse sequence TCCCCGGTGACAGTGAGAAC, designated herein as SEQ ID NO: 6; probe sequence AAGCCCCCAAGGAGCATAAGTACAAAGCTG, designated herein as SEQ ID NO: 7) or human primer probe set RTS40528 (forward sequence GTGCACGGATCCTCCATC, designated herein as SEQ ID NO: 8; reverse sequence CAGCTTGGTCCTCACACAC, designated herein as SEQ ID NO: 9; probe sequence AATCACCCTGGCACGCATCG, designated herein as SEQ ID NO: 10) was used to measure RNA levels. FXII RNA levels were normalized to total RNA content, as measured by RIBOGREEN®. Reduction of FXII RNA is presented in the tables below as percent FXII RNA relative to the amount in untreated control cells (% UTC). The symbol "†" indicates that the modified oligonucleotide is complementary to the target transcript within the amplicon region of the primer probe set. In such instances, additional assays using alternative primer probes must be performed to accurately assess the potency and efficacy of such modified oligonucleotides.

TABLE 1

Reduction of FXII RNA by 5-10-5 MOE gapmers with full PS internucleoside linkages (Huh7, lipofectin, 120 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413577 | 1 | 20 | 1 | 20 | CCAGGAGTCCAGATCAATAG | 62 | 20 |
| 413578 | 67 | 86 | 67 | 86 | TCACCAGCAGGAACCCCAGG | 21 | 21 |
| 413579 | 92 | 111 | N/A | N/A | GGAATCGAAAGTGTTGACTC | 19† | 22 |
| 413580 | 159 | 178 | N/A | N/A | GGTGACAGTGAGAACGACTG | 6† | 23 |
| 413581 | 164 | 183 | 3515 | 3534 | TCCCCGGTGACAGTGAGAAC | 3† | 24 |
| 413582 | 217 | 236 | 3568 | 3587 | GGGTACATTTGTGGTACAGC | 19 | 25 |
| 413583 | 227 | 246 | 3578 | 3597 | CGGCCCTTGTGGGTACATTT | 30 | 26 |
| 413584 | 237 | 256 | 3588 | 3607 | AGGGCCTGGCCGGCCCTTGT | 67 | 27 |
| 413585 | 291 | 310 | 3798 | 3817 | GTATCCCCATCGCTGGTCCT | 14 | 28 |
| 413586 | 325 | 344 | N/A | N/A | TGCAGTGGTCTTTCACTTTC | 19 | 29 |
| 413587 | 399 | 418 | 4207 | 4226 | TTGTGGACAGAGACAGTGGG | 27 | 30 |
| 413588 | 409 | 428 | 4217 | 4236 | CAGTGAGGTGTTGTGGACAG | 14 | 31 |
| 413589 | 452 | 471 | 4397 | 4416 | AGAAGCTGAGGCTCAAAGCA | 38 | 32 |
| 413590 | 462 | 481 | 4407 | 4426 | GAAAACCGGAGAAGCTGAG | 24 | 33 |
| 413591 | 515 | 534 | 4460 | 4479 | TGGCATCTGGCCACAGCTGC | 20 | 34 |
| 413592 | 520 | 539 | 4465 | 4484 | TGCACTGGCATCTGGCCACA | 33 | 35 |
| 413593 | 528 | 547 | 4473 | 4492 | AGGACCCTTGCACTGGCATC | 24 | 36 |
| 413594 | 538 | 557 | 4483 | 4502 | AGTGGGCATCAGGACCCTTG | 22 | 37 |
| 413595 | 548 | 567 | 4493 | 4512 | AGCCGCTGGCAGTGGGCATC | 57 | 38 |
| 413596 | 562 | 581 | N/A | N/A | AGGCCTGGCTGGCCAGCCGC | 112 | 39 |
| 413597 | 567 | 586 | N/A | N/A | GCGGCAGGCCTGGCTGGCCA | 31 | 40 |
| 413598 | 572 | 591 | N/A | N/A | TTGGTGCGGCAGGCCTGGCT | 48 | 41 |
| 413599 | 587 | 606 | 4671 | 4690 | CCATGGAGGCACGGGTTGGT | 19 | 42 |
| 413600 | 608 | 627 | 4692 | 4711 | TCCACCTCTAGGCAGCGACC | 19 | 43 |
| 413601 | 626 | 645 | 4710 | 4729 | TGGCACAGGCGGTGGCCCTC | 39 | 44 |
| 413602 | 695 | 714 | 4924 | 4943 | CCGCGGCCATCATAGCAGCT | 24 | 45 |
| 413603 | 700 | 719 | 4929 | 4948 | TGAGCCCGCGGCCATCATAG | 33 | 46 |
| 413604 | 705 | 724 | 4934 | 4953 | GTAGCTGAGCCCGCGGCCAT | 28 | 47 |
| 413605 | 713 | 732 | 4942 | 4961 | AGGCCGCGGTAGCTGAGCCC | 38 | 48 |
| 413606 | 718 | 737 | 4947 | 4966 | TGGCCAGGCCGCGGTAGCTG | 30 | 49 |
| 413607 | 723 | 742 | 4952 | 4971 | GGTCCTGGCCAGGCCGCGGT | 23 | 50 |
| 413608 | 746 | 765 | 4975 | 4994 | TGACAGGGCGCACCCGAGAG | 33 | 51 |
| 413609 | 751 | 770 | 4980 | 4999 | ACGGCTGACAGGGCGCACCC | 28 | 52 |
| 413610 | 808 | 827 | 5037 | 5056 | GTCCCAGTTCCGCGCTTGC | 21 | 53 |
| 413611 | 818 | 837 | 5047 | 5066 | TGGCCGCCCAGTCCCCAGTT | 29 | 54 |

TABLE 1-continued

Reduction of FXII RNA by 5-10-5 MOE gapmers with full PS internucleoside linkages (Huh7, lipofectin, 120 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413612 | 839 | 858 | N/A | N/A | TCCGGGTTCCGGCAGAAGGC | 20 | 55 |
| 413613 | 863 | 882 | 5177 | 5196 | AAGCACCACGGGCGGATGTC | 29 | 56 |
| 413614 | 871 | 890 | 5185 | 5204 | TCAGCACGAAGCACCACGGG | 13 | 57 |
| 413615 | 978 | 997 | 5292 | 5311 | CATGAGTGGGACATGAAGCC | 38 | 58 |
| 413616 | 1119 | 1138 | 5538 | 5557 | GAGCCGCTGCCCGCAGCTCA | 31 | 59 |
| 413617 | 1132 | 1151 | 5551 | 5570 | ACAGACTCTTGCGGAGCCGC | 19 | 60 |
| 413618 | 1137 | 1156 | 5556 | 5575 | CGAAGACAGACTCTTGCGGA | 22 | 61 |
| 413619 | 1142 | 1161 | 5561 | 5580 | GTCATCGAAGACAGACTCTT | 28 | 62 |
| 413620 | 1211 | 1230 | 5630 | 5649 | TGGCCCCAGTACAGCGCGGC | 27 | 63 |
| 413621 | 1231 | 1250 | 5650 | 5669 | GGCTGCCGGCGCAGAAACTG | 32 | 64 |
| 413622 | 1236 | 1255 | 5655 | 5674 | GATGAGGCTGCCGGCGCAGA | 25 | 65 |
| 413623 | 1283 | 1302 | N/A | N/A | GGCCGGTCCTGCAGGCAGTG | 28 | 66 |
| 413624 | 1304 | 1323 | 5964 | 5983 | ACCGTCAGATCCTCGGGTGC | 33 | 67 |
| 413625 | 1379 | 1398 | 6039 | 6058 | TGCAAGCGGTAGGAGCGCAC | 32 | 68 |
| 413626 | 1429 | 1448 | N/A | N/A | GGCGCAACAGAGCCAGGTCG | 100 | 69 |
| 413627 | 1455 | 1474 | 6198 | 6217 | GCAGCTGCCGTCCGCATCCT | 28 | 70 |
| 413628 | 1466 | 1485 | 6209 | 6228 | GACAGGAGCGCGCAGCTGCC | 25 | 71 |
| 413629 | 1492 | 1511 | 6235 | 6254 | GCAGGCACACCGGCTGAACG | 19 | 72 |
| 413630 | 1502 | 1521 | 6245 | 6264 | GCGCCGCTTGGCAGGCACAC | 28 | 73 |
| 413631 | 1559 | 1578 | 6302 | 6321 | TCGAACTGGTGGCCCCAGCC | 30 | 74 |
| 413632 | 1679 | 1698 | 6977 | 6996 | CCTGCGCAGAGCATGCCGGG | 50 | 75 |
| 413633 | 1684 | 1703 | 6982 | 7001 | GGAACCCTGCGCAGAGCATG | 17 | 76 |
| 413634 | 1689 | 1708 | 6987 | 7006 | CTCGAGGAACCCTGCGCAGA | 36 | 77 |
| 413635 | 1695 | 1714 | 6993 | 7012 | GCCGCCCTCGAGGAACCCTG | 14 | 78 |
| 413636 | 1743 | 1762 | 7131 | 7150 | GTCCTCACACACCAGCGGGC | 16 | 79 |
| 413637 | 1748 | 1767 | 7136 | 7155 | GCTTGGTCCTCACACACCAG | 18 | 80 |
| 413638 | 1774 | 1793 | 7162 | 7181 | CTTGCAGGGTGAGCCGGCGC | 45 | 81 |
| 413639 | 1779 | 1798 | 7167 | 7186 | GATGCCTTGCAGGGTGAGCC | 29 | 82 |
| 413640 | 1809 | 1828 | 7197 | 7216 | GCGGTCACCACAGCCCGATC | 25 | 83 |
| 413641 | 1814 | 1833 | 7202 | 7221 | TTGTTGCGGTCACCACAGCC | 23 | 84 |
| 413642 | 1820 | 1839 | 7208 | 7227 | CCTGGCTTGTTGCGGTCACC | 141 | 85 |
| 413643 | 1839 | 1858 | 7227 | 7246 | GGCCACATCGGTGTAGACGC | 16 | 86 |
| 413644 | 1844 | 1863 | 7232 | 7251 | TAGTAGGCCACATCGGTGTA | 32 | 87 |
| 413645 | 1849 | 1868 | 7237 | 7256 | CCAGGTAGTAGGCCACATCG | 21 | 88 |
| 413646 | 1854 | 1873 | 7242 | 7261 | CCAGGCCAGGTAGTAGGCCA | 38 | 89 |

TABLE 1-continued

Reduction of FXII RNA by 5-10-5 MOE gapmers with full PS internucleoside linkages (Huh7, lipofectin, 120 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413647 | 1859 | 1878 | 7247 | 7266 | CGGATCCAGGCCAGGTAGTA | 33 | 90 |
| 413648 | 1891 | 1910 | 7279 | 7298 | AGTCCCTGAGCAATCAGGAA | 19 | 91 |
| 413649 | 1901 | 1920 | 7289 | 7308 | GGGAAAGATGAGTCCCTGAG | 14 | 92 |
| 413650 | 1992 | 2011 | 7380 | 7399 | ATCCTGGCGCGGAGCTGGCC | 13 | 93 |
| 413651 | 2002 | 2021 | 7390 | 7409 | TTCCTGCGCCATCCTGGCGC | 23 | 94 |
| 413652 | 2012 | 2031 | 7400 | 7419 | CTTTATTGAGTTCCTGCGCC | 15 | 95 |
| 413653 | 2022 | 2041 | 7410 | 7429 | TTTCAAAGCACTTTATTGAG | 11 | 96 |
| 413654 | 2027 | 2046 | 7415 | 7434 | AGCATTTTCAAAGCACTTTA | 23 | 97 |

TABLE 2

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413627 | 1455 | 1474 | 6198 | 6217 | GCAGCTGCCGTCCGCATCCT | 27 | 70 |
| 413633 | 1684 | 1703 | 6982 | 7001 | GGAACCCTGCGCAGAGCATG | 41 | 76 |
| 413635 | 1695 | 1714 | 6993 | 7012 | GCCGCCCTCGAGGAACCCTG | 34 | 78 |
| 413643 | 1839 | 1858 | 7227 | 7246 | GGCCACATCGGTGTAGACGC | 23 | 86 |
| 413648 | 1891 | 1910 | 7279 | 7298 | AGTCCCTGAGCAATCAGGAA | 33 | 91 |
| 413649 | 1901 | 1920 | 7289 | 7308 | GGGAAAGATGAGTCCCTGAG | 18 | 92 |
| 413652 | 2012 | 2031 | 7400 | 7419 | CTTTATTGAGTTCCTGCGCC | 14 | 95 |
| 462131 | 1128 | 1147 | 5547 | 5566 | ACTCTTGCGGAGCCGCTGCC | 23 | 98 |
| 462132 | 1145 | 1164 | 5564 | 5583 | CGGGTCATCGAAGACAGACT | 39 | 99 |
| 462133 | 1148 | 1167 | 5567 | 5586 | ACGCGGGTCATCGAAGACAG | 24 | 100 |
| 462134 | 1151 | 1170 | 5570 | 5589 | ACGACGCGGGTCATCGAAGA | 52 | 101 |
| 462135 | 1154 | 1173 | 5573 | 5592 | CCAACGACGCGGGTCATCGA | 57 | 102 |
| 462136 | 1157 | 1176 | 5576 | 5595 | CCGCCAACGACGCGGGTCAT | 51 | 103 |
| 462137 | 1160 | 1179 | 5579 | 5598 | AGCCCGCCAACGACGCGGGT | 59 | 104 |
| 462138 | 1163 | 1182 | 5582 | 5601 | ACCAGCCCGCCAACGACGCG | 45 | 105 |
| 462139 | 1166 | 1185 | 5585 | 5604 | GCCACCAGCCCGCCAACGAC | 46 | 106 |
| 462140 | 1202 | 1221 | 5621 | 5640 | TACAGCGCGGCGATGTAGGG | 44 | 107 |
| 462141 | 1205 | 1224 | 5624 | 5643 | CAGTACAGCGCGGCGATGTA | 61 | 108 |
| 462142 | 1208 | 1227 | 5627 | 5646 | CCCCAGTACAGCGCGGCGAT | 30 | 109 |

TABLE 2-continued

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 462143 | 1214 | 1233 | 5633 | 5652 | CTGTGGCCCCAGTACAGCGC | 28 | 110 |
| 462144 | 1217 | 1236 | 5636 | 5655 | AAACTGTGGCCCCAGTACAG | 42 | 111 |
| 462145 | 1223 | 1242 | 5642 | 5661 | GCGCAGAAACTGTGGCCCCA | 20 | 112 |
| 462146 | 1226 | 1245 | 5645 | 5664 | CCGGCGCAGAAACTGTGGCC | 41 | 113 |
| 462147 | 1239 | 1258 | 5658 | 5677 | GGCGATGAGGCTGCCGGCGC | 22 | 114 |
| 462148 | 1374 | 1393 | 6034 | 6053 | GCGGTAGGAGCGCACGGCCA | 32 | 115 |
| 462149 | 1432 | 1451 | N/A | N/A | GAAGGCGCAACAGAGCCAGG | 61 | 116 |
| 462150 | 1435 | 1454 | N/A | N/A | CCTGAAGGCGCAACAGAGCC | 56 | 117 |
| 462151 | 1438 | 1457 | 6181 | 6200 | CCTCCTGAAGGCGCAACAGA | 48 | 118 |
| 462152 | 1444 | 1463 | 6187 | 6206 | CCGCATCCTCCTGAAGGCGC | 25 | 119 |
| 462153 | 1447 | 1466 | 6190 | 6209 | CGTCCGCATCCTCCTGAAGG | 50 | 120 |
| 462154 | 1450 | 1469 | 6193 | 6212 | TGCCGTCCGCATCCTCCTGA | 37 | 121 |
| 462155 | 1453 | 1472 | 6196 | 6215 | AGCTGCCGTCCGCATCCTCC | 39 | 122 |
| 462156 | 1454 | 1473 | 6197 | 6216 | CAGCTGCCGTCCGCATCCTC | 36 | 123 |
| 462157 | 1456 | 1475 | 6199 | 6218 | CGCAGCTGCCGTCCGCATCC | 22 | 124 |
| 462158 | 1457 | 1476 | 6200 | 6219 | GCGCAGCTGCCGTCCGCATC | 31 | 125 |
| 462159 | 1458 | 1477 | 6201 | 6220 | CGCGCAGCTGCCGTCCGCAT | 28 | 126 |
| 462160 | 1461 | 1480 | 6204 | 6223 | GAGCGCGCAGCTGCCGTCCG | 41 | 127 |
| 462161 | 1469 | 1488 | 6212 | 6231 | GGCGACAGGAGCGCGCAGCT | 25 | 128 |
| 462162 | 1472 | 1491 | 6215 | 6234 | TAAGGCGACAGGAGCGCGCA | 41 | 129 |
| 462163 | 1495 | 1514 | 6238 | 6257 | TTGGCAGGCACACCGGCTGA | 32 | 130 |
| 462164 | 1498 | 1517 | 6241 | 6260 | CGCTTGGCAGGCACACCGGC | 36 | 131 |
| 462165 | 1518 | 1537 | 6261 | 6280 | CTCGGAGGGTCGCGCGGCGC | 28 | 132 |
| 462166 | 1562 | 1581 | 6305 | 6324 | CCCTCGAACTGGTGGCCCCA | 42 | 133 |
| 462167 | 1596 | 1615 | 6894 | 6913 | CGCCTCCTGCAGGAAGCTGG | 33 | 134 |
| 462168 | 1599 | 1618 | 6897 | 6916 | CTGCGCCTCCTGCAGGAAGC | 38 | 135 |
| 462169 | 1602 | 1621 | 6900 | 6919 | TACCTGCGCCTCCTGCAGGA | 67 | 136 |
| 462170 | 1682 | 1701 | 6980 | 6999 | AACCCTGCGCAGAGCATGCC | 28 | 137 |
| 462171 | 1685 | 1704 | 6983 | 7002 | AGGAACCCTGCGCAGAGCAT | 36 | 138 |
| 462172 | 1686 | 1705 | 6984 | 7003 | GAGGAACCCTGCGCAGAGCA | 27 | 139 |
| 462173 | 1692 | 1711 | 6990 | 7009 | GCCCTCGAGGAACCCTGCGC | 38 | 140 |
| 462174 | 1693 | 1712 | 6991 | 7010 | CGCCCTCGAGGAACCCTGCG | 39 | 141 |
| 462175 | 1697 | 1716 | 6995 | 7014 | GTGCCGCCCTCGAGGAACCC | 44 | 142 |
| 462176 | 1698 | 1717 | 6996 | 7015 | GGTGCCGCCCTCGAGGAACC | 19 | 143 |
| 462177 | 1702 | 1721 | 7000 | 7019 | CATCGGTGCCGCCCTCGAGG | 50 | 144 |

TABLE 2-continued

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 462178 | 1840 | 1859 | 7228 | 7247 | AGGCCACATCGGTGTAGACG | 30 | 145 |
| 462179 | 1841 | 1860 | 7229 | 7248 | TAGGCCACATCGGTGTAGAC | 36 | 146 |
| 462180 | 1889 | 1908 | 7277 | 7296 | TCCCTGAGCAATCAGGAAAC | 31 | 147 |
| 462181 | 1890 | 1909 | 7278 | 7297 | GTCCCTGAGCAATCAGGAAA | 29 | 148 |
| 462182 | 1892 | 1911 | 7280 | 7299 | GAGTCCCTGAGCAATCAGGA | 39 | 149 |
| 462183 | 1893 | 1912 | 7281 | 7300 | TGAGTCCCTGAGCAATCAGG | 16 | 150 |
| 462184 | 1899 | 1918 | 7287 | 7306 | GAAAGATGAGTCCCTGAGCA | 34 | 151 |
| 462185 | 1900 | 1919 | 7288 | 7307 | GGAAAGATGAGTCCCTGAGC | 24 | 152 |
| 462186 | 1902 | 1921 | 7290 | 7309 | AGGGAAAGATGAGTCCCTGA | 25 | 153 |
| 462187 | 1903 | 1922 | 7291 | 7310 | GAGGGAAAGATGAGTCCCTG | 24 | 154 |
| 462188 | 1904 | 1923 | 7292 | 7311 | GGAGGGAAAGATGAGTCCCT | 21 | 155 |
| 462189 | 1947 | 1966 | 7335 | 7354 | TGCCTTCCATGCCCCAGCCA | 17 | 156 |
| 462190 | 1995 | 2014 | 7383 | 7402 | GCCATCCTGGCGCGGAGCTG | 23 | 157 |
| 462191 | 1998 | 2017 | 7386 | 7405 | TGCGCCATCCTGGCGCGGAG | 50 | 158 |
| 462192 | 2005 | 2024 | 7393 | 7412 | GAGTTCCTGCGCCATCCTGG | 13 | 159 |
| 462193 | 2008 | 2027 | 7396 | 7415 | ATTGAGTTCCTGCGCCATCC | 17 | 160 |
| 462194 | 2011 | 2030 | 7399 | 7418 | TTTATTGAGTTCCTGCGCCA | 22 | 161 |
| 462195 | 2013 | 2032 | 7401 | 7420 | ACTTTATTGAGTTCCTGCGC | 16 | 162 |
| 462196 | 2014 | 2033 | 7402 | 7421 | CACTTTATTGAGTTCCTGCG | 8 | 163 |
| 462197 | 2015 | 2034 | 7403 | 7422 | GCACTTTATTGAGTTCCTGC | 6 | 164 |
| 462198 | 2018 | 2037 | 7406 | 7425 | AAAGCACTTTATTGAGTTCC | 7 | 165 |
| 462199 | 2030 | 2049 | 7418 | 7437 | CTCAGCATTTTCAAAGCACT | 22 | 166 |

TABLE 3

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413582 | 217 | 236 | 3568 | 3587 | GGGTACATTTGTGGTACAGC | 42 | 5 |
| 413592 | 520 | 539 | 4465 | 4484 | TGCACTGGCATCTGGCCACA | 57 | 35 |
| 413610 | 808 | 827 | 5037 | 5056 | GTCCCCAGTTCCGCGCTTGC | 45 | 43 |
| 413611 | 818 | 837 | 5047 | 5066 | TGGCCGCCCAGTCCCCAGTT | 77 | 54 |
| 413612 | 839 | 858 | N/A | N/A | TCCGGGTTCCGGCAGAAGGC | 68 | 55 |

TABLE 3-continued

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 413652 | 2012 | 2031 | 7400 | 7419 | CTTTATTGAGTTCCTGCGCC | 30 | 95 |
| 462056 | 55 | 74 | 55 | 74 | ACCCCAGGAGCAGCAGAGCC | 58 | 167 |
| 462057 | 58 | 77 | 58 | 77 | GGAACCCCAGGAGCAGCAGA | 67 | 168 |
| 462058 | 61 | 80 | 61 | 80 | GCAGGAACCCCAGGAGCAGC | 62 | 169 |
| 462059 | 64 | 83 | 64 | 83 | CCAGCAGGAACCCCAGGAGC | 76 | 170 |
| 462060 | 95 | 114 | N/A | N/A | GGTGGAATCGAAAGTGTTGA | 65† | 171 |
| 462061 | 98 | 117 | N/A | N/A | CAAGGTGGAATCGAAAGTGT | 63† | 172 |
| 462062 | 137 | 156 | 504 | 523 | TGCTCTTCAGCTTTGTACTT | 23† | 173 |
| 462063 | 140 | 159 | 507 | 526 | GTGTGCTCTTCAGCTTTGTA | 6† | 174 |
| 462064 | 143 | 162 | 510 | 529 | ACTGTGTGCTCTTCAGCTTT | 10† | 175 |
| 462065 | 146 | 165 | N/A | N/A | ACGACTGTGTGCTCTTCAGC | 9† | 176 |
| 462067 | 155 | 174 | N/A | N/A | ACAGTGAGAACGACTGTGTG | 30† | 177 |
| 462068 | 167 | 186 | 3518 | 3537 | GGCTCCCCGGTGACAGTGAG | 13† | 178 |
| 462069 | 170 | 189 | 3521 | 3540 | CAGGGCTCCCCGGTGACAGT | 14† | 179 |
| 462070 | 173 | 192 | 3524 | 3543 | TGGCAGGGCTCCCCGGTGAC | 16† | 180 |
| 462071 | 176 | 195 | 3527 | 3546 | AAGTGGCAGGGCTCCCCGGT | 70† | 181 |
| 462072 | 215 | 234 | 3566 | 3585 | GTACATTTGTGGTACAGCTG | 16 | 182 |
| 462073 | 216 | 235 | 3567 | 3586 | GGTACATTTGTGGTACAGCT | 24 | 183 |
| 462074 | 219 | 238 | 3570 | 3589 | GTGGGTACATTTGTGGTACA | 38 | 184 |
| 462075 | 223 | 242 | 3574 | 3593 | CCTTGTGGGTACATTTGTGG | 48 | 185 |
| 462076 | 230 | 249 | 3581 | 3600 | GGCCGGCCCTTGTGGGTACA | 65 | 186 |
| 462077 | 315 | 334 | 3822 | 3841 | TTTCACTTTCTTGGGCTCCA | 46 | 187 |
| 462078 | 318 | 337 | N/A | N/A | GTCTTTCACTTTCTTGGGCT | 59 | 188 |
| 462079 | 321 | 340 | N/A | N/A | GTGGTCTTTCACTTTCTTGG | 69 | 189 |
| 462080 | 448 | 467 | 4393 | 4412 | GCTGAGGCTCAAAGCACTTC | 42 | 190 |
| 462081 | 455 | 474 | 4400 | 4419 | CGGAGAAGCTGAGGCTCAAA | 71 | 191 |
| 462082 | 458 | 477 | 4403 | 4422 | AACCGGAGAAGCTGAGGCTC | 60 | 192 |
| 462083 | 465 | 484 | 4410 | 4429 | GTGGAAAACCGGAGAAGCT | 46 | 193 |
| 462084 | 486 | 505 | 4431 | 4450 | TCTATACCATATCTCATTCT | 57 | 194 |
| 462085 | 507 | 526 | 4452 | 4471 | GGCCACAGCTGCTTGCTCAG | 44 | 195 |
| 462086 | 518 | 537 | 4463 | 4482 | CACTGGCATCTGGCCACAGC | 51 | 196 |
| 462087 | 519 | 538 | 4464 | 4483 | GCACTGGCATCTGGCCACAG | 62 | 197 |
| 462088 | 521 | 540 | 4466 | 4485 | TTGCACTGGCATCTGGCCAC | 37 | 198 |
| 462089 | 522 | 541 | 4467 | 4486 | CTTGCACTGGCATCTGGCCA | 55 | 199 |
| 462090 | 523 | 542 | 4468 | 4487 | CCTTGCACTGGCATCTGGCC | 81 | 200 |

TABLE 3-continued

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 462091 | 534 | 553 | 4479 | 4498 | GGCATCAGGACCCTTGCACT | 35 | 201 |
| 462092 | 541 | 560 | 4486 | 4505 | GGCAGTGGGCATCAGGACCC | 59 | 202 |
| 462093 | 544 | 563 | 4489 | 4508 | GCTGGCAGTGGGCATCAGGA | 85 | 203 |
| 462094 | 575 | 594 | N/A | N/A | GGGTTGGTGCGGCAGGCCTG | 68 | 204 |
| 462095 | 578 | 597 | 4662 | 4681 | CACGGGTTGGTGCGGCAGGC | 65 | 205 |
| 462096 | 581 | 600 | 4665 | 4684 | AGGCACGGGTTGGTGCGGCA | 65 | 206 |
| 462097 | 584 | 603 | 4668 | 4687 | TGGAGGCACGGGTTGGTGCG | 105 | 207 |
| 462098 | 590 | 609 | 4674 | 4693 | CCCCCATGGAGGCACGGGTT | 32 | 208 |
| 462099 | 593 | 612 | 4677 | 4696 | CGACCCCATGGAGGCACGG | 51 | 209 |
| 462100 | 596 | 615 | 4680 | 4699 | CAGCGACCCCATGGAGGCA | 59 | 210 |
| 462101 | 599 | 618 | 4683 | 4702 | AGGCAGCGACCCCCATGGAG | 51 | 211 |
| 462102 | 602 | 621 | 4686 | 4705 | TCTAGGCAGCGACCCCCATG | 50 | 212 |
| 462103 | 605 | 624 | 4689 | 4708 | ACCTCTAGGCAGCGACCCCC | 59 | 213 |
| 462104 | 611 | 630 | 4695 | 4714 | CCCTCCACCTCTAGGCAGCG | 60 | 214 |
| 462105 | 614 | 633 | 4698 | 4717 | TGGCCCTCCACCTCTAGGCA | 47 | 215 |
| 462106 | 620 | 639 | 4704 | 4723 | AGGCGGTGGCCCTCCACCTC | 73 | 216 |
| 462107 | 623 | 642 | 4707 | 4726 | CACAGGCGGTGGCCCTCCAC | 27 | 217 |
| 462108 | 629 | 648 | 4713 | 4732 | CAGTGGCACAGGCGGTGGCC | 45 | 218 |
| 462109 | 632 | 651 | 4716 | 4735 | GGGCAGTGGCACAGGCGGTG | 54 | 219 |
| 462110 | 708 | 727 | 4937 | 4956 | GCGGTAGCTGAGCCCGCGGC | 81 | 220 |
| 462111 | 726 | 745 | 4955 | 4974 | CGTGGTCCTGGCCAGGCCGC | 61 | 221 |
| 462112 | 803 | 822 | 5032 | 5051 | CAGTTCCGCGCTTGCTCGGC | 51 | 222 |
| 462113 | 806 | 825 | 5035 | 5054 | CCCCAGTTCCGCGCTTGCTC | 44 | 223 |
| 462114 | 807 | 826 | 5036 | 5055 | TCCCCAGTTCCGCGCTTGCT | 69 | 224 |
| 462115 | 809 | 828 | 5038 | 5057 | AGTCCCCAGTTCCGCGCTTG | 55 | 225 |
| 462116 | 810 | 829 | 5039 | 5058 | CAGTCCCCAGTTCCGCGCTT | 56 | 226 |
| 462117 | 811 | 830 | 5040 | 5059 | CCAGTCCCCAGTTCCGCGCT | 40 | 227 |
| 462118 | 814 | 833 | 5043 | 5062 | CGCCCAGTCCCCAGTTCCGC | 60 | 228 |
| 462119 | 817 | 836 | 5046 | 5065 | GGCCGCCCAGTCCCCAGTTC | 57 | 229 |
| 462120 | 820 | 839 | 5049 | 5068 | CGTGGCCGCCCAGTCCCCAG | 43 | 230 |
| 462121 | 838 | 857 | N/A | N/A | CCGGGTTCCGGCAGAAGGCG | 59 | 231 |
| 462122 | 841 | 860 | N/A | N/A | TGTCCGGGTTCCGGCAGAAG | 95 | 232 |
| 462123 | 842 | 861 | N/A | N/A | TTGTCCGGGTTCCGGCAGAA | 96 | 233 |
| 462124 | 866 | 885 | 5180 | 5199 | ACGAAGCACCACGGGCGGAT | 85 | 234 |
| 462125 | 1002 | 1021 | 5316 | 5335 | CTTCGGCGGTGCCGGCTGCG | 57 | 235 |

TABLE 3-continued

Reduction of FXII RNA by 5-10-5 MOE gapmers with full PS internucleoside linkages (Huh7, oligofectamine, 200 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS2992 | SEQ ID NO |
|---|---|---|---|---|---|---|---|
| 462126 | 1122 | 1141 | 5541 | 5560 | GCGGAGCCGCTGCCCGCAGC | 80 | 236 |
| 462127 | 1125 | 1144 | 5544 | 5563 | CTTGCGGAGCCGCTGCCCGC | 79 | 237 |

TABLE 4

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 413612 | 839 | 858 | N/A | N/A | TCCGGGTTCCGGCAGAAGGC | 31 | 55 |
| 462073 | 216 | 235 | 3567 | 3586 | GGTACATTTGTGGTACAGCT | 10 | 183 |
| 462192 | 2005 | 2024 | 7393 | 7412 | GAGTTCCTGCGCCATCCTGG | 22 | 159 |
| 1124163 | 32 | 51 | 32 | 51 | ATGGCATCCGTCCGTTGGTC | 70 | 238 |
| 1124191 | 78 | 97 | 78 | 97 | TGACTCCAAGCTCACCAGCA | 79 | 239 |
| 1124219 | 135 | 154 | 502 | 521 | CTCTTCAGCTTTGTACTTAT | 60 | 240 |
| 1124245 | 171 | 190 | 3522 | 3541 | GCAGGGCTCCCCGGTGACAG | 42 | 241 |
| 1124268 | 225 | 244 | 3576 | 3595 | GCCCTTGTGGGTACATTTGT | 79 | 242 |
| 1124296 | 290 | 309 | 3797 | 3816 | TATCCCCATCGCTGGTCCTG | 31 | 243 |
| 1124324 | 331 | 350 | N/A | N/A | GTTTGCTGCAGTGGTCTTTC | 25 | 244 |
| 1124352 | 404 | 423 | 4212 | 4231 | AGGTGTTGTGGACAGAGACA | 60 | 245 |
| 1124380 | 446 | 465 | 4391 | 4410 | TGAGGCTCAAAGCACTTCTC | 43 | 246 |
| 1124407 | 489 | 508 | 4434 | 4453 | AGTTCTATACCATATCTCAT | 32 | 247 |
| 1124435 | 532 | 551 | 4477 | 4496 | CATCAGGACCCTTGCACTGG | 54 | 248 |
| 1124462 | 566 | 585 | N/A | N/A | CGGCAGGCCTGGCTGGCCAG | 33 | 249 |
| 1124489 | 606 | 625 | 4690 | 4709 | CACCTCTAGGCAGCGACCCC | 21 | 250 |
| 1124517 | 653 | 672 | 4737 | 4756 | AAGGCTCCGGTGTAGCCCAC | 48 | 251 |
| 1124545 | 709 | 728 | 4938 | 4957 | CGCGGTAGCTGAGCCCGCGG | 65 | 252 |
| 1124572 | 762 | 781 | 4991 | 5010 | CTCCGAGGCCCACGGCTGAC | 39 | 253 |
| 1124620 | 902 | 921 | 5216 | 5235 | TCGCAGTACTCCCAGCTCAG | 19 | 254 |
| 1124648 | 993 | 1012 | 5307 | 5326 | TGCCGGCTGCGCGGGCATGA | 37 | 255 |
| 1124676 | 1071 | 1090 | 5490 | 5509 | CTGCTCCCGCTTCGCCGGCA | 79 | 256 |
| 1124704 | 1116 | 1135 | 5535 | 5554 | CCGCTGCCCGCAGCTCAGTG | 50 | 257 |
| 1124730 | 1152 | 1171 | 5571 | 5590 | AACGACGCGGGTCATCGAAG | 27 | 258 |
| 1124757 | 1224 | 1243 | 5643 | 5662 | GGCGCAGAAACTGTGGCCCC | 32 | 259 |

TABLE 4-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1124784 | 1311 | 1330 | 5971 | 5990 | GAGCACCACCGTCAGATCCT | 30 | 260 |
| 1124812 | 1380 | 1399 | 6040 | 6059 | GTGCAAGCGGTAGGAGCGCA | 48 | 261 |
| 1124839 | 1459 | 1478 | 6202 | 6221 | GCGCGCAGCTGCCGTCCGCA | 27 | 262 |
| 1124863 | 1548 | 1567 | 6291 | 6310 | GCCCCAGCCGGCCACCTGGC | 149 | 263 |
| 1124890 | 1578 | 1597 | N/A | N/A | GGCATATTCCTCCGCCCCCT | 37 | 264 |
| 1124917 | 1620 | 1639 | 6918 | 6937 | CTCCAGGGAGAGGAACGGTA | 116 | 265 |
| 1124943 | 1746 | 1765 | 7134 | 7153 | TTGGTCCTCACACACCAGCG | 10† | 266 |
| 1124970 | 1793 | 1812 | 7181 | 7200 | GATCCCCAGCTGATGATGCC | 94 | 267 |
| 1124996 | 1823 | 1842 | 7211 | 7230 | ACGCCTGGCTTGTTGCGGTC | 24 | 268 |
| 1125021 | 1870 | 1889 | 7258 | 7277 | CGGTGTGCTCCCGGATCCAG | 50 | 269 |
| 1125047 | 1915 | 1934 | 7303 | 7322 | GGAATCACCAAGGAGGGAAA | 14 | 270 |
| 1125074 | 1950 | 1969 | 7338 | 7357 | TCTTGCCTTCCATGCCCCAG | 18 | 271 |
| 1125122 | N/A | N/A | 94 | 113 | CACTCACCGAAAGTGTTGAC | 40 | 272 |
| 1125150 | N/A | N/A | 178 | 197 | CCACAGGTCATGAGCAGAGG | 63 | 273 |
| 1125178 | N/A | N/A | 274 | 293 | TGCCCTTGTATCCACCCAGT | 71 | 274 |
| 1125206 | N/A | N/A | 368 | 387 | CCCAGAAATGCAGAGATTTC | 103 | 275 |
| 1125234 | N/A | N/A | 457 | 476 | AATCTACAAGGGAGAGAAGA | 51 | 276 |
| 1125262 | N/A | N/A | 603 | 622 | GGCACTAGACTAGACTGCCC | 33 | 277 |
| 1125290 | N/A | N/A | 690 | 709 | CTTAGACACAGCCCATACCC | 25 | 278 |
| 1125318 | N/A | N/A | 859 | 878 | ATTGAAGGCCCTGGCCTCTG | 37 | 279 |
| 1125346 | N/A | N/A | 957 | 976 | TCAAATCCCTCGCCCAGAGT | 56 | 280 |
| 1125374 | N/A | N/A | 1064 | 1083 | CAGGTGATGGGCTGAATACC | 123 | 281 |
| 1125402 | N/A | N/A | 1197 | 1216 | AATTTAGTGTCTGGAAGAAT | 44 | 282 |
| 1125430 | N/A | N/A | 1575 | 1594 | CCCCACCAAGTCAGGCCCAC | 66 | 283 |
| 1125458 | N/A | N/A | 1747 | 1766 | TGGACGGACAGAGAGGAGGG | 127 | 284 |
| 1125486 | N/A | N/A | 2123 | 2142 | AGGACCAAACCAGAACTAGG | 119 | 285 |
| 1125514 | N/A | N/A | 2253 | 2272 | TGTCTTCTTCAGAGGAATTG | 47 | 286 |
| 1125542 | N/A | N/A | 2341 | 2360 | GGCTCACAGGAACCTAATAC | 36 | 287 |
| 1125570 | N/A | N/A | 2479 | 2498 | GATTCAGGTGTGTGCTATAG | 13 | 288 |
| 1125598 | N/A | N/A | 2609 | 2628 | GTTTTTCACACTTTGTGCTT | 31 | 289 |
| 1125626 | N/A | N/A | 2734 | 2753 | GGGCATGCACAGAGCAGTGA | 47 | 290 |
| 1125654 | N/A | N/A | 2832 | 2851 | CTCATTCTTCTCTGGTTCTA | 32 | 291 |
| 1125682 | N/A | N/A | 2939 | 2958 | TAGGCACTTAATAATACTTG | 51 | 292 |
| 1125710 | N/A | N/A | 3042 | 3061 | GGAGTCAGATAGCTGGAGTA | 163 | 293 |
| 1125738 | N/A | N/A | 3436 | 3455 | CTCAGGGTCTGGTCAGGAAA | 62 | 294 |

TABLE 4-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1125766 | N/A | N/A | 3631 | 3650 | CAGGCCCCTGCTCCAACTCC | 107 | 295 |
| 1125794 | N/A | N/A | 3743 | 3762 | GAGACAAGGCTTCCCTGCTC | 38 | 296 |
| 1125822 | N/A | N/A | 3889 | 3908 | GATACCAGGAGAGTAATGAG | 103 | 297 |
| 1125850 | N/A | N/A | 4015 | 4034 | AAGCTTGGTTTACCCACCTG | 94 | 298 |
| 1125878 | N/A | N/A | 4122 | 4141 | GAGAGATGGACATGGTGGAA | 79 | 299 |
| 1125906 | N/A | N/A | 4310 | 4329 | CCAGCAACCTATTCTGTAGG | 47 | 300 |
| 1125934 | N/A | N/A | 4535 | 4554 | CTCCCTGGCCCGTTCCCAAC | 30 | 301 |
| 1125962 | N/A | N/A | 4632 | 4651 | AACGCAGTGAGCCACCCCTG | 61 | 302 |
| 1125990 | N/A | N/A | 4859 | 4878 | CTGGGCTCTCCTGCCTCCCT | 80 | 303 |
| 1126018 | N/A | N/A | 5383 | 5402 | TTCCCCCCCCCACTTCCTAA | 187 | 304 |
| 1126046 | N/A | N/A | 5751 | 5770 | GAGACGGAGGAGCCGCGGCC | 120 | 305 |
| 1126074 | N/A | N/A | 6158 | 6177 | AACCCGGGCGGAGAGGAGCG | 170 | 306 |
| 1126102 | N/A | N/A | 6373 | 6392 | GGCTTCTTCCGCCTAACCCA | 111 | 307 |
| 1126130 | N/A | N/A | 6481 | 6500 | TGAATCCCAGGCCCTGGGAT | 73 | 308 |
| 1126158 | N/A | N/A | 6621 | 6640 | GAGTCGCAGAACCTGGCTCC | 84 | 309 |
| 1126186 | N/A | N/A | 6712 | 6731 | ATTTCATAGGCAAGGAGGCT | 53 | 310 |
| 1126214 | N/A | N/A | 6839 | 6858 | CTTCACACCCCATCTGACAA | 82 | 311 |
| 1126242 | N/A | N/A | 7106 | 7125 | GAATCACCCTGGGTCGGAAA | 43† | 312 |

TABLE 5

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 413643 | 1839 | 1858 | 7227 | 7246 | GGCCACATCGGTGTAGACGC | 14 | 86 |
| 462073 | 216 | 235 | 3567 | 3586 | GGTACATTTGTGGTACAGCT | 36 | 183 |
| 626671 | 840 | 859 | N/A | N/A | GTCCGGGTTCCGGCAGAAGG | 19 | 313 |
| 1124164 | 33 | 52 | 33 | 52 | CATGGCATCCGTCCGTTGGT | 24 | 314 |
| 1124192 | 79 | 98 | 79 | 98 | TTGACTCCAAGCTCACCAGC | 95 | 315 |
| 1124220 | 136 | 155 | 503 | 522 | GCTCTTCAGCTTTGTACTTA | 93 | 316 |
| 1124246 | 172 | 191 | 3523 | 3542 | GGCAGGGCTCCCCGGTGACA | 36 | 317 |
| 1124269 | 226 | 245 | 3577 | 3596 | GGCCCTTGTGGGTACATTTG | 34 | 318 |
| 1124297 | 292 | 311 | 3799 | 3818 | AGTATCCCCATCGCTGGTCC | 24 | 319 |
| 1124325 | 332 | 351 | N/A | N/A | TGTTTGCTGCAGTGGTCTTT | 92 | 320 |

TABLE 5-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1124353 | 405 | 424 | 4213 | 4232 | GAGGTGTTGTGGACAGAGAC | 24 | 321 |
| 1124381 | 447 | 466 | 4392 | 4411 | CTGAGGCTCAAAGCACTTCT | 27 | 322 |
| 1124408 | 493 | 512 | 4438 | 4457 | GCTCAGTTCTATACCATATC | 18 | 323 |
| 1124436 | 533 | 552 | 4478 | 4497 | GCATCAGGACCCTTGCACTG | 78 | 324 |
| 1124463 | 568 | 587 | N/A | N/A | TGCGGCAGGCCTGGCTGGCC | 65 | 325 |
| 1124490 | 607 | 626 | 4691 | 4710 | CCACCTCTAGGCAGCGACCC | 17 | 326 |
| 1124518 | 654 | 673 | 4738 | 4757 | GAAGGCTCCGGTGTAGCCCA | 75 | 327 |
| 1124546 | 710 | 729 | 4939 | 4958 | CCGCGGTAGCTGAGCCCGCG | 170 | 328 |
| 1124573 | 763 | 782 | 4992 | 5011 | CCTCCGAGGCCCACGGCTGA | 27 | 329 |
| 1124621 | 903 | 922 | 5217 | 5236 | GTCGCAGTACTCCCAGCTCA | 23 | 330 |
| 1124649 | 994 | 1013 | 5308 | 5327 | GTGCCGGCTGCGCGGGCATG | 42 | 331 |
| 1124677 | 1072 | 1091 | 5491 | 5510 | GCTGCTCCCGCTTCGCCGGC | 23 | 332 |
| 1124705 | 1117 | 1136 | 5536 | 5555 | GCCGCTGCCCGCAGCTCAGT | 40 | 333 |
| 1124731 | 1153 | 1172 | 5572 | 5591 | CAACGACGCGGGTCATCGAA | 64 | 334 |
| 1124758 | 1225 | 1244 | 5644 | 5663 | CGGCGCAGAAACTGTGGCCC | 35 | 335 |
| 1124785 | 1312 | 1331 | 5972 | 5991 | CGAGCACCACCGTCAGATCC | 30 | 336 |
| 1124813 | 1381 | 1400 | 6041 | 6060 | CGTGCAAGCGGTAGGAGCGC | 18 | 337 |
| 1124840 | 1460 | 1479 | 6203 | 6222 | AGCGCGCAGCTGCCGTCCGC | 59 | 338 |
| 1124864 | 1549 | 1568 | 6292 | 6311 | GGCCCCAGCCGGCCACCTGG | 54 | 339 |
| 1124891 | 1579 | 1598 | N/A | N/A | TGGCATATTCCTCCGCCCCC | 34 | 340 |
| 1124918 | 1621 | 1640 | 6919 | 6938 | GCTCCAGGGAGAGGAACGGT | 84 | 341 |
| 1124944 | 1747 | 1766 | 7135 | 7154 | CTTGGTCCTCACACACCAGC | 7† | 342 |
| 1124971 | 1794 | 1813 | 7182 | 7201 | CGATCCCCAGCTGATGATGC | 66 | 343 |
| 1125022 | 1871 | 1890 | 7259 | 7278 | ACGGTGTGCTCCCGGATCCA | 26 | 344 |
| 1125048 | 1916 | 1935 | 7304 | 7323 | CGGAATCACCAAGGAGGGAA | 35 | 345 |
| 1125075 | 1951 | 1970 | 7339 | 7358 | ATCTTGCCTTCCATGCCCCA | 23 | 346 |
| 1125101 | 2006 | 2025 | 7394 | 7413 | TGAGTTCCTGCGCCATCCTG | 7 | 347 |
| 1125123 | N/A | N/A | 97 | 116 | CAGCACTCACCGAAAGTGTT | 67 | 348 |
| 1125151 | N/A | N/A | 181 | 200 | GACCCACAGGTCATGAGCAG | 50 | 349 |
| 1125179 | N/A | N/A | 277 | 296 | CTGTGCCCTTGTATCCACCC | 67 | 350 |
| 1125207 | N/A | N/A | 371 | 390 | CAGCCCAGAAATGCAGAGAT | 45 | 351 |
| 1125235 | N/A | N/A | 460 | 479 | TGGAATCTACAAGGGAGAGA | 125 | 352 |
| 1125263 | N/A | N/A | 606 | 625 | GTAGGCACTAGACTAGACTG | 129 | 353 |
| 1125291 | N/A | N/A | 693 | 712 | GCACTTAGACACAGCCCATA | 69 | 354 |
| 1125319 | N/A | N/A | 862 | 881 | CCCATTGAAGGCCCTGGCCT | 38 | 355 |

TABLE 5-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1125347 | N/A | N/A | 960 | 979 | AACTCAAATCCCTCGCCCAG | 77 | 356 |
| 1125375 | N/A | N/A | 1067 | 1086 | CACCAGGTGATGGGCTGAAT | 86 | 357 |
| 1125403 | N/A | N/A | 1200 | 1219 | GGTAATTTAGTGTCTGGAAG | 130 | 358 |
| 1125431 | N/A | N/A | 1578 | 1597 | CAACCCCACCAAGTCAGGCC | 74 | 359 |
| 1125459 | N/A | N/A | 1750 | 1769 | GGATGGACGGACAGAGAGGA | 60 | 360 |
| 1125487 | N/A | N/A | 2126 | 2145 | CCAAGGACCAAACCAGAACT | 84 | 361 |
| 1125515 | N/A | N/A | 2256 | 2275 | CTGTGTCTTCTTCAGAGGAA | 50 | 362 |
| 1125543 | N/A | N/A | 2370 | 2389 | TGTTGGTTGATGAAAATGTT | 55 | 363 |
| 1125571 | N/A | N/A | 2482 | 2501 | CTTGATTCAGGTGTGTGCTA | 73 | 364 |
| 1125599 | N/A | N/A | 2628 | 2647 | TCAGTCTACTTAGTGCAACG | 98 | 365 |
| 1125627 | N/A | N/A | 2739 | 2758 | TTTGTGGGCATGCACAGAGC | 31 | 366 |
| 1125655 | N/A | N/A | 2835 | 2854 | ATCCTCATTCTTCTCTGGTT | 26 | 367 |
| 1125683 | N/A | N/A | 2942 | 2961 | AAGTAGGCACTTAATAATAC | 73 | 368 |
| 1125711 | N/A | N/A | 3045 | 3064 | TCAGGAGTCAGATAGCTGGA | 100 | 369 |
| 1125739 | N/A | N/A | 3439 | 3458 | TCCCTCAGGGTCTGGTCAGG | 25 | 370 |
| 1125767 | N/A | N/A | 3637 | 3656 | GTCTCCCAGGCCCCTGCTCC | 77 | 371 |
| 1125795 | N/A | N/A | 3749 | 3768 | TAGAAAGAGACAAGGCTTCC | 102 | 372 |
| 1125823 | N/A | N/A | 3892 | 3911 | GGTGATACCAGGAGAGTAAT | 93 | 373 |
| 1125851 | N/A | N/A | 4018 | 4037 | TCCAAGCTTGGTTTACCCAC | 38 | 374 |
| 1125879 | N/A | N/A | 4125 | 4144 | TCTGAGAGATGGACATGGTG | 69 | 375 |
| 1125907 | N/A | N/A | 4313 | 4332 | TATCCAGCAACCTATTCTGT | 152 | 376 |
| 1125935 | N/A | N/A | 4538 | 4557 | CTCCTCCCTGGCCCGTTCCC | 64 | 377 |
| 1125963 | N/A | N/A | 4635 | 4654 | GGGAACGCAGTGAGCCACCC | 97 | 378 |
| 1125991 | N/A | N/A | 4862 | 4881 | AGGCTGGGCTCTCCTGCCTC | 105 | 379 |
| 1126019 | N/A | N/A | 5386 | 5405 | TCCTTCCCCCCCCCACTTCC | 37 | 380 |
| 1126047 | N/A | N/A | 5754 | 5773 | TGGGAGACGGAGGAGCCGCG | 87 | 381 |
| 1126075 | N/A | N/A | 6161 | 6180 | GCTAACCCGGGCGGAGAGGA | 36 | 382 |
| 1126103 | N/A | N/A | 6376 | 6395 | GCGGGCTTCTTCCGCCTAAC | 66 | 383 |
| 1126131 | N/A | N/A | 6484 | 6503 | CAGTGAATCCCAGGCCCTGG | 34 | 384 |
| 1126159 | N/A | N/A | 6624 | 6643 | CCAGAGTCGCAGAACCTGGC | 34 | 385 |
| 1126187 | N/A | N/A | 6715 | 6734 | TCAATTTCATAGGCAAGGAG | 28 | 386 |
| 1126215 | N/A | N/A | 6842 | 6861 | CTTCTTCACACCCCATCTGA | 100 | 387 |
| 1126243 | N/A | N/A | 7109 | 7128 | CCGGAATCACCCTGGGTCGG | 28† | 388 |

TABLE 6

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 413637 | 1748 | 1767 | 7136 | 7155 | GCTTGGTCCTCACACACCAG | 12† | 80 |
| 462073 | 216 | 235 | 3567 | 3586 | GGTACATTTGTGGTACAGCT | 20 | 183 |
| 1124193 | 80 | 99 | 80 | 99 | GTTGACTCCAAGCTCACCAG | 34 | 389 |
| 1124221 | 138 | 157 | 505 | 524 | GTGCTCTTCAGCTTTGTACT | 37 | 390 |
| 1124247 | 174 | 193 | 3525 | 3544 | GTGGCAGGGCTCCCCGGTGA | 54 | 391 |
| 1124270 | 228 | 247 | 3579 | 3598 | CCGGCCCTTGTGGGTACATT | 51 | 392 |
| 1124298 | 293 | 312 | 3800 | 3819 | CAGTATCCCCATCGCTGGTC | 36 | 393 |
| 1124326 | 333 | 352 | N/A | N/A | GTGTTTGCTGCAGTGGTCTT | 56 | 394 |
| 1124354 | 406 | 425 | 4214 | 4233 | TGAGGTGTTGTGGACAGAGA | 56 | 395 |
| 1124382 | 449 | 468 | 4394 | 4413 | AGCTGAGGCTCAAAGCACTT | 38 | 396 |
| 1124409 | 494 | 513 | 4439 | 4458 | TGCTCAGTTCTATACCATAT | 31 | 397 |
| 1124437 | 535 | 554 | 4480 | 4499 | GGGCATCAGGACCCTTGCAC | 66 | 398 |
| 1124464 | 569 | 588 | N/A | N/A | GTGCGGCAGGCCTGGCTGGC | 70 | 399 |
| 1124491 | 609 | 628 | 4693 | 4712 | CTCCACCTCTAGGCAGCGAC | 28 | 400 |
| 1124519 | 655 | 674 | 4739 | 4758 | AGAAGGCTCCGGTGTAGCCC | 102 | 401 |
| 1124547 | 711 | 730 | 4940 | 4959 | GCCGCGGTAGCTGAGCCCGC | 58 | 402 |
| 1124574 | 765 | 784 | 4994 | 5013 | GGCCTCCGAGGCCCACGGCT | 44 | 403 |
| 1124597 | 843 | 862 | N/A | N/A | GTTGTCCGGGTTCCGGCAGA | 45 | 404 |
| 1124622 | 904 | 923 | 5218 | 5237 | GGTCGCAGTACTCCCAGCTC | 42 | 405 |
| 1124650 | 996 | 1015 | 5310 | 5329 | CGGTGCCGGCTGCGCGGGCA | 90 | 406 |
| 1124678 | 1073 | 1092 | 5492 | 5511 | GGCTGCTCCCGCTTCGCCGG | 92 | 407 |
| 1124706 | 1118 | 1137 | 5537 | 5556 | AGCCGCTGCCCGCAGCTCAG | 39 | 408 |
| 1124732 | 1155 | 1174 | 5574 | 5593 | GCCAACGACGCGGGTCATCG | 38 | 409 |
| 1124759 | 1227 | 1246 | 5646 | 5665 | GCCGGCGCAGAAACTGTGGC | 55 | 410 |
| 1124786 | 1313 | 1332 | 5973 | 5992 | CCGAGCACCACCGTCAGATC | 40 | 411 |
| 1124814 | 1399 | 1418 | 6059 | 6078 | TGACGGGCGAGAAGGCCTCG | 59 | 412 |
| 1124841 | 1462 | 1481 | 6205 | 6224 | GGAGCGCGCAGCTGCCGTCC | 44 | 413 |
| 1124865 | 1550 | 1569 | 6293 | 6312 | TGGCCCCAGCCGGCCACCTG | 53 | 414 |
| 1124892 | 1581 | 1600 | 6879 | 6898 | GCTGGCATATTCCTCCGCCC | 78 | 415 |
| 1124919 | 1622 | 1641 | 6920 | 6939 | CGCTCCAGGGAGAGGAACGG | 80 | 416 |
| 1124972 | 1795 | 1814 | 7183 | 7202 | CCGATCCCCAGCTGATGATG | 41 | 417 |
| 1124997 | 1842 | 1861 | 7230 | 7249 | GTAGGCCACATCGGTGTAGA | 39 | 418 |
| 1125023 | 1873 | 1892 | 7261 | 7280 | AAACGGTGTGCTCCCGGATC | 26 | 419 |
| 1125049 | 1917 | 1936 | 7305 | 7324 | GCGGAATCACCAAGGAGGGA | 20 | 420 |
| 1125076 | 1952 | 1971 | 7340 | 7359 | AATCTTGCCTTCCATGCCCC | 22 | 421 |

TABLE 6-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
| --- | --- | --- | --- | --- | --- | --- | --- |
| 1125102 | 2007 | 2026 | 7395 | 7414 | TTGAGTTCCTGCGCCATCCT | 15 | 422 |
| 1125124 | N/A | N/A | 100 | 119 | CCACAGCACTCACCGAAAGT | 102 | 423 |
| 1125152 | N/A | N/A | 184 | 203 | CTGGACCCACAGGTCATGAG | 87 | 424 |
| 1125180 | N/A | N/A | 280 | 299 | AGGCTGTGCCCTTGTATCCA | 109 | 425 |
| 1125208 | N/A | N/A | 374 | 393 | TCACAGCCCAGAAATGCAGA | 82 | 426 |
| 1125236 | N/A | N/A | 463 | 482 | AGGTGGAATCTACAAGGGAG | 100 | 427 |
| 1125264 | N/A | N/A | 609 | 628 | CAGGTAGGCACTAGACTAGA | 81 | 428 |
| 1125292 | N/A | N/A | 696 | 715 | TGGGCACTTAGACACAGCCC | 52 | 429 |
| 1125320 | N/A | N/A | 865 | 884 | TTGCCCATTGAAGGCCCTGG | 39 | 430 |
| 1125348 | N/A | N/A | 963 | 982 | GAGAACTCAAATCCCTCGCC | 50 | 431 |
| 1125376 | N/A | N/A | 1070 | 1089 | ATGCACCAGGTGATGGGCTG | 62 | 432 |
| 1125404 | N/A | N/A | 1203 | 1222 | GTAGGTAATTTAGTGTCTGG | 59 | 433 |
| 1125432 | N/A | N/A | 1581 | 1600 | ACTCAACCCCACCAAGTCAG | 52 | 434 |
| 1125460 | N/A | N/A | 1753 | 1772 | ATGGGATGGACGGACAGAGA | 58 | 435 |
| 1125488 | N/A | N/A | 2129 | 2148 | TTGCCAAGGACCAAACCAGA | 72 | 436 |
| 1125516 | N/A | N/A | 2259 | 2278 | TGCCTGTGTCTTCTTCAGAG | 61 | 437 |
| 1125544 | N/A | N/A | 2373 | 2392 | TGCTGTTGGTTGATGAAAAT | 62 | 438 |
| 1125572 | N/A | N/A | 2485 | 2504 | ACACTTGATTCAGGTGTGTG | 74 | 439 |
| 1125600 | N/A | N/A | 2634 | 2653 | TCCTTCTCAGTCTACTTAGT | 49 | 440 |
| 1125628 | N/A | N/A | 2742 | 2761 | CCATTTGTGGGCATGCACAG | 75 | 441 |
| 1125656 | N/A | N/A | 2838 | 2857 | TTGATCCTCATTCTTCTCTG | 77 | 442 |
| 1125684 | N/A | N/A | 2950 | 2969 | TTGCCACAAAGTAGGCACTT | 51 | 443 |
| 1125712 | N/A | N/A | 3048 | 3067 | GGTTCAGGAGTCAGATAGCT | 66 | 444 |
| 1125740 | N/A | N/A | 3442 | 3461 | CTGTCCCTCAGGGTCTGGTC | 61 | 445 |
| 1125768 | N/A | N/A | 3640 | 3659 | CATGTCTCCCAGGCCCTGC | 73 | 446 |
| 1125796 | N/A | N/A | 3752 | 3771 | CTGTAGAAAGAGACAAGGCT | 59 | 447 |
| 1125824 | N/A | N/A | 3895 | 3914 | TCTGGTGATACCAGGAGAGT | 48 | 448 |
| 1125852 | N/A | N/A | 4021 | 4040 | GTTTCCAAGCTTGGTTTACC | 54 | 449 |
| 1125880 | N/A | N/A | 4128 | 4147 | TGGTCTGAGAGATGGACATG | 59 | 450 |
| 1125908 | N/A | N/A | 4316 | 4335 | GAGTATCCAGCAACCTATTC | 67 | 451 |
| 1125936 | N/A | N/A | 4541 | 4560 | ACGCTCCTCCCTGGCCCGTT | 60 | 452 |
| 1125964 | N/A | N/A | 4638 | 4657 | GGAGGGAACGCAGTGAGCCA | 127 | 453 |
| 1125992 | N/A | N/A | 4866 | 4885 | GCCAAGGCTGGGCTCTCCTG | 57 | 454 |
| 1126020 | N/A | N/A | 5389 | 5408 | TCCTCCTTCCCCCCCCCACT | 82 | 455 |
| 1126048 | N/A | N/A | 5757 | 5776 | CGCTGGGAGACGGAGGAGCC | 116 | 456 |

TABLE 6-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1126076 | N/A | N/A | 6164 | 6183 | AGAGCTAACCCGGGCGGAGA | 120 | 457 |
| 1126104 | N/A | N/A | 6379 | 6398 | GTCGCGGGCTTCTTCCGCCT | 54 | 458 |
| 1126132 | N/A | N/A | 6487 | 6506 | CAGCAGTGAATCCCAGGCCC | 96 | 459 |
| 1126160 | N/A | N/A | 6627 | 6646 | CATCCAGAGTCGCAGAACCT | 105 | 460 |
| 1126188 | N/A | N/A | 6718 | 6737 | AATTCAATTTCATAGGCAAG | 73 | 461 |
| 1126216 | N/A | N/A | 6845 | 6864 | CGCCTTCTTCACACCCCATC | 68 | 462 |
| 1126244 | N/A | N/A | 7112 | 7131 | CCTCCGGAATCACCCTGGGT | 31† | 463 |

TABLE 7

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 462073 | 216 | 235 | 3567 | 3586 | GGTACATTTGTGGTACAGCT | 15 | 183 |
| 564842 | 1463 | 1482 | 6206 | 6225 | AGGAGCGCGCAGCTGCCGTC | 44 | 464 |
| 1124194 | 82 | 101 | 82 | 101 | GTGTTGACTCCAAGCTCACC | 63 | 465 |
| 1124222 | 139 | 158 | 506 | 525 | TGTGCTCTTCAGCTTTGTAC | 25 | 466 |
| 1124248 | 175 | 194 | 3526 | 3545 | AGTGGCAGGGCTCCCCGGTG | 48 | 467 |
| 1124271 | 229 | 248 | 3580 | 3599 | GCCGGCCCTTGTGGGTACAT | 49 | 468 |
| 1124299 | 294 | 313 | 3801 | 3820 | ACAGTATCCCCATCGCTGGT | 46 | 469 |
| 1124327 | 334 | 353 | 4142 | 4161 | TGTGTTTGCTGCAGTGGTCT | 52 | 470 |
| 1124355 | 407 | 426 | 4215 | 4234 | GTGAGGTGTTGTGGACAGAG | 110 | 471 |
| 1124383 | 450 | 469 | 4395 | 4414 | AAGCTGAGGCTCAAAGCACT | 55 | 472 |
| 1124410 | 495 | 514 | 4440 | 4459 | TTGCTCAGTTCTATACCATA | 36 | 473 |
| 1124438 | 536 | 555 | 4481 | 4500 | TGGGCATCAGGACCCTTGCA | 51 | 474 |
| 1124465 | 570 | 589 | N/A | N/A | GGTGCGGCAGGCCTGGCTGG | 140 | 475 |
| 1124492 | 610 | 629 | 4694 | 4713 | CCTCCACCTCTAGGCAGCGA | 38 | 476 |
| 1124520 | 656 | 675 | 4740 | 4759 | CAGAAGGCTCCGGTGTAGCC | 63 | 477 |
| 1124548 | 712 | 731 | 4941 | 4960 | GGCCGCGGTAGCTGAGCCCG | 66 | 478 |
| 1124575 | 766 | 785 | 4995 | 5014 | TGGCCTCCGAGGCCCACGGC | 65 | 479 |
| 1124598 | 844 | 863 | N/A | N/A | CGTTGTCCGGGTTCCGGCAG | 33 | 480 |
| 1124623 | 905 | 924 | 5219 | 5238 | AGGTCGCAGTACTCCCAGCT | 47 | 481 |
| 1124651 | 997 | 1016 | 5311 | 5330 | GCGGTGCCGGCTGCGCGGGC | 57 | 482 |
| 1124679 | 1075 | 1094 | 5494 | 5513 | GCGGCTGCTCCCGCTTCGCC | 45 | 483 |

TABLE 7-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1124707 | 1120 | 1139 | 5539 | 5558 | GGAGCCGCTGCCCGCAGCTC | 47 | 484 |
| 1124733 | 1156 | 1175 | 5575 | 5594 | CGCCAACGACGCGGGTCATC | 42 | 485 |
| 1124760 | 1228 | 1247 | 5647 | 5666 | TGCCGGCGCAGAAACTGTGG | 64 | 486 |
| 1124787 | 1314 | 1333 | 5974 | 5993 | GCCGAGCACCACCGTCAGAT | 36 | 487 |
| 1124815 | 1400 | 1419 | 6060 | 6079 | CTGACGGGCGAGAAGGCCTC | 45 | 488 |
| 1124866 | 1551 | 1570 | 6294 | 6313 | GTGGCCCCAGCCGGCCACCT | 118 | 489 |
| 1124893 | 1582 | 1601 | 6880 | 6899 | AGCTGGCATATTCCTCCGCC | 81 | 490 |
| 1124920 | 1623 | 1642 | 6921 | 6940 | GCGCTCCAGGGAGAGGAACG | 79 | 491 |
| 1124945 | 1749 | 1768 | 7137 | 7156 | AGCTTGGTCCTCACACACCA | 121 | 492 |
| 1124973 | 1796 | 1815 | 7184 | 7203 | CCCGATCCCCAGCTGATGAT | 39 | 493 |
| 1124998 | 1843 | 1862 | 7231 | 7250 | AGTAGGCCACATCGGTGTAG | 31 | 494 |
| 1125024 | 1874 | 1893 | 7262 | 7281 | GAAACGGTGTGCTCCCGGAT | 34 | 495 |
| 1125050 | 1918 | 1937 | 7306 | 7325 | TGCGGAATCACCAAGGAGGG | 23 | 496 |
| 1125077 | 1954 | 1973 | 7342 | 7361 | ACAATCTTGCCTTCCATGCC | 23 | 497 |
| 1125103 | 2009 | 2028 | 7397 | 7416 | TATTGAGTTCCTGCGCCATC | 25 | 498 |
| 1125125 | N/A | N/A | 103 | 122 | TTCCCACAGCACTCACCGAA | 84 | 499 |
| 1125153 | N/A | N/A | 187 | 206 | CACCTGGACCCACAGGTCAT | 110 | 500 |
| 1125181 | N/A | N/A | 283 | 302 | TGCAGGCTGTGCCCTTGTAT | 78 | 501 |
| 1125209 | N/A | N/A | 377 | 396 | CTCTCACAGCCCAGAAATGC | 68 | 502 |
| 1125237 | N/A | N/A | 466 | 485 | CCAAGGTGGAATCTACAAGG | 78 | 503 |
| 1125265 | N/A | N/A | 612 | 631 | CACCAGGTAGGCACTAGACT | 64 | 504 |
| 1125293 | N/A | N/A | 716 | 735 | CCTGCTCCGAGCCAGGCTCG | 74 | 505 |
| 1125321 | N/A | N/A | 868 | 887 | TCCTTGCCCATTGAAGGCCC | 65 | 506 |
| 1125349 | N/A | N/A | 966 | 985 | TTGGAGAACTCAAATCCCTC | 66 | 507 |
| 1125377 | N/A | N/A | 1073 | 1092 | TCCATGCACCAGGTGATGGG | 58 | 508 |
| 1125405 | N/A | N/A | 1206 | 1225 | CATGTAGGTAATTTAGTGTC | 90 | 509 |
| 1125433 | N/A | N/A | 1584 | 1603 | GAGACTCAACCCCACCAAGT | 88 | 510 |
| 1125461 | N/A | N/A | 1756 | 1775 | CAGATGGGATGGACGGACAG | 65 | 511 |
| 1125489 | N/A | N/A | 2132 | 2151 | CACTTGCCAAGGACCAAACC | 86 | 512 |
| 1125517 | N/A | N/A | 2262 | 2281 | AATTGCCTGTGTCTTCTTCA | 57 | 513 |
| 1125545 | N/A | N/A | 2376 | 2395 | ATATGCTGTTGGTTGATGAA | 55 | 514 |
| 1125573 | N/A | N/A | 2488 | 2507 | TAGACACTTGATTCAGGTGT | 57 | 515 |
| 1125601 | N/A | N/A | 2637 | 2656 | GTGTCCTTCTCAGTCTACTT | 68 | 516 |
| 1125629 | N/A | N/A | 2745 | 2764 | TGGCCATTTGTGGGCATGCA | 54 | 517 |
| 1125657 | N/A | N/A | 2841 | 2860 | CAGTTGATCCTCATTCTTCT | 59 | 518 |

TABLE 7-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1125685 | N/A | N/A | 2953 | 2972 | CACTTGCCACAAAGTAGGCA | 51 | 519 |
| 1125713 | N/A | N/A | 3051 | 3070 | TTGGGTTCAGGAGTCAGATA | 116 | 520 |
| 1125741 | N/A | N/A | 3445 | 3464 | GCACTGTCCCTCAGGGTCTG | 68 | 521 |
| 1125769 | N/A | N/A | 3643 | 3662 | GTACATGTCTCCCAGGCCCC | 57 | 522 |
| 1125797 | N/A | N/A | 3755 | 3774 | CACCTGTAGAAAGAGACAAG | 148 | 523 |
| 1125825 | N/A | N/A | 3898 | 3917 | GGGTCTGGTGATACCAGGAG | 56 | 524 |
| 1125853 | N/A | N/A | 4024 | 4043 | CAAGTTTCCAAGCTTGGTTT | 53 | 525 |
| 1125881 | N/A | N/A | 4131 | 4150 | CAGTGGTCTGAGAGATGGAC | 56 | 526 |
| 1125909 | N/A | N/A | 4319 | 4338 | TCCGAGTATCCAGCAACCTA | 88 | 527 |
| 1125937 | N/A | N/A | 4557 | 4576 | CCAGCCTGTCTTCCTGACGC | 63 | 528 |
| 1125965 | N/A | N/A | 4657 | 4676 | GTTGGTGCGGCAGGCTTGGG | 60 | 529 |
| 1125993 | N/A | N/A | 4869 | 4888 | GCAGCCAAGGCTGGGCTCTC | 75 | 530 |
| 1126021 | N/A | N/A | 5392 | 5411 | GGCTCCTCCTTCCCCCCCCC | 54 | 531 |
| 1126049 | N/A | N/A | 5760 | 5779 | CTGCGCTGGGAGACGGAGGA | 181 | 532 |
| 1126077 | N/A | N/A | 6167 | 6186 | AACAGAGCTAACCCGGGCGG | 67 | 533 |
| 1126105 | N/A | N/A | 6382 | 6401 | AAAGTCGCGGGCTTCTTCCG | 59 | 534 |
| 1126133 | N/A | N/A | 6490 | 6509 | TCCCAGCAGTGAATCCCAGG | 88 | 535 |
| 1126161 | N/A | N/A | 6630 | 6649 | ACCCATCCAGAGTCGCAGAA | 72 | 536 |
| 1126189 | N/A | N/A | 6721 | 6740 | ATTAATTCAATTTCATAGGC | 76 | 537 |
| 1126217 | N/A | N/A | 6862 | 6881 | CCCCTGCGAACACAGAGCGC | 105 | 538 |

TABLE 8

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 413644 | 1844 | 1863 | 7232 | 7251 | TAGTAGGCCACATCGGTGTA | 32 | 87 |
| 462073 | 216 | 235 | 3567 | 3586 | GGTACATTTGTGGTACAGCT | 48 | 183 |
| 564822 | 862 | 881 | 5176 | 5195 | AGCACCACGGGCGGATGTCG | 69 | 539 |
| 1124167 | 36 | 55 | 36 | 55 | CCTCATGGCATCCGTCCGTT | 42 | 540 |
| 1124195 | 83 | 102 | 83 | 102 | AGTGTTGACTCCAAGCTCAC | 45 | 541 |
| 1124223 | 141 | 160 | 508 | 527 | TGTGTGCTCTTCAGCTTTGT | 32 | 542 |
| 1124249 | 177 | 196 | 3528 | 3547 | GAAGTGGCAGGGCTCCCCGG | 54 | 543 |

TABLE 8-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1124272 | 231 | 250 | 3582 | 3601 | TGGCCGGCCCTTGTGGGTAC | 141 | 544 |
| 1124300 | 296 | 315 | 3803 | 3822 | AAACAGTATCCCCATCGCTG | 66 | 545 |
| 1124328 | 335 | 354 | 4143 | 4162 | CTGTGTTTGCTGCAGTGGTC | 38 | 546 |
| 1124356 | 408 | 427 | 4216 | 4235 | AGTGAGGTGTTGTGGACAGA | 73 | 547 |
| 1124384 | 451 | 470 | 4396 | 4415 | GAAGCTGAGGCTCAAAGCAC | 32 | 548 |
| 1124411 | 496 | 515 | 4441 | 4460 | CTTGCTCAGTTCTATACCAT | 52 | 549 |
| 1124439 | 537 | 556 | 4482 | 4501 | GTGGGCATCAGGACCCTTGC | 45 | 550 |
| 1124466 | 571 | 590 | N/A | N/A | TGGTGCGGCAGGCCTGGCTG | 146 | 551 |
| 1124493 | 612 | 631 | 4696 | 4715 | GCCCTCCACCTCTAGGCAGC | 70 | 552 |
| 1124521 | 657 | 676 | 4741 | 4760 | GCAGAAGGCTCCGGTGTAGC | 97 | 553 |
| 1124549 | 714 | 733 | 4943 | 4962 | CAGGCCGCGGTAGCTGAGCC | 99 | 554 |
| 1124576 | 767 | 786 | 4996 | 5015 | GTGGCCTCCGAGGCCCACGG | 78 | 555 |
| 1124624 | 907 | 926 | 5221 | 5240 | CCAGGTCGCAGTACTCCCAG | 51 | 556 |
| 1124652 | 998 | 1017 | 5312 | 5331 | GGCGGTGCCGGCTGCGCGGG | 70 | 557 |
| 1124680 | 1076 | 1095 | 5495 | 5514 | GGCGGCTGCTCCCGCTTCGC | 67 | 558 |
| 1124708 | 1121 | 1140 | 5540 | 5559 | CGGAGCCGCTGCCCGCAGCT | 136 | 559 |
| 1124734 | 1158 | 1177 | 5577 | 5596 | CCCGCCAACGACGCGGGTCA | 51 | 560 |
| 1124761 | 1229 | 1248 | 5648 | 5667 | CTGCCGGCGCAGAAACTGTG | 54 | 561 |
| 1124788 | 1315 | 1334 | 5975 | 5994 | GGCCGAGCACCACCGTCAGA | 100 | 562 |
| 1124816 | 1401 | 1420 | 6061 | 6080 | GCTGACGGGCGAGAAGGCCT | 70 | 563 |
| 1124842 | 1464 | 1483 | 6207 | 6226 | CAGGAGCGCGCAGCTGCCGT | 40 | 564 |
| 1124867 | 1552 | 1571 | 6295 | 6314 | GGTGGCCCCAGCCGGCCACC | 66 | 565 |
| 1124894 | 1583 | 1602 | 6881 | 6900 | AAGCTGGCATATTCCTCCGC | 80 | 566 |
| 1124921 | 1657 | 1676 | 6955 | 6974 | GGATGGAGGATCCGTGCACG | 30† | 567 |
| 1124946 | 1750 | 1769 | 7138 | 7157 | CAGCTTGGTCCTCACACACC | 18† | 568 |
| 1124974 | 1797 | 1816 | 7185 | 7204 | GCCCGATCCCCAGCTGATGA | 43 | 569 |
| 1125025 | 1876 | 1895 | 7264 | 7283 | AGGAAACGGTGTGCTCCCGG | 42 | 570 |
| 1125051 | 1919 | 1938 | 7307 | 7326 | CTGCGGAATCACCAAGGAGG | 26 | 571 |
| 1125078 | 1955 | 1974 | 7343 | 7362 | CACAATCTTGCCTTCCATGC | 37 | 572 |
| 1125104 | 2010 | 2029 | 7398 | 7417 | TTATTGAGTTCCTGCGCCAT | 22 | 573 |
| 1125126 | N/A | N/A | 106 | 125 | TGGTTCCCACAGCACTCACC | 73 | 574 |
| 1125154 | N/A | N/A | 190 | 209 | AGTCACCTGGACCCACAGGT | 78 | 575 |
| 1125182 | N/A | N/A | 286 | 305 | AAATGCAGGCTGTGCCCTTG | 69 | 576 |
| 1125210 | N/A | N/A | 380 | 399 | TTCCTCTCACAGCCCAGAAA | 60 | 577 |
| 1125238 | N/A | N/A | 469 | 488 | TTCCCAAGGTGGAATCTACA | 84 | 578 |

TABLE 8-continued

Reduction of FXII RNA by 5-10-5 MOE gapmers with full PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) RTS40528 | SEQ ID NO |
|---|---|---|---|---|---|---|---|
| 1125266 | N/A | N/A | 615 | 634 | TAGCACCAGGTAGGCACTAG | 66 | 579 |
| 1125294 | N/A | N/A | 721 | 740 | AAGCACCTGCTCCGAGCCAG | 56 | 580 |
| 1125322 | N/A | N/A | 871 | 890 | CCTTCCTTGCCCATTGAAGG | 60 | 581 |
| 1125350 | N/A | N/A | 969 | 988 | AGCTTGGAGAACTCAAATCC | 62 | 582 |
| 1125378 | N/A | N/A | 1076 | 1095 | ATTTCCATGCACCAGGTGAT | 62 | 583 |
| 1125406 | N/A | N/A | 1209 | 1228 | TGGCATGTAGGTAATTTAGT | 63 | 584 |
| 1125434 | N/A | N/A | 1587 | 1606 | TTAGAGACTCAACCCCACCA | 143 | 585 |
| 1125462 | N/A | N/A | 1759 | 1778 | ATGCAGATGGGATGGACGGA | 167 | 586 |
| 1125490 | N/A | N/A | 2135 | 2154 | GTGCACTTGCCAAGGACCAA | 73 | 587 |
| 1125518 | N/A | N/A | 2265 | 2284 | GAGAATTGCCTGTGTCTTCT | 55 | 588 |
| 1125546 | N/A | N/A | 2379 | 2398 | ATTATATGCTGTTGGTTGAT | 123 | 589 |
| 1125574 | N/A | N/A | 2513 | 2532 | GCTACCTTAGGGAGAAAGCG | 121 | 590 |
| 1125602 | N/A | N/A | 2640 | 2659 | TGAGTGTCCTTCTCAGTCTA | 69 | 591 |
| 1125630 | N/A | N/A | 2748 | 2767 | TCATGGCCATTTGTGGGCAT | 89 | 592 |
| 1125658 | N/A | N/A | 2845 | 2864 | AGTACAGTTGATCCTCATTC | 162 | 593 |
| 1125686 | N/A | N/A | 2956 | 2975 | GAGCACTTGCCACAAAGTAG | 91 | 594 |
| 1125714 | N/A | N/A | 3054 | 3073 | AACTTGGGTTCAGGAGTCAG | 105 | 595 |
| 1125742 | N/A | N/A | 3448 | 3467 | CAGGCACTGTCCCTCAGGGT | 141 | 596 |
| 1125770 | N/A | N/A | 3649 | 3668 | GGCAGGGTACATGTCTCCCA | 68 | 597 |
| 1125798 | N/A | N/A | 3758 | 3777 | GCACACCTGTAGAAAGAGAC | 82 | 598 |
| 1125826 | N/A | N/A | 3916 | 3935 | CAGAATCCCAGGTGTGTGGG | 54 | 599 |
| 1125854 | N/A | N/A | 4027 | 4046 | CTCCAAGTTTCCAAGCTTGG | 116 | 600 |
| 1125882 | N/A | N/A | 4134 | 4153 | CTGCAGTGGTCTGAGAGATG | 102 | 601 |
| 1125910 | N/A | N/A | 4325 | 4344 | CAAGTCTCCGAGTATCCAGC | 96 | 602 |
| 1125938 | N/A | N/A | 4560 | 4579 | CTGCCAGCCTGTCTTCCTGA | 80 | 603 |
| 1125966 | N/A | N/A | 4660 | 4679 | CGGGTTGGTGCGGCAGGCTT | 95 | 604 |
| 1125994 | N/A | N/A | 4875 | 4894 | CCCTGGGCAGCCAAGGCTGG | 67 | 605 |
| 1126022 | N/A | N/A | 5395 | 5414 | CTCGGCTCCTCCTTCCCCCC | 61 | 606 |
| 1126050 | N/A | N/A | 5763 | 5782 | AAGCTGCGCTGGGAGACGGA | 123 | 607 |
| 1126078 | N/A | N/A | 6170 | 6189 | CGCAACAGAGCTAACCCGGG | 76 | 608 |
| 1126106 | N/A | N/A | 6385 | 6404 | ACCAAAGTCGCGGGCTTCTT | 150 | 609 |
| 1126134 | N/A | N/A | 6493 | 6512 | GGATCCCAGCAGTGAATCCC | 70 | 610 |
| 1126162 | N/A | N/A | 6633 | 6652 | ACCACCCATCCAGAGTCGCA | 60 | 611 |
| 1126190 | N/A | N/A | 6724 | 6743 | GCCATTAATTCAATTTCATA | 72 | 612 |
| 1126218 | N/A | N/A | 6865 | 6884 | CCGCCCCTGCGAACACAGAG | 66 | 613 |

TABLE 9

Reduction of FXII RNA by 5-10-5 MOE gapmers with full PS internucleoside linkages (Huh7, oligofectamine, 200 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 462200 | 10845 | 10864 | N/A | N/A | CTTCTCAGCATTTTCAAAGC | 63 | 614 |
| 462201 | 10848 | 10867 | N/A | N/A | TTCCTTCTCAGCATTTTCAA | 63 | 615 |

TABLE 10

Reduction of FXII RNA by 5-10-5 MOE gapmers with full PS internucleoside linkages (Huh7, electroporation, 5000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1126246 | 10849 | 10868 | N/A | N/A | TTTCCTTCTCAGCATTTTCA | 130 | 616 |

TABLE 11

Reduction of FXII RNA by 5-10-5 MOE gapmers with full PS internucleoside linkages electroporation, 5000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1124165 | 3458 | 3477 | 34 | 53 | TCATGGCATCCGTCCGTTGG | 60 | 617 |
| 1126245 | 10846 | 10865 | N/A | N/A | CCTTCTCAGCATTTTCAAAG | 77 | 618 |
| 1124166 | 3459 | 3478 | 35 | 54 | CTCATGGCATCCGTCCGTTG | 52 | 619 |

Example 2: Effects of 5-10-5 MOE Gapmers on Human FXII RNA In Vitro, Single Dose Modified oligonucleotides complementary to a FXII nucleic acid were synthesized and tested for their effect on FXII RNA levels in vitro. The modified oligonucleotides were tested in a series of experiments using similar culture conditions. The results for each separate experiment are presented in separate tables below.

The modified oligonucleotides in the tables below 5-10-5 MOE gapmers (i.e., they have a central region of ten 2'-deoxynucleosides flanked on each side by wings, each comprising five 2'-MOE nucleosides). The motif for the gapmers is (from 5' to 3'): eeeeedddddddddddeeeee; wherein "d" represents a 2'-β-D-deoxyribosyl sugar moiety, and 'e' represents a 2'-MOE sugar moiety. The internucleoside linkage motif for the gapmers is (from 5' to 3'): soooossssssssssooss; wherein 'o' represents a phosphodiester internucleoside linkage and 's' represents a phosphorothioate internucleoside linkage. Each cytosine residue is a 5-methyl cytosine.

"Start site" indicates the 5'-most nucleoside of the target sequence to which the modified oligonucleotide is complementary. "Stop site" indicates the 3'-most nucleoside of the target sequence to which the modified oligonucleotide is complementary. As shown in the tables below, the modified oligonucleotides are 100% complementary to one or more of human FXII target sequences including the human FXII mRNA sequence designated herein as SEQ ID NO: 1 (ENSEMBL ID ENST00000253496.3 from ENSEMBL version 99: January 2020), the human FXII genomic sequence, designated herein as SEQ ID NO: 2 (ENSEMBL ID ENSG00000131187.9 from ENSEMBL version 99: January 2020), the human FXII genomic sequence, designated herein as SEQ ID No. 3 (the complement of GENBANK Accession No. NC_000005.10 truncated from truncated from nucleotides 177399001 to 177413000), and the human FXII mRNA sequence designated herein as SEQ ID No: 4 (GENBANK Accession No. NM 000505.3). 'N/A' indicates that the modified oligonucleotide is not complementary to that particular target sequence with 100% complementarity.

Cultured Huh7 cells, at a density of 20,000 cells per well, were transfected using electroporation with either 5000 nM or 2000 nM modified oligonucleotide. After a treatment period of approximately 24 hours, RNA was isolated from the cells and FXII RNA levels were measured by quantitative real-time RTPCR. Human primer probe set RTS40528 (described herein above) was used to measure RNA levels. FXII RNA levels were normalized to total RNA content, as measured by RIBOGREEN®. Reduction of FXII RNA is presented in the tables below as percent FXII RNA relative to the amount in untreated control cells (% UTC). The symbol "†" indicates that the modified oligonucleotide is complementary to the target transcript within the amplicon region of the primer probe set. In such instances, additional assays using alternative primer probes must be performed to accurately assess the potency and efficacy of such modified oligonucleotides.

TABLE 12

Reduction of FXII RNA by 5-10-5 MOE gapmers with
mixed PO/PS internucleoside linkages (Huh7,
electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130742 | 2 | 21 | 2 | 21 | TCCAGGAGTCCAGATCAATA | 67 | 620 |
| 1130770 | 37 | 56 | 37 | 56 | CCCTCATGGCATCCGTCCGT | 68 | 621 |
| 1130798 | 84 | 103 | 84 | 103 | AAGTGTTGACTCCAAGCTCA | 90 | 622 |
| 1130826 | 142 | 161 | 509 | 528 | CTGTGTGCTCTTCAGCTTTG | 13 | 623 |
| 1130854 | 178 | 197 | 3529 | 3548 | GGAAGTGGCAGGGCTCCCCG | 47 | 624 |
| 1130871 | 216 | 235 | 3567 | 3586 | GGTACATTTGTGGTACAGCT | 18 | 183 |
| 1130883 | 232 | 251 | 3583 | 3602 | CTGGCCGGCCCTTGTGGGTA | 21 | 625 |
| 1130911 | 297 | 316 | 3804 | 3823 | CAAACAGTATCCCCATCGCT | 28 | 626 |
| 1130939 | 338 | 357 | 4146 | 4165 | GGGCTGTGTTTGCTGCAGTG | 22 | 627 |
| 1130967 | 410 | 429 | 4218 | 4237 | CCAGTGAGGTGTTGTGGACA | 68 | 628 |
| 1130995 | 453 | 472 | 4398 | 4417 | GAGAAGCTGAGGCTCAAAGC | 38 | 629 |
| 1131023 | 498 | 517 | 4443 | 4462 | TGCTTGCTCAGTTCTATACC | 20 | 630 |
| 1131051 | 538 | 557 | 4483 | 4502 | AGTGGGCATCAGGACCCTTG | 93 | 277 |
| 1131079 | 573 | 592 | N/A | N/A | GTTGGTGCGGCAGGCCTGGC | 37 | 631 |
| 1131107 | 613 | 632 | 4697 | 4716 | GGCCCTCCACCTCTAGGCAG | 28 | 632 |
| 1131135 | 658 | 677 | 4742 | 4761 | CGCAGAAGGCTCCGGTGTAG | 54 | 633 |
| 1131163 | 715 | 734 | 4944 | 4963 | CCAGGCCGCGGTAGCTGAGC | 40 | 634 |
| 1131191 | 768 | 787 | 4997 | 5016 | GGTGGCCTCCGAGGCCCACG | 83 | 635 |
| 1131219 | 864 | 883 | 5178 | 5197 | GAAGCACCACGGGCGGATGT | 44 | 636 |
| 1131247 | 908 | 927 | 5222 | 5241 | GCCAGGTCGCAGTACTCCCA | 19 | 637 |
| 1131275 | 999 | 1018 | 5313 | 5332 | CGGCGGTGCCGGCTGCGCGG | 70 | 638 |
| 1131303 | 1077 | 1096 | 5496 | 5515 | AGGCGGCTGCTCCCGCTTCG | 38 | 639 |
| 1131331 | 1123 | 1142 | 5542 | 5561 | TGCGGAGCCGCTGCCCGCAG | 125 | 640 |
| 1131359 | 1159 | 1178 | 5578 | 5597 | GCCCGCCAACGACGCGGGTC | 56 | 641 |
| 1131387 | 1230 | 1249 | 5649 | 5668 | GCTGCCGGCGCAGAAACTGT | 57 | 642 |
| 1131415 | 1316 | 1335 | 5976 | 5995 | TGGCCGAGCACCACCGTCAG | 51 | 643 |
| 1131443 | 1402 | 1421 | 6062 | 6081 | AGCTGACGGGCGAGAAGGCC | 36 | 644 |
| 1131471 | 1465 | 1484 | 6208 | 6227 | ACAGGAGCGCGCAGCTGCCG | 30 | 645 |
| 1131499 | 1553 | 1572 | 6296 | 6315 | TGGTGGCCCCAGCCGGCCAC | 61 | 646 |
| 1131527 | 1585 | 1604 | 6883 | 6902 | GGAAGCTGGCATATTCCTCC | 57 | 647 |
| 1131555 | 1660 | 1679 | 6958 | 6977 | GGAGGATGGAGGATCCGTGC | 7† | 648 |
| 1131583 | 1751 | 1770 | 7139 | 7158 | GCAGCTTGGTCCTCACACAC | 8† | 649 |
| 1131611 | 1798 | 1817 | 7186 | 7205 | AGCCCGATCCCCAGCTGATG | 33 | 650 |
| 1131639 | 1845 | 1864 | 7233 | 7252 | GTAGTAGGCCACATCGGTGT | 62 | 651 |
| 1131667 | 1877 | 1896 | 7265 | 7284 | CAGGAAACGGTGTGCTCCCG | 28 | 652 |

TABLE 12-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131695 | 1921 | 1940 | 7309 | 7328 | CACTGCGGAATCACCAAGGA | 13 | 653 |
| 1131723 | 1956 | 1975 | 7344 | 7363 | ACACAATCTTGCCTTCCATG | 26 | 654 |
| 1131751 | 2012 | 2031 | 7400 | 7419 | CTTTATTGAGTTCCTGCGCC | 20 | 95 |
| 1131779 | N/A | N/A | 109 | 128 | TCCTGGTTCCCACAGCACTC | 71 | 655 |
| 1131807 | N/A | N/A | 193 | 212 | CCTAGTCACCTGGACCCACA | 56 | 656 |
| 1131835 | N/A | N/A | 289 | 308 | CAGAAATGCAGGCTGTGCCC | 71 | 657 |
| 1131863 | N/A | N/A | 386 | 405 | TGCAGCTTCCTCTCACAGCC | 120 | 658 |
| 1131891 | N/A | N/A | 513 | 532 | CCGACTGTGTGCTCTTCAGC | 21 | 659 |
| 1131919 | N/A | N/A | 618 | 637 | ACCTAGCACCAGGTAGGCAC | 39 | 660 |
| 1131947 | N/A | N/A | 724 | 743 | CTCAAGCACCTGCTCCGAGC | 54 | 661 |
| 1131975 | N/A | N/A | 874 | 893 | GATCCTTCCTTGCCCATTGA | 122 | 662 |
| 1132003 | N/A | N/A | 972 | 991 | TGAAGCTTGGAGAACTCAAA | 76 | 663 |
| 1132031 | N/A | N/A | 1079 | 1098 | AGCATTTCCATGCACCAGGT | 70 | 664 |
| 1132059 | N/A | N/A | 1212 | 1231 | GCCTGGCATGTAGGTAATTT | 60 | 665 |
| 1132087 | N/A | N/A | 1590 | 1609 | TGCTTAGAGACTCAACCCCA | 67 | 666 |
| 1132115 | N/A | N/A | 1762 | 1781 | AAGATGCAGATGGGATGGAC | 79 | 667 |
| 1132143 | N/A | N/A | 2138 | 2157 | AAAGTGCACTTGCCAAGGAC | 60 | 668 |
| 1132171 | N/A | N/A | 2268 | 2287 | AATGAGAATTGCCTGTGTCT | 41 | 669 |
| 1132199 | N/A | N/A | 2382 | 2401 | CAGATTATATGCTGTTGGTT | 49 | 670 |
| 1132227 | N/A | N/A | 2516 | 2535 | AAGGCTACCTTAGGGAGAAA | 48 | 671 |
| 1132255 | N/A | N/A | 2643 | 2662 | GAATGAGTGTCCTTCTCAGT | 46 | 672 |
| 1132283 | N/A | N/A | 2751 | 2770 | TTTTCATGGCCATTTGTGGG | 60 | 673 |
| 1132311 | N/A | N/A | 2848 | 2867 | AATAGTACAGTTGATCCTCA | 46 | 674 |
| 1132339 | N/A | N/A | 2959 | 2978 | GAAGAGCACTTGCCACAAAG | 106 | 675 |
| 1132367 | N/A | N/A | 3060 | 3079 | AAAAAAAACTTGGGTTCAGG | 133 | 676 |
| 1132395 | N/A | N/A | 3451 | 3470 | GCTCAGGCACTGTCCCTCAG | 41 | 677 |
| 1132423 | N/A | N/A | 3652 | 3671 | ACAGGCAGGGTACATGTCTC | 45 | 678 |
| 1132451 | N/A | N/A | 3761 | 3780 | GTAGCACACCTGTAGAAAGA | 45 | 679 |
| 1132479 | N/A | N/A | 3919 | 3938 | GTCCAGAATCCCAGGTGTGT | 46 | 680 |
| 1132507 | N/A | N/A | 4030 | 4049 | CTACTCCAAGTTTCCAAGCT | 97 | 681 |
| 1132535 | N/A | N/A | 4137 | 4156 | TTGCTGCAGTGGTCTGAGAG | 36 | 682 |
| 1132563 | N/A | N/A | 4328 | 4347 | TGCCAAGTCTCCGAGTATCC | 56 | 683 |
| 1132591 | N/A | N/A | 4563 | 4582 | CTCCTGCCAGCCTGTCTTCC | 70 | 684 |
| 1132619 | N/A | N/A | 4763 | 4782 | CAGACCCTCACTCACCCACG | 67 | 685 |
| 1132647 | N/A | N/A | 4878 | 4897 | GCTCCCTGGGCAGCCAAGGC | 37 | 686 |

TABLE 12-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132675 | N/A | N/A | 5398 | 5417 | CCTCTCGGCTCCTCCTTCCC | 78 | 687 |
| 1132703 | N/A | N/A | 5766 | 5785 | TGGAAGCTGCGCTGGGAGAC | 122 | 688 |
| 1132731 | N/A | N/A | 6173 | 6192 | AGGCGCAACAGAGCTAACCC | 32 | 689 |
| 1132759 | N/A | N/A | 6388 | 6407 | GATACCAAAGTCGCGGGCTT | 100 | 690 |
| 1132787 | N/A | N/A | 6512 | 6531 | GTATCCCCAGGAGATTTGGG | 66 | 691 |
| 1132815 | N/A | N/A | 6636 | 6655 | CCCACCACCCATCCAGAGTC | 56 | 692 |
| 1132843 | N/A | N/A | 6727 | 6746 | GGTGCCATTAATTCAATTTC | 109 | 693 |
| 1132871 | N/A | N/A | 6868 | 6887 | CCTCCGCCCCTGCAACACA | 55 | 694 |

TABLE 13

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130743 | 3 | 22 | 3 | 22 | ATCCAGGAGTCCAGATCAAT | 48 | 695 |
| 1130771 | 38 | 57 | 38 | 57 | GCCCTCATGGCATCCGTCCG | 57 | 696 |
| 1130799 | 85 | 104 | 85 | 104 | AAAGTGTTGACTCCAAGCTC | 53 | 697 |
| 1130827 | 144 | 163 | 511 | 530 | GACTGTGTGCTCTTCAGCTT | 32 | 698 |
| 1130855 | 197 | 216 | 3548 | 3567 | TGCCGGTGGTACTGGAAGGG | 53 | 699 |
| 1130871 | 216 | 235 | 3567 | 3586 | GGTACATTTGTGGTACAGCT | 13 | 183 |
| 1130884 | 233 | 252 | 3584 | 3603 | CCTGGCCGGCCCTTGTGGGT | 50 | 700 |
| 1130912 | 298 | 317 | 3805 | 3824 | CCAAACAGTATCCCCATCGC | 25 | 701 |
| 1130940 | 357 | 376 | 4165 | 4184 | GGTCCCTCCTTTCTGGCAGG | 76 | 702 |
| 1130968 | 411 | 430 | 4219 | 4238 | TCCAGTGAGGTGTTGTGGAC | 42 | 703 |
| 1130996 | 456 | 475 | 4401 | 4420 | CCGGAGAAGCTGAGGCTCAA | 22 | 704 |
| 1131024 | 499 | 518 | 4444 | 4463 | CTGCTTGCTCAGTTCTATAC | 14 | 705 |
| 1131052 | 539 | 558 | 4484 | 4503 | CAGTGGGCATCAGGACCCTT | 46 | 706 |
| 1131080 | 574 | 593 | N/A | N/A | GGTTGGTGCGGCAGGCCTGG | 22 | 707 |
| 1131108 | 615 | 634 | 4699 | 4718 | GTGGCCCTCCACCTCTAGGC | 62 | 708 |
| 1131136 | 660 | 679 | 4744 | 4763 | GTCGCAGAAGGCTCCGGTGT | 64 | 709 |
| 1131164 | 716 | 735 | 4945 | 4964 | GCCAGGCCGCGGTAGCTGAG | 46 | 710 |
| 1131192 | 772 | 791 | 5001 | 5020 | GGTAGGTGGCCTCCGAGGCC | 52 | 711 |
| 1131220 | 865 | 884 | 5179 | 5198 | CGAAGCACCACGGGCGGATG | 95 | 712 |
| 1131248 | 909 | 928 | 5223 | 5242 | TGCCAGGTCGCAGTACTCCC | 29 | 713 |

TABLE 13-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131276 | 1000 | 1019 | 5314 | 5333 | TCGGCGGTGCCGGCTGCGCG | 39 | 714 |
| 1131304 | 1078 | 1097 | 5497 | 5516 | AAGGCGGCTGCTCCCGCTTC | 78 | 715 |
| 1131332 | 1124 | 1143 | 5543 | 5562 | TTGCGGAGCCGCTGCCCGCA | 65 | 716 |
| 1131360 | 1161 | 1180 | 5580 | 5599 | CAGCCCGCCAACGACGCGGG | 62 | 717 |
| 1131388 | 1232 | 1251 | 5651 | 5670 | AGGCTGCCGGCGCAGAAACT | 34 | 718 |
| 1131416 | 1317 | 1336 | 5977 | 5996 | CTGGCCGAGCACCACCGTCA | 13 | 719 |
| 1131444 | 1405 | 1424 | 6065 | 6084 | GGTAGCTGACGGGCGAGAAG | 48 | 720 |
| 1131472 | 1467 | 1486 | 6210 | 6229 | CGACAGGAGCGCGCAGCTGC | 59 | 721 |
| 1131500 | 1554 | 1573 | 6297 | 6316 | CTGGTGGCCCCAGCCGGCCA | 53 | 722 |
| 1131528 | 1586 | 1605 | 6884 | 6903 | AGGAAGCTGGCATATTCCTC | 47 | 723 |
| 1131556 | 1679 | 1698 | 6977 | 6996 | CCTGCGCAGAGCATGCCGGG | 71† | 75 |
| 1131584 | 1752 | 1771 | 7140 | 7159 | TGCAGCTTGGTCCTCACACA | 17† | 724 |
| 1131612 | 1799 | 1818 | 7187 | 7206 | CAGCCCGATCCCCAGCTGAT | 80 | 725 |
| 1131640 | 1846 | 1865 | 7234 | 7253 | GGTAGTAGGCCACATCGGTG | 19 | 726 |
| 1131668 | 1878 | 1897 | 7266 | 7285 | TCAGGAAACGGTGTGCTCCC | 46 | 727 |
| 1131696 | 1922 | 1941 | 7310 | 7329 | TCACTGCGGAATCACCAAGG | 21 | 728 |
| 1131724 | 1958 | 1977 | 7346 | 7365 | GGACACAATCTTGCCTTCCA | 7 | 729 |
| 1131752 | 2013 | 2032 | 7401 | 7420 | ACTTTATTGAGTTCCTGCGC | 11 | 162 |
| 1131780 | N/A | N/A | 112 | 131 | CAATCCTGGTTCCCACAGCA | 64 | 730 |
| 1131808 | N/A | N/A | 196 | 215 | CCTCCTAGTCACCTGGACCC | 60 | 731 |
| 1131836 | N/A | N/A | 292 | 311 | CCCCAGAAATGCAGGCTGTG | 114 | 732 |
| 1131864 | N/A | N/A | 389 | 408 | GTCTGCAGCTTCCTCTCACA | 56 | 733 |
| 1131892 | N/A | N/A | 516 | 535 | TTACCGACTGTGTGCTCTTC | 18 | 734 |
| 1131920 | N/A | N/A | 621 | 640 | AAGACCTAGCACCAGGTAGG | 58 | 735 |
| 1131948 | N/A | N/A | 727 | 746 | TATCTCAAGCACCTGCTCCG | 25 | 736 |
| 1131976 | N/A | N/A | 877 | 896 | CTTGATCCTTCCTTGCCCAT | 58 | 737 |
| 1132004 | N/A | N/A | 975 | 994 | AATTGAAGCTTGGAGAACTC | 99 | 738 |
| 1132032 | N/A | N/A | 1082 | 1101 | TAAAGCATTTCCATGCACCA | 93 | 739 |
| 1132060 | N/A | N/A | 1215 | 1234 | CATGCCTGGCATGTAGGTAA | 53 | 740 |
| 1132088 | N/A | N/A | 1593 | 1612 | CCATGCTTAGAGACTCAACC | 82 | 741 |
| 1132116 | N/A | N/A | 1765 | 1784 | AAAAAGATGCAGATGGGATG | 86 | 742 |
| 1132144 | N/A | N/A | 2141 | 2160 | GGCAAAGTGCACTTGCCAAG | 85 | 743 |
| 1132172 | N/A | N/A | 2271 | 2290 | AATAATGAGAATTGCCTGTG | 117 | 744 |
| 1132200 | N/A | N/A | 2385 | 2404 | AACCAGATTATATGCTGTTG | 41 | 745 |
| 1132228 | N/A | N/A | 2519 | 2538 | AAGAAGGCTACCTTAGGGAG | 40 | 746 |
| 1132256 | N/A | N/A | 2646 | 2665 | ATTGAATGAGTGTCCTTCTC | 50 | 747 |

TABLE 13-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132284 | N/A | N/A | 2754 | 2773 | ATGTTTTCATGGCCATTTGT | 45 | 748 |
| 1132312 | N/A | N/A | 2851 | 2870 | AATAATAGTACAGTTGATCC | 62 | 749 |
| 1132340 | N/A | N/A | 2962 | 2981 | CAGGAAGAGCACTTGCCACA | 52 | 750 |
| 1132368 | N/A | N/A | 3370 | 3389 | CTCTAAAAGTTGGGTTCAGG | 51 | 751 |
| 1132396 | N/A | N/A | 3457 | 3476 | TCAACTGCTCAGGCACTGTC | 53 | 752 |
| 1132424 | N/A | N/A | 3655 | 3674 | AGGACAGGCAGGGTACATGT | 51 | 753 |
| 1132452 | N/A | N/A | 3764 | 3783 | GTGGTAGCACACCTGTAGAA | 28 | 754 |
| 1132480 | N/A | N/A | 3922 | 3941 | TGGGTCCAGAATCCCAGGTG | 59 | 755 |
| 1132508 | N/A | N/A | 4033 | 4052 | TTGCTACTCCAAGTTTCCAA | 50 | 756 |
| 1132536 | N/A | N/A | 4140 | 4159 | TGTTTGCTGCAGTGGTCTGA | 21 | 757 |
| 1132564 | N/A | N/A | 4334 | 4353 | GGACCATGCCAAGTCTCCGA | 41 | 758 |
| 1132592 | N/A | N/A | 4566 | 4585 | GGCCTCCTGCCAGCCTGTCT | 49 | 759 |
| 1132620 | N/A | N/A | 4766 | 4785 | CCCCAGACCCTCACTCACCC | 90 | 760 |
| 1132648 | N/A | N/A | 4899 | 4918 | TGGTGTCTGAGGAGAAAGGG | 71 | 761 |
| 1132676 | N/A | N/A | 5401 | 5420 | CGCCCTCTCGGCTCCTCCTT | 44 | 762 |
| 1132704 | N/A | N/A | 5841 | 5860 | CTCCCCGGGAGCTCCGGAGG | 123 | 763 |
| 1132732 | N/A | N/A | 6176 | 6195 | TGAAGGCGCAACAGAGCTAA | 21 | 764 |
| 1132760 | N/A | N/A | 6394 | 6413 | CGGAACGATACCAAAGTCGC | 85 | 765 |
| 1132788 | N/A | N/A | 6515 | 6534 | CCTGTATCCCCAGGAGATTT | 21 | 766 |
| 1132816 | N/A | N/A | 6639 | 6658 | TCCCCCACCACCCATCCAGA | 87 | 767 |
| 1132844 | N/A | N/A | 6730 | 6749 | GGAGGTGCCATTAATTCAAT | 46 | 768 |
| 1132872 | N/A | N/A | 6871 | 6890 | ATTCCTCCGCCCCTGCGAAC | 150 | 769 |

TABLE 14

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130800 | 89 | 108 | N/A | N/A | ATCGAAAGTGTTGACTCCAA | 28 | 770 |
| 1130828 | 145 | 164 | 512 | 531 | CGACTGTGTGCTCTTCAGCT | 14 | 771 |
| 1130856 | 199 | 218 | 3550 | 3569 | GCTGCCGGTGGTACTGGAAG | 22 | 772 |
| 1130871 | 216 | 235 | 3567 | 3586 | GGTACATTTGTGGTACAGCT | 21 | 183 |
| 1130885 | 234 | 253 | 3585 | 3604 | GCCTGGCCGGCCCTTGTGGG | 51 | 773 |
| 1130913 | 304 | 323 | 3811 | 3830 | TGGGCTCCAAACAGTATCCC | 22 | 774 |

TABLE 14-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130941 | 359 | 378 | 4167 | 4186 | CAGGTCCCTCCTTTCTGGCA | 46 | 775 |
| 1130969 | 413 | 432 | 4221 | 4240 | TTTCCAGTGAGGTGTTGTGG | 25 | 776 |
| 1130997 | 457 | 476 | 4402 | 4421 | ACCGGAGAAGCTGAGGCTCA | 19 | 777 |
| 1131025 | 500 | 519 | 4445 | 4464 | GCTGCTTGCTCAGTTCTATA | 19 | 778 |
| 1131053 | 540 | 559 | 4485 | 4504 | GCAGTGGGCATCAGGACCCT | 22 | 779 |
| 1131081 | 576 | 595 | N/A | N/A | CGGGTTGGTGCGGCAGGCCT | 65 | 780 |
| 1131109 | 616 | 635 | 4700 | 4719 | GGTGGCCCTCCACCTCTAGG | 38 | 781 |
| 1131137 | 661 | 680 | 4745 | 4764 | CGTCGCAGAAGGCTCCGGTG | 94 | 782 |
| 1131165 | 717 | 736 | 4946 | 4965 | GGCCAGGCCGCGGTAGCTGA | 35 | 783 |
| 1131193 | 773 | 792 | 5002 | 5021 | CGGTAGGTGGCCTCCGAGGC | 30 | 784 |
| 1131221 | 867 | 886 | 5181 | 5200 | CACGAAGCACCACGGGCGGA | 38 | 785 |
| 1131249 | 911 | 930 | 5225 | 5244 | TGTGCCAGGTCGCAGTACTC | 24 | 786 |
| 1131277 | 1001 | 1020 | 5315 | 5334 | TTCGGCGGTGCCGGCTGCGC | 25 | 787 |
| 1131305 | 1079 | 1098 | 5498 | 5517 | GAAGGCGGCTGCTCCCGCTT | 39 | 788 |
| 1131333 | 1126 | 1145 | 5545 | 5564 | TCTTGCGGAGCCGCTGCCCG | 34 | 789 |
| 1131361 | 1162 | 1181 | 5581 | 5600 | CCAGCCCGCCAACGACGCGG | 31 | 790 |
| 1131389 | 1233 | 1252 | 5652 | 5671 | GAGGCTGCCGGCGCAGAAAC | 39 | 791 |
| 1131417 | 1318 | 1337 | 5978 | 5997 | CCTGGCCGAGCACCACCGTC | 26 | 792 |
| 1131445 | 1408 | 1427 | 6068 | 6087 | GCTGGTAGCTGACGGGCGAG | 26 | 793 |
| 1131473 | 1468 | 1487 | 6211 | 6230 | GCGACAGGAGCGCGCAGCTG | 21 | 794 |
| 1131501 | 1555 | 1574 | 6298 | 6317 | ACTGGTGGCCCCAGCCGGCC | 51 | 795 |
| 1131529 | 1587 | 1606 | 6885 | 6904 | CAGGAAGCTGGCATATTCCT | 82 | 796 |
| 1131557 | 1680 | 1699 | 6978 | 6997 | CCCTGCGCAGAGCATGCCGG | 28† | 797 |
| 1131585 | 1753 | 1772 | 7141 | 7160 | CTGCAGCTTGGTCCTCACAC | 6† | 798 |
| 1131613 | 1800 | 1819 | 7188 | 7207 | ACAGCCCGATCCCCAGCTGA | 39 | 799 |
| 1131641 | 1847 | 1866 | 7235 | 7254 | AGGTAGTAGGCCACATCGGT | 19 | 800 |
| 1131669 | 1879 | 1898 | 7267 | 7286 | ATCAGGAAACGGTGTGCTCC | 24 | 801 |
| 1131697 | 1923 | 1942 | 7311 | 7330 | CTCACTGCGGAATCACCAAG | 8 | 802 |
| 1131725 | 1960 | 1979 | 7348 | 7367 | TGGGACACAATCTTGCCTTC | 12 | 803 |
| 1131753 | 2014 | 2033 | 7402 | 7421 | CACTTTATTGAGTTCCTGCG | 15 | 163 |
| 1131781 | N/A | N/A | 115 | 134 | GGACAATCCTGGTTCCCACA | 71 | 804 |
| 1131809 | N/A | N/A | 199 | 218 | AGGCCTCCTAGTCACCTGGA | 58 | 805 |
| 1131837 | N/A | N/A | 302 | 321 | GGCCCATCTCCCCCAGAAAT | 50 | 806 |
| 1131865 | N/A | N/A | 392 | 411 | CTAGTCTGCAGCTTCCTCTC | 48 | 807 |
| 1131893 | N/A | N/A | 519 | 538 | CACTTACCGACTGTGTGCTC | 24 | 808 |

TABLE 14-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131921 | N/A | N/A | 627 | 646 | GGGCATAAGACCTAGCACCA | 46 | 809 |
| 1131949 | N/A | N/A | 730 | 749 | ACATATCTCAAGCACCTGCT | 63 | 810 |
| 1131977 | N/A | N/A | 880 | 899 | GCTCTTGATCCTTCCTTGCC | 54 | 811 |
| 1132005 | N/A | N/A | 997 | 1016 | AACCTGGTTTCACAGAAGGG | 54 | 812 |
| 1132033 | N/A | N/A | 1085 | 1104 | TTGTAAAGCATTTCCATGCA | 37 | 813 |
| 1132061 | N/A | N/A | 1512 | 1531 | ACTCTAGGTAAATTTTTTTT | 86 | 814 |
| 1132089 | N/A | N/A | 1612 | 1631 | AATGTGCTGGGCCTCAACGC | 49 | 815 |
| 1132117 | N/A | N/A | 1908 | 1927 | AAGTTGTGTGCCTGTAATCC | 50 | 816 |
| 1132145 | N/A | N/A | 2144 | 2163 | CAAGGCAAAGTGCACTTGCC | 39 | 817 |
| 1132173 | N/A | N/A | 2274 | 2293 | GCGAATAATGAGAATTGCCT | 38 | 818 |
| 1132201 | N/A | N/A | 2388 | 2407 | TAAAACCAGATTATATGCTG | 67 | 819 |
| 1132229 | N/A | N/A | 2522 | 2541 | CACAAGAAGGCTACCTTAGG | 55 | 820 |
| 1132257 | N/A | N/A | 2649 | 2668 | CCTATTGAATGAGTGTCCTT | 48 | 821 |
| 1132285 | N/A | N/A | 2760 | 2779 | CTTGAAATGTTTTCATGGCC | 59 | 822 |
| 1132313 | N/A | N/A | 2854 | 2873 | AGTAATAATAGTACAGTTGA | 59 | 823 |
| 1132341 | N/A | N/A | 2965 | 2984 | GGCCAGGAAGAGCACTTGCC | 59 | 824 |
| 1132369 | N/A | N/A | 3373 | 3392 | CTGCTCTAAAAGTTGGGTTC | 40 | 825 |
| 1132397 | N/A | N/A | 3460 | 3479 | TACTCAACTGCTCAGGCACT | 34 | 826 |
| 1132425 | N/A | N/A | 3658 | 3677 | AGAAGGACAGGCAGGGTACA | 67 | 827 |
| 1132453 | N/A | N/A | 3824 | 3843 | CCTTTCACTTTCTTGGGCTC | 16 | 828 |
| 1132481 | N/A | N/A | 3925 | 3944 | GGCTGGGTCCAGAATCCCAG | 40 | 829 |
| 1132509 | N/A | N/A | 4036 | 4055 | ACCTTGCTACTCCAAGTTTC | 36 | 830 |
| 1132537 | N/A | N/A | 4236 | 4255 | CCTTTCTGGCAGTGGTTTCC | 20 | 831 |
| 1132565 | N/A | N/A | 4337 | 4356 | CTAGGACCATGCCAAGTCTC | 89 | 832 |
| 1132593 | N/A | N/A | 4569 | 4588 | CCCGGCCTCCTGCCAGCCTG | 40 | 833 |
| 1132621 | N/A | N/A | 4769 | 4788 | TTGCCCCAGACCCTCACTCA | 47 | 834 |
| 1132649 | N/A | N/A | 4902 | 4921 | CCTTGGTGTCTGAGGAGAAA | 59 | 835 |
| 1132677 | N/A | N/A | 5418 | 5437 | GAATCTAGCTCGCCCGGCGC | 58 | 836 |
| 1132705 | N/A | N/A | 5844 | 5863 | TTCCTCCCCGGGAGCTCCGG | 65 | 837 |
| 1132733 | N/A | N/A | 6306 | 6325 | ACCCTCGAACTGGTGGCCCC | 59 | 838 |
| 1132761 | N/A | N/A | 6397 | 6416 | ACCCGGAACGATACCAAAGT | 61 | 839 |
| 1132789 | N/A | N/A | 6518 | 6537 | CTCCCTGTATCCCCAGGAGA | 77 | 840 |
| 1132817 | N/A | N/A | 6643 | 6662 | CCCCTCCCCCACCACCCATC | 46 | 841 |

TABLE 14-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132845 | N/A | N/A | 6733 | 6752 | GGAGGAGGTGCCATTAATTC | 61 | 842 |
| 1132873 | N/A | N/A | 6874 | 6893 | CATATTCCTCCGCCCCTGCG | 90 | 843 |

TABLE 15

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130745 | 5 | 24 | 5 | 24 | CTATCCAGGAGTCCAGATCA | 58 | 844 |
| 1130773 | 42 | 61 | 42 | 61 | CAGAGCCCTCATGGCATCCG | 33 | 845 |
| 1130801 | 90 | 109 | N/A | N/A | AATCGAAAGTGTTGACTCCA | 33 | 846 |
| 1130829 | 146 | 165 | N/A | N/A | ACGACTGTGTGCTCTTCAGC | 20 | 176 |
| 1130857 | 200 | 219 | 3551 | 3570 | AGCTGCCGGTGGTACTGGAA | 43 | 847 |
| 1130871 | 216 | 235 | 3567 | 3586 | GGTACATTTGTGGTACAGCT | 18 | 183 |
| 1130886 | 235 | 254 | 3586 | 3605 | GGCCTGGCCGGCCCTTGTGG | 49 | 848 |
| 1130914 | 305 | 324 | 3812 | 3831 | TTGGGCTCCAAACAGTATCC | 20 | 849 |
| 1130942 | 361 | 380 | 4169 | 4188 | CACAGGTCCCTCCTTTCTGG | 62 | 850 |
| 1130970 | 417 | 436 | 4225 | 4244 | GTGGTTTCCAGTGAGGTGTT | 19 | 851 |
| 1130998 | 459 | 478 | 4404 | 4423 | AAACCGGAGAAGCTGAGGCT | 21 | 852 |
| 1131026 | 501 | 520 | 4446 | 4465 | AGCTGCTTGCTCAGTTCTAT | 41 | 853 |
| 1131054 | 542 | 561 | 4487 | 4506 | TGGCAGTGGGCATCAGGACC | 60 | 854 |
| 1131082 | 577 | 596 | N/A | N/A | ACGGGTTGGTGCGGCAGGCC | 31 | 855 |
| 1131110 | 617 | 636 | 4701 | 4720 | CGGTGGCCCTCCACCTCTAG | 44 | 856 |
| 1131138 | 679 | 698 | N/A | N/A | AGCTTGCCTTGGTGTCCACG | 38 | 857 |
| 1131166 | 719 | 738 | 4948 | 4967 | CTGGCCAGGCCGCGGTAGCT | 92 | 858 |
| 1131194 | 774 | 793 | 5003 | 5022 | CCGGTAGGTGGCCTCCGAGG | 44 | 859 |
| 1131222 | 868 | 887 | 5182 | 5201 | GCACGAAGCACCACGGGCGG | 30 | 860 |
| 1131250 | 912 | 931 | 5226 | 5245 | CTGTGCCAGGTCGCAGTACT | 38 | 861 |
| 1131278 | 1003 | 1022 | 5317 | 5336 | GCTTCGGCGGTGCCGGCTGC | 33 | 862 |
| 1131306 | 1080 | 1099 | 5499 | 5518 | GGAAGGCGGCTGCTCCCGCT | 36 | 863 |
| 1131334 | 1127 | 1146 | 5546 | 5565 | CTCTTGCGGAGCCGCTGCCC | 46 | 864 |
| 1131362 | 1164 | 1183 | 5583 | 5602 | CACCAGCCCGCCAACGACGC | 24 | 865 |
| 1131390 | 1234 | 1253 | 5653 | 5672 | TGAGGCTGCCGGCGCAGAAA | 40 | 866 |

TABLE 15-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131418 | 1319 | 1338 | 5979 | 5998 | TCCTGGCCGAGCACCACCGT | 34 | 867 |
| 1131446 | 1410 | 1429 | 6070 | 6089 | GTGCTGGTAGCTGACGGGCG | 26 | 868 |
| 1131474 | 1470 | 1489 | 6213 | 6232 | AGGCGACAGGAGCGCGCAGC | 21 | 869 |
| 1131502 | 1556 | 1575 | 6299 | 6318 | AACTGGTGGCCCCAGCCGGC | 47 | 870 |
| 1131530 | 1588 | 1607 | 6886 | 6905 | GCAGGAAGCTGGCATATTCC | 58 | 871 |
| 1131558 | 1681 | 1700 | 6979 | 6998 | ACCCTGCGCAGAGCATGCCG | 20† | 872 |
| 1131586 | 1755 | 1774 | 7143 | 7162 | CTCTGCAGCTTGGTCCTCAC | 14† | 873 |
| 1131614 | 1801 | 1820 | 7189 | 7208 | CACAGCCCGATCCCCAGCTG | 38 | 874 |
| 1131642 | 1848 | 1867 | 7236 | 7255 | CAGGTAGTAGGCCACATCGG | 35 | 875 |
| 1131670 | 1881 | 1900 | 7269 | 7288 | CAATCAGGAAACGGTGTGCT | 47 | 876 |
| 1131698 | 1924 | 1943 | 7312 | 7331 | TCTCACTGCGGAATCACCAA | 6 | 877 |
| 1131726 | 1961 | 1980 | 7349 | 7368 | ATGGGACACAATCTTGCCTT | 34 | 878 |
| 1131754 | 2015 | 2034 | 7403 | 7422 | GCACTTTATTGAGTTCCTGC | 4 | 164 |
| 1131782 | N/A | N/A | 118 | 137 | CTGGGACAATCCTGGTTCCC | 56 | 879 |
| 1131810 | N/A | N/A | 202 | 221 | CATAGGCCTCCTAGTCACCT | 94 | 880 |
| 1131838 | N/A | N/A | 305 | 324 | TAAGGCCCATCTCCCCCAGA | 41 | 881 |
| 1131866 | N/A | N/A | 395 | 414 | TTGCTAGTCTGCAGCTTCCT | 60 | 882 |
| 1131894 | N/A | N/A | 523 | 542 | AGGCCACTTACCGACTGTGT | 109 | 883 |
| 1131922 | N/A | N/A | 630 | 649 | CATGGGCATAAGACCTAGCA | 65 | 884 |
| 1131950 | N/A | N/A | 733 | 752 | AGCACATATCTCAAGCACCT | 85 | 885 |
| 1131978 | N/A | N/A | 886 | 905 | AGACAAGCTCTTGATCCTTC | 79 | 886 |
| 1132006 | N/A | N/A | 1000 | 1019 | ATCAACCTGGTTTCACAGAA | 48 | 887 |
| 1132034 | N/A | N/A | 1088 | 1107 | TATTTGTAAAGCATTTCCAT | 67 | 888 |
| 1132062 | N/A | N/A | 1515 | 1534 | CACACTCTAGGTAAATTTTT | 59 | 889 |
| 1132090 | N/A | N/A | 1615 | 1634 | TGGAATGTGCTGGGCCTCAA | 59 | 890 |
| 1132118 | N/A | N/A | 1911 | 1930 | ATGAAGTTGTGTGCCTGTAA | 61 | 891 |
| 1132146 | N/A | N/A | 2147 | 2166 | GTTCAAGGCAAAGTGCACTT | 56 | 892 |
| 1132174 | N/A | N/A | 2277 | 2296 | ATCGCGAATAATGAGAATTG | 68 | 893 |
| 1132202 | N/A | N/A | 2391 | 2410 | ACATAAAACCAGATTATATG | 52 | 894 |
| 1132230 | N/A | N/A | 2525 | 2544 | AAGCACAAGAAGGCTACCTT | 33 | 895 |
| 1132258 | N/A | N/A | 2652 | 2671 | TCTCCTATTGAATGAGTGTC | 36 | 896 |
| 1132286 | N/A | N/A | 2765 | 2784 | CAATACTTGAAATGTTTTCA | 47 | 897 |
| 1132314 | N/A | N/A | 2857 | 2876 | GGCAGTAATAATAGTACAGT | 38 | 898 |
| 1132342 | N/A | N/A | 2968 | 2987 | CAAGGCCAGGAAGAGCACTT | 76 | 899 |
| 1132370 | N/A | N/A | 3376 | 3395 | TTTCTGCTCTAAAAGTTGGG | 35 | 900 |

TABLE 15-continued

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132398 | N/A | N/A | 3463 | 3482 | CTGTACTCAACTGCTCAGGC | 60 | 901 |
| 1132426 | N/A | N/A | 3661 | 3680 | GACAGAAGGACAGGCAGGGT | 52 | 902 |
| 1132454 | N/A | N/A | 3827 | 3846 | GCACCTTTCACTTTCTTGGG | 24 | 903 |
| 1132482 | N/A | N/A | 3945 | 3964 | TATTGTGGAGGGAGAGAAGG | 83 | 904 |
| 1132510 | N/A | N/A | 4039 | 4058 | GTGACCTTGCTACTCCAAGT | 74 | 905 |
| 1132538 | N/A | N/A | 4239 | 4258 | TCACCTTTCTGGCAGTGGTT | 44 | 906 |
| 1132566 | N/A | N/A | 4340 | 4359 | AGTCTAGGACCATGCCAAGT | 34 | 907 |
| 1132594 | N/A | N/A | 4572 | 4591 | CCACCCGGCCTCCTGCCAGC | 75 | 908 |
| 1132622 | N/A | N/A | 4772 | 4791 | TGCTTGCCCCAGACCCTCAC | 54 | 909 |
| 1132650 | N/A | N/A | 4905 | 4924 | TTGCCTTGGTGTCTGAGGAG | 44 | 910 |
| 1132678 | N/A | N/A | 5421 | 5440 | CCGGAATCTAGCTCGCCCGG | 50 | 911 |
| 1132706 | N/A | N/A | 5847 | 5866 | AGCTTCCTCCCCGGGAGCTC | 64 | 912 |
| 1132734 | N/A | N/A | 6309 | 6328 | CCTACCCTCGAACTGGTGGC | 61 | 913 |
| 1132762 | N/A | N/A | 6400 | 6419 | GGCACCCGGAACGATACCAA | 63 | 914 |
| 1132790 | N/A | N/A | 6521 | 6540 | ATTCTCCTGTATCCCCAGG | 58 | 915 |
| 1132818 | N/A | N/A | 6646 | 6665 | AAACCCCTCCCCCACCACCC | 41 | 916 |
| 1132846 | N/A | N/A | 6752 | 6771 | CTCGCAGCAAGCCCGAAGGG | 38 | 917 |
| 1132874 | N/A | N/A | 6877 | 6896 | TGGCATATTCCTCCGCCCCT | 49 | 918 |

TABLE 16

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130746 | 7 | 26 | 7 | 26 | GCCTATCCAGGAGTCCAGAT | 29 | 919 |
| 1130774 | 46 | 65 | 46 | 65 | GCAGCAGAGCCCTCATGGCA | 22 | 920 |
| 1130802 | 91 | 110 | N/A | N/A | GAATCGAAAGTGTTGACTCC | 40 | 921 |
| 1130830 | 147 | 166 | N/A | N/A | AACGACTGTGTGCTCTTCAG | 9 | 922 |
| 1130858 | 201 | 220 | 3552 | 3571 | CAGCTGCCGGTGGTACTGGA | 22 | 923 |
| 1130871 | 216 | 235 | 3567 | 3586 | GGTACATTTGTGGTACAGCT | 22 | 183 |
| 1130887 | 236 | 255 | 3587 | 3606 | GGGCCTGGCCGGCCCTTGTG | 41 | 924 |
| 1130915 | 306 | 325 | 3813 | 3832 | CTTGGGCTCCAAACAGTATC | 26 | 925 |
| 1130943 | 362 | 381 | 4170 | 4189 | ACACAGGTCCCTCCTTTCTG | 32 | 926 |
| 1130971 | 419 | 438 | 4227 | 4246 | CAGTGGTTTCCAGTGAGGTG | 38 | 927 |

TABLE 16-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130999 | 460 | 479 | 4405 | 4424 | AAAACCGGAGAAGCTGAGGC | 26 | 928 |
| 1131027 | 502 | 521 | 4447 | 4466 | CAGCTGCTTGCTCAGTTCTA | 35 | 929 |
| 1131055 | 543 | 562 | 4488 | 4507 | CTGGCAGTGGGCATCAGGAC | 33 | 930 |
| 1131083 | 579 | 598 | 4663 | 4682 | GCACGGGTTGGTGCGGCAGG | 29 | 931 |
| 1131111 | 618 | 637 | 4702 | 4721 | GCGGTGGCCCTCCACCTCTA | 54 | 932 |
| 1131139 | 680 | 699 | N/A | N/A | CAGCTTGCCTTGGTGTCCAC | 30 | 933 |
| 1131167 | 720 | 739 | 4949 | 4968 | CCTGGCCAGGCCGCGGTAGC | 80 | 934 |
| 1131195 | 775 | 794 | 5004 | 5023 | TCCGGTAGGTGGCCTCCGAG | 33 | 935 |
| 1131223 | 869 | 888 | 5183 | 5202 | AGCACGAAGCACCACGGGCG | 17 | 936 |
| 1131251 | 913 | 932 | 5227 | 5246 | ACTGTGCCAGGTCGCAGTAC | 26 | 937 |
| 1131279 | 1004 | 1023 | 5318 | 5337 | GGCTTCGGCGGTGCCGGCTG | 24 | 938 |
| 1131307 | 1081 | 1100 | 5500 | 5519 | GGGAAGGCGGCTGCTCCCGC | 40 | 939 |
| 1131335 | 1128 | 1147 | 5547 | 5566 | ACTCTTGCGGAGCCGCTGCC | 43 | 98 |
| 1131363 | 1165 | 1184 | 5584 | 5603 | CCACCAGCCCGCCAACGACG | 59 | 940 |
| 1131391 | 1235 | 1254 | 5654 | 5673 | ATGAGGCTGCCGGCGCAGAA | 49 | 941 |
| 1131419 | 1320 | 1339 | 5980 | 5999 | TTCCTGGCCGAGCACCACCG | 24 | 942 |
| 1131447 | 1411 | 1430 | 6071 | 6090 | CGTGCTGGTAGCTGACGGGC | 25 | 943 |
| 1131475 | 1471 | 1490 | 6214 | 6233 | AAGGCGACAGGAGCGCGCAG | 28 | 944 |
| 1131503 | 1557 | 1576 | 6300 | 6319 | GAACTGGTGGCCCCAGCCGG | 65 | 945 |
| 1131531 | 1592 | 1611 | 6890 | 6909 | TCCTGCAGGAAGCTGGCATA | 88 | 946 |
| 1131559 | 1683 | 1702 | 6981 | 7000 | GAACCCTGCGCAGAGCATGC | 56† | 947 |
| 1131587 | 1757 | 1776 | 7145 | 7164 | CGCTCTGCAGCTTGGTCCTC | 19† | 948 |
| 1131615 | 1802 | 1821 | 7190 | 7209 | CCACAGCCCGATCCCCAGCT | 40 | 949 |
| 1131643 | 1849 | 1868 | 7237 | 7256 | CCAGGTAGTAGGCCACATCG | 44 | 88 |
| 1131671 | 1882 | 1901 | 7270 | 7289 | GCAATCAGGAAACGGTGTGC | 12 | 950 |
| 1131699 | 1926 | 1945 | 7314 | 7333 | TCTCTCACTGCGGAATCACC | 7 | 951 |
| 1131727 | 1962 | 1981 | 7350 | 7369 | AATGGGACACAATCTTGCCT | 25 | 952 |
| 1131755 | 2016 | 2035 | 7404 | 7423 | AGCACTTTATTGAGTTCCTG | 3 | 953 |
| 1131783 | N/A | N/A | 121 | 140 | ATCCTGGGACAATCCTGGTT | 41 | 954 |
| 1131811 | N/A | N/A | 205 | 224 | CCACATAGGCCTCCTAGTCA | 48 | 955 |
| 1131839 | N/A | N/A | 308 | 327 | TCTTAAGGCCCATCTCCCCC | 46 | 956 |
| 1131867 | N/A | N/A | 398 | 417 | CTGTTGCTAGTCTGCAGCTT | 85 | 957 |
| 1131895 | N/A | N/A | 526 | 545 | GCCAGGCCACTTACCGACTG | 40 | 958 |
| 1131923 | N/A | N/A | 633 | 652 | GCCCATGGGCATAAGACCTA | 37 | 959 |
| 1131951 | N/A | N/A | 736 | 755 | AGCAGCACATATCTCAAGCA | 68 | 960 |

TABLE 16-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131979 | N/A | N/A | 889 | 908 | CAGAGACAAGCTCTTGATCC | 44 | 961 |
| 1132007 | N/A | N/A | 1003 | 1022 | GTTATCAACCTGGTTTCACA | 27 | 962 |
| 1132035 | N/A | N/A | 1097 | 1116 | AAAAGCTAATATTTGTAAAG | 42 | 963 |
| 1132063 | N/A | N/A | 1518 | 1537 | TGCCACACTCTAGGTAAATT | 43 | 964 |
| 1132091 | N/A | N/A | 1618 | 1637 | GGTTGGAATGTGCTGGGCCT | 48 | 965 |
| 1132119 | N/A | N/A | 1914 | 1933 | AGCATGAAGTTGTGTGCCTG | 79 | 966 |
| 1132147 | N/A | N/A | 2150 | 2169 | TTTGTTCAAGGCAAAGTGCA | 34 | 967 |
| 1132175 | N/A | N/A | 2280 | 2299 | ACCATCGCGAATAATGAGAA | 32 | 968 |
| 1132203 | N/A | N/A | 2394 | 2413 | CATACATAAAACCAGATTAT | 67 | 969 |
| 1132231 | N/A | N/A | 2533 | 2552 | TAGTTCCTAAGCACAAGAAG | 98 | 970 |
| 1132259 | N/A | N/A | 2655 | 2674 | AGCTCTCCTATTGAATGAGT | 36 | 971 |
| 1132287 | N/A | N/A | 2768 | 2787 | AGTCAATACTTGAAATGTTT | 84 | 972 |
| 1132315 | N/A | N/A | 2860 | 2879 | AACGGCAGTAATAATAGTAC | 55 | 973 |
| 1132343 | N/A | N/A | 2971 | 2990 | TCCCAAGGCCAGGAAGAGCA | 32 | 974 |
| 1132371 | N/A | N/A | 3379 | 3398 | CACTTTCTGCTCTAAAAGTT | 28 | 975 |
| 1132399 | N/A | N/A | 3466 | 3485 | CCCCTGTACTCAACTGCTCA | 42 | 976 |
| 1132427 | N/A | N/A | 3664 | 3683 | TTGGACAGAAGGACAGGCAG | 58 | 977 |
| 1132455 | N/A | N/A | 3830 | 3849 | GTAGCACCTTTCACTTTCTT | 16 | 978 |
| 1132483 | N/A | N/A | 3954 | 3973 | TCCAAAGGGTATTGTGGAGG | 38 | 979 |
| 1132511 | N/A | N/A | 4042 | 4061 | CTTGTGACCTTGCTACTCCA | 28 | 980 |
| 1132539 | N/A | N/A | 4242 | 4261 | TCCTCACCTTTCTGGCAGTG | 27 | 981 |
| 1132567 | N/A | N/A | 4343 | 4362 | GAGAGTCTAGGACCATGCCA | 80 | 982 |
| 1132595 | N/A | N/A | 4575 | 4594 | ACACCACCCGGCCTCCTGCC | 58 | 983 |
| 1132623 | N/A | N/A | 4775 | 4794 | TTCTGCTTGCCCCAGACCCT | 70 | 984 |
| 1132651 | N/A | N/A | 4908 | 4927 | AGCTTGCCTTGGTGTCTGAG | 19 | 985 |
| 1132679 | N/A | N/A | 5424 | 5443 | TGGCCGGAATCTAGCTCGCC | 61 | 986 |
| 1132707 | N/A | N/A | 5850 | 5869 | TCCAGCTTCCTCCCCGGGAG | 51 | 987 |
| 1132735 | N/A | N/A | 6312 | 6331 | GTGCCTACCCTCGAACTGGT | 45 | 988 |
| 1132763 | N/A | N/A | 6403 | 6422 | GTAGGCACCCGGAACGATAC | 27 | 989 |
| 1132791 | N/A | N/A | 6524 | 6543 | TCGATTCTCCCTGTATCCCC | 69 | 990 |
| 1132819 | N/A | N/A | 6649 | 6668 | CAGAAACCCCTCCCCCACCA | 50 | 991 |
| 1132847 | N/A | N/A | 6755 | 6774 | TCTCTCGCAGCAAGCCCGAA | 48 | 992 |
| 1132875 | N/A | N/A | 7010 | 7029 | ACCTGGCACGCATCGGTGCC | 29† | 993 |

TABLE 17

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130747 | 10 | 29 | 10 | 29 | GCTGCCTATCCAGGAGTCCA | 45 | 994 |
| 1130775 | 47 | 66 | 47 | 66 | AGCAGCAGAGCCCTCATGGC | 43 | 995 |
| 1130803 | 93 | 112 | N/A | N/A | TGGAATCGAAAGTGTTGACT | 25 | 996 |
| 1130831 | 148 | 167 | N/A | N/A | GAACGACTGTGTGCTCTTCA | 18 | 997 |
| 1130859 | 203 | 222 | 3554 | 3573 | TACAGCTGCCGGTGGTACTG | 28 | 998 |
| 1130871 | 216 | 235 | 3567 | 3586 | GGTACATTTGTGGTACAGCT | 8 | 183 |
| 1130888 | 238 | 257 | 3589 | 3608 | GAGGGCCTGGCCGGCCCTTG | 77 | 999 |
| 1130916 | 307 | 326 | 3814 | 3833 | TCTTGGGCTCCAAACAGTAT | 33 | 1000 |
| 1130944 | 363 | 382 | 4171 | 4190 | CACACAGGTCCCTCCTTTCT | 53 | 1001 |
| 1130972 | 420 | 439 | 4228 | 4247 | GCAGTGGTTTCCAGTGAGGT | 19 | 1002 |
| 1131000 | 461 | 480 | 4406 | 4425 | AAAAACCGGAGAAGCTGAGG | 25 | 1003 |
| 1131028 | 505 | 524 | 4450 | 4469 | CCACAGCTGCTTGCTCAGTT | 23 | 1004 |
| 1131056 | 545 | 564 | 4490 | 4509 | CGCTGGCAGTGGGCATCAGG | 24 | 1005 |
| 1131084 | 580 | 599 | 4664 | 4683 | GGCACGGGTTGGTGCGGCAG | 19 | 1006 |
| 1131112 | 619 | 638 | 4703 | 4722 | GGCGGTGGCCCTCCACCTCT | 36 | 1007 |
| 1131140 | 681 | 700 | N/A | N/A | GCAGCTTGCCTTGGTGTCCA | 21 | 1008 |
| 1131168 | 721 | 740 | 4950 | 4969 | TCCTGGCCAGGCCGCGGTAG | 37 | 1009 |
| 1131196 | 777 | 796 | 5006 | 5025 | GTTCCGGTAGGTGGCCTCCG | 46 | 1010 |
| 1131224 | 870 | 889 | 5184 | 5203 | CAGCACGAAGCACCACGGGC | 35 | 1011 |
| 1131252 | 914 | 933 | 5228 | 5247 | CACTGTGCCAGGTCGCAGTA | 60 | 1012 |
| 1131280 | 1005 | 1024 | 5319 | 5338 | AGGCTTCGGCGGTGCCGGCT | 31 | 1013 |
| 1131308 | 1085 | 1104 | 5504 | 5523 | GTCAGGGAAGGCGGCTGCTC | 25 | 1014 |
| 1131336 | 1129 | 1148 | 5548 | 5567 | GACTCTTGCGGAGCCGCTGC | 40 | 1015 |
| 1131364 | 1167 | 1186 | 5586 | 5605 | CGCCACCAGCCCGCCAACGA | 43 | 1016 |
| 1131392 | 1237 | 1256 | 5656 | 5675 | CGATGAGGCTGCCGGCGCAG | 30 | 1017 |
| 1131420 | 1322 | 1341 | 5982 | 6001 | CGTTCCTGGCCGAGCACCAC | 34 | 1018 |
| 1131448 | 1430 | 1449 | N/A | N/A | AGGCGCAACAGAGCCAGGTC | 38 | 1019 |
| 1131476 | 1473 | 1492 | 6216 | 6235 | GTAAGGCGACAGGAGCGCGC | 37 | 1020 |
| 1131504 | 1558 | 1577 | 6301 | 6320 | CGAACTGGTGGCCCCAGCCG | 76 | 1021 |
| 1131532 | 1594 | 1613 | 6892 | 6911 | CCTCCTGCAGGAAGCTGGCA | 112 | 1022 |
| 1131560 | 1687 | 1706 | 6985 | 7004 | CGAGGAACCCTGCGCAGAGC | 6† | 1023 |
| 1131588 | 1758 | 1777 | 7146 | 7165 | GCGCTCTGCAGCTTGGTCCT | 16† | 1024 |
| 1131616 | 1803 | 1822 | 7191 | 7210 | ACCACAGCCCGATCCCCAGC | 39 | 1025 |
| 1131644 | 1850 | 1869 | 7238 | 7257 | GCCAGGTAGTAGGCCACATC | 34 | 1026 |
| 1131672 | 1883 | 1902 | 7271 | 7290 | AGCAATCAGGAAACGGTGTG | 24 | 1027 |

TABLE 17-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131700 | 1927 | 1946 | 7315 | 7334 | CTCTCTCACTGCGGAATCAC | 7 | 1028 |
| 1131728 | 1963 | 1982 | 7351 | 7370 | GAATGGGACACAATCTTGCC | 21 | 1029 |
| 1131756 | 2017 | 2036 | 7405 | 7424 | AAGCACTTTATTGAGTTCCT | 5 | 1030 |
| 1131784 | N/A | N/A | 124 | 143 | ACAATCCTGGGACAATCCTG | 85 | 1031 |
| 1131812 | N/A | N/A | 208 | 227 | TTTCCACATAGGCCTCCTAG | 42 | 1032 |
| 1131840 | N/A | N/A | 311 | 330 | TCTTCTTAAGGCCCATCTCC | 79 | 1033 |
| 1131868 | N/A | N/A | 401 | 420 | GATCTGTTGCTAGTCTGCAG | 82 | 1034 |
| 1131896 | N/A | N/A | 529 | 548 | GGAGCCAGGCCACTTACCGA | 45 | 1035 |
| 1131924 | N/A | N/A | 636 | 655 | AGTGCCCATGGGCATAAGAC | 52 | 1036 |
| 1131952 | N/A | N/A | 739 | 758 | GCCAGCAGCACATATCTCAA | 55 | 1037 |
| 1131980 | N/A | N/A | 892 | 911 | TGCCAGAGACAAGCTCTTGA | 73 | 1038 |
| 1132008 | N/A | N/A | 1006 | 1025 | ACTGTTATCAACCTGGTTTC | 60 | 1039 |
| 1132036 | N/A | N/A | 1105 | 1124 | TTCATAATAAAAGCTAATAT | 68 | 1040 |
| 1132064 | N/A | N/A | 1521 | 1540 | ATGTGCCACACTCTAGGTAA | 51 | 1041 |
| 1132092 | N/A | N/A | 1622 | 1641 | CCAGGGTTGGAATGTGCTGG | 56 | 1042 |
| 1132120 | N/A | N/A | 1917 | 1936 | CTGAGCATGAAGTTGTGTGC | 44 | 1043 |
| 1132148 | N/A | N/A | 2166 | 2185 | AAGCTTTTGCCACTATTTTG | 36 | 1044 |
| 1132176 | N/A | N/A | 2283 | 2302 | ATAACCATCGCGAATAATGA | 50 | 1045 |
| 1132204 | N/A | N/A | 2397 | 2416 | AATCATACATAAAACCAGAT | 75 | 1046 |
| 1132232 | N/A | N/A | 2536 | 2555 | GTGTAGTTCCTAAGCACAAG | 37 | 1047 |
| 1132260 | N/A | N/A | 2658 | 2677 | TTCAGCTCTCCTATTGAATG | 37 | 1048 |
| 1132288 | N/A | N/A | 2771 | 2790 | CCAAGTCAATACTTGAAATG | 42 | 1049 |
| 1132316 | N/A | N/A | 2863 | 2882 | TAAAACGGCAGTAATAATAG | 62 | 1050 |
| 1132344 | N/A | N/A | 2974 | 2993 | CAGTCCCAAGGCCAGGAAGA | 38 | 1051 |
| 1132372 | N/A | N/A | 3382 | 3401 | AAACACTTTCTGCTCTAAAA | 67 | 1052 |
| 1132400 | N/A | N/A | 3469 | 3488 | CTTCCCCTGTACTCAACTGC | 43 | 1053 |
| 1132428 | N/A | N/A | 3667 | 3686 | TCCTTGGACAGAAGGACAGG | 75 | 1054 |
| 1132456 | N/A | N/A | 3833 | 3852 | TGTGTAGCACCTTTCACTTT | 41 | 1055 |
| 1132484 | N/A | N/A | 3957 | 3976 | ACTTCCAAAGGGTATTGTGG | 56 | 1056 |
| 1132512 | N/A | N/A | 4045 | 4064 | TGCCTTGTGACCTTGCTACT | 34 | 1057 |
| 1132540 | N/A | N/A | 4245 | 4264 | ATCTCCTCACCTTTCTGGCA | 82 | 1058 |
| 1132568 | N/A | N/A | 4346 | 4365 | CAGGAGAGTCTAGGACCATG | 78 | 1059 |
| 1132596 | N/A | N/A | 4578 | 4597 | GGCACACCACCCGGCCTCCT | 48 | 1060 |
| 1132624 | N/A | N/A | 4778 | 4797 | GCCTTCTGCTTGCCCCAGAC | 48 | 1061 |
| 1132652 | N/A | N/A | 4911 | 4930 | AGCAGCTTGCCTTGGTGTCT | 25 | 1062 |

TABLE 17-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132680 | N/A | N/A | 5427 | 5446 | GGCTGGCCGGAATCTAGCTC | 69 | 1063 |
| 1132708 | N/A | N/A | 5853 | 5872 | TGTTCCAGCTTCCTCCCCGG | 37 | 1064 |
| 1132736 | N/A | N/A | 6315 | 6334 | GTTGTGCCTACCCTCGAACT | 85 | 1065 |
| 1132764 | N/A | N/A | 6406 | 6425 | TCTGTAGGCACCCGGAACGA | 58 | 1066 |
| 1132792 | N/A | N/A | 6527 | 6546 | AGTTCGATTCTCCCTGTATC | 54 | 1067 |
| 1132820 | N/A | N/A | 6652 | 6671 | AAACAGAAACCCCTCCCCCA | 73 | 1068 |
| 1132848 | N/A | N/A | 6758 | 6777 | TCCTCTCTCGCAGCAAGCCC | 57 | 1069 |
| 1132876 | N/A | N/A | 7013 | 7032 | CTCACCTGGCACGCATCGGT | 64† | 1070 |

TABLE 18

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130749 | 12 | 31 | 12 | 31 | CAGCTGCCTATCCAGGAGTC | 57 | 1071 |
| 1130777 | 49 | 68 | 49 | 68 | GGAGCAGCAGAGCCCTCATG | 40 | 1072 |
| 1130805 | 96 | 115 | N/A | N/A | AGGTGGAATCGAAAGTGTTG | 34 | 1073 |
| 1130833 | 151 | 170 | N/A | N/A | TGAGAACGACTGTGTGCTCT | 27 | 1074 |
| 1130861 | 205 | 224 | 3556 | 3575 | GGTACAGCTGCCGGTGGTAC | 31 | 1075 |
| 1130871 | 216 | 235 | 3567 | 3586 | GGTACATTTGTGGTACAGCT | 10 | 183 |
| 1130890 | 240 | 259 | 3591 | 3610 | CTGAGGGCCTGGCCGGCCCT | 40 | 1076 |
| 1130918 | 310 | 329 | 3817 | 3836 | CTTTCTTGGGCTCCAAACAG | 36 | 1077 |
| 1130946 | 366 | 385 | 4174 | 4193 | GTTCACACAGGTCCCTCCTT | 48 | 1078 |
| 1130974 | 423 | 442 | 4231 | 4250 | CTGGCAGTGGTTTCCAGTGA | 28 | 1079 |
| 1131002 | 464 | 483 | 4409 | 4428 | TGGAAAAACCGGAGAAGCTG | 22 | 1080 |
| 1131030 | 508 | 527 | 4453 | 4472 | TGGCCACAGCTGCTTGCTCA | 48 | 1081 |
| 1131058 | 547 | 566 | 4492 | 4511 | GCCGCTGGCAGTGGGCATCA | 42 | 1082 |
| 1131086 | 583 | 602 | 4667 | 4686 | GGAGGCACGGGTTGGTGCGG | 27 | 1083 |
| 1131114 | 622 | 641 | 4706 | 4725 | ACAGGCGGTGGCCCTCCACC | 58 | 1084 |
| 1131142 | 685 | 704 | 4914 | 4933 | CATAGCAGCTTGCCTTGGTG | 22 | 1085 |
| 1131170 | 724 | 743 | 4953 | 4972 | TGGTCCTGGCCAGGCCGCGG | 77 | 1086 |
| 1131198 | 796 | 815 | 5025 | 5044 | GCGCTTGCTCGGCAGTCACG | 18 | 1087 |
| 1131226 | 873 | 892 | 5187 | 5206 | GTTCAGCACGAAGCACCACG | 21 | 1088 |
| 1131254 | 916 | 935 | 5230 | 5249 | GGCACTGTGCCAGGTCGCAG | 39 | 1089 |

TABLE 18-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131282 | 1007 | 1026 | 5321 | 5340 | TGAGGCTTCGGCGGTGCCGG | 43 | 1090 |
| 1131310 | 1089 | 1108 | 5508 | 5527 | CCTGGTCAGGGAAGGCGGCT | 27 | 1091 |
| 1131338 | 1131 | 1150 | 5550 | 5569 | CAGACTCTTGCGGAGCCGCT | 22 | 1092 |
| 1131366 | 1203 | 1222 | 5622 | 5641 | GTACAGCGCGGCGATGTAGG | 41 | 1093 |
| 1131394 | 1239 | 1258 | 5658 | 5677 | GGCGATGAGGCTGCCGGCGC | 31 | 114 |
| 1131422 | 1341 | 1360 | 6001 | 6020 | CTCACAGCTGTGGTTACGGC | 23 | 1094 |
| 1131450 | 1433 | 1452 | N/A | N/A | TGAAGGCGCAACAGAGCCAG | 46 | 1095 |
| 1131478 | 1492 | 1511 | 6235 | 6254 | GCAGGCACACCGGCTGAACG | 36 | 72 |
| 1131506 | 1560 | 1579 | 6303 | 6322 | CTCGAACTGGTGGCCCCAGC | 53 | 1096 |
| 1131534 | 1597 | 1616 | 6895 | 6914 | GCGCCTCCTGCAGGAAGCTG | 92 | 1097 |
| 1131562 | 1690 | 1709 | 6988 | 7007 | CCTCGAGGAACCCTGCGCAG | 27† | 1098 |
| 1131590 | 1776 | 1795 | 7164 | 7183 | GCCTTGCAGGGTGAGCCGGC | 43 | 1099 |
| 1131618 | 1805 | 1824 | 7193 | 7212 | TCACCACAGCCCGATCCCCA | 40 | 1100 |
| 1131646 | 1852 | 1871 | 7240 | 7259 | AGGCCAGGTAGTAGGCCACA | 63 | 1101 |
| 1131674 | 1888 | 1907 | 7276 | 7295 | CCCTGAGCAATCAGGAAACG | 35 | 1102 |
| 1131702 | 1930 | 1949 | 7318 | 7337 | CCACTCTCTCACTGCGGAAT | 9 | 1103 |
| 1131730 | 1984 | 2003 | 7372 | 7391 | GCGGAGCTGGCCGCACTGGG | 18 | 1104 |
| 1131758 | 2019 | 2038 | 7407 | 7426 | CAAAGCACTTTATTGAGTTC | 9 | 1105 |
| 1131786 | N/A | N/A | 130 | 149 | CCCAGAACAATCCTGGGACA | 70 | 1106 |
| 1131814 | N/A | N/A | 214 | 233 | CTCACCTTTCCACATAGGCC | 82 | 1107 |
| 1131842 | N/A | N/A | 317 | 336 | CCGTTGTCTTCTTAAGGCCC | 82 | 1108 |
| 1131870 | N/A | N/A | 407 | 426 | GCCACCGATCTGTTGCTAGT | 67 | 1109 |
| 1131898 | N/A | N/A | 538 | 557 | CCGGGAGGAGGAGCCAGGCC | 67 | 1110 |
| 1131926 | N/A | N/A | 642 | 661 | CACTCTAGTGCCCATGGGCA | 83 | 1111 |
| 1131954 | N/A | N/A | 760 | 779 | CAGGAGCCCAGGTGTGATGG | 47 | 1112 |
| 1131982 | N/A | N/A | 898 | 917 | TTCAGATGCCAGAGACAAGC | 54 | 1113 |
| 1132010 | N/A | N/A | 1012 | 1031 | AGGTTTACTGTTATCAACCT | 48 | 1114 |
| 1132038 | N/A | N/A | 1111 | 1130 | GGTAGTTTCATAATAAAAGC | 36 | 1115 |
| 1132066 | N/A | N/A | 1527 | 1546 | CCTGCTATGTGCCACACTCT | 59 | 1116 |
| 1132094 | N/A | N/A | 1637 | 1656 | GGAGGCTGAGGGAGTCCAGG | 90 | 1117 |
| 1132122 | N/A | N/A | 1923 | 1942 | AATTAGCTGAGCATGAAGTT | 54 | 1118 |
| 1132150 | N/A | N/A | 2172 | 2191 | CTCAATAAGCTTTTGCCACT | 57 | 1119 |
| 1132178 | N/A | N/A | 2289 | 2308 | TAGAACATAACCATCGCGAA | 33 | 1120 |
| 1132206 | N/A | N/A | 2411 | 2430 | ATGTCTTTAAACAGAATCAT | 32 | 1121 |
| 1132234 | N/A | N/A | 2542 | 2561 | AGAGCTGTGTAGTTCCTAAG | 65 | 1122 |

TABLE 18-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132262 | N/A | N/A | 2664 | 2683 | GCTTGTTTCAGCTCTCCTAT | 78 | 1123 |
| 1132290 | N/A | N/A | 2777 | 2796 | TAACTCCCAAGTCAATACTT | 76 | 1124 |
| 1132318 | N/A | N/A | 2890 | 2909 | TGATCTGAGCCTTGGTTTCC | 69 | 1125 |
| 1132346 | N/A | N/A | 2980 | 2999 | AGTCTTCAGTCCCAAGGCCA | 71 | 1126 |
| 1132374 | N/A | N/A | 3388 | 3407 | CATTGAAAACACTTTCTGCT | 70 | 1127 |
| 1132402 | N/A | N/A | 3475 | 3494 | TGAGGACTTCCCCTGTACTC | 40 | 1128 |
| 1132430 | N/A | N/A | 3673 | 3692 | CAGAGTTCCTTGGACAGAAG | 38 | 1129 |
| 1132458 | N/A | N/A | 3839 | 3858 | AGGCTGTGTGTAGCACCTTT | 54 | 1130 |
| 1132486 | N/A | N/A | 3963 | 3982 | CTCTGGACTTCCAAAGGGTA | 37 | 1131 |
| 1132514 | N/A | N/A | 4051 | 4070 | CCTACTTGCCTTGTGACCTT | 37 | 1132 |
| 1132542 | N/A | N/A | 4251 | 4270 | CTCCACATCTCCTCACCTTT | 39 | 1133 |
| 1132570 | N/A | N/A | 4352 | 4371 | TGGTCTCAGGAGAGTCTAGG | 59 | 1134 |
| 1132598 | N/A | N/A | 4584 | 4603 | CTTCCTGGCACACCACCCGG | 60 | 1135 |
| 1132626 | N/A | N/A | 4784 | 4803 | GGGCTGGCCTTCTGCTTGCC | 36 | 1136 |
| 1132654 | N/A | N/A | 5070 | 5089 | ACGCGGCGCACCGGCAGAAG | 61 | 1137 |
| 1132682 | N/A | N/A | 5436 | 5455 | CCCGCGGCCGGCTGGCCGGA | 118 | 1138 |
| 1132710 | N/A | N/A | 5859 | 5878 | ATCCCGTGTTCCAGCTTCCT | 67 | 1139 |
| 1132738 | N/A | N/A | 6321 | 6340 | CTAGCAGTTGTGCCTACCCT | 49 | 1140 |
| 1132766 | N/A | N/A | 6412 | 6431 | ACCCATTCTGTAGGCACCCG | 78 | 1141 |
| 1132794 | N/A | N/A | 6533 | 6552 | AGAGCAAGTTCGATTCTCCC | 88 | 1142 |
| 1132822 | N/A | N/A | 6658 | 6677 | GAGCGGAAACAGAAACCCCT | 52 | 1143 |
| 1132850 | N/A | N/A | 6764 | 6783 | TGCCCTTCCTCTCTCGCAGC | 95 | 1144 |
| 1132878 | N/A | N/A | 7019 | 7038 | TAAGAGCTCACCTGGCACGC | 85† | 1145 |

TABLE 19

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130748 | 11 | 30 | 11 | 30 | AGCTGCCTATCCAGGAGTCC | 62 | 1146 |
| 1130776 | 48 | 67 | 48 | 67 | GAGCAGCAGAGCCCTCATGG | 67 | 1147 |
| 1130804 | 94 | 113 | N/A | N/A | GTGGAATCGAAAGTGTTGAC | 58 | 1148 |
| 1130832 | 150 | 169 | N/A | N/A | GAGAACGACTGTGTGCTCTT | 12 | 1149 |

TABLE 19-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130860 | 204 | 223 | 3555 | 3574 | GTACAGCTGCCGGTGGTACT | 35 | 1150 |
| 1130871 | 216 | 235 | 3567 | 3586 | GGTACATTTGTGGTACAGCT | 16 | 183 |
| 1130889 | 239 | 258 | 3590 | 3609 | TGAGGGCCTGGCCGGCCCTT | 54 | 1151 |
| 1130917 | 308 | 327 | 3815 | 3834 | TTCTTGGGCTCCAAACAGTA | 25 | 1152 |
| 1130945 | 365 | 384 | 4173 | 4192 | TTCACACAGGTCCCTCCTTT | 37 | 1153 |
| 1130973 | 421 | 440 | 4229 | 4248 | GGCAGTGGTTTCCAGTGAGG | 14 | 1154 |
| 1131001 | 463 | 482 | 4408 | 4427 | GGAAAAACCGGAGAAGCTGA | 26 | 1155 |
| 1131029 | 506 | 525 | 4451 | 4470 | GCCACAGCTGCTTGCTCAGT | 35 | 1156 |
| 1131057 | 546 | 565 | 4491 | 4510 | CCGCTGGCAGTGGGCATCAG | 32 | 1157 |
| 1131085 | 582 | 601 | 4666 | 4685 | GAGGCACGGGTTGGTGCGGC | 32 | 1158 |
| 1131113 | 621 | 640 | 4705 | 4724 | CAGGCGGTGGCCCTCCACCT | 25 | 1159 |
| 1131141 | 682 | 701 | N/A | N/A | AGCAGCTTGCCTTGGTGTCC | 29 | 1160 |
| 1131169 | 722 | 741 | 4951 | 4970 | GTCCTGGCCAGGCCGCGGTA | 42 | 1161 |
| 1131197 | 778 | 797 | 5007 | 5026 | CGTTCCGGTAGGTGGCCTCC | 28 | 1162 |
| 1131225 | 872 | 891 | 5186 | 5205 | TTCAGCACGAAGCACCACGG | 27 | 1163 |
| 1131253 | 915 | 934 | 5229 | 5248 | GCACTGTGCCAGGTCGCAGT | 36 | 1164 |
| 1131281 | 1006 | 1025 | 5320 | 5339 | GAGGCTTCGGCGGTGCCGGC | 26 | 1165 |
| 1131309 | 1087 | 1106 | 5506 | 5525 | TGGTCAGGGAAGGCGGCTGC | 8 | 1166 |
| 1131337 | 1130 | 1149 | 5549 | 5568 | AGACTCTTGCGGAGCCGCTG | 24 | 1167 |
| 1131365 | 1168 | 1187 | 5587 | 5606 | GCGCCACCAGCCCGCCAACG | 33 | 1168 |
| 1131393 | 1238 | 1257 | 5657 | 5676 | GCGATGAGGCTGCCGGCGCA | 26 | 1169 |
| 1131421 | 1340 | 1359 | 6000 | 6019 | TCACAGCTGTGGTTACGGCG | 38 | 1170 |
| 1131449 | 1431 | 1450 | N/A | N/A | AAGGCGCAACAGAGCCAGGT | 55 | 1171 |
| 1131477 | 1474 | 1493 | 6217 | 6236 | CGTAAGGCGACAGGAGCGCG | 25 | 1172 |
| 1131505 | 1559 | 1578 | 6302 | 6321 | TCGAACTGGTGGCCCCAGCC | 86 | 74 |
| 1131533 | 1595 | 1614 | 6893 | 6912 | GCCTCCTGCAGGAAGCTGGC | 53 | 1173 |
| 1131561 | 1688 | 1707 | 6986 | 7005 | TCGAGGAACCCTGCGCAGAG | 21† | 1174 |
| 1131589 | 1775 | 1794 | 7163 | 7182 | CCTTGCAGGGTGAGCCGGCG | 30 | 1175 |
| 1131617 | 1804 | 1823 | 7192 | 7211 | CACCACAGCCCGATCCCCAG | 28 | 1176 |
| 1131645 | 1851 | 1870 | 7239 | 7258 | GGCCAGGTAGTAGGCCACAT | 63 | 1177 |
| 1131673 | 1886 | 1905 | 7274 | 7293 | CTGAGCAATCAGGAAACGGT | 16 | 1178 |
| 1131701 | 1928 | 1947 | 7316 | 7335 | ACTCTCTCACTGCGGAATCA | 7 | 1179 |
| 1131729 | 1964 | 1983 | 7352 | 7371 | GGAATGGGACACAATCTTGC | 26 | 1180 |
| 1131757 | 2018 | 2037 | 7406 | 7425 | AAAGCACTTTATTGAGTTCC | 3 | 165 |
| 1131785 | N/A | N/A | 127 | 146 | AGAACAATCCTGGGACAATC | 69 | 1181 |

TABLE 19-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131813 | N/A | N/A | 211 | 230 | ACCTTTCCACATAGGCCTCC | 99 | 1182 |
| 1131841 | N/A | N/A | 314 | 333 | TTGTCTTCTTAAGGCCCATC | 49 | 1183 |
| 1131869 | N/A | N/A | 404 | 423 | ACCGATCTGTTGCTAGTCTG | 72 | 1184 |
| 1131897 | N/A | N/A | 535 | 554 | GGAGGAGGAGCCAGGCCACT | 94 | 1185 |
| 1131925 | N/A | N/A | 639 | 658 | TCTAGTGCCCATGGGCATAA | 38 | 1186 |
| 1131953 | N/A | N/A | 757 | 776 | GAGCCCAGGTGTGATGGCGC | 87 | 1187 |
| 1131981 | N/A | N/A | 895 | 914 | AGATGCCAGAGACAAGCTCT | 49 | 1188 |
| 1132009 | N/A | N/A | 1009 | 1028 | TTTACTGTTATCAACCTGGT | 38 | 1189 |
| 1132037 | N/A | N/A | 1108 | 1127 | AGTTTCATAATAAAAGCTAA | 83 | 1190 |
| 1132065 | N/A | N/A | 1524 | 1543 | GCTATGTGCCACACTCTAGG | 102 | 1191 |
| 1132093 | N/A | N/A | 1625 | 1644 | AGTCCAGGGTTGGAATGTGC | 80 | 1192 |
| 1132121 | N/A | N/A | 1920 | 1939 | TAGCTGAGCATGAAGTTGTG | 52 | 1193 |
| 1132149 | N/A | N/A | 2169 | 2188 | AATAAGCTTTTGCCACTATT | 59 | 1194 |
| 1132177 | N/A | N/A | 2286 | 2305 | AACATAACCATCGCGAATAA | 53 | 1195 |
| 1132205 | N/A | N/A | 2400 | 2419 | CAGAATCATACATAAAACCA | 45 | 1196 |
| 1132233 | N/A | N/A | 2539 | 2558 | GCTGTGTAGTTCCTAAGCAC | 70 | 1197 |
| 1132261 | N/A | N/A | 2661 | 2680 | TGTTTCAGCTCTCCTATTGA | 53 | 1198 |
| 1132289 | N/A | N/A | 2774 | 2793 | CTCCCAAGTCAATACTTGAA | 93 | 1199 |
| 1132317 | N/A | N/A | 2870 | 2889 | TTATCTGTAAAACGGCAGTA | 38 | 1200 |
| 1132345 | N/A | N/A | 2977 | 2996 | CTTCAGTCCCAAGGCCAGGA | 64 | 1201 |
| 1132373 | N/A | N/A | 3385 | 3404 | TGAAAACACTTTCTGCTCTA | 51 | 1202 |
| 1132401 | N/A | N/A | 3472 | 3491 | GGACTTCCCCTGTACTCAAC | 72 | 1203 |
| 1132429 | N/A | N/A | 3670 | 3689 | AGTTCCTTGGACAGAAGGAC | 50 | 1204 |
| 1132457 | N/A | N/A | 3836 | 3855 | CTGTGTGTAGCACCTTTCAC | 73 | 1205 |
| 1132485 | N/A | N/A | 3960 | 3979 | TGGACTTCCAAAGGGTATTG | 39 | 1206 |
| 1132513 | N/A | N/A | 4048 | 4067 | ACTTGCCTTGTGACCTTGCT | 58 | 1207 |
| 1132541 | N/A | N/A | 4248 | 4267 | CACATCTCCTCACCTTTCTG | 98 | 1208 |
| 1132569 | N/A | N/A | 4349 | 4368 | TCTCAGGAGAGTCTAGGACC | 59 | 1209 |
| 1132597 | N/A | N/A | 4581 | 4600 | CCTGGCACACCACCCGGCCT | 70 | 1210 |
| 1132625 | N/A | N/A | 4781 | 4800 | CTGGCCTTCTGCTTGCCCCA | 46 | 1211 |
| 1132653 | N/A | N/A | 5067 | 5086 | CGGCGCACCGGCAGAAGGCG | 37 | 1212 |
| 1132681 | N/A | N/A | 5430 | 5449 | GCCGGCTGGCCGGAATCTAG | 77 | 1213 |
| 1132709 | N/A | N/A | 5856 | 5875 | CCGTGTTCCAGCTTCCTCCC | 160 | 1214 |
| 1132737 | N/A | N/A | 6318 | 6337 | GCAGTTGTGCCTACCCTCGA | 49 | 1215 |
| 1132765 | N/A | N/A | 6409 | 6428 | CATTCTGTAGGCACCCGGAA | 47 | 1216 |

TABLE 19-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132793 | N/A | N/A | 6530 | 6549 | GCAAGTTCGATTCTCCCTGT | 72 | 1217 |
| 1132821 | N/A | N/A | 6655 | 6674 | CGGAAACAGAAACCCCTCCC | 47 | 1218 |
| 1132849 | N/A | N/A | 6761 | 6780 | CCTTCCTCTCTCGCAGCAAG | 59 | 1219 |
| 1132877 | N/A | N/A | 7016 | 7035 | GAGCTCACCTGGCACGCATC | 85† | 1220 |

TABLE 20

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130750 | 13 | 32 | 13 | 32 | CCAGCTGCCTATCCAGGAGT | 48 | 1221 |
| 1130778 | 50 | 69 | 50 | 69 | AGGAGCAGCAGAGCCCTCAT | 38 | 1222 |
| 1130806 | 97 | 116 | N/A | N/A | AAGGTGGAATCGAAAGTGTT | 67 | 1223 |
| 1130834 | 152 | 171 | N/A | N/A | GTGAGAACGACTGTGTGCTC | 20 | 1224 |
| 1130862 | 206 | 225 | 3557 | 3576 | TGGTACAGCTGCCGGTGGTA | 26 | 1225 |
| 1130871 | 216 | 235 | 3567 | 3586 | GGTACATTTGTGGTACAGCT | 13 | 183 |
| 1130891 | 241 | 260 | 3592 | 3611 | GCTGAGGGCCTGGCCGGCCC | 51 | 1226 |
| 1130919 | 311 | 330 | 3818 | 3837 | ACTTTCTTGGGCTCCAAACA | 49 | 1227 |
| 1130947 | 367 | 386 | 4175 | 4194 | TGTTCACACAGGTCCCTCCT | 28 | 1228 |
| 1130975 | 426 | 445 | 4234 | 4253 | TTTCTGGCAGTGGTTTCCAG | 24 | 1229 |
| 1131003 | 469 | 488 | 4414 | 4433 | TCTTGTGGAAAAACCGGAGA | 36 | 1230 |
| 1131031 | 509 | 528 | 4454 | 4473 | CTGGCCACAGCTGCTTGCTC | 46 | 1231 |
| 1131059 | 549 | 568 | 4494 | 4513 | CAGCCGCTGGCAGTGGGCAT | 71 | 1232 |
| 1131087 | 585 | 604 | 4669 | 4688 | ATGGAGGCACGGGTTGGTGC | 64 | 1233 |
| 1131115 | 624 | 643 | 4708 | 4727 | GCACAGGCGGTGGCCCTCCA | 34 | 1234 |
| 1131143 | 686 | 705 | 4915 | 4934 | TCATAGCAGCTTGCCTTGGT | 28 | 1235 |
| 1131171 | 725 | 744 | 4954 | 4973 | GTGGTCCTGGCCAGGCCGCG | 64 | 1236 |
| 1131199 | 797 | 816 | 5026 | 5045 | CGCGCTTGCTCGGCAGTCAC | 17 | 1237 |
| 1131227 | 874 | 893 | 5188 | 5207 | GGTTCAGCACGAAGCACCAC | 23 | 1238 |
| 1131255 | 917 | 936 | 5231 | 5250 | TGGCACTGTGCCAGGTCGCA | 18 | 1239 |
| 1131283 | 1008 | 1027 | 5322 | 5341 | CTGAGGCTTCGGCGGTGCCG | 21 | 1240 |
| 1131311 | 1090 | 1109 | 5509 | 5528 | TCCTGGTCAGGGAAGGCGGC | 26 | 1241 |
| 1131339 | 1132 | 1151 | 5551 | 5570 | ACAGACTCTTGCGGAGCCGC | 20 | 60 |
| 1131367 | 1204 | 1223 | 5623 | 5642 | AGTACAGCGCGGCGATGTAG | 42 | 1242 |

TABLE 20-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131395 | 1240 | 1259 | 5659 | 5678 | GGGCGATGAGGCTGCCGGCG | 53 | 1243 |
| 1131423 | 1342 | 1361 | 6002 | 6021 | GCTCACAGCTGTGGTTACGG | 19 | 1244 |
| 1131451 | 1434 | 1453 | N/A | N/A | CTGAAGGCGCAACAGAGCCA | 46 | 1245 |
| 1131479 | 1493 | 1512 | 6236 | 6255 | GGCAGGCACACCGGCTGAAC | 31 | 1246 |
| 1131507 | 1561 | 1580 | 6304 | 6323 | CCTCGAACTGGTGGCCCCAG | 153 | 1247 |
| 1131535 | 1598 | 1617 | 6896 | 6915 | TGCGCCTCCTGCAGGAAGCT | 116 | 1248 |
| 1131563 | 1691 | 1710 | 6989 | 7008 | CCCTCGAGGAACCCTGCGCA | 23† | 1249 |
| 1131591 | 1777 | 1796 | 7165 | 7184 | TGCCTTGCAGGGTGAGCCGG | 19 | 1250 |
| 1131619 | 1806 | 1825 | 7194 | 7213 | GTCACCACAGCCCGATCCCC | 37 | 1251 |
| 1131647 | 1853 | 1872 | 7241 | 7260 | CAGGCCAGGTAGTAGGCCAC | 48 | 1252 |
| 1131675 | 1893 | 1912 | 7281 | 7300 | TGAGTCCCTGAGCAATCAGG | 19 | 150 |
| 1131703 | 1932 | 1951 | 7320 | 7339 | AGCCACTCTCTCACTGCGGA | 24 | 1253 |
| 1131731 | 1985 | 2004 | 7373 | 7392 | CGCGGAGCTGGCCGCACTGG | 30 | 1254 |
| 1131759 | 2020 | 2039 | 7408 | 7427 | TCAAAGCACTTTATTGAGTT | 11 | 1255 |
| 1131787 | N/A | N/A | 133 | 152 | CCCCCCAGAACAATCCTGGG | 80 | 1256 |
| 1131815 | N/A | N/A | 217 | 236 | GGCCTCACCTTTCCACATAG | 66 | 1257 |
| 1131843 | N/A | N/A | 320 | 339 | CCCCCGTTGTCTTCTTAAGG | 47 | 1258 |
| 1131871 | N/A | N/A | 410 | 429 | CCTGCCACCGATCTGTTGCT | 124 | 1259 |
| 1131899 | N/A | N/A | 541 | 560 | TTCCCGGGAGGAGGAGCCAG | 46 | 1260 |
| 1131927 | N/A | N/A | 645 | 664 | GATCACTCTAGTGCCCATGG | 48 | 1261 |
| 1131955 | N/A | N/A | 763 | 782 | TGGCAGGAGCCCAGGTGTGA | 66 | 1262 |
| 1131983 | N/A | N/A | 901 | 920 | GCATTCAGATGCCAGAGACA | 77 | 1263 |
| 1132011 | N/A | N/A | 1015 | 1034 | AAGAGGTTTACTGTTATCAA | 55 | 1264 |
| 1132039 | N/A | N/A | 1114 | 1133 | AAAGGTAGTTTCATAATAAA | 44 | 1265 |
| 1132067 | N/A | N/A | 1530 | 1549 | GGCCCTGCTATGTGCCACAC | 93 | 1266 |
| 1132095 | N/A | N/A | 1640 | 1659 | AGAGGAGGCTGAGGGAGTCC | 52 | 1267 |
| 1132123 | N/A | N/A | 2075 | 2094 | ACCTTTAAGATGCAAATGGG | 51 | 1268 |
| 1132151 | N/A | N/A | 2175 | 2194 | CTGCTCAATAAGCTTTTGCC | 54 | 1269 |
| 1132179 | N/A | N/A | 2292 | 2311 | TTATAGAACATAACCATCGC | 68 | 1270 |
| 1132207 | N/A | N/A | 2426 | 2445 | CATATACTAAATAAAATGTC | 99 | 1271 |
| 1132235 | N/A | N/A | 2545 | 2564 | TGAAGAGCTGTGTAGTTCCT | 58 | 1272 |
| 1132263 | N/A | N/A | 2667 | 2686 | GCTGCTTGTTTCAGCTCTCC | 55 | 1273 |
| 1132291 | N/A | N/A | 2780 | 2799 | TTGTAACTCCCAAGTCAATA | 78 | 1274 |
| 1132319 | N/A | N/A | 2893 | 2912 | CTCTGATCTGAGCCTTGGTT | 95 | 1275 |
| 1132347 | N/A | N/A | 2983 | 3002 | GTAAGTCTTCAGTCCCAAGG | 86 | 1276 |

TABLE 20-continued

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132375 | N/A | N/A | 3391 | 3410 | GTGCATTGAAAACACTTTCT | 41 | 1277 |
| 1132403 | N/A | N/A | 3478 | 3497 | CTCTGAGGACTTCCCCTGTA | 166 | 1278 |
| 1132431 | N/A | N/A | 3676 | 3695 | AAGCAGAGTTCCTTGGACAG | 57 | 1279 |
| 1132459 | N/A | N/A | 3842 | 3861 | CAGAGGCTGTGTGTAGCACC | 76 | 1280 |
| 1132487 | N/A | N/A | 3966 | 3985 | TCCCTCTGGACTTCCAAAGG | 47 | 1281 |
| 1132515 | N/A | N/A | 4054 | 4073 | GAACCTACTTGCCTTGTGAC | 59 | 1282 |
| 1132543 | N/A | N/A | 4254 | 4273 | GTCCTCCACATCTCCTCACC | 47 | 1283 |
| 1132571 | N/A | N/A | 4355 | 4374 | TAGTGGTCTCAGGAGAGTCT | 92 | 1284 |
| 1132599 | N/A | N/A | 4587 | 4606 | CTCCTTCCTGGCACACCACC | 38 | 1285 |
| 1132627 | N/A | N/A | 4803 | 4822 | GCAAGCCCGTCCCACCTGGG | 47 | 1286 |
| 1132655 | N/A | N/A | 5073 | 5092 | CCCACGCGGCGCACCGGCAG | 48 | 1287 |
| 1132683 | N/A | N/A | 5439 | 5458 | GAGCCCGCGGCCGGCTGGCC | 68 | 1288 |
| 1132711 | N/A | N/A | 5862 | 5881 | CCAATCCCGTGTTCCAGCTT | 37 | 1289 |
| 1132739 | N/A | N/A | 6324 | 6343 | CCCCTAGCAGTTGTGCCTAC | 138 | 1290 |
| 1132767 | N/A | N/A | 6415 | 6434 | GCCACCCATTCTGTAGGCAC | 59 | 1291 |
| 1132795 | N/A | N/A | 6536 | 6555 | CCAAGAGCAAGTTCGATTCT | 50 | 1292 |
| 1132823 | N/A | N/A | 6661 | 6680 | GCGGAGCGGAAACAGAAACC | 88 | 1293 |
| 1132851 | N/A | N/A | 6767 | 6786 | TCATGCCCTTCCTCTCTCGC | 39 | 1294 |
| 1132879 | N/A | N/A | 7025 | 7044 | CCGGGCTAAGAGCTCACCTG | 59† | 1295 |

TABLE 21

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130752 | 15 | 34 | 15 | 34 | GTCCAGCTGCCTATCCAGGA | 49 | 1296 |
| 1130780 | 57 | 76 | 57 | 76 | GAACCCCAGGAGCAGCAGAG | 72 | 1297 |
| 1130808 | 103 | 122 | N/A | N/A | CTTCCCAAGGTGGAATCGAA | 62 | 1298 |
| 1130836 | 154 | 173 | N/A | N/A | CAGTGAGAACGACTGTGTGC | 41 | 1299 |
| 1130864 | 208 | 227 | 3559 | 3578 | TGTGGTACAGCTGCCGGTGG | 42 | 1300 |
| 1130871 | 216 | 235 | 3567 | 3586 | GGTACATTTGTGGTACAGCT | 21 | 183 |
| 1130893 | 254 | 273 | N/A | N/A | GTAGCACACCAGGGCTGAGG | 54 | 1301 |
| 1130921 | 313 | 332 | 3820 | 3839 | TCACTTTCTTGGGCTCCAAA | 41 | 1302 |

TABLE 21-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
| --- | --- | --- | --- | --- | --- | --- | --- |
| 1130949 | 371 | 390 | 4179 | 4198 | GGCATGTTCACACAGGTCCC | 42 | 1303 |
| 1130977 | 428 | 447 | N/A | N/A | TCTTTCTGGCAGTGGTTTCC | 48 | 1304 |
| 1131005 | 471 | 490 | 4416 | 4435 | ATTCTTGTGGAAAAACCGGA | 39 | 1305 |
| 1131033 | 511 | 530 | 4456 | 4475 | ATCTGGCCACAGCTGCTTGC | 53 | 1306 |
| 1131061 | 551 | 570 | 4496 | 4515 | GCCAGCCGCTGGCAGTGGGC | 58 | 1307 |
| 1131089 | 588 | 607 | 4672 | 4691 | CCCATGGAGGCACGGGTTGG | 40 | 1308 |
| 1131117 | 627 | 646 | 4711 | 4730 | GTGGCACAGGCGGTGGCCCT | 71 | 1309 |
| 1131145 | 690 | 709 | 4919 | 4938 | GCCATCATAGCAGCTTGCCT | 36 | 1310 |
| 1131173 | 745 | 764 | 4974 | 4993 | GACAGGGCGCACCCGAGAGC | 52 | 1311 |
| 1131201 | 799 | 818 | 5028 | 5047 | TCCGCGCTTGCTCGGCAGTC | 74 | 1312 |
| 1131229 | 882 | 901 | 5196 | 5215 | CCGGTCGCGGTTCAGCACGA | 46 | 1313 |
| 1131257 | 920 | 939 | 5234 | 5253 | GTCTGGCACTGTGCCAGGTC | 74 | 1314 |
| 1131285 | 1011 | 1030 | 5325 | 5344 | GGGCTGAGGCTTCGGCGGTG | 31 | 1315 |
| 1131313 | 1092 | 1111 | 5511 | 5530 | GTTCCTGGTCAGGGAAGGCG | 52 | 1316 |
| 1131341 | 1134 | 1153 | 5553 | 5572 | AGACAGACTCTTGCGGAGCC | 37 | 1317 |
| 1131369 | 1207 | 1226 | 5626 | 5645 | CCCAGTACAGCGCGGCGATG | 32 | 1318 |
| 1131397 | 1281 | 1300 | 5700 | 5719 | CCGGTCCTGCAGGCAGTGAG | 59 | 1319 |
| 1131425 | 1345 | 1364 | 6005 | 6024 | ACGGCTCACAGCTGTGGTTA | 49 | 1320 |
| 1131453 | 1437 | 1456 | 6180 | 6199 | CTCCTGAAGGCGCAACAGAG | 66 | 1321 |
| 1131481 | 1496 | 1515 | 6239 | 6258 | CTTGGCAGGCACACCGGCTG | 24 | 1322 |
| 1131509 | 1564 | 1583 | N/A | N/A | CCCCCTCGAACTGGTGGCCC | 76 | 1323 |
| 1131537 | 1603 | 1622 | 6901 | 6920 | GTACCTGCGCCTCCTGCAGG | 126 | 1324 |
| 1131565 | 1696 | 1715 | 6994 | 7013 | TGCCGCCCTCGAGGAACCCT | 8† | 1325 |
| 1131593 | 1780 | 1799 | 7168 | 7187 | TGATGCCTTGCAGGGTGAGC | 17 | 1326 |
| 1131621 | 1808 | 1827 | 7196 | 7215 | CGGTCACCACAGCCCGATCC | 35 | 1327 |
| 1131649 | 1856 | 1875 | 7244 | 7263 | ATCCAGGCCAGGTAGTAGGC | 70 | 1328 |
| 1131677 | 1895 | 1914 | 7283 | 7302 | GATGAGTCCCTGAGCAATCA | 35 | 1329 |
| 1131705 | 1935 | 1954 | 7323 | 7342 | CCCAGCCACTCTCTCACTGC | 37 | 1330 |
| 1131733 | 1989 | 2008 | 7377 | 7396 | CTGGCGCGGAGCTGGCCGCA | 49 | 1331 |
| 1131761 | 2023 | 2042 | 7411 | 7430 | TTTTCAAAGCACTTTATTGA | 28 | 1332 |
| 1131789 | N/A | N/A | 139 | 158 | TAGCGACCCCCCAGAACAAT | 101 | 1333 |
| 1131817 | N/A | N/A | 223 | 242 | CGGGCTGGCCTCACCTTTCC | 74 | 1334 |
| 1131845 | N/A | N/A | 326 | 345 | TACCTCCCCCGTTGTCTTC | 105 | 1335 |
| 1131873 | N/A | N/A | 416 | 435 | TCATAGCCTGCCACCGATCT | 77 | 1336 |
| 1131901 | N/A | N/A | 560 | 579 | ACACATCCCCACCCAAGGGT | 61 | 1337 |

TABLE 21-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131929 | N/A | N/A | 651 | 670 | GCTCACGATCACTCTAGTGC | 44 | 1338 |
| 1131957 | N/A | N/A | 770 | 789 | GGAAGGCTGGCAGGAGCCCA | 81 | 1339 |
| 1131985 | N/A | N/A | 910 | 929 | GCTTCAGAGGCATTCAGATG | 84 | 1340 |
| 1132013 | N/A | N/A | 1021 | 1040 | AACCCTAAGAGGTTTACTGT | 105 | 1341 |
| 1132041 | N/A | N/A | 1120 | 1139 | CATCTAAAAGGTAGTTTCAT | 90 | 1342 |
| 1132069 | N/A | N/A | 1536 | 1555 | TTCACAGGCCCTGCTATGTG | 101 | 1343 |
| 1132097 | N/A | N/A | 1667 | 1686 | GGAGAAACTTTTGGGTGTGG | 86 | 1344 |
| 1132125 | N/A | N/A | 2081 | 2100 | AGATGGACCTTTAAGATGCA | 79 | 1345 |
| 1132153 | N/A | N/A | 2181 | 2200 | AAGTACCTGCTCAATAAGCT | 61 | 1346 |
| 1132181 | N/A | N/A | 2299 | 2318 | TGTGATTTTATAGAACATAA | 71 | 1347 |
| 1132209 | N/A | N/A | 2437 | 2456 | AATCAGCAACACATATACTA | 73 | 1348 |
| 1132237 | N/A | N/A | 2551 | 2570 | TCCTGCTGAAGAGCTGTGTA | 66 | 1349 |
| 1132265 | N/A | N/A | 2673 | 2692 | GCTGCTGCTGCTTGTTTCAG | 42 | 1350 |
| 1132293 | N/A | N/A | 2786 | 2805 | TTTTATTTGTAACTCCCAAG | 100 | 1351 |
| 1132321 | N/A | N/A | 2899 | 2918 | TAACCACTCTGATCTGAGCC | 80 | 1352 |
| 1132349 | N/A | N/A | 2989 | 3008 | CCTTGGGTAAGTCTTCAGTC | 107 | 1353 |
| 1132377 | N/A | N/A | 3397 | 3416 | GTCGCTGTGCATTGAAAACA | 98 | 1354 |
| 1132405 | N/A | N/A | 3484 | 3503 | CACACTCTCTGAGGACTTCC | 83 | 1355 |
| 1132433 | N/A | N/A | 3682 | 3701 | CTCTCCAAGCAGAGTTCCTT | 89 | 1356 |
| 1132461 | N/A | N/A | 3848 | 3867 | CCACCCCAGAGGCTGTGTGT | 90 | 1357 |
| 1132489 | N/A | N/A | 3972 | 3991 | GAACTCTCCCTCTGGACTTC | 61 | 1358 |
| 1132517 | N/A | N/A | 4060 | 4079 | CTTCTTGAACCTACTTGCCT | 66 | 1359 |
| 1132545 | N/A | N/A | 4260 | 4279 | GCCCAGGTCCTCCACATCTC | 60 | 1360 |
| 1132573 | N/A | N/A | 4361 | 4380 | GAGGGATAGTGGTCTCAGGA | 76 | 1361 |
| 1132601 | N/A | N/A | 4593 | 4612 | AGAGCTCTCCTTCCTGGCAC | 60 | 1362 |
| 1132629 | N/A | N/A | 4809 | 4828 | TTCCTGGCAAGCCCGTCCCA | 50 | 1363 |
| 1132657 | N/A | N/A | 5079 | 5098 | CCCAGCCCCACGCGGCGCAC | 105 | 1364 |
| 1132685 | N/A | N/A | 5445 | 5464 | GACGGAGAGCCCGCGGCCGG | 109 | 1365 |
| 1132713 | N/A | N/A | 5868 | 5887 | CGAACCCCAATCCCGTGTTC | 81 | 1366 |
| 1132741 | N/A | N/A | 6330 | 6349 | CCCCTGCCCCTAGCAGTTGT | 111 | 1367 |
| 1132769 | N/A | N/A | 6436 | 6455 | CTCACAACCCATCAGGTCAG | 97 | 1368 |
| 1132797 | N/A | N/A | 6542 | 6561 | AGGGAACCAAGAGCAAGTTC | 26 | 1369 |
| 1132825 | N/A | N/A | 6667 | 6686 | GAATGGGCGGAGCGGAAACA | 73 | 1370 |
| 1132853 | N/A | N/A | 6773 | 6792 | ACCCACTCATGCCCTTCCTC | 42 | 1371 |
| 1132881 | N/A | N/A | 7031 | 7050 | CGCCAACCGGGCTAAGAGCT | 82† | 1372 |

TABLE 22

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130753 | 16 | 35 | 16 | 35 | GGTCCAGCTGCCTATCCAGG | 37 | 1373 |
| 1130781 | 60 | 79 | 60 | 79 | CAGGAACCCCAGGAGCAGCA | 65 | 1374 |
| 1130809 | 104 | 123 | N/A | N/A | GCTTCCCAAGGTGGAATCGA | 67 | 1375 |
| 1130837 | 156 | 175 | N/A | N/A | GACAGTGAGAACGACTGTGT | 43 | 1376 |
| 1130865 | 210 | 229 | 3561 | 3580 | TTTGTGGTACAGCTGCCGGT | 52 | 1377 |
| 1130871 | 216 | 235 | 3567 | 3586 | GGTACATTTGTGGTACAGCT | 20 | 183 |
| 1130894 | 257 | 276 | N/A | N/A | GTGGTAGCACACCAGGGCTG | 19 | 1378 |
| 1130922 | 314 | 333 | 3821 | 3840 | TTCACTTTCTTGGGCTCCAA | 36 | 1379 |
| 1130950 | 372 | 391 | 4180 | 4199 | TGGCATGTTCACACAGGTCC | 42 | 1380 |
| 1130978 | 429 | 448 | N/A | N/A | CTCTTTCTGGCAGTGGTTTC | 45 | 1381 |
| 1131006 | 472 | 491 | 4417 | 4436 | CATTCTTGTGGAAAAACCGG | 22 | 1382 |
| 1131034 | 512 | 531 | 4457 | 4476 | CATCTGGCCACAGCTGCTTG | 42 | 1383 |
| 1131062 | 552 | 571 | 4497 | 4516 | GGCCAGCCGCTGGCAGTGGG | 87 | 1384 |
| 1131090 | 589 | 608 | 4673 | 4692 | CCCCATGGAGGCACGGGTTG | 36 | 1385 |
| 1131118 | 628 | 647 | 4712 | 4731 | AGTGGCACAGGCGGTGGCCC | 32 | 1386 |
| 1131146 | 691 | 710 | 4920 | 4939 | GGCCATCATAGCAGCTTGCC | 27 | 1387 |
| 1131174 | 747 | 766 | 4976 | 4995 | CTGACAGGGCGCACCCGAGA | 49 | 1388 |
| 1131202 | 800 | 819 | 5029 | 5048 | TTCCGCGCTTGCTCGGCAGT | 35 | 1389 |
| 1131230 | 883 | 902 | 5197 | 5216 | GCCGGTCGCGGTTCAGCACG | 42 | 1390 |
| 1131258 | 921 | 940 | 5235 | 5254 | GGTCTGGCACTGTGCCAGGT | 34 | 1391 |
| 1131286 | 1012 | 1031 | 5326 | 5345 | TGGGCTGAGGCTTCGGCGGT | 45 | 1392 |
| 1131314 | 1093 | 1112 | 5512 | 5531 | CGTTCCTGGTCAGGGAAGGC | 15 | 1393 |
| 1131342 | 1135 | 1154 | 5554 | 5573 | AAGACAGACTCTTGCGGAGC | 29 | 1394 |
| 1131370 | 1209 | 1228 | 5628 | 5647 | GCCCCAGTACAGCGCGGCGA | 53 | 1395 |
| 1131398 | 1282 | 1301 | 5701 | 5720 | GCCGGTCCTGCAGGCAGTGA | 48 | 1396 |
| 1131426 | 1346 | 1365 | 6006 | 6025 | CACGGCTCACAGCTGTGGTT | 28 | 1397 |
| 1131454 | 1439 | 1458 | 6182 | 6201 | TCCTCCTGAAGGCGCAACAG | 33 | 1398 |
| 1131482 | 1497 | 1516 | 6240 | 6259 | GCTTGGCAGGCACACCGGCT | 41 | 1399 |
| 1131510 | 1565 | 1584 | N/A | N/A | GCCCCCTCGAACTGGTGGCC | 49 | 1400 |
| 1131538 | 1604 | 1623 | 6902 | 6921 | GGTACCTGCGCCTCCTGCAG | 154 | 1401 |
| 1131566 | 1699 | 1718 | 6997 | 7016 | CGGTGCCGCCCTCGAGGAAC | 6† | 1402 |
| 1131594 | 1781 | 1800 | 7169 | 7188 | ATGATGCCTTGCAGGGTGAG | 29 | 1403 |
| 1131622 | 1810 | 1829 | 7198 | 7217 | TGCGGTCACCACAGCCCGAT | 37 | 1404 |
| 1131650 | 1857 | 1876 | 7245 | 7264 | GATCCAGGCCAGGTAGTAGG | 29 | 1405 |
| 1131678 | 1896 | 1915 | 7284 | 7303 | AGATGAGTCCCTGAGCAATC | 32 | 1406 |

TABLE 22-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131706 | 1938 | 1957 | 7326 | 7345 | TGCCCCAGCCACTCTCTCAC | 25 | 1407 |
| 1131734 | 1990 | 2009 | 7378 | 7397 | CCTGGCGCGGAGCTGGCCGC | 44 | 1408 |
| 1131762 | 2024 | 2043 | 7412 | 7431 | ATTTTCAAAGCACTTTATTG | 32 | 1409 |
| 1131790 | N/A | N/A | 142 | 161 | TGATAGCGACCCCCCAGAAC | 80 | 1410 |
| 1131818 | N/A | N/A | 229 | 248 | GCCTTCCGGGCTGGCCTCAC | 91 | 1411 |
| 1131846 | N/A | N/A | 329 | 348 | TTCTACCTCCCCCGTTGTC | 106 | 1412 |
| 1131874 | N/A | N/A | 419 | 438 | AAGTCATAGCCTGCCACCGA | 105 | 1413 |
| 1131902 | N/A | N/A | 563 | 582 | CATACACATCCCCACCCAAG | 85 | 1414 |
| 1131930 | N/A | N/A | 654 | 673 | ACAGCTCACGATCACTCTAG | 67 | 1415 |
| 1131958 | N/A | N/A | 773 | 792 | TGAGGAAGGCTGGCAGGAGC | 76 | 1416 |
| 1131986 | N/A | N/A | 913 | 932 | TGGGCTTCAGAGGCATTCAG | 50 | 1417 |
| 1132014 | N/A | N/A | 1024 | 1043 | AACAACCCTAAGAGGTTTAC | 62 | 1418 |
| 1132042 | N/A | N/A | 1123 | 1142 | CTTCATCTAAAAGGTAGTTT | 48 | 1419 |
| 1132070 | N/A | N/A | 1539 | 1558 | TGGTTCACAGGCCCTGCTAT | 66 | 1420 |
| 1132098 | N/A | N/A | 1670 | 1689 | AGAGGAGAAACTTTTGGGTG | 68 | 1421 |
| 1132126 | N/A | N/A | 2084 | 2103 | CTGAGATGGACCTTTAAGAT | 54 | 1422 |
| 1132154 | N/A | N/A | 2188 | 2207 | TGGCACAAAGTACCTGCTCA | 53 | 1423 |
| 1132182 | N/A | N/A | 2302 | 2321 | CACTGTGATTTTATAGAACA | 65 | 1424 |
| 1132210 | N/A | N/A | 2440 | 2459 | ATGAATCAGCAACACATATA | 58 | 1425 |
| 1132238 | N/A | N/A | 2554 | 2573 | GCCTCCTGCTGAAGAGCTGT | 61 | 1426 |
| 1132266 | N/A | N/A | 2676 | 2695 | CACGCTGCTGCTGCTTGTTT | 75 | 1427 |
| 1132294 | N/A | N/A | 2789 | 2808 | GAATTTTATTTGTAACTCCC | 84 | 1428 |
| 1132322 | N/A | N/A | 2902 | 2921 | TGTTAACCACTCTGATCTGA | 59 | 1429 |
| 1132350 | N/A | N/A | 2992 | 3011 | TGACCTTGGGTAAGTCTTCA | 93 | 1430 |
| 1132378 | N/A | N/A | 3400 | 3419 | AAGGTCGCTGTGCATTGAAA | 84 | 1431 |
| 1132406 | N/A | N/A | 3487 | 3506 | CAACACACTCTCTGAGGACT | 55 | 1432 |
| 1132434 | N/A | N/A | 3685 | 3704 | CCTCTCTCCAAGCAGAGTTC | 49 | 1433 |
| 1132462 | N/A | N/A | 3851 | 3870 | AGGCCACCCCAGAGGCTGTG | 38 | 1434 |
| 1132490 | N/A | N/A | 3975 | 3994 | CCAGAACTCTCCCTCTGGAC | 74 | 1435 |
| 1132518 | N/A | N/A | 4063 | 4082 | GCCCTTCTTGAACCTACTTG | 73 | 1436 |
| 1132546 | N/A | N/A | 4263 | 4282 | CCCGCCCAGGTCCTCCACAT | 59 | 1437 |
| 1132574 | N/A | N/A | 4364 | 4383 | AAAGAGGGATAGTGGTCTCA | 74 | 1438 |
| 1132602 | N/A | N/A | 4596 | 4615 | CAGAGAGCTCTCCTTCCTGG | 81 | 1439 |
| 1132630 | N/A | N/A | 4812 | 4831 | TCCTTCCTGGCAAGCCCGTC | 40 | 1440 |
| 1132658 | N/A | N/A | 5082 | 5101 | TCACCCAGCCCCACGCGGCG | 44 | 1441 |

TABLE 22-continued

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132686 | N/A | N/A | 5448 | 5467 | GAGGACGGAGAGCCCGCGGC | 75 | 1442 |
| 1132714 | N/A | N/A | 5871 | 5890 | TCCCGAACCCCAATCCCGTG | 83 | 1443 |
| 1132742 | N/A | N/A | 6333 | 6352 | CTACCCCTGCCCCTAGCAGT | 70 | 1444 |
| 1132770 | N/A | N/A | 6439 | 6458 | ATTCTCACAACCCATCAGGT | 103 | 1445 |
| 1132798 | N/A | N/A | 6548 | 6567 | GCCCAGAGGGAACCAAGAGC | 85 | 1446 |
| 1132826 | N/A | N/A | 6670 | 6689 | TTTGAATGGGCGGAGCGGAA | 86 | 1447 |
| 1132854 | N/A | N/A | 6776 | 6795 | TAAACCCACTCATGCCCTTC | 87 | 1448 |
| 1132882 | N/A | N/A | 7057 | 7076 | TTGTGCCTGACGGCCTCGGG | 84† | 1449 |

TABLE 23

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130751 | 14 | 33 | 14 | 33 | TCCAGCTGCCTATCCAGGAG | 65 | 1450 |
| 1130779 | 51 | 70 | 51 | 70 | CAGGAGCAGCAGAGCCCTCA | 39 | 1451 |
| 1130807 | 99 | 118 | N/A | N/A | CCAAGGTGGAATCGAAAGTG | 37 | 1452 |
| 1130835 | 153 | 172 | N/A | N/A | AGTGAGAACGACTGTGTGCT | 29 | 1453 |
| 1130863 | 207 | 226 | 3558 | 3577 | GTGGTACAGCTGCCGGTGGT | 23 | 1454 |
| 1130871 | 216 | 235 | 3567 | 3586 | GGTACATTTGTGGTACAGCT | 8 | 183 |
| 1130892 | 242 | 261 | 3593 | 3612 | GGCTGAGGGCCTGGCCGGCC | 54 | 1455 |
| 1130920 | 312 | 331 | 3819 | 3838 | CACTTTCTTGGGCTCCAAAC | 17 | 1456 |
| 1130948 | 370 | 389 | 4178 | 4197 | GCATGTTCACACAGGTCCCT | 36 | 1457 |
| 1130976 | 427 | 446 | 4235 | 4254 | CTTTCTGGCAGTGGTTTCCA | 25 | 1458 |
| 1131004 | 470 | 489 | 4415 | 4434 | TTCTTGTGGAAAAACCGGAG | 28 | 1459 |
| 1131032 | 510 | 529 | 4455 | 4474 | TCTGGCCACAGCTGCTTGCT | 26 | 1460 |
| 1131060 | 550 | 569 | 4495 | 4514 | CCAGCCGCTGGCAGTGGGCA | 53 | 1461 |
| 1131088 | 586 | 605 | 4670 | 4689 | CATGGAGGCACGGGTTGGTG | 89 | 1462 |
| 1131116 | 625 | 644 | 4709 | 4728 | GGCACAGGCGGTGGCCCTCC | 47 | 1463 |
| 1131144 | 688 | 707 | 4917 | 4936 | CATCATAGCAGCTTGCCTTG | 40 | 1464 |
| 1131172 | 744 | 763 | 4973 | 4992 | ACAGGGCGCACCCGAGAGCG | 50 | 1465 |
| 1131200 | 798 | 817 | 5027 | 5046 | CCGCGCTTGCTCGGCAGTCA | 31 | 1466 |
| 1131228 | 876 | 895 | 5190 | 5209 | GCGGTTCAGCACGAAGCACC | 47 | 1467 |
| 1131256 | 919 | 938 | 5233 | 5252 | TCTGGCACTGTGCCAGGTCG | 43 | 1468 |

TABLE 23-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131284 | 1010 | 1029 | 5324 | 5343 | GGCTGAGGCTTCGGCGGTGC | 27 | 1469 |
| 1131312 | 1091 | 1110 | 5510 | 5529 | TTCCTGGTCAGGGAAGGCGG | 35 | 1470 |
| 1131340 | 1133 | 1152 | 5552 | 5571 | GACAGACTCTTGCGGAGCCG | 19 | 1471 |
| 1131368 | 1206 | 1225 | 5625 | 5644 | CCAGTACAGCGCGGCGATGT | 17 | 1472 |
| 1131396 | 1280 | 1299 | 5699 | 5718 | CGGTCCTGCAGGCAGTGAGC | 26 | 1473 |
| 1131424 | 1344 | 1363 | 6004 | 6023 | CGGCTCACAGCTGTGGTTAC | 19 | 1474 |
| 1131452 | 1436 | 1455 | 6179 | 6198 | TCCTGAAGGCGCAACAGAGC | 39 | 1475 |
| 1131480 | 1494 | 1513 | 6237 | 6256 | TGGCAGGCACACCGGCTGAA | 22 | 1476 |
| 1131508 | 1563 | 1582 | N/A | N/A | CCCCTCGAACTGGTGGCCCC | 132 | 1477 |
| 1131536 | 1601 | 1620 | 6899 | 6918 | ACCTGCGCCTCCTGCAGGAA | 108 | 1478 |
| 1131564 | 1694 | 1713 | 6992 | 7011 | CCGCCCTCGAGGAACCCTGC | 10† | 1479 |
| 1131592 | 1778 | 1797 | 7166 | 7185 | ATGCCTTGCAGGGTGAGCCG | 24 | 1480 |
| 1131620 | 1807 | 1826 | 7195 | 7214 | GGTCACCACAGCCCGATCCC | 23 | 1481 |
| 1131648 | 1855 | 1874 | 7243 | 7262 | TCCAGGCCAGGTAGTAGGCC | 81 | 1482 |
| 1131676 | 1894 | 1913 | 7282 | 7301 | ATGAGTCCCTGAGCAATCAG | 44 | 1483 |
| 1131704 | 1933 | 1952 | 7321 | 7340 | CAGCCACTCTCTCACTGCGG | 11 | 1484 |
| 1131732 | 1986 | 2005 | 7374 | 7393 | GCGCGGAGCTGGCCGCACTG | 24 | 1485 |
| 1131760 | 2021 | 2040 | 7409 | 7428 | TTCAAAGCACTTTATTGAGT | 6 | 1486 |
| 1131788 | N/A | N/A | 136 | 155 | CGACCCCCAGAACAATCCT | 54 | 1487 |
| 1131816 | N/A | N/A | 220 | 239 | GCTGGCCTCACCTTTCCACA | 69 | 1488 |
| 1131844 | N/A | N/A | 323 | 342 | CTCCCCCCGTTGTCTTCTTA | 87 | 1489 |
| 1131872 | N/A | N/A | 413 | 432 | TAGCCTGCCACCGATCTGTT | 59 | 1490 |
| 1131900 | N/A | N/A | 557 | 576 | CATCCCCACCCAAGGGTTCC | 80 | 1491 |
| 1131928 | N/A | N/A | 648 | 667 | CACGATCACTCTAGTGCCCA | 67 | 1492 |
| 1131956 | N/A | N/A | 767 | 786 | AGGCTGGCAGGAGCCCAGGT | 61 | 1493 |
| 1131984 | N/A | N/A | 904 | 923 | GAGGCATTCAGATGCCAGAG | 101 | 1494 |
| 1132012 | N/A | N/A | 1018 | 1037 | CCTAAGAGGTTTACTGTTAT | 46 | 1495 |
| 1132040 | N/A | N/A | 1117 | 1136 | CTAAAAGGTAGTTTCATAAT | 70 | 1496 |
| 1132068 | N/A | N/A | 1533 | 1552 | ACAGGCCCTGCTATGTGCCA | 67 | 1497 |
| 1132096 | N/A | N/A | 1647 | 1666 | GGTGAAGAGAGGAGGCTGAG | 68 | 1498 |
| 1132124 | N/A | N/A | 2078 | 2097 | TGGACCTTTAAGATGCAAAT | 53 | 1499 |
| 1132152 | N/A | N/A | 2178 | 2197 | TACCTGCTCAATAAGCTTTT | 54 | 1500 |
| 1132180 | N/A | N/A | 2295 | 2314 | ATTTTATAGAACATAACCAT | 125 | 1501 |
| 1132208 | N/A | N/A | 2430 | 2449 | AACACATATACTAAATAAAA | 88 | 1502 |
| 1132236 | N/A | N/A | 2548 | 2567 | TGCTGAAGAGCTGTGTAGTT | 77 | 1503 |

TABLE 23-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132264 | N/A | N/A | 2670 | 2689 | GCTGCTGCTTGTTTCAGCTC | 72 | 1504 |
| 1132292 | N/A | N/A | 2783 | 2802 | TATTTGTAACTCCCAAGTCA | 66 | 1505 |
| 1132320 | N/A | N/A | 2896 | 2915 | CCACTCTGATCTGAGCCTTG | 87 | 1506 |
| 1132348 | N/A | N/A | 2986 | 3005 | TGGGTAAGTCTTCAGTCCCA | 64 | 1507 |
| 1132376 | N/A | N/A | 3394 | 3413 | GCTGTGCATTGAAAACACTT | 32 | 1508 |
| 1132404 | N/A | N/A | 3481 | 3500 | ACTCTCTGAGGACTTCCCCT | 48 | 1509 |
| 1132432 | N/A | N/A | 3679 | 3698 | TCCAAGCAGAGTTCCTTGGA | 102 | 1510 |
| 1132460 | N/A | N/A | 3845 | 3864 | CCCCAGAGGCTGTGTGTAGC | 80 | 1511 |
| 1132488 | N/A | N/A | 3969 | 3988 | CTCTCCCTCTGGACTTCCAA | 52 | 1512 |
| 1132516 | N/A | N/A | 4057 | 4076 | CTTGAACCTACTTGCCTTGT | 53 | 1513 |
| 1132544 | N/A | N/A | 4257 | 4276 | CAGGTCCTCCACATCTCCTC | 57 | 1514 |
| 1132572 | N/A | N/A | 4358 | 4377 | GGATAGTGGTCTCAGGAGAG | 82 | 1515 |
| 1132600 | N/A | N/A | 4590 | 4609 | GCTCTCCTTCCTGGCACACC | 73 | 1516 |
| 1132628 | N/A | N/A | 4806 | 4825 | CTGGCAAGCCCGTCCCACCT | 52 | 1517 |
| 1132656 | N/A | N/A | 5076 | 5095 | AGCCCCACGCGGCGCACCGG | 60 | 1518 |
| 1132684 | N/A | N/A | 5442 | 5461 | GGAGAGCCCGCGGCCGGCTG | 72 | 1519 |
| 1132712 | N/A | N/A | 5865 | 5884 | ACCCCAATCCCGTGTTCCAG | 64 | 1520 |
| 1132740 | N/A | N/A | 6327 | 6346 | CTGCCCCTAGCAGTTGTGCC | 93 | 1521 |
| 1132768 | N/A | N/A | 6433 | 6452 | ACAACCCATCAGGTCAGCGC | 109 | 1522 |
| 1132796 | N/A | N/A | 6539 | 6558 | GAACCAAGAGCAAGTTCGAT | 67 | 1523 |
| 1132824 | N/A | N/A | 6664 | 6683 | TGGGCGGAGCGGAAACAGAA | 46 | 1524 |
| 1132852 | N/A | N/A | 6770 | 6789 | CACTCATGCCCTTCCTCTCT | 39 | 1525 |
| 1132880 | N/A | N/A | 7028 | 7047 | CAACCGGGCTAAGAGCTCAC | 56† | 1526 |

TABLE 24

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130754 | 18 | 37 | 18 | 37 | TTGGTCCAGCTGCCTATCCA | 28 | 1527 |
| 1130782 | 65 | 84 | 65 | 84 | ACCAGCAGGAACCCCAGGAG | 94 | 1528 |
| 1130810 | 106 | 125 | 473 | 492 | GGGCTTCCCAAGGTGGAATC | 19 | 1529 |
| 1130838 | 157 | 176 | N/A | N/A | TGACAGTGAGAACGACTGTG | 33 | 1530 |

TABLE 24-continued

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130866 | 211 | 230 | 3562 | 3581 | ATTTGTGGTACAGCTGCCGG | 23 | 1531 |
| 1130871 | 216 | 235 | 3567 | 3586 | GGTACATTTGTGGTACAGCT | 11 | 183 |
| 1130895 | 258 | 277 | N/A | N/A | GGTGGTAGCACACCAGGGCT | 48 | 1532 |
| 1130923 | 316 | 335 | 3823 | 3842 | CTTTCACTTTCTTGGGCTCC | 19 | 1533 |
| 1130951 | 374 | 393 | 4182 | 4201 | CTTGGCATGTTCACACAGGT | 26 | 1534 |
| 1130979 | 430 | 449 | N/A | N/A | TCTCTTTCTGGCAGTGGTTT | 17 | 1535 |
| 1131007 | 473 | 492 | 4418 | 4437 | TCATTCTTGTGGAAAAACCG | 18 | 1536 |
| 1131035 | 513 | 532 | 4458 | 4477 | GCATCTGGCCACAGCTGCTT | 38 | 1537 |
| 1131063 | 553 | 572 | 4498 | 4517 | TGGCCAGCCGCTGGCAGTGG | 67 | 1538 |
| 1131091 | 590 | 609 | 4674 | 4693 | CCCCCATGGAGGCACGGGTT | 42 | 208 |
| 1131119 | 630 | 649 | 4714 | 4733 | GCAGTGGCACAGGCGGTGGC | 30 | 1539 |
| 1131147 | 693 | 712 | 4922 | 4941 | GCGGCCATCATAGCAGCTTG | 46 | 1540 |
| 1131175 | 748 | 767 | 4977 | 4996 | GCTGACAGGGCGCACCCGAG | 32 | 1541 |
| 1131203 | 801 | 820 | 5030 | 5049 | GTTCCGCGCTTGCTCGGCAG | 30 | 1542 |
| 1131231 | 884 | 903 | 5198 | 5217 | AGCCGGTCGCGGTTCAGCAC | 25 | 1543 |
| 1131259 | 922 | 941 | 5236 | 5255 | GGGTCTGGCACTGTGCCAGG | 22 | 1544 |
| 1131287 | 1013 | 1032 | 5327 | 5346 | GTGGGCTGAGGCTTCGGCGG | 49 | 1545 |
| 1131315 | 1094 | 1113 | 5513 | 5532 | CCGTTCCTGGTCAGGGAAGG | 46 | 1546 |
| 1131343 | 1136 | 1155 | 5555 | 5574 | GAAGACAGACTCTTGCGGAG | 38 | 1547 |
| 1131371 | 1210 | 1229 | 5629 | 5648 | GGCCCCAGTACAGCGCGGCG | 54 | 1548 |
| 1131399 | 1284 | 1303 | N/A | N/A | GGGCCGGTCCTGCAGGCAGT | 64 | 1549 |
| 1131427 | 1347 | 1366 | 6007 | 6026 | GCACGGCTCACAGCTGTGGT | 50 | 1550 |
| 1131455 | 1440 | 1459 | 6183 | 6202 | ATCCTCCTGAAGGCGCAACA | 29 | 1551 |
| 1131483 | 1499 | 1518 | 6242 | 6261 | CCGCTTGGCAGGCACACCGG | 29 | 1552 |
| 1131511 | 1566 | 1585 | N/A | N/A | CGCCCCCTCGAACTGGTGGC | 126 | 1553 |
| 1131539 | 1605 | 1624 | 6903 | 6922 | CGGTACCTGCGCCTCCTGCA | 79 | 1554 |
| 1131567 | 1700 | 1719 | 6998 | 7017 | TCGGTGCCGCCCTCGAGGAA | 5† | 1555 |
| 1131595 | 1782 | 1801 | 7170 | 7189 | GATGATGCCTTGCAGGGTGA | 15 | 1556 |
| 1131623 | 1811 | 1830 | 7199 | 7218 | TTGCGGTCACCACAGCCCGA | 32 | 1557 |
| 1131651 | 1858 | 1877 | 7246 | 7265 | GGATCCAGGCCAGGTAGTAG | 64 | 1558 |
| 1131679 | 1897 | 1916 | 7285 | 7304 | AAGATGAGTCCCTGAGCAAT | 30 | 1559 |
| 1131707 | 1939 | 1958 | 7327 | 7346 | ATGCCCCAGCCACTCTCTCA | 24 | 1560 |
| 1131735 | 1991 | 2010 | 7379 | 7398 | TCCTGGCGCGGAGCTGGCCG | 25 | 1561 |
| 1131763 | 2026 | 2045 | 7414 | 7433 | GCATTTTCAAAGCACTTTAT | 9 | 1562 |
| 1131791 | N/A | N/A | 145 | 164 | CTGTGATAGCGACCCCCCAG | 57 | 1563 |

TABLE 24-continued

Reduction of FXII RNA by 5-10-5 MOE gapmers with mixed
PO/PS internucleoside linkages (Huh7, electroporation,
5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131819 | N/A | N/A | 241 | 260 | TCCTCTGCCTGGGCCTTCCG | 83 | 1564 |
| 1131847 | N/A | N/A | 332 | 351 | CCTTTCTACCTCCCCCGTT | 78 | 1565 |
| 1131875 | N/A | N/A | 422 | 441 | TATAAGTCATAGCCTGCCAC | 61 | 1566 |
| 1131903 | N/A | N/A | 566 | 585 | CACCATACACATCCCCACCC | 74 | 1567 |
| 1131931 | N/A | N/A | 657 | 676 | CACACAGCTCACGATCACTC | 90 | 1568 |
| 1131959 | N/A | N/A | 776 | 795 | AACTGAGGAAGGCTGGCAGG | 59 | 1569 |
| 1131987 | N/A | N/A | 919 | 938 | TAAAGCTGGGCTTCAGAGGC | 73 | 1570 |
| 1132015 | N/A | N/A | 1027 | 1046 | CTCAACAACCCTAAGAGGTT | 122 | 1571 |
| 1132043 | N/A | N/A | 1126 | 1145 | ACCCTTCATCTAAAAGGTAG | 42 | 1572 |
| 1132071 | N/A | N/A | 1542 | 1561 | ATCTGGTTCACAGGCCCTGC | 44 | 1573 |
| 1132099 | N/A | N/A | 1673 | 1692 | GAGAGAGGAGAAACTTTTGG | 51 | 1574 |
| 1132127 | N/A | N/A | 2087 | 2106 | GATCTGAGATGGACCTTTAA | 68 | 1575 |
| 1132155 | N/A | N/A | 2191 | 2210 | GTCTGGCACAAAGTACCTGC | 66 | 1576 |
| 1132183 | N/A | N/A | 2308 | 2327 | AATGTTCACTGTGATTTTAT | 86 | 1577 |
| 1132211 | N/A | N/A | 2443 | 2462 | TTGATGAATCAGCAACACAT | 86 | 1578 |
| 1132239 | N/A | N/A | 2557 | 2576 | TGAGCCTCCTGCTGAAGAGC | 64 | 1579 |
| 1132267 | N/A | N/A | 2679 | 2698 | CGTCACGCTGCTGCTGCTTG | 92 | 1580 |
| 1132295 | N/A | N/A | 2792 | 2811 | GCTGAATTTTATTTGTAACT | 101 | 1581 |
| 1132323 | N/A | N/A | 2905 | 2924 | CACTGTTAACCACTCTGATC | 49 | 1582 |
| 1132351 | N/A | N/A | 3009 | 3028 | ACAACCTGCTAGCTGTGTGA | 65 | 1583 |
| 1132379 | N/A | N/A | 3403 | 3422 | AAAAAGGTCGCTGTGCATTG | 55 | 1584 |
| 1132407 | N/A | N/A | 3490 | 3509 | GGACAACACACTCTCTGAGG | 54 | 1585 |
| 1132435 | N/A | N/A | 3688 | 3707 | TCCCCTCTCTCCAAGCAGAG | 53 | 1586 |
| 1132463 | N/A | N/A | 3855 | 3874 | CCCCAGGCCACCCCAGAGGC | 67 | 1587 |
| 1132491 | N/A | N/A | 3978 | 3997 | TTCCCAGAACTCTCCCTCTG | 59 | 1588 |
| 1132519 | N/A | N/A | 4066 | 4085 | AAGGCCCTTCTTGAACCTAC | 50 | 1589 |
| 1132547 | N/A | N/A | 4266 | 4285 | CACCCCGCCCAGGTCCTCCA | 99 | 1590 |
| 1132575 | N/A | N/A | 4387 | 4406 | GCTCAAAGCACTTCTCTGGG | 25 | 1591 |
| 1132603 | N/A | N/A | 4599 | 4618 | CCCCAGAGAGCTCTCCTTCC | 76 | 1592 |
| 1132631 | N/A | N/A | 4816 | 4835 | CTCCTCCTTCCTGGCAAGCC | 43 | 1593 |
| 1132659 | N/A | N/A | 5085 | 5104 | GGGTCACCCAGCCCCACGCG | 65 | 1594 |
| 1132687 | N/A | N/A | 5451 | 5470 | GCTGAGGACGGAGAGCCCGC | 88 | 1595 |
| 1132715 | N/A | N/A | 5874 | 5893 | TGCTCCCGAACCCCAATCCC | 43 | 1596 |
| 1132743 | N/A | N/A | 6336 | 6355 | CCCCTACCCCTGCCCCTAGC | 65 | 1597 |
| 1132771 | N/A | N/A | 6442 | 6461 | CACATTCTCACAACCCATCA | 72 | 1598 |

TABLE 24-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132799 | N/A | N/A | 6566 | 6585 | TGGCCTTTGCAGCCCGGCGC | 84 | 1599 |
| 1132827 | N/A | N/A | 6673 | 6692 | GGATTTGAATGGGCGGAGCG | 49 | 1600 |
| 1132855 | N/A | N/A | 6779 | 6798 | TTGTAAACCCACTCATGCCC | 52 | 1601 |
| 1132883 | N/A | N/A | 7060 | 7079 | GATTTGTGCCTGACGGCCTC | 42† | 1602 |

TABLE 25

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130783 | 66 | 85 | 66 | 85 | CACCAGCAGGAACCCCAGGA | 57 | 1603 |
| 1130811 | 125 | 144 | 492 | 511 | TTGTACTTATGCTCCTTGGG | 30 | 1604 |
| 1130839 | 158 | 177 | N/A | N/A | GTGACAGTGAGAACGACTGT | 14 | 1605 |
| 1130867 | 212 | 231 | 3563 | 3582 | CATTTGTGGTACAGCTGCCG | 22 | 1606 |
| 1130871 | 216 | 235 | 3567 | 3586 | GGTACATTTGTGGTACAGCT | 17 | 183 |
| 1130896 | 278 | 297 | 3785 | 3804 | TGGTCCTGATCAAAGTTGGG | 44 | 1607 |
| 1130924 | 317 | 336 | N/A | N/A | TCTTTCACTTTCTTGGGCTC | 30 | 1608 |
| 1130952 | 375 | 394 | 4183 | 4202 | GCTTGGCATGTTCACACAGG | 15 | 1609 |
| 1130980 | 431 | 450 | N/A | N/A | TTCTCTTTCTGGCAGTGGTT | 44 | 1610 |
| 1131008 | 474 | 493 | 4419 | 4438 | CTCATTCTTGTGGAAAAACC | 25 | 1611 |
| 1131036 | 514 | 533 | 4459 | 4478 | GGCATCTGGCCACAGCTGCT | 20 | 1612 |
| 1131064 | 554 | 573 | 4499 | 4518 | CTGGCCAGCCGCTGGCAGTG | 102 | 1613 |
| 1131092 | 591 | 610 | 4675 | 4694 | ACCCCCATGGAGGCACGGGT | 45 | 1614 |
| 1131120 | 631 | 650 | 4715 | 4734 | GGCAGTGGCACAGGCGGTGG | 20 | 1615 |
| 1131148 | 696 | 715 | 4925 | 4944 | CCCGCGGCCATCATAGCAGC | 57 | 1616 |
| 1131176 | 749 | 768 | 4978 | 4997 | GGCTGACAGGGCGCACCCGA | 31 | 1617 |
| 1131204 | 802 | 821 | 5031 | 5050 | AGTTCCGCGCTTGCTCGGCA | 13 | 1618 |
| 1131232 | 886 | 905 | 5200 | 5219 | TCAGCCGGTCGCGGTTCAGC | 39 | 1619 |
| 1131260 | 974 | 993 | 5288 | 5307 | AGTGGGACATGAAGCCTAGG | 34 | 1620 |
| 1131288 | 1060 | 1079 | N/A | N/A | TCGCCGGCAAGGCTCCCGGG | 68 | 1621 |
| 1131316 | 1095 | 1114 | 5514 | 5533 | GCCGTTCCTGGTCAGGGAAG | 27 | 1622 |
| 1131344 | 1138 | 1157 | 5557 | 5576 | TCGAAGACAGACTCTTGCGG | 15 | 1623 |
| 1131372 | 1212 | 1231 | 5631 | 5650 | GTGGCCCCAGTACAGCGCGG | 32 | 1624 |

TABLE 25-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131400 | 1285 | 1304 | N/A | N/A | CGGGCCGGTCCTGCAGGCAG | 34 | 1625 |
| 1131428 | 1351 | 1370 | 6011 | 6030 | TCTGGCACGGCTCACAGCTG | 17 | 1626 |
| 1131456 | 1441 | 1460 | 6184 | 6203 | CATCCTCCTGAAGGCGCAAC | 51 | 1627 |
| 1131484 | 1500 | 1519 | 6243 | 6262 | GCCGCTTGGCAGGCACACCG | 17 | 1628 |
| 1131512 | 1567 | 1586 | N/A | N/A | CCGCCCCCTCGAACTGGTGG | 125 | 1629 |
| 1131540 | 1609 | 1628 | 6907 | 6926 | GGAACGGTACCTGCGCCTCC | 62 | 1630 |
| 1131568 | 1701 | 1720 | 6999 | 7018 | ATCGGTGCCGCCCTCGAGGA | 43† | 1631 |
| 1131596 | 1783 | 1802 | 7171 | 7190 | TGATGATGCCTTGCAGGGTG | 21 | 1632 |
| 1131624 | 1812 | 1831 | 7200 | 7219 | GTTGCGGTCACCACAGCCCG | 20 | 1633 |
| 1131652 | 1860 | 1879 | 7248 | 7267 | CCGGATCCAGGCCAGGTAGT | 30 | 1634 |
| 1131680 | 1898 | 1917 | 7286 | 7305 | AAAGATGAGTCCCTGAGCAA | 20 | 1635 |
| 1131708 | 1940 | 1959 | 7328 | 7347 | CATGCCCCAGCCACTCTCTC | 25 | 1636 |
| 1131736 | 1993 | 2012 | 7381 | 7400 | CATCCTGGCGCGGAGCTGGC | 16 | 1637 |
| 1131764 | 2027 | 2046 | 7415 | 7434 | AGCATTTTCAAAGCACTTTA | 9 | 97 |
| 1131792 | N/A | N/A | 148 | 167 | TGGCTGTGATAGCGACCCCC | 50 | 1638 |
| 1131820 | N/A | N/A | 244 | 263 | GTCTCCTCTGCCTGGGCCTT | 61 | 1639 |
| 1131848 | N/A | N/A | 335 | 354 | AACCCTTTCTACCTCCCCCC | 76 | 1640 |
| 1131876 | N/A | N/A | 425 | 444 | GACTATAAGTCATAGCCTGC | 145 | 1641 |
| 1131904 | N/A | N/A | 569 | 588 | CTGCACCATACACATCCCCA | 37 | 1642 |
| 1131932 | N/A | N/A | 660 | 679 | GATCACACAGCTCACGATCA | 54 | 1643 |
| 1131960 | N/A | N/A | 779 | 798 | GGAAACTGAGGAAGGCTGGC | 85 | 1644 |
| 1131988 | N/A | N/A | 922 | 941 | TGATAAAGCTGGGCTTCAGA | 69 | 1645 |
| 1132016 | N/A | N/A | 1031 | 1050 | CCTTCTCAACAACCCTAAGA | 59 | 1646 |
| 1132044 | N/A | N/A | 1129 | 1148 | GGTACCCTTCATCTAAAAGG | 56 | 1647 |
| 1132072 | N/A | N/A | 1545 | 1564 | TCCATCTGGTTCACAGGCCC | 66 | 1648 |
| 1132100 | N/A | N/A | 1676 | 1695 | CAAGAGAGAGGAGAAACTTT | 108 | 1649 |
| 1132128 | N/A | N/A | 2090 | 2109 | ATGGATCTGAGATGGACCTT | 34 | 1650 |
| 1132156 | N/A | N/A | 2194 | 2213 | AGTGTCTGGCACAAAGTACC | 28 | 1651 |
| 1132184 | N/A | N/A | 2311 | 2330 | TTCAATGTTCACTGTGATTT | 52 | 1652 |
| 1132212 | N/A | N/A | 2446 | 2465 | GCATTGATGAATCAGCAACA | 55 | 1653 |
| 1132240 | N/A | N/A | 2560 | 2579 | CTCTGAGCCTCCTGCTGAAG | 33 | 1654 |
| 1132268 | N/A | N/A | 2697 | 2716 | AGTTAAGGTTCAACAAGGCG | 36 | 1655 |
| 1132296 | N/A | N/A | 2802 | 2821 | GTGCCTACTTGCTGAATTTT | 68 | 1656 |
| 1132324 | N/A | N/A | 2908 | 2927 | AGTCACTGTTAACCACTCTG | 41 | 1657 |
| 1132352 | N/A | N/A | 3012 | 3031 | TCCACAACCTGCTAGCTGTG | 29 | 1658 |

TABLE 25-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132380 | N/A | N/A | 3406 | 3425 | CTCAAAAAGGTCGCTGTGCA | 36 | 1659 |
| 1132408 | N/A | N/A | 3493 | 3512 | CAGGGACAACACACTCTCTG | 86 | 1660 |
| 1132436 | N/A | N/A | 3691 | 3710 | CAGTCCCCTCTCTCCAAGCA | 55 | 1661 |
| 1132464 | N/A | N/A | 3859 | 3878 | AGAGCCCCAGGCCACCCCAG | 39 | 1662 |
| 1132492 | N/A | N/A | 3981 | 4000 | TCCTTCCCAGAACTCTCCCT | 53 | 1663 |
| 1132520 | N/A | N/A | 4069 | 4088 | GCCAAGGCCCTTCTTGAACC | 25 | 1664 |
| 1132548 | N/A | N/A | 4269 | 4288 | CAGCACCCCGCCCAGGTCCT | 73 | 1665 |
| 1132576 | N/A | N/A | 4505 | 4524 | CCCTGGCTGGCCAGCCGCTG | 46 | 1666 |
| 1132604 | N/A | N/A | 4602 | 4621 | CCCCCCCAGAGAGCTCTCCT | 120 | 1667 |
| 1132632 | N/A | N/A | 4819 | 4838 | TCCCTCCTCCTTCCTGGCAA | 30 | 1668 |
| 1132660 | N/A | N/A | 5112 | 5131 | CCGGGAGCCCGGAGCCCTGG | 68 | 1669 |
| 1132688 | N/A | N/A | 5471 | 5490 | AAGGCTGTGGAGGAGCAGGG | 69 | 1670 |
| 1132716 | N/A | N/A | 5877 | 5896 | CCCTGCTCCCGAACCCCAAT | 69 | 1671 |
| 1132744 | N/A | N/A | 6343 | 6362 | GTCTCCTCCCCTACCCCTGC | 63 | 1672 |
| 1132772 | N/A | N/A | 6445 | 6464 | CTACACATTCTCACAACCCA | 57 | 1673 |
| 1132800 | N/A | N/A | 6569 | 6588 | AGTTGGCCTTTGCAGCCCGG | 34 | 1674 |
| 1132828 | N/A | N/A | 6676 | 6695 | CCAGGATTTGAATGGGCGGA | 65 | 1675 |
| 1132856 | N/A | N/A | 6782 | 6801 | CGCTTGTAAACCCACTCATG | 51 | 1676 |
| 1132884 | N/A | N/A | 7063 | 7082 | TGAGATTTGTGCCTGACGGC | 126† | 1677 |

TABLE 26

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130757 | 21 | 40 | 21 | 40 | CCGTTGGTCCAGCTGCCTAT | 42 | 1678 |
| 1130785 | 69 | 88 | 69 | 88 | GCTCACCAGCAGGAACCCCA | 25 | 1679 |
| 1130813 | 127 | 146 | 494 | 513 | CTTTGTACTTATGCTCCTTG | 55 | 1680 |
| 1130841 | 161 | 180 | N/A | N/A | CCGGTGACAGTGAGAACGAC | 11 | 1681 |
| 1130869 | 214 | 233 | 3565 | 3584 | TACATTTGTGGTACAGCTGC | 13 | 1682 |
| 1130871 | 216 | 235 | 3567 | 3586 | GGTACATTTGTGGTACAGCT | 10 | 183 |
| 1130898 | 281 | 300 | 3788 | 3807 | CGCTGGTCCTGATCAAAGTT | 14 | 1683 |

TABLE 26-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130926 | 320 | 339 | N/A | N/A | TGGTCTTTCACTTTCTTGGG | 23 | 1684 |
| 1130954 | 377 | 396 | 4185 | 4204 | CCGCTTGGCATGTTCACACA | 15 | 1685 |
| 1130982 | 435 | 454 | N/A | N/A | GCACTTCTCTTTCTGGCAGT | 21 | 1686 |
| 1131010 | 476 | 495 | 4421 | 4440 | ATCTCATTCTTGTGGAAAAA | 29 | 1687 |
| 1131038 | 517 | 536 | 4462 | 4481 | ACTGGCATCTGGCCACAGCT | 36 | 1688 |
| 1131066 | 556 | 575 | 4501 | 4520 | GGCTGGCCAGCCGCTGGCAG | 51 | 1689 |
| 1131094 | 594 | 613 | 4678 | 4697 | GCGACCCCCATGGAGGCACG | 26 | 1690 |
| 1131122 | 635 | 654 | 4719 | 4738 | ACCGGGCAGTGGCACAGGCG | 50 | 1691 |
| 1131150 | 698 | 717 | 4927 | 4946 | AGCCCGCGGCCATCATAGCA | 56 | 1692 |
| 1131178 | 751 | 770 | 4980 | 4999 | ACGGCTGACAGGGCGCACCC | 29 | 52 |
| 1131206 | 805 | 824 | 5034 | 5053 | CCCAGTTCCGCGCTTGCTCG | 28 | 1693 |
| 1131234 | 889 | 908 | 5203 | 5222 | AGCTCAGCCGGTCGCGGTTC | 25 | 1694 |
| 1131262 | 976 | 995 | 5290 | 5309 | TGAGTGGGACATGAAGCCTA | 25 | 1695 |
| 1131290 | 1062 | 1081 | N/A | N/A | CTTCGCCGGCAAGGCTCCCG | 36 | 1696 |
| 1131318 | 1104 | 1123 | 5523 | 5542 | GCTCAGTGGGCCGTTCCTGG | 31 | 1697 |
| 1131346 | 1140 | 1159 | 5559 | 5578 | CATCGAAGACAGACTCTTGC | 15 | 1698 |
| 1131374 | 1215 | 1234 | 5634 | 5653 | ACTGTGGCCCCAGTACAGCG | 22 | 1699 |
| 1131402 | 1288 | 1307 | N/A | N/A | GTGCGGGCCGGTCCTGCAGG | 79 | 1700 |
| 1131430 | 1353 | 1372 | 6013 | 6032 | CGTCTGGCACGGCTCACAGC | 22 | 1701 |
| 1131458 | 1443 | 1462 | 6186 | 6205 | CGCATCCTCCTGAAGGCGCA | 11 | 1702 |
| 1131486 | 1520 | 1539 | 6263 | 6282 | GTCTCGGAGGGTCGCGCGGC | 47 | 1703 |
| 1131514 | 1569 | 1588 | N/A | N/A | CTCCGCCCCCTCGAACTGGT | 61 | 1704 |
| 1131542 | 1612 | 1631 | 6910 | 6929 | AGAGGAACGGTACCTGCGCC | 155 | 1705 |
| 1131570 | 1704 | 1723 | 7002 | 7021 | CGCATCGGTGCCGCCCTCGA | 20† | 1706 |
| 1131598 | 1785 | 1804 | 7173 | 7192 | GCTGATGATGCCTTGCAGGG | 21 | 1707 |
| 1131626 | 1815 | 1834 | 7203 | 7222 | CTTGTTGCGGTCACCACAGC | 53 | 1708 |
| 1131654 | 1862 | 1881 | 7250 | 7269 | TCCCGGATCCAGGCCAGGTA | 60 | 1709 |
| 1131682 | 1905 | 1924 | 7293 | 7312 | AGGAGGGAAAGATGAGTCCC | 17 | 1710 |
| 1131710 | 1942 | 1961 | 7330 | 7349 | TCCATGCCCCAGCCACTCTC | 10 | 1711 |
| 1131738 | 1995 | 2014 | 7383 | 7402 | GCCATCCTGGCGCGGAGCTG | 21 | 157 |
| 1131766 | 2029 | 2048 | 7417 | 7436 | TCAGCATTTTCAAAGCACTT | 9 | 1712 |
| 1131794 | N/A | N/A | 154 | 173 | GGCTCATGGCTGTGATAGCG | 36 | 1713 |
| 1131822 | N/A | N/A | 250 | 269 | TTGTCTGTCTCCTCTGCCTG | 79 | 1714 |
| 1131850 | N/A | N/A | 341 | 360 | GACCCAAACCCTTTCTACCT | 37 | 1715 |
| 1131878 | N/A | N/A | 431 | 450 | GGAACTGACTATAAGTCATA | 68 | 1716 |

TABLE 26-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131906 | N/A | N/A | 576 | 595 | GCACACACTGCACCATACAC | 74 | 1717 |
| 1131934 | N/A | N/A | 666 | 685 | CTCAAGGATCACACAGCTCA | 55 | 1718 |
| 1131962 | N/A | N/A | 835 | 854 | GCATGAATGATGCCCATGAG | 85 | 1719 |
| 1131990 | N/A | N/A | 928 | 947 | CATAAGTGATAAAGCTGGGC | 42 | 1720 |
| 1132018 | N/A | N/A | 1037 | 1056 | GGTTTCCCTTCTCAACAACC | 58 | 1721 |
| 1132046 | N/A | N/A | 1135 | 1154 | ATGGCAGGTACCCTTCATCT | 85 | 1722 |
| 1132074 | N/A | N/A | 1551 | 1570 | GTAAGGTCCATCTGGTTCAC | 61 | 1723 |
| 1132102 | N/A | N/A | 1682 | 1701 | GTAAGGCAAGAGAGAGGAGA | 35 | 1724 |
| 1132130 | N/A | N/A | 2096 | 2115 | ATGGAAATGGATCTGAGATG | 53 | 1725 |
| 1132158 | N/A | N/A | 2204 | 2223 | AATGCTGAGCAGTGTCTGGC | 59 | 1726 |
| 1132186 | N/A | N/A | 2317 | 2336 | TGCTAGTTCAATGTTCACTG | 31 | 1727 |
| 1132214 | N/A | N/A | 2452 | 2471 | AGCTTAGCATTGATGAATCA | 49 | 1728 |
| 1132242 | N/A | N/A | 2567 | 2586 | AAATGGCCTCTGAGCCTCCT | 67 | 1729 |
| 1132270 | N/A | N/A | 2703 | 2722 | ATTCCCAGTTAAGGTTCAAC | 45 | 1730 |
| 1132298 | N/A | N/A | 2808 | 2827 | GAGAATGTGCCTACTTGCTG | 39 | 1731 |
| 1132326 | N/A | N/A | 2914 | 2933 | TGTTGAAGTCACTGTTAACC | 91 | 1732 |
| 1132354 | N/A | N/A | 3018 | 3037 | CCTGACTCCACAACCTGCTA | 36 | 1733 |
| 1132382 | N/A | N/A | 3412 | 3431 | CAGACCCTCAAAAAGGTCGC | 29 | 1734 |
| 1132410 | N/A | N/A | 3502 | 3521 | TGAGAACTGCAGGGACAACA | 76 | 1735 |
| 1132438 | N/A | N/A | 3697 | 3716 | CTATCACAGTCCCCTCTCTC | 64 | 1736 |
| 1132466 | N/A | N/A | 3865 | 3884 | GAGGAGAGAGCCCCAGGCCA | 51 | 1737 |
| 1132494 | N/A | N/A | 3987 | 4006 | GACCACTCCTTCCCAGAACT | 56 | 1738 |
| 1132522 | N/A | N/A | 4093 | 4112 | GGGAGCTGAGTCACACAGCT | 67 | 1739 |
| 1132550 | N/A | N/A | 4283 | 4302 | TTGCCCCTGTCCCCCAGCAC | 71 | 1740 |
| 1132578 | N/A | N/A | 4511 | 4530 | TGCTCACCCTGGCTGGCCAG | 48 | 1741 |
| 1132606 | N/A | N/A | 4608 | 4627 | TAAAGACCCCCCCAGAGAGC | 30 | 1742 |
| 1132634 | N/A | N/A | 4826 | 4845 | CGCACTCTCCCTCCTCCTTC | 51 | 1743 |
| 1132662 | N/A | N/A | 5146 | 5165 | TCCTGTAGCCACACGACGGG | 52 | 1744 |
| 1132690 | N/A | N/A | 5480 | 5499 | TTCGCCGGCAAGGCTGTGGA | 64 | 1745 |
| 1132718 | N/A | N/A | 5883 | 5902 | GAAGCCCCCTGCTCCCGAAC | 26 | 1746 |
| 1132746 | N/A | N/A | 6349 | 6368 | TCAAAGGTCTCCTCCCCTAC | 45 | 1747 |
| 1132774 | N/A | N/A | 6451 | 6470 | ATTCACCTACACATTCTCAC | 82 | 1748 |
| 1132802 | N/A | N/A | 6575 | 6594 | CGTCCTAGTTGGCCTTTGCA | 86 | 1749 |
| 1132830 | N/A | N/A | 6685 | 6704 | AGAGAAAAGCCAGGATTTGA | 93 | 1750 |

TABLE 26-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132858 | N/A | N/A | 6802 | 6821 | ATGGACAAAGCTGCTCCAGG | 30 | 1751 |
| 1132886 | N/A | N/A | 7069 | 7088 | TGGACCTGAGATTTGTGCCT | 77† | 1752 |

TABLE 27

Reduction of FXII RNA by 5-10-5 MOE gapmers with mixed PO/PS internucleoside linkages (Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130784 | 68 | 87 | 68 | 87 | CTCACCAGCAGGAACCCCAG | 106 | 1753 |
| 1130812 | 126 | 145 | 493 | 512 | TTTGTACTTATGCTCCTTGG | 18 | 1754 |
| 1130840 | 160 | 179 | N/A | N/A | CGGTGACAGTGAGAACGACT | 18 | 1755 |
| 1130868 | 213 | 232 | 3564 | 3583 | ACATTTGTGGTACAGCTGCC | 18 | 1756 |
| 1130871 | 216 | 235 | 3567 | 3586 | GGTACATTTGTGGTACAGCT | 16 | 183 |
| 1130897 | 280 | 299 | 3787 | 3806 | GCTGGTCCTGATCAAAGTTG | 22 | 1757 |
| 1130925 | 319 | 338 | N/A | N/A | GGTCTTTCACTTTCTTGGGC | 16 | 1758 |
| 1130953 | 376 | 395 | 4184 | 4203 | CGCTTGGCATGTTCACACAG | 40 | 1759 |
| 1130981 | 434 | 453 | N/A | N/A | CACTTCTCTTTCTGGCAGTG | 15 | 1760 |
| 1131009 | 475 | 494 | 4420 | 4439 | TCTCATTCTTGTGGAAAAAC | 18 | 1761 |
| 1131037 | 516 | 535 | 4461 | 4480 | CTGGCATCTGGCCACAGCTG | 25 | 1762 |
| 1131065 | 555 | 574 | 4500 | 4519 | GCTGGCCAGCCGCTGGCAGT | 131 | 1763 |
| 1131093 | 592 | 611 | 4676 | 4695 | GACCCCATGGAGGCACGGG | 36 | 1764 |
| 1131121 | 633 | 652 | 4717 | 4736 | CGGGCAGTGGCACAGGCGGT | 20 | 1765 |
| 1131149 | 697 | 716 | 4926 | 4945 | GCCCGCGGCCATCATAGCAG | 35 | 1766 |
| 1131177 | 750 | 769 | 4979 | 4998 | CGGCTGACAGGGCGCACCCG | 26 | 1767 |
| 1131205 | 804 | 823 | 5033 | 5052 | CCAGTTCCGCGCTTGCTCGG | 26 | 1768 |
| 1131233 | 888 | 907 | 5202 | 5221 | GCTCAGCCGGTCGCGGTTCA | 21 | 1769 |
| 1131261 | 975 | 994 | 5289 | 5308 | GAGTGGGACATGAAGCCTAG | 24 | 1770 |
| 1131289 | 1061 | 1080 | N/A | N/A | TTCGCCGGCAAGGCTCCCGG | 40 | 1771 |
| 1131317 | 1102 | 1121 | 5521 | 5540 | TCAGTGGGCCGTTCCTGGTC | 31 | 1772 |
| 1131345 | 1139 | 1158 | 5558 | 5577 | ATCGAAGACAGACTCTTGCG | 19 | 1773 |
| 1131373 | 1213 | 1232 | 5632 | 5651 | TGTGGCCCCAGTACAGCGCG | 43 | 1774 |
| 1131401 | 1286 | 1305 | N/A | N/A | GCGGGCCGGTCCTGCAGGCA | 28 | 1775 |
| 1131429 | 1352 | 1371 | 6012 | 6031 | GTCTGGCACGGCTCACAGCT | 16 | 1776 |

TABLE 27-continued

Reduction of FXII RNA by 5-10-5 MOE gapmers with mixed PO/PS internucleoside linkages (Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131457 | 1442 | 1461 | 6185 | 6204 | GCATCCTCCTGAAGGCGCAA | 24 | 1777 |
| 1131485 | 1501 | 1520 | 6244 | 6263 | CGCCGCTTGGCAGGCACACC | 45 | 1778 |
| 1131513 | 1568 | 1587 | N/A | N/A | TCCGCCCCCTCGAACTGGTG | 70 | 1779 |
| 1131541 | 1610 | 1629 | 6908 | 6927 | AGGAACGGTACCTGCGCCTC | 66 | 1780 |
| 1131597 | 1784 | 1803 | 7172 | 7191 | CTGATGATGCCTTGCAGGGT | 24 | 1781 |
| 1131625 | 1813 | 1832 | 7201 | 7220 | TGTTGCGGTCACCACAGCCC | 15 | 1782 |
| 1131653 | 1861 | 1880 | 7249 | 7268 | CCCGGATCCAGGCCAGGTAG | 40 | 1783 |
| 1131681 | 1901 | 1920 | 7289 | 7308 | GGGAAAGATGAGTCCCTGAG | 19 | 92 |
| 1131709 | 1941 | 1960 | 7329 | 7348 | CCATGCCCCAGCCACTCTCT | 18 | 1784 |
| 1131737 | 1994 | 2013 | 7382 | 7401 | CCATCCTGGCGCGGAGCTGG | 17 | 1785 |
| 1131765 | 2028 | 2047 | 7416 | 7435 | CAGCATTTTCAAAGCACTTT | 39 | 1786 |
| 1131793 | N/A | N/A | 151 | 170 | TCATGGCTGTGATAGCGACC | 80 | 1787 |
| 1131821 | N/A | N/A | 247 | 266 | TCTGTCTCCTCTGCCTGGGC | 91 | 1788 |
| 1131849 | N/A | N/A | 338 | 357 | CCAAACCCTTTCTACCTCCC | 103 | 1789 |
| 1131877 | N/A | N/A | 428 | 447 | ACTGACTATAAGTCATAGCC | 77 | 1790 |
| 1131905 | N/A | N/A | 572 | 591 | ACACTGCACCATACACATCC | 59 | 1791 |
| 1131933 | N/A | N/A | 663 | 682 | AAGGATCACACAGCTCACGA | 64 | 1792 |
| 1131961 | N/A | N/A | 832 | 851 | TGAATGATGCCCATGAGACG | 33 | 1793 |
| 1131989 | N/A | N/A | 925 | 944 | AAGTGATAAAGCTGGGCTTC | 61 | 1794 |
| 1132017 | N/A | N/A | 1034 | 1053 | TTCCCTTCTCAACAACCCTA | 49 | 1795 |
| 1132045 | N/A | N/A | 1132 | 1151 | GCAGGTACCCTTCATCTAAA | 44 | 1796 |
| 1132073 | N/A | N/A | 1548 | 1567 | AGGTCCATCTGGTTCACAGG | 41 | 1797 |
| 1132101 | N/A | N/A | 1679 | 1698 | AGGCAAGAGAGAGGAGAAAC | 37 | 1798 |
| 1132129 | N/A | N/A | 2093 | 2112 | GAAATGGATCTGAGATGGAC | 65 | 1799 |
| 1132157 | N/A | N/A | 2201 | 2220 | GCTGAGCAGTGTCTGGCACA | 35 | 1800 |
| 1132185 | N/A | N/A | 2314 | 2333 | TAGTTCAATGTTCACTGTGA | 44 | 1801 |
| 1132213 | N/A | N/A | 2449 | 2468 | TTAGCATTGATGAATCAGCA | 46 | 1802 |
| 1132241 | N/A | N/A | 2564 | 2583 | TGGCCTCTGAGCCTCCTGCT | 60 | 1803 |
| 1132269 | N/A | N/A | 2700 | 2719 | CCCAGTTAAGGTTCAACAAG | 62 | 1804 |
| 1132297 | N/A | N/A | 2805 | 2824 | AATGTGCCTACTTGCTGAAT | 77 | 1805 |
| 1132325 | N/A | N/A | 2911 | 2930 | TGAAGTCACTGTTAACCACT | 45 | 1806 |
| 1132353 | N/A | N/A | 3015 | 3034 | GACTCCACAACCTGCTAGCT | 62 | 1807 |
| 1132381 | N/A | N/A | 3409 | 3428 | ACCCTCAAAAAGGTCGCTGT | 58 | 1808 |
| 1132409 | N/A | N/A | 3499 | 3518 | GAACTGCAGGGACAACACAC | 48 | 1809 |

TABLE 27-continued

Reduction of FXII RNA by 5-10-5 MOE gapmers with mixed PO/PS internucleoside linkages (Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132437 | N/A | N/A | 3694 | 3713 | TCACAGTCCCCTCTCTCCAA | 63 | 1810 |
| 1132465 | N/A | N/A | 3862 | 3881 | GAGAGAGCCCCAGGCCACCC | 41 | 1811 |
| 1132493 | N/A | N/A | 3984 | 4003 | CACTCCTTCCCAGAACTCTC | 52 | 1812 |
| 1132521 | N/A | N/A | 4090 | 4109 | AGCTGAGTCACACAGCTGGG | 69 | 1813 |
| 1132549 | N/A | N/A | 4272 | 4291 | CCCCAGCACCCCGCCCAGGT | 113 | 1814 |
| 1132577 | N/A | N/A | 4508 | 4527 | TCACCCTGGCTGGCCAGCCG | 103 | 1815 |
| 1132605 | N/A | N/A | 4605 | 4624 | AGACCCCCCCAGAGAGCTCT | 72 | 1816 |
| 1132633 | N/A | N/A | 4823 | 4842 | ACTCTCCCTCCTCCTTCCTG | 42 | 1817 |
| 1132661 | N/A | N/A | 5115 | 5134 | GCGCCGGGAGCCCGGAGCCC | 92 | 1818 |
| 1132689 | N/A | N/A | 5474 | 5493 | GGCAAGGCTGTGGAGGAGCA | 82 | 1819 |
| 1132717 | N/A | N/A | 5880 | 5899 | GCCCCCTGCTCCCGAACCCC | 65 | 1820 |
| 1132745 | N/A | N/A | 6346 | 6365 | AAGGTCTCCTCCCCTACCCC | 68 | 1821 |
| 1132773 | N/A | N/A | 6448 | 6467 | CACCTACACATTCTCACAAC | 66 | 1822 |
| 1132801 | N/A | N/A | 6572 | 6591 | CCTAGTTGGCCTTTGCAGCC | 67 | 1823 |
| 1132829 | N/A | N/A | 6679 | 6698 | AAGCCAGGATTTGAATGGGC | 50 | 1824 |
| 1132857 | N/A | N/A | 6799 | 6818 | GACAAAGCTGCTCCAGGCGC | 74 | 1825 |
| 1131569 | 1703 | 1722 | 7001 | 7020 | GCATCGGTGCCGCCCTCGAG | 8† | 1826 |
| 1132885 | N/A | N/A | 7066 | 7085 | ACCTGAGATTTGTGCCTGAC | 72† | 1827 |

TABLE 28

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130758 | 22 | 41 | 22 | 41 | TCCGTTGGTCCAGCTGCCTA | 70 | 1828 |
| 1130786 | 70 | 89 | 70 | 89 | AGCTCACCAGCAGGAACCCC | 55 | 1829 |
| 1130814 | 128 | 147 | 495 | 514 | GCTTTGTACTTATGCTCCTT | 30 | 1830 |
| 1130842 | 162 | 181 | N/A | N/A | CCCGGTGACAGTGAGAACGA | 43 | 1831 |
| 1130870 | 215 | 234 | 3566 | 3585 | GTACATTTGTGGTACAGCTG | 19 | 182 |
| 1130871 | 216 | 235 | 3567 | 3586 | GGTACATTTGTGGTACAGCT | 10 | 183 |
| 1130899 | 282 | 301 | 3789 | 3808 | TCGCTGGTCCTGATCAAAGT | 30 | 1832 |
| 1130927 | 322 | 341 | N/A | N/A | AGTGGTCTTTCACTTTCTTG | 41 | 1833 |
| 1130955 | 378 | 397 | 4186 | 4205 | GCCGCTTGGCATGTTCACAC | 46 | 1834 |
| 1130983 | 436 | 455 | N/A | N/A | AGCACTTCTCTTTCTGGCAG | 14 | 1835 |

TABLE 28-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131011 | 478 | 497 | 4423 | 4442 | ATATCTCATTCTTGTGGAAA | 39 | 1836 |
| 1131039 | 524 | 543 | 4469 | 4488 | CCCTTGCACTGGCATCTGGC | 38 | 1837 |
| 1131067 | 557 | 576 | 4502 | 4521 | TGGCTGGCCAGCCGCTGGCA | 45 | 1838 |
| 1131095 | 595 | 614 | 4679 | 4698 | AGCGACCCCCATGGAGGCAC | 21 | 1839 |
| 1131123 | 637 | 656 | 4721 | 4740 | CCACCGGGCAGTGGCACAGG | 42 | 1840 |
| 1131151 | 699 | 718 | 4928 | 4947 | GAGCCCGCGGCCATCATAGC | 85 | 1841 |
| 1131179 | 752 | 771 | 4981 | 5000 | CACGGCTGACAGGGCGCACC | 94 | 1842 |
| 1131207 | 808 | 827 | 5037 | 5056 | GTCCCCAGTTCCGCGCTTGC | 90 | 53 |
| 1131235 | 891 | 910 | 5205 | 5224 | CCAGCTCAGCCGGTCGCGGT | 72 | 1843 |
| 1131263 | 977 | 996 | 5291 | 5310 | ATGAGTGGGACATGAAGCCT | 51 | 1844 |
| 1131291 | 1063 | 1082 | N/A | N/A | GCTTCGCCGGCAAGGCTCCC | 41 | 1845 |
| 1131319 | 1106 | 1125 | 5525 | 5544 | CAGCTCAGTGGGCCGTTCCT | 66 | 1846 |
| 1131347 | 1141 | 1160 | 5560 | 5579 | TCATCGAAGACAGACTCTTG | 27 | 1847 |
| 1131375 | 1216 | 1235 | 5635 | 5654 | AACTGTGGCCCCAGTACAGC | 17 | 1848 |
| 1131403 | 1289 | 1308 | N/A | N/A | GGTGCGGGCCGGTCCTGCAG | 79 | 1849 |
| 1131431 | 1371 | 1390 | 6031 | 6050 | GTAGGAGCGCACGGCCAACG | 46 | 1850 |
| 1131459 | 1445 | 1464 | 6188 | 6207 | TCCGCATCCTCCTGAAGGCG | 40 | 1851 |
| 1131487 | 1521 | 1540 | 6264 | 6283 | GGTCTCGGAGGGTCGCGCGG | 61 | 1852 |
| 1131515 | 1570 | 1589 | N/A | N/A | CCTCCGCCCCTCGAACTGG | 258 | 1853 |
| 1131543 | 1613 | 1632 | 6911 | 6930 | GAGAGGAACGGTACCTGCGC | 80 | 1854 |
| 1131571 | 1707 | 1726 | 7005 | 7024 | GCACGCATCGGTGCCGCCCT | 22† | 1855 |
| 1131599 | 1786 | 1805 | 7174 | 7193 | AGCTGATGATGCCTTGCAGG | 25 | 1856 |
| 1131627 | 1816 | 1835 | 7204 | 7223 | GCTTGTTGCGGTCACCACAG | 21 | 1857 |
| 1131655 | 1863 | 1882 | 7251 | 7270 | CTCCCGGATCCAGGCCAGGT | 81 | 1858 |
| 1131683 | 1906 | 1925 | 7294 | 7313 | AAGGAGGGAAAGATGAGTCC | 48 | 1859 |
| 1131711 | 1943 | 1962 | 7331 | 7350 | TTCCATGCCCCAGCCACTCT | 20 | 1860 |
| 1131739 | 1996 | 2015 | 7384 | 7403 | CGCCATCCTGGCGCGGAGCT | 15 | 1861 |
| 1131795 | N/A | N/A | 157 | 176 | CATGGCTCATGGCTGTGATA | 82 | 1862 |
| 1131823 | N/A | N/A | 253 | 272 | TGGTTGTCTGTCTCCTCTGC | 70 | 1863 |
| 1131851 | N/A | N/A | 344 | 363 | CAAGACCCAAACCCTTTCTA | 154 | 1864 |
| 1131879 | N/A | N/A | 434 | 453 | CAGGGAACTGACTATAAGTC | 74 | 1865 |
| 1131907 | N/A | N/A | 579 | 598 | ACTGCACACTGCACCATA | 78 | 1866 |
| 1131935 | N/A | N/A | 669 | 688 | GCCCTCAAGGATCACACAGC | 80 | 1867 |
| 1131963 | N/A | N/A | 838 | 857 | GTGGCATGAATGATGCCCAT | 153 | 1868 |
| 1131991 | N/A | N/A | 931 | 950 | GCTCATAAGTGATAAAGCTG | 36 | 1869 |

TABLE 28-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132019 | N/A | N/A | 1043 | 1062 | CACATGGGTTTCCCTTCTCA | 100 | 1870 |
| 1132047 | N/A | N/A | 1138 | 1157 | GAAATGGCAGGTACCCTTCA | 46 | 1871 |
| 1132075 | N/A | N/A | 1554 | 1573 | AGGGTAAGGTCCATCTGGTT | 85 | 1872 |
| 1132103 | N/A | N/A | 1688 | 1707 | GTTTGGGTAAGGCAAGAGAG | 47 | 1873 |
| 1132131 | N/A | N/A | 2099 | 2118 | TAAATGGAAATGGATCTGAG | 37 | 1874 |
| 1132159 | N/A | N/A | 2207 | 2226 | TGAAATGCTGAGCAGTGTCT | 84 | 1875 |
| 1132187 | N/A | N/A | 2320 | 2339 | GTTTGCTAGTTCAATGTTCA | 56 | 1876 |
| 1132215 | N/A | N/A | 2455 | 2474 | ATCAGCTTAGCATTGATGAA | 44 | 1877 |
| 1132243 | N/A | N/A | 2570 | 2589 | TGGAAATGGCCTCTGAGCCT | 52 | 1878 |
| 1132271 | N/A | N/A | 2706 | 2725 | CACATTCCCAGTTAAGGTTC | 30 | 1879 |
| 1132299 | N/A | N/A | 2811 | 2830 | ATTGAGAATGTGCCTACTTG | 87 | 1880 |
| 1132327 | N/A | N/A | 2917 | 2936 | GAATGTTGAAGTCACTGTTA | 74 | 1881 |
| 1132355 | N/A | N/A | 3021 | 3040 | ACTCCTGACTCCACAACCTG | 49 | 1882 |
| 1132383 | N/A | N/A | 3415 | 3434 | GGACAGACCCTCAAAAAGGT | 72 | 1883 |
| 1132411 | N/A | N/A | 3505 | 3524 | CAGTGAGAACTGCAGGGACA | 73 | 1884 |
| 1132439 | N/A | N/A | 3700 | 3719 | GCCCTATCACAGTCCCCTCT | 61 | 1885 |
| 1132467 | N/A | N/A | 3868 | 3887 | CGGGAGGAGAGAGCCCCAGG | 46 | 1886 |
| 1132495 | N/A | N/A | 3990 | 4009 | TGGGACCACTCCTTCCCAGA | 65 | 1887 |
| 1132523 | N/A | N/A | 4096 | 4115 | GCAGGGAGCTGAGTCACACA | 121 | 1888 |
| 1132551 | N/A | N/A | 4286 | 4305 | GGGTTGCCCCTGTCCCCCAG | 59 | 1889 |
| 1132579 | N/A | N/A | 4514 | 4533 | ATCTGCTCACCCTGGCTGGC | 48 | 1890 |
| 1132607 | N/A | N/A | 4611 | 4630 | GCCTAAAGACCCCCCCAGAG | 75 | 1891 |
| 1132635 | N/A | N/A | 4832 | 4851 | GCTTTCCGCACTCTCCCTCC | 54 | 1892 |
| 1132663 | N/A | N/A | 5149 | 5168 | GGTTCCTGTAGCCACACGAC | 86 | 1893 |
| 1132691 | N/A | N/A | 5483 | 5502 | CGCTTCGCCGGCAAGGCTGT | 41 | 1894 |
| 1132719 | N/A | N/A | 5910 | 5929 | CTCAGACCTGGCCACAAGCG | 89 | 1895 |
| 1132747 | N/A | N/A | 6352 | 6371 | TGATCAAAGGTCTCCTCCCC | 118 | 1896 |
| 1132775 | N/A | N/A | 6454 | 6473 | GGGATTCACCTACACATTCT | 119 | 1897 |
| 1132803 | N/A | N/A | 6600 | 6619 | ACACTAGCCCGGAGCGCGGG | 62 | 1898 |
| 1132831 | N/A | N/A | 6688 | 6707 | TCCAGAGAAAGCCAGGATT | 86 | 1899 |
| 1132859 | N/A | N/A | 6805 | 6824 | ACGATGGACAAAGCTGCTCC | 55 | 1900 |
| 1132887 | N/A | N/A | 7072 | 7091 | CTGTGGACCTGAGATTTGTG | 155† | 1901 |

TABLE 29

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130759 | 24 | 43 | 24 | 43 | CGTCCGTTGGTCCAGCTGCC | 35 | 1902 |
| 1130787 | 71 | 90 | 71 | 90 | AAGCTCACCAGCAGGAACCC | 47 | 1903 |
| 1130815 | 129 | 148 | 496 | 515 | AGCTTTGTACTTATGCTCCT | 44 | 1904 |
| 1130843 | 163 | 182 | N/A | N/A | CCCCGGTGACAGTGAGAACG | 27 | 1905 |
| 1130871 | 216 | 235 | 3567 | 3586 | GGTACATTTGTGGTACAGCT | 17 | 183 |
| 1130872 | 217 | 236 | 3568 | 3587 | GGGTACATTTGTGGTACAGC | 23 | 25 |
| 1130900 | 283 | 302 | 3790 | 3809 | ATCGCTGGTCCTGATCAAAG | 22 | 1906 |
| 1130928 | 323 | 342 | N/A | N/A | CAGTGGTCTTTCACTTTCTT | 12 | 1907 |
| 1130956 | 379 | 398 | 4187 | 4206 | GGCCGCTTGGCATGTTCACA | 66 | 1908 |
| 1130984 | 438 | 457 | N/A | N/A | AAAGCACTTCTCTTTCTGGC | 33 | 1909 |
| 1131012 | 479 | 498 | 4424 | 4443 | CATATCTCATTCTTGTGGAA | 38 | 1910 |
| 1131040 | 525 | 544 | 4470 | 4489 | ACCCTTGCACTGGCATCTGG | 22 | 1911 |
| 1131068 | 558 | 577 | 4503 | 4522 | CTGGCTGGCCAGCCGCTGGC | 26 | 1912 |
| 1131096 | 597 | 616 | 4681 | 4700 | GCAGCGACCCCATGGAGGC | 23 | 1913 |
| 1131124 | 638 | 657 | 4722 | 4741 | CCCACCGGGCAGTGGCACAG | 45 | 1914 |
| 1131152 | 701 | 720 | 4930 | 4949 | CTGAGCCCGCGGCCATCATA | 35 | 1915 |
| 1131180 | 753 | 772 | 4982 | 5001 | CCACGGCTGACAGGGCGCAC | 36 | 1916 |
| 1131208 | 812 | 831 | 5041 | 5060 | CCCAGTCCCCAGTTCCGCGC | 22 | 1917 |
| 1131236 | 892 | 911 | 5206 | 5225 | CCCAGCTCAGCCGGTCGCGG | 71 | 1918 |
| 1131264 | 979 | 998 | 5293 | 5312 | GCATGAGTGGGACATGAAGC | 47 | 1919 |
| 1131292 | 1064 | 1083 | N/A | N/A | CGCTTCGCCGGCAAGGCTCC | 55 | 1920 |
| 1131320 | 1107 | 1126 | 5526 | 5545 | GCAGCTCAGTGGGCCGTTCC | 71 | 1921 |
| 1131348 | 1143 | 1162 | 5562 | 5581 | GGTCATCGAAGACAGACTCT | 22 | 1922 |
| 1131376 | 1218 | 1237 | 5637 | 5656 | GAAACTGTGGCCCCAGTACA | 32 | 1923 |
| 1131404 | 1302 | 1321 | 5962 | 5981 | CGTCAGATCCTCGGGTGCGG | 29 | 1924 |
| 1131432 | 1372 | 1391 | 6032 | 6051 | GGTAGGAGCGCACGGCCAAC | 22 | 1925 |
| 1131460 | 1446 | 1465 | 6189 | 6208 | GTCCGCATCCTCCTGAAGGC | 31 | 1926 |
| 1131488 | 1522 | 1541 | 6265 | 6284 | TGGTCTCGGAGGGTCGCGCG | 40 | 1927 |
| 1131516 | 1571 | 1590 | N/A | N/A | TCCTCCGCCCCCTCGAACTG | 425 | 1928 |
| 1131544 | 1614 | 1633 | 6912 | 6931 | GGAGAGGAACGGTACCTGCG | 87 | 1929 |
| 1131572 | 1709 | 1728 | 7007 | 7026 | TGGCACGCATCGGTGCCGCC | 63[†] | 1930 |
| 1131600 | 1787 | 1806 | 7175 | 7194 | CAGCTGATGATGCCTTGCAG | 90 | 1931 |
| 1131628 | 1817 | 1836 | 7205 | 7224 | GGCTTGTTGCGGTCACCACA | 40 | 1932 |
| 1131656 | 1864 | 1883 | 7252 | 7271 | GCTCCCGGATCCAGGCCAGG | 56 | 1933 |
| 1131684 | 1907 | 1926 | 7295 | 7314 | CAAGGAGGGAAAGATGAGTC | 33 | 1934 |
| 1131712 | 1944 | 1963 | 7332 | 7351 | CTTCCATGCCCCAGCCACTC | 20 | 1935 |

TABLE 29-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131740 | 1997 | 2016 | 7385 | 7404 | GCGCCATCCTGGCGCGGAGC | 38 | 1936 |
| 1131796 | N/A | N/A | 160 | 179 | GGCCATGGCTCATGGCTGTG | 79 | 1937 |
| 1131824 | N/A | N/A | 256 | 275 | GTCTGGTTGTCTGTCTCCTC | 63 | 1938 |
| 1131852 | N/A | N/A | 347 | 366 | TCCCAAGACCCAAACCCTTT | 57 | 1939 |
| 1131880 | N/A | N/A | 437 | 456 | AGGCAGGGAACTGACTATAA | 33 | 1940 |
| 1131908 | N/A | N/A | 582 | 601 | GAGACTGCACACACTGCACC | 40 | 1941 |
| 1131936 | N/A | N/A | 672 | 691 | CCTGCCCTCAAGGATCACAC | 45 | 1942 |
| 1131964 | N/A | N/A | 841 | 860 | TGTGTGGCATGAATGATGCC | 85 | 1943 |
| 1131992 | N/A | N/A | 934 | 953 | CCAGCTCATAAGTGATAAAG | 36 | 1944 |
| 1132020 | N/A | N/A | 1046 | 1065 | CCTCACATGGGTTTCCCTTC | 26 | 1945 |
| 1132048 | N/A | N/A | 1159 | 1178 | TGGCAGAGCTTGAGGAAGGG | 31 | 1946 |
| 1132076 | N/A | N/A | 1557 | 1576 | ACCAGGGTAAGGTCCATCTG | 65 | 1947 |
| 1132104 | N/A | N/A | 1691 | 1710 | CAAGTTTGGGTAAGGCAAGA | 40 | 1948 |
| 1132132 | N/A | N/A | 2102 | 2121 | CAGTAAATGGAAATGGATCT | 64 | 1949 |
| 1132160 | N/A | N/A | 2210 | 2229 | CCATGAAATGCTGAGCAGTG | 46 | 1950 |
| 1132188 | N/A | N/A | 2323 | 2342 | ACTGTTTGCTAGTTCAATGT | 25 | 1951 |
| 1132216 | N/A | N/A | 2458 | 2477 | GCCATCAGCTTAGCATTGAT | 38 | 1952 |
| 1132244 | N/A | N/A | 2573 | 2592 | TTTTGGAAATGGCCTCTGAG | 71 | 1953 |
| 1132272 | N/A | N/A | 2709 | 2728 | TTGCACATTCCCAGTTAAGG | 58 | 1954 |
| 1132300 | N/A | N/A | 2814 | 2833 | TACATTGAGAATGTGCCTAC | 116 | 1955 |
| 1132328 | N/A | N/A | 2920 | 2939 | GTTGAATGTTGAAGTCACTG | 47 | 1956 |
| 1132356 | N/A | N/A | 3024 | 3043 | TAGACTCCTGACTCCACAAC | 110 | 1957 |
| 1132384 | N/A | N/A | 3418 | 3437 | AAAGGACAGACCCTCAAAAA | 113 | 1958 |
| 1132412 | N/A | N/A | 3508 | 3527 | TGACAGTGAGAACTGCAGGG | 30 | 1959 |
| 1132440 | N/A | N/A | 3703 | 3722 | CCTGCCCTATCACAGTCCCC | 84 | 1960 |
| 1132468 | N/A | N/A | 3871 | 3890 | AGGCGGGAGGAGAGAGCCCC | 62 | 1961 |
| 1132496 | N/A | N/A | 3993 | 4012 | AAATGGGACCACTCCTTCCC | 41 | 1962 |
| 1132524 | N/A | N/A | 4099 | 4118 | AGAGCAGGGAGCTGAGTCAC | 60 | 1963 |
| 1132552 | N/A | N/A | 4289 | 4308 | CCAGGGTTGCCCCTGTCCCC | 190 | 1964 |
| 1132580 | N/A | N/A | 4517 | 4536 | ACCATCTGCTCACCCTGGCT | 67 | 1965 |
| 1132608 | N/A | N/A | 4614 | 4633 | TGGGCCTAAAGACCCCCCCA | 74 | 1966 |
| 1132636 | N/A | N/A | 4835 | 4854 | TCTGCTTTCCGCACTCTCCC | 36 | 1967 |
| 1132664 | N/A | N/A | 5152 | 5171 | CCGGGTTCCTGTAGCCACAC | 53 | 1968 |
| 1132692 | N/A | N/A | 5702 | 5721 | CGCCGGTCCTGCAGGCAGTG | 54 | 1969 |
| 1132720 | N/A | N/A | 5913 | 5932 | GCTCTCAGACCTGGCCACAA | 94 | 1970 |

TABLE 29-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132748 | N/A | N/A | 6355 | 6374 | CAGTGATCAAAGGTCTCCTC | 73 | 1971 |
| 1132776 | N/A | N/A | 6457 | 6476 | CCTGGGATTCACCTACACAT | 46 | 1972 |
| 1132804 | N/A | N/A | 6603 | 6622 | CCCACACTAGCCCGGAGCGC | 52 | 1973 |
| 1132832 | N/A | N/A | 6691 | 6710 | AGGTCCAGAGAAAAGCCAGG | 60 | 1974 |
| 1132860 | N/A | N/A | 6808 | 6827 | CGGACGATGGACAAAGCTGC | 37 | 1975 |
| 1132888 | N/A | N/A | 7075 | 7094 | GCGCTGTGGACCTGAGATTT | 87† | 1976 |

TABLE 30

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130788 | 72 | 91 | 72 | 91 | CAAGCTCACCAGCAGGAACC | 44 | 1977 |
| 1130816 | 130 | 149 | 497 | 516 | CAGCTTTGTACTTATGCTCC | 46 | 1978 |
| 1130844 | 164 | 183 | 3515 | 3534 | TCCCCGGTGACAGTGAGAAC | 43 | 24 |
| 1130871 | 216 | 235 | 3567 | 3586 | GGTACATTTGTGGTACAGCT | 12 | 183 |
| 1130873 | 218 | 237 | 3569 | 3588 | TGGGTACATTTGTGGTACAG | 22 | 1979 |
| 1130901 | 284 | 303 | 3791 | 3810 | CATCGCTGGTCCTGATCAAA | 26 | 1980 |
| 1130929 | 324 | 343 | N/A | N/A | GCAGTGGTCTTTCACTTTCT | 35 | 1981 |
| 1130957 | 380 | 399 | 4188 | 4207 | GGGCCGCTTGGCATGTTCAC | 32 | 1982 |
| 1130985 | 439 | 458 | N/A | N/A | CAAAGCACTTCTCTTTCTGG | 34 | 1983 |
| 1131013 | 481 | 500 | 4426 | 4445 | ACCATATCTCATTCTTGTGG | 21 | 1984 |
| 1131041 | 526 | 545 | 4471 | 4490 | GACCCTTGCACTGGCATCTG | 27 | 1985 |
| 1131069 | 559 | 578 | 4504 | 4523 | CCTGGCTGGCCAGCCGCTGG | 76 | 1986 |
| 1131097 | 598 | 617 | 4682 | 4701 | GGCAGCGACCCCCATGGAGG | 24 | 1987 |
| 1131125 | 640 | 659 | 4724 | 4743 | AGCCCACCGGGCAGTGGCAC | 57 | 1988 |
| 1131153 | 702 | 721 | 4931 | 4950 | GCTGAGCCCGCGGCCATCAT | 36 | 1989 |
| 1131181 | 754 | 773 | 4983 | 5002 | CCCACGGCTGACAGGGCGCA | 37 | 1990 |
| 1131209 | 813 | 832 | 5042 | 5061 | GCCCAGTCCCCAGTTCCGCG | 41 | 1991 |
| 1131237 | 893 | 912 | 5207 | 5226 | TCCCAGCTCAGCCGGTCGCG | 40 | 1992 |
| 1131265 | 980 | 999 | 5294 | 5313 | GGCATGAGTGGGACATGAAG | 28 | 1993 |
| 1131293 | 1065 | 1084 | N/A | N/A | CCGCTTCGCCGGCAAGGCTC | 35 | 1994 |
| 1131321 | 1108 | 1127 | 5527 | 5546 | CGCAGCTCAGTGGGCCGTTC | 32 | 1995 |
| 1131349 | 1144 | 1163 | 5563 | 5582 | GGGTCATCGAAGACAGACTC | 44 | 1996 |

TABLE 30-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131377 | 1219 | 1238 | 5638 | 5657 | AGAAACTGTGGCCCCAGTAC | 46 | 1997 |
| 1131405 | 1303 | 1322 | 5963 | 5982 | CCGTCAGATCCTCGGGTGCG | 28 | 1998 |
| 1131433 | 1373 | 1392 | 6033 | 6052 | CGGTAGGAGCGCACGGCCAA | 21 | 1999 |
| 1131461 | 1448 | 1467 | 6191 | 6210 | CCGTCCGCATCCTCCTGAAG | 42 | 2000 |
| 1131489 | 1523 | 1542 | 6266 | 6285 | GTGGTCTCGGAGGGTCGCGC | 41 | 2001 |
| 1131517 | 1572 | 1591 | N/A | N/A | TTCCTCCGCCCCCTCGAACT | 194 | 2002 |
| 1131545 | 1615 | 1634 | 6913 | 6932 | GGGAGAGGAACGGTACCTGC | 65 | 2003 |
| 1131573 | 1710 | 1729 | 7008 | 7027 | CTGGCACGCATCGGTGCCGC | 121† | 2004 |
| 1131601 | 1788 | 1807 | 7176 | 7195 | CCAGCTGATGATGCCTTGCA | 22 | 2005 |
| 1131629 | 1818 | 1837 | 7206 | 7225 | TGGCTTGTTGCGGTCACCAC | 26 | 2006 |
| 1131657 | 1865 | 1884 | 7253 | 7272 | TGCTCCCGGATCCAGGCCAG | 44 | 2007 |
| 1131685 | 1908 | 1927 | 7296 | 7315 | CCAAGGAGGGAAAGATGAGT | 22 | 2008 |
| 1131713 | 1945 | 1964 | 7333 | 7352 | CCTTCCATGCCCCAGCCACT | 15 | 2009 |
| 1131741 | 1999 | 2018 | 7387 | 7406 | CTGCGCCATCCTGGCGCGGA | 83 | 2010 |
| 1131797 | N/A | N/A | 163 | 182 | AGAGGCCATGGCTCATGGCT | 91 | 2011 |
| 1131825 | N/A | N/A | 259 | 278 | CCAGTCTGGTTGTCTGTCTC | 60 | 2012 |
| 1131853 | N/A | N/A | 350 | 369 | TCTTCCCAAGACCCAAACCC | 65 | 2013 |
| 1131881 | N/A | N/A | 440 | 459 | AGAAGGCAGGGAACTGACTA | 84 | 2014 |
| 1131909 | N/A | N/A | 585 | 604 | CCTGAGACTGCACACACTGC | 56 | 2015 |
| 1131937 | N/A | N/A | 675 | 694 | TACCCTGCCCTCAAGGATCA | 42 | 2016 |
| 1131965 | N/A | N/A | 844 | 863 | CTCTGTGTGGCATGAATGAT | 71 | 2017 |
| 1131993 | N/A | N/A | 937 | 956 | CACCCAGCTCATAAGTGATA | 63 | 2018 |
| 1132021 | N/A | N/A | 1049 | 1068 | ATACCTCACATGGGTTTCCC | 59 | 2019 |
| 1132049 | N/A | N/A | 1162 | 1181 | CTATGGCAGAGCTTGAGGAA | 62 | 2020 |
| 1132077 | N/A | N/A | 1560 | 1579 | CCCACCAGGGTAAGGTCCAT | 54 | 2021 |
| 1132105 | N/A | N/A | 1694 | 1713 | CACCAAGTTTGGGTAAGGCA | 34 | 2022 |
| 1132133 | N/A | N/A | 2105 | 2124 | GGACAGTAAATGGAAATGGA | 45 | 2023 |
| 1132161 | N/A | N/A | 2219 | 2238 | GAGATAATGCCATGAAATGC | 56 | 2024 |
| 1132189 | N/A | N/A | 2326 | 2345 | AATACTGTTTGCTAGTTCAA | 52 | 2025 |
| 1132217 | N/A | N/A | 2461 | 2480 | AGTGCCATCAGCTTAGCATT | 51 | 2026 |
| 1132245 | N/A | N/A | 2576 | 2595 | GGCTTTTGGAAATGGCCTCT | 46 | 2027 |
| 1132273 | N/A | N/A | 2712 | 2731 | AATTTGCACATTCCCAGTTA | 64 | 2028 |
| 1132301 | N/A | N/A | 2817 | 2836 | TTCTACATTGAGAATGTGCC | 43 | 2029 |
| 1132329 | N/A | N/A | 2923 | 2942 | CTTGTTGAATGTTGAAGTCA | 50 | 2030 |
| 1132357 | N/A | N/A | 3027 | 3046 | GAGTAGACTCCTGACTCCAC | 73 | 2031 |

TABLE 30-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132385 | N/A | N/A | 3421 | 3440 | GGAAAAGGACAGACCCTCAA | 72 | 2032 |
| 1132413 | N/A | N/A | 3511 | 3530 | CGGTGACAGTGAGAACTGCA | 32 | 2033 |
| 1132441 | N/A | N/A | 3706 | 3725 | CACCCTGCCCTATCACAGTC | 74 | 2034 |
| 1132469 | N/A | N/A | 3874 | 3893 | ATGAGGCGGGAGGAGAGAGC | 72 | 2035 |
| 1132497 | N/A | N/A | 3996 | 4015 | GCAAAATGGGACCACTCCTT | 42 | 2036 |
| 1132525 | N/A | N/A | 4102 | 4121 | GGAAGAGCAGGGAGCTGAGT | 102 | 2037 |
| 1132553 | N/A | N/A | 4292 | 4311 | GGCCCAGGGTTGCCCCTGTC | 75 | 2038 |
| 1132581 | N/A | N/A | 4520 | 4539 | CCAACCATCTGCTCACCCTG | 72 | 2039 |
| 1132609 | N/A | N/A | 4617 | 4636 | CCCTGGGCCTAAAGACCCCC | 115 | 2040 |
| 1132637 | N/A | N/A | 4838 | 4857 | TCATCTGCTTTCCGCACTCT | 44 | 2041 |
| 1132665 | N/A | N/A | 5155 | 5174 | TGTCCGGGTTCCTGTAGCCA | 43 | 2042 |
| 1132693 | N/A | N/A | 5705 | 5724 | ACTCGCCGGTCCTGCAGGCA | 29 | 2043 |
| 1132721 | N/A | N/A | 6089 | 6108 | GCCCCACGCACCCAGGTCG | 132 | 2044 |
| 1132749 | N/A | N/A | 6358 | 6377 | ACCCAGTGATCAAAGGTCTC | 56 | 2045 |
| 1132777 | N/A | N/A | 6460 | 6479 | CTACCTGGGATTCACCTACA | 51 | 2046 |
| 1132805 | N/A | N/A | 6606 | 6625 | GCTCCCACACTAGCCCGGAG | 52 | 2047 |
| 1132833 | N/A | N/A | 6694 | 6713 | CTGAGGTCCAGAGAAAAGCC | 25 | 2048 |
| 1132861 | N/A | N/A | 6811 | 6830 | GCCCGGACGATGGACAAAGC | 86 | 2049 |
| 1132889 | N/A | N/A | 7091 | 7110 | GGAAACACGCAGCTCAGCGC | 87† | 2050 |

TABLE 31

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130761 | 27 | 46 | 27 | 46 | ATCCGTCCGTTGGTCCAGCT | 24 | 2051 |
| 1130789 | 73 | 92 | 73 | 92 | CCAAGCTCACCAGCAGGAAC | 47 | 2052 |
| 1130817 | 131 | 150 | 498 | 517 | TCAGCTTTGTACTTATGCTC | 43 | 2053 |
| 1130845 | 165 | 184 | 3516 | 3535 | CTCCCCGGTGACAGTGAGAA | 68 | 2054 |
| 1130871 | 216 | 235 | 3567 | 3586 | GGTACATTTGTGGTACAGCT | 16 | 183 |
| 1130874 | 220 | 239 | 3571 | 3590 | TGTGGGTACATTTGTGGTAC | 21 | 2055 |
| 1130902 | 286 | 305 | 3793 | 3812 | CCCATCGCTGGTCCTGATCA | 25 | 2056 |
| 1130930 | 326 | 345 | N/A | N/A | CTGCAGTGGTCTTTCACTTT | 56 | 2057 |
| 1130958 | 400 | 419 | 4208 | 4227 | GTTGTGGACAGAGACAGTGG | 37 | 2058 |

TABLE 31-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130986 | 440 | 459 | N/A | N/A | TCAAAGCACTTCTCTTTCTG | 41 | 2059 |
| 1131014 | 484 | 503 | 4429 | 4448 | TATACCATATCTCATTCTTG | 41 | 2060 |
| 1131042 | 527 | 546 | 4472 | 4491 | GGACCCTTGCACTGGCATCT | 39 | 2061 |
| 1131070 | 560 | 579 | N/A | N/A | GCCTGGCTGGCCAGCCGCTG | 82 | 2062 |
| 1131098 | 600 | 619 | 4684 | 4703 | TAGGCAGCGACCCCCATGGA | 47 | 2063 |
| 1131126 | 643 | 662 | 4727 | 4746 | TGTAGCCCACCGGGCAGTGG | 24 | 2064 |
| 1131154 | 703 | 722 | 4932 | 4951 | AGCTGAGCCCGCGGCCATCA | 29 | 2065 |
| 1131182 | 756 | 775 | 4985 | 5004 | GGCCCACGGCTGACAGGGCG | 61 | 2066 |
| 1131210 | 815 | 834 | 5044 | 5063 | CCGCCCAGTCCCCAGTTCCG | 27 | 2067 |
| 1131238 | 894 | 913 | 5208 | 5227 | CTCCCAGCTCAGCCGGTCGC | 66 | 2068 |
| 1131266 | 989 | 1008 | 5303 | 5322 | GGCTGCGCGGGCATGAGTGG | 66 | 2069 |
| 1131294 | 1066 | 1085 | 5485 | 5504 | CCCGCTTCGCCGGCAAGGCT | 49 | 2070 |
| 1131322 | 1109 | 1128 | 5528 | 5547 | CCGCAGCTCAGTGGGCCGTT | 67 | 2071 |
| 1131350 | 1146 | 1165 | 5565 | 5584 | GCGGGTCATCGAAGACAGAC | 23 | 2072 |
| 1131378 | 1220 | 1239 | 5639 | 5658 | CAGAAACTGTGGCCCCAGTA | 51 | 2073 |
| 1131406 | 1305 | 1324 | 5965 | 5984 | CACCGTCAGATCCTCGGGTG | 31 | 2074 |
| 1131434 | 1375 | 1394 | 6035 | 6054 | AGCGGTAGGAGCGCACGGCC | 24 | 2075 |
| 1131462 | 1449 | 1468 | 6192 | 6211 | GCCGTCCGCATCCTCCTGAA | 17 | 2076 |
| 1131490 | 1524 | 1543 | 6267 | 6286 | CGTGGTCTCGGAGGGTCGCG | 28 | 2077 |
| 1131518 | 1573 | 1592 | N/A | N/A | ATTCCTCCGCCCCCTCGAAC | 238 | 2078 |
| 1131546 | 1616 | 1635 | 6914 | 6933 | AGGGAGAGGAACGGTACCTG | 50 | 2079 |
| 1131574 | 1712 | 1731 | N/A | N/A | CCCTGGCACGCATCGGTGCC | 56[†] | 2080 |
| 1131602 | 1789 | 1808 | 7177 | 7196 | CCCAGCTGATGATGCCTTGC | 45 | 2081 |
| 1131630 | 1819 | 1838 | 7207 | 7226 | CTGGCTTGTTGCGGTCACCA | 16 | 2082 |
| 1131658 | 1866 | 1885 | 7254 | 7273 | GTGCTCCCGGATCCAGGCCA | 32 | 2083 |
| 1131686 | 1909 | 1928 | 7297 | 7316 | ACCAAGGAGGGAAAGATGAG | 19 | 2084 |
| 1131714 | 1946 | 1965 | 7334 | 7353 | GCCTTCCATGCCCCAGCCAC | 30 | 2085 |
| 1131742 | 2000 | 2019 | 7388 | 7407 | CCTGCGCCATCCTGGCGCGG | 113 | 2086 |
| 1131798 | N/A | N/A | 166 | 185 | AGCAGAGGCCATGGCTCATG | 38 | 2087 |
| 1131826 | N/A | N/A | 262 | 281 | CACCCAGTCTGGTTGTCTGT | 71 | 2088 |
| 1131854 | N/A | N/A | 353 | 372 | ATTTCTTCCCAAGACCCAAA | 74 | 2089 |
| 1131882 | N/A | N/A | 443 | 462 | AGAAGAAGGCAGGGAACTGA | 120 | 2090 |
| 1131910 | N/A | N/A | 591 | 610 | GACTGCCCTGAGACTGCACA | 59 | 2091 |
| 1131938 | N/A | N/A | 678 | 697 | CCATACCCTGCCCTCAAGGA | 46 | 2092 |
| 1131966 | N/A | N/A | 847 | 866 | GGCCTCTGTGTGGCATGAAT | 31 | 2093 |
| 1131994 | N/A | N/A | 941 | 960 | GAGTCACCCAGCTCATAAGT | 80 | 2094 |

TABLE 31-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1132022 | N/A | N/A | 1052 | 1071 | TGAATACCTCACATGGGTTT | 34 | 2095 |
| 1132050 | N/A | N/A | 1165 | 1184 | GAGCTATGGCAGAGCTTGAG | 51 | 2096 |
| 1132078 | N/A | N/A | 1563 | 1582 | AGGCCCACCAGGGTAAGGTC | 61 | 2097 |
| 1132106 | N/A | N/A | 1702 | 1721 | GGATAGGGCACCAAGTTTGG | 77 | 2098 |
| 1132134 | N/A | N/A | 2108 | 2127 | CTAGGACAGTAAATGGAAAT | 33 | 2099 |
| 1132162 | N/A | N/A | 2222 | 2241 | CATGAGATAATGCCATGAAA | 50 | 2100 |
| 1132190 | N/A | N/A | 2329 | 2348 | CCTAATACTGTTTGCTAGTT | 36 | 2101 |
| 1132218 | N/A | N/A | 2464 | 2483 | TATAGTGCCATCAGCTTAGC | 43 | 2102 |
| 1132246 | N/A | N/A | 2579 | 2598 | TTTGGCTTTTGGAAATGGCC | 29 | 2103 |
| 1132274 | N/A | N/A | 2715 | 2734 | AAAAATTTGCACATTCCCAG | 85 | 2104 |
| 1132302 | N/A | N/A | 2820 | 2839 | TGGTTCTACATTGAGAATGT | 76 | 2105 |
| 1132330 | N/A | N/A | 2926 | 2945 | ATACTTGTTGAATGTTGAAG | 52 | 2106 |
| 1132358 | N/A | N/A | 3030 | 3049 | CTGGAGTAGACTCCTGACTC | 62 | 2107 |
| 1132386 | N/A | N/A | 3424 | 3443 | TCAGGAAAAGGACAGACCCT | 36 | 2108 |
| 1132414 | N/A | N/A | 3514 | 3533 | CCCCGGTGACAGTGAGAACT | 33 | 2109 |
| 1132442 | N/A | N/A | 3709 | 3728 | GCCCACCCTGCCCTATCACA | 40 | 2110 |
| 1132470 | N/A | N/A | 3877 | 3896 | GTAATGAGGCGGGAGGAGAG | 46 | 2111 |
| 1132498 | N/A | N/A | 3999 | 4018 | CCTGCAAAATGGGACCACTC | 60 | 2112 |
| 1132526 | N/A | N/A | 4105 | 4124 | GAAGGAAGAGCAGGGAGCTG | 58 | 2113 |
| 1132554 | N/A | N/A | 4295 | 4314 | GTAGGCCCAGGGTTGCCCCT | 71 | 2114 |
| 1132582 | N/A | N/A | 4523 | 4542 | TTCCCAACCATCTGCTCACC | 72 | 2115 |
| 1132610 | N/A | N/A | 4620 | 4639 | CACCCCTGGGCCTAAAGACC | 79 | 2116 |
| 1132638 | N/A | N/A | 4841 | 4860 | CTCTCATCTGCTTTCCGCAC | 60 | 2117 |
| 1132666 | N/A | N/A | 5158 | 5177 | CGTTGTCCGGGTTCCTGTAG | 59 | 2118 |
| 1132694 | N/A | N/A | 5708 | 5727 | GGTACTCGCCGGTCCTGCAG | 37 | 2119 |
| 1132722 | N/A | N/A | 6111 | 6130 | TCTCTTCCCGTCCCCGCGGG | 60 | 2120 |
| 1132750 | N/A | N/A | 6361 | 6380 | CTAACCCAGTGATCAAAGGT | 75 | 2121 |
| 1132778 | N/A | N/A | 6463 | 6482 | ATTCTACCTGGGATTCACCT | 34 | 2122 |
| 1132806 | N/A | N/A | 6609 | 6628 | CTGGCTCCCACACTAGCCCG | 44 | 2123 |
| 1132834 | N/A | N/A | 6697 | 6716 | AGGCTGAGGTCCAGAGAAAA | 96 | 2124 |
| 1132862 | N/A | N/A | 6814 | 6833 | GCCGCCCGGACGATGGACAA | 97 | 2125 |
| 1132890 | N/A | N/A | 7094 | 7113 | GTCGGAAACACGCAGCTCAG | 90† | 2126 |

TABLE 32

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130762 | 28 | 47 | 28 | 47 | CATCCGTCCGTTGGTCCAGC | 46 | 2127 |
| 1130790 | 74 | 93 | 74 | 93 | TCCAAGCTCACCAGCAGGAA | 41 | 2128 |
| 1130818 | 132 | 151 | 499 | 518 | TTCAGCTTTGTACTTATGCT | 63 | 2129 |
| 1130846 | 166 | 185 | 3517 | 3536 | GCTCCCCGGTGACAGTGAGA | 16 | 2130 |
| 1130871 | 216 | 235 | 3567 | 3586 | GGTACATTTGTGGTACAGCT | 15 | 183 |
| 1130875 | 221 | 240 | 3572 | 3591 | TTGTGGGTACATTTGTGGTA | 31 | 2131 |
| 1130903 | 287 | 306 | 3794 | 3813 | CCCCATCGCTGGTCCTGATC | 20 | 2132 |
| 1130931 | 328 | 347 | N/A | N/A | TGCTGCAGTGGTCTTTCACT | 55 | 2133 |
| 1130959 | 401 | 420 | 4209 | 4228 | TGTTGTGGACAGAGACAGTG | 67 | 2134 |
| 1130987 | 443 | 462 | N/A | N/A | GGCTCAAAGCACTTCTCTTT | 15 | 2135 |
| 1131015 | 485 | 504 | 4430 | 4449 | CTATACCATATCTCATTCTT | 20 | 2136 |
| 1131043 | 529 | 548 | 4474 | 4493 | CAGGACCCTTGCACTGGCAT | 38 | 2137 |
| 1131071 | 561 | 580 | N/A | N/A | GGCCTGGCTGGCCAGCCGCT | 114 | 2138 |
| 1131099 | 601 | 620 | 4685 | 4704 | CTAGGCAGCGACCCCATGG | 40 | 2139 |
| 1131127 | 648 | 667 | 4732 | 4751 | TCCGGTGTAGCCCACCGGGC | 104 | 2140 |
| 1131155 | 704 | 723 | 4933 | 4952 | TAGCTGAGCCCGCGGCCATC | 22 | 2141 |
| 1131183 | 759 | 778 | 4988 | 5007 | CGAGGCCCACGGCTGACAGG | 51 | 2142 |
| 1131211 | 816 | 835 | 5045 | 5064 | GCCGCCCAGTCCCCAGTTCC | 41 | 2143 |
| 1131239 | 896 | 915 | 5210 | 5229 | TACTCCCAGCTCAGCCGGTC | 49 | 2144 |
| 1131267 | 990 | 1009 | 5304 | 5323 | CGGCTGCGCGGGCATGAGTG | 71 | 2145 |
| 1131295 | 1067 | 1086 | 5486 | 5505 | TCCCGCTTCGCCGGCAAGGC | 36 | 2146 |
| 1131323 | 1110 | 1129 | 5529 | 5548 | CCCGCAGCTCAGTGGGCCGT | 33 | 2147 |
| 1131351 | 1147 | 1166 | 5566 | 5585 | CGCGGGTCATCGAAGACAGA | 39 | 2148 |
| 1131379 | 1221 | 1240 | 5640 | 5659 | GCAGAAACTGTGGCCCCAGT | 56 | 2149 |
| 1131407 | 1308 | 1327 | 5968 | 5987 | CACCACCGTCAGATCCTCGG | 40 | 2150 |
| 1131435 | 1376 | 1395 | 6036 | 6055 | AAGCGGTAGGAGCGCACGGC | 25 | 2151 |
| 1131463 | 1451 | 1470 | 6194 | 6213 | CTGCCGTCCGCATCCTCCTG | 22 | 2152 |
| 1131491 | 1542 | 1561 | 6285 | 6304 | GCCGGCCACCTGGCAGAGCG | 87 | 2153 |
| 1131519 | 1574 | 1593 | N/A | N/A | TATTCCTCCGCCCCCTCGAA | 316 | 2154 |
| 1131547 | 1617 | 1636 | 6915 | 6934 | CAGGGAGAGGAACGGTACCT | 116 | 2155 |
| 1131575 | 1743 | 1762 | 7131 | 7150 | GTCCTCACACACCAGCGGGC | 14† | 79 |
| 1131603 | 1790 | 1809 | 7178 | 7197 | CCCCAGCTGATGATGCCTTG | 50 | 2156 |
| 1131631 | 1820 | 1839 | 7208 | 7227 | CCTGGCTTGTTGCGGTCACC | 38 | 85 |
| 1131659 | 1867 | 1886 | 7255 | 7274 | TGTGCTCCCGGATCCAGGCC | 42 | 2157 |
| 1131687 | 1911 | 1930 | 7299 | 7318 | TCACCAAGGAGGGAAAGATG | 17 | 2158 |
| 1131715 | 1947 | 1966 | 7335 | 7354 | TGCCTTCCATGCCCCAGCCA | 36 | 156 |

TABLE 32-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1131743 | 2001 | 2020 | 7389 | 7408 | TCCTGCGCCATCCTGGCGCG | 30 | 2159 |
| 1131799 | N/A | N/A | 169 | 188 | ATGAGCAGAGGCCATGGCTC | 99 | 2160 |
| 1131827 | N/A | N/A | 265 | 284 | ATCCACCCAGTCTGGTTGTC | 89 | 2161 |
| 1131855 | N/A | N/A | 356 | 375 | GAGATTTCTTCCCAAGACCC | 107 | 2162 |
| 1131883 | N/A | N/A | 446 | 465 | GAGAGAAGAAGGCAGGGAAC | 126 | 2163 |
| 1131911 | N/A | N/A | 594 | 613 | CTAGACTGCCCTGAGACTGC | 72 | 2164 |
| 1131939 | N/A | N/A | 681 | 700 | AGCCCATACCCTGCCCTCAA | 38 | 2165 |
| 1131967 | N/A | N/A | 850 | 869 | CCTGGCCTCTGTGTGGCATG | 63 | 2166 |
| 1131995 | N/A | N/A | 947 | 966 | CGCCCAGAGTCACCCAGCTC | 34 | 2167 |
| 1132023 | N/A | N/A | 1055 | 1074 | GGCTGAATACCTCACATGGG | 74 | 2168 |
| 1132051 | N/A | N/A | 1188 | 1207 | TCTGGAAGAATGAAAGCAAT | 62 | 2169 |
| 1132079 | N/A | N/A | 1566 | 1585 | GTCAGGCCCACCAGGGTAAG | 47 | 2170 |
| 1132107 | N/A | N/A | 1705 | 1724 | CAAGGATAGGGCACCAAGTT | 56 | 2171 |
| 1132135 | N/A | N/A | 2114 | 2133 | CCAGAACTAGGACAGTAAAT | 52 | 2172 |
| 1132163 | N/A | N/A | 2225 | 2244 | CTTCATGAGATAATGCCATG | 46 | 2173 |
| 1132191 | N/A | N/A | 2332 | 2351 | GAACCTAATACTGTTTGCTA | 27 | 2174 |
| 1132219 | N/A | N/A | 2467 | 2486 | TGCTATAGTGCCATCAGCTT | 60 | 2175 |
| 1132247 | N/A | N/A | 2582 | 2601 | GGATTTGGCTTTTGGAAATG | 42 | 2176 |
| 1132275 | N/A | N/A | 2718 | 2737 | GTGAAAAATTTGCACATTCC | 50 | 2177 |
| 1132303 | N/A | N/A | 2823 | 2842 | CTCTGGTTCTACATTGAGAA | 36 | 2178 |
| 1132331 | N/A | N/A | 2929 | 2948 | ATAATACTTGTTGAATGTTG | 39 | 2179 |
| 1132359 | N/A | N/A | 3033 | 3052 | TAGCTGGAGTAGACTCCTGA | 92 | 2180 |
| 1132387 | N/A | N/A | 3427 | 3446 | TGGTCAGGAAAAGGACAGAC | 21 | 2181 |
| 1132415 | N/A | N/A | 3605 | 3624 | TAGTCTTACCAGGGCTGAGG | 50 | 2182 |
| 1132443 | N/A | N/A | 3734 | 3753 | CTTCCCTGCTCTACCCAGGG | 56 | 2183 |
| 1132471 | N/A | N/A | 3880 | 3899 | AGAGTAATGAGGCGGGAGGA | 44 | 2184 |
| 1132499 | N/A | N/A | 4002 | 4021 | CCACCTGCAAAATGGGACCA | 29 | 2185 |
| 1132527 | N/A | N/A | 4110 | 4129 | TGGTGGAAGGAAGAGCAGGG | 90 | 2186 |
| 1132555 | N/A | N/A | 4298 | 4317 | TCTGTAGGCCCAGGGTTGCC | 73 | 2187 |
| 1132583 | N/A | N/A | 4526 | 4545 | CCGTTCCCAACCATCTGCTC | 42 | 2188 |
| 1132611 | N/A | N/A | 4623 | 4642 | AGCCACCCCTGGGCCTAAAG | 150 | 2189 |
| 1132639 | N/A | N/A | 4844 | 4863 | TCCCTCTCATCTGCTTTCCG | 26 | 2190 |
| 1132667 | N/A | N/A | 5374 | 5393 | CCACTTCCTAACCTCCCGGG | 129 | 2191 |
| 1132695 | N/A | N/A | 5711 | 5730 | GCGGGTACTCGCCGGTCCTG | 58 | 2192 |
| 1132723 | N/A | N/A | 6114 | 6133 | AGCTCTCTTCCCGTCCCCGC | 67 | 2193 |

TABLE 32-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1132751 | N/A | N/A | 6364 | 6383 | CGCCTAACCCAGTGATCAAA | 91 | 2194 |
| 1132779 | N/A | N/A | 6472 | 6491 | GGCCCTGGGATTCTACCTGG | 50 | 2195 |
| 1132807 | N/A | N/A | 6612 | 6631 | AACCTGGCTCCCACACTAGC | 51 | 2196 |
| 1132835 | N/A | N/A | 6703 | 6722 | GCAAGGAGGCTGAGGTCCAG | 39 | 2197 |
| 1132863 | N/A | N/A | 6817 | 6836 | CTTGCCGCCCGGACGATGGA | 50 | 2198 |
| 1132891 | N/A | N/A | 7097 | 7116 | TGGGTCGGAAACACGCAGCT | 115† | 2199 |

TABLE 33

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130763 | 30 | 49 | 30 | 49 | GGCATCCGTCCGTTGGTCCA | 21 | 2200 |
| 1130791 | 75 | 94 | 75 | 94 | CTCCAAGCTCACCAGCAGGA | 37 | 2201 |
| 1130819 | 133 | 152 | 500 | 519 | CTTCAGCTTTGTACTTATGC | 70 | 2202 |
| 1130847 | 168 | 187 | 3519 | 3538 | GGGCTCCCCGGTGACAGTGA | 33 | 2203 |
| 1130871 | 216 | 235 | 3567 | 3586 | GGTACATTTGTGGTACAGCT | 14 | 183 |
| 1130876 | 222 | 241 | 3573 | 3592 | CTTGTGGGTACATTTGTGGT | 28 | 2204 |
| 1130904 | 288 | 307 | 3795 | 3814 | TCCCCATCGCTGGTCCTGAT | 43 | 2205 |
| 1130932 | 329 | 348 | N/A | N/A | TTGCTGCAGTGGTCTTTCAC | 24 | 2206 |
| 1130960 | 402 | 421 | 4210 | 4229 | GTGTTGTGGACAGAGACAGT | 34 | 2207 |
| 1130988 | 444 | 463 | N/A | N/A | AGGCTCAAAGCACTTCTCTT | 23 | 2208 |
| 1131016 | 487 | 506 | 4432 | 4451 | TTCTATACCATATCTCATTC | 30 | 2209 |
| 1131044 | 530 | 549 | 4475 | 4494 | TCAGGACCCTTGCACTGGCA | 31 | 2210 |
| 1131072 | 563 | 582 | N/A | N/A | CAGGCCTGGCTGGCCAGCCG | 41 | 2211 |
| 1131100 | 603 | 622 | 4687 | 4706 | CTCTAGGCAGCGACCCCCAT | 22 | 2212 |
| 1131128 | 649 | 668 | 4733 | 4752 | CTCCGGTGTAGCCCACCGGG | 44 | 2213 |
| 1131156 | 706 | 725 | 4935 | 4954 | GGTAGCTGAGCCCGCGGCCA | 29 | 2214 |
| 1131184 | 760 | 779 | 4989 | 5008 | CCGAGGCCCACGGCTGACAG | 78 | 2215 |
| 1131212 | 819 | 838 | 5048 | 5067 | GTGGCCGCCCAGTCCCCAGT | 52 | 2216 |
| 1131240 | 897 | 916 | 5211 | 5230 | GTACTCCCAGCTCAGCCGGT | 33 | 2217 |
| 1131268 | 991 | 1010 | 5305 | 5324 | CCGGCTGCGCGGGCATGAGT | 29 | 2218 |
| 1131296 | 1068 | 1087 | 5487 | 5506 | CTCCCGCTTCGCCGGCAAGG | 35 | 2219 |
| 1131324 | 1113 | 1132 | 5532 | 5551 | CTGCCCGCAGCTCAGTGGGC | 53 | 2220 |
| 1131352 | 1149 | 1168 | 5568 | 5587 | GACGCGGGTCATCGAAGACA | 30 | 2221 |

TABLE 33-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1131380 | 1222 | 1241 | 5641 | 5660 | CGCAGAAACTGTGGCCCCAG | 31 | 2222 |
| 1131408 | 1309 | 1328 | 5969 | 5988 | GCACCACCGTCAGATCCTCG | 49 | 2223 |
| 1131436 | 1377 | 1396 | 6037 | 6056 | CAAGCGGTAGGAGCGCACGG | 33 | 2224 |
| 1131464 | 1452 | 1471 | 6195 | 6214 | GCTGCCGTCCGCATCCTCCT | 38 | 2225 |
| 1131492 | 1544 | 1563 | 6287 | 6306 | CAGCCGGCCACCTGGCAGAG | 63 | 2226 |
| 1131520 | 1575 | 1594 | N/A | N/A | ATATTCCTCCGCCCCCTCGA | 216 | 2227 |
| 1131548 | 1618 | 1637 | 6916 | 6935 | CCAGGGAGAGGAACGGTACC | 119 | 2228 |
| 1131604 | 1791 | 1810 | 7179 | 7198 | TCCCCAGCTGATGATGCCTT | 29 | 2229 |
| 1131632 | 1821 | 1840 | 7209 | 7228 | GCCTGGCTTGTTGCGGTCAC | 27 | 2230 |
| 1131660 | 1868 | 1887 | 7256 | 7275 | GTGTGCTCCCGGATCCAGGC | 43 | 2231 |
| 1131688 | 1913 | 1932 | 7301 | 7320 | AATCACCAAGGAGGGAAAGA | 14 | 2232 |
| 1131716 | 1948 | 1967 | 7336 | 7355 | TTGCCTTCCATGCCCCAGCC | 19 | 2233 |
| 1131744 | 2003 | 2022 | 7391 | 7410 | GTTCCTGCGCCATCCTGGCG | 7 | 2234 |
| 1131772 | N/A | N/A | 88 | 107 | CCGAAAGTGTTGACTCCAAG | 64 | 2235 |
| 1131800 | N/A | N/A | 172 | 191 | GTCATGAGCAGAGGCCATGG | 43 | 2236 |
| 1131828 | N/A | N/A | 268 | 287 | TGTATCCACCCAGTCTGGTT | 70 | 2237 |
| 1131856 | N/A | N/A | 359 | 378 | GCAGAGATTTCTTCCCAAGA | 53 | 2238 |
| 1131884 | N/A | N/A | 451 | 470 | CAAGGGAGAGAAGAAGGCAG | 75 | 2239 |
| 1131912 | N/A | N/A | 597 | 616 | AGACTAGACTGCCCTGAGAC | 40 | 2240 |
| 1131940 | N/A | N/A | 684 | 703 | CACAGCCCATACCCTGCCCT | 57 | 2241 |
| 1131968 | N/A | N/A | 853 | 872 | GGCCCTGGCCTCTGTGTGGC | 70 | 2242 |
| 1131996 | N/A | N/A | 951 | 970 | CCCTCGCCCAGAGTCACCCA | 58 | 2243 |
| 1132024 | N/A | N/A | 1058 | 1077 | ATGGGCTGAATACCTCACAT | 44 | 2244 |
| 1132052 | N/A | N/A | 1191 | 1210 | GTGTCTGGAAGAATGAAAGC | 45 | 2245 |
| 1132080 | N/A | N/A | 1569 | 1588 | CAAGTCAGGCCCACCAGGGT | 47 | 2246 |
| 1132108 | N/A | N/A | 1708 | 1727 | AGGCAAGGATAGGGCACCAA | 44 | 2247 |
| 1132136 | N/A | N/A | 2117 | 2136 | AAACCAGAACTAGGACAGTA | 52 | 2248 |
| 1132164 | N/A | N/A | 2228 | 2247 | GGGCTTCATGAGATAATGCC | 63 | 2249 |
| 1132192 | N/A | N/A | 2335 | 2354 | CAGGAACCTAATACTGTTTG | 66 | 2250 |
| 1132220 | N/A | N/A | 2470 | 2489 | GTGTGCTATAGTGCCATCAG | 44 | 2251 |
| 1132248 | N/A | N/A | 2601 | 2620 | CACTTTGTGCTTTTGCTGGG | 59 | 2252 |
| 1132276 | N/A | N/A | 2721 | 2740 | GCAGTGAAAAATTTGCACAT | 41 | 2253 |
| 1132304 | N/A | N/A | 2826 | 2845 | CTTCTCTGGTTCTACATTGA | 52 | 2254 |
| 1132332 | N/A | N/A | 2933 | 2952 | CTTAATAATACTTGTTGAAT | 56 | 2255 |
| 1132360 | N/A | N/A | 3036 | 3055 | AGATAGCTGGAGTAGACTCC | 57 | 2256 |

TABLE 33-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1132388 | N/A | N/A | 3430 | 3449 | GTCTGGTCAGGAAAAGGACA | 74 | 2257 |
| 1132416 | N/A | N/A | 3625 | 3644 | CCTGCTCCAACTCCTCTGCG | 27 | 2258 |
| 1132444 | N/A | N/A | 3737 | 3756 | AGGCTTCCCTGCTCTACCCA | 61 | 2259 |
| 1132472 | N/A | N/A | 3883 | 3902 | AGGAGAGTAATGAGGCGGGA | 46 | 2260 |
| 1132500 | N/A | N/A | 4009 | 4028 | GGTTTACCCACCTGCAAAAT | 36 | 2261 |
| 1132528 | N/A | N/A | 4113 | 4132 | ACATGGTGGAAGGAAGAGCA | 35 | 2262 |
| 1132556 | N/A | N/A | 4301 | 4320 | TATTCTGTAGGCCCAGGGTT | 71 | 2263 |
| 1132584 | N/A | N/A | 4529 | 4548 | GGCCCGTTCCCAACCATCTG | 43 | 2264 |
| 1132612 | N/A | N/A | 4626 | 4645 | GTGAGCCACCCCTGGGCCTA | 80 | 2265 |
| 1132640 | N/A | N/A | 4848 | 4867 | TGCCTCCCTCTCATCTGCTT | 74 | 2266 |
| 1132668 | N/A | N/A | 5377 | 5396 | CCCCCACTTCCTAACCTCCC | 60 | 2267 |
| 1132696 | N/A | N/A | 5745 | 5764 | GAGGAGCCGCGGCCCCTGGG | 70 | 2268 |
| 1132724 | N/A | N/A | 6117 | 6136 | CCAAGCTCTCTTCCCGTCCC | 60 | 2269 |
| 1132752 | N/A | N/A | 6367 | 6386 | TTCCGCCTAACCCAGTGATC | 68 | 2270 |
| 1132780 | N/A | N/A | 6475 | 6494 | CCAGGCCCTGGGATTCTACC | 46 | 2271 |
| 1132808 | N/A | N/A | 6615 | 6634 | CAGAACCTGGCTCCCACACT | 83 | 2272 |
| 1132836 | N/A | N/A | 6706 | 6725 | TAGGCAAGGAGGCTGAGGTC | 80 | 2273 |
| 1132864 | N/A | N/A | 6820 | 6839 | ACGCTTGCCGCCCGGACGAT | 83 | 2274 |
| 1132892 | N/A | N/A | 7100 | 7119 | CCCTGGGTCGGAAACACGCA | 50† | 2275 |

TABLE 34

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130764 | 31 | 50 | 31 | 50 | TGGCATCCGTCCGTTGGTCC | 45 | 2276 |
| 1130792 | 77 | 96 | 77 | 96 | GACTCCAAGCTCACCAGCAG | 69 | 2277 |
| 1130820 | 134 | 153 | 501 | 520 | TCTTCAGCTTTGTACTTATG | 43 | 2278 |
| 1130848 | 169 | 188 | 3520 | 3539 | AGGGCTCCCCGGTGACAGTG | 30 | 2279 |
| 1130871 | 216 | 235 | 3567 | 3586 | GGTACATTTGTGGTACAGCT | 17 | 183 |
| 1130877 | 224 | 243 | 3575 | 3594 | CCCTTGTGGGTACATTTGTG | 45 | 2280 |
| 1130905 | 289 | 308 | 3796 | 3815 | ATCCCCATCGCTGGTCCTGA | 48 | 2281 |
| 1130933 | 330 | 349 | N/A | N/A | TTTGCTGCAGTGGTCTTTCA | 37 | 2282 |
| 1130961 | 403 | 422 | 4211 | 4230 | GGTGTTGTGGACAGAGACAG | 43 | 2283 |
| 1130989 | 445 | 464 | 4390 | 4409 | GAGGCTCAAAGCACTTCTCT | 32 | 2284 |

TABLE 34-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1131017 | 488 | 507 | 4433 | 4452 | GTTCTATACCATATCTCATT | 37 | 2285 |
| 1131045 | 531 | 550 | 4476 | 4495 | ATCAGGACCCTTGCACTGGC | 38 | 2286 |
| 1131073 | 564 | 583 | N/A | N/A | GCAGGCCTGGCTGGCCAGCC | 50 | 2287 |
| 1131101 | 604 | 623 | 4688 | 4707 | CCTCTAGGCAGCGACCCCCA | 41 | 2288 |
| 1131129 | 651 | 670 | 4735 | 4754 | GGCTCCGGTGTAGCCCACCG | 60 | 2289 |
| 1131157 | 707 | 726 | 4936 | 4955 | CGGTAGCTGAGCCCGCGGCC | 55 | 2290 |
| 1131185 | 761 | 780 | 4990 | 5009 | TCCGAGGCCCACGGCTGACA | 49 | 2291 |
| 1131213 | 836 | 855 | N/A | N/A | GGGTTCCGGCAGAAGGCGTG | 66 | 2292 |
| 1131241 | 899 | 918 | 5213 | 5232 | CAGTACTCCCAGCTCAGCCG | 38 | 2293 |
| 1131269 | 992 | 1011 | 5306 | 5325 | GCCGGCTGCGCGGGCATGAG | 51 | 2294 |
| 1131297 | 1070 | 1089 | 5489 | 5508 | TGCTCCCGCTTCGCCGGCAA | 30 | 2295 |
| 1131325 | 1115 | 1134 | 5534 | 5553 | CGCTGCCCGCAGCTCAGTGG | 45 | 2296 |
| 1131353 | 1150 | 1169 | 5569 | 5588 | CGACGCGGGTCATCGAAGAC | 67 | 2297 |
| 1131381 | 1223 | 1242 | 5642 | 5661 | GCGCAGAAACTGTGGCCCCA | 47 | 112 |
| 1131409 | 1310 | 1329 | 5970 | 5989 | AGCACCACCGTCAGATCCTC | 18 | 2298 |
| 1131437 | 1378 | 1397 | 6038 | 6057 | GCAAGCGGTAGGAGCGCACG | 50 | 2299 |
| 1131465 | 1455 | 1474 | 6198 | 6217 | GCAGCTGCCGTCCGCATCCT | 45 | 70 |
| 1131493 | 1547 | 1566 | 6290 | 6309 | CCCCAGCCGGCCACCTGGCA | 74 | 2300 |
| 1131521 | 1577 | 1596 | N/A | N/A | GCATATTCCTCCGCCCCCTC | 148 | 2301 |
| 1131549 | 1619 | 1638 | 6917 | 6936 | TCCAGGGAGAGGAACGGTAC | 130 | 2302 |
| 1131577 | 1745 | 1764 | 7133 | 7152 | TGGTCCTCACACACCAGCGG | 6† | 2303 |
| 1131605 | 1792 | 1811 | 7180 | 7199 | ATCCCCAGCTGATGATGCCT | 28 | 2304 |
| 1131633 | 1822 | 1841 | 7210 | 7229 | CGCCTGGCTTGTTGCGGTCA | 34 | 2305 |
| 1131661 | 1869 | 1888 | 7257 | 7276 | GGTGTGCTCCCGGATCCAGG | 39 | 2306 |
| 1131689 | 1914 | 1933 | 7302 | 7321 | GAATCACCAAGGAGGGAAAG | 21 | 2307 |
| 1131717 | 1949 | 1968 | 7337 | 7356 | CTTGCCTTCCATGCCCCAGC | 24 | 2308 |
| 1131745 | 2004 | 2023 | 7392 | 7411 | AGTTCCTGCGCCATCCTGGC | 25 | 2309 |
| 1131773 | N/A | N/A | 91 | 110 | TCACCGAAAGTGTTGACTCC | 87 | 2310 |
| 1131801 | N/A | N/A | 175 | 194 | CAGGTCATGAGCAGAGGCCA | 70 | 2311 |
| 1131829 | N/A | N/A | 271 | 290 | CCTTGTATCCACCCAGTCTG | 76 | 2312 |
| 1131857 | N/A | N/A | 365 | 384 | AGAAATGCAGAGATTTCTTC | 91 | 2313 |
| 1131885 | N/A | N/A | 454 | 473 | CTACAAGGGAGAGAAGAAGG | 88 | 2314 |
| 1131913 | N/A | N/A | 600 | 619 | ACTAGACTAGACTGCCCTGA | 77 | 2315 |
| 1131941 | N/A | N/A | 687 | 706 | AGACACAGCCCATACCCTGC | 41 | 2316 |
| 1131969 | N/A | N/A | 856 | 875 | GAAGGCCCTGGCCTCTGTGT | 31 | 2317 |

TABLE 34-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1131997 | N/A | N/A | 954 | 973 | AATCCCTCGCCCAGAGTCAC | 90 | 2318 |
| 1132025 | N/A | N/A | 1061 | 1080 | GTGATGGGCTGAATACCTCA | 49 | 2319 |
| 1132053 | N/A | N/A | 1194 | 1213 | TTAGTGTCTGGAAGAATGAA | 60 | 2320 |
| 1132081 | N/A | N/A | 1572 | 1591 | CACCAAGTCAGGCCCACCAG | 80 | 2321 |
| 1132109 | N/A | N/A | 1711 | 1730 | ATTAGGCAAGGATAGGGCAC | 32 | 2322 |
| 1132137 | N/A | N/A | 2120 | 2139 | ACCAAACCAGAACTAGGACA | 56 | 2323 |
| 1132165 | N/A | N/A | 2250 | 2269 | CTTCTTCAGAGGAATTGTCG | 59 | 2324 |
| 1132193 | N/A | N/A | 2338 | 2357 | TCACAGGAACCTAATACTGT | 61 | 2325 |
| 1132221 | N/A | N/A | 2473 | 2492 | GGTGTGTGCTATAGTGCCAT | 59 | 2326 |
| 1132249 | N/A | N/A | 2604 | 2623 | TCACACTTTGTGCTTTTGCT | 35 | 2327 |
| 1132277 | N/A | N/A | 2724 | 2743 | AGAGCAGTGAAAAATTTGCA | 44 | 2328 |
| 1132305 | N/A | N/A | 2829 | 2848 | ATTCTTCTCTGGTTCTACAT | 56 | 2329 |
| 1132333 | N/A | N/A | 2936 | 2955 | GCACTTAATAATACTTGTTG | 41 | 2330 |
| 1132361 | N/A | N/A | 3039 | 3058 | GTCAGATAGCTGGAGTAGAC | 36 | 2331 |
| 1132389 | N/A | N/A | 3433 | 3452 | AGGGTCTGGTCAGGAAAAGG | 47 | 2332 |
| 1132417 | N/A | N/A | 3628 | 3647 | GCCCCTGCTCCAACTCCTCT | 63 | 2333 |
| 1132445 | N/A | N/A | 3740 | 3759 | ACAAGGCTTCCCTGCTCTAC | 102 | 2334 |
| 1132473 | N/A | N/A | 3886 | 3905 | ACCAGGAGAGTAATGAGGCG | 47 | 2335 |
| 1132501 | N/A | N/A | 4012 | 4031 | CTTGGTTTACCCACCTGCAA | 59 | 2336 |
| 1132529 | N/A | N/A | 4116 | 4135 | TGGACATGGTGGAAGGAAGA | 94 | 2337 |
| 1132557 | N/A | N/A | 4304 | 4323 | ACCTATTCTGTAGGCCCAGG | 53 | 2338 |
| 1132585 | N/A | N/A | 4532 | 4551 | CCTGGCCCGTTCCCAACCAT | 64 | 2339 |
| 1132613 | N/A | N/A | 4629 | 4648 | GCAGTGAGCCACCCCTGGGC | 72 | 2340 |
| 1132641 | N/A | N/A | 4851 | 4870 | TCCTGCCTCCCTCTCATCTG | 66 | 2341 |
| 1132669 | N/A | N/A | 5380 | 5399 | CCCCCCCCACTTCCTAACCT | 84 | 2342 |
| 1132697 | N/A | N/A | 5748 | 5767 | ACGGAGGAGCCGCGGCCCCT | 52 | 2343 |
| 1132725 | N/A | N/A | 6120 | 6139 | GCCCCAAGCTCTCTTCCCGT | 120 | 2344 |
| 1132753 | N/A | N/A | 6370 | 6389 | TTCTTCCGCCTAACCCAGTG | 71 | 2345 |
| 1132781 | N/A | N/A | 6478 | 6497 | ATCCCAGGCCCTGGGATTCT | 79 | 2346 |
| 1132809 | N/A | N/A | 6618 | 6637 | TCGCAGAACCTGGCTCCCAC | 60 | 2347 |
| 1132837 | N/A | N/A | 6709 | 6728 | TCATAGGCAAGGAGGCTGAG | 78 | 2348 |
| 1132865 | N/A | N/A | 6836 | 6855 | CACACCCCATCTGACAACGC | 82 | 2349 |
| 1132893 | N/A | N/A | 7103 | 7122 | TCACCCTGGGTCGGAAACAC | 73† | 2350 |

TABLE 35

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130793 | 78 | 97 | 78 | 97 | TGACTCCAAGCTCACCAGCA | 34 | 239 |
| 1130821 | 135 | 154 | 502 | 521 | CTCTTCAGCTTTGTACTTAT | 42 | 240 |
| 1130849 | 171 | 190 | 3522 | 3541 | GCAGGGCTCCCCGGTGACAG | 34 | 241 |
| 1130871 | 216 | 235 | 3567 | 3586 | GGTACATTTGTGGTACAGCT | 11 | 183 |
| 1130878 | 225 | 244 | 3576 | 3595 | GCCCTTGTGGGTACATTTGT | 33 | 242 |
| 1130906 | 290 | 309 | 3797 | 3816 | TATCCCCATCGCTGGTCCTG | 26 | 243 |
| 1130934 | 331 | 350 | N/A | N/A | GTTTGCTGCAGTGGTCTTTC | 21 | 244 |
| 1130962 | 404 | 423 | 4212 | 4231 | AGGTGTTGTGGACAGAGACA | 45 | 245 |
| 1130990 | 446 | 465 | 4391 | 4410 | TGAGGCTCAAAGCACTTCTC | 18 | 246 |
| 1131018 | 489 | 508 | 4434 | 4453 | AGTTCTATACCATATCTCAT | 13 | 247 |
| 1131046 | 532 | 551 | 4477 | 4496 | CATCAGGACCCTTGCACTGG | 26 | 248 |
| 1131074 | 566 | 585 | N/A | N/A | CGGCAGGCCTGGCTGGCCAG | 70 | 249 |
| 1131102 | 606 | 625 | 4690 | 4709 | CACCTCTAGGCAGCGACCCC | 28 | 250 |
| 1131130 | 653 | 672 | 4737 | 4756 | AAGGCTCCGGTGTAGCCCAC | 66 | 251 |
| 1131158 | 709 | 728 | 4938 | 4957 | CGCGGTAGCTGAGCCCGCGG | 98 | 252 |
| 1131186 | 762 | 781 | 4991 | 5010 | CTCCGAGGCCCACGGCTGAC | 40 | 253 |
| 1131214 | 839 | 858 | N/A | N/A | TCCGGGTTCCGGCAGAAGGC | 39 | 55 |
| 1131242 | 902 | 921 | 5216 | 5235 | TCGCAGTACTCCCAGCTCAG | 16 | 254 |
| 1131270 | 993 | 1012 | 5307 | 5326 | TGCCGGCTGCGCGGGCATGA | 41 | 255 |
| 1131298 | 1071 | 1090 | 5490 | 5509 | CTGCTCCCGCTTCGCCGGCA | 27 | 256 |
| 1131326 | 1116 | 1135 | 5535 | 5554 | CCGCTGCCCGCAGCTCAGTG | 34 | 257 |
| 1131354 | 1152 | 1171 | 5571 | 5590 | AACGACGCGGGTCATCGAAG | 36 | 258 |
| 1131382 | 1224 | 1243 | 5643 | 5662 | GGCGCAGAAACTGTGGCCCC | 59 | 259 |
| 1131410 | 1311 | 1330 | 5971 | 5990 | GAGCACCACCGTCAGATCCT | 18 | 260 |
| 1131438 | 1380 | 1399 | 6040 | 6059 | GTGCAAGCGGTAGGAGCGCA | 40 | 261 |
| 1131466 | 1459 | 1478 | 6202 | 6221 | GCGCGCAGCTGCCGTCCGCA | 36 | 262 |
| 1131494 | 1548 | 1567 | 6291 | 6310 | GCCCCAGCCGGCCACCTGGC | 62 | 263 |
| 1131522 | 1578 | 1597 | N/A | N/A | GGCATATTCCTCCGCCCCCT | 79 | 264 |
| 1131550 | 1620 | 1639 | 6918 | 6937 | CTCCAGGGAGAGGAACGGTA | 74 | 265 |
| 1131578 | 1746 | 1765 | 7134 | 7153 | TTGGTCCTCACACACCAGCG | 8† | 266 |
| 1131606 | 1793 | 1812 | 7181 | 7200 | GATCCCCAGCTGATGATGCC | 31 | 267 |
| 1131634 | 1823 | 1842 | 7211 | 7230 | ACGCCTGGCTTGTTGCGGTC | 31 | 268 |
| 1131662 | 1870 | 1889 | 7258 | 7277 | CGGTGTGCTCCCGGATCCAG | 22 | 269 |
| 1131690 | 1915 | 1934 | 7303 | 7322 | GGAATCACCAAGGAGGGAAA | 20 | 270 |
| 1131718 | 1950 | 1969 | 7338 | 7357 | TCTTGCCTTCCATGCCCCAG | 17 | 271 |
| 1131746 | 2005 | 2024 | 7393 | 7412 | GAGTTCCTGCGCCATCCTGG | 7 | 159 |

TABLE 35-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131774 | N/A | N/A | 94 | 113 | CACTCACCGAAAGTGTTGAC | 78 | 272 |
| 1131802 | N/A | N/A | 178 | 197 | CCACAGGTCATGAGCAGAGG | 58 | 273 |
| 1131830 | N/A | N/A | 274 | 293 | TGCCCTTGTATCCACCCAGT | 97 | 274 |
| 1131858 | N/A | N/A | 368 | 387 | CCCAGAAATGCAGAGATTTC | 98 | 275 |
| 1131886 | N/A | N/A | 457 | 476 | AATCTACAAGGGAGAGAAGA | 79 | 276 |
| 1131914 | N/A | N/A | 603 | 622 | GGCACTAGACTAGACTGCCC | 67 | ?77 |
| 1131942 | N/A | N/A | 690 | 709 | CTTAGACACAGCCCATACCC | 60 | 278 |
| 1131970 | N/A | N/A | 859 | 878 | ATTGAAGGCCCTGGCCTCTG | 62 | 279 |
| 1131998 | N/A | N/A | 957 | 976 | TCAAATCCCTCGCCCAGAGT | 81 | 280 |
| 1132026 | N/A | N/A | 1064 | 1083 | CAGGTGATGGGCTGAATACC | 81 | 281 |
| 1132054 | N/A | N/A | 1197 | 1216 | AATTTAGTGTCTGGAAGAAT | 70 | 282 |
| 1132082 | N/A | N/A | 1575 | 1594 | CCCCACCAAGTCAGGCCCAC | 78 | 283 |
| 1132110 | N/A | N/A | 1747 | 1766 | TGGACGGACAGAGAGGAGGG | 71 | 284 |
| 1132138 | N/A | N/A | 2123 | 2142 | AGGACCAAACCAGAACTAGG | 58 | 285 |
| 1132166 | N/A | N/A | 2253 | 2272 | TGTCTTCTTCAGAGGAATTG | 66 | 286 |
| 1132194 | N/A | N/A | 2341 | 2360 | GGCTCACAGGAACCTAATAC | 47 | 287 |
| 1132222 | N/A | N/A | 2479 | 2498 | GATTCAGGTGTGTGCTATAG | 53 | 288 |
| 1132250 | N/A | N/A | 2609 | 2628 | GTTTTTCACACTTTGTGCTT | 51 | 289 |
| 1132278 | N/A | N/A | 2734 | 2753 | GGGCATGCACAGAGCAGTGA | 52 | 290 |
| 1132306 | N/A | N/A | 2832 | 2851 | CTCATTCTTCTCTGGTTCTA | 48 | 291 |
| 1132334 | N/A | N/A | 2939 | 2958 | TAGGCACTTAATAATACTTG | 56 | 292 |
| 1132362 | N/A | N/A | 3042 | 3061 | GGAGTCAGATAGCTGGAGTA | 69 | 293 |
| 1132390 | N/A | N/A | 3436 | 3455 | CTCAGGGTCTGGTCAGGAAA | 70 | 294 |
| 1132418 | N/A | N/A | 3631 | 3650 | CAGGCCCCTGCTCCAACTCC | 65 | 295 |
| 1132446 | N/A | N/A | 3743 | 3762 | GAGACAAGGCTTCCCTGCTC | 71 | 296 |
| 1132474 | N/A | N/A | 3889 | 3908 | GATACCAGGAGAGTAATGAG | 55 | 297 |
| 1132502 | N/A | N/A | 4015 | 4034 | AAGCTTGGTTTACCCACCTG | 46 | 298 |
| 1132530 | N/A | N/A | 4122 | 4141 | GAGAGATGGACATGGTGGAA | 67 | 299 |
| 1132558 | N/A | N/A | 4310 | 4329 | CCAGCAACCTATTCTGTAGG | 56 | 300 |
| 1132586 | N/A | N/A | 4535 | 4554 | CTCCCTGGCCCGTTCCCAAC | 68 | 301 |
| 1132614 | N/A | N/A | 4632 | 4651 | AACGCAGTGAGCCACCCCTG | 32 | 302 |
| 1132642 | N/A | N/A | 4859 | 4878 | CTGGGCTCTCCTGCCTCCCT | 31 | 303 |
| 1132670 | N/A | N/A | 5383 | 5402 | TTCCCCCCCCACTTCCTAA | 106 | 304 |
| 1132698 | N/A | N/A | 5751 | 5770 | GAGACGGAGGAGCCGCGGCC | 72 | 305 |
| 1132726 | N/A | N/A | 6158 | 6177 | AACCCGGGCGGAGAGGAGCG | 98 | 306 |

TABLE 35-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132754 | N/A | N/A | 6373 | 6392 | GGCTTCTTCCGCCTAACCCA | 72 | 307 |
| 1132782 | N/A | N/A | 6481 | 6500 | TGAATCCCAGGCCCTGGGAT | 101 | 308 |
| 1132810 | N/A | N/A | 6621 | 6640 | GAGTCGCAGAACCTGGCTCC | 71 | 309 |
| 1132838 | N/A | N/A | 6712 | 6731 | ATTTCATAGGCAAGGAGGCT | 66 | 310 |
| 1132866 | N/A | N/A | 6839 | 6858 | CTTCACACCCCATCTGACAA | 108 | 311 |
| 1132894 | N/A | N/A | 7106 | 7125 | GAATCACCCTGGGTCGGAAA | 76† | 312 |

TABLE 36

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130794 | 79 | 98 | 79 | 98 | TTGACTCCAAGCTCACCAGC | 41 | 315 |
| 1130822 | 136 | 155 | 503 | 522 | GCTCTTCAGCTTTGTACTTA | 34 | 316 |
| 1130850 | 172 | 191 | 3523 | 3542 | GGCAGGGCTCCCCGGTGACA | 19 | 317 |
| 1130871 | 216 | 235 | 3567 | 3586 | GGTACATTTGTGGTACAGCT | 12 | 183 |
| 1130879 | 226 | 245 | 3577 | 3596 | GGCCCTTGTGGGTACATTTG | 66 | 318 |
| 1130907 | 292 | 311 | 3799 | 3818 | AGTATCCCCATCGCTGGTCC | 19 | 319 |
| 1130935 | 332 | 351 | N/A | N/A | TGTTTGCTGCAGTGGTCTTT | 27 | 320 |
| 1130963 | 405 | 424 | 4213 | 4232 | GAGGTGTTGTGGACAGAGAC | 47 | 321 |
| 1130991 | 447 | 466 | 4392 | 4411 | CTGAGGCTCAAAGCACTTCT | 29 | 322 |
| 1131019 | 493 | 512 | 4438 | 4457 | GCTCAGTTCTATACCATATC | 17 | 323 |
| 1131047 | 533 | 552 | 4478 | 4497 | GCATCAGGACCCTTGCACTG | 26 | 324 |
| 1131075 | 568 | 587 | N/A | N/A | TGCGGCAGGCCTGGCTGGCC | 50 | 325 |
| 1131103 | 607 | 626 | 4691 | 4710 | CCACCTCTAGGCAGCGACCC | 29 | 326 |
| 1131131 | 654 | 673 | 4738 | 4757 | GAAGGCTCCGGTGTAGCCCA | 56 | 327 |
| 1131159 | 710 | 729 | 4939 | 4958 | CCGCGGTAGCTGAGCCCGCG | 77 | 328 |
| 1131187 | 763 | 782 | 4992 | 5011 | CCTCCGAGGCCCACGGCTGA | 47 | 329 |
| 1131215 | 840 | 859 | N/A | N/A | GTCCGGGTTCCGGCAGAAGG | 38 | 313 |
| 1131243 | 903 | 922 | 5217 | 5236 | GTCGCAGTACTCCCAGCTCA | 12 | 330 |
| 1131271 | 994 | 1013 | 5308 | 5327 | GTGCCGGCTGCGCGGGCATG | 63 | 331 |
| 1131299 | 1072 | 1091 | 5491 | 5510 | GCTGCTCCCGCTTCGCCGGC | 26 | 332 |
| 1131327 | 1117 | 1136 | 5536 | 5555 | GCCGCTGCCCGCAGCTCAGT | 30 | 333 |
| 1131355 | 1153 | 1172 | 5572 | 5591 | CAACGACGCGGGTCATCGAA | 53 | 334 |
| 1131383 | 1225 | 1244 | 5644 | 5663 | CGGCGCAGAAACTGTGGCCC | 46 | 335 |

TABLE 36-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131411 | 1312 | 1331 | 5972 | 5991 | CGAGCACCACCGTCAGATCC | 17 | 336 |
| 1131439 | 1381 | 1400 | 6041 | 6060 | CGTGCAAGCGGTAGGAGCGC | 27 | 337 |
| 1131467 | 1460 | 1479 | 6203 | 6222 | AGCGCGCAGCTGCCGTCCGC | 42 | 338 |
| 1131495 | 1549 | 1568 | 6292 | 6311 | GGCCCCAGCCGGCCACCTGG | 82 | 339 |
| 1131523 | 1579 | 1598 | N/A | N/A | TGGCATATTCCTCCGCCCCC | 67 | 340 |
| 1131551 | 1621 | 1640 | 6919 | 6938 | GCTCCAGGGAGAGGAACGGT | 66 | 341 |
| 1131579 | 1747 | 1766 | 7135 | 7154 | CTTGGTCCTCACACACCAGC | 36† | 342 |
| 1131607 | 1794 | 1813 | 7182 | 7201 | CGATCCCCAGCTGATGATGC | 41 | 343 |
| 1131635 | 1839 | 1858 | 7227 | 7246 | GGCCACATCGGTGTAGACGC | 18 | 86 |
| 1131663 | 1871 | 1890 | 7259 | 7278 | ACGGTGTGCTCCCGGATCCA | 16 | 344 |
| 1131691 | 1916 | 1935 | 7304 | 7323 | CGGAATCACCAAGGAGGGAA | 15 | 345 |
| 1131719 | 1951 | 1970 | 7339 | 7358 | ATCTTGCCTTCCATGCCCCA | 28 | 346 |
| 1131747 | 2006 | 2025 | 7394 | 7413 | TGAGTTCCTGCGCCATCCTG | 17 | 347 |
| 1131775 | N/A | N/A | 97 | 116 | CAGCACTCACCGAAAGTGTT | 84 | 348 |
| 1131803 | N/A | N/A | 181 | 200 | GACCCACAGGTCATGAGCAG | 87 | 349 |
| 1131831 | N/A | N/A | 277 | 296 | CTGTGCCCTTGTATCCACCC | 61 | 350 |
| 1131859 | N/A | N/A | 371 | 390 | CAGCCCAGAAATGCAGAGAT | 69 | 351 |
| 1131887 | N/A | N/A | 460 | 479 | TGGAATCTACAAGGGAGAGA | 89 | 352 |
| 1131915 | N/A | N/A | 606 | 625 | GTAGGCACTAGACTAGACTG | 52 | 353 |
| 1131943 | N/A | N/A | 693 | 712 | GCACTTAGACACAGCCCATA | 64 | 354 |
| 1131971 | N/A | N/A | 862 | 881 | CCCATTGAAGGCCCTGGCCT | 49 | 355 |
| 1131999 | N/A | N/A | 960 | 979 | AACTCAAATCCCTCGCCCAG | 59 | 356 |
| 1132027 | N/A | N/A | 1067 | 1086 | CACCAGGTGATGGGCTGAAT | 49 | 357 |
| 1132055 | N/A | N/A | 1200 | 1219 | GGTAATTTAGTGTCTGGAAG | 46 | 358 |
| 1132083 | N/A | N/A | 1578 | 1597 | CAACCCCACCAAGTCAGGCC | 69 | 359 |
| 1132111 | N/A | N/A | 1750 | 1769 | GGATGGACGGACAGAGAGGA | 63 | 360 |
| 1132139 | N/A | N/A | 2126 | 2145 | CCAAGGACCAAACCAGAACT | 56 | 361 |
| 1132167 | N/A | N/A | 2256 | 2275 | CTGTGTCTTCTTCAGAGGAA | 50 | 362 |
| 1132195 | N/A | N/A | 2370 | 2389 | TGTTGGTTGATGAAAATGTT | 54 | 363 |
| 1132223 | N/A | N/A | 2482 | 2501 | CTTGATTCAGGTGTGTGCTA | 50 | 364 |
| 1132251 | N/A | N/A | 2628 | 2647 | TCAGTCTACTTAGTGCAACG | 51 | 365 |
| 1132279 | N/A | N/A | 2739 | 2758 | TTTGTGGGCATGCACAGAGC | 53 | 366 |
| 1132307 | N/A | N/A | 2835 | 2854 | ATCCTCATTCTTCTCTGGTT | 53 | 367 |
| 1132335 | N/A | N/A | 2942 | 2961 | AAGTAGGCACTTAATAATAC | 67 | 368 |
| 1132363 | N/A | N/A | 3045 | 3064 | TCAGGAGTCAGATAGCTGGA | 77 | 369 |

TABLE 36-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132391 | N/A | N/A | 3439 | 3458 | TCCCTCAGGGTCTGGTCAGG | 54 | 370 |
| 1132419 | N/A | N/A | 3637 | 3656 | GTCTCCCAGGCCCCTGCTCC | 56 | 371 |
| 1132447 | N/A | N/A | 3749 | 3768 | TAGAAAGAGACAAGGCTTCC | 61 | 372 |
| 1132475 | N/A | N/A | 3892 | 3911 | GGTGATACCAGGAGAGTAAT | 47 | 373 |
| 1132503 | N/A | N/A | 4018 | 4037 | TCCAAGCTTGGTTTACCCAC | 38 | 374 |
| 1132531 | N/A | N/A | 4125 | 4144 | TCTGAGAGATGGACATGGTG | 68 | 375 |
| 1132559 | N/A | N/A | 4313 | 4332 | TATCCAGCAACCTATTCTGT | 69 | 376 |
| 1132587 | N/A | N/A | 4538 | 4557 | CTCCTCCCTGGCCCGTTCCC | 70 | 377 |
| 1132615 | N/A | N/A | 4635 | 4654 | GGGAACGCAGTGAGCCACCC | 49 | 378 |
| 1132643 | N/A | N/A | 4862 | 4881 | AGGCTGGGCTCTCCTGCCTC | 75 | 379 |
| 1132671 | N/A | N/A | 5386 | 5405 | TCCTTCCCCCCCCCACTTCC | 92 | 380 |
| 1132699 | N/A | N/A | 5754 | 5773 | TGGGAGACGGAGGAGCCGCG | 61 | 381 |
| 1132727 | N/A | N/A | 6161 | 6180 | GCTAACCCGGGCGGAGAGGA | 101 | 382 |
| 1132755 | N/A | N/A | 6376 | 6395 | GCGGGCTTCTTCCGCCTAAC | 56 | 383 |
| 1132783 | N/A | N/A | 6484 | 6503 | CAGTGAATCCCAGGCCCTGG | 66 | 384 |
| 1132811 | N/A | N/A | 6624 | 6643 | CCAGAGTCGCAGAACCTGGC | 56 | 385 |
| 1132839 | N/A | N/A | 6715 | 6734 | TCAATTTCATAGGCAAGGAG | 64 | 386 |
| 1132867 | N/A | N/A | 6842 | 6861 | CTTCTTCACACCCCATCTGA | 88 | 387 |
| 1132895 | N/A | N/A | 7109 | 7128 | CCGGAATCACCCTGGGTCGG | 28† | 388 |

TABLE 37

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130795 | 80 | 99 | 80 | 99 | GTTGACTCCAAGCTCACCAG | 40 | 389 |
| 1130823 | 138 | 157 | 505 | 524 | GTGCTCTTCAGCTTTGTACT | 38 | 390 |
| 1130851 | 174 | 193 | 3525 | 3544 | GTGGCAGGGCTCCCCGGTGA | 80 | 391 |
| 1130871 | 216 | 235 | 3567 | 3586 | GGTACATTTGTGGTACAGCT | 11 | 183 |
| 1130880 | 228 | 247 | 3579 | 3598 | CCGGCCCTTGTGGGTACATT | 42 | 392 |
| 1130908 | 293 | 312 | 3800 | 3819 | CAGTATCCCCATCGCTGGTC | 24 | 393 |
| 1130936 | 333 | 352 | N/A | N/A | GTGTTTGCTGCAGTGGTCTT | 32 | 394 |
| 1130964 | 406 | 425 | 4214 | 4233 | TGAGGTGTTGTGGACAGAGA | 112 | 395 |
| 1130992 | 449 | 468 | 4394 | 4413 | AGCTGAGGCTCAAAGCACTT | 45 | 396 |
| 1131020 | 494 | 513 | 4439 | 4458 | TGCTCAGTTCTATACCATAT | 23 | 397 |

TABLE 37-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
| --- | --- | --- | --- | --- | --- | --- | --- |
| 1131048 | 535 | 554 | 4480 | 4499 | GGGCATCAGGACCCTTGCAC | 81 | 398 |
| 1131076 | 569 | 588 | N/A | N/A | GTGCGGCAGGCCTGGCTGGC | 54 | 399 |
| 1131104 | 609 | 628 | 4693 | 4712 | CTCCACCTCTAGGCAGCGAC | 45 | 400 |
| 1131132 | 655 | 674 | 4739 | 4758 | AGAAGGCTCCGGTGTAGCCC | 69 | 401 |
| 1131160 | 711 | 730 | 4940 | 4959 | GCCGCGGTAGCTGAGCCCGC | 97 | 402 |
| 1131188 | 765 | 784 | 4994 | 5013 | GGCCTCCGAGGCCCACGGCT | 45 | 403 |
| 1131216 | 843 | 862 | N/A | N/A | GTTGTCCGGGTTCCGGCAGA | 20 | 404 |
| 1131244 | 904 | 923 | 5218 | 5237 | GGTCGCAGTACTCCCAGCTC | 32 | 405 |
| 1131272 | 996 | 1015 | 5310 | 5329 | CGGTGCCGGCTGCGCGGGCA | 59 | 406 |
| 1131300 | 1073 | 1092 | 5492 | 5511 | GGCTGCTCCCGCTTCGCCGG | 50 | 407 |
| 1131328 | 1118 | 1137 | 5537 | 5556 | AGCCGCTGCCCGCAGCTCAG | 83 | 408 |
| 1131356 | 1155 | 1174 | 5574 | 5593 | GCCAACGACGCGGGTCATCG | 38 | 409 |
| 1131384 | 1227 | 1246 | 5646 | 5665 | GCCGGCGCAGAAACTGTGGC | 68 | 410 |
| 1131412 | 1313 | 1332 | 5973 | 5992 | CCGAGCACCACCGTCAGATC | 47 | 411 |
| 1131440 | 1399 | 1418 | 6059 | 6078 | TGACGGGCGAGAAGGCCTCG | 59 | 412 |
| 1131468 | 1462 | 1481 | 6205 | 6224 | GGAGCGCGCAGCTGCCGTCC | 44 | 413 |
| 1131496 | 1550 | 1569 | 6293 | 6312 | TGGCCCCAGCCGGCCACCTG | 96 | 414 |
| 1131524 | 1581 | 1600 | 6879 | 6898 | GCTGGCATATTCCTCCGCCC | 64 | 415 |
| 1131552 | 1622 | 1641 | 6920 | 6939 | CGCTCCAGGGAGAGGAACGG | 107 | 416 |
| 1131580 | 1748 | 1767 | 7136 | 7155 | GCTTGGTCCTCACACACCAG | 10† | 80 |
| 1131608 | 1795 | 1814 | 7183 | 7202 | CCGATCCCCAGCTGATGATG | 28 | 417 |
| 1131636 | 1842 | 1861 | 7230 | 7249 | GTAGGCCACATCGGTGTAGA | 51 | 418 |
| 1131664 | 1873 | 1892 | 7261 | 7280 | AAACGGTGTGCTCCCGGATC | 81 | 419 |
| 1131692 | 1917 | 1936 | 7305 | 7324 | GCGGAATACCAAGGAGGGA | 18 | 420 |
| 1131720 | 1952 | 1971 | 7340 | 7359 | AATCTTGCCTTCCATGCCCC | 30 | 421 |
| 1131748 | 2007 | 2026 | 7395 | 7414 | TTGAGTTCCTGCGCCATCCT | 11 | 422 |
| 1131776 | N/A | N/A | 100 | 119 | CCACAGCACTCACCGAAAGT | 116 | 423 |
| 1131804 | N/A | N/A | 184 | 203 | CTGGACCCACAGGTCATGAG | 48 | 424 |
| 1131832 | N/A | N/A | 280 | 299 | AGGCTGTGCCCTTGTATCCA | 45 | 425 |
| 1131860 | N/A | N/A | 374 | 393 | TCACAGCCCAGAAATGCAGA | 144 | 426 |
| 1131888 | N/A | N/A | 463 | 482 | AGGTGGAATCTACAAGGGAG | 72 | 427 |
| 1131916 | N/A | N/A | 609 | 628 | CAGGTAGGCACTAGACTAGA | 85 | 428 |
| 1131944 | N/A | N/A | 696 | 715 | TGGGCACTTAGACACAGCCC | 56 | 429 |
| 1131972 | N/A | N/A | 865 | 884 | TTGCCCATTGAAGGCCCTGG | 60 | 430 |
| 1132000 | N/A | N/A | 963 | 982 | GAGAACTCAAATCCCTCGCC | 77 | 431 |

TABLE 37-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132028 | N/A | N/A | 1070 | 1089 | ATGCACCAGGTGATGGGCTG | 65 | 432 |
| 1132056 | N/A | N/A | 1203 | 1222 | GTAGGTAATTTAGTGTCTGG | 89 | 433 |
| 1132084 | N/A | N/A | 1581 | 1600 | ACTCAACCCCACCAAGTCAG | 75 | 434 |
| 1132112 | N/A | N/A | 1753 | 1772 | ATGGGATGGACGGACAGAGA | 60 | 435 |
| 1132140 | N/A | N/A | 2129 | 2148 | TTGCCAAGGACCAAACCAGA | 87 | 436 |
| 1132168 | N/A | N/A | 2259 | 2278 | TGCCTGTGTCTTCTTCAGAG | 51 | 437 |
| 1132196 | N/A | N/A | 2373 | 2392 | TGCTGTTGGTTGATGAAAAT | 51 | 438 |
| 1132224 | N/A | N/A | 2485 | 2504 | ACACTTGATTCAGGTGTGTG | 64 | 439 |
| 1132252 | N/A | N/A | 2634 | 2653 | TCCTTCTCAGTCTACTTAGT | 53 | 440 |
| 1132280 | N/A | N/A | 2742 | 2761 | CCATTTGTGGGCATGCACAG | 60 | 441 |
| 1132308 | N/A | N/A | 2838 | 2857 | TTGATCCTCATTCTTCTCTG | 44 | 442 |
| 1132336 | N/A | N/A | 2950 | 2969 | TTGCCACAAAGTAGGCACTT | 66 | 443 |
| 1132364 | N/A | N/A | 3048 | 3067 | GGTTCAGGAGTCAGATAGCT | 74 | 444 |
| 1132392 | N/A | N/A | 3442 | 3461 | CTGTCCCTCAGGGTCTGGTC | 74 | 445 |
| 1132420 | N/A | N/A | 3640 | 3659 | CATGTCTCCCAGGCCCTGC | 49 | 446 |
| 1132448 | N/A | N/A | 3752 | 3771 | CTGTAGAAAGAGACAAGGCT | 52 | 447 |
| 1132476 | N/A | N/A | 3895 | 3914 | TCTGGTGATACCAGGAGAGT | 50 | 448 |
| 1132504 | N/A | N/A | 4021 | 4040 | GTTTCCAAGCTTGGTTTACC | 61 | 449 |
| 1132532 | N/A | N/A | 4128 | 4147 | TGGTCTGAGAGATGGACATG | 40 | 450 |
| 1132560 | N/A | N/A | 4316 | 4335 | GAGTATCCAGCAACCTATTC | 46 | 451 |
| 1132588 | N/A | N/A | 4541 | 4560 | ACGCTCCTCCCTGGCCCGTT | 85 | 452 |
| 1132616 | N/A | N/A | 4638 | 4657 | GGAGGGAACGCAGTGAGCCA | 83 | 453 |
| 1132644 | N/A | N/A | 4866 | 4885 | GCCAAGGCTGGGCTCTCCTG | 43 | 454 |
| 1132672 | N/A | N/A | 5389 | 5408 | TCCTCCTTCCCCCCCCCACT | 99 | 455 |
| 1132700 | N/A | N/A | 5757 | 5776 | CGCTGGGAGACGGAGGAGCC | 98 | 456 |
| 1132728 | N/A | N/A | 6164 | 6183 | AGAGCTAACCCGGGCGGAGA | 69 | 457 |
| 1132756 | N/A | N/A | 6379 | 6398 | GTCGCGGGCTTCTTCCGCCT | 46 | 458 |
| 1132784 | N/A | N/A | 6487 | 6506 | CAGCAGTGAATCCCAGGCCC | 63 | 459 |
| 1132812 | N/A | N/A | 6627 | 6646 | CATCCAGAGTCGCAGAACCT | 48 | 460 |
| 1132840 | N/A | N/A | 6718 | 6737 | AATTCAATTTCATAGGCAAG | 69 | 461 |
| 1132868 | N/A | N/A | 6845 | 6864 | CGCCTTCTTCACACCCCATC | 97 | 462 |
| 1132896 | N/A | N/A | 7112 | 7131 | CCTCCGGAATCACCCTGGGT | 53† | 463 |

TABLE 38

Reduction of FXII RNA by 5-10-5 MOE gapmers with mixed PO/PS internucleoside linkages
(Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130796 | 82 | 101 | 82 | 101 | GTGTTGACTCCAAGCTCACC | 34 | 465 |
| 1130824 | 139 | 158 | 506 | 525 | TGTGCTCTTCAGCTTTGTAC | 21 | 466 |
| 1130852 | 175 | 194 | 3526 | 3545 | AGTGGCAGGGCTCCCCGGTG | 59 | 467 |
| 1130871 | 216 | 235 | 3567 | 3586 | GGTACATTTGTGGTACAGCT | 16 | 183 |
| 1130881 | 229 | 248 | 3580 | 3599 | GCCGGCCCTTGTGGGTACAT | 52 | 468 |
| 1130909 | 294 | 313 | 3801 | 3820 | ACAGTATCCCCATCGCTGGT | 46 | 469 |
| 1130937 | 334 | 353 | 4142 | 4161 | TGTGTTTGCTGCAGTGGTCT | 63 | 470 |
| 1130965 | 407 | 426 | 4215 | 4234 | GTGAGGTGTTGTGGACAGAG | 40 | 471 |
| 1130993 | 450 | 469 | 4395 | 4414 | AAGCTGAGGCTCAAAGCACT | 37 | 472 |
| 1131021 | 495 | 514 | 4440 | 4459 | TTGCTCAGTTCTATACCATA | 16 | 473 |
| 1131049 | 536 | 555 | 4481 | 4500 | TGGGCATCAGGACCCTTGCA | 47 | 474 |
| 1131077 | 570 | 589 | N/A | N/A | GGTGCGGCAGGCCTGGCTGG | 52 | 475 |
| 1131105 | 610 | 629 | 4694 | 4713 | CCTCCACCTCTAGGCAGCGA | 48 | 476 |
| 1131133 | 656 | 675 | 4740 | 4759 | CAGAAGGCTCCGGTGTAGCC | 89 | 477 |
| 1131161 | 712 | 731 | 4941 | 4960 | GGCCGCGGTAGCTGAGCCCG | 59 | 478 |
| 1131189 | 766 | 785 | 4995 | 5014 | TGGCCTCCGAGGCCCACGGC | 75 | 479 |
| 1131217 | 844 | 863 | N/A | N/A | CGTTGTCCGGGTTCCGGCAG | 32 | 480 |
| 1131245 | 905 | 924 | 5219 | 5238 | AGGTCGCAGTACTCCCAGCT | 37 | 481 |
| 1131273 | 997 | 1016 | 5311 | 5330 | GCGGTGCCGGCTGCGCGGGC | 49 | 482 |
| 1131301 | 1075 | 1094 | 5494 | 5513 | GCGGCTGCTCCCGCTTCGCC | 48 | 483 |
| 1131329 | 1120 | 1139 | 5539 | 5558 | GGAGCCGCTGCCCGCAGCTC | 51 | 484 |
| 1131357 | 1156 | 1175 | 5575 | 5594 | CGCCAACGACGCGGGTCATC | 23 | 485 |
| 1131385 | 1228 | 1247 | 5647 | 5666 | TGCCGGCGCAGAAACTGTGG | 61 | 486 |
| 1131413 | 1314 | 1333 | 5974 | 5993 | GCCGAGCACCACCGTCAGAT | 35 | 487 |
| 1131441 | 1400 | 1419 | 6060 | 6079 | CTGACGGGCGAGAAGGCCTC | 37 | 488 |
| 1131469 | 1463 | 1482 | 6206 | 6225 | AGGAGCGCGCAGCTGCCGTC | 77 | 464 |
| 1131497 | 1551 | 1570 | 6294 | 6313 | GTGGCCCCAGCCGGCCACCT | 114 | 489 |
| 1131525 | 1582 | 1601 | 6880 | 6899 | AGCTGGCATATTCCTCCGCC | 113 | 490 |
| 1131553 | 1623 | 1642 | 6921 | 6940 | GCGCTCCAGGGAGAGGAACG | 90 | 491 |
| 1131581 | 1749 | 1768 | 7137 | 7156 | AGCTTGGTCCTCACACACCA | 7† | 492 |
| 1131609 | 1796 | 1815 | 7184 | 7203 | CCCGATCCCCAGCTGATGAT | 33 | 493 |
| 1131637 | 1843 | 1862 | 7231 | 7250 | AGTAGGCCACATCGGTGTAG | 37 | 494 |
| 1131665 | 1874 | 1893 | 7262 | 7281 | GAAACGGTGTGCTCCCGGAT | 36 | 495 |
| 1131693 | 1918 | 1937 | 7306 | 7325 | TGCGGAATCACCAAGGAGGG | 11 | 496 |
| 1131721 | 1954 | 1973 | 7342 | 7361 | ACAATCTTGCCTTCCATGCC | 25 | 497 |
| 1131749 | 2009 | 2028 | 7397 | 7416 | TATTGAGTTCCTGCGCCATC | 13 | 498 |

TABLE 38-continued

Reduction of FXII RNA by 5-10-5 MOE gapmers with mixed PO/PS internucleoside linkages (Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131777 | N/A | N/A | 103 | 122 | TTCCCACAGCACTCACCGAA | 77 | 499 |
| 1131805 | N/A | N/A | 187 | 206 | CACCTGGACCCACAGGTCAT | 88 | 500 |
| 1131833 | N/A | N/A | 283 | 302 | TGCAGGCTGTGCCCTTGTAT | 115 | 501 |
| 1131861 | N/A | N/A | 377 | 396 | CTCTCACAGCCCAGAAATGC | 73 | 502 |
| 1131889 | N/A | N/A | 466 | 485 | CCAAGGTGGAATCTACAAGG | 30 | 503 |
| 1131917 | N/A | N/A | 612 | 631 | CACCAGGTAGGCACTAGACT | 42 | 504 |
| 1131945 | N/A | N/A | 716 | 735 | CCTGCTCCGAGCCAGGCTCG | 62 | 505 |
| 1131973 | N/A | N/A | 868 | 887 | TCCTTGCCCATTGAAGGCCC | 43 | 506 |
| 1132001 | N/A | N/A | 966 | 985 | TTGGAGAACTCAAATCCCTC | 52 | 507 |
| 1132029 | N/A | N/A | 1073 | 1092 | TCCATGCACCAGGTGATGGG | 54 | 508 |
| 1132057 | N/A | N/A | 1206 | 1225 | CATGTAGGTAATTTAGTGTC | 47 | 509 |
| 1132085 | N/A | N/A | 1584 | 1603 | GAGACTCAACCCCACCAAGT | 60 | 510 |
| 1132113 | N/A | N/A | 1756 | 1775 | CAGATGGGATGGACGGACAG | 74 | 511 |
| 1132141 | N/A | N/A | 2132 | 2151 | CACTTGCCAAGGACCAAACC | 69 | 512 |
| 1132169 | N/A | N/A | 2262 | 2281 | AATTGCCTGTGTCTTCTTCA | 51 | 513 |
| 1132197 | N/A | N/A | 2376 | 2395 | ATATGCTGTTGGTTGATGAA | 48 | 514 |
| 1132225 | N/A | N/A | 2488 | 2507 | TAGACACTTGATTCAGGTGT | 43 | 515 |
| 1132253 | N/A | N/A | 2637 | 2656 | GTGTCCTTCTCAGTCTACTT | 45 | 516 |
| 1132281 | N/A | N/A | 2745 | 2764 | TGGCCATTTGTGGGCATGCA | 69 | 517 |
| 1132309 | N/A | N/A | 2841 | 2860 | CAGTTGATCCTCATTCTTCT | 57 | 518 |
| 1132337 | N/A | N/A | 2953 | 2972 | CACTTGCCACAAAGTAGGCA | 44 | 519 |
| 1132365 | N/A | N/A | 3051 | 3070 | TTGGGTTCAGGAGTCAGATA | 73 | 520 |
| 1132393 | N/A | N/A | 3445 | 3464 | GCACTGTCCCTCAGGGTCTG | 47 | 521 |
| 1132421 | N/A | N/A | 3643 | 3662 | GTACATGTCTCCCAGGCCCC | 50 | 522 |
| 1132449 | N/A | N/A | 3755 | 3774 | CACCTGTAGAAAGAGACAAG | 58 | 523 |
| 1132477 | N/A | N/A | 3898 | 3917 | GGGTCTGGTGATACCAGGAG | 44 | 524 |
| 1132505 | N/A | N/A | 4024 | 4043 | CAAGTTTCCAAGCTTGGTTT | 29 | 525 |
| 1132533 | N/A | N/A | 4131 | 4150 | CAGTGGTCTGAGAGATGGAC | 46 | 526 |
| 1132561 | N/A | N/A | 4319 | 4338 | TCCGAGTATCCAGCAACCTA | 50 | 527 |
| 1132589 | N/A | N/A | 4557 | 4576 | CCAGCCTGTCTTCCTGACGC | 67 | 528 |
| 1132617 | N/A | N/A | 4657 | 4676 | GTTGGTGCGGCAGGCTTGGG | 59 | 529 |
| 1132645 | N/A | N/A | 4869 | 4888 | GCAGCCAAGGCTGGGCTCTC | 59 | 530 |
| 1132673 | N/A | N/A | 5392 | 5411 | GGCTCCTCCTTCCCCCCCCC | 41 | 531 |
| 1132701 | N/A | N/A | 5760 | 5779 | CTGCGCTGGGAGACGGAGGA | 70 | 532 |
| 1132729 | N/A | N/A | 6167 | 6186 | AACAGAGCTAACCCGGGCGG | 65 | 533 |

TABLE 38-continued

Reduction of FXII RNA by 5-10-5 MOE gapmers with mixed PO/PS internucleoside linkages (Huh7, electroporation 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132757 | N/A | N/A | 6382 | 6401 | AAAGTCGCGGGCTTCTTCCG | 31 | 534 |
| 1132785 | N/A | N/A | 6490 | 6509 | TCCCAGCAGTGAATCCCAGG | 69 | 535 |
| 1132813 | N/A | N/A | 6630 | 6649 | ACCCATCCAGAGTCGCAGAA | 43 | 536 |
| 1132841 | N/A | N/A | 6721 | 6740 | ATTAATTCAATTTCATAGGC | 68 | 537 |
| 1132869 | N/A | N/A | 6862 | 6881 | CCCCTGCGAACACAGAGCGC | 59 | 538 |

TABLE 39

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130797 | 83 | 102 | 83 | 102 | AGTGTTGACTCCAAGCTCAC | 27 | 541 |
| 1130825 | 141 | 160 | 508 | 527 | TGTGTGCTCTTCAGCTTTGT | 14 | 542 |
| 1130853 | 177 | 196 | 3528 | 3547 | GAAGTGGCAGGGCTCCCCGG | 33 | 543 |
| 1130871 | 216 | 235 | 3567 | 3586 | GGTACATTTGTGGTACAGCT | 9 | 183 |
| 1130882 | 231 | 250 | 3582 | 3601 | TGGCCGGCCCTTGTGGGTAC | 23 | 544 |
| 1130910 | 296 | 315 | 3803 | 3822 | AAACAGTATCCCCATCGCTG | 36 | 545 |
| 1130938 | 335 | 354 | 4143 | 4162 | CTGTGTTTGCTGCAGTGGTC | 13 | 546 |
| 1130966 | 408 | 427 | 4216 | 4235 | AGTGAGGTGTTGTGGACAGA | 48 | 547 |
| 1130994 | 451 | 470 | 4396 | 4415 | GAAGCTGAGGCTCAAAGCAC | 22 | 548 |
| 1131022 | 496 | 515 | 4441 | 4460 | CTTGCTCAGTTCTATACCAT | 23 | 549 |
| 1131050 | 537 | 556 | 4482 | 4501 | GTGGGCATCAGGACCCTTGC | 41 | 550 |
| 1131078 | 571 | 590 | N/A | N/A | TGGTGCGGCAGGCCTGGCTG | 33 | 551 |
| 1131106 | 612 | 631 | 4696 | 4715 | GCCCTCCACCTCTAGGCAGC | 26 | 552 |
| 1131134 | 657 | 676 | 4741 | 4760 | GCAGAAGGCTCCGGTGTAGC | 23 | 553 |
| 1131162 | 714 | 733 | 4943 | 4962 | CAGGCCGCGGTAGCTGAGCC | 34 | 554 |
| 1131190 | 767 | 786 | 4996 | 5015 | GTGGCCTCCGAGGCCCACGG | 50 | 555 |
| 1131218 | 862 | 881 | 5176 | 5195 | AGCACCACGGGCGGATGTCG | 25 | 539 |
| 1131246 | 907 | 926 | 5221 | 5240 | CCAGGTCGCAGTACTCCCAG | 26 | 556 |
| 1131274 | 998 | 1017 | 5312 | 5331 | GGCGGTGCCGGCTGCGCGGG | 71 | 557 |
| 1131302 | 1076 | 1095 | 5495 | 5514 | GGCGGCTGCTCCCGCTTCGC | 20 | 558 |
| 1131330 | 1121 | 1140 | 5540 | 5559 | CGGAGCCGCTGCCCGCAGCT | 33 | 559 |
| 1131358 | 1158 | 1177 | 5577 | 5596 | CCCGCCAACGACGCGGGTCA | 19 | 560 |
| 1131386 | 1229 | 1248 | 5648 | 5667 | CTGCCGGCGCAGAAACTGTG | 46 | 561 |
| 1131414 | 1315 | 1334 | 5975 | 5994 | GGCCGAGCACCACCGTCAGA | 32 | 562 |

TABLE 39-continued

Reduction of FXII RNA by 5-10-5 MOE gapmers with mixed PO/PS internucleoside linkages
(Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1131442 | 1401 | 1420 | 6061 | 6080 | GCTGACGGGCGAGAAGGCCT | 19 | 563 |
| 1131470 | 1464 | 1483 | 6207 | 6226 | CAGGAGCGCGCAGCTGCCGT | 33 | 564 |
| 1131498 | 1552 | 1571 | 6295 | 6314 | GGTGGCCCCAGCCGGCCACC | 46 | 565 |
| 1131526 | 1583 | 1602 | 6881 | 6900 | AAGCTGGCATATTCCTCCGC | 136 | 566 |
| 1131554 | 1657 | 1676 | 6955 | 6974 | GGATGGAGGATCCGTGCACG | 15† | 567 |
| 1131582 | 1750 | 1769 | 7138 | 7157 | CAGCTTGGTCCTCACACACC | 11† | 568 |
| 1131610 | 1797 | 1816 | 7185 | 7204 | GCCCGATCCCCAGCTGATGA | 39 | 569 |
| 1131638 | 1844 | 1863 | 7232 | 7251 | TAGTAGGCCACATCGGTGTA | 25 | 87 |
| 1131666 | 1876 | 1895 | 7264 | 7283 | AGGAAACGGTGTGCTCCCGG | 31 | 570 |
| 1131694 | 1919 | 1938 | 7307 | 7326 | CTGCGGAATCACCAAGGAGG | 10 | 571 |
| 1131722 | 1955 | 1974 | 7343 | 7362 | CACAATCTTGCCTTCCATGC | 18 | 572 |
| 1131750 | 2010 | 2029 | 7398 | 7417 | TTATTGAGTTCCTGCGCCAT | 23 | 573 |
| 1131778 | N/A | N/A | 106 | 125 | TGGTTCCCACAGCACTCACC | 42 | 574 |
| 1131806 | N/A | N/A | 190 | 209 | AGTCACCTGGACCCACAGGT | 28 | 575 |
| 1131834 | N/A | N/A | 286 | 305 | AAATGCAGGCTGTGCCCTTG | 33 | 576 |
| 1131862 | N/A | N/A | 380 | 399 | TTCCTCTCACAGCCCAGAAA | 41 | 577 |
| 1131890 | N/A | N/A | 469 | 488 | TTCCCAAGGTGGAATCTACA | 74 | 578 |
| 1131918 | N/A | N/A | 615 | 634 | TAGCACCAGGTAGGCACTAG | 45 | 579 |
| 1131946 | N/A | N/A | 721 | 740 | AAGCACCTGCTCCGAGCCAG | 33 | 580 |
| 1131974 | N/A | N/A | 871 | 890 | CCTTCCTTGCCCATTGAAGG | 46 | 581 |
| 1132002 | N/A | N/A | 969 | 988 | AGCTTGGAGAACTCAAATCC | 56 | 582 |
| 1132030 | N/A | N/A | 1076 | 1095 | ATTTCCATGCACCAGGTGAT | 58 | 583 |
| 1132058 | N/A | N/A | 1209 | 1228 | TGGCATGTAGGTAATTTAGT | 34 | 584 |
| 1132086 | N/A | N/A | 1587 | 1606 | TTAGAGACTCAACCCCACCA | 55 | 585 |
| 1132114 | N/A | N/A | 1759 | 1778 | ATGCAGATGGGATGGACGGA | 48 | 586 |
| 1132142 | N/A | N/A | 2135 | 2154 | GTGCACTTGCCAAGGACCAA | 25 | 587 |
| 1132170 | N/A | N/A | 2265 | 2284 | GAGAATTGCCTGTGTCTTCT | 40 | 588 |
| 1132198 | N/A | N/A | 2379 | 2398 | ATTATATGCTGTTGGTTGAT | 28 | 589 |
| 1132226 | N/A | N/A | 2513 | 2532 | GCTACCTTAGGGAGAAAGCG | 53 | 590 |
| 1132254 | N/A | N/A | 2640 | 2659 | TGAGTGTCCTTCTCAGTCTA | 47 | 591 |
| 1132282 | N/A | N/A | 2748 | 2767 | TCATGGCCATTTGTGGGCAT | 46 | 592 |
| 1132310 | N/A | N/A | 2845 | 2864 | AGTACAGTTGATCCTCATTC | 56 | 593 |
| 1132338 | N/A | N/A | 2956 | 2975 | GAGCACTTGCCACAAAGTAG | 30 | 594 |
| 1132366 | N/A | N/A | 3054 | 3073 | AACTTGGGTTCAGGAGTCAG | 42 | 595 |
| 1132394 | N/A | N/A | 3448 | 3467 | CAGGCACTGTCCCTCAGGGT | 32 | 596 |

TABLE 39-continued

Reduction of FXII RNA by 5-10-5 MOE gapmers with mixed PO/PS internucleoside linkages (Huh7, electroporation, 5000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132422 | N/A | N/A | 3649 | 3668 | GGCAGGGTACATGTCTCCCA | 36 | 597 |
| 1132450 | N/A | N/A | 3758 | 3777 | GCACACCTGTAGAAAGAGAC | 39 | 598 |
| 1132478 | N/A | N/A | 3916 | 3935 | CAGAATCCCAGGTGTGTGGG | 64 | 599 |
| 1132506 | N/A | N/A | 4027 | 4046 | CTCCAAGTTTCCAAGCTTGG | 38 | 600 |
| 1132534 | N/A | N/A | 4134 | 4153 | CTGCAGTGGTCTGAGAGATG | 36 | 601 |
| 1132562 | N/A | N/A | 4325 | 4344 | CAAGTCTCCGAGTATCCAGC | 49 | 602 |
| 1132590 | N/A | N/A | 4560 | 4579 | CTGCCAGCCTGTCTTCCTGA | 30 | 603 |
| 1132618 | N/A | N/A | 4660 | 4679 | CGGGTTGGTGCGGCAGGCTT | 30 | 604 |
| 1132646 | N/A | N/A | 4875 | 4894 | CCCTGGGCAGCCAAGGCTGG | 53 | 605 |
| 1132674 | N/A | N/A | 5395 | 5414 | CTCGGCTCCTCCTTCCCCCC | 45 | 606 |
| 1132702 | N/A | N/A | 5763 | 5782 | AAGCTGCGCTGGGAGACGGA | 45 | 607 |
| 1132730 | N/A | N/A | 6170 | 6189 | CGCAACAGAGCTAACCCGGG | 45 | 608 |
| 1132758 | N/A | N/A | 6385 | 6404 | ACCAAAGTCGCGGGCTTCTT | 43 | 609 |
| 1132786 | N/A | N/A | 6493 | 6512 | GGATCCCAGCAGTGAATCCC | 59 | 610 |
| 1132814 | N/A | N/A | 6633 | 6652 | ACCACCCATCCAGAGTCGCA | 44 | 611 |
| 1132842 | N/A | N/A | 6724 | 6743 | GCCATTAATTCAATTTCATA | 45 | 612 |
| 1132870 | N/A | N/A | 6865 | 6884 | CCGCCCTGCGAACACAGAG | 44 | 613 |

TABLE 40

Reduction of FXII RNA by 5-10-5 MOE gapmers with mixed PO/PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130868 | 213 | 232 | 3564 | 3583 | ACATTTGTGGTACAGCTGCC | 84 | 1756 |
| 1130987 | 443 | 462 | N/A | N/A | GGCTCAAAGCACTTCTCTTT | 93 | 2135 |
| 1131593 | 1780 | 1799 | 7168 | 7187 | TGATGCCTTGCAGGGTGAGC | 37 | 1326 |
| 1131694 | 1919 | 1938 | 7307 | 7326 | CTGCGGAATCACCAAGGAGG | 57 | 571 |
| 1131701 | 1928 | 1947 | 7316 | 7335 | ACTCTCTCACTGCGGAATCA | 42 | 1179 |
| 1131746 | 2005 | 2024 | 7393 | 7412 | GAGTTCCTGCGCCATCCTGG | 40 | 159 |
| 1131754 | 2015 | 2034 | 7403 | 7422 | GCACTTTATTGAGTTCCTGC | 35 | 164 |
| 1131756 | 2017 | 2036 | 7405 | 7424 | AAGCACTTTATTGAGTTCCT | 11 | 1030 |
| 1131757 | 2018 | 2037 | 7406 | 7425 | AAAGCACTTTATTGAGTTCC | 36 | 165 |
| 1131763 | 2026 | 2045 | 7414 | 7433 | GCATTTTCAAAGCACTTTAT | 41 | 1562 |
| 1131891 | N/A | N/A | 513 | 532 | CCGACTGTGTGCTCTTCAGC | 88 | 659 |
| 1132188 | N/A | N/A | 2323 | 2342 | ACTGTTTGCTAGTTCAATGT | 106 | 1951 |

TABLE 40-continued

Reduction of FXII RNA by 5-10-5 MOE gapmers with mixed PO/PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1132271 | N/A | N/A | 2706 | 2725 | CACATTCCCAGTTAAGGTTC | 93 | 1879 |
| 1132505 | N/A | N/A | 4024 | 4043 | CAAGTTTCCAAGCTTGGTTT | 104 | 525 |
| 1132651 | N/A | N/A | 4908 | 4927 | AGCTTGCCTTGGTGTCTGAG | 79 | 985 |
| 1132797 | N/A | N/A | 6542 | 6561 | AGGGAACCAAGAGCAAGTTC | 72 | 1369 |
| 1194299 | N/A | N/A | 2318 | 2337 | TTGCTAGTTCAATGTTCACT | 95 | 2351 |
| 1194300 | N/A | N/A | 2319 | 2338 | TTTGCTAGTTCAATGTTCAC | 67 | 2352 |
| 1194301 | N/A | N/A | 2321 | 2340 | TGTTTGCTAGTTCAATGTTC | 102 | 2353 |
| 1194302 | N/A | N/A | 2322 | 2341 | CTGTTTGCTAGTTCAATGTT | 97 | 2354 |
| 1194303 | N/A | N/A | 2324 | 2343 | TACTGTTTGCTAGTTCAATG | 95 | 2355 |
| 1194304 | N/A | N/A | 2325 | 2344 | ATACTGTTTGCTAGTTCAAT | 97 | 2356 |
| 1194305 | N/A | N/A | 2327 | 2346 | TAATACTGTTTGCTAGTTCA | 96 | 2357 |
| 1194306 | N/A | N/A | 2328 | 2347 | CTAATACTGTTTGCTAGTTC | 93 | 2358 |
| 1194307 | N/A | N/A | 2701 | 2720 | TCCCAGTTAAGGTTCAACAA | 99 | 2359 |
| 1194308 | N/A | N/A | 2702 | 2721 | TTCCCAGTTAAGGTTCAACA | 96 | 2360 |
| 1194309 | N/A | N/A | 2704 | 2723 | CATTCCCAGTTAAGGTTCAA | 79 | 2361 |
| 1194310 | N/A | N/A | 2705 | 2724 | ACATTCCCAGTTAAGGTTCA | 81 | 2362 |
| 1194311 | N/A | N/A | 2707 | 2726 | GCACATTCCCAGTTAAGGTT | 100 | 2363 |
| 1194312 | N/A | N/A | 2708 | 2727 | TGCACATTCCCAGTTAAGGT | 95 | 2364 |
| 1194313 | N/A | N/A | 2710 | 2729 | TTTGCACATTCCCAGTTAAG | 92 | 2365 |
| 1194314 | N/A | N/A | 2711 | 2730 | ATTTGCACATTCCCAGTTAA | 105 | 2366 |
| 1194315 | N/A | N/A | 4019 | 4038 | TTCCAAGCTTGGTTTACCCA | 113 | 2367 |
| 1194316 | N/A | N/A | 4020 | 4039 | TTTCCAAGCTTGGTTTACCC | 109 | 2368 |
| 1194317 | N/A | N/A | 4022 | 4041 | AGTTTCCAAGCTTGGTTTAC | 87 | 2369 |
| 1194318 | N/A | N/A | 4023 | 4042 | AAGTTTCCAAGCTTGGTTTA | 84 | 2370 |
| 1194319 | N/A | N/A | 4025 | 4044 | CCAAGTTTCCAAGCTTGGTT | 102 | 2371 |
| 1194320 | N/A | N/A | 4026 | 4045 | TCCAAGTTTCCAAGCTTGGT | 81 | 2372 |
| 1194321 | N/A | N/A | 4028 | 4047 | ACTCCAAGTTTCCAAGCTTG | 95 | 2373 |
| 1194322 | N/A | N/A | 4029 | 4048 | TACTCCAAGTTTCCAAGCTT | 98 | 2374 |
| 1194323 | N/A | N/A | 4903 | 4922 | GCCTTGGTGTCTGAGGAGAA | 83 | 2375 |
| 1194324 | N/A | N/A | 4904 | 4923 | TGCCTTGGTGTCTGAGGAGA | 80 | 2376 |
| 1194325 | N/A | N/A | 4906 | 4925 | CTTGCCTTGGTGTCTGAGGA | 75 | 2377 |
| 1194326 | N/A | N/A | 4907 | 4926 | GCTTGCCTTGGTGTCTGAGG | 77 | 2378 |
| 1194327 | N/A | N/A | 4909 | 4928 | CAGCTTGCCTTGGTGTCTGA | 78 | 2379 |
| 1194328 | N/A | N/A | 4910 | 4929 | GCAGCTTGCCTTGGTGTCTG | 87 | 2380 |
| 1194329 | 683 | 702 | 4912 | 4931 | TAGCAGCTTGCCTTGGTGTC | 99 | 2381 |

TABLE 40-continued

Reduction of FXII RNA by 5-10-5 MOE gapmers with mixed PO/PS internucleoside linkages
(Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1194330 | 684 | 703 | 4913 | 4932 | ATAGCAGCTTGCCTTGGTGT | 93 | 2382 |
| 1194331 | N/A | N/A | 6537 | 6556 | ACCAAGAGCAAGTTCGATTC | 60 | 2383 |
| 1194332 | N/A | N/A | 6538 | 6557 | AACCAAGAGCAAGTTCGATT | 56 | 2384 |
| 1194333 | N/A | N/A | 6540 | 6559 | GGAACCAAGAGCAAGTTCGA | 73 | 2385 |
| 1194334 | N/A | N/A | 6541 | 6560 | GGGAACCAAGAGCAAGTTCG | 69 | 2386 |
| 1194335 | N/A | N/A | 6543 | 6562 | GAGGGAACCAAGAGCAAGTT | 74 | 2387 |
| 1194336 | N/A | N/A | 6544 | 6563 | AGAGGGAACCAAGAGCAAGT | 69 | 2388 |
| 1194337 | N/A | N/A | 6545 | 6564 | CAGAGGGAACCAAGAGCAAG | 85 | 2389 |
| 1194338 | N/A | N/A | 6546 | 6565 | CCAGAGGGAACCAAGAGCAA | 68 | 2390 |
| 1194339 | N/A | N/A | 6547 | 6566 | CCCAGAGGGAACCAAGAGCA | 57 | 2391 |
| 1206452 | 143 | 162 | 510 | 529 | ACTGTGTGCTCTTCAGCTTT | 78 | 175 |
| 1206453 | 209 | 228 | 3560 | 3579 | TTGTGGTACAGCTGCCGGTG | 79 | 2392 |
| 1206454 | 1912 | 1931 | 7300 | 7319 | ATCACCAAGGAGGGAAAGAT | 53 | 2393 |
| 1206455 | 1920 | 1939 | 7308 | 7327 | ACTGCGGAATCACCAAGGAG | 39 | 2394 |
| 1206456 | 1925 | 1944 | 7313 | 7332 | CTCTCACTGCGGAATCACCA | 28 | 2395 |
| 1206457 | 1929 | 1948 | 7317 | 7336 | CACTCTCTCACTGCGGAATC | 17 | 2396 |
| 1206458 | 1931 | 1950 | 7319 | 7338 | GCCACTCTCTCACTGCGGAA | 25 | 2397 |
| 1206459 | 1934 | 1953 | 7322 | 7341 | CCAGCCACTCTCTCACTGCG | 42 | 2398 |
| 1206460 | N/A | N/A | 514 | 533 | ACCGACTGTGTGCTCTTCAG | 82 | 2399 |
| 1206461 | N/A | N/A | 515 | 534 | TACCGACTGTGTGCTCTTCA | 90 | 2400 |
| 1206462 | N/A | N/A | 517 | 536 | CTTACCGACTGTGTGCTCTT | 102 | 2401 |
| 1206463 | N/A | N/A | 518 | 537 | ACTTACCGACTGTGTGCTCT | 68 | 2402 |
| 1206464 | N/A | N/A | 2313 | 2332 | AGTTCAATGTTCACTGTGAT | 105 | 2403 |
| 1206465 | N/A | N/A | 2333 | 2352 | GGAACCTAATACTGTTTGCT | 92 | 2404 |
| 1206466 | N/A | N/A | 2696 | 2715 | GTTAAGGTTCAACAAGGCGT | 81 | 2405 |
| 1206467 | N/A | N/A | 2716 | 2735 | GAAAAATTTGCACATTCCCA | 92 | 2406 |
| 1206468 | N/A | N/A | 4014 | 4033 | AGCTTGGTTTACCCACCTGC | 95 | 2407 |
| 1206469 | N/A | N/A | 4034 | 4053 | CTTGCTACTCCAAGTTTCCA | 80 | 2408 |
| 1206470 | N/A | N/A | 4898 | 4917 | GGTGTCTGAGGAGAAAGGGG | 82 | 2409 |
| 1206471 | N/A | N/A | 6532 | 6551 | GAGCAAGTTCGATTCTCCCT | 67 | 2410 |
| 1206472 | N/A | N/A | 6552 | 6571 | CGGCGCCCAGAGGGAACCAA | 95 | 2411 |

TABLE 41

Reduction of FXII RNA by 5-10-5 MOE gapmers with mixed PO/PS internucleoside linkages (Huh7, electroporation, 5000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1131768 | N/A | N/A | 2033 | 2052 | TTTCTCAGCATTTTCAAAGC | 35 | 2412 |
| 1131767 | 10843 | 10862 | 2031 | 2050 | TCTCAGCATTTTCAAAGCAC | 25 | 2413 |
| 1131770 | N/A | N/A | 2036 | 2055 | TTTTTTCTCAGCATTTTCAA | 54 | 2414 |
| 1131771 | N/A | N/A | 2037 | 2056 | TTTTTTTCTCAGCATTTTCA | 83 | 2415 |
| 1130767 | 3458 | 3477 | 34 | 53 | TCATGGCATCCGTCCGTTGG | 36 | 617 |
| 1130768 | 3459 | 3478 | 35 | 54 | CTCATGGCATCCGTCCGTTG | 90 | 619 |
| 1132897 | 10846 | 10865 | N/A | N/A | CCTTCTCAGCATTTTCAAAG | 62 | 618 |
| 1130769 | 3460 | 3479 | 36 | 55 | CCTCATGGCATCCGTCCGTT | 22 | 540 |
| 1132898 | 10849 | 10868 | N/A | N/A | TTTCCTTCTCAGCATTTTCA | 61 | 616 |

TABLE 42

Reduction of FXII RNA by 5-10-5 MOE gapmers with mixed PO/PS internucleoside linkages (Huh7, electroporation, 5000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1130744 | 3428 | 3447 | 4 | 23 | TATCCAGGAGTCCAGATCAA | 61 | 2416 |
| 1130772 | 3463 | 3482 | 39 | 58 | AGCCCTCATGGCATCCGTCC | 35 | 2417 |
| 1130755 | 3443 | 3462 | 19 | 38 | GTTGGTCCAGCTGCCTATCC | 64 | 2418 |
| 1130756 | 3444 | 3463 | 20 | 39 | CGTTGGTCCAGCTGCCTATC | 50 | 2419 |
| 1130760 | 3450 | 3469 | 26 | 45 | TCCGTCCGTTGGTCCAGCTG | 37 | 2420 |
| 1130765 | 3456 | 3475 | 32 | 51 | ATGGCATCCGTCCGTTGGTC | 43 | 238 |
| 1130766 | 3457 | 3476 | 33 | 52 | CATGGCATCCGTCCGTTGGT | 50 | 314 |

Example 3: Effects of 3-10-3 cET Gapmers on Human FXII RNA In Vitro, Single Dose Modified oligonucleotides complementary to an FXII nucleic acid were synthesized and tested for their effect on FXII RNA levels in vitro. The modified oligonucleotides were tested in a series of experiments using similar culture conditions. The results for each separate experiment are presented in separate tables below.

The modified oligonucleotides in the tables below are 3-10-3 cEt gapmers (i.e., they have a central region of ten 2'-deoxynucleosides flanked on each side by wings, each comprising three cEt modified nucleosides). The internucleoside linkages throughout each modified oligonucleotide are phosphorothioate (P=S) linkages. All cytosine nucleobases throughout each modified oligonucleotide are 5-methylcytosines.

"Start site" indicates the 5'-most nucleoside of the target sequence to which the modified oligonucleotide is complementary. "Stop site" indicates the 3'-most nucleoside of the target sequence to which the modified oligonucleotide is complementary. As shown in the tables below, the modified oligonucleotides are 100% complementary to one or more of human FXII target sequences including the human FXII mRNA sequence designated herein as SEQ ID NO: 1 (ENSEMBL ID ENST00000253496.3 from ENSEMBL version 99: January 2020), the human FXII genomic sequence, designated herein as SEQ ID NO: 2 (ENSEMBL ID ENSG00000131187.9 from ENSEML version 99: January 2020), the human FXII genomic sequence, designated herein as SEQ ID No. 3 (the complement of GENBANK Accession No. NC_000005.10 truncated from truncated from nucleotides 177399001 to 177413000), and the human FXII mRNA sequence designated herein as SEQ ID No: 4 (GENBANK Accession No. NM 000505.3) 'N/A' indicates that the modified oligonucleotide is not complementary to that particular target sequence with 100% complementarity.

Cultured Huh7 cells, at a density of 20,000 cells per well, were transfected using electroporation with either 2000 nM or 3000 nM modified oligonucleotide. After a treatment period of approximately 24 hours, RNA was isolated from the cells and FXII RNA levels were measured by quantitative real-time RTPCR. Human primer probe set RTS40528 (described herein above) was used to measure RNA levels. FXII RNA levels were normalized to total RNA content, as measured by RIBOGREEN®. Reduction of FXII RNA is presented in the tables below as percent FXII RNA relative to the amount in untreated control cells (% UTC). The symbol "†" indicates that the modified oligonucleotide is complementary to the target transcript within the amplicon region of the primer probe set. In such instances, additional assays using alternative primer probes must be performed to accurately assess the potency and efficacy of such modified oligonucleotides.

TABLE 43

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128712 | 3 | 18 | 3 | 18 | AGGAGTCCAGATCAAT | 50 | 2421 |
| 1128732 | 80 | 95 | 80 | 95 | ACTCCAAGCTCACCAG | 37 | 2422 |
| 1128752 | 125 | 140 | 492 | 507 | ACTTATGCTCCTTGGG | 39 | 2423 |
| 1128772 | 156 | 171 | N/A | N/A | GTGAGAACGACTGTGT | 39 | 2424 |
| 1128792 | 200 | 215 | 3551 | 3566 | GCCGGTGGTACTGGAA | 57 | 2425 |
| 1128802 | 218 | 233 | 3569 | 3584 | TACATTTGTGGTACAG | 12 | 2426 |
| 1128813 | 231 | 246 | 3582 | 3597 | CGGCCCTTGTGGGTAC | 79 | 2427 |
| 1128833 | 294 | 309 | 3801 | 3816 | TATCCCCATCGCTGGT | 51 | 2428 |
| 1128853 | 409 | 424 | 4217 | 4232 | GAGGTGTTGTGGACAG | 45 | 2429 |
| 1128873 | 482 | 497 | 4427 | 4442 | ATATCTCATTCTTGTG | 22 | 2430 |
| 1128893 | 545 | 560 | 4490 | 4505 | GGCAGTGGGCATCAGG | 40 | 2431 |
| 1128913 | 598 | 613 | 4682 | 4697 | GCGACCCCATGGAGG | 39 | 2432 |
| 1128933 | 634 | 649 | 4718 | 4733 | GCAGTGGCACAGGCGG | 36 | 2433 |
| 1128953 | 664 | 679 | 4748 | 4763 | GTCGCAGAAGGCTCCG | 64 | 2434 |
| 1128973 | 713 | 728 | 4942 | 4957 | CGCGGTAGCTGAGCCC | 68 | 2435 |
| 1128993 | 759 | 774 | 4988 | 5003 | GCCCACGGCTGACAGG | 62 | 2436 |
| 1129013 | 807 | 822 | 5036 | 5051 | CAGTTCCGCGCTTGCT | 60 | 2437 |
| 1129033 | 863 | 878 | 5177 | 5192 | ACCACGGGCGGATGTC | 54 | 2438 |
| 1129053 | 892 | 907 | 5206 | 5221 | GCTCAGCCGGTCGCGG | 51 | 2439 |
| 1129073 | 982 | 997 | 5296 | 5311 | CATGAGTGGGACATGA | 45 | 2440 |
| 1129093 | 1043 | 1058 | 5357 | 5372 | TCTGGGACTGAGGCGG | 33 | 2441 |
| 1129113 | 1089 | 1104 | 5508 | 5523 | GTCAGGGAAGGCGGCT | 38 | 2442 |
| 1129133 | 1129 | 1144 | 5548 | 5563 | CTTGCGGAGCCGCTGC | 37 | 2443 |
| 1129153 | 1152 | 1167 | 5571 | 5586 | ACGCGGGTCATCGAAG | 53 | 2444 |
| 1129173 | 1209 | 1224 | 5628 | 5643 | CAGTACAGCGCGGCGA | 35 | 2445 |
| 1129193 | 1240 | 1255 | 5659 | 5674 | GATGAGGCTGCCGGCG | 81 | 2446 |
| 1129213 | 1319 | 1334 | 5979 | 5994 | GGCCGAGCACCACCGT | 44 | 2447 |
| 1129233 | 1384 | 1399 | 6044 | 6059 | GTGCAAGCGGTAGGAG | 76 | 2448 |
| 1129253 | 1438 | 1453 | 6181 | 6196 | CTGAAGGCGCAACAGA | 61 | 2449 |
| 1129273 | 1463 | 1478 | 6206 | 6221 | GCGCGCAGCTGCCGTC | 39 | 2450 |

TABLE 43-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129293 | 1497 | 1512 | 6240 | 6255 | GGCAGGCACACCGGCT | 93 | 2451 |
| 1129313 | 1558 | 1573 | 6301 | 6316 | CTGGTGGCCCCAGCCG | 96 | 2452 |
| 1129333 | 1580 | 1595 | 6878 | 6893 | CATATTCCTCCGCCCC | 78 | 2453 |
| 1129353 | 1619 | 1634 | 6917 | 6932 | GGGAGAGGAACGGTAC | 126 | 2454 |
| 1129373 | 1693 | 1708 | 6991 | 7006 | CTCGAGGAACCCTGCG | 27† | 2455 |
| 1129393 | 1748 | 1763 | 7136 | 7151 | GGTCCTCACACACCAG | 44† | 2456 |
| 1129413 | 1798 | 1813 | 7186 | 7201 | CGATCCCCAGCTGATG | 27 | 2457 |
| 1129433 | 1839 | 1854 | 7227 | 7242 | ACATCGGTGTAGACGC | 28 | 2458 |
| 1129453 | 1866 | 1881 | 7254 | 7269 | TCCCGGATCCAGGCCA | 41 | 2459 |
| 1129473 | 1898 | 1913 | 7286 | 7301 | ATGAGTCCCTGAGCAA | 26 | 2460 |
| 1129493 | 1931 | 1946 | 7319 | 7334 | CTCTCTCACTGCGGAA | 15 | 2461 |
| 1129513 | 1990 | 2005 | 7378 | 7393 | GCGCGGAGCTGGCCGC | 46 | 2462 |
| 1129533 | 2011 | 2026 | 7399 | 7414 | TTGAGTTCCTGCGCCA | 23 | 2463 |
| 1129553 | N/A | N/A | 97 | 112 | ACTCACCGAAAGTGTT | 78 | 2464 |
| 1129573 | N/A | N/A | 197 | 212 | CCTAGTCACCTGGACC | 63 | 2465 |
| 1129593 | N/A | N/A | 328 | 343 | CCTCCCCCCGTTGTCT | 49 | 2466 |
| 1129613 | N/A | N/A | 434 | 449 | GAACTGACTATAAGTC | 61 | 2467 |
| 1129633 | N/A | N/A | 606 | 621 | GCACTAGACTAGACTG | 54 | 2468 |
| 1129653 | N/A | N/A | 652 | 667 | CACGATCACTCTAGTG | 51 | 2469 |
| 1129673 | N/A | N/A | 908 | 923 | GAGGCATTCAGATGCC | 61 | 2470 |
| 1129693 | N/A | N/A | 1055 | 1070 | GAATACCTCACATGGG | 86 | 2471 |
| 1129713 | N/A | N/A | 1557 | 1572 | GGGTAAGGTCCATCTG | 61 | 2472 |
| 1129733 | N/A | N/A | 1709 | 1724 | CAAGGATAGGGCACCA | 50 | 2473 |
| 1129753 | N/A | N/A | 2146 | 2161 | AGGCAAAGTGCACTTG | 55 | 2474 |
| 1129773 | N/A | N/A | 2450 | 2465 | GCATTGATGAATCAGC | 47 | 2475 |
| 1129793 | N/A | N/A | 2527 | 2542 | GCACAAGAAGGCTACC | 54 | 2476 |
| 1129813 | N/A | N/A | 2852 | 2867 | AATAGTACAGTTGATC | 54 | 2477 |
| 1129833 | N/A | N/A | 3048 | 3063 | CAGGAGTCAGATAGCT | 64 | 2478 |
| 1129853 | N/A | N/A | 3652 | 3667 | GCAGGGTACATGTCTC | 68 | 2479 |
| 1129873 | N/A | N/A | 4015 | 4030 | TTGGTTTACCCACCTG | 73 | 2480 |
| 1129893 | N/A | N/A | 4316 | 4331 | ATCCAGCAACCTATTC | 67 | 2481 |
| 1129913 | N/A | N/A | 4360 | 4375 | ATAGTGGTCTCAGGAG | 64 | 2482 |
| 1129933 | N/A | N/A | 4619 | 4634 | CTGGGCCTAAAGACCC | 62 | 2483 |
| 1129953 | N/A | N/A | 5070 | 5085 | GGCGCACCGGCAGAAG | 52 | 2484 |
| 1129973 | N/A | N/A | 5418 | 5433 | CTAGCTCGCCCGGCGC | 76 | 2485 |

TABLE 43-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129993 | N/A | N/A | 5450 | 5465 | GGACGGAGAGCCCGCG | 74 | 2486 |
| 1130013 | N/A | N/A | 5755 | 5770 | GAGACGGAGGAGCCGC | 54 | 2487 |
| 1130033 | N/A | N/A | 5869 | 5884 | ACCCCAATCCCGTGTT | 61 | 2488 |
| 1130053 | N/A | N/A | 6170 | 6185 | ACAGAGCTAACCCGGG | 96 | 2489 |
| 1130073 | N/A | N/A | 6330 | 6345 | TGCCCCTAGCAGTTGT | 65 | 2490 |
| 1130093 | N/A | N/A | 6389 | 6404 | ACCAAAGTCGCGGGCT | 137 | 2491 |
| 1130113 | N/A | N/A | 6413 | 6428 | CATTCTGTAGGCACCC | 83 | 2492 |
| 1130133 | N/A | N/A | 6538 | 6553 | AAGAGCAAGTTCGATT | 51 | 2493 |
| 1130153 | N/A | N/A | 6624 | 6639 | AGTCGCAGAACCTGGC | 49 | 2494 |
| 1130173 | N/A | N/A | 6676 | 6691 | GATTTGAATGGGCGGA | 55 | 2495 |
| 1130193 | N/A | N/A | 6812 | 6827 | CGGACGATGGACAAAG | 64 | 2496 |
| 1130213 | N/A | N/A | 6876 | 6891 | TATTCCTCCGCCCCTG | 131 | 2497 |
| 1130233 | N/A | N/A | 7078 | 7093 | CGCTGTGGACCTGAGA | 89† | 2498 |

TABLE 44

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128713 | 4 | 19 | 4 | 19 | CAGGAGTCCAGATCAA | 35 | 2499 |
| 1128733 | 81 | 96 | 81 | 96 | GACTCCAAGCTCACCA | 38 | 2500 |
| 1128753 | 126 | 141 | 493 | 508 | TACTTATGCTCCTTGG | 35 | 2501 |
| 1128773 | 157 | 172 | N/A | N/A | AGTGAGAACGACTGTG | 31 | 2502 |
| 1128793 | 201 | 216 | 3552 | 3567 | TGCCGGTGGTACTGGA | 41 | 2503 |
| 1128802 | 218 | 233 | 3569 | 3584 | TACATTTGTGGTACAG | 18 | 2426 |
| 1128814 | 233 | 248 | 3584 | 3599 | GCCGGCCCTTGTGGGT | 55 | 2504 |
| 1128834 | 295 | 310 | 3802 | 3817 | GTATCCCCATCGCTGG | 35 | 2505 |
| 1128854 | 411 | 426 | 4219 | 4234 | GTGAGGTGTTGTGGAC | 38 | 2506 |
| 1128874 | 484 | 499 | 4429 | 4444 | CCATATCTCATTCTTG | 24 | 2507 |
| 1128894 | 551 | 566 | 4496 | 4511 | GCCGCTGGCAGTGGGC | 51 | 2508 |
| 1128914 | 599 | 614 | 4683 | 4698 | AGCGACCCCATGGAG | 37 | 2509 |
| 1128934 | 639 | 654 | 4723 | 4738 | ACCGGGCAGTGGCACA | 46 | 2510 |
| 1128954 | 665 | 680 | 4749 | 4764 | CGTCGCAGAAGGCTCC | 45 | 2511 |
| 1128974 | 714 | 729 | 4943 | 4958 | CCGCGGTAGCTGAGCC | 90 | 2512 |
| 1128994 | 761 | 776 | 4990 | 5005 | AGGCCCACGGCTGACA | 44 | 2513 |

TABLE 44-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129014 | 808 | 823 | 5037 | 5052 | CCAGTTCCGCGCTTGC | 33 | 2514 |
| 1129034 | 864 | 879 | 5178 | 5193 | CACCACGGGCGGATGT | 56 | 2515 |
| 1129054 | 896 | 911 | 5210 | 5225 | CCCAGCTCAGCCGGTC | 57 | 2516 |
| 1129074 | 989 | 1004 | 5303 | 5318 | GCGCGGGCATGAGTGG | 37 | 2517 |
| 1129094 | 1044 | 1059 | 5358 | 5373 | GTCTGGGACTGAGGCG | 26 | 2518 |
| 1129114 | 1090 | 1105 | 5509 | 5524 | GGTCAGGGAAGGCGGC | 21 | 2519 |
| 1129134 | 1130 | 1145 | 5549 | 5564 | TCTTGCGGAGCCGCTG | 38 | 2520 |
| 1129154 | 1153 | 1168 | 5572 | 5587 | GACGCGGGTCATCGAA | 47 | 2521 |
| 1129174 | 1210 | 1225 | 5629 | 5644 | CCAGTACAGCGCGGCG | 27 | 2522 |
| 1129194 | 1241 | 1256 | 5660 | 5675 | CGATGAGGCTGCCGGC | 53 | 2523 |
| 1129214 | 1320 | 1335 | 5980 | 5995 | TGGCCGAGCACCACCG | 38 | 2524 |
| 1129234 | 1385 | 1400 | 6045 | 6060 | CGTGCAAGCGGTAGGA | 38 | 2525 |
| 1129254 | 1439 | 1454 | 6182 | 6197 | CCTGAAGGCGCAACAG | 37 | 2526 |
| 1129274 | 1464 | 1479 | 6207 | 6222 | AGCGCGCAGCTGCCGT | 30 | 2527 |
| 1129294 | 1498 | 1513 | 6241 | 6256 | TGGCAGGCACACCGGC | 20 | 2528 |
| 1129314 | 1559 | 1574 | 6302 | 6317 | ACTGGTGGCCCCAGCC | 73 | 2529 |
| 1129334 | 1581 | 1596 | 6879 | 6894 | GCATATTCCTCCGCCC | 83 | 2530 |
| 1129354 | 1620 | 1635 | 6918 | 6933 | AGGGAGAGGAACGGTA | 69 | 2531 |
| 1129374 | 1694 | 1709 | 6992 | 7007 | CCTCGAGGAACCCTGC | 18† | 2532 |
| 1129394 | 1749 | 1764 | 7137 | 7152 | TGGTCCTCACACACCA | 41† | 2533 |
| 1129414 | 1800 | 1815 | 7188 | 7203 | CCCGATCCCCAGCTGA | 47 | 2534 |
| 1129434 | 1840 | 1855 | 7228 | 7243 | CACATCGGTGTAGACG | 34 | 2535 |
| 1129454 | 1867 | 1882 | 7255 | 7270 | CTCCCGGATCCAGGCC | 47 | 2536 |
| 1129474 | 1899 | 1914 | 7287 | 7302 | GATGAGTCCCTGAGCA | 27 | 2537 |
| 1129494 | 1946 | 1961 | 7334 | 7349 | TCCATGCCCCAGCCAC | 25 | 2538 |
| 1129514 | 1991 | 2006 | 7379 | 7394 | GGCGCGGAGCTGGCCG | 77 | 2539 |
| 1129534 | 2012 | 2027 | 7400 | 7415 | ATTGAGTTCCTGCGCC | 15 | 2540 |
| 1129554 | N/A | N/A | 99 | 114 | GCACTCACCGAAAGTG | 78 | 2541 |
| 1129574 | N/A | N/A | 198 | 213 | TCCTAGTCACCTGGAC | 53 | 2542 |
| 1129594 | N/A | N/A | 329 | 344 | ACCTCCCCCGTTGTC | 62 | 2543 |
| 1129614 | N/A | N/A | 435 | 450 | GGAACTGACTATAAGT | 53 | 2544 |
| 1129634 | N/A | N/A | 607 | 622 | GGCACTAGACTAGACT | 64 | 2545 |
| 1129654 | N/A | N/A | 653 | 668 | TCACGATCACTCTAGT | 41 | 2546 |
| 1129674 | N/A | N/A | 953 | 968 | CTCGCCCAGAGTCACC | 72 | 2547 |
| 1129694 | N/A | N/A | 1056 | 1071 | TGAATACCTCACATGG | 48 | 2548 |

TABLE 44-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129714 | N/A | N/A | 1558 | 1573 | AGGGTAAGGTCCATCT | 35 | 2549 |
| 1129734 | N/A | N/A | 1710 | 1725 | GCAAGGATAGGGCACC | 57 | 2550 |
| 1129754 | N/A | N/A | 2250 | 2265 | TTCAGAGGAATTGTCG | 52 | 2551 |
| 1129774 | N/A | N/A | 2452 | 2467 | TAGCATTGATGAATCA | 72 | 2552 |
| 1129794 | N/A | N/A | 2540 | 2555 | GTGTAGTTCCTAAGCA | 57 | 2553 |
| 1129814 | N/A | N/A | 2862 | 2877 | CGGCAGTAATAATAGT | 77 | 2554 |
| 1129834 | N/A | N/A | 3373 | 3388 | TCTAAAAGTTGGGTTC | 51 | 2555 |
| 1129854 | N/A | N/A | 3704 | 3719 | GCCCTATCACAGTCCC | 53 | 2556 |
| 1129874 | N/A | N/A | 4017 | 4032 | GCTTGGTTTACCCACC | 70 | 2557 |
| 1129894 | N/A | N/A | 4318 | 4333 | GTATCCAGCAACCTAT | 48 | 2558 |
| 1129914 | N/A | N/A | 4361 | 4376 | GATAGTGGTCTCAGGA | 58 | 2559 |
| 1129934 | N/A | N/A | 4620 | 4635 | CCTGGGCCTAAAGACC | 85 | 2560 |
| 1129954 | N/A | N/A | 5071 | 5086 | CGGCGCACCGGCAGAA | 42 | 2561 |
| 1129974 | N/A | N/A | 5419 | 5434 | TCTAGCTCGCCCGGCG | 61 | 2562 |
| 1129994 | N/A | N/A | 5451 | 5466 | AGGACGGAGAGCCCGC | 49 | 2563 |
| 1130014 | N/A | N/A | 5762 | 5777 | GCGCTGGGAGACGGAG | 101 | 2564 |
| 1130034 | N/A | N/A | 5870 | 5885 | AACCCCAATCCCGTGT | 54 | 2565 |
| 1130054 | N/A | N/A | 6171 | 6186 | AACAGAGCTAACCCGG | 62 | 2566 |
| 1130074 | N/A | N/A | 6331 | 6346 | CTGCCCCTAGCAGTTG | 118 | 2567 |
| 1130094 | N/A | N/A | 6390 | 6405 | TACCAAAGTCGCGGGC | 46 | 2568 |
| 1130114 | N/A | N/A | 6420 | 6435 | CGCCACCCATTCTGTA | 54 | 2569 |
| 1130134 | N/A | N/A | 6539 | 6554 | CAAGAGCAAGTTCGAT | 69 | 2570 |
| 1130154 | N/A | N/A | 6626 | 6641 | AGAGTCGCAGAACCTG | 51 | 2571 |
| 1130174 | N/A | N/A | 6677 | 6692 | GGATTTGAATGGGCGG | 48 | 2572 |
| 1130194 | N/A | N/A | 6813 | 6828 | CCGGACGATGGACAAA | 56 | 2573 |
| 1130214 | N/A | N/A | 6877 | 6892 | ATATTCCTCCGCCCCT | 78 | 2574 |
| 1130234 | N/A | N/A | 7091 | 7106 | ACACGCAGCTCAGCGC | 56† | 2575 |

TABLE 45

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128714 | 6 | 21 | 6 | 21 | TCCAGGAGTCCAGATC | 85 | 2576 |
| 1128734 | 82 | 97 | 82 | 97 | TGACTCCAAGCTCACC | 30 | 2577 |

TABLE 45-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128754 | 127 | 142 | 494 | 509 | GTACTTATGCTCCTTG | 16 | 2578 |
| 1128774 | 158 | 173 | N/A | N/A | CAGTGAGAACGACTGT | 36 | 2579 |
| 1128794 | 202 | 217 | 3553 | 3568 | CTGCCGGTGGTACTGG | 22 | 2580 |
| 1128802 | 218 | 233 | 3569 | 3584 | TACATTTGTGGTACAG | 12 | 2426 |
| 1128815 | 235 | 250 | 3586 | 3601 | TGGCCGGCCCTTGTGG | 57 | 2581 |
| 1128835 | 297 | 312 | 3804 | 3819 | CAGTATCCCCATCGCT | 16 | 2582 |
| 1128855 | 412 | 427 | 4220 | 4235 | AGTGAGGTGTTGTGGA | 38 | 2583 |
| 1128875 | 487 | 502 | 4432 | 4447 | ATACCATATCTCATTC | 18 | 2584 |
| 1128895 | 552 | 567 | 4497 | 4512 | AGCCGCTGGCAGTGGG | 49 | 2585 |
| 1128915 | 600 | 615 | 4684 | 4699 | CAGCGACCCCCATGGA | 30 | 2586 |
| 1128935 | 640 | 655 | 4724 | 4739 | CACCGGGCAGTGGCAC | 32 | 2587 |
| 1128955 | 679 | 694 | N/A | N/A | TGCCTTGGTGTCCACG | 31 | 2588 |
| 1128975 | 715 | 730 | 4944 | 4959 | GCCGCGGTAGCTGAGC | 52 | 2589 |
| 1128995 | 762 | 777 | 4991 | 5006 | GAGGCCCACGGCTGAC | 31 | 2590 |
| 1129015 | 809 | 824 | 5038 | 5053 | CCCAGTTCCGCGCTTG | 18 | 2591 |
| 1129035 | 866 | 881 | 5180 | 5195 | AGCACCACGGGCGGAT | 26 | 2592 |
| 1129055 | 897 | 912 | 5211 | 5226 | TCCCAGCTCAGCCGGT | 27 | 2593 |
| 1129075 | 990 | 1005 | 5304 | 5319 | TGCGCGGGCATGAGTG | 24 | 2594 |
| 1129095 | 1060 | 1075 | N/A | N/A | CGGCAAGGCTCCCGGG | 35 | 2595 |
| 1129115 | 1099 | 1114 | 5518 | 5533 | GCCGTTCCTGGTCAGG | 25 | 2596 |
| 1129135 | 1131 | 1146 | 5550 | 5565 | CTCTTGCGGAGCCGCT | 22 | 2597 |
| 1129155 | 1154 | 1169 | 5573 | 5588 | CGACGCGGGTCATCGA | 58 | 2598 |
| 1129175 | 1211 | 1226 | 5630 | 5645 | CCCAGTACAGCGCGGC | 22 | 2599 |
| 1129195 | 1242 | 1257 | 5661 | 5676 | GCGATGAGGCTGCCGG | 30 | 2600 |
| 1129215 | 1321 | 1336 | 5981 | 5996 | CTGGCCGAGCACCACC | 23 | 2601 |
| 1129235 | 1399 | 1414 | 6059 | 6074 | GGGCGAGAAGGCCTCG | 60 | 2602 |
| 1129255 | 1440 | 1455 | 6183 | 6198 | TCCTGAAGGCGCAACA | 22 | 2603 |
| 1129275 | 1465 | 1480 | 6208 | 6223 | GAGCGCGCAGCTGCCG | 18 | 2604 |
| 1129295 | 1499 | 1514 | 6242 | 6257 | TTGGCAGGCACACCGG | 20 | 2605 |
| 1129315 | 1560 | 1575 | 6303 | 6318 | AACTGGTGGCCCCAGC | 38 | 2606 |
| 1129335 | 1582 | 1597 | 6880 | 6895 | GGCATATTCCTCCGCC | 42 | 2607 |
| 1129355 | 1621 | 1636 | 6919 | 6934 | CAGGGAGAGGAACGGT | 43 | 2608 |
| 1129375 | 1695 | 1710 | 6993 | 7008 | CCCTCGAGGAACCCTG | 9† | 2609 |
| 1129395 | 1750 | 1765 | 7138 | 7153 | TTGGTCCTCACACACC | 24† | 2610 |
| 1129415 | 1801 | 1816 | 7189 | 7204 | GCCCGATCCCCAGCTG | 33 | 2611 |

TABLE 45-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129435 | 1841 | 1856 | 7229 | 7244 | CCACATCGGTGTAGAC | 20 | 2612 |
| 1129455 | 1868 | 1883 | 7256 | 7271 | GCTCCCGGATCCAGGC | 34 | 2613 |
| 1129475 | 1900 | 1915 | 7288 | 7303 | AGATGAGTCCCTGAGC | 10 | 2614 |
| 1129495 | 1947 | 1962 | 7335 | 7350 | TTCCATGCCCCAGCCA | 20 | 2615 |
| 1129515 | 1992 | 2007 | 7380 | 7395 | TGGCGCGGAGCTGGCC | 49 | 2616 |
| 1129535 | 2013 | 2028 | 7401 | 7416 | TATTGAGTTCCTGCGC | 8 | 2617 |
| 1129555 | N/A | N/A | 100 | 115 | AGCACTCACCGAAAGT | 105 | 2618 |
| 1129575 | N/A | N/A | 199 | 214 | CTCCTAGTCACCTGGA | 80 | 2619 |
| 1129595 | N/A | N/A | 332 | 347 | TCTACCTCCCCCCGTT | 117 | 2620 |
| 1129615 | N/A | N/A | 436 | 451 | GGGAACTGACTATAAG | 153 | 2621 |
| 1129635 | N/A | N/A | 608 | 623 | AGGCACTAGACTAGAC | 62 | 2622 |
| 1129655 | N/A | N/A | 654 | 669 | CTCACGATCACTCTAG | 56 | 2623 |
| 1129675 | N/A | N/A | 955 | 970 | CCCTCGCCCAGAGTCA | 58 | 2624 |
| 1129695 | N/A | N/A | 1059 | 1074 | GGCTGAATACCTCACA | 36 | 2625 |
| 1129715 | N/A | N/A | 1559 | 1574 | CAGGGTAAGGTCCATC | 33 | 2626 |
| 1129735 | N/A | N/A | 1711 | 1726 | GGCAAGGATAGGGCAC | 50 | 2627 |
| 1129755 | N/A | N/A | 2279 | 2294 | CGCGAATAATGAGAAT | 64 | 2628 |
| 1129775 | N/A | N/A | 2457 | 2472 | CAGCTTAGCATTGATG | 52 | 2629 |
| 1129795 | N/A | N/A | 2543 | 2558 | GCTGTGTAGTTCCTAA | 56 | 2630 |
| 1129815 | N/A | N/A | 2863 | 2878 | ACGGCAGTAATAATAG | 49 | 2631 |
| 1129835 | N/A | N/A | 3375 | 3390 | GCTCTAAAAGTTGGGT | 60 | 2632 |
| 1129855 | N/A | N/A | 3764 | 3779 | TAGCACACCTGTAGAA | 83 | 2633 |
| 1129875 | N/A | N/A | 4018 | 4033 | AGCTTGGTTTACCCAC | 42 | 2634 |
| 1129895 | N/A | N/A | 4320 | 4335 | GAGTATCCAGCAACCT | 49 | 2635 |
| 1129915 | N/A | N/A | 4362 | 4377 | GGATAGTGGTCTCAGG | 65 | 2636 |
| 1129935 | N/A | N/A | 4622 | 4637 | CCCCTGGGCCTAAAGA | 72 | 2637 |
| 1129955 | N/A | N/A | 5072 | 5087 | GCGGCGCACCGGCAGA | 55 | 2638 |
| 1129975 | N/A | N/A | 5420 | 5435 | ATCTAGCTCGCCCGGC | 37 | 2639 |
| 1129995 | N/A | N/A | 5452 | 5467 | GAGGACGGAGAGCCCG | 88 | 2640 |
| 1130015 | N/A | N/A | 5763 | 5778 | TGCGCTGGGAGACGGA | 73 | 2641 |
| 1130035 | N/A | N/A | 5871 | 5886 | GAACCCCAATCCCGTG | 49 | 2642 |
| 1130055 | N/A | N/A | 6172 | 6187 | CAACAGAGCTAACCCG | 59 | 2643 |
| 1130075 | N/A | N/A | 6355 | 6370 | GATCAAAGGTCTCCTC | 41 | 2644 |
| 1130095 | N/A | N/A | 6391 | 6406 | ATACCAAAGTCGCGGG | 80 | 2645 |
| 1130115 | N/A | N/A | 6434 | 6449 | ACCCATCAGGTCAGCG | 59 | 2646 |
| 1130135 | N/A | N/A | 6540 | 6555 | CCAAGAGCAAGTTCGA | 47 | 2647 |

TABLE 45-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130155 | N/A | N/A | 6627 | 6642 | CAGAGTCGCAGAACCT | 48 | 2648 |
| 1130175 | N/A | N/A | 6678 | 6693 | AGGATTTGAATGGGCG | 38 | 2649 |
| 1130195 | N/A | N/A | 6814 | 6829 | CCCGGACGATGGACAA | 68 | 2650 |
| 1130215 | N/A | N/A | 7015 | 7030 | CACCTGGCACGCATCG | 24† | 2651 |
| 1130235 | N/A | N/A | 7093 | 7108 | AAACACGCAGCTCAGC | 81† | 2652 |

TABLE 46

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128715 | 9 | 24 | 9 | 24 | CTATCCAGGAGTCCAG | 70 | 2653 |
| 1128735 | 87 | 102 | 87 | 102 | AGTGTTGACTCCAAGC | 22 | 2654 |
| 1128755 | 128 | 143 | 495 | 510 | TGTACTTATGCTCCTT | 23 | 2655 |
| 1128775 | 159 | 174 | N/A | N/A | ACAGTGAGAACGACTG | 48 | 2656 |
| 1128795 | 210 | 225 | 3561 | 3576 | TGGTACAGCTGCCGGT | 17 | 2657 |
| 1128802 | 218 | 233 | 3569 | 3584 | TACATTTGTGGTACAG | 8 | 2426 |
| 1128816 | 236 | 251 | 3587 | 3602 | CTGGCCGGCCCTTGTG | 35 | 2658 |
| 1128836 | 298 | 313 | 3805 | 3820 | ACAGTATCCCCATCGC | 16 | 2659 |
| 1128856 | 413 | 428 | 4221 | 4236 | CAGTGAGGTGTTGTGG | 34 | 2660 |
| 1128876 | 489 | 504 | 4434 | 4449 | CTATACCATATCTCAT | 20 | 2661 |
| 1128896 | 556 | 571 | 4501 | 4516 | GGCCAGCCGCTGGCAG | 74 | 2662 |
| 1128916 | 601 | 616 | 4685 | 4700 | GCAGCGACCCCCATGG | 19 | 2663 |
| 1128936 | 641 | 656 | 4725 | 4740 | CCACCGGGCAGTGGCA | 28 | 2664 |
| 1128956 | 683 | 698 | 4912 | 4927 | AGCTTGCCTTGGTGTC | 22 | 2665 |
| 1128976 | 716 | 731 | 4945 | 4960 | GGCCGCGGTAGCTGAG | 62 | 2666 |
| 1128996 | 765 | 780 | 4994 | 5009 | TCCGAGGCCCACGGCT | 30 | 2667 |
| 1129016 | 810 | 825 | 5039 | 5054 | CCCCAGTTCCGCGCTT | 36 | 2668 |
| 1129036 | 867 | 882 | 5181 | 5196 | AAGCACCACGGGCGGA | 25 | 2669 |
| 1129056 | 905 | 920 | 5219 | 5234 | CGCAGTACTCCCAGCT | 20 | 2670 |
| 1129076 | 991 | 1006 | 5305 | 5320 | CTGCGCGGGCATGAGT | 23 | 2671 |
| 1129096 | 1061 | 1076 | N/A | N/A | CCGGCAAGGCTCCCGG | 66 | 2672 |
| 1129116 | 1102 | 1117 | 5521 | 5536 | TGGGCCGTTCCTGGTC | 31 | 2673 |
| 1129136 | 1132 | 1147 | 5551 | 5566 | ACTCTTGCGGAGCCGC | 16 | 2674 |

TABLE 46-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129156 | 1156 | 1171 | 5575 | 5590 | AACGACGCGGGTCATC | 54 | 2675 |
| 1129176 | 1212 | 1227 | 5631 | 5646 | CCCCAGTACAGCGCGG | 41 | 2676 |
| 1129196 | 1243 | 1258 | 5662 | 5677 | GGCGATGAGGCTGCCG | 79 | 2677 |
| 1129216 | 1323 | 1338 | 5983 | 5998 | TCCTGGCCGAGCACCA | 32 | 2678 |
| 1129236 | 1400 | 1415 | 6060 | 6075 | CGGGCGAGAAGGCCTC | 46 | 2679 |
| 1129256 | 1441 | 1456 | 6184 | 6199 | CTCCTGAAGGCGCAAC | 34 | 2680 |
| 1129276 | 1467 | 1482 | 6210 | 6225 | AGGAGCGCGCAGCTGC | 18 | 2681 |
| 1129296 | 1502 | 1517 | 6245 | 6260 | CGCTTGGCAGGCACAC | 29 | 2682 |
| 1129316 | 1561 | 1576 | 6304 | 6319 | GAACTGGTGGCCCCAG | 32 | 2683 |
| 1129336 | 1583 | 1598 | 6881 | 6896 | TGGCATATTCCTCCGC | 37 | 2684 |
| 1129356 | 1657 | 1672 | 6955 | 6970 | GGAGGATCCGTGCACG | 3† | 2685 |
| 1129376 | 1696 | 1711 | 6994 | 7009 | GCCCTCGAGGAACCCT | 11† | 2686 |
| 1129396 | 1751 | 1766 | 7139 | 7154 | CTTGGTCCTCACACAC | 9† | 2687 |
| 1129416 | 1802 | 1817 | 7190 | 7205 | AGCCCGATCCCCAGCT | 36 | 2688 |
| 1129436 | 1842 | 1857 | 7230 | 7245 | GCCACATCGGTGTAGA | 23 | 2689 |
| 1129456 | 1876 | 1891 | 7264 | 7279 | AACGGTGTGCTCCCGG | 17 | 2690 |
| 1129476 | 1901 | 1916 | 7289 | 7304 | AAGATGAGTCCCTGAG | 7 | 2691 |
| 1129496 | 1948 | 1963 | 7336 | 7351 | CTTCCATGCCCCAGCC | 16 | 2692 |
| 1129516 | 1993 | 2008 | 7381 | 7396 | CTGGCGCGGAGCTGGC | 12 | 2693 |
| 1129536 | 2014 | 2029 | 7402 | 7417 | TTATTGAGTTCCTGCG | 10 | 2694 |
| 1129556 | N/A | N/A | 101 | 116 | CAGCACTCACCGAAAG | 55 | 2695 |
| 1129576 | N/A | N/A | 204 | 219 | TAGGCCTCCTAGTCAC | 57 | 2696 |
| 1129596 | N/A | N/A | 333 | 348 | TTCTACCTCCCCCCGT | 92 | 2697 |
| 1129616 | N/A | N/A | 439 | 454 | GCAGGGAACTGACTAT | 143 | 2698 |
| 1129636 | N/A | N/A | 610 | 625 | GTAGGCACTAGACTAG | 52 | 2699 |
| 1129656 | N/A | N/A | 655 | 670 | GCTCACGATCACTCTA | 33 | 2700 |
| 1129676 | N/A | N/A | 957 | 972 | ATCCCTCGCCCAGAGT | 66 | 2701 |
| 1129696 | N/A | N/A | 1061 | 1076 | TGGGCTGAATACCTCA | 52 | 2702 |
| 1129716 | N/A | N/A | 1560 | 1575 | CCAGGGTAAGGTCCAT | 45 | 2703 |
| 1129736 | N/A | N/A | 1713 | 1728 | TAGGCAAGGATAGGGC | 66 | 2704 |
| 1129756 | N/A | N/A | 2280 | 2295 | TCGCGAATAATGAGAA | 38 | 2705 |
| 1129776 | N/A | N/A | 2459 | 2474 | ATCAGCTTAGCATTGA | 55 | 2706 |
| 1129796 | N/A | N/A | 2628 | 2643 | TCTACTTAGTGCAACG | 30 | 2707 |
| 1129816 | N/A | N/A | 2910 | 2925 | TCACTGTTAACCACTC | 52 | 2708 |
| 1129836 | N/A | N/A | 3376 | 3391 | TGCTCTAAAAGTTGGG | 63 | 2709 |
| 1129856 | N/A | N/A | 3770 | 3785 | GGGTGGTAGCACACCT | 55 | 2710 |

TABLE 46-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129876 | N/A | N/A | 4019 | 4034 | AAGCTTGGTTTACCCA | 49 | 2711 |
| 1129896 | N/A | N/A | 4321 | 4336 | CGAGTATCCAGCAACC | 83 | 2712 |
| 1129916 | N/A | N/A | 4363 | 4378 | GGGATAGTGGTCTCAG | 32 | 2713 |
| 1129936 | N/A | N/A | 4624 | 4639 | CACCCCTGGGCCTAAA | 75 | 2714 |
| 1129956 | N/A | N/A | 5073 | 5088 | CGCGGCGCACCGGCAG | 55 | 2715 |
| 1129976 | N/A | N/A | 5421 | 5436 | AATCTAGCTCGCCCGG | 39 | 2716 |
| 1129996 | N/A | N/A | 5453 | 5468 | TGAGGACGGAGAGCCC | 53 | 2717 |
| 1130016 | N/A | N/A | 5764 | 5779 | CTGCGCTGGGAGACGG | 64 | 2718 |
| 1130036 | N/A | N/A | 5872 | 5887 | CGAACCCCAATCCCGT | 57 | 2719 |
| 1130056 | N/A | N/A | 6174 | 6189 | CGCAACAGAGCTAACC | 43 | 2720 |
| 1130076 | N/A | N/A | 6360 | 6375 | CCAGTGATCAAAGGTC | 71 | 2721 |
| 1130096 | N/A | N/A | 6392 | 6407 | GATACCAAAGTCGCGG | 44 | 2722 |
| 1130116 | N/A | N/A | 6437 | 6452 | ACAACCCATCAGGTCA | 54 | 2723 |
| 1130136 | N/A | N/A | 6541 | 6556 | ACCAAGAGCAAGTTCG | 51 | 2724 |
| 1130156 | N/A | N/A | 6628 | 6643 | CCAGAGTCGCAGAACC | 47 | 2725 |
| 1130176 | N/A | N/A | 6752 | 6767 | CAGCAAGCCCGAAGGG | 60 | 2726 |
| 1130196 | N/A | N/A | 6815 | 6830 | GCCCGGACGATGGACA | 47 | 2727 |
| 1130216 | N/A | N/A | 7016 | 7031 | TCACCTGGCACGCATC | 32† | 2728 |
| 1130236 | N/A | N/A | 7094 | 7109 | GAAACACGCAGCTCAG | 74† | 2729 |

TABLE 47

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128716 | 11 | 26 | 11 | 26 | GCCTATCCAGGAGTCC | 73 | 2730 |
| 1128736 | 89 | 104 | 89 | 104 | AAAGTGTTGACTCCAA | 21 | 2731 |
| 1128756 | 129 | 144 | 496 | 511 | TTGTACTTATGCTCCT | 34 | 2732 |
| 1128776 | 160 | 175 | N/A | N/A | GACAGTGAGAACGACT | 14 | 2733 |
| 1128796 | 212 | 227 | 3563 | 3578 | TGTGGTACAGCTGCCG | 11 | 2734 |
| 1128802 | 218 | 233 | 3569 | 3584 | TACATTTGTGGTACAG | 7 | 2426 |
| 1128817 | 238 | 253 | 3589 | 3604 | GCCTGGCCGGCCCTTG | 46 | 2735 |
| 1128837 | 299 | 314 | 3806 | 3821 | AACAGTATCCCCATCG | 30 | 2736 |
| 1128857 | 414 | 429 | 4222 | 4237 | CCAGTGAGGTGTTGTG | 29 | 2737 |

TABLE 47-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128877 | 492 | 507 | 4437 | 4452 | GTTCTATACCATATCT | 24 | 2738 |
| 1128897 | 572 | 587 | N/A | N/A | TGCGGCAGGCCTGGCT | 72 | 2739 |
| 1128917 | 602 | 617 | 4686 | 4701 | GGCAGCGACCCCCATG | 24 | 2740 |
| 1128937 | 642 | 657 | 4726 | 4741 | CCCACCGGGCAGTGGC | 50 | 2741 |
| 1128957 | 686 | 701 | 4915 | 4930 | AGCAGCTTGCCTTGGT | 19 | 2742 |
| 1128977 | 718 | 733 | 4947 | 4962 | CAGGCCGCGGTAGCTG | 70 | 2743 |
| 1128997 | 766 | 781 | 4995 | 5010 | CTCCGAGGCCCACGGC | 43 | 2744 |
| 1129017 | 811 | 826 | 5040 | 5055 | TCCCCAGTTCCGCGCT | 47 | 2745 |
| 1129037 | 869 | 884 | 5183 | 5198 | CGAAGCACCACGGGCG | 14 | 2746 |
| 1129057 | 906 | 921 | 5220 | 5235 | TCGCAGTACTCCCAGC | 15 | 2747 |
| 1129077 | 993 | 1008 | 5307 | 5322 | GGCTGCGCGGGCATGA | 26 | 2748 |
| 1129097 | 1062 | 1077 | N/A | N/A | GCCGGCAAGGCTCCCG | 34 | 2749 |
| 1129117 | 1104 | 1119 | 5523 | 5538 | AGTGGGCCGTTCCTGG | 23 | 2750 |
| 1129137 | 1133 | 1148 | 5552 | 5567 | GACTCTTGCGGAGCCG | 16 | 2751 |
| 1129157 | 1157 | 1172 | 5576 | 5591 | CAACGACGCGGGTCAT | 39 | 2752 |
| 1129177 | 1215 | 1230 | 5634 | 5649 | TGGCCCCAGTACAGCG | 60 | 2753 |
| 1129197 | 1244 | 1259 | 5663 | 5678 | GGGCGATGAGGCTGCC | 67 | 2754 |
| 1129217 | 1349 | 1364 | 6009 | 6024 | ACGGCTCACAGCTGTG | 67 | 2755 |
| 1129237 | 1401 | 1416 | 6061 | 6076 | ACGGGCGAGAAGGCCT | 51 | 2756 |
| 1129257 | 1442 | 1457 | 6185 | 6200 | CCTCCTGAAGGCGCAA | 33 | 2757 |
| 1129277 | 1468 | 1483 | 6211 | 6226 | CAGGAGCGCGCAGCTG | 29 | 2758 |
| 1129297 | 1503 | 1518 | 6246 | 6261 | CCGCTTGGCAGGCACA | 26 | 2759 |
| 1129317 | 1562 | 1577 | 6305 | 6320 | CGAACTGGTGGCCCCA | 35 | 2760 |
| 1129337 | 1584 | 1599 | 6882 | 6897 | CTGGCATATTCCTCCG | 47 | 2761 |
| 1129357 | 1658 | 1673 | 6956 | 6971 | TGGAGGATCCGTGCAC | 4† | 2762 |
| 1129377 | 1697 | 1712 | 6995 | 7010 | CGCCCTCGAGGAACCC | 13† | 2763 |
| 1129397 | 1752 | 1767 | 7140 | 7155 | GCTTGGTCCTCACACA | 6† | 2764 |
| 1129417 | 1803 | 1818 | 7191 | 7206 | CAGCCCGATCCCCAGC | 24 | 2765 |
| 1129437 | 1843 | 1858 | 7231 | 7246 | GGCCACATCGGTGTAG | 45 | 2766 |
| 1129457 | 1877 | 1892 | 7265 | 7280 | AAACGGTGTGCTCCCG | 15 | 2767 |
| 1129477 | 1902 | 1917 | 7290 | 7305 | AAAGATGAGTCCCTGA | 9 | 2768 |
| 1129497 | 1949 | 1964 | 7337 | 7352 | CCTTCCATGCCCCAGC | 4 | 2769 |
| 1129517 | 1994 | 2009 | 7382 | 7397 | CCTGGCGCGGAGCTGG | 20 | 2770 |
| 1129537 | 2016 | 2031 | 7404 | 7419 | CTTTATTGAGTTCCTG | 4 | 2771 |
| 1129557 | N/A | N/A | 119 | 134 | GGACAATCCTGGTTCC | 55 | 2772 |
| 1129577 | N/A | N/A | 206 | 221 | CATAGGCCTCCTAGTC | 88 | 2773 |

TABLE 47-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129597 | N/A | N/A | 334 | 349 | TTTCTACCTCCCCCCG | 77 | 2774 |
| 1129617 | N/A | N/A | 463 | 478 | GGAATCTACAAGGGAG | 76 | 2775 |
| 1129637 | N/A | N/A | 612 | 627 | AGGTAGGCACTAGACT | 67 | 2776 |
| 1129657 | N/A | N/A | 659 | 674 | CACAGCTCACGATCAC | 58 | 2777 |
| 1129677 | N/A | N/A | 958 | 973 | AATCCCTCGCCCAGAG | 71 | 2778 |
| 1129697 | N/A | N/A | 1125 | 1140 | TCATCTAAAAGGTAGT | 47 | 2779 |
| 1129717 | N/A | N/A | 1561 | 1576 | ACCAGGGTAAGGTCCA | 56 | 2780 |
| 1129737 | N/A | N/A | 1716 | 1731 | GATTAGGCAAGGATAG | 66 | 2781 |
| 1129757 | N/A | N/A | 2281 | 2296 | ATCGCGAATAATGAGA | 58 | 2782 |
| 1129777 | N/A | N/A | 2468 | 2483 | TATAGTGCCATCAGCT | 60 | 2783 |
| 1129797 | N/A | N/A | 2629 | 2644 | GTCTACTTAGTGCAAC | 64 | 2784 |
| 1129817 | N/A | N/A | 2912 | 2927 | AGTCACTGTTAACCAC | 51 | 2785 |
| 1129837 | N/A | N/A | 3401 | 3416 | GTCGCTGTGCATTGAA | 42 | 2786 |
| 1129857 | N/A | N/A | 3881 | 3896 | GTAATGAGGCGGGAGG | 62 | 2787 |
| 1129877 | N/A | N/A | 4035 | 4050 | GCTACTCCAAGTTTCC | 40 | 2788 |
| 1129897 | N/A | N/A | 4322 | 4337 | CCGAGTATCCAGCAAC | 53 | 2789 |
| 1129917 | N/A | N/A | 4365 | 4380 | GAGGGATAGTGGTCTC | 95 | 2790 |
| 1129937 | N/A | N/A | 4634 | 4649 | CGCAGTGAGCCACCCC | 71 | 2791 |
| 1129957 | N/A | N/A | 5074 | 5089 | ACGCGGCGCACCGGCA | 55 | 2792 |
| 1129977 | N/A | N/A | 5422 | 5437 | GAATCTAGCTCGCCCG | 78 | 2793 |
| 1129997 | N/A | N/A | 5482 | 5497 | CGCCGGCAAGGCTGTG | 77 | 2794 |
| 1130017 | N/A | N/A | 5766 | 5781 | AGCTGCGCTGGGAGAC | 79 | 2795 |
| 1130037 | N/A | N/A | 5873 | 5888 | CCGAACCCCAATCCCG | 97 | 2796 |
| 1130057 | N/A | N/A | 6175 | 6190 | GCGCAACAGAGCTAAC | 57 | 2797 |
| 1130077 | N/A | N/A | 6367 | 6382 | GCCTAACCCAGTGATC | 95 | 2798 |
| 1130097 | N/A | N/A | 6393 | 6408 | CGATACCAAAGTCGCG | 97 | 2799 |
| 1130117 | N/A | N/A | 6438 | 6453 | CACAACCCATCAGGTC | 57 | 2800 |
| 1130137 | N/A | N/A | 6567 | 6582 | CCTTTGCAGCCCGGCG | 69 | 2801 |
| 1130157 | N/A | N/A | 6629 | 6644 | TCCAGAGTCGCAGAAC | 61 | 2802 |
| 1130177 | N/A | N/A | 6753 | 6768 | GCAGCAAGCCCGAAGG | 65 | 2803 |
| 1130197 | N/A | N/A | 6816 | 6831 | CGCCCGGACGATGGAC | 59 | 2804 |
| 1130217 | N/A | N/A | 7017 | 7032 | CTCACCTGGCACGCAT | 64† | 2805 |
| 1130237 | N/A | N/A | 7095 | 7110 | GGAAACACGCAGCTCA | 73† | 2806 |

TABLE 48

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128717 | 12 | 27 | 12 | 27 | TGCCTATCCAGGAGTC | 97 | 2807 |
| 1128737 | 90 | 105 | 90 | 105 | GAAAGTGTTGACTCCA | 24 | 2808 |
| 1128757 | 131 | 146 | 498 | 513 | CTTTGTACTTATGCTC | 46 | 2809 |
| 1128777 | 161 | 176 | N/A | N/A | TGACAGTGAGAACGAC | 31 | 2810 |
| 1128797 | 213 | 228 | 3564 | 3579 | TTGTGGTACAGCTGCC | 15 | 2811 |
| 1128802 | 218 | 233 | 3569 | 3584 | TACATTTGTGGTACAG | 18 | 2426 |
| 1128818 | 243 | 258 | 3594 | 3609 | TGAGGGCCTGGCCGGC | 68 | 2812 |
| 1128838 | 300 | 315 | 3807 | 3822 | AAACAGTATCCCCATC | 57 | 2813 |
| 1128858 | 415 | 430 | 4223 | 4238 | TCCAGTGAGGTGTTGT | 35 | 2814 |
| 1128878 | 493 | 508 | 4438 | 4453 | AGTTCTATACCATATC | 15 | 2815 |
| 1128898 | 581 | 596 | 4665 | 4680 | ACGGGTTGGTGCGGCA | 44 | 2816 |
| 1128918 | 603 | 618 | 4687 | 4702 | AGGCAGCGACCCCCAT | 33 | 2817 |
| 1128938 | 643 | 658 | 4727 | 4742 | GCCCACCGGGCAGTGG | 83 | 2818 |
| 1128958 | 689 | 704 | 4918 | 4933 | CATAGCAGCTTGCCTT | 17 | 2819 |
| 1128978 | 720 | 735 | 4949 | 4964 | GCCAGGCCGCGGTAGC | 63 | 2820 |
| 1128998 | 767 | 782 | 4996 | 5011 | CCTCCGAGGCCCACGG | 35 | 2821 |
| 1129018 | 812 | 827 | 5041 | 5056 | GTCCCCAGTTCCGCGC | 66 | 2822 |
| 1129038 | 870 | 885 | 5184 | 5199 | ACGAAGCACCACGGGC | 30 | 2823 |
| 1129058 | 907 | 922 | 5221 | 5236 | GTCGCAGTACTCCCAG | 19 | 2824 |
| 1129078 | 995 | 1010 | 5309 | 5324 | CCGGCTGCGCGGGCAT | 33 | 2825 |
| 1129098 | 1063 | 1078 | N/A | N/A | CGCCGGCAAGGCTCCC | 42 | 2826 |
| 1129118 | 1106 | 1121 | 5525 | 5540 | TCAGTGGGCCGTTCCT | 30 | 2827 |
| 1129138 | 1134 | 1149 | 5553 | 5568 | AGACTCTTGCGGAGCC | 21 | 2828 |
| 1129158 | 1158 | 1173 | 5577 | 5592 | CCAACGACGCGGGTCA | 29 | 2829 |
| 1129178 | 1220 | 1235 | 5639 | 5654 | AACTGTGGCCCCAGTA | 42 | 2830 |
| 1129198 | 1261 | 1276 | 5680 | 5695 | CGTCAGCACCCAGCAG | 54 | 2831 |
| 1129218 | 1352 | 1367 | 6012 | 6027 | GGCACGGCTCACAGCT | 34 | 2832 |
| 1129238 | 1402 | 1417 | 6062 | 6077 | GACGGGCGAGAAGGCC | 42 | 2833 |
| 1129258 | 1443 | 1458 | 6186 | 6201 | TCCTCCTGAAGGCGCA | 38 | 2834 |
| 1129278 | 1469 | 1484 | 6212 | 6227 | ACAGGAGCGCGCAGCT | 37 | 2835 |
| 1129298 | 1504 | 1519 | 6247 | 6262 | GCCGCTTGGCAGGCAC | 77 | 2836 |
| 1129318 | 1563 | 1578 | 6306 | 6321 | TCGAACTGGTGGCCCC | 76 | 2837 |
| 1129338 | 1591 | 1606 | 6889 | 6904 | CAGGAAGCTGGCATAT | 59 | 2838 |
| 1129358 | 1659 | 1674 | 6957 | 6972 | ATGGAGGATCCGTGCA | 10[†] | 2839 |
| 1129378 | 1698 | 1713 | 6996 | 7011 | CCGCCCTCGAGGAACC | 16[†] | 2840 |
| 1129398 | 1753 | 1768 | 7141 | 7156 | AGCTTGGTCCTCACAC | 22[†] | 2841 |

TABLE 48-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129418 | 1806 | 1821 | 7194 | 7209 | CCACAGCCCGATCCCC | 36 | 2842 |
| 1129438 | 1844 | 1859 | 7232 | 7247 | AGGCCACATCGGTGTA | 34 | 2843 |
| 1129458 | 1878 | 1893 | 7266 | 7281 | GAAACGGTGTGCTCCC | 21 | 2844 |
| 1129478 | 1903 | 1918 | 7291 | 7306 | GAAAGATGAGTCCCTG | 15 | 2845 |
| 1129498 | 1950 | 1965 | 7338 | 7353 | GCCTTCCATGCCCCAG | 16 | 2846 |
| 1129518 | 1995 | 2010 | 7383 | 7398 | TCCTGGCGCGGAGCTG | 22 | 2847 |
| 1129538 | 2017 | 2032 | 7405 | 7420 | ACTTTATTGAGTTCCT | 9 | 2848 |
| 1129558 | N/A | N/A | 126 | 141 | AATCCTGGGACAATCC | 77 | 2849 |
| 1129578 | N/A | N/A | 207 | 222 | ACATAGGCCTCCTAGT | 83 | 2850 |
| 1129598 | N/A | N/A | 405 | 420 | GATCTGTTGCTAGTCT | 77 | 2851 |
| 1129618 | N/A | N/A | 466 | 481 | GGTGGAATCTACAAGG | 107 | 2852 |
| 1129638 | N/A | N/A | 613 | 628 | CAGGTAGGCACTAGAC | 76 | 2853 |
| 1129658 | N/A | N/A | 660 | 675 | ACACAGCTCACGATCA | 63 | 2854 |
| 1129678 | N/A | N/A | 959 | 974 | AAATCCCTCGCCCAGA | 62 | 2855 |
| 1129698 | N/A | N/A | 1132 | 1147 | GTACCCTTCATCTAAA | 83 | 2856 |
| 1129718 | N/A | N/A | 1562 | 1577 | CACCAGGGTAAGGTCC | 64 | 2857 |
| 1129738 | N/A | N/A | 1717 | 1732 | GGATTAGGCAAGGATA | 76 | 2858 |
| 1129758 | N/A | N/A | 2282 | 2297 | CATCGCGAATAATGAG | 49 | 2859 |
| 1129778 | N/A | N/A | 2469 | 2484 | CTATAGTGCCATCAGC | 56 | 2860 |
| 1129798 | N/A | N/A | 2631 | 2646 | CAGTCTACTTAGTGCA | 63 | 2861 |
| 1129818 | N/A | N/A | 2963 | 2978 | GAAGAGCACTTGCCAC | 51 | 2862 |
| 1129838 | N/A | N/A | 3404 | 3419 | AAGGTCGCTGTGCATT | 58 | 2863 |
| 1129858 | N/A | N/A | 3882 | 3897 | AGTAATGAGGCGGGAG | 58 | 2864 |
| 1129878 | N/A | N/A | 4045 | 4060 | TTGTGACCTTGCTACT | 50 | 2865 |
| 1129898 | N/A | N/A | 4323 | 4338 | TCCGAGTATCCAGCAA | 68 | 2866 |
| 1129918 | N/A | N/A | 4366 | 4381 | AGAGGGATAGTGGTCT | 88 | 2867 |
| 1129938 | N/A | N/A | 4635 | 4650 | ACGCAGTGAGCCACCC | 43 | 2868 |
| 1129958 | N/A | N/A | 5075 | 5090 | CACGCGGCGCACCGGC | 66 | 2869 |
| 1129978 | N/A | N/A | 5423 | 5438 | GGAATCTAGCTCGCCC | 74 | 2870 |
| 1129998 | N/A | N/A | 5483 | 5498 | TCGCCGGCAAGGCTGT | 80 | 2871 |
| 1130018 | N/A | N/A | 5772 | 5787 | CGTGGAAGCTGCGCTG | 75 | 2872 |
| 1130038 | N/A | N/A | 5877 | 5892 | GCTCCCGAACCCCAAT | 69 | 2873 |
| 1130058 | N/A | N/A | 6176 | 6191 | GGCGCAACAGAGCTAA | 59 | 2874 |
| 1130078 | N/A | N/A | 6368 | 6383 | CGCCTAACCCAGTGAT | 71 | 2875 |
| 1130098 | N/A | N/A | 6394 | 6409 | ACGATACCAAAGTCGC | 68 | 2876 |

TABLE 48-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130118 | N/A | N/A | 6457 | 6472 | GGATTCACCTACACAT | 73 | 2877 |
| 1130138 | N/A | N/A | 6568 | 6583 | GCCTTTGCAGCCCGGC | 98 | 2878 |
| 1130158 | N/A | N/A | 6630 | 6645 | ATCCAGAGTCGCAGAA | 62 | 2879 |
| 1130178 | N/A | N/A | 6754 | 6769 | CGCAGCAAGCCCGAAG | 69 | 2880 |
| 1130198 | N/A | N/A | 6817 | 6832 | CCGCCCGGACGATGGA | 78 | 2881 |
| 1130218 | N/A | N/A | 7018 | 7033 | GCTCACCTGGCACGCA | 98† | 2882 |
| 1130238 | N/A | N/A | 7096 | 7111 | CGGAAACACGCAGCTC | 79† | 2883 |

TABLE 49

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128738 | 92 | 107 | N/A | N/A | TCGAAAGTGTTGACTC | 15 | 2884 |
| 1128758 | 132 | 147 | 499 | 514 | GCTTTGTACTTATGCT | 63 | 2885 |
| 1128778 | 163 | 178 | N/A | N/A | GGTGACAGTGAGAACG | 19 | 2886 |
| 1128798 | 214 | 229 | 3565 | 3580 | TTTGTGGTACAGCTGC | 28 | 2887 |
| 1128802 | 218 | 233 | 3569 | 3584 | TACATTTGTGGTACAG | 16 | 2426 |
| 1128819 | 245 | 260 | 3596 | 3611 | GCTGAGGGCCTGGCCG | 59 | 2888 |
| 1128839 | 301 | 316 | 3808 | 3823 | CAAACAGTATCCCCAT | 24 | 2889 |
| 1128859 | 424 | 439 | 4232 | 4247 | GCAGTGGTTTCCAGTG | 17 | 2890 |
| 1128879 | 494 | 509 | 4439 | 4454 | CAGTTCTATACCATAT | 15 | 2891 |
| 1128899 | 582 | 597 | 4666 | 4681 | CACGGGTTGGTGCGGC | 33 | 2892 |
| 1128919 | 604 | 619 | 4688 | 4703 | TAGGCAGCGACCCCCA | 31 | 2893 |
| 1128939 | 645 | 660 | 4729 | 4744 | TAGCCCACCGGGCAGT | 40 | 2894 |
| 1128959 | 690 | 705 | 4919 | 4934 | TCATAGCAGCTTGCCT | 22 | 2895 |
| 1128979 | 744 | 759 | 4973 | 4988 | GGCGCACCCGAGAGCG | 32 | 2896 |
| 1128999 | 768 | 783 | 4997 | 5012 | GCCTCCGAGGCCCACG | 46 | 2897 |
| 1129019 | 813 | 828 | 5042 | 5057 | AGTCCCCAGTTCCGCG | 39 | 2898 |
| 1129039 | 871 | 886 | 5185 | 5200 | CACGAAGCACCACGGG | 16 | 2899 |
| 1129059 | 908 | 923 | 5222 | 5237 | GGTCGCAGTACTCCCA | 18 | 2900 |
| 1129079 | 996 | 1011 | 5310 | 5325 | GCCGGCTGCGCGGGCA | 35 | 2901 |
| 1129099 | 1064 | 1079 | N/A | N/A | TCGCCGGCAAGGCTCC | 36 | 2902 |
| 1129119 | 1107 | 1122 | 5526 | 5541 | CTCAGTGGGCCGTTCC | 17 | 2903 |
| 1129139 | 1135 | 1150 | 5554 | 5569 | CAGACTCTTGCGGAGC | 12 | 2904 |

TABLE 49-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129159 | 1159 | 1174 | 5578 | 5593 | GCCAACGACGCGGGTC | 27 | 2905 |
| 1129179 | 1222 | 1237 | 5641 | 5656 | GAAACTGTGGCCCCAG | 18 | 2906 |
| 1129199 | 1286 | 1301 | 5705 | 5720 | GCCGGTCCTGCAGGCA | 33 | 2907 |
| 1129219 | 1353 | 1368 | 6013 | 6028 | TGGCACGGCTCACAGC | 27 | 2908 |
| 1129239 | 1403 | 1418 | 6063 | 6078 | TGACGGGCGAGAAGGC | 47 | 2909 |
| 1129259 | 1445 | 1460 | 6188 | 6203 | CATCCTCCTGAAGGCG | 32 | 2910 |
| 1129279 | 1470 | 1485 | 6213 | 6228 | GACAGGAGCGCGCAGC | 27 | 2911 |
| 1129299 | 1505 | 1520 | 6248 | 6263 | CGCCGCTTGGCAGGCA | 59 | 2912 |
| 1129319 | 1564 | 1579 | 6307 | 6322 | CTCGAACTGGTGGCCC | 37 | 2913 |
| 1129339 | 1592 | 1607 | 6890 | 6905 | GCAGGAAGCTGGCATA | 72 | 2914 |
| 1129359 | 1660 | 1675 | 6958 | 6973 | GATGGAGGATCCGTGC | 11† | 2915 |
| 1129379 | 1699 | 1714 | 6997 | 7012 | GCCGCCCTCGAGGAAC | 6† | 2916 |
| 1129399 | 1754 | 1769 | 7142 | 7157 | CAGCTTGGTCCTCACA | 26† | 2917 |
| 1129419 | 1808 | 1823 | 7196 | 7211 | CACCACAGCCCGATCC | 37 | 2918 |
| 1129439 | 1845 | 1860 | 7233 | 7248 | TAGGCCACATCGGTGT | 31 | 2919 |
| 1129459 | 1879 | 1894 | 7267 | 7282 | GGAAACGGTGTGCTCC | 41 | 2920 |
| 1129479 | 1904 | 1919 | 7292 | 7307 | GGAAAGATGAGTCCCT | 15 | 2921 |
| 1129499 | 1951 | 1966 | 7339 | 7354 | TGCCTTCCATGCCCCA | 8 | 2922 |
| 1129519 | 1996 | 2011 | 7384 | 7399 | ATCCTGGCGCGGAGCT | 29 | 2923 |
| 1129539 | 2018 | 2033 | 7406 | 7421 | CACTTTATTGAGTTCC | 6 | 2924 |
| 1129559 | N/A | N/A | 138 | 153 | ACCCCCCAGAACAATC | 45 | 2925 |
| 1129579 | N/A | N/A | 208 | 223 | CACATAGGCCTCCTAG | 24 | 2926 |
| 1129599 | N/A | N/A | 408 | 423 | ACCGATCTGTTGCTAG | 79 | 2927 |
| 1129619 | N/A | N/A | 469 | 484 | CAAGGTGGAATCTACA | 50 | 2928 |
| 1129639 | N/A | N/A | 614 | 629 | CCAGGTAGGCACTAGA | 36 | 2929 |
| 1129659 | N/A | N/A | 693 | 708 | TTAGACACAGCCCATA | 56 | 2930 |
| 1129679 | N/A | N/A | 960 | 975 | CAAATCCCTCGCCCAG | 30 | 2931 |
| 1129699 | N/A | N/A | 1134 | 1149 | AGGTACCCTTCATCTA | 79 | 2932 |
| 1129719 | N/A | N/A | 1583 | 1598 | TCAACCCCACCAAGTC | 59 | 2933 |
| 1129739 | N/A | N/A | 1757 | 1772 | ATGGGATGGACGGACA | 44 | 2934 |
| 1129759 | N/A | N/A | 2283 | 2298 | CCATCGCGAATAATGA | 50 | 2935 |
| 1129779 | N/A | N/A | 2470 | 2485 | GCTATAGTGCCATCAG | 25 | 2936 |
| 1129799 | N/A | N/A | 2651 | 2666 | TATTGAATGAGTGTCC | 36 | 2937 |
| 1129819 | N/A | N/A | 2987 | 3002 | GTAAGTCTTCAGTCCC | 56 | 2938 |
| 1129839 | N/A | N/A | 3405 | 3420 | AAAGGTCGCTGTGCAT | 58 | 2939 |

TABLE 49-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129859 | N/A | N/A | 3883 | 3898 | GAGTAATGAGGCGGGA | 55 | 2940 |
| 1129879 | N/A | N/A | 4058 | 4073 | GAACCTACTTGCCTTG | 42 | 2941 |
| 1129899 | N/A | N/A | 4324 | 4339 | CTCCGAGTATCCAGCA | 28 | 2942 |
| 1129919 | N/A | N/A | 4367 | 4382 | AAGAGGGATAGTGGTC | 48 | 2943 |
| 1129939 | N/A | N/A | 4636 | 4651 | AACGCAGTGAGCCACC | 55 | 2944 |
| 1129959 | N/A | N/A | 5076 | 5091 | CCACGCGGCGCACCGG | 61 | 2945 |
| 1129979 | N/A | N/A | 5424 | 5439 | CGGAATCTAGCTCGCC | 45 | 2946 |
| 1129999 | N/A | N/A | 5484 | 5499 | TTCGCCGGCAAGGCTG | 50 | 2947 |
| 1130019 | N/A | N/A | 5800 | 5815 | AGAAGGTAGGGCACGG | 78 | 2948 |
| 1130039 | N/A | N/A | 6089 | 6104 | CCACGCACCCAGGTCG | 87 | 2949 |
| 1130059 | N/A | N/A | 6177 | 6192 | AGGCGCAACAGAGCTA | 32 | 2950 |
| 1130079 | N/A | N/A | 6369 | 6384 | CCGCCTAACCCAGTGA | 28 | 2951 |
| 1130099 | N/A | N/A | 6395 | 6410 | AACGATACCAAAGTCG | 42 | 2952 |
| 1130119 | N/A | N/A | 6459 | 6474 | TGGGATTCACCTACAC | 94 | 2953 |
| 1130139 | N/A | N/A | 6576 | 6591 | CCTAGTTGGCCTTTGC | 46 | 2954 |
| 1130159 | N/A | N/A | 6634 | 6649 | ACCCATCCAGAGTCGC | 66 | 2955 |
| 1130179 | N/A | N/A | 6755 | 6770 | TCGCAGCAAGCCCGAA | 53 | 2956 |
| 1130199 | N/A | N/A | 6818 | 6833 | GCCGCCCGGACGATGG | 84 | 2957 |
| 1130219 | N/A | N/A | 7026 | 7041 | GGCTAAGAGCTCACCT | 81† | 2958 |
| 1130239 | N/A | N/A | 7097 | 7112 | TCGGAAACACGCAGCT | 65† | 2959 |

TABLE 50

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128739 | 93 | 108 | N/A | N/A | ATCGAAAGTGTTGACT | 23 | 2960 |
| 1128759 | 133 | 148 | 500 | 515 | AGCTTTGTACTTATGC | 13 | 2961 |
| 1128779 | 164 | 179 | 3515 | 3530 | CGGTGACAGTGAGAAC | 14 | 2962 |
| 1128799 | 215 | 230 | 3566 | 3581 | ATTTGTGGTACAGCTG | 7 | 2963 |
| 1128802 | 218 | 233 | 3569 | 3584 | TACATTTGTGGTACAG | 4 | 2426 |
| 1128820 | 257 | 272 | N/A | N/A | TAGCACACCAGGGCTG | 40 | 2964 |
| 1128840 | 302 | 317 | 3809 | 3824 | CCAAACAGTATCCCCA | 10 | 2965 |
| 1128860 | 431 | 446 | 4239 | 4254 | CTTTCTGGCAGTGGTT | 12 | 2966 |
| 1128880 | 497 | 512 | 4442 | 4457 | GCTCAGTTCTATACCA | 2 | 2967 |

TABLE 50-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128900 | 583 | 598 | 4667 | 4682 | GCACGGGTTGGTGCGG | 38 | 2968 |
| 1128920 | 607 | 622 | 4691 | 4706 | CTCTAGGCAGCGACCC | 18 | 2969 |
| 1128940 | 646 | 661 | 4730 | 4745 | GTAGCCCACCGGGCAG | 33 | 2970 |
| 1128960 | 691 | 706 | 4920 | 4935 | ATCATAGCAGCTTGCC | 15 | 2971 |
| 1128980 | 745 | 760 | 4974 | 4989 | GGGCGCACCCGAGAGC | 10 | 2972 |
| 1129000 | 776 | 791 | 5005 | 5020 | GGTAGGTGGCCTCCGA | 10 | 2973 |
| 1129020 | 814 | 829 | 5043 | 5058 | CAGTCCCCAGTTCCGC | 8 | 2974 |
| 1129040 | 872 | 887 | 5186 | 5201 | GCACGAAGCACCACGG | 18 | 2975 |
| 1129060 | 910 | 925 | 5224 | 5239 | CAGGTCGCAGTACTCC | 24 | 2976 |
| 1129080 | 998 | 1013 | 5312 | 5327 | GTGCCGGCTGCGCGGG | 15 | 2977 |
| 1129100 | 1065 | 1080 | N/A | N/A | TTCGCCGGCAAGGCTC | 36 | 2978 |
| 1129120 | 1108 | 1123 | 5527 | 5542 | GCTCAGTGGGCCGTTC | 10 | 2979 |
| 1129140 | 1136 | 1151 | 5555 | 5570 | ACAGACTCTTGCGGAG | 16 | 2980 |
| 1129160 | 1160 | 1175 | 5579 | 5594 | CGCCAACGACGCGGGT | 21 | 2981 |
| 1129180 | 1223 | 1238 | 5642 | 5657 | AGAAACTGTGGCCCCA | 10 | 2982 |
| 1129200 | 1288 | 1303 | N/A | N/A | GGGCCGGTCCTGCAGG | 15 | 2983 |
| 1129220 | 1354 | 1369 | 6014 | 6029 | CTGGCACGGCTCACAG | 23 | 2984 |
| 1129240 | 1404 | 1419 | 6064 | 6079 | CTGACGGGCGAGAAGG | 46 | 2985 |
| 1129260 | 1446 | 1461 | 6189 | 6204 | GCATCCTCCTGAAGGC | 10 | 2986 |
| 1129280 | 1471 | 1486 | 6214 | 6229 | CGACAGGAGCGCGCAG | 39 | 2987 |
| 1129300 | 1518 | 1533 | 6261 | 6276 | GAGGGTCGCGCGGCGC | 24 | 2988 |
| 1129320 | 1565 | 1580 | 6308 | 6323 | CCTCGAACTGGTGGCC | 48 | 2989 |
| 1129340 | 1602 | 1617 | 6900 | 6915 | TGCGCCTCCTGCAGGA | 70 | 2990 |
| 1129360 | 1662 | 1677 | 6960 | 6975 | AGGATGGAGGATCCGT | 43† | 2991 |
| 1129380 | 1700 | 1715 | 6998 | 7013 | TGCCGCCCTCGAGGAA | 10† | 2992 |
| 1129400 | 1755 | 1770 | 7143 | 7158 | GCAGCTTGGTCCTCAC | 8† | 2993 |
| 1129420 | 1811 | 1826 | 7199 | 7214 | GGTCACCACAGCCCGA | 9 | 2994 |
| 1129440 | 1846 | 1861 | 7234 | 7249 | GTAGGCCACATCGGTG | 12 | 2995 |
| 1129460 | 1880 | 1895 | 7268 | 7283 | AGGAAACGGTGTGCTC | 7 | 2996 |
| 1129480 | 1905 | 1920 | 7293 | 7308 | GGGAAAGATGAGTCCC | 39 | 2997 |
| 1129500 | 1952 | 1967 | 7340 | 7355 | TTGCCTTCCATGCCCC | 4 | 2998 |
| 1129520 | 1997 | 2012 | 7385 | 7400 | CATCCTGGCGCGGAGC | 15 | 2999 |
| 1129540 | 2019 | 2034 | 7407 | 7422 | GCACTTTATTGAGTTC | 3 | 3000 |
| 1129560 | N/A | N/A | 139 | 154 | GACCCCCAGAACAAT | 20 | 3001 |
| 1129580 | N/A | N/A | 216 | 231 | CACCTTTCCACATAGG | 44 | 3002 |

TABLE 50-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129600 | N/A | N/A | 409 | 424 | CACCGATCTGTTGCTA | 77 | 3003 |
| 1129620 | N/A | N/A | 470 | 485 | CCAAGGTGGAATCTAC | 34 | 3004 |
| 1129640 | N/A | N/A | 615 | 630 | ACCAGGTAGGCACTAG | 23 | 3005 |
| 1129660 | N/A | N/A | 694 | 709 | CTTAGACACAGCCCAT | 58 | 3006 |
| 1129680 | N/A | N/A | 963 | 978 | ACTCAAATCCCTCGCC | 23 | 3007 |
| 1129700 | N/A | N/A | 1136 | 1151 | GCAGGTACCCTTCATC | 22 | 3008 |
| 1129720 | N/A | N/A | 1586 | 1601 | GACTCAACCCCACCAA | 32 | 3009 |
| 1129740 | N/A | N/A | 1758 | 1773 | GATGGGATGGACGGAC | 16 | 3010 |
| 1129760 | N/A | N/A | 2284 | 2299 | ACCATCGCGAATAATG | 14 | 3011 |
| 1129780 | N/A | N/A | 2487 | 2502 | ACTTGATTCAGGTGTG | 29 | 3012 |
| 1129800 | N/A | N/A | 2652 | 2667 | CTATTGAATGAGTGTC | 47 | 3013 |
| 1129820 | N/A | N/A | 2989 | 3004 | GGGTAAGTCTTCAGTC | 33 | 3014 |
| 1129840 | N/A | N/A | 3406 | 3421 | AAAAGGTCGCTGTGCA | 49 | 3015 |
| 1129860 | N/A | N/A | 3884 | 3899 | AGAGTAATGAGGCGGG | 27 | 3016 |
| 1129880 | N/A | N/A | 4059 | 4074 | TGAACCTACTTGCCTT | 21 | 3017 |
| 1129900 | N/A | N/A | 4325 | 4340 | TCTCCGAGTATCCAGC | 34 | 3018 |
| 1129920 | N/A | N/A | 4529 | 4544 | CGTTCCCAACCATCTG | 56 | 3019 |
| 1129940 | N/A | N/A | 4637 | 4652 | GAACGCAGTGAGCCAC | 21 | 3020 |
| 1129960 | N/A | N/A | 5078 | 5093 | CCCCACGCGGCGCACC | 44 | 3021 |
| 1129980 | N/A | N/A | 5425 | 5440 | CCGGAATCTAGCTCGC | 32 | 3022 |
| 1130000 | N/A | N/A | 5706 | 5721 | CGCCGGTCCTGCAGGC | 32 | 3023 |
| 1130020 | N/A | N/A | 5801 | 5816 | GAGAAGGTAGGGCACG | 30 | 3024 |
| 1130040 | N/A | N/A | 6112 | 6127 | CTTCCCGTCCCCGCGG | 45 | 3025 |
| 1130060 | N/A | N/A | 6178 | 6193 | AAGGCGCAACAGAGCT | 19 | 3026 |
| 1130080 | N/A | N/A | 6370 | 6385 | TCCGCCTAACCCAGTG | 76 | 3027 |
| 1130100 | N/A | N/A | 6396 | 6411 | GAACGATACCAAAGTC | 38 | 3028 |
| 1130120 | N/A | N/A | 6462 | 6477 | ACCTGGGATTCACCTA | 31 | 3029 |
| 1130140 | N/A | N/A | 6577 | 6592 | TCCTAGTTGGCCTTTG | 23 | 3030 |
| 1130160 | N/A | N/A | 6659 | 6674 | CGGAAACAGAAACCCC | 57 | 3031 |
| 1130180 | N/A | N/A | 6756 | 6771 | CTCGCAGCAAGCCCGA | 46 | 3032 |
| 1130200 | N/A | N/A | 6819 | 6834 | TGCCGCCCGGACGATG | 26 | 3033 |
| 1130220 | N/A | N/A | 7028 | 7043 | CGGGCTAAGAGCTCAC | 26† | 3034 |
| 1130240 | N/A | N/A | 7098 | 7113 | GTCGGAAACACGCAGC | 15† | 3035 |

TABLE 51

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128740 | 94 | 109 | N/A | N/A | AATCGAAAGTGTTGAC | 55 | 3036 |
| 1128760 | 143 | 158 | 510 | 525 | TGTGCTCTTCAGCTTT | 23 | 3037 |
| 1128780 | 165 | 180 | 3516 | 3531 | CCGGTGACAGTGAGAA | 29 | 3038 |
| 1128800 | 216 | 231 | 3567 | 3582 | CATTTGTGGTACAGCT | 20 | 3039 |
| 1128802 | 218 | 233 | 3569 | 3584 | TACATTTGTGGTACAG | 16 | 2426 |
| 1128821 | 261 | 276 | N/A | N/A | GTGGTAGCACACCAGG | 19 | 3040 |
| 1128841 | 303 | 318 | 3810 | 3825 | TCCAAACAGTATCCCC | 16 | 3041 |
| 1128861 | 432 | 447 | N/A | N/A | TCTTTCTGGCAGTGGT | 31 | 3042 |
| 1128881 | 528 | 543 | 4473 | 4488 | CCCTTGCACTGGCATC | 17 | 3043 |
| 1128901 | 584 | 599 | 4668 | 4683 | GGCACGGGTTGGTGCG | 69 | 3044 |
| 1128921 | 608 | 623 | 4692 | 4707 | CCTCTAGGCAGCGACC | 32 | 3045 |
| 1128941 | 648 | 663 | 4732 | 4747 | GTGTAGCCCACCGGGC | 84 | 3046 |
| 1128961 | 692 | 707 | 4921 | 4936 | CATCATAGCAGCTTGC | 28 | 3047 |
| 1128981 | 746 | 761 | 4975 | 4990 | AGGGCGCACCCGAGAG | 25 | 3048 |
| 1129001 | 777 | 792 | 5006 | 5021 | CGGTAGGTGGCCTCCG | 57 | 3049 |
| 1129021 | 815 | 830 | 5044 | 5059 | CCAGTCCCCAGTTCCG | 39 | 3050 |
| 1129041 | 873 | 888 | 5187 | 5202 | AGCACGAAGCACCACG | 25 | 3051 |
| 1129061 | 911 | 926 | 5225 | 5240 | CCAGGTCGCAGTACTC | 21 | 3052 |
| 1129081 | 1001 | 1016 | 5315 | 5330 | GCGGTGCCGGCTGCGC | 73 | 3053 |
| 1129101 | 1066 | 1081 | 5485 | 5500 | CTTCGCCGGCAAGGCT | 36 | 3054 |
| 1129121 | 1112 | 1127 | 5531 | 5546 | CGCAGCTCAGTGGGCC | 46 | 3055 |
| 1129141 | 1137 | 1152 | 5556 | 5571 | GACAGACTCTTGCGGA | 23 | 3056 |
| 1129161 | 1161 | 1176 | 5580 | 5595 | CCGCCAACGACGCGGG | 38 | 3057 |
| 1129181 | 1224 | 1239 | 5643 | 5658 | CAGAAACTGTGGCCCC | 29 | 3058 |
| 1129201 | 1289 | 1304 | N/A | N/A | CGGGCCGGTCCTGCAG | 58 | 3059 |
| 1129221 | 1357 | 1372 | 6017 | 6032 | CGTCTGGCACGGCTCA | 12 | 3060 |
| 1129241 | 1405 | 1420 | 6065 | 6080 | GCTGACGGGCGAGAAG | 30 | 3061 |
| 1129261 | 1448 | 1463 | 6191 | 6206 | CCGCATCCTCCTGAAG | 46 | 3062 |
| 1129281 | 1472 | 1487 | 6215 | 6230 | GCGACAGGAGCGCGCA | 59 | 3063 |
| 1129301 | 1519 | 1534 | 6262 | 6277 | GGAGGGTCGCGCGGCG | 61 | 3064 |
| 1129321 | 1566 | 1581 | 6309 | 6324 | CCCTCGAACTGGTGGC | 70 | 3065 |
| 1129341 | 1606 | 1621 | 6904 | 6919 | TACCTGCGCCTCCTGC | 90 | 3066 |
| 1129361 | 1663 | 1678 | 6961 | 6976 | GAGGATGGAGGATCCG | 43† | 3067 |
| 1129381 | 1704 | 1719 | 7002 | 7017 | TCGGTGCCGCCCTCGA | 32† | 3068 |
| 1129401 | 1759 | 1774 | 7147 | 7162 | CTCTGCAGCTTGGTCC | 32† | 3069 |
| 1129421 | 1814 | 1829 | 7202 | 7217 | TGCGGTCACCACAGCC | 22 | 3070 |

TABLE 51-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129441 | 1847 | 1862 | 7235 | 7250 | AGTAGGCCACATCGGT | 13 | 3071 |
| 1129461 | 1881 | 1896 | 7269 | 7284 | CAGGAAACGGTGTGCT | 25 | 3072 |
| 1129481 | 1906 | 1921 | 7294 | 7309 | AGGGAAAGATGAGTCC | 10 | 3073 |
| 1129501 | 1954 | 1969 | 7342 | 7357 | TCTTGCCTTCCATGCC | 14 | 3074 |
| 1129521 | 1998 | 2013 | 7386 | 7401 | CCATCCTGGCGCGGAG | 28 | 3075 |
| 1129541 | 2020 | 2035 | 7408 | 7423 | AGCACTTTATTGAGTT | 8 | 3076 |
| 1129561 | N/A | N/A | 140 | 155 | CGACCCCCAGAACAA | 72 | 3077 |
| 1129581 | N/A | N/A | 229 | 244 | TCCGGGCTGGCCTCAC | 81 | 3078 |
| 1129601 | N/A | N/A | 410 | 425 | CCACCGATCTGTTGCT | 56 | 3079 |
| 1129621 | N/A | N/A | 520 | 535 | TTACCGACTGTGTGCT | 30 | 3080 |
| 1129641 | N/A | N/A | 619 | 634 | TAGCACCAGGTAGGCA | 64 | 3081 |
| 1129661 | N/A | N/A | 697 | 712 | GCACTTAGACACAGCC | 88 | 3082 |
| 1129681 | N/A | N/A | 964 | 979 | AACTCAAATCCCTCGC | 70 | 3083 |
| 1129701 | N/A | N/A | 1137 | 1152 | GGCAGGTACCCTTCAT | 151 | 3084 |
| 1129721 | N/A | N/A | 1590 | 1605 | TAGAGACTCAACCCCA | 62 | 3085 |
| 1129741 | N/A | N/A | 1761 | 1776 | GCAGATGGGATGGACG | 42 | 3086 |
| 1129761 | N/A | N/A | 2285 | 2300 | AACCATCGCGAATAAT | 50 | 3087 |
| 1129781 | N/A | N/A | 2489 | 2504 | ACACTTGATTCAGGTG | 49 | 3088 |
| 1129801 | N/A | N/A | 2653 | 2668 | CCTATTGAATGAGTGT | 54 | 3089 |
| 1129821 | N/A | N/A | 2991 | 3006 | TTGGGTAAGTCTTCAG | 51 | 3090 |
| 1129841 | N/A | N/A | 3407 | 3422 | AAAAAGGTCGCTGTGC | 52 | 3091 |
| 1129861 | N/A | N/A | 3885 | 3900 | GAGAGTAATGAGGCGG | 54 | 3092 |
| 1129881 | N/A | N/A | 4060 | 4075 | TTGAACCTACTTGCCT | 62 | 3093 |
| 1129901 | N/A | N/A | 4326 | 4341 | GTCTCCGAGTATCCAG | 106 | 3094 |
| 1129921 | N/A | N/A | 4532 | 4547 | GCCCGTTCCCAACCAT | 63 | 3095 |
| 1129941 | N/A | N/A | 4639 | 4654 | GGGAACGCAGTGAGCC | 47 | 3096 |
| 1129961 | N/A | N/A | 5080 | 5095 | AGCCCCACGCGGCGCA | 112 | 3097 |
| 1129981 | N/A | N/A | 5426 | 5441 | GCCGGAATCTAGCTCG | 49 | 3098 |
| 1130001 | N/A | N/A | 5707 | 5722 | TCGCCGGTCCTGCAGG | 60 | 3099 |
| 1130021 | N/A | N/A | 5806 | 5821 | GGCGGGAGAAGGTAGG | 51 | 3100 |
| 1130041 | N/A | N/A | 6158 | 6173 | CGGGCGGAGAGGAGCG | 118 | 3101 |
| 1130061 | N/A | N/A | 6310 | 6325 | ACCCTCGAACTGGTGG | 45 | 3102 |
| 1130081 | N/A | N/A | 6371 | 6386 | TTCCGCCTAACCCAGT | 113 | 3103 |
| 1130101 | N/A | N/A | 6397 | 6412 | GGAACGATACCAAAGT | 75 | 3104 |
| 1130121 | N/A | N/A | 6463 | 6478 | TACCTGGGATTCACCT | 59 | 3105 |

TABLE 51-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130141 | N/A | N/A | 6578 | 6593 | GTCCTAGTTGGCCTTT | 29 | 3106 |
| 1130161 | N/A | N/A | 6664 | 6679 | CGGAGCGGAAACAGAA | 109 | 3107 |
| 1130181 | N/A | N/A | 6757 | 6772 | TCTCGCAGCAAGCCCG | 99 | 3108 |
| 1130201 | N/A | N/A | 6823 | 6838 | CGCTTGCCGCCCGGAC | 48 | 3109 |
| 1130221 | N/A | N/A | 7029 | 7044 | CCGGGCTAAGAGCTCA | 48† | 3110 |
| 1130241 | N/A | N/A | 7099 | 7114 | GGTCGGAAACACGCAG | 77† | 3111 |

TABLE 52

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128761 | 145 | 160 | 512 | 527 | TGTGTGCTCTTCAGCT | 19 | 3112 |
| 1128781 | 166 | 181 | 3517 | 3532 | CCCGGTGACAGTGAGA | 18 | 3113 |
| 1128801 | 217 | 232 | 3568 | 3583 | ACATTTGTGGTACAGC | 8 | 3114 |
| 1128802 | 218 | 233 | 3569 | 3584 | TACATTTGTGGTACAG | 9 | 2426 |
| 1128862 | 462 | 477 | 4407 | 4422 | AACCGGAGAAGCTGAG | 24 | 3115 |
| 1128882 | 529 | 544 | 4474 | 4489 | ACCCTTGCACTGGCAT | 32 | 3116 |
| 1128902 | 585 | 600 | 4669 | 4684 | AGGCACGGGTTGGTGC | 70 | 3117 |
| 1128922 | 609 | 624 | 4693 | 4708 | ACCTCTAGGCAGCGAC | 19 | 3118 |
| 1128942 | 650 | 665 | 4734 | 4749 | CGGTGTAGCCCACCGG | 67 | 3119 |
| 1128962 | 693 | 708 | 4922 | 4937 | CCATCATAGCAGCTTG | 22 | 3120 |
| 1128982 | 747 | 762 | 4976 | 4991 | CAGGGCGCACCCGAGA | 27 | 3121 |
| 1129002 | 778 | 793 | 5007 | 5022 | CCGGTAGGTGGCCTCC | 32 | 3122 |
| 1129022 | 823 | 838 | 5052 | 5067 | GTGGCCGCCCAGTCCC | 17 | 3123 |
| 1129042 | 874 | 889 | 5188 | 5203 | CAGCACGAAGCACCAC | 21 | 3124 |
| 1129062 | 912 | 927 | 5226 | 5241 | GCCAGGTCGCAGTACT | 25 | 3125 |
| 1129082 | 1003 | 1018 | 5317 | 5332 | CGGCGGTGCCGGCTGC | 25 | 3126 |
| 1129102 | 1068 | 1083 | 5487 | 5502 | CGCTTCGCCGGCAAGG | 30 | 3127 |
| 1129122 | 1113 | 1128 | 5532 | 5547 | CCGCAGCTCAGTGGGC | 40 | 3128 |
| 1129142 | 1138 | 1153 | 5557 | 5572 | AGACAGACTCTTGCGG | 15 | 3129 |
| 1129162 | 1162 | 1177 | 5581 | 5596 | CCCGCCAACGACGCGG | 43 | 3130 |
| 1129182 | 1225 | 1240 | 5644 | 5659 | GCAGAAACTGTGGCCC | 33 | 3131 |
| 1129222 | 1371 | 1386 | 6031 | 6046 | GAGCGCACGGCCAACG | 23 | 3132 |
| 1129242 | 1406 | 1421 | 6066 | 6081 | AGCTGACGGGCGAGAA | 59 | 3133 |

TABLE 52-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129262 | 1449 | 1464 | 6192 | 6207 | TCCGCATCCTCCTGAA | 55 | 3134 |
| 1129282 | 1473 | 1488 | 6216 | 6231 | GGCGACAGGAGCGCGC | 34 | 3135 |
| 1129302 | 1520 | 1535 | 6263 | 6278 | CGGAGGGTCGCGCGGC | 65 | 3136 |
| 1129342 | 1607 | 1622 | 6905 | 6920 | GTACCTGCGCCTCCTG | 82 | 3137 |
| 1129362 | 1679 | 1694 | 6977 | 6992 | CGCAGAGCATGCCGGG | 6† | 3138 |
| 1129382 | 1705 | 1720 | 7003 | 7018 | ATCGGTGCCGCCCTCG | 8† | 3139 |
| 1129402 | 1774 | 1789 | 7162 | 7177 | CAGGGTGAGCCGGCGC | 31 | 3140 |
| 1129422 | 1815 | 1830 | 7203 | 7218 | TTGCGGTCACCACAGC | 27 | 3141 |
| 1129442 | 1848 | 1863 | 7236 | 7251 | TAGTAGGCCACATCGG | 19 | 3142 |
| 1129462 | 1882 | 1897 | 7270 | 7285 | TCAGGAAACGGTGTGC | 18 | 3143 |
| 1129482 | 1908 | 1923 | 7296 | 7311 | GGAGGGAAAGATGAGT | 15 | 3144 |
| 1129502 | 1955 | 1970 | 7343 | 7358 | ATCTTGCCTTCCATGC | 9 | 3145 |
| 1129522 | 1999 | 2014 | 7387 | 7402 | GCCATCCTGGCGCGGA | 51 | 3146 |
| 1129542 | 2021 | 2036 | 7409 | 7424 | AAGCACTTTATTGAGT | 12 | 3147 |
| 1129562 | N/A | N/A | 141 | 156 | GCGACCCCCAGAACA | 72 | 3148 |
| 1129582 | N/A | N/A | 230 | 245 | TTCCGGGCTGGCCTCA | 52 | 3149 |
| 1129602 | N/A | N/A | 411 | 426 | GCCACCGATCTGTTGC | 82 | 3150 |
| 1129622 | N/A | N/A | 521 | 536 | CTTACCGACTGTGTGC | 52 | 3151 |
| 1129642 | N/A | N/A | 623 | 638 | GACCTAGCACCAGGTA | 103 | 3152 |
| 1129662 | N/A | N/A | 699 | 714 | GGGCACTTAGACACAG | 55 | 3153 |
| 1129682 | N/A | N/A | 965 | 980 | GAACTCAAATCCCTCG | 49 | 3154 |
| 1129702 | N/A | N/A | 1138 | 1153 | TGGCAGGTACCCTTCA | 62 | 3155 |
| 1129722 | N/A | N/A | 1591 | 1606 | TTAGAGACTCAACCCC | 62 | 3156 |
| 1129742 | N/A | N/A | 1916 | 1931 | CATGAAGTTGTGTGCC | 67 | 3157 |
| 1129762 | N/A | N/A | 2287 | 2302 | ATAACCATCGCGAATA | 36 | 3158 |
| 1129782 | N/A | N/A | 2490 | 2505 | GACACTTGATTCAGGT | 45 | 3159 |
| 1129802 | N/A | N/A | 2654 | 2669 | TCCTATTGAATGAGTG | 23 | 3160 |
| 1129822 | N/A | N/A | 3016 | 3031 | TCCACAACCTGCTAGC | 74 | 3161 |
| 1129842 | N/A | N/A | 3408 | 3423 | CAAAAGGTCGCTGTG | 59 | 3162 |
| 1129862 | N/A | N/A | 3886 | 3901 | GGAGAGTAATGAGGCG | 44 | 3163 |
| 1129882 | N/A | N/A | 4061 | 4076 | CTTGAACCTACTTGCC | 50 | 3164 |
| 1129902 | N/A | N/A | 4328 | 4343 | AAGTCTCCGAGTATCC | 61 | 3165 |
| 1129922 | N/A | N/A | 4534 | 4549 | TGGCCCGTTCCCAACC | 46 | 3166 |
| 1129942 | N/A | N/A | 4805 | 4820 | AAGCCCGTCCCACCTG | 46 | 3167 |
| 1129962 | N/A | N/A | 5084 | 5099 | ACCCAGCCCCACGCGG | 60 | 3168 |

TABLE 52-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129982 | N/A | N/A | 5428 | 5443 | TGGCCGGAATCTAGCT | 119 | 3169 |
| 1130002 | N/A | N/A | 5708 | 5723 | CTCGCCGGTCCTGCAG | 54 | 3170 |
| 1130022 | N/A | N/A | 5823 | 5838 | CGTGGAAAGAAGGGTG | 78 | 3171 |
| 1130042 | N/A | N/A | 6159 | 6174 | CCGGGCGGAGAGGAGC | 87 | 3172 |
| 1130062 | N/A | N/A | 6311 | 6326 | TACCCTCGAACTGGTG | 69 | 3173 |
| 1130082 | N/A | N/A | 6373 | 6388 | TCTTCCGCCTAACCCA | 74 | 3174 |
| 1130102 | N/A | N/A | 6398 | 6413 | CGGAACGATACCAAAG | 47 | 3175 |
| 1130122 | N/A | N/A | 6464 | 6479 | CTACCTGGGATTCACC | 85 | 3176 |
| 1130142 | N/A | N/A | 6579 | 6594 | CGTCCTAGTTGGCCTT | 33 | 3177 |
| 1130162 | N/A | N/A | 6665 | 6680 | GCGGAGCGGAAACAGA | 67 | 3178 |
| 1130182 | N/A | N/A | 6759 | 6774 | TCTCTCGCAGCAAGCC | 47 | 3179 |
| 1130202 | N/A | N/A | 6836 | 6851 | CCCCATCTGACAACGC | 103 | 3180 |
| 1130222 | N/A | N/A | 7030 | 7045 | ACCGGGCTAAGAGCTC | 69† | 3181 |
| 1130242 | N/A | N/A | 7100 | 7115 | GGGTCGGAAACACGCA | 94† | 3182 |
| 1128741 | 95 | 110 | N/A | N/A | GAATCGAAAGTGTTGA | 28 | 3183 |
| 1128822 | 263 | 278 | N/A | N/A | GGGTGGTAGCACACCA | 36 | 3184 |
| 1128842 | 327 | 342 | N/A | N/A | CAGTGGTCTTTCACTT | 91 | 3185 |
| 1129202 | 1291 | 1306 | N/A | N/A | TGCGGGCCGGTCCTGC | 63 | 3186 |
| 1129322 | 1567 | 1582 | N/A | N/A | CCCCTCGAACTGGTGG | 86 | 3187 |

TABLE 53

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1128722 | 27 | 42 | 27 | 42 | GTCCGTTGGTCCAGCT | 34 | 3188 |
| 1128742 | 96 | 111 | N/A | N/A | GGAATCGAAAGTGTTG | 19 | 3189 |
| 1128762 | 146 | 161 | 513 | 528 | CTGTGTGCTCTTCAGC | 11 | 3190 |
| 1128782 | 168 | 183 | 3519 | 3534 | TCCCCGGTGACAGTGA | 16 | 3191 |
| 1128802 | 218 | 233 | 3569 | 3584 | TACATTTGTGGTACAG | 7 | 2426 |
| 1128803 | 219 | 234 | 3570 | 3585 | GTACATTTGTGGTACA | 41 | 3192 |
| 1128823 | 278 | 293 | 3785 | 3800 | CCTGATCAAAGTTGGG | 25 | 3193 |
| 1128843 | 328 | 343 | N/A | N/A | GCAGTGGTCTTTCACT | 34 | 3194 |
| 1128863 | 463 | 478 | 4408 | 4423 | AAACCGGAGAAGCTGA | 34 | 3195 |
| 1128883 | 531 | 546 | 4476 | 4491 | GGACCCTTGCACTGGC | 33 | 3196 |

TABLE 53-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1128903 | 586 | 601 | 4670 | 4685 | GAGGCACGGGTTGGTG | 33 | 3197 |
| 1128923 | 610 | 625 | 4694 | 4709 | CACCTCTAGGCAGCGA | 26 | 3198 |
| 1128943 | 651 | 666 | 4735 | 4750 | CCGGTGTAGCCCACCG | 45 | 3199 |
| 1128963 | 695 | 710 | 4924 | 4939 | GGCCATCATAGCAGCT | 35 | 3200 |
| 1128983 | 748 | 763 | 4977 | 4992 | ACAGGGCGCACCCGAG | 19 | 3201 |
| 1129003 | 779 | 794 | 5008 | 5023 | TCCGGTAGGTGGCCTC | 32 | 3202 |
| 1129023 | 838 | 853 | N/A | N/A | GTTCCGGCAGAAGGCG | 20 | 3203 |
| 1129043 | 877 | 892 | 5191 | 5206 | GTTCAGCACGAAGCAC | 14 | 3204 |
| 1129063 | 913 | 928 | 5227 | 5242 | TGCCAGGTCGCAGTAC | 37 | 3205 |
| 1129083 | 1004 | 1019 | 5318 | 5333 | TCGGCGGTGCCGGCTG | 18 | 3206 |
| 1129103 | 1069 | 1084 | 5488 | 5503 | CCGCTTCGCCGGCAAG | 44 | 3207 |
| 1129123 | 1114 | 1129 | 5533 | 5548 | CCCGCAGCTCAGTGGG | 35 | 3208 |
| 1129143 | 1139 | 1154 | 5558 | 5573 | AAGACAGACTCTTGCG | 16 | 3209 |
| 1129163 | 1163 | 1178 | 5582 | 5597 | GCCCGCCAACGACGCG | 39 | 3210 |
| 1129183 | 1226 | 1241 | 5645 | 5660 | CGCAGAAACTGTGGCC | 36 | 3211 |
| 1129203 | 1292 | 1307 | N/A | N/A | GTGCGGGCCGGTCCTG | 62 | 3212 |
| 1129223 | 1373 | 1388 | 6033 | 6048 | AGGAGCGCACGGCCAA | 27 | 3213 |
| 1129243 | 1411 | 1426 | 6071 | 6086 | CTGGTAGCTGACGGGC | 24 | 3214 |
| 1129263 | 1450 | 1465 | 6193 | 6208 | GTCCGCATCCTCCTGA | 40 | 3215 |
| 1129283 | 1474 | 1489 | 6217 | 6232 | AGGCGACAGGAGCGCG | 20 | 3216 |
| 1129303 | 1521 | 1536 | 6264 | 6279 | TCGGAGGGTCGCGCGG | 48 | 3217 |
| 1129323 | 1568 | 1583 | N/A | N/A | CCCCCTCGAACTGGTG | 58 | 3218 |
| 1129343 | 1609 | 1624 | 6907 | 6922 | CGGTACCTGCGCCTCC | 87 | 3219 |
| 1129363 | 1680 | 1695 | 6978 | 6993 | GCGCAGAGCATGCCGG | 44† | 3220 |
| 1129383 | 1706 | 1721 | 7004 | 7019 | CATCGGTGCCGCCCTC | 15† | 3221 |
| 1129403 | 1775 | 1790 | 7163 | 7178 | GCAGGGTGAGCCGGCG | 27 | 3222 |
| 1129423 | 1817 | 1832 | 7205 | 7220 | TGTTGCGGTCACCACA | 11 | 3223 |
| 1129443 | 1849 | 1864 | 7237 | 7252 | GTAGTAGGCCACATCG | 20 | 3224 |
| 1129463 | 1883 | 1898 | 7271 | 7286 | ATCAGGAAACGGTGTG | 38 | 3225 |
| 1129483 | 1919 | 1934 | 7307 | 7322 | GGAATCACCAAGGAGG | 5 | 3226 |
| 1129503 | 1957 | 1972 | 7345 | 7360 | CAATCTTGCCTTCCAT | 14 | 3227 |
| 1129523 | 2000 | 2015 | 7388 | 7403 | CGCCATCCTGGCGCGG | 57 | 3228 |
| 1129543 | 2022 | 2037 | 7410 | 7425 | AAAGCACTTTATTGAG | 9 | 3229 |
| 1129563 | N/A | N/A | 142 | 157 | AGCGACCCCCAGAAC | 42 | 3230 |
| 1129583 | N/A | N/A | 232 | 247 | CCTTCCGGGCTGGCCT | 55 | 3231 |

TABLE 53-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1129603 | N/A | N/A | 412 | 427 | TGCCACCGATCTGTTG | 60 | 3232 |
| 1129623 | N/A | N/A | 526 | 541 | GGCCACTTACCGACTG | 78 | 3233 |
| 1129643 | N/A | N/A | 624 | 639 | AGACCTAGCACCAGGT | 53 | 3234 |
| 1129663 | N/A | N/A | 701 | 716 | GTGGGCACTTAGACAC | 63 | 3235 |
| 1129683 | N/A | N/A | 1003 | 1018 | TCAACCTGGTTTCACA | 20 | 3236 |
| 1129703 | N/A | N/A | 1139 | 1154 | ATGGCAGGTACCCTTC | 21 | 3237 |
| 1129723 | N/A | N/A | 1592 | 1607 | CTTAGAGACTCAACCC | 36 | 3238 |
| 1129743 | N/A | N/A | 1917 | 1932 | GCATGAAGTTGTGTGC | 72 | 3239 |
| 1129763 | N/A | N/A | 2288 | 2303 | CATAACCATCGCGAAT | 29 | 3240 |
| 1129783 | N/A | N/A | 2494 | 2509 | GTTAGACACTTGATTC | 21 | 3241 |
| 1129803 | N/A | N/A | 2655 | 2670 | CTCCTATTGAATGAGT | 64 | 3242 |
| 1129823 | N/A | N/A | 3031 | 3046 | GAGTAGACTCCTGACT | 80 | 3243 |
| 1129843 | N/A | N/A | 3409 | 3424 | TCAAAAGGTCGCTGT | 64 | 3244 |
| 1129863 | N/A | N/A | 3895 | 3910 | GTGATACCAGGAGAGT | 36 | 3245 |
| 1129883 | N/A | N/A | 4062 | 4077 | TCTTGAACCTACTTGC | 32 | 3246 |
| 1129903 | N/A | N/A | 4330 | 4345 | CCAAGTCTCCGAGTAT | 68 | 3247 |
| 1129923 | N/A | N/A | 4535 | 4550 | CTGGCCCGTTCCCAAC | 41 | 3248 |
| 1129943 | N/A | N/A | 4808 | 4823 | GGCAAGCCCGTCCCAC | 21 | 3249 |
| 1129963 | N/A | N/A | 5148 | 5163 | CTGTAGCCACACGACG | 85 | 3250 |
| 1129983 | N/A | N/A | 5429 | 5444 | CTGGCCGGAATCTAGC | 92 | 3251 |
| 1130003 | N/A | N/A | 5709 | 5724 | ACTCGCCGGTCCTGCA | 36 | 3252 |
| 1130023 | N/A | N/A | 5841 | 5856 | CCGGGAGCTCCGGAGG | 69 | 3253 |
| 1130043 | N/A | N/A | 6160 | 6175 | CCCGGGCGGAGAGGAG | 85 | 3254 |
| 1130063 | N/A | N/A | 6312 | 6327 | CTACCCTCGAACTGGT | 52 | 3255 |
| 1130083 | N/A | N/A | 6375 | 6390 | CTTCTTCCGCCTAACC | 51 | 3256 |
| 1130103 | N/A | N/A | 6399 | 6414 | CCGGAACGATACCAAA | 72 | 3257 |
| 1130123 | N/A | N/A | 6475 | 6490 | GCCCTGGGATTCTACC | 54 | 3258 |
| 1130143 | N/A | N/A | 6600 | 6615 | TAGCCCGGAGCGCGGG | 61 | 3259 |
| 1130163 | N/A | N/A | 6666 | 6681 | GGCGGAGCGGAAACAG | 49 | 3260 |
| 1130183 | N/A | N/A | 6760 | 6775 | CTCTCTCGCAGCAAGC | 43 | 3261 |
| 1130203 | N/A | N/A | 6838 | 6853 | CACCCCATCTGACAAC | 45 | 3262 |
| 1130223 | N/A | N/A | 7031 | 7046 | AACCGGGCTAAGAGCT | 62† | 3263 |
| 1130243 | N/A | N/A | 7101 | 7116 | TGGGTCGGAAACACGC | 33† | 3264 |

TABLE 54

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1128723 | 29 | 44 | 29 | 44 | CCGTCCGTTGGTCCAG | 25 | 3265 |
| 1128743 | 97 | 112 | N/A | N/A | TGGAATCGAAAGTGTT | 42 | 3266 |
| 1128763 | 147 | 162 | 514 | 529 | ACTGTGTGCTCTTCAG | 20 | 3267 |
| 1128783 | 169 | 184 | 3520 | 3535 | CTCCCCGGTGACAGTG | 36 | 3268 |
| 1128802 | 218 | 233 | 3569 | 3584 | TACATTTGTGGTACAG | 12 | 2426 |
| 1128804 | 220 | 235 | 3571 | 3586 | GGTACATTTGTGGTAC | 39 | 3269 |
| 1128824 | 279 | 294 | 3786 | 3801 | TCCTGATCAAAGTTGG | 32 | 3270 |
| 1128844 | 330 | 345 | N/A | N/A | CTGCAGTGGTCTTTCA | 87 | 3271 |
| 1128864 | 464 | 479 | 4409 | 4424 | AAAACCGGAGAAGCTG | 32 | 3272 |
| 1128884 | 535 | 550 | 4480 | 4495 | ATCAGGACCCTTGCAC | 32 | 3273 |
| 1128904 | 587 | 602 | 4671 | 4686 | GGAGGCACGGGTTGGT | 41 | 3274 |
| 1128924 | 612 | 627 | 4696 | 4711 | TCCACCTCTAGGCAGC | 26 | 3275 |
| 1128944 | 652 | 667 | 4736 | 4751 | TCCGGTGTAGCCCACC | 31 | 3276 |
| 1128964 | 697 | 712 | 4926 | 4941 | GCGGCCATCATAGCAG | 70 | 3277 |
| 1128984 | 749 | 764 | 4978 | 4993 | GACAGGGCGCACCCGA | 28 | 3278 |
| 1129004 | 780 | 795 | 5009 | 5024 | TTCCGGTAGGTGGCCT | 38 | 3279 |
| 1129024 | 839 | 854 | N/A | N/A | GGTTCCGGCAGAAGGC | 27 | 3280 |
| 1129044 | 881 | 896 | 5195 | 5210 | CGCGGTTCAGCACGAA | 21 | 3281 |
| 1129064 | 941 | 956 | 5255 | 5270 | GCGCCGCCTGGGTTGG | 48 | 3282 |
| 1129084 | 1005 | 1020 | 5319 | 5334 | TTCGGCGGTGCCGGCT | 17 | 3283 |
| 1129104 | 1070 | 1085 | 5489 | 5504 | CCCGCTTCGCCGGCAA | 20 | 3284 |
| 1129124 | 1115 | 1130 | 5534 | 5549 | GCCCGCAGCTCAGTGG | 39 | 3285 |
| 1129144 | 1141 | 1156 | 5560 | 5575 | CGAAGACAGACTCTTG | 20 | 3286 |
| 1129164 | 1165 | 1180 | 5584 | 5599 | CAGCCCGCCAACGACG | 47 | 3287 |
| 1129184 | 1227 | 1242 | 5646 | 5661 | GCGCAGAAACTGTGGC | 51 | 3288 |
| 1129204 | 1302 | 1317 | 5962 | 5977 | AGATCCTCGGGTGCGG | 22 | 3289 |
| 1129224 | 1374 | 1389 | 6034 | 6049 | TAGGAGCGCACGGCCA | 27 | 3290 |
| 1129244 | 1412 | 1427 | 6072 | 6087 | GCTGGTAGCTGACGGG | 44 | 3291 |
| 1129264 | 1452 | 1467 | 6195 | 6210 | CCGTCCGCATCCTCCT | 24 | 3292 |
| 1129284 | 1475 | 1490 | 6218 | 6233 | AAGGCGACAGGAGCGC | 21 | 3293 |
| 1129304 | 1522 | 1537 | 6265 | 6280 | CTCGGAGGGTCGCGCG | 26 | 3294 |
| 1129324 | 1569 | 1584 | N/A | N/A | GCCCCCTCGAACTGGT | 110 | 3295 |
| 1129344 | 1610 | 1625 | 6908 | 6923 | ACGGTACCTGCGCCTC | 63 | 3296 |
| 1129364 | 1681 | 1696 | 6979 | 6994 | TGCGCAGAGCATGCCG | 44† | 3297 |
| 1129384 | 1707 | 1722 | 7005 | 7020 | GCATCGGTGCCGCCCT | 36† | 3298 |
| 1129404 | 1776 | 1791 | 7164 | 7179 | TGCAGGGTGAGCCGGC | 54 | 3299 |

TABLE 54-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1129424 | 1819 | 1834 | 7207 | 7222 | CTTGTTGCGGTCACCA | 17 | 3300 |
| 1129444 | 1850 | 1865 | 7238 | 7253 | GGTAGTAGGCCACATC | 23 | 3301 |
| 1129464 | 1884 | 1899 | 7272 | 7287 | AATCAGGAAACGGTGT | 28 | 3302 |
| 1129484 | 1920 | 1935 | 7308 | 7323 | CGGAATCACCAAGGAG | 9 | 3303 |
| 1129504 | 1958 | 1973 | 7346 | 7361 | ACAATCTTGCCTTCCA | 15 | 3304 |
| 1129524 | 2002 | 2017 | 7390 | 7405 | TGCGCCATCCTGGCGC | 42 | 3305 |
| 1129544 | 2023 | 2038 | 7411 | 7426 | CAAAGCACTTTATTGA | 21 | 3306 |
| 1129564 | N/A | N/A | 143 | 158 | TAGCGACCCCCAGAA | 34 | 3307 |
| 1129584 | N/A | N/A | 271 | 286 | GTATCCACCCAGTCTG | 67 | 3308 |
| 1129604 | N/A | N/A | 415 | 430 | GCCTGCCACCGATCTG | 81 | 3309 |
| 1129624 | N/A | N/A | 528 | 543 | CAGGCCACTTACCGAC | 37 | 3310 |
| 1129644 | N/A | N/A | 626 | 641 | TAAGACCTAGCACCAG | 69 | 3311 |
| 1129664 | N/A | N/A | 702 | 717 | CGTGGGCACTTAGACA | 47 | 3312 |
| 1129684 | N/A | N/A | 1004 | 1019 | ATCAACCTGGTTTCAC | 33 | 3313 |
| 1129704 | N/A | N/A | 1203 | 1218 | GTAATTTAGTGTCTGG | 38 | 3314 |
| 1129724 | N/A | N/A | 1593 | 1608 | GCTTAGAGACTCAACC | 60 | 3315 |
| 1129744 | N/A | N/A | 2082 | 2097 | TGGACCTTTAAGATGC | 26 | 3316 |
| 1129764 | N/A | N/A | 2289 | 2304 | ACATAACCATCGCGAA | 45 | 3317 |
| 1129784 | N/A | N/A | 2499 | 2514 | CGTGTGTTAGACACTT | 42 | 3318 |
| 1129804 | N/A | N/A | 2656 | 2671 | TCTCCTATTGAATGAG | 79 | 3319 |
| 1129824 | N/A | N/A | 3032 | 3047 | GGAGTAGACTCCTGAC | 85 | 3320 |
| 1129844 | N/A | N/A | 3410 | 3425 | CTCAAAAGGTCGCTG | 43 | 3321 |
| 1129864 | N/A | N/A | 3897 | 3912 | TGGTGATACCAGGAGA | 21 | 3322 |
| 1129884 | N/A | N/A | 4066 | 4081 | CCCTTCTTGAACCTAC | 58 | 3323 |
| 1129904 | N/A | N/A | 4332 | 4347 | TGCCAAGTCTCCGAGT | 52 | 3324 |
| 1129924 | N/A | N/A | 4583 | 4598 | TGGCACACCACCCGGC | 51 | 3325 |
| 1129944 | N/A | N/A | 4809 | 4824 | TGGCAAGCCCGTCCCA | 41 | 3326 |
| 1129964 | N/A | N/A | 5149 | 5164 | CCTGTAGCCACACGAC | 61 | 3327 |
| 1129984 | N/A | N/A | 5433 | 5448 | CCGGCTGGCCGGAATC | 63 | 3328 |
| 1130004 | N/A | N/A | 5710 | 5725 | TACTCGCCGGTCCTGC | 34 | 3329 |
| 1130024 | N/A | N/A | 5842 | 5857 | CCCGGGAGCTCCGGAG | 138 | 3330 |
| 1130044 | N/A | N/A | 6161 | 6176 | ACCCGGGCGGAGAGGA | 38 | 3331 |
| 1130064 | N/A | N/A | 6313 | 6328 | CCTACCCTCGAACTGG | 62 | 3332 |
| 1130084 | N/A | N/A | 6380 | 6395 | GCGGGCTTCTTCCGCC | 103 | 3333 |
| 1130104 | N/A | N/A | 6400 | 6415 | CCCGGAACGATACCAA | 75 | 3334 |

TABLE 54-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID No. |
|---|---|---|---|---|---|---|---|
| 1130124 | N/A | N/A | 6527 | 6542 | CGATTCTCCCTGTATC | 34 | 3335 |
| 1130144 | N/A | N/A | 6602 | 6617 | ACTAGCCCGGAGCGCG | 56 | 3336 |
| 1130164 | N/A | N/A | 6667 | 6682 | GGGCGGAGCGGAAACA | 87 | 3337 |
| 1130184 | N/A | N/A | 6781 | 6796 | GTAAACCCACTCATGC | 63 | 3338 |
| 1130204 | N/A | N/A | 6841 | 6856 | TCACACCCCATCTGAC | 52 | 3339 |
| 1130224 | N/A | N/A | 7032 | 7047 | CAACCGGGCTAAGAGC | 74† | 3340 |
| 1130244 | N/A | N/A | 7102 | 7117 | CTGGGTCGGAAACACG | 57† | 3341 |

TABLE 55

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128744 | 98 | 113 | N/A | N/A | GTGGAATCGAAAGTGT | 37 | 3342 |
| 1128764 | 148 | 163 | 515 | 530 | GACTGTGTGCTCTTCA | 12 | 3343 |
| 1128784 | 170 | 185 | 3521 | 3536 | GCTCCCCGGTGACAGT | 44 | 3344 |
| 1128802 | 218 | 233 | 3569 | 3584 | TACATTTGTGGTACAG | 13 | 2426 |
| 1128805 | 221 | 236 | 3572 | 3587 | GGGTACATTTGTGGTA | 35 | 3345 |
| 1128825 | 284 | 299 | 3791 | 3806 | GCTGGTCCTGATCAAA | 31 | 3346 |
| 1128845 | 365 | 380 | 4173 | 4188 | CACAGGTCCCTCCTTT | 41 | 3347 |
| 1128865 | 465 | 480 | 4410 | 4425 | AAAAACCGGAGAAGCT | 57 | 3348 |
| 1128885 | 536 | 551 | 4481 | 4496 | CATCAGGACCCTTGCA | 51 | 3349 |
| 1128905 | 589 | 604 | 4673 | 4688 | ATGGAGGCACGGGTTG | 34 | 3350 |
| 1128925 | 619 | 634 | 4703 | 4718 | GTGGCCCTCCACCTCT | 37 | 3351 |
| 1128945 | 653 | 668 | 4737 | 4752 | CTCCGGTGTAGCCCAC | 51 | 3352 |
| 1128965 | 698 | 713 | 4927 | 4942 | CGCGGCCATCATAGCA | 76 | 3353 |
| 1128985 | 750 | 765 | 4979 | 4994 | TGACAGGGCGCACCCG | 43 | 3354 |
| 1129005 | 781 | 796 | 5010 | 5025 | GTTCCGGTAGGTGGCC | 49 | 3355 |
| 1129025 | 840 | 855 | N/A | N/A | GGGTTCCGGCAGAAGG | 37 | 3356 |
| 1129045 | 882 | 897 | 5196 | 5211 | TCGCGGTTCAGCACGA | 41 | 3357 |
| 1129065 | 973 | 988 | 5287 | 5302 | GACATGAAGCCTAGGG | 17 | 3358 |
| 1129085 | 1006 | 1021 | 5320 | 5335 | CTTCGGCGGTGCCGGC | 41 | 3359 |
| 1129105 | 1071 | 1086 | 5490 | 5505 | TCCCGCTTCGCCGGCA | 35 | 3360 |
| 1129125 | 1117 | 1132 | 5536 | 5551 | CTGCCCGCAGCTCAGT | 36 | 3361 |
| 1129145 | 1142 | 1157 | 5561 | 5576 | TCGAAGACAGACTCTT | 31 | 3362 |

TABLE 55-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129165 | 1168 | 1183 | 5587 | 5602 | CACCAGCCCGCCAACG | 53 | 3363 |
| 1129185 | 1228 | 1243 | 5647 | 5662 | GGCGCAGAAACTGTGG | 42 | 3364 |
| 1129205 | 1304 | 1319 | 5964 | 5979 | TCAGATCCTCGGGTGC | 29 | 3365 |
| 1129225 | 1375 | 1390 | 6035 | 6050 | GTAGGAGCGCACGGCC | 32 | 3366 |
| 1129245 | 1413 | 1428 | 6073 | 6088 | TGCTGGTAGCTGACGG | 36 | 3367 |
| 1129265 | 1454 | 1469 | 6197 | 6212 | TGCCGTCCGCATCCTC | 40 | 3368 |
| 1129285 | 1476 | 1491 | 6219 | 6234 | TAAGGCGACAGGAGCG | 33 | 3369 |
| 1129305 | 1523 | 1538 | 6266 | 6281 | TCTCGGAGGGTCGCGC | 39 | 3370 |
| 1129325 | 1570 | 1585 | N/A | N/A | CGCCCCTCGAACTGG | 131 | 3371 |
| 1129345 | 1611 | 1626 | 6909 | 6924 | AACGGTACCTGCGCCT | 82 | 3372 |
| 1129365 | 1684 | 1699 | 6982 | 6997 | CCCTGCGCAGAGCATG | 21† | 3373 |
| 1129385 | 1708 | 1723 | 7006 | 7021 | CGCATCGGTGCCGCCC | 17† | 3374 |
| 1129405 | 1777 | 1792 | 7165 | 7180 | TTGCAGGGTGAGCGG | 40 | 3375 |
| 1129425 | 1820 | 1835 | 7208 | 7223 | GCTTGTTGCGGTCACC | 27 | 3376 |
| 1129445 | 1851 | 1866 | 7239 | 7254 | AGGTAGTAGGCCACAT | 23 | 3377 |
| 1129465 | 1885 | 1900 | 7273 | 7288 | CAATCAGGAAACGGTG | 29 | 3378 |
| 1129485 | 1921 | 1936 | 7309 | 7324 | GCGGAATCACCAAGGA | 7 | 3379 |
| 1129505 | 1962 | 1977 | 7350 | 7365 | GGACACAATCTTGCCT | 34 | 3380 |
| 1129525 | 2003 | 2018 | 7391 | 7406 | CTGCGCCATCCTGGCG | 65 | 3381 |
| 1129545 | 2024 | 2039 | 7412 | 7427 | TCAAAGCACTTTATTG | 15 | 3382 |
| 1129565 | N/A | N/A | 144 | 159 | ATAGCGACCCCCCAGA | 46 | 3383 |
| 1129585 | N/A | N/A | 273 | 288 | TTGTATCCACCCAGTC | 93 | 3384 |
| 1129605 | N/A | N/A | 420 | 435 | TCATAGCCTGCCACCG | 73 | 3385 |
| 1129625 | N/A | N/A | 554 | 569 | ACCCAAGGGTTCCCGG | 142 | 3386 |
| 1129645 | N/A | N/A | 629 | 644 | GCATAAGACCTAGCAC | 80 | 3387 |
| 1129665 | N/A | N/A | 725 | 740 | AAGCACCTGCTCCGAG | 78 | 3388 |
| 1129685 | N/A | N/A | 1009 | 1024 | CTGTTATCAACCTGGT | 64 | 3389 |
| 1129705 | N/A | N/A | 1204 | 1219 | GGTAATTTAGTGTCTG | 48 | 3390 |
| 1129725 | N/A | N/A | 1594 | 1609 | TGCTTAGAGACTCAAC | 76 | 3391 |
| 1129745 | N/A | N/A | 2084 | 2099 | GATGGACCTTTAAGAT | 72 | 3392 |
| 1129765 | N/A | N/A | 2290 | 2305 | AACATAACCATCGCGA | 55 | 3393 |
| 1129785 | N/A | N/A | 2513 | 2528 | CCTTAGGGAGAAAGCG | 51 | 3394 |
| 1129805 | N/A | N/A | 2659 | 2674 | AGCTCTCCTATTGAAT | 69 | 3395 |
| 1129825 | N/A | N/A | 3034 | 3049 | CTGGAGTAGACTCCTG | 66 | 3396 |
| 1129845 | N/A | N/A | 3411 | 3426 | CCTCAAAAGGTCGCT | 59 | 3397 |

TABLE 55-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129865 | N/A | N/A | 3900 | 3915 | GTCTGGTGATACCAGG | 54 | 3398 |
| 1129885 | N/A | N/A | 4069 | 4084 | AGGCCCTTCTTGAACC | 72 | 3399 |
| 1129905 | N/A | N/A | 4333 | 4348 | ATGCCAAGTCTCCGAG | 68 | 3400 |
| 1129925 | N/A | N/A | 4584 | 4599 | CTGGCACACCACCCGG | 68 | 3401 |
| 1129945 | N/A | N/A | 4810 | 4825 | CTGGCAAGCCCGTCCC | 48 | 3402 |
| 1129965 | N/A | N/A | 5150 | 5165 | TCCTGTAGCCACACGA | 109 | 3403 |
| 1129985 | N/A | N/A | 5434 | 5449 | GCCGGCTGGCCGGAAT | 89 | 3404 |
| 1130005 | N/A | N/A | 5711 | 5726 | GTACTCGCCGGTCCTG | 76 | 3405 |
| 1130025 | N/A | N/A | 5843 | 5858 | CCCCGGGAGCTCCGGA | 77 | 3406 |
| 1130045 | N/A | N/A | 6162 | 6177 | AACCCGGGCGGAGAGG | 96 | 3407 |
| 1130065 | N/A | N/A | 6314 | 6329 | GCCTACCCTCGAACTG | 85 | 3408 |
| 1130085 | N/A | N/A | 6381 | 6396 | CGCGGGCTTCTTCCGC | 88 | 3409 |
| 1130105 | N/A | N/A | 6401 | 6416 | ACCCGGAACGATACCA | 69 | 3410 |
| 1130125 | N/A | N/A | 6529 | 6544 | TTCGATTCTCCCTGTA | 77 | 3411 |
| 1130145 | N/A | N/A | 6603 | 6618 | CACTAGCCCGGAGCGC | 80 | 3412 |
| 1130165 | N/A | N/A | 6668 | 6683 | TGGGCGGAGCGGAAAC | 80 | 3413 |
| 1130185 | N/A | N/A | 6783 | 6798 | TTGTAAACCCACTCAT | 82 | 3414 |
| 1130205 | N/A | N/A | 6862 | 6877 | TGCGAACACAGAGCGC | 113 | 3415 |
| 1130225 | N/A | N/A | 7033 | 7048 | CCAACCGGGCTAAGAG | 65† | 3416 |
| 1130245 | N/A | N/A | 7103 | 7118 | CCTGGGTCGGAAACAC | 80† | 3417 |

TABLE 56

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128745 | 99 | 114 | N/A | N/A | GGTGGAATCGAAAGTG | 45 | 3418 |
| 1128765 | 149 | 164 | 516 | 531 | CGACTGTGTGCTCTTC | 13 | 3419 |
| 1128785 | 171 | 186 | 3522 | 3537 | GGCTCCCCGGTGACAG | 37 | 3420 |
| 1128802 | 218 | 233 | 3569 | 3584 | TACATTTGTGGTACAG | 14 | 2426 |
| 1128806 | 222 | 237 | 3573 | 3588 | TGGGTACATTTGTGGT | 33 | 3421 |
| 1128826 | 285 | 300 | 3792 | 3807 | CGCTGGTCCTGATCAA | 23 | 3422 |
| 1128846 | 366 | 381 | 4174 | 4189 | ACACAGGTCCCTCCTT | 48 | 3423 |
| 1128866 | 466 | 481 | 4411 | 4426 | GAAAACCGGAGAAGC | 46 | 3424 |
| 1128886 | 537 | 552 | 4482 | 4497 | GCATCAGGACCCTTGC | 67 | 3425 |

TABLE 56-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128906 | 590 | 605 | 4674 | 4689 | CATGGAGGCACGGGTT | 29 | 3426 |
| 1128926 | 623 | 638 | 4707 | 4722 | GGCGGTGGCCCTCCAC | 38 | 3427 |
| 1128946 | 654 | 669 | 4738 | 4753 | GCTCCGGTGTAGCCCA | 69 | 3428 |
| 1128966 | 699 | 714 | 4928 | 4943 | CCGCGGCCATCATAGC | 77 | 3429 |
| 1128986 | 751 | 766 | 4980 | 4995 | CTGACAGGGCGCACCC | 38 | 3430 |
| 1129006 | 799 | 814 | 5028 | 5043 | CGCTTGCTCGGCAGTC | 23 | 3431 |
| 1129026 | 841 | 856 | N/A | N/A | CGGGTTCCGGCAGAAG | 40 | 3432 |
| 1129046 | 883 | 898 | 5197 | 5212 | GTCGCGGTTCAGCACG | 24 | 3433 |
| 1129066 | 974 | 989 | 5288 | 5303 | GGACATGAAGCCTAGG | 23 | 3434 |
| 1129086 | 1007 | 1022 | 5321 | 5336 | GCTTCGGCGGTGCCGG | 33 | 3435 |
| 1129106 | 1073 | 1088 | 5492 | 5507 | GCTCCCGCTTCGCCGG | 52 | 3436 |
| 1129126 | 1119 | 1134 | 5538 | 5553 | CGCTGCCCGCAGCTCA | 31 | 3437 |
| 1129146 | 1143 | 1158 | 5562 | 5577 | ATCGAAGACAGACTCT | 25 | 3438 |
| 1129166 | 1171 | 1186 | 5590 | 5605 | CGCCACCAGCCCGCCA | 45 | 3439 |
| 1129186 | 1229 | 1244 | 5648 | 5663 | CGGCGCAGAAACTGTG | 36 | 3440 |
| 1129206 | 1306 | 1321 | 5966 | 5981 | CGTCAGATCCTCGGGT | 30 | 3441 |
| 1129226 | 1377 | 1392 | 6037 | 6052 | CGGTAGGAGCGCACGG | 25 | 3442 |
| 1129246 | 1429 | 1444 | N/A | N/A | CAACAGAGCCAGGTCG | 36 | 3443 |
| 1129266 | 1455 | 1470 | 6198 | 6213 | CTGCCGTCCGCATCCT | 42 | 3444 |
| 1129286 | 1477 | 1492 | 6220 | 6235 | GTAAGGCGACAGGAGC | 23 | 3445 |
| 1129306 | 1524 | 1539 | 6267 | 6282 | GTCTCGGAGGGTCGCG | 33 | 3446 |
| 1129326 | 1571 | 1586 | N/A | N/A | CCGCCCCTCGAACTG | 69 | 3447 |
| 1129346 | 1612 | 1627 | 6910 | 6925 | GAACGGTACCTGCGCC | 96 | 3448 |
| 1129366 | 1685 | 1700 | 6983 | 6998 | ACCCTGCGCAGAGCAT | 19† | 3449 |
| 1129386 | 1709 | 1724 | 7007 | 7022 | ACGCATCGGTGCCGCC | 17† | 3450 |
| 1129406 | 1780 | 1795 | 7168 | 7183 | GCCTTGCAGGGTGAGC | 25 | 3451 |
| 1129426 | 1821 | 1836 | 7209 | 7224 | GGCTTGTTGCGGTCAC | 16 | 3452 |
| 1129446 | 1852 | 1867 | 7240 | 7255 | CAGGTAGTAGGCCACA | 25 | 3453 |
| 1129466 | 1888 | 1903 | 7276 | 7291 | GAGCAATCAGGAAACG | 20 | 3454 |
| 1129486 | 1922 | 1937 | 7310 | 7325 | TGCGGAATCACCAAGG | 9 | 3455 |
| 1129506 | 1964 | 1979 | 7352 | 7367 | TGGGACACAATCTTGC | 25 | 3456 |
| 1129526 | 2004 | 2019 | 7392 | 7407 | CCTGCGCCATCCTGGC | 21 | 3457 |
| 1129546 | 2031 | 2046 | 7419 | 7434 | AGCATTTTCAAAGCAC | 51 | 3458 |
| 1129566 | N/A | N/A | 145 | 160 | GATAGCGACCCCCCAG | 53 | 3459 |
| 1129586 | N/A | N/A | 277 | 292 | GCCCTTGTATCCACCC | 80 | 3460 |

TABLE 56-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
| --- | --- | --- | --- | --- | --- | --- | --- |
| 1129606 | N/A | N/A | 422 | 437 | AGTCATAGCCTGCCAC | 110 | 3461 |
| 1129626 | N/A | N/A | 555 | 570 | CACCCAAGGGTTCCCG | 81 | 3462 |
| 1129646 | N/A | N/A | 630 | 645 | GGCATAAGACCTAGCA | 73 | 3463 |
| 1129666 | N/A | N/A | 727 | 742 | TCAAGCACCTGCTCCG | 53 | 3464 |
| 1129686 | N/A | N/A | 1010 | 1025 | ACTGTTATCAACCTGG | 54 | 3465 |
| 1129706 | N/A | N/A | 1206 | 1221 | TAGGTAATTTAGTGTC | 55 | 3466 |
| 1129726 | N/A | N/A | 1596 | 1611 | CATGCTTAGAGACTCA | 51 | 3467 |
| 1129746 | N/A | N/A | 2092 | 2107 | GGATCTGAGATGGACC | 43 | 3468 |
| 1129766 | N/A | N/A | 2291 | 2306 | GAACATAACCATCGCG | 60 | 3469 |
| 1129786 | N/A | N/A | 2519 | 2534 | AGGCTACCTTAGGGAG | 64 | 3470 |
| 1129806 | N/A | N/A | 2683 | 2698 | CGTCACGCTGCTGCTG | 45 | 3471 |
| 1129826 | N/A | N/A | 3035 | 3050 | GCTGGAGTAGACTCCT | 54 | 3472 |
| 1129846 | N/A | N/A | 3412 | 3427 | CCCTCAAAAAGGTCGC | 71 | 3473 |
| 1129866 | N/A | N/A | 3956 | 3971 | CAAAGGGTATTGTGGA | 48 | 3474 |
| 1129886 | N/A | N/A | 4306 | 4321 | CTATTCTGTAGGCCCA | 62 | 3475 |
| 1129906 | N/A | N/A | 4343 | 4358 | GTCTAGGACCATGCCA | 95 | 3476 |
| 1129926 | N/A | N/A | 4607 | 4622 | ACCCCCCCAGAGAGCT | 91 | 3477 |
| 1129946 | N/A | N/A | 4812 | 4827 | TCCTGGCAAGCCCGTC | 37 | 3478 |
| 1129966 | N/A | N/A | 5157 | 5172 | TCCGGGTTCCTGTAGC | 60 | 3479 |
| 1129986 | N/A | N/A | 5436 | 5451 | CGGCCGGCTGGCCGGA | 84 | 3480 |
| 1130006 | N/A | N/A | 5712 | 5727 | GGTACTCGCCGGTCCT | 50 | 3481 |
| 1130026 | N/A | N/A | 5844 | 5859 | TCCCCGGGAGCTCCGG | 102 | 3482 |
| 1130046 | N/A | N/A | 6163 | 6178 | TAACCCGGGCGGAGAG | 88 | 3483 |
| 1130066 | N/A | N/A | 6315 | 6330 | TGCCTACCCTCGAACT | 100 | 3484 |
| 1130086 | N/A | N/A | 6382 | 6397 | TCGCGGGCTTCTTCCG | 56 | 3485 |
| 1130106 | N/A | N/A | 6402 | 6417 | CACCCGGAACGATACC | 67 | 3486 |
| 1130126 | N/A | N/A | 6531 | 6546 | AGTTCGATTCTCCCTG | 57 | 3487 |
| 1130146 | N/A | N/A | 6604 | 6619 | ACACTAGCCCGGAGCG | 66 | 3488 |
| 1130166 | N/A | N/A | 6669 | 6684 | ATGGGCGGAGCGGAAA | 108 | 3489 |
| 1130186 | N/A | N/A | 6784 | 6799 | CTTGTAAACCCACTCA | 57 | 3490 |
| 1130206 | N/A | N/A | 6863 | 6878 | CTGCGAACACAGAGCG | 100 | 3491 |
| 1130226 | N/A | N/A | 7034 | 7049 | GCCAACCGGGCTAAGA | 134† | 3492 |
| 1130246 | N/A | N/A | 7104 | 7119 | CCCTGGGTCGGAAACA | 87† | 3493 |

TABLE 57

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128746 | 101 | 116 | N/A | N/A | AAGGTGGAATCGAAAG | 68 | 3494 |
| 1128766 | 150 | 165 | N/A | N/A | ACGACTGTGTGCTCTT | 20 | 3495 |
| 1128786 | 175 | 190 | 3526 | 3541 | GCAGGGCTCCCCGGTG | 45 | 3496 |
| 1128802 | 218 | 233 | 3569 | 3584 | TACATTTGTGGTACAG | 38 | 2426 |
| 1128807 | 223 | 238 | 3574 | 3589 | GTGGGTACATTTGTGG | 57 | 3497 |
| 1128827 | 287 | 302 | 3794 | 3809 | ATCGCTGGTCCTGATC | 57 | 3498 |
| 1128847 | 370 | 385 | 4178 | 4193 | GTTCACACAGGTCCCT | 40 | 3499 |
| 1128867 | 467 | 482 | 4412 | 4427 | GGAAAAACCGGAGAAG | 63 | 3500 |
| 1128887 | 538 | 553 | 4483 | 4498 | GGCATCAGGACCCTTG | 58 | 3501 |
| 1128907 | 591 | 606 | 4675 | 4690 | CCATGGAGGCACGGGT | 50 | 3502 |
| 1128927 | 624 | 639 | 4708 | 4723 | AGGCGGTGGCCCTCCA | 69 | 3503 |
| 1128947 | 655 | 670 | 4739 | 4754 | GGCTCCGGTGTAGCCC | 97 | 3504 |
| 1128967 | 700 | 715 | 4929 | 4944 | CCCGCGGCCATCATAG | 100 | 3505 |
| 1128987 | 752 | 767 | 4981 | 4996 | GCTGACAGGGCGCACC | 48 | 3506 |
| 1129007 | 801 | 816 | 5030 | 5045 | CGCGCTTGCTCGGCAG | 71 | 3507 |
| 1129027 | 842 | 857 | N/A | N/A | CCGGGTTCCGGCAGAA | 51 | 3508 |
| 1129047 | 884 | 899 | 5198 | 5213 | GGTCGCGGTTCAGCAC | 44 | 3509 |
| 1129067 | 976 | 991 | 5290 | 5305 | TGGGACATGAAGCCTA | 61 | 3510 |
| 1129087 | 1008 | 1023 | 5322 | 5337 | GGCTTCGGCGGTGCCG | 79 | 3511 |
| 1129107 | 1079 | 1094 | 5498 | 5513 | GCGGCTGCTCCCGCTT | 75 | 3512 |
| 1129127 | 1121 | 1136 | 5540 | 5555 | GCCGCTGCCCGCAGCT | 59 | 3513 |
| 1129147 | 1144 | 1159 | 5563 | 5578 | CATCGAAGACAGACTC | 45 | 3514 |
| 1129167 | 1202 | 1217 | 5621 | 5636 | GCGCGGCGATGTAGGG | 57 | 3515 |
| 1129187 | 1230 | 1245 | 5649 | 5664 | CCGGCGCAGAAACTGT | 73 | 3516 |
| 1129207 | 1309 | 1324 | 5969 | 5984 | CACCGTCAGATCCTCG | 52 | 3517 |
| 1129227 | 1378 | 1393 | 6038 | 6053 | GCGGTAGGAGCGCACG | 41 | 3518 |
| 1129247 | 1431 | 1446 | N/A | N/A | CGCAACAGAGCCAGGT | 48 | 3519 |
| 1129267 | 1456 | 1471 | 6199 | 6214 | GCTGCCGTCCGCATCC | 61 | 3520 |
| 1129287 | 1478 | 1493 | 6221 | 6236 | CGTAAGGCGACAGGAG | 36 | 3521 |
| 1129307 | 1525 | 1540 | 6268 | 6283 | GGTCTCGGAGGGTCGC | 69 | 3522 |
| 1129327 | 1572 | 1587 | N/A | N/A | TCCGCCCCCTCGAACT | 128 | 3523 |
| 1129347 | 1613 | 1628 | 6911 | 6926 | GGAACGGTACCTGCGC | 181 | 3524 |
| 1129367 | 1686 | 1701 | 6984 | 6999 | AACCCTGCGCAGAGCA | 17† | 3525 |
| 1129387 | 1710 | 1725 | 7008 | 7023 | CACGCATCGGTGCCGC | 30† | 3526 |
| 1129407 | 1781 | 1796 | 7169 | 7184 | TGCCTTGCAGGGTGAG | 23 | 3527 |
| 1129427 | 1822 | 1837 | 7210 | 7225 | TGGCTTGTTGCGGTCA | 59 | 3528 |

TABLE 57-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
| --- | --- | --- | --- | --- | --- | --- | --- |
| 1129447 | 1853 | 1868 | 7241 | 7256 | CCAGGTAGTAGGCCAC | 56 | 3529 |
| 1129467 | 1892 | 1907 | 7280 | 7295 | CCCTGAGCAATCAGGA | 48 | 3530 |
| 1129487 | 1923 | 1938 | 7311 | 7326 | CTGCGGAATCACCAAG | 30 | 3531 |
| 1129507 | 1965 | 1980 | 7353 | 7368 | ATGGGACACAATCTTG | 70 | 3532 |
| 1129527 | 2005 | 2020 | 7393 | 7408 | TCCTGCGCCATCCTGG | 33 | 3533 |
| 1129547 | 2033 | 2048 | 7421 | 7436 | TCAGCATTTTCAAAGC | 40 | 3534 |
| 1129567 | N/A | N/A | 146 | 161 | TGATAGCGACCCCCCA | 67 | 3535 |
| 1129587 | N/A | N/A | 279 | 294 | GTGCCCTTGTATCCAC | 76 | 3536 |
| 1129607 | N/A | N/A | 423 | 438 | AAGTCATAGCCTGCCA | 115 | 3537 |
| 1129627 | N/A | N/A | 571 | 586 | GCACCATACACATCCC | 57 | 3538 |
| 1129647 | N/A | N/A | 631 | 646 | GGGCATAAGACCTAGC | 76 | 3539 |
| 1129667 | N/A | N/A | 736 | 751 | GCACATATCTCAAGCA | 53 | 3540 |
| 1129687 | N/A | N/A | 1017 | 1032 | GAGGTTTACTGTTATC | 78 | 3541 |
| 1129707 | N/A | N/A | 1207 | 1222 | GTAGGTAATTTAGTGT | 73 | 3542 |
| 1129727 | N/A | N/A | 1599 | 1614 | CGCCATGCTTAGAGAC | 82 | 3543 |
| 1129747 | N/A | N/A | 2132 | 2147 | TGCCAAGGACCAAACC | 72 | 3544 |
| 1129767 | N/A | N/A | 2292 | 2307 | AGAACATAACCATCGC | 63 | 3545 |
| 1129787 | N/A | N/A | 2520 | 2535 | AAGGCTACCTTAGGGA | 94 | 3546 |
| 1129807 | N/A | N/A | 2697 | 2712 | AAGGTTCAACAAGGCG | 61 | 3547 |
| 1129827 | N/A | N/A | 3036 | 3051 | AGCTGGAGTAGACTCC | 75 | 3548 |
| 1129847 | N/A | N/A | 3469 | 3484 | CCCTGTACTCAACTGC | 65 | 3549 |
| 1129867 | N/A | N/A | 3957 | 3972 | CCAAAGGGTATTGTGG | 74 | 3550 |
| 1129887 | N/A | N/A | 4308 | 4323 | ACCTATTCTGTAGGCC | 88 | 3551 |
| 1129907 | N/A | N/A | 4344 | 4359 | AGTCTAGGACCATGCC | 100 | 3552 |
| 1129927 | N/A | N/A | 4611 | 4626 | AAAGACCCCCCCAGAG | 116 | 3553 |
| 1129947 | N/A | N/A | 4837 | 4852 | TGCTTTCCGCACTCTC | 54 | 3554 |
| 1129967 | N/A | N/A | 5158 | 5173 | GTCCGGGTTCCTGTAG | 85 | 3555 |
| 1129987 | N/A | N/A | 5438 | 5453 | CGCGGCCGGCTGGCCG | 89 | 3556 |
| 1130007 | N/A | N/A | 5713 | 5728 | GGGTACTCGCCGGTCC | 62 | 3557 |
| 1130027 | N/A | N/A | 5862 | 5877 | TCCCGTGTTCCAGCTT | 80 | 3558 |
| 1130047 | N/A | N/A | 6164 | 6179 | CTAACCCGGGCGGAGA | 80 | 3559 |
| 1130067 | N/A | N/A | 6316 | 6331 | GTGCCTACCCTCGAAC | 112 | 3560 |
| 1130087 | N/A | N/A | 6383 | 6398 | GTCGCGGGCTTCTTCC | 54 | 3561 |
| 1130107 | N/A | N/A | 6403 | 6418 | GCACCCGGAACGATAC | 80 | 3562 |
| 1130127 | N/A | N/A | 6532 | 6547 | AAGTTCGATTCTCCCT | 70 | 3563 |

TABLE 57-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130147 | N/A | N/A | 6605 | 6620 | CACACTAGCCCGGAGC | 86 | 3564 |
| 1130167 | N/A | N/A | 6670 | 6685 | AATGGGCGGAGCGGAA | 79 | 3565 |
| 1130187 | N/A | N/A | 6785 | 6800 | GCTTGTAAACCCACTC | 73 | 3566 |
| 1130207 | N/A | N/A | 6865 | 6880 | CCCTGCGAACACAGAG | 91 | 3567 |
| 1130227 | N/A | N/A | 7035 | 7050 | CGCCAACCGGGCTAAG | 98† | 3568 |
| 1130247 | N/A | N/A | 7105 | 7120 | ACCCTGGGTCGGAAAC | 96† | 3569 |

TABLE 58

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128747 | 102 | 117 | N/A | N/A | CAAGGTGGAATCGAAA | 21 | 3570 |
| 1128767 | 151 | 166 | N/A | N/A | AACGACTGTGTGCTCT | 43 | 3571 |
| 1128787 | 176 | 191 | 3527 | 3542 | GGCAGGGCTCCCCGGT | 45 | 3572 |
| 1128802 | 218 | 233 | 3569 | 3584 | TACATTTGTGGTACAG | 20 | 2426 |
| 1128808 | 224 | 239 | 3575 | 3590 | TGTGGGTACATTTGTG | 30 | 3573 |
| 1128828 | 288 | 303 | 3795 | 3810 | CATCGCTGGTCCTGAT | 46 | 3574 |
| 1128848 | 373 | 388 | 4181 | 4196 | CATGTTCACACAGGTC | 31 | 3575 |
| 1128868 | 468 | 483 | 4413 | 4428 | TGGAAAACCGGAGAA | 47 | 3576 |
| 1128888 | 539 | 554 | 4484 | 4499 | GGGCATCAGGACCCTT | 69 | 3577 |
| 1128908 | 592 | 607 | 4676 | 4691 | CCCATGGAGGCACGGG | 76 | 3578 |
| 1128928 | 625 | 640 | 4709 | 4724 | CAGGCGGTGGCCCTCC | 44 | 3579 |
| 1128948 | 657 | 672 | 4741 | 4756 | AAGGCTCCGGTGTAGC | 73 | 3580 |
| 1128968 | 701 | 716 | 4930 | 4945 | GCCCGCGGCCATCATA | 52 | 3581 |
| 1128988 | 753 | 768 | 4982 | 4997 | GGCTGACAGGGCGCAC | 40 | 3582 |
| 1129008 | 802 | 817 | 5031 | 5046 | CCGCGCTTGCTCGGCA | 35 | 3583 |
| 1129028 | 843 | 858 | N/A | N/A | TCCGGGTTCCGGCAGA | 35 | 3584 |
| 1129048 | 885 | 900 | 5199 | 5214 | CGGTCGCGGTTCAGCA | 39 | 3585 |
| 1129068 | 977 | 992 | 5291 | 5306 | GTGGGACATGAAGCCT | 31 | 3586 |
| 1129088 | 1009 | 1024 | 5323 | 5338 | AGGCTTCGGCGGTGCC | 78 | 3587 |
| 1129108 | 1082 | 1097 | 5501 | 5516 | AAGGCGGCTGCTCCCG | 46 | 3588 |
| 1129128 | 1124 | 1139 | 5543 | 5558 | GGAGCCGCTGCCCGCA | 40 | 3589 |
| 1129148 | 1145 | 1160 | 5564 | 5579 | TCATCGAAGACAGACT | 36 | 3590 |
| 1129168 | 1203 | 1218 | 5622 | 5637 | AGCGCGGCGATGTAGG | 54 | 3591 |

TABLE 58-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129188 | 1231 | 1246 | 5650 | 5665 | GCCGGCGCAGAAACTG | 81 | 3592 |
| 1129208 | 1311 | 1326 | 5971 | 5986 | ACCACCGTCAGATCCT | 48 | 3593 |
| 1129228 | 1379 | 1394 | 6039 | 6054 | AGCGGTAGGAGCGCAC | 48 | 3594 |
| 1129248 | 1433 | 1448 | N/A | N/A | GGCGCAACAGAGCCAG | 63 | 3595 |
| 1129268 | 1457 | 1472 | 6200 | 6215 | AGCTGCCGTCCGCATC | 42 | 3596 |
| 1129288 | 1492 | 1507 | 6235 | 6250 | GCACACCGGCTGAACG | 52 | 3597 |
| 1129308 | 1542 | 1557 | 6285 | 6300 | GCCACCTGGCAGAGCG | 73 | 3598 |
| 1129328 | 1573 | 1588 | N/A | N/A | CTCCGCCCCTCGAAC | 135 | 3599 |
| 1129348 | 1614 | 1629 | 6912 | 6927 | AGGAACGGTACCTGCG | 127 | 3600 |
| 1129368 | 1688 | 1703 | 6986 | 7001 | GGAACCCTGCGCAGAG | 7† | 3601 |
| 1129388 | 1711 | 1726 | 7009 | 7024 | GCACGCATCGGTGCCG | 84† | 3602 |
| 1129408 | 1785 | 1800 | 7173 | 7188 | ATGATGCCTTGCAGGG | 16 | 3603 |
| 1129428 | 1823 | 1838 | 7211 | 7226 | CTGGCTTGTTGCGGTC | 48 | 3604 |
| 1129448 | 1854 | 1869 | 7242 | 7257 | GCCAGGTAGTAGGCCA | 64 | 3605 |
| 1129468 | 1893 | 1908 | 7281 | 7296 | TCCCTGAGCAATCAGG | 45 | 3606 |
| 1129488 | 1924 | 1939 | 7312 | 7327 | ACTGCGGAATCACCAA | 20 | 3607 |
| 1129508 | 1967 | 1982 | 7355 | 7370 | GAATGGGACACAATCT | 63 | 3608 |
| 1129528 | 2006 | 2021 | 7394 | 7409 | TTCCTGCGCCATCCTG | 35 | 3609 |
| 1129548 | N/A | N/A | 92 | 107 | CCGAAAGTGTTGACTC | 44 | 3610 |
| 1129568 | N/A | N/A | 147 | 162 | GTGATAGCGACCCCCC | 58 | 3611 |
| 1129588 | N/A | N/A | 323 | 338 | CCCCGTTGTCTTCTTA | 80 | 3612 |
| 1129608 | N/A | N/A | 425 | 440 | ATAAGTCATAGCCTGC | 93 | 3613 |
| 1129628 | N/A | N/A | 598 | 613 | CTAGACTGCCCTGAGA | 55 | 3614 |
| 1129648 | N/A | N/A | 636 | 651 | CCCATGGGCATAAGAC | 89 | 3615 |
| 1129668 | N/A | N/A | 737 | 752 | AGCACATATCTCAAGC | 75 | 3616 |
| 1129688 | N/A | N/A | 1022 | 1037 | CCTAAGAGGTTTACTG | 78 | 3617 |
| 1129708 | N/A | N/A | 1208 | 1223 | TGTAGGTAATTTAGTG | 67 | 3618 |
| 1129728 | N/A | N/A | 1695 | 1710 | CAAGTTTGGGTAAGGC | 57 | 3619 |
| 1129748 | N/A | N/A | 2137 | 2152 | GCACTTGCCAAGGACC | 42 | 3620 |
| 1129768 | N/A | N/A | 2293 | 2308 | TAGAACATAACCATCG | 59 | 3621 |
| 1129788 | N/A | N/A | 2521 | 2536 | GAAGGCTACCTTAGGG | 61 | 3622 |
| 1129808 | N/A | N/A | 2700 | 2715 | GTTAAGGTTCAACAAG | 59 | 3623 |
| 1129828 | N/A | N/A | 3037 | 3052 | TAGCTGGAGTAGACTC | 62 | 3624 |
| 1129848 | N/A | N/A | 3476 | 3491 | GGACTTCCCCTGTACT | 70 | 3625 |
| 1129868 | N/A | N/A | 3958 | 3973 | TCCAAAGGGTATTGTG | 64 | 3626 |

TABLE 58-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129888 | N/A | N/A | 4309 | 4324 | AACCTATTCTGTAGGC | 74 | 3627 |
| 1129908 | N/A | N/A | 4345 | 4360 | GAGTCTAGGACCATGC | 85 | 3628 |
| 1129928 | N/A | N/A | 4613 | 4628 | CTAAAGACCCCCCAG | 77 | 3629 |
| 1129948 | N/A | N/A | 4840 | 4855 | ATCTGCTTTCCGCACT | 23 | 3630 |
| 1129968 | N/A | N/A | 5159 | 5174 | TGTCCGGGTTCCTGTA | 59 | 3631 |
| 1129988 | N/A | N/A | 5440 | 5455 | CCCGCGGCCGGCTGGC | 91 | 3632 |
| 1130008 | N/A | N/A | 5715 | 5730 | GCGGGTACTCGCCGGT | 66 | 3633 |
| 1130028 | N/A | N/A | 5864 | 5879 | AATCCCGTGTTCCAGC | 62 | 3634 |
| 1130048 | N/A | N/A | 6165 | 6180 | GCTAACCCGGGCGGAG | 97 | 3635 |
| 1130068 | N/A | N/A | 6322 | 6337 | GCAGTTGTGCCTACCC | 53 | 3636 |
| 1130088 | N/A | N/A | 6384 | 6399 | AGTCGCGGGCTTCTTC | 78 | 3637 |
| 1130108 | N/A | N/A | 6405 | 6420 | AGGCACCCGGAACGAT | 62 | 3638 |
| 1130128 | N/A | N/A | 6533 | 6548 | CAAGTTCGATTCTCCC | 58 | 3639 |
| 1130148 | N/A | N/A | 6606 | 6621 | CCACACTAGCCCGGAG | 81 | 3640 |
| 1130168 | N/A | N/A | 6671 | 6686 | GAATGGGCGGAGCGGA | 86 | 3641 |
| 1130188 | N/A | N/A | 6786 | 6801 | CGCTTGTAAACCCACT | 58 | 3642 |
| 1130208 | N/A | N/A | 6866 | 6881 | CCCCTGCGAACACAGA | 111 | 3643 |
| 1130228 | N/A | N/A | 7036 | 7051 | GCGCCAACCGGGCTAA | 78† | 3644 |
| 1130248 | N/A | N/A | 7106 | 7121 | CACCCTGGGTCGGAAA | 67† | 3645 |

TABLE 59

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128748 | 103 | 118 | N/A | N/A | CCAAGGTGGAATCGAA | 49 | 3646 |
| 1128768 | 152 | 167 | N/A | N/A | GAACGACTGTGTGCTC | 29 | 3647 |
| 1128788 | 177 | 192 | 3528 | 3543 | TGGCAGGGCTCCCCGG | 55 | 3648 |
| 1128802 | 218 | 233 | 3569 | 3584 | TACATTTGTGGTACAG | 35 | 2426 |
| 1128809 | 225 | 240 | 3576 | 3591 | TTGTGGGTACATTTGT | 51 | 3649 |
| 1128829 | 290 | 305 | 3797 | 3812 | CCCATCGCTGGTCCTG | 49 | 3650 |
| 1128849 | 380 | 395 | 4188 | 4203 | CGCTTGGCATGTTCAC | 41 | 3651 |
| 1128869 | 469 | 484 | 4414 | 4429 | GTGGAAAAACCGGAGA | 58 | 3652 |
| 1128889 | 540 | 555 | 4485 | 4500 | TGGGCATCAGGACCCT | 79 | 3653 |
| 1128909 | 593 | 608 | 4677 | 4692 | CCCCATGGAGGCACGG | 52 | 3654 |

TABLE 59-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128929 | 626 | 641 | 4710 | 4725 | ACAGGCGGTGGCCCTC | 48 | 3655 |
| 1128949 | 660 | 675 | 4744 | 4759 | CAGAAGGCTCCGGTGT | 79 | 3656 |
| 1128969 | 703 | 718 | 4932 | 4947 | GAGCCCGCGGCCATCA | 68 | 3657 |
| 1128989 | 754 | 769 | 4983 | 4998 | CGGCTGACAGGGCGCA | 56 | 3658 |
| 1129009 | 803 | 818 | 5032 | 5047 | TCCGCGCTTGCTCGGC | 57 | 3659 |
| 1129029 | 844 | 859 | N/A | N/A | GTCCGGGTTCCGGCAG | 51 | 3660 |
| 1129049 | 886 | 901 | 5200 | 5215 | CCGGTCGCGGTTCAGC | 55 | 3661 |
| 1129069 | 978 | 993 | 5292 | 5307 | AGTGGGACATGAAGCC | 41 | 3662 |
| 1129089 | 1010 | 1025 | 5324 | 5339 | GAGGCTTCGGCGGTGC | 59 | 3663 |
| 1129109 | 1083 | 1098 | 5502 | 5517 | GAAGGCGGCTGCTCCC | 54 | 3664 |
| 1129129 | 1125 | 1140 | 5544 | 5559 | CGGAGCCGCTGCCCGC | 70 | 3665 |
| 1129149 | 1146 | 1161 | 5565 | 5580 | GTCATCGAAGACAGAC | 58 | 3666 |
| 1129169 | 1204 | 1219 | 5623 | 5638 | CAGCGCGGCGATGTAG | 61 | 3667 |
| 1129189 | 1233 | 1248 | 5652 | 5667 | CTGCCGGCGCAGAAAC | 65 | 3668 |
| 1129209 | 1312 | 1327 | 5972 | 5987 | CACCACCGTCAGATCC | 64 | 3669 |
| 1129229 | 1380 | 1395 | 6040 | 6055 | AAGCGGTAGGAGCGCA | 66 | 3670 |
| 1129249 | 1434 | 1449 | N/A | N/A | AGGCGCAACAGAGCCA | 74 | 3671 |
| 1129269 | 1458 | 1473 | 6201 | 6216 | CAGCTGCCGTCCGCAT | 55 | 3672 |
| 1129289 | 1493 | 1508 | 6236 | 6251 | GGCACACCGGCTGAAC | 56 | 3673 |
| 1129309 | 1545 | 1560 | 6288 | 6303 | CCGGCCACCTGGCAGA | 120 | 3674 |
| 1129329 | 1575 | 1590 | N/A | N/A | TCCTCCGCCCCCTCGA | 145 | 3675 |
| 1129349 | 1615 | 1630 | 6913 | 6928 | GAGGAACGGTACCTGC | 95 | 3676 |
| 1129369 | 1689 | 1704 | 6987 | 7002 | AGGAACCCTGCGCAGA | 20† | 3677 |
| 1129389 | 1713 | 1728 | 7011 | 7026 | TGGCACGCATCGGTGC | 65† | 3678 |
| 1129409 | 1788 | 1803 | 7176 | 7191 | CTGATGATGCCTTGCA | 37 | 3679 |
| 1129429 | 1824 | 1839 | 7212 | 7227 | CCTGGCTTGTTGCGGT | 52 | 3680 |
| 1129449 | 1855 | 1870 | 7243 | 7258 | GGCCAGGTAGTAGGCC | 88 | 3681 |
| 1129469 | 1894 | 1909 | 7282 | 7297 | GTCCCTGAGCAATCAG | 40 | 3682 |
| 1129489 | 1925 | 1940 | 7313 | 7328 | CACTGCGGAATCACCA | 29 | 3683 |
| 1129509 | 1968 | 1983 | 7356 | 7371 | GGAATGGGACACAATC | 45 | 3684 |
| 1129529 | 2007 | 2022 | 7395 | 7410 | GTTCCTGCGCCATCCT | 37 | 3685 |
| 1129549 | N/A | N/A | 93 | 108 | ACCGAAAGTGTTGACT | 63 | 3686 |
| 1129569 | N/A | N/A | 148 | 163 | TGTGATAGCGACCCCC | 74 | 3687 |
| 1129589 | N/A | N/A | 324 | 339 | CCCCCGTTGTCTTCTT | 117 | 3688 |
| 1129609 | N/A | N/A | 426 | 441 | TATAAGTCATAGCCTG | 66 | 3689 |

TABLE 59-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129629 | N/A | N/A | 600 | 615 | GACTAGACTGCCCTGA | 84 | 3690 |
| 1129649 | N/A | N/A | 637 | 652 | GCCCATGGGCATAAGA | 83 | 3691 |
| 1129669 | N/A | N/A | 744 | 759 | CGCCAGCAGCACATAT | 78 | 3692 |
| 1129689 | N/A | N/A | 1023 | 1038 | CCCTAAGAGGTTTACT | 98 | 3693 |
| 1129709 | N/A | N/A | 1214 | 1229 | CTGGCATGTAGGTAAT | 75 | 3694 |
| 1129729 | N/A | N/A | 1696 | 1711 | CCAAGTTTGGGTAAGG | 80 | 3695 |
| 1129749 | N/A | N/A | 2139 | 2154 | GTGCACTTGCCAAGGA | 80 | 3696 |
| 1129769 | N/A | N/A | 2321 | 2336 | TGCTAGTTCAATGTTC | 51 | 3697 |
| 1129789 | N/A | N/A | 2523 | 2538 | AAGAAGGCTACCTTAG | 88 | 3698 |
| 1129809 | N/A | N/A | 2703 | 2718 | CCAGTTAAGGTTCAAC | 64 | 3699 |
| 1129829 | N/A | N/A | 3038 | 3053 | ATAGCTGGAGTAGACT | 80 | 3700 |
| 1129849 | N/A | N/A | 3495 | 3510 | GGGACAACACACTCTC | 68 | 3701 |
| 1129869 | N/A | N/A | 3963 | 3978 | GGACTTCCAAAGGGTA | 66 | 3702 |
| 1129889 | N/A | N/A | 4310 | 4325 | CAACCTATTCTGTAGG | 65 | 3703 |
| 1129909 | N/A | N/A | 4347 | 4362 | GAGAGTCTAGGACCAT | 106 | 3704 |
| 1129929 | N/A | N/A | 4615 | 4630 | GCCTAAAGACCCCCCC | 88 | 3705 |
| 1129949 | N/A | N/A | 4844 | 4859 | TCTCATCTGCTTTCCG | 35 | 3706 |
| 1129969 | N/A | N/A | 5160 | 5175 | TTGTCCGGGTTCCTGT | 67 | 3707 |
| 1129989 | N/A | N/A | 5443 | 5458 | GAGCCCGCGGCCGGCT | 93 | 3708 |
| 1130009 | N/A | N/A | 5716 | 5731 | GGCGGGTACTCGCCGG | 96 | 3709 |
| 1130029 | N/A | N/A | 5865 | 5880 | CAATCCCGTGTTCCAG | 70 | 3710 |
| 1130049 | N/A | N/A | 6166 | 6181 | AGCTAACCCGGGCGGA | 105 | 3711 |
| 1130069 | N/A | N/A | 6324 | 6339 | TAGCAGTTGTGCCTAC | 70 | 3712 |
| 1130089 | N/A | N/A | 6385 | 6400 | AAGTCGCGGGCTTCTT | 93 | 3713 |
| 1130109 | N/A | N/A | 6407 | 6422 | GTAGGCACCCGGAACG | 79 | 3714 |
| 1130129 | N/A | N/A | 6534 | 6549 | GCAAGTTCGATTCTCC | 70 | 3715 |
| 1130149 | N/A | N/A | 6608 | 6623 | TCCCACACTAGCCCGG | 83 | 3716 |
| 1130169 | N/A | N/A | 6672 | 6687 | TGAATGGGCGGAGCGG | 88 | 3717 |
| 1130189 | N/A | N/A | 6787 | 6802 | GCGCTTGTAAACCCAC | 91 | 3718 |
| 1130209 | N/A | N/A | 6867 | 6882 | GCCCCTGCGAACACAG | 85 | 3719 |
| 1130229 | N/A | N/A | 7057 | 7072 | GCCTGACGGCCTCGGG | 77[†] | 3720 |
| 1130249 | N/A | N/A | 7107 | 7122 | TCACCCTGGGTCGGAA | 86[†] | 3721 |

TABLE 60

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128749 | 104 | 119 | N/A | N/A | CCCAAGGTGGAATCGA | 63 | 3722 |
| 1128769 | 153 | 168 | N/A | N/A | AGAACGACTGTGTGCT | 33 | 3723 |
| 1128789 | 178 | 193 | 3529 | 3544 | GTGGCAGGGCTCCCCG | 44 | 3724 |
| 1128802 | 218 | 233 | 3569 | 3584 | TACATTTGTGGTACAG | 24 | 2426 |
| 1128810 | 226 | 241 | 3577 | 3592 | CTTGTGGGTACATTTG | 40 | 3725 |
| 1128830 | 291 | 306 | 3798 | 3813 | CCCCATCGCTGGTCCT | 40 | 3726 |
| 1128850 | 381 | 396 | 4189 | 4204 | CCGCTTGGCATGTTCA | 49 | 3727 |
| 1128870 | 470 | 485 | 4415 | 4430 | TGTGGAAAAACCGGAG | 27 | 3728 |
| 1128890 | 541 | 556 | 4486 | 4501 | GTGGGCATCAGGACCC | 91 | 3729 |
| 1128910 | 594 | 609 | 4678 | 4693 | CCCCCATGGAGGCACG | 63 | 3730 |
| 1128930 | 627 | 642 | 4711 | 4726 | CACAGGCGGTGGCCCT | 53 | 3731 |
| 1128950 | 661 | 676 | 4745 | 4760 | GCAGAAGGCTCCGGTG | 118 | 3732 |
| 1128970 | 706 | 721 | 4935 | 4950 | GCTGAGCCCGCGGCCA | 61 | 3733 |
| 1128990 | 755 | 770 | 4984 | 4999 | ACGGCTGACAGGGCGC | 61 | 3734 |
| 1129010 | 804 | 819 | 5033 | 5048 | TTCCGCGCTTGCTCGG | 129 | 3735 |
| 1129030 | 845 | 860 | N/A | N/A | TGTCCGGGTTCCGGCA | 52 | 3736 |
| 1129050 | 887 | 902 | 5201 | 5216 | GCCGGTCGCGGTTCAG | 47 | 3737 |
| 1129070 | 979 | 994 | 5293 | 5308 | GAGTGGGACATGAAGC | 74 | 3738 |
| 1129090 | 1013 | 1028 | 5327 | 5342 | GCTGAGGCTTCGGCGG | 52 | 3739 |
| 1129110 | 1085 | 1100 | 5504 | 5519 | GGGAAGGCGGCTGCTC | 68 | 3740 |
| 1129130 | 1126 | 1141 | 5545 | 5560 | GCGGAGCCGCTGCCCG | 76 | 3741 |
| 1129150 | 1147 | 1162 | 5566 | 5581 | GGTCATCGAAGACAGA | 52 | 3742 |
| 1129170 | 1206 | 1221 | 5625 | 5640 | TACAGCGCGGCGATGT | 106 | 3743 |
| 1129190 | 1236 | 1251 | 5655 | 5670 | AGGCTGCCGGCGCAGA | 51 | 3744 |
| 1129210 | 1314 | 1329 | 5974 | 5989 | AGCACCACCGTCAGAT | 72 | 3745 |
| 1129230 | 1381 | 1396 | 6041 | 6056 | CAAGCGGTAGGAGCGC | 61 | 3746 |
| 1129250 | 1435 | 1450 | N/A | N/A | AAGGCGCAACAGAGCC | 60 | 3747 |
| 1129270 | 1459 | 1474 | 6202 | 6217 | GCAGCTGCCGTCCGCA | 54 | 3748 |
| 1129290 | 1494 | 1509 | 6237 | 6252 | AGGCACACCGGCTGAA | 63 | 3749 |
| 1129310 | 1546 | 1561 | 6289 | 6304 | GCCGGCCACCTGGCAG | 93 | 3750 |
| 1129330 | 1577 | 1592 | N/A | N/A | ATTCCTCCGCCCCCTC | 189 | 3751 |
| 1129350 | 1616 | 1631 | 6914 | 6929 | AGAGGAACGGTACCTG | 99 | 3752 |
| 1129370 | 1690 | 1705 | 6988 | 7003 | GAGGAACCCTGCGCAG | 17† | 3753 |
| 1129390 | 1714 | 1729 | 7012 | 7027 | CTGGCACGCATCGGTG | 30† | 3754 |
| 1129410 | 1789 | 1804 | 7177 | 7192 | GCTGATGATGCCTTGC | 42 | 3755 |
| 1129430 | 1825 | 1840 | 7213 | 7228 | GCCTGGCTTGTTGCGG | 60 | 3756 |

TABLE 60-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129450 | 1856 | 1871 | 7244 | 7259 | AGGCCAGGTAGTAGGC | 92 | 3757 |
| 1129470 | 1895 | 1910 | 7283 | 7298 | AGTCCCTGAGCAATCA | 53 | 3758 |
| 1129490 | 1926 | 1941 | 7314 | 7329 | TCACTGCGGAATCACC | 17 | 3759 |
| 1129510 | 1984 | 1999 | 7372 | 7387 | AGCTGGCCGCACTGGG | 36 | 3760 |
| 1129530 | 2008 | 2023 | 7396 | 7411 | AGTTCCTGCGCCATCC | 19 | 3761 |
| 1129550 | N/A | N/A | 94 | 109 | CACCGAAAGTGTTGAC | 118 | 3762 |
| 1129570 | N/A | N/A | 149 | 164 | CTGTGATAGCGACCCC | 96 | 3763 |
| 1129590 | N/A | N/A | 325 | 340 | CCCCCCGTTGTCTTCT | 118 | 3764 |
| 1129610 | N/A | N/A | 427 | 442 | CTATAAGTCATAGCCT | 139 | 3765 |
| 1129630 | N/A | N/A | 602 | 617 | TAGACTAGACTGCCCT | 78 | 3766 |
| 1129650 | N/A | N/A | 644 | 659 | CTCTAGTGCCCATGGG | 75 | 3767 |
| 1129670 | N/A | N/A | 866 | 881 | CCCATTGAAGGCCCTG | 75 | 3768 |
| 1129690 | N/A | N/A | 1024 | 1039 | ACCCTAAGAGGTTTAC | 106 | 3769 |
| 1129710 | N/A | N/A | 1522 | 1537 | TGCCACACTCTAGGTA | 98 | 3770 |
| 1129730 | N/A | N/A | 1699 | 1714 | GCACCAAGTTTGGGTA | 100 | 3771 |
| 1129750 | N/A | N/A | 2141 | 2156 | AAGTGCACTTGCCAAG | 107 | 3772 |
| 1129770 | N/A | N/A | 2376 | 2391 | GCTGTTGGTTGATGAA | 85 | 3773 |
| 1129790 | N/A | N/A | 2524 | 2539 | CAAGAAGGCTACCTTA | 146 | 3774 |
| 1129810 | N/A | N/A | 2708 | 2723 | CATTCCCAGTTAAGGT | 85 | 3775 |
| 1129830 | N/A | N/A | 3039 | 3054 | GATAGCTGGAGTAGAC | 108 | 3776 |
| 1129850 | N/A | N/A | 3609 | 3624 | TAGTCTTACCAGGGCT | 82 | 3777 |
| 1129870 | N/A | N/A | 3995 | 4010 | ATGGGACCACTCCTTC | 76 | 3778 |
| 1129890 | N/A | N/A | 4311 | 4326 | GCAACCTATTCTGTAG | 109 | 3779 |
| 1129910 | N/A | N/A | 4348 | 4363 | GGAGAGTCTAGGACCA | 115 | 3780 |
| 1129930 | N/A | N/A | 4616 | 4631 | GGCCTAAAGACCCCCC | 143 | 3781 |
| 1129950 | N/A | N/A | 5067 | 5082 | GCACCGGCAGAAGGCG | 63 | 3782 |
| 1129970 | N/A | N/A | 5374 | 5389 | TTCCTAACCTCCCGGG | 97 | 3783 |
| 1129990 | N/A | N/A | 5446 | 5461 | GGAGAGCCCGCGGCCG | 95 | 3784 |
| 1130010 | N/A | N/A | 5752 | 5767 | ACGGAGGAGCCGCGGC | 62 | 3785 |
| 1130030 | N/A | N/A | 5866 | 5881 | CCAATCCCGTGTTCCA | 84 | 3786 |
| 1130050 | N/A | N/A | 6167 | 6182 | GAGCTAACCCGGGCGG | 96 | 3787 |
| 1130070 | N/A | N/A | 6327 | 6342 | CCCTAGCAGTTGTGCC | 104 | 3788 |
| 1130090 | N/A | N/A | 6386 | 6401 | AAAGTCGCGGGCTTCT | 92 | 3789 |
| 1130110 | N/A | N/A | 6409 | 6424 | CTGTAGGCACCCGGAA | 164 | 3790 |
| 1130130 | N/A | N/A | 6535 | 6550 | AGCAAGTTCGATTCTC | 80 | 3791 |

TABLE 60-continued

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1130150 | N/A | N/A | 6621 | 6636 | CGCAGAACCTGGCTCC | 95 | 3792 |
| 1130170 | N/A | N/A | 6673 | 6688 | TTGAATGGGCGGAGCG | 126 | 3793 |
| 1130190 | N/A | N/A | 6809 | 6824 | ACGATGGACAAAGCTG | 147 | 3794 |
| 1130210 | N/A | N/A | 6870 | 6885 | TCCGCCCTGCGAACA | 143 | 3795 |
| 1130230 | N/A | N/A | 7064 | 7079 | GATTTGTGCCTGACGG | 93† | 3796 |
| 1130250 | N/A | N/A | 7109 | 7124 | AATCACCCTGGGTCGG | 115† | 3797 |

TABLE 61

Reduction of FXII RNA by 3-10-3 cEt gapmers with uniform PS internucleoside linkages
(Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128750 | 105 | 120 | N/A | N/A | TCCCAAGGTGGAATCG | 66 | 3798 |
| 1128770 | 154 | 169 | N/A | N/A | GAGAACGACTGTGTGC | 47 | 3799 |
| 1128790 | 198 | 213 | 3549 | 3564 | CGGTGGTACTGGAAGG | 45 | 3800 |
| 1128802 | 218 | 233 | 3569 | 3584 | TACATTTGTGGTACAG | 28 | 2426 |
| 1128811 | 228 | 243 | 3579 | 3594 | CCCTTGTGGGTACATT | 75 | 3801 |
| 1128831 | 292 | 307 | 3799 | 3814 | TCCCCATCGCTGGTCC | 70 | 3802 |
| 1128851 | 382 | 397 | 4190 | 4205 | GCCGCTTGGCATGTTC | 53 | 3803 |
| 1128871 | 472 | 487 | 4417 | 4432 | CTTGTGGAAAAACCGG | 37 | 3804 |
| 1128891 | 542 | 557 | 4487 | 4502 | AGTGGGCATCAGGACC | 64 | 3805 |
| 1128911 | 595 | 610 | 4679 | 4694 | ACCCCCATGGAGGCAC | 49 | 3806 |
| 1128931 | 628 | 643 | 4712 | 4727 | GCACAGGCGGTGGCCC | 66 | 3807 |
| 1128951 | 662 | 677 | 4746 | 4761 | CGCAGAAGGCTCCGGT | 95 | 3808 |
| 1128971 | 711 | 726 | 4940 | 4955 | CGGTAGCTGAGCCCGC | 102 | 3809 |
| 1128991 | 756 | 771 | 4985 | 5000 | CACGGCTGACAGGGCG | 53 | 3810 |
| 1129011 | 805 | 820 | 5034 | 5049 | GTTCCGCGCTTGCTCG | 43 | 3811 |
| 1129031 | 846 | 861 | N/A | N/A | TTGTCCGGGTTCCGGC | 47 | 3812 |
| 1129051 | 888 | 903 | 5202 | 5217 | AGCCGGTCGCGGTTCA | 18 | 3813 |
| 1129071 | 980 | 995 | 5294 | 5309 | TGAGTGGGACATGAAG | 50 | 3814 |
| 1129091 | 1014 | 1029 | 5328 | 5343 | GGCTGAGGCTTCGGCG | 54 | 3815 |
| 1129111 | 1086 | 1101 | 5505 | 5520 | AGGGAAGGCGGCTGCT | 44 | 3816 |
| 1129131 | 1127 | 1142 | 5546 | 5561 | TGCGGAGCCGCTGCCC | 59 | 3817 |
| 1129151 | 1150 | 1165 | 5569 | 5584 | GCGGGTCATCGAAGAC | 52 | 3818 |
| 1129171 | 1207 | 1222 | 5626 | 5641 | GTACAGCGCGGCGATG | 57 | 3819 |

TABLE 61-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129191 | 1238 | 1253 | 5657 | 5672 | TGAGGCTGCCGGCGCA | 65 | 3820 |
| 1129211 | 1315 | 1330 | 5975 | 5990 | GAGCACCACCGTCAGA | 36 | 3821 |
| 1129231 | 1382 | 1397 | 6042 | 6057 | GCAAGCGGTAGGAGCG | 53 | 3822 |
| 1129251 | 1436 | 1451 | 6179 | 6194 | GAAGGCGCAACAGAGC | 60 | 3823 |
| 1129271 | 1460 | 1475 | 6203 | 6218 | CGCAGCTGCCGTCCGC | 50 | 3824 |
| 1129291 | 1495 | 1510 | 6238 | 6253 | CAGGCACACCGGCTGA | 53 | 3825 |
| 1129311 | 1554 | 1569 | 6297 | 6312 | TGGCCCCAGCCGGCCA | 78 | 3826 |
| 1129331 | 1578 | 1593 | N/A | N/A | TATTCCTCCGCCCCCT | 140 | 3827 |
| 1129351 | 1617 | 1632 | 6915 | 6930 | GAGAGGAACGGTACCT | 120 | 3828 |
| 1129371 | 1691 | 1706 | 6989 | 7004 | CGAGGAACCCTGCGCA | 41† | 3829 |
| 1129391 | 1746 | 1761 | 7134 | 7149 | TCCTCACACACCAGCG | 15† | 3830 |
| 1129411 | 1790 | 1805 | 7178 | 7193 | AGCTGATGATGCCTTG | 40 | 3831 |
| 1129431 | 1826 | 1841 | 7214 | 7229 | CGCCTGGCTTGTTGCG | 83 | 3832 |
| 1129451 | 1864 | 1879 | 7252 | 7267 | CCGGATCCAGGCCAGG | 66 | 3833 |
| 1129471 | 1896 | 1911 | 7284 | 7299 | GAGTCCCTGAGCAATC | 43 | 3834 |
| 1129491 | 1927 | 1942 | 7315 | 7330 | CTCACTGCGGAATCAC | 21 | 3835 |
| 1129511 | 1988 | 2003 | 7376 | 7391 | GCGGAGCTGGCCGCAC | 56 | 3836 |
| 1129531 | 2009 | 2024 | 7397 | 7412 | GAGTTCCTGCGCCATC | 18 | 3837 |
| 1129551 | N/A | N/A | 95 | 110 | TCACCGAAAGTGTTGA | 86 | 3838 |
| 1129571 | N/A | N/A | 150 | 165 | GCTGTGATAGCGACCC | 78 | 3839 |
| 1129591 | N/A | N/A | 326 | 341 | TCCCCCCGTTGTCTTC | 116 | 3840 |
| 1129611 | N/A | N/A | 428 | 443 | ACTATAAGTCATAGCC | 95 | 3841 |
| 1129631 | N/A | N/A | 603 | 618 | CTAGACTAGACTGCCC | 92 | 3842 |
| 1129651 | N/A | N/A | 645 | 660 | ACTCTAGTGCCCATGG | 86 | 3843 |
| 1129671 | N/A | N/A | 867 | 882 | GCCCATTGAAGGCCCT | 83 | 3844 |
| 1129691 | N/A | N/A | 1053 | 1068 | ATACCTCACATGGGTT | 145 | 3845 |
| 1129711 | N/A | N/A | 1555 | 1570 | GTAAGGTCCATCTGGT | 72 | 3846 |
| 1129731 | N/A | N/A | 1704 | 1719 | ATAGGGCACCAAGTTT | 93 | 3847 |
| 1129751 | N/A | N/A | 2143 | 2158 | CAAAGTGCACTTGCCA | 73 | 3848 |
| 1129771 | N/A | N/A | 2445 | 2460 | GATGAATCAGCAACAC | 56 | 3849 |
| 1129791 | N/A | N/A | 2525 | 2540 | ACAAGAAGGCTACCTT | 79 | 3850 |
| 1129811 | N/A | N/A | 2746 | 2761 | CCATTTGTGGGCATGC | 64 | 3851 |
| 1129831 | N/A | N/A | 3040 | 3055 | AGATAGCTGGAGTAGA | 87 | 3852 |
| 1129851 | N/A | N/A | 3610 | 3625 | GTAGTCTTACCAGGGC | 72 | 3853 |
| 1129871 | N/A | N/A | 3996 | 4011 | AATGGGACCACTCCTT | 60 | 3854 |

TABLE 61-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129891 | N/A | N/A | 4312 | 4327 | AGCAACCTATTCTGTA | 95 | 3855 |
| 1129911 | N/A | N/A | 4349 | 4364 | AGGAGAGTCTAGGACC | 116 | 3856 |
| 1129931 | N/A | N/A | 4617 | 4632 | GGGCCTAAAGACCCCC | 94 | 3857 |
| 1129951 | N/A | N/A | 5068 | 5083 | CGCACCGGCAGAAGGC | 75 | 3858 |
| 1129971 | N/A | N/A | 5375 | 5390 | CTTCCTAACCTCCCGG | 76 | 3859 |
| 1129991 | N/A | N/A | 5448 | 5463 | ACGGAGAGCCCGCGGC | 94 | 3860 |
| 1130011 | N/A | N/A | 5753 | 5768 | GACGGAGGAGCCGCGG | 98 | 3861 |
| 1130031 | N/A | N/A | 5867 | 5882 | CCCAATCCCGTGTTCC | 76 | 3862 |
| 1130051 | N/A | N/A | 6168 | 6183 | AGAGCTAACCCGGGCG | 91 | 3863 |
| 1130071 | N/A | N/A | 6328 | 6343 | CCCCTAGCAGTTGTGC | 76 | 3864 |
| 1130091 | N/A | N/A | 6387 | 6402 | CAAAGTCGCGGGCTTC | 67 | 3865 |
| 1130111 | N/A | N/A | 6410 | 6425 | TCTGTAGGCACCCGGA | 73 | 3866 |
| 1130131 | N/A | N/A | 6536 | 6551 | GAGCAAGTTCGATTCT | 81 | 3867 |
| 1130151 | N/A | N/A | 6622 | 6637 | TCGCAGAACCTGGCTC | 76 | 3868 |
| 1130171 | N/A | N/A | 6674 | 6689 | TTTGAATGGGCGGAGC | 84 | 3869 |
| 1130191 | N/A | N/A | 6810 | 6825 | GACGATGGACAAAGCT | 82 | 3870 |
| 1130211 | N/A | N/A | 6871 | 6886 | CTCCGCCCTGCGAAC | 122 | 3871 |
| 1130231 | N/A | N/A | 7065 | 7080 | AGATTTGTGCCTGACG | 84† | 3872 |
| 1130251 | N/A | N/A | 7111 | 7126 | GGAATCACCCTGGGTC | 55† | 3873 |

TABLE 62

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128751 | 107 | 122 | 474 | 489 | CTTCCCAAGGTGGAAT | 89 | 3874 |
| 1128771 | 155 | 170 | N/A | N/A | TGAGAACGACTGTGTG | 49 | 3875 |
| 1128791 | 199 | 214 | 3550 | 3565 | CCGGTGGTACTGGAAG | 55 | 3876 |
| 1128802 | 218 | 233 | 3569 | 3584 | TACATTTGTGGTACAG | 12 | 2426 |
| 1128812 | 229 | 244 | 3580 | 3595 | GCCCTTGTGGGTACAT | 56 | 3877 |
| 1128832 | 293 | 308 | 3800 | 3815 | ATCCCCATCGCTGGTC | 36 | 3878 |
| 1128852 | 383 | 398 | 4191 | 4206 | GGCCGCTTGGCATGTT | 54 | 3879 |
| 1128872 | 480 | 495 | 4425 | 4440 | ATCTCATTCTTGTGGA | 32 | 3880 |
| 1128892 | 543 | 558 | 4488 | 4503 | CAGTGGGCATCAGGAC | 48 | 3881 |
| 1128912 | 597 | 612 | 4681 | 4696 | CGACCCCATGGAGGC | 36 | 3882 |

TABLE 62-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128932 | 630 | 645 | 4714 | 4729 | TGGCACAGGCGGTGGC | 52 | 3883 |
| 1128952 | 663 | 678 | 4747 | 4762 | TCGCAGAAGGCTCCGG | 87 | 3884 |
| 1128972 | 712 | 727 | 4941 | 4956 | GCGGTAGCTGAGCCCG | 66 | 3885 |
| 1128992 | 758 | 773 | 4987 | 5002 | CCCACGGCTGACAGGG | 73 | 3886 |
| 1129012 | 806 | 821 | 5035 | 5050 | AGTTCCGCGCTTGCTC | 34 | 3887 |
| 1129032 | 862 | 877 | 5176 | 5191 | CCACGGGCGGATGTCG | 43 | 3888 |
| 1129052 | 889 | 904 | 5203 | 5218 | CAGCCGGTCGCGGTTC | 38 | 3889 |
| 1129072 | 981 | 996 | 5295 | 5310 | ATGAGTGGGACATGAA | 55 | 3890 |
| 1129092 | 1016 | 1031 | 5330 | 5345 | TGGGCTGAGGCTTCGG | 25 | 3891 |
| 1129112 | 1088 | 1103 | 5507 | 5522 | TCAGGGAAGGCGGCTG | 45 | 3892 |
| 1129132 | 1128 | 1143 | 5547 | 5562 | TTGCGGAGCCGCTGCC | 58 | 3893 |
| 1129152 | 1151 | 1166 | 5570 | 5585 | CGCGGGTCATCGAAGA | 44 | 3894 |
| 1129172 | 1208 | 1223 | 5627 | 5642 | AGTACAGCGCGGCGAT | 31 | 3895 |
| 1129192 | 1239 | 1254 | 5658 | 5673 | ATGAGGCTGCCGGCGC | 43 | 3896 |
| 1129212 | 1318 | 1333 | 5978 | 5993 | GCCGAGCACCACCGTC | 40 | 3897 |
| 1129232 | 1383 | 1398 | 6043 | 6058 | TGCAAGCGGTAGGAGC | 33 | 3898 |
| 1129252 | 1437 | 1452 | 6180 | 6195 | TGAAGGCGCAACAGAG | 44 | 3899 |
| 1129272 | 1462 | 1477 | 6205 | 6220 | CGCGCAGCTGCCGTCC | 43 | 3900 |
| 1129292 | 1496 | 1511 | 6239 | 6254 | GCAGGCACACCGGCTG | 34 | 3901 |
| 1129312 | 1556 | 1571 | 6299 | 6314 | GGTGGCCCCAGCCGGC | 60 | 3902 |
| 1129332 | 1579 | 1594 | N/A | N/A | ATATTCCTCCGCCCCC | 89 | 3903 |
| 1129352 | 1618 | 1633 | 6916 | 6931 | GGAGAGGAACGGTACC | 89 | 3904 |
| 1129372 | 1692 | 1707 | 6990 | 7005 | TCGAGGAACCCTGCGC | 46† | 3905 |
| 1129392 | 1747 | 1762 | 7135 | 7150 | GTCCTCACACACCAGC | 5† | 3906 |
| 1129412 | 1797 | 1812 | 7185 | 7200 | GATCCCCAGCTGATGA | 43 | 3907 |
| 1129432 | 1827 | 1842 | 7215 | 7230 | ACGCCTGGCTTGTTGC | 43 | 3908 |
| 1129452 | 1865 | 1880 | 7253 | 7268 | CCCGGATCCAGGCCAG | 41 | 3909 |
| 1129472 | 1897 | 1912 | 7285 | 7300 | TGAGTCCCTGAGCAAT | 24 | 3910 |
| 1129492 | 1928 | 1943 | 7316 | 7331 | TCTCACTGCGGAATCA | 14 | 3911 |
| 1129512 | 1989 | 2004 | 7377 | 7392 | CGCGGAGCTGGCCGCA | 39 | 3912 |
| 1129532 | 2010 | 2025 | 7398 | 7413 | TGAGTTCCTGCGCCAT | 16 | 3913 |
| 1129552 | N/A | N/A | 96 | 111 | CTCACCGAAAGTGTTG | 88 | 3914 |
| 1129572 | N/A | N/A | 186 | 201 | GGACCCACAGGTCATG | 28 | 3915 |
| 1129592 | N/A | N/A | 327 | 342 | CTCCCCCGTTGTCTT | 85 | 3916 |
| 1129612 | N/A | N/A | 429 | 444 | GACTATAAGTCATAGC | 101 | 3917 |

TABLE 62-continued

Reduction of FXII RNA by 3-10-3 cEt gapmers with uniform PS internucleoside linkages (Huh7, electroporation, 3000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1129632 | N/A | N/A | 604 | 619 | ACTAGACTAGACTGCC | 79 | 3918 |
| 1129652 | N/A | N/A | 649 | 664 | GATCACTCTAGTGCCC | 49 | 3919 |
| 1129672 | N/A | N/A | 889 | 904 | GACAAGCTCTTGATCC | 40 | 3920 |
| 1129692 | N/A | N/A | 1054 | 1069 | AATACCTCACATGGGT | 51 | 3921 |
| 1129712 | N/A | N/A | 1556 | 1571 | GGTAAGGTCCATCTGG | 47 | 3922 |
| 1129732 | N/A | N/A | 1708 | 1723 | AAGGATAGGGCACCAA | 53 | 3923 |
| 1129752 | N/A | N/A | 2145 | 2160 | GGCAAAGTGCACTTGC | 80 | 3924 |
| 1129772 | N/A | N/A | 2449 | 2464 | CATTGATGAATCAGCA | 53 | 3925 |
| 1129792 | N/A | N/A | 2526 | 2541 | CACAAGAAGGCTACCT | 69 | 3926 |
| 1129812 | N/A | N/A | 2806 | 2821 | GTGCCTACTTGCTGAA | 72 | 3927 |
| 1129832 | N/A | N/A | 3041 | 3056 | CAGATAGCTGGAGTAG | 39 | 3928 |
| 1129852 | N/A | N/A | 3647 | 3662 | GTACATGTCTCCCAGG | 55 | 3929 |
| 1129872 | N/A | N/A | 4014 | 4029 | TGGTTTACCCACCTGC | 59 | 3930 |
| 1129892 | N/A | N/A | 4313 | 4328 | CAGCAACCTATTCTGT | 88 | 3931 |
| 1129912 | N/A | N/A | 4350 | 4365 | CAGGAGAGTCTAGGAC | 69 | 3932 |
| 1129932 | N/A | N/A | 4618 | 4633 | TGGGCCTAAAGACCCC | 96 | 3933 |
| 1129952 | N/A | N/A | 5069 | 5084 | GCGCACCGGCAGAAGG | 101 | 3934 |
| 1129972 | N/A | N/A | 5376 | 5391 | ACTTCCTAACCTCCCG | 56 | 3935 |
| 1129992 | N/A | N/A | 5449 | 5464 | GACGGAGAGCCCGCGG | 88 | 3936 |
| 1130012 | N/A | N/A | 5754 | 5769 | AGACGGAGGAGCCGCG | 59 | 3937 |
| 1130032 | N/A | N/A | 5868 | 5883 | CCCCAATCCCGTGTTC | 82 | 3938 |
| 1130052 | N/A | N/A | 6169 | 6184 | CAGAGCTAACCCGGGC | 69 | 3939 |
| 1130072 | N/A | N/A | 6329 | 6344 | GCCCCTAGCAGTTGTG | 86 | 3940 |
| 1130092 | N/A | N/A | 6388 | 6403 | CCAAAGTCGCGGGCTT | 54 | 3941 |
| 1130112 | N/A | N/A | 6412 | 6427 | ATTCTGTAGGCACCCG | 46 | 3942 |
| 1130132 | N/A | N/A | 6537 | 6552 | AGAGCAAGTTCGATTC | 51 | 3943 |
| 1130152 | N/A | N/A | 6623 | 6638 | GTCGCAGAACCTGGCT | 60 | 3944 |
| 1130172 | N/A | N/A | 6675 | 6690 | ATTTGAATGGGCGGAG | 44 | 3945 |
| 1130192 | N/A | N/A | 6811 | 6826 | GGACGATGGACAAAGC | 66 | 3946 |
| 1130212 | N/A | N/A | 6873 | 6888 | TCCTCCGCCCCTGCGA | 152 | 3947 |
| 1130232 | N/A | N/A | 7066 | 7081 | GAGATTTGTGCCTGAC | 65[†] | 3948 |
| 1130252 | N/A | N/A | 7112 | 7127 | CGGAATCACCCTGGGT | 22[†] | 3949 |

TABLE 63

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 124 | 2426 |
| 1129531 | 2009 | 2024 | 7397 | 7412 | GAGTTCCTGCGCCATC | 13 | 3837 |
| 1129948 | N/A | N/A | 4840 | 4855 | ATCTGCTTTCCGCACT | 134 | 3630 |
| 1194296 | N/A | N/A | 4848 | 4863 | TCCCTCTCATCTGCTT | 55 | 3950 |
| 1206493 | N/A | N/A | 4830 | 4845 | CGCACTCTCCCTCCTC | 105 | 3951 |
| 1208291 | N/A | N/A | 130 | 145 | GAACAATCCTGGGACA | 84 | 3952 |
| 1208323 | N/A | N/A | 200 | 215 | CCTCCTAGTCACCTGG | 44 | 3953 |
| 1208358 | N/A | N/A | 269 | 284 | ATCCACCCAGTCTGGT | 123 | 3954 |
| 1208388 | N/A | N/A | 315 | 330 | TCTTCTTAAGGCCCAT | 76 | 3955 |
| 1208422 | N/A | N/A | 407 | 422 | CCGATCTGTTGCTAGT | 113 | 3956 |
| 1208453 | N/A | N/A | 442 | 457 | AAGGCAGGGAACTGAC | 91 | 3957 |
| 1208484 | N/A | N/A | 531 | 546 | AGCCAGGCCACTTACC | 123 | 3958 |
| 1208512 | N/A | N/A | 599 | 614 | ACTAGACTGCCCTGAG | 102 | 3959 |
| 1208540 | N/A | N/A | 632 | 647 | TGGGCATAAGACCTAG | 113 | 3960 |
| 1208572 | N/A | N/A | 662 | 677 | TCACACAGCTCACGAT | 77 | 3961 |
| 1208588 | N/A | N/A | 734 | 749 | ACATATCTCAAGCACC | 119 | 3962 |
| 1208601 | N/A | N/A | 841 | 856 | TGGCATGAATGATGCC | 127 | 3963 |
| 1208614 | N/A | N/A | 887 | 902 | CAAGCTCTTGATCCTT | 56 | 3964 |
| 1208627 | N/A | N/A | 927 | 942 | GTGATAAAGCTGGGCT | 101 | 3965 |
| 1208640 | N/A | N/A | 969 | 984 | TGGAGAACTCAAATCC | 52 | 3966 |
| 1208653 | N/A | N/A | 1015 | 1030 | GGTTTACTGTTATCAA | 120 | 3967 |
| 1208666 | N/A | N/A | 1057 | 1072 | CTGAATACCTCACATG | 107 | 3968 |
| 1208679 | N/A | N/A | 1126 | 1141 | TTCATCTAAAAGGTAG | 73 | 3969 |
| 1208692 | N/A | N/A | 1165 | 1180 | TATGGCAGAGCTTGAG | 72 | 3970 |
| 1208705 | N/A | N/A | 1517 | 1532 | CACTCTAGGTAAATTT | 84 | 3971 |
| 1208718 | N/A | N/A | 1567 | 1582 | AGGCCCACCAGGGTAA | 111 | 3972 |
| 1208735 | N/A | N/A | 1597 | 1612 | CCATGCTTAGAGACTC | 83 | 3973 |
| 1208762 | N/A | N/A | 1690 | 1705 | TTGGGTAAGGCAAGAG | 48 | 3974 |
| 1208789 | N/A | N/A | 1718 | 1733 | GGGATTAGGCAAGGAT | 74 | 3975 |
| 1208813 | N/A | N/A | 1921 | 1936 | CTGAGCATGAAGTTGT | 80 | 3976 |
| 1208840 | N/A | N/A | 2094 | 2109 | ATGGATCTGAGATGGA | 52 | 3977 |
| 1208868 | N/A | N/A | 2126 | 2141 | GGACCAAACCAGAACT | 98 | 3978 |
| 1208895 | N/A | N/A | 2149 | 2164 | TCAAGGCAAAGTGCAC | 47 | 3979 |
| 1208918 | N/A | N/A | 2182 | 2197 | TACCTGCTCAATAAGC | 46 | 3980 |
| 1208944 | N/A | N/A | 2251 | 2266 | CTTCAGAGGAATTGTC | 64 | 3981 |
| 1208971 | N/A | N/A | 2320 | 2335 | GCTAGTTCAATGTTCA | 98 | 3982 |

TABLE 63-continued

Reduction of FXII RNA by 3-10-3 cEt gapmers with uniform PS internucleoside linkages
(Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208997 | N/A | N/A | 2337 | 2352 | GGAACCTAATACTGTT | 73 | 3983 |
| 1209023 | N/A | N/A | 2389 | 2404 | AACCAGATTATATGCT | 80 | 3984 |
| 1209048 | N/A | N/A | 2461 | 2476 | CCATCAGCTTAGCATT | 53 | 3985 |
| 1209073 | N/A | N/A | 2493 | 2508 | TTAGACACTTGATTCA | 76 | 3986 |
| 1209100 | N/A | N/A | 2548 | 2563 | GAAGAGCTGTGTAGTT | 95 | 3987 |
| 1209126 | N/A | N/A | 2647 | 2662 | GAATGAGTGTCCTTCT | 43 | 3988 |
| 1209152 | N/A | N/A | 2707 | 2722 | ATTCCCAGTTAAGGTT | 78 | 3989 |
| 1209180 | N/A | N/A | 2750 | 2765 | ATGGCCATTTGTGGGC | 98 | 3990 |
| 1209206 | N/A | N/A | 2785 | 2800 | TTTGTAACTCCCAAGT | 80 | 3991 |
| 1209229 | N/A | N/A | 2817 | 2832 | ACATTGAGAATGTGCC | 99 | 3992 |
| 1209253 | N/A | N/A | 2896 | 2911 | TCTGATCTGAGCCTTG | 103 | 3993 |
| 1209277 | N/A | N/A | 2957 | 2972 | CACTTGCCACAAAGTA | 74 | 3994 |
| 1209303 | N/A | N/A | 3019 | 3034 | GACTCCACAACCTGCT | 130 | 3995 |
| 1209329 | N/A | N/A | 3371 | 3386 | TAAAAGTTGGGTTCAG | 78 | 3996 |
| 1209347 | N/A | N/A | 3441 | 3456 | CCTCAGGGTCTGGTCA | 117 | 3997 |
| 1209360 | N/A | N/A | 3474 | 3489 | ACTTCCCCTGTACTCA | 143 | 3998 |
| 1209373 | N/A | N/A | 3511 | 3526 | GACAGTGAGAACTGCA | 123 | 3999 |
| 1209386 | N/A | N/A | 3658 | 3673 | GGACAGGCAGGGTACA | 76 | 4000 |
| 1209399 | N/A | N/A | 3703 | 3718 | CCCTATCACAGTCCCC | 64 | 4001 |
| 1209412 | N/A | N/A | 3879 | 3894 | AATGAGGCGGGAGGAG | 122 | 4002 |
| 1209425 | N/A | N/A | 3923 | 3938 | GTCCAGAATCCCAGGT | 86 | 4003 |
| 1209438 | N/A | N/A | 3998 | 4013 | AAAATGGGACCACTCC | 144 | 4004 |
| 1209451 | N/A | N/A | 4034 | 4049 | CTACTCCAAGTTTCCA | 71 | 4005 |
| 1209464 | N/A | N/A | 4067 | 4082 | GCCCTTCTTGAACCTA | 88 | 4006 |
| 1209477 | N/A | N/A | 4269 | 4284 | ACCCCGCCCAGGTCCT | 48 | 4007 |
| 1209490 | N/A | N/A | 4331 | 4346 | GCCAAGTCTCCGAGTA | 76 | 4008 |
| 1209503 | N/A | N/A | 4364 | 4379 | AGGGATAGTGGTCTCA | 73 | 4009 |
| 1209516 | N/A | N/A | 4609 | 4624 | AGACCCCCCAGAGAG | 71 | 4010 |
| 1209529 | N/A | N/A | 4803 | 4818 | GCCCGTCCCACCTGGG | 78 | 4011 |
| 1209542 | N/A | N/A | 5119 | 5134 | GCGCCGGGAGCCCGGA | 62 | 4012 |
| 1209555 | N/A | N/A | 5430 | 5445 | GCTGGCCGGAATCTAG | 61 | 4013 |
| 1209568 | N/A | N/A | 5745 | 5760 | AGCCGCGGCCCCTGGG | 49 | 4014 |
| 1209581 | N/A | N/A | 5860 | 5875 | CCGTGTTCCAGCTTCC | 53 | 4015 |
| 1209594 | N/A | N/A | 6095 | 6110 | GCGCCCCACGCACCC | 74 | 4016 |
| 1209607 | N/A | N/A | 6357 | 6372 | GTGATCAAAGGTCTCC | 26 | 4017 |

TABLE 63-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209620 | N/A | N/A | 6436 | 6451 | CAACCCATCAGGTCAG | 41 | 4018 |
| 1209633 | N/A | N/A | 6474 | 6489 | CCCTGGGATTCTACCT | 65 | 4019 |
| 1209646 | N/A | N/A | 6542 | 6557 | AACCAAGAGCAAGTTC | 38 | 4020 |
| 1209659 | N/A | N/A | 6625 | 6640 | GAGTCGCAGAACCTGG | 25 | 4021 |
| 1209672 | N/A | N/A | 6680 | 6695 | CCAGGATTTGAATGGG | 83 | 4022 |
| 1209685 | N/A | N/A | 6780 | 6795 | TAAACCCACTCATGCC | 44 | 4023 |
| 1209698 | N/A | N/A | 6839 | 6854 | ACACCCCATCTGACAA | 63 | 4024 |
| 1209711 | N/A | N/A | 7027 | 7042 | GGGCTAAGAGCTCACC | 88† | 4025 |

TABLE 64

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 88 | 2426 |
| 1129531 | 2009 | 2024 | 7397 | 7412 | GAGTTCCTGCGCCATC | 7 | 3837 |
| 1129948 | N/A | N/A | 4840 | 4855 | ATCTGCTTTCCGCACT | 84 | 3630 |
| 1194286 | N/A | N/A | 4835 | 4850 | CTTTCCGCACTCTCCC | 97 | 4026 |
| 1194297 | N/A | N/A | 4849 | 4864 | CTCCCTCTCATCTGCT | 54 | 4027 |
| 1208292 | N/A | N/A | 131 | 146 | AGAACAATCCTGGGAC | 91 | 4028 |
| 1208327 | N/A | N/A | 201 | 216 | GCCTCCTAGTCACCTG | 108 | 4029 |
| 1208361 | N/A | N/A | 270 | 285 | TATCCACCCAGTCTGG | 73 | 4030 |
| 1208392 | N/A | N/A | 316 | 331 | GTCTTCTTAAGGCCCA | 79 | 4031 |
| 1208426 | N/A | N/A | 413 | 428 | CTGCCACCGATCTGTT | 57 | 4032 |
| 1208454 | N/A | N/A | 460 | 475 | ATCTACAAGGGAGAGA | 107 | 4033 |
| 1208487 | N/A | N/A | 546 | 561 | GTTCCCGGGAGGAGGA | 69 | 4034 |
| 1208513 | N/A | N/A | 601 | 616 | AGACTAGACTGCCCTG | 43 | 4035 |
| 1208544 | N/A | N/A | 633 | 648 | ATGGGCATAAGACCTA | 60 | 4036 |
| 1208575 | N/A | N/A | 664 | 679 | GATCACACAGCTCACG | 112 | 4037 |
| 1208589 | N/A | N/A | 735 | 750 | CACATATCTCAAGCAC | 65 | 4038 |
| 1208602 | N/A | N/A | 842 | 857 | GTGGCATGAATGATGC | 94 | 4039 |
| 1208615 | N/A | N/A | 888 | 903 | ACAAGCTCTTGATCCT | 96 | 4040 |
| 1208628 | N/A | N/A | 928 | 943 | AGTGATAAAGCTGGGC | 89 | 4041 |
| 1208641 | N/A | N/A | 970 | 985 | TTGGAGAACTCAAATC | 81 | 4042 |
| 1208654 | N/A | N/A | 1016 | 1031 | AGGTTTACTGTTATCA | 95 | 4043 |

TABLE 64-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208667 | N/A | N/A | 1058 | 1073 | GCTGAATACCTCACAT | 74 | 4044 |
| 1208680 | N/A | N/A | 1128 | 1143 | CCTTCATCTAAAAGGT | 113 | 4045 |
| 1208693 | N/A | N/A | 1166 | 1181 | CTATGGCAGAGCTTGA | 111 | 4046 |
| 1208706 | N/A | N/A | 1518 | 1533 | ACACTCTAGGTAAATT | 83 | 4047 |
| 1208719 | N/A | N/A | 1573 | 1588 | CAAGTCAGGCCCACCA | 168 | 4048 |
| 1208738 | N/A | N/A | 1598 | 1613 | GCCATGCTTAGAGACT | 47 | 4049 |
| 1208764 | N/A | N/A | 1691 | 1706 | TTTGGGTAAGGCAAGA | 53 | 4050 |
| 1208792 | N/A | N/A | 1751 | 1766 | TGGACGGACAGAGAGG | 64 | 4051 |
| 1208816 | N/A | N/A | 1922 | 1937 | GCTGAGCATGAAGTTG | 38 | 4052 |
| 1208843 | N/A | N/A | 2111 | 2126 | TAGGACAGTAAATGGA | 64 | 4053 |
| 1208870 | N/A | N/A | 2127 | 2142 | AGGACCAAACCAGAAC | 125 | 4054 |
| 1208896 | N/A | N/A | 2151 | 2166 | GTTCAAGGCAAAGTGC | 68 | 4055 |
| 1208921 | N/A | N/A | 2183 | 2198 | GTACCTGCTCAATAAG | 102 | 4056 |
| 1208947 | N/A | N/A | 2266 | 2281 | AATTGCCTGTGTCTTC | 47 | 4057 |
| 1208973 | N/A | N/A | 2322 | 2337 | TTGCTAGTTCAATGTT | 60 | 4058 |
| 1209000 | N/A | N/A | 2338 | 2353 | AGGAACCTAATACTGT | 104 | 4059 |
| 1209024 | N/A | N/A | 2390 | 2405 | AAACCAGATTATATGC | 75 | 4060 |
| 1209050 | N/A | N/A | 2463 | 2478 | TGCCATCAGCTTAGCA | 72 | 4061 |
| 1209076 | N/A | N/A | 2495 | 2510 | TGTTAGACACTTGATT | 92 | 4062 |
| 1209101 | N/A | N/A | 2549 | 2564 | TGAAGAGCTGTGTAGT | 83 | 4063 |
| 1209127 | N/A | N/A | 2648 | 2663 | TGAATGAGTGTCCTTC | 131 | 4064 |
| 1209155 | N/A | N/A | 2709 | 2724 | ACATTCCCAGTTAAGG | 93 | 4065 |
| 1209183 | N/A | N/A | 2771 | 2786 | GTCAATACTTGAAATG | 88 | 4066 |
| 1209207 | N/A | N/A | 2786 | 2801 | ATTTGTAACTCCCAAG | 108 | 4067 |
| 1209232 | N/A | N/A | 2818 | 2833 | TACATTGAGAATGTGC | 72 | 4068 |
| 1209254 | N/A | N/A | 2901 | 2916 | ACCACTCTGATCTGAG | 70 | 4069 |
| 1209280 | N/A | N/A | 2962 | 2977 | AAGAGCACTTGCCACA | 77 | 4070 |
| 1209305 | N/A | N/A | 3028 | 3043 | TAGACTCCTGACTCCA | 141 | 4071 |
| 1209332 | N/A | N/A | 3372 | 3387 | CTAAAAGTTGGGTTCA | 77 | 4072 |
| 1209348 | N/A | N/A | 3460 | 3475 | CAACTGCTCAGGCACT | 117 | 4073 |
| 1209361 | N/A | N/A | 3485 | 3500 | ACTCTCTGAGGACTTC | 101 | 4074 |
| 1209374 | N/A | N/A | 3605 | 3620 | CTTACCAGGGCTGAGG | 93 | 4075 |
| 1209387 | N/A | N/A | 3660 | 3675 | AAGGACAGGCAGGGTA | 86 | 4076 |
| 1209400 | N/A | N/A | 3705 | 3720 | TGCCCTATCACAGTCC | 96 | 4077 |
| 1209413 | N/A | N/A | 3880 | 3895 | TAATGAGGCGGGAGGA | 106 | 4078 |

TABLE 64-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209426 | N/A | N/A | 3949 | 3964 | TATTGTGGAGGGAGAG | 131 | 4079 |
| 1209439 | N/A | N/A | 3999 | 4014 | CAAAATGGGACCACTC | 58 | 4080 |
| 1209452 | N/A | N/A | 4036 | 4051 | TGCTACTCCAAGTTTC | 72 | 4081 |
| 1209465 | N/A | N/A | 4068 | 4083 | GGCCCTTCTTGAACCT | 47 | 4082 |
| 1209478 | N/A | N/A | 4271 | 4286 | GCACCCCGCCCAGGTC | 90 | 4083 |
| 1209491 | N/A | N/A | 4334 | 4349 | CATGCCAAGTCTCCGA | 73 | 4084 |
| 1209504 | N/A | N/A | 4368 | 4383 | AAAGAGGGATAGTGGT | 47 | 4085 |
| 1209517 | N/A | N/A | 4612 | 4627 | TAAAGACCCCCCCAGA | 95 | 4086 |
| 1209530 | N/A | N/A | 4804 | 4819 | AGCCCGTCCCACCTGG | 97 | 4087 |
| 1209543 | N/A | N/A | 5146 | 5161 | GTAGCCACACGACGGG | 31 | 4088 |
| 1209556 | N/A | N/A | 5431 | 5446 | GGCTGGCCGGAATCTA | 37 | 4089 |
| 1209569 | N/A | N/A | 5746 | 5761 | GAGCCGCGGCCCCTGG | 67 | 4090 |
| 1209582 | N/A | N/A | 5863 | 5878 | ATCCCGTGTTCCAGCT | 58 | 4091 |
| 1209595 | N/A | N/A | 6111 | 6126 | TTCCCGTCCCCGCGGG | 82 | 4092 |
| 1209608 | N/A | N/A | 6359 | 6374 | CAGTGATCAAAGGTCT | 34 | 4093 |
| 1209621 | N/A | N/A | 6439 | 6454 | TCACAACCCATCAGGT | 43 | 4094 |
| 1209634 | N/A | N/A | 6476 | 6491 | GGCCCTGGGATTCTAC | 89 | 4095 |
| 1209647 | N/A | N/A | 6543 | 6558 | GAACCAAGAGCAAGTT | 64 | 4096 |
| 1209660 | N/A | N/A | 6631 | 6646 | CATCCAGAGTCGCAGA | 36 | 4097 |
| 1209673 | N/A | N/A | 6681 | 6696 | GCCAGGATTTGAATGG | 84 | 4098 |
| 1209686 | N/A | N/A | 6782 | 6797 | TGTAAACCCACTCATG | 101 | 4099 |
| 1209699 | N/A | N/A | 6840 | 6855 | CACACCCCATCTGACA | 86 | 4100 |
| 1209712 | N/A | N/A | 7058 | 7073 | TGCCTGACGGCCTCGG | 47† | 4101 |

TABLE 65

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 102 | 2426 |
| 1129531 | 2009 | 2024 | 7397 | 7412 | GAGTTCCTGCGCCATC | 25 | 3837 |
| 1129948 | N/A | N/A | 4840 | 4855 | ATCTGCTTTCCGCACT | 76 | 3630 |
| 1194287 | N/A | N/A | 4836 | 4851 | GCTTTCCGCACTCTCC | 48 | 4102 |
| 1206494 | N/A | N/A | 4854 | 4869 | CCTGCCTCCCTCTCAT | 92 | 4103 |
| 1208296 | N/A | N/A | 133 | 148 | CCAGAACAATCCTGGG | 62 | 4104 |

TABLE 65-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208328 | N/A | N/A | 203 | 218 | AGGCCTCCTAGTCACC | 56 | 4105 |
| 1208363 | N/A | N/A | 274 | 289 | CTTGTATCCACCCAGT | 79 | 4106 |
| 1208393 | N/A | N/A | 321 | 336 | CCGTTGTCTTCTTAAG | 67 | 4107 |
| 1208427 | N/A | N/A | 414 | 429 | CCTGCCACCGATCTGT | 94 | 4108 |
| 1208458 | N/A | N/A | 461 | 476 | AATCTACAAGGGAGAG | 55 | 4109 |
| 1208489 | N/A | N/A | 547 | 562 | GGTTCCCGGGAGGAGG | 51 | 4110 |
| 1208515 | N/A | N/A | 605 | 620 | CACTAGACTAGACTGC | 69 | 4111 |
| 1208545 | N/A | N/A | 634 | 649 | CATGGGCATAAGACCT | 52 | 4112 |
| 1208577 | N/A | N/A | 672 | 687 | CCCTCAAGGATCACAC | 68 | 4113 |
| 1208590 | N/A | N/A | 738 | 753 | CAGCACATATCTCAAG | 64 | 4114 |
| 1208603 | N/A | N/A | 862 | 877 | TTGAAGGCCCTGGCCT | 45 | 4115 |
| 1208616 | N/A | N/A | 895 | 910 | GCCAGAGACAAGCTCT | 87 | 4116 |
| 1208629 | N/A | N/A | 932 | 947 | CATAAGTGATAAAGCT | 79 | 4117 |
| 1208642 | N/A | N/A | 975 | 990 | GAAGCTTGGAGAACTC | 88 | 4118 |
| 1208655 | N/A | N/A | 1018 | 1033 | AGAGGTTTACTGTTAT | 57 | 4119 |
| 1208668 | N/A | N/A | 1062 | 1077 | ATGGGCTGAATACCTC | 95 | 4120 |
| 1208681 | N/A | N/A | 1129 | 1144 | CCCTTCATCTAAAAGG | 133 | 4121 |
| 1208694 | N/A | N/A | 1167 | 1182 | GCTATGGCAGAGCTTG | 84 | 4122 |
| 1208707 | N/A | N/A | 1519 | 1534 | CACACTCTAGGTAAAT | 76 | 4123 |
| 1208720 | N/A | N/A | 1574 | 1589 | CCAAGTCAGGCCCACC | 74 | 4124 |
| 1208739 | N/A | N/A | 1600 | 1615 | ACGCCATGCTTAGAGA | 76 | 4125 |
| 1208766 | N/A | N/A | 1692 | 1707 | GTTTGGGTAAGGCAAG | 60 | 4126 |
| 1208795 | N/A | N/A | 1756 | 1771 | TGGGATGGACGGACAG | 83 | 4127 |
| 1208817 | N/A | N/A | 1923 | 1938 | AGCTGAGCATGAAGTT | 144 | 4128 |
| 1208844 | N/A | N/A | 2112 | 2127 | CTAGGACAGTAAATGG | 73 | 4129 |
| 1208873 | N/A | N/A | 2129 | 2144 | CAAGGACCAAACCAGA | 91 | 4130 |
| 1208898 | N/A | N/A | 2152 | 2167 | TGTTCAAGGCAAAGTG | 72 | 4131 |
| 1208922 | N/A | N/A | 2190 | 2205 | GCACAAAGTACCTGCT | 71 | 4132 |
| 1208948 | N/A | N/A | 2267 | 2282 | GAATTGCCTGTGTCTT | 72 | 4133 |
| 1208976 | N/A | N/A | 2323 | 2338 | TTTGCTAGTTCAATGT | 62 | 4134 |
| 1209001 | N/A | N/A | 2339 | 2354 | CAGGAACCTAATACTG | 61 | 4135 |
| 1209027 | N/A | N/A | 2442 | 2457 | GAATCAGCAACACATA | 85 | 4136 |
| 1209051 | N/A | N/A | 2465 | 2480 | AGTGCCATCAGCTTAG | 111 | 4137 |
| 1209077 | N/A | N/A | 2496 | 2511 | GTGTTAGACACTTGAT | 76 | 4138 |
| 1209104 | N/A | N/A | 2551 | 2566 | GCTGAAGAGCTGTGTA | 74 | 4139 |

TABLE 65-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209130 | N/A | N/A | 2649 | 2664 | TTGAATGAGTGTCCTT | 102 | 4140 |
| 1209156 | N/A | N/A | 2710 | 2725 | CACATTCCCAGTTAAG | 100 | 4141 |
| 1209184 | N/A | N/A | 2774 | 2789 | CAAGTCAATACTTGAA | 50 | 4142 |
| 1209209 | N/A | N/A | 2803 | 2818 | CCTACTTGCTGAATTT | 96 | 4143 |
| 1209234 | N/A | N/A | 2819 | 2834 | CTACATTGAGAATGTG | 55 | 4144 |
| 1209257 | N/A | N/A | 2902 | 2917 | AACCACTCTGATCTGA | 68 | 4145 |
| 1209281 | N/A | N/A | 2964 | 2979 | GGAAGAGCACTTGCCA | 79 | 4146 |
| 1209307 | N/A | N/A | 3029 | 3044 | GTAGACTCCTGACTCC | 79 | 4147 |
| 1209333 | N/A | N/A | 3374 | 3389 | CTCTAAAAGTTGGGTT | 55 | 4148 |
| 1209349 | N/A | N/A | 3461 | 3476 | TCAACTGCTCAGGCAC | 73 | 4149 |
| 1209362 | N/A | N/A | 3491 | 3506 | CAACACACTCTCTGAG | 69 | 4150 |
| 1209375 | N/A | N/A | 3606 | 3621 | TCTTACCAGGGCTGAG | 90 | 4151 |
| 1209388 | N/A | N/A | 3669 | 3684 | CTTGGACAGAAGGACA | 93 | 4152 |
| 1209401 | N/A | N/A | 3706 | 3721 | CTGCCCTATCACAGTC | 65 | 4153 |
| 1209414 | N/A | N/A | 3887 | 3902 | AGGAGAGTAATGAGGC | 80 | 4154 |
| 1209427 | N/A | N/A | 3950 | 3965 | GTATTGTGGAGGGAGA | 70 | 4155 |
| 1209440 | N/A | N/A | 4003 | 4018 | CCTGCAAAATGGGACC | 69 | 4156 |
| 1209453 | N/A | N/A | 4037 | 4052 | TTGCTACTCCAAGTTT | 69 | 4157 |
| 1209466 | N/A | N/A | 4070 | 4085 | AAGGCCCTTCTTGAAC | 62 | 4158 |
| 1209479 | N/A | N/A | 4272 | 4287 | AGCACCCCGCCCAGGT | 73 | 4159 |
| 1209492 | N/A | N/A | 4335 | 4350 | CCATGCCAAGTCTCCG | 87 | 4160 |
| 1209505 | N/A | N/A | 4369 | 4384 | CAAAGAGGGATAGTGG | 92 | 4161 |
| 1209518 | N/A | N/A | 4623 | 4638 | ACCCCTGGGCCTAAAG | 91 | 4162 |
| 1209531 | N/A | N/A | 4806 | 4821 | CAAGCCCGTCCCACCT | 52 | 4163 |
| 1209544 | N/A | N/A | 5151 | 5166 | TTCCTGTAGCCACACG | 50 | 4164 |
| 1209557 | N/A | N/A | 5432 | 5447 | CGGCTGGCCGGAATCT | 46 | 4165 |
| 1209570 | N/A | N/A | 5747 | 5762 | GGAGCCGCGGCCCCTG | 62 | 4166 |
| 1209583 | N/A | N/A | 5876 | 5891 | CTCCCGAACCCCAATC | 52 | 4167 |
| 1209596 | N/A | N/A | 6114 | 6129 | CTCTTCCCGTCCCCGC | 53 | 4168 |
| 1209609 | N/A | N/A | 6362 | 6377 | ACCCAGTGATCAAAGG | 40 | 4169 |
| 1209622 | N/A | N/A | 6440 | 6455 | CTCACAACCCATCAGG | 42 | 4170 |
| 1209635 | N/A | N/A | 6477 | 6492 | AGGCCCTGGGATTCTA | 39 | 4171 |
| 1209648 | N/A | N/A | 6544 | 6559 | GGAACCAAGAGCAAGT | 40 | 4172 |
| 1209661 | N/A | N/A | 6632 | 6647 | CCATCCAGAGTCGCAG | 38 | 4173 |
| 1209674 | N/A | N/A | 6712 | 6727 | CATAGGCAAGGAGGCT | 34 | 4174 |
| 1209687 | N/A | N/A | 6799 | 6814 | AAGCTGCTCCAGGCGC | 57 | 4175 |

TABLE 65-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209700 | N/A | N/A | 6849 | 6864 | CGCCTTCTTCACACCC | 117 | 4176 |
| 1209713 | N/A | N/A | 7059 | 7074 | GTGCCTGACGGCCTCG | 68† | 4177 |

TABLE 66

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 99 | 2426 |
| 1129531 | 2009 | 2024 | 7397 | 7412 | GAGTTCCTGCGCCATC | 16 | 3837 |
| 1129947 | N/A | N/A | 4837 | 4852 | TGCTTTCCGCACTCTC | 51 | 3554 |
| 1129948 | N/A | N/A | 4840 | 4855 | ATCTGCTTTCCGCACT | 70 | 3630 |
| 1208266 | N/A | N/A | 98 | 113 | CACTCACCGAAAGTGT | 65 | 4178 |
| 1208297 | N/A | N/A | 136 | 151 | CCCCCAGAACAATCCT | 84 | 4179 |
| 1208332 | N/A | N/A | 205 | 220 | ATAGGCCTCCTAGTCA | 97 | 4180 |
| 1208366 | N/A | N/A | 275 | 290 | CCTTGTATCCACCCAG | 55 | 4181 |
| 1208397 | N/A | N/A | 322 | 337 | CCCGTTGTCTTCTTAA | 87 | 4182 |
| 1208431 | N/A | N/A | 417 | 432 | TAGCCTGCCACCGATC | 78 | 4183 |
| 1208459 | N/A | N/A | 462 | 477 | GAATCTACAAGGGAGA | 52 | 4184 |
| 1208492 | N/A | N/A | 556 | 571 | CCACCCAAGGGTTCCC | 81 | 4185 |
| 1208516 | N/A | N/A | 609 | 624 | TAGGCACTAGACTAGA | 97 | 4186 |
| 1208549 | N/A | N/A | 635 | 650 | CCATGGGCATAAGACC | 38 | 4187 |
| 1208578 | N/A | N/A | 674 | 689 | TGCCCTCAAGGATCAC | 46 | 4188 |
| 1208591 | N/A | N/A | 740 | 755 | AGCAGCACATATCTCA | 95 | 4189 |
| 1208604 | N/A | N/A | 863 | 878 | ATTGAAGGCCCTGGCC | 47 | 4190 |
| 1208617 | N/A | N/A | 896 | 911 | TGCCAGAGACAAGCTC | 43 | 4191 |
| 1208630 | N/A | N/A | 934 | 949 | CTCATAAGTGATAAAG | 58 | 4192 |
| 1208643 | N/A | N/A | 977 | 992 | TTGAAGCTTGGAGAAC | 52 | 4193 |
| 1208656 | N/A | N/A | 1019 | 1034 | AAGAGGTTTACTGTTA | 76 | 4194 |
| 1208669 | N/A | N/A | 1063 | 1078 | GATGGGCTGAATACCT | 51 | 4195 |
| 1208682 | N/A | N/A | 1130 | 1145 | ACCCTTCATCTAAAAG | 56 | 4196 |
| 1208695 | N/A | N/A | 1168 | 1183 | AGCTATGGCAGAGCTT | 98 | 4197 |
| 1208708 | N/A | N/A | 1520 | 1535 | CCACACTCTAGGTAAA | 44 | 4198 |
| 1208721 | N/A | N/A | 1575 | 1590 | ACCAAGTCAGGCCCAC | 92 | 4199 |

TABLE 66-continued

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208742 | N/A | N/A | 1620 | 1635 | TTGGAATGTGCTGGGC | 58 | 4200 |
| 1208768 | N/A | N/A | 1693 | 1708 | AGTTTGGGTAAGGCAA | 62 | 4201 |
| 1208796 | N/A | N/A | 1759 | 1774 | AGATGGGATGGACGGA | 47 | 4202 |
| 1208820 | N/A | N/A | 1924 | 1939 | TAGCTGAGCATGAAGT | 43 | 4203 |
| 1208847 | N/A | N/A | 2113 | 2128 | ACTAGGACAGTAAATG | 50 | 4204 |
| 1208874 | N/A | N/A | 2130 | 2145 | CCAAGGACCAAACCAG | 67 | 4205 |
| 1208899 | N/A | N/A | 2169 | 2184 | AGCTTTTGCCACTATT | 90 | 4206 |
| 1208925 | N/A | N/A | 2191 | 2206 | GGCACAAAGTACCTGC | 71 | 4207 |
| 1208951 | N/A | N/A | 2269 | 2284 | GAGAATTGCCTGTGTC | 92 | 4208 |
| 1208977 | N/A | N/A | 2325 | 2340 | TGTTTGCTAGTTCAAT | 27 | 4209 |
| 1209004 | N/A | N/A | 2340 | 2355 | ACAGGAACCTAATACT | 74 | 4210 |
| 1209028 | N/A | N/A | 2446 | 2461 | TGATGAATCAGCAACA | 59 | 4211 |
| 1209053 | N/A | N/A | 2467 | 2482 | ATAGTGCCATCAGCTT | 50 | 4212 |
| 1209080 | N/A | N/A | 2498 | 2513 | GTGTGTTAGACACTTG | 50 | 4213 |
| 1209105 | N/A | N/A | 2570 | 2585 | AATGGCCTCTGAGCCT | 46 | 4214 |
| 1209131 | N/A | N/A | 2650 | 2665 | ATTGAATGAGTGTCCT | 117 | 4215 |
| 1209159 | N/A | N/A | 2711 | 2726 | GCACATTCCCAGTTAA | 49 | 4216 |
| 1209187 | N/A | N/A | 2775 | 2790 | CCAAGTCAATACTTGA | 45 | 4217 |
| 1209210 | N/A | N/A | 2804 | 2819 | GCCTACTTGCTGAATT | 35 | 4218 |
| 1209236 | N/A | N/A | 2824 | 2839 | TGGTTCTACATTGAGA | 93 | 4219 |
| 1209258 | N/A | N/A | 2903 | 2918 | TAACCACTCTGATCTG | 49 | 4220 |
| 1209284 | N/A | N/A | 2965 | 2980 | AGGAAGAGCACTTGCC | 55 | 4221 |
| 1209309 | N/A | N/A | 3030 | 3045 | AGTAGACTCCTGACTC | 49 | 4222 |
| 1209336 | N/A | N/A | 3377 | 3392 | CTGCTCTAAAAGTTGG | 64 | 4223 |
| 1209350 | N/A | N/A | 3462 | 3477 | CTCAACTGCTCAGGCA | 61 | 4224 |
| 1209363 | N/A | N/A | 3492 | 3507 | ACAACACACTCTCTGA | 48 | 4225 |
| 1209376 | N/A | N/A | 3607 | 3622 | GTCTTACCAGGGCTGA | 59 | 4226 |
| 1209389 | N/A | N/A | 3670 | 3685 | CCTTGGACAGAAGGAC | 49 | 4227 |
| 1209402 | N/A | N/A | 3707 | 3722 | CCTGCCCTATCACAGT | 92 | 4228 |
| 1209415 | N/A | N/A | 3889 | 3904 | CCAGGAGAGTAATGAG | 49 | 4229 |
| 1209428 | N/A | N/A | 3951 | 3966 | GGTATTGTGGAGGGAG | 56 | 4230 |
| 1209441 | N/A | N/A | 4012 | 4027 | GTTTACCCACCTGCAA | 39 | 4231 |
| 1209454 | N/A | N/A | 4038 | 4053 | CTTGCTACTCCAAGTT | 108 | 4232 |
| 1209467 | N/A | N/A | 4073 | 4088 | GCCAAGGCCCTTCTTG | 56 | 4233 |
| 1209480 | N/A | N/A | 4295 | 4310 | GCCCAGGGTTGCCCCT | 65 | 4234 |
| 1209493 | N/A | N/A | 4336 | 4351 | ACCATGCCAAGTCTCC | 46 | 4235 |

TABLE 66-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209506 | N/A | N/A | 4370 | 4385 | ACAAAGAGGGATAGTG | 67 | 4236 |
| 1209519 | N/A | N/A | 4625 | 4640 | CCACCCCTGGGCCTAA | 134 | 4237 |
| 1209532 | N/A | N/A | 4807 | 4822 | GCAAGCCCGTCCCACC | 81 | 4238 |
| 1209545 | N/A | N/A | 5152 | 5167 | GTTCCTGTAGCCACAC | 23 | 4239 |
| 1209558 | N/A | N/A | 5435 | 5450 | GGCCGGCTGGCCGGAA | 84 | 4240 |
| 1209571 | N/A | N/A | 5748 | 5763 | AGGAGCCGCGGCCCCT | 64 | 4241 |
| 1209584 | N/A | N/A | 5878 | 5893 | TGCTCCCGAACCCCAA | 35 | 4242 |
| 1209597 | N/A | N/A | 6120 | 6135 | CAAGCTCTCTTCCCGT | 53 | 4243 |
| 1209610 | N/A | N/A | 6365 | 6380 | CTAACCCAGTGATCAA | 29 | 4244 |
| 1209623 | N/A | N/A | 6443 | 6458 | ATTCTCACAACCCATC | 64 | 4245 |
| 1209636 | N/A | N/A | 6486 | 6501 | GTGAATCCCAGGCCCT | 41 | 4246 |
| 1209649 | N/A | N/A | 6553 | 6568 | CGCCCAGAGGGAACCA | 116 | 4247 |
| 1209662 | N/A | N/A | 6633 | 6648 | CCCATCCAGAGTCGCA | 30 | 4248 |
| 1209675 | N/A | N/A | 6713 | 6728 | TCATAGGCAAGGAGGC | 36 | 4249 |
| 1209688 | N/A | N/A | 6800 | 6815 | AAAGCTGCTCCAGGCG | 27 | 4250 |
| 1209701 | N/A | N/A | 6850 | 6865 | GCGCCTTCTTCACACC | 85 | 4251 |
| 1209714 | N/A | N/A | 7063 | 7078 | ATTTGTGCCTGACGGC | 53[†] | 4252 |

TABLE 67

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 29 | 2426 |
| 1129531 | 2009 | 2024 | 7397 | 7412 | GAGTTCCTGCGCCATC | 33 | 3837 |
| 1129948 | N/A | N/A | 4840 | 4855 | ATCTGCTTTCCGCACT | 52 | 3630 |
| 1194288 | N/A | N/A | 4838 | 4853 | CTGCTTTCCGCACTCT | 27 | 4253 |
| 1208267 | N/A | N/A | 104 | 119 | CCACAGCACTCACCGA | 128 | 4254 |
| 1208301 | N/A | N/A | 137 | 152 | CCCCCCAGAACAATCC | 177 | 4255 |
| 1208333 | N/A | N/A | 213 | 228 | CTTTCCACATAGGCCT | 68 | 4256 |
| 1208370 | N/A | N/A | 276 | 291 | CCCTTGTATCCACCCA | 41 | 4257 |
| 1208398 | N/A | N/A | 331 | 346 | CTACCTCCCCCCGTTG | 91 | 4258 |
| 1208432 | N/A | N/A | 418 | 433 | ATAGCCTGCCACCGAT | 116 | 4259 |
| 1208463 | N/A | N/A | 465 | 480 | GTGGAATCTACAAGGG | 34 | 4260 |

TABLE 67-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208494 | N/A | N/A | 557 | 572 | CCCACCCAAGGGTTCC | 44 | 4261 |
| 1208519 | N/A | N/A | 616 | 631 | CACCAGGTAGGCACTA | 93 | 4262 |
| 1208550 | N/A | N/A | 638 | 653 | TGCCCATGGGCATAAG | 43 | 4263 |
| 1208579 | N/A | N/A | 685 | 700 | AGCCCATACCCTGCCC | 77 | 4264 |
| 1208592 | N/A | N/A | 741 | 756 | CAGCAGCACATATCTC | 64 | 4265 |
| 1208605 | N/A | N/A | 864 | 879 | CATTGAAGGCCCTGGC | 90 | 4266 |
| 1208618 | N/A | N/A | 897 | 912 | ATGCCAGAGACAAGCT | 56 | 4267 |
| 1208631 | N/A | N/A | 935 | 950 | GCTCATAAGTGATAAA | 54 | 4268 |
| 1208644 | N/A | N/A | 1002 | 1017 | CAACCTGGTTTCACAG | 32 | 4269 |
| 1208657 | N/A | N/A | 1020 | 1035 | TAAGAGGTTTACTGTT | 44 | 4270 |
| 1208670 | N/A | N/A | 1066 | 1081 | GGTGATGGGCTGAATA | 52 | 4271 |
| 1208683 | N/A | N/A | 1131 | 1146 | TACCCTTCATCTAAAA | 80 | 4272 |
| 1208696 | N/A | N/A | 1169 | 1184 | GAGCTATGGCAGAGCT | 67 | 4273 |
| 1208709 | N/A | N/A | 1529 | 1544 | TGCTATGTGCCACACT | 61 | 4274 |
| 1208722 | N/A | N/A | 1578 | 1593 | CCCACCAAGTCAGGCC | 56 | 4275 |
| 1208744 | N/A | N/A | 1621 | 1636 | GTTGGAATGTGCTGGG | 42 | 4276 |
| 1208771 | N/A | N/A | 1694 | 1709 | AAGTTTGGGTAAGGCA | 81 | 4277 |
| 1208799 | N/A | N/A | 1760 | 1775 | CAGATGGGATGGACGG | 57 | 4278 |
| 1208821 | N/A | N/A | 2075 | 2090 | TTAAGATGCAAATGGG | 31 | 4279 |
| 1208848 | N/A | N/A | 2115 | 2130 | GAACTAGGACAGTAAA | 40 | 4280 |
| 1208877 | N/A | N/A | 2131 | 2146 | GCCAAGGACCAAACCA | 34 | 4281 |
| 1208901 | N/A | N/A | 2170 | 2185 | AAGCTTTTGCCACTAT | 49 | 4282 |
| 1208926 | N/A | N/A | 2192 | 2207 | TGGCACAAAGTACCTG | 73 | 4283 |
| 1208952 | N/A | N/A | 2270 | 2285 | TGAGAATTGCCTGTGT | 59 | 4284 |
| 1208980 | N/A | N/A | 2326 | 2341 | CTGTTTGCTAGTTCAA | 47 | 4285 |
| 1209005 | N/A | N/A | 2342 | 2357 | TCACAGGAACCTAATA | 101 | 4286 |
| 1209031 | N/A | N/A | 2447 | 2462 | TTGATGAATCAGCAAC | 39 | 4287 |
| 1209054 | N/A | N/A | 2471 | 2486 | TGCTATAGTGCCATCA | 49 | 4288 |
| 1209081 | N/A | N/A | 2517 | 2532 | GCTACCTTAGGGAGAA | 48 | 4289 |
| 1209108 | N/A | N/A | 2572 | 2587 | GAAATGGCCTCTGAGC | 30 | 4290 |
| 1209134 | N/A | N/A | 2657 | 2672 | CTCTCCTATTGAATGA | 18 | 4291 |
| 1209160 | N/A | N/A | 2713 | 2728 | TTGCACATTCCCAGTT | 34 | 4292 |
| 1209188 | N/A | N/A | 2776 | 2791 | CCCAAGTCAATACTTG | 43 | 4293 |
| 1209212 | N/A | N/A | 2805 | 2820 | TGCCTACTTGCTGAAT | 87 | 4294 |
| 1209238 | N/A | N/A | 2825 | 2840 | CTGGTTCTACATTGAG | 20 | 4295 |
| 1209261 | N/A | N/A | 2905 | 2920 | GTTAACCACTCTGATC | 79 | 4296 |

TABLE 67-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209285 | N/A | N/A | 2985 | 3000 | AAGTCTTCAGTCCCAA | 47 | 4297 |
| 1209312 | N/A | N/A | 3033 | 3048 | TGGAGTAGACTCCTGA | 72 | 4298 |
| 1209337 | N/A | N/A | 3413 | 3428 | ACCCTCAAAAAGGTCG | 45 | 4299 |
| 1209351 | N/A | N/A | 3463 | 3478 | ACTCAACTGCTCAGGC | 87 | 4300 |
| 1209364 | N/A | N/A | 3493 | 3508 | GACAACACACTCTCTG | 44 | 4301 |
| 1209377 | N/A | N/A | 3608 | 3623 | AGTCTTACCAGGGCTG | 88 | 4302 |
| 1209390 | N/A | N/A | 3673 | 3688 | GTTCCTTGGACAGAAG | 96 | 4303 |
| 1209403 | N/A | N/A | 3709 | 3724 | ACCCTGCCCTATCACA | 29 | 4304 |
| 1209416 | N/A | N/A | 3890 | 3905 | ACCAGGAGAGTAATGA | 31 | 4305 |
| 1209429 | N/A | N/A | 3954 | 3969 | AAGGGTATTGTGGAGG | 45 | 4306 |
| 1209442 | N/A | N/A | 4016 | 4031 | CTTGGTTTACCCACCT | 49 | 4307 |
| 1209455 | N/A | N/A | 4041 | 4056 | GACCTTGCTACTCCAA | 21 | 4308 |
| 1209468 | N/A | N/A | 4074 | 4089 | GGCCAAGGCCCTTCTT | 128 | 4309 |
| 1209481 | N/A | N/A | 4298 | 4313 | TAGGCCCAGGGTTGCC | 135 | 4310 |
| 1209494 | N/A | N/A | 4337 | 4352 | GACCATGCCAAGTCTC | 40 | 4311 |
| 1209507 | N/A | N/A | 4528 | 4543 | GTTCCCAACCATCTGC | 42 | 4312 |
| 1209520 | N/A | N/A | 4631 | 4646 | AGTGAGCCACCCCTGG | 91 | 4313 |
| 1209533 | N/A | N/A | 4813 | 4828 | TTCCTGGCAAGCCCGT | 60 | 4314 |
| 1209546 | N/A | N/A | 5156 | 5171 | CCGGGTTCCTGTAGCC | 58 | 4315 |
| 1209559 | N/A | N/A | 5437 | 5452 | GCGGCCGGCTGGCCGG | 56 | 4316 |
| 1209572 | N/A | N/A | 5749 | 5764 | GAGGAGCCGCGGCCCC | 40 | 4317 |
| 1209585 | N/A | N/A | 5879 | 5894 | CTGCTCCCGAACCCCA | 48 | 4318 |
| 1209598 | N/A | N/A | 6121 | 6136 | CCAAGCTCTCTTCCCG | 61 | 4319 |
| 1209611 | N/A | N/A | 6366 | 6381 | CCTAACCCAGTGATCA | 48 | 4320 |
| 1209624 | N/A | N/A | 6453 | 6468 | TCACCTACACATTCTC | 37 | 4321 |
| 1209637 | N/A | N/A | 6487 | 6502 | AGTGAATCCCAGGCCC | 138 | 4322 |
| 1209650 | N/A | N/A | 6554 | 6569 | GCGCCCAGAGGGAACC | 50 | 4323 |
| 1209663 | N/A | N/A | 6635 | 6650 | CACCCATCCAGAGTCG | 51 | 4324 |
| 1209676 | N/A | N/A | 6714 | 6729 | TTCATAGGCAAGGAGG | 45 | 4325 |
| 1209689 | N/A | N/A | 6803 | 6818 | GACAAAGCTGCTCCAG | 99 | 4326 |
| 1209702 | N/A | N/A | 6864 | 6879 | CCTGCGAACACAGAGC | 43 | 4327 |
| 1209715 | N/A | N/A | 7067 | 7082 | TGAGATTTGTGCCTGA | 44[†] | 4328 |

TABLE 68

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 37 | 2426 |
| 1129531 | 2009 | 2024 | 7397 | 7412 | GAGTTCCTGCGCCATC | 25 | 3837 |
| 1129948 | N/A | N/A | 4840 | 4855 | ATCTGCTTTCCGCACT | 44 | 3630 |
| 1194289 | N/A | N/A | 4839 | 4854 | TCTGCTTTCCGCACTC | 28 | 4329 |
| 1208271 | N/A | N/A | 116 | 131 | CAATCCTGGTTCCCAC | 68 | 4330 |
| 1208302 | N/A | N/A | 154 | 169 | CATGGCTGTGATAGCG | 73 | 4331 |
| 1208337 | N/A | N/A | 215 | 230 | ACCTTTCCACATAGGC | 81 | 4332 |
| 1208371 | N/A | N/A | 278 | 293 | TGCCCTTGTATCCACC | 43 | 4333 |
| 1208402 | N/A | N/A | 342 | 357 | CCAAACCCTTTCTACC | 59 | 4334 |
| 1208435 | N/A | N/A | 419 | 434 | CATAGCCTGCCACCGA | 29 | 4335 |
| 1208464 | N/A | N/A | 467 | 482 | AGGTGGAATCTACAAG | 38 | 4336 |
| 1208497 | N/A | N/A | 558 | 573 | CCCCACCCAAGGGTTC | 68 | 4337 |
| 1208520 | N/A | N/A | 617 | 632 | GCACCAGGTAGGCACT | 44 | 4338 |
| 1208554 | N/A | N/A | 646 | 661 | CACTCTAGTGCCCATG | 111 | 4339 |
| 1208580 | N/A | N/A | 695 | 710 | ACTTAGACACAGCCCA | 43 | 4340 |
| 1208593 | N/A | N/A | 745 | 760 | GCGCCAGCAGCACATA | 55 | 4341 |
| 1208606 | N/A | N/A | 865 | 880 | CCATTGAAGGCCCTGG | 39 | 4342 |
| 1208619 | N/A | N/A | 898 | 913 | GATGCCAGAGACAAGC | 26 | 4343 |
| 1208632 | N/A | N/A | 936 | 951 | AGCTCATAAGTGATAA | 73 | 4344 |
| 1208645 | N/A | N/A | 1005 | 1020 | TATCAACCTGGTTTCA | 47 | 4345 |
| 1208658 | N/A | N/A | 1021 | 1036 | CTAAGAGGTTTACTGT | 35 | 4346 |
| 1208671 | N/A | N/A | 1072 | 1087 | GCACCAGGTGATGGGC | 40 | 4347 |
| 1208684 | N/A | N/A | 1133 | 1148 | GGTACCCTTCATCTAA | 121 | 4348 |
| 1208697 | N/A | N/A | 1200 | 1215 | ATTTAGTGTCTGGAAG | 41 | 4349 |
| 1208710 | N/A | N/A | 1541 | 1556 | GTTCACAGGCCCTGCT | 55 | 4350 |
| 1208723 | N/A | N/A | 1579 | 1594 | CCCCACCAAGTCAGGC | 95 | 4351 |
| 1208745 | N/A | N/A | 1624 | 1639 | AGGGTTGGAATGTGCT | 44 | 4352 |
| 1208773 | N/A | N/A | 1697 | 1712 | ACCAAGTTTGGGTAAG | 39 | 4353 |
| 1208800 | N/A | N/A | 1762 | 1777 | TGCAGATGGGATGGAC | 51 | 4354 |
| 1208824 | N/A | N/A | 2080 | 2095 | GACCTTTAAGATGCAA | 40 | 4355 |
| 1208851 | N/A | N/A | 2116 | 2131 | AGAACTAGGACAGTAA | 33 | 4356 |
| 1208878 | N/A | N/A | 2133 | 2148 | TTGCCAAGGACCAAAC | 36 | 4357 |
| 1208902 | N/A | N/A | 2171 | 2186 | TAAGCTTTTGCCACTA | 29 | 4358 |
| 1208929 | N/A | N/A | 2193 | 2208 | CTGGCACAAAGTACCT | 58 | 4359 |
| 1208955 | N/A | N/A | 2271 | 2286 | ATGAGAATTGCCTGTG | 29 | 4360 |
| 1208981 | N/A | N/A | 2327 | 2342 | ACTGTTTGCTAGTTCA | 44 | 4361 |

TABLE 68-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209008 | N/A | N/A | 2375 | 2390 | CTGTTGGTTGATGAAA | 83 | 4362 |
| 1209032 | N/A | N/A | 2448 | 2463 | ATTGATGAATCAGCAA | 68 | 4363 |
| 1209057 | N/A | N/A | 2472 | 2487 | GTGCTATAGTGCCATC | 25 | 4364 |
| 1209084 | N/A | N/A | 2518 | 2533 | GGCTACCTTAGGGAGA | 57 | 4365 |
| 1209109 | N/A | N/A | 2579 | 2594 | GCTTTTGGAAATGGCC | 27 | 4366 |
| 1209135 | N/A | N/A | 2673 | 2688 | CTGCTGCTTGTTTCAG | 82 | 4367 |
| 1209163 | N/A | N/A | 2716 | 2731 | AATTTGCACATTCCCA | 71 | 4368 |
| 1209191 | N/A | N/A | 2777 | 2792 | TCCCAAGTCAATACTT | 77 | 4369 |
| 1209213 | N/A | N/A | 2808 | 2823 | ATGTGCCTACTTGCTG | 58 | 4370 |
| 1209240 | N/A | N/A | 2827 | 2842 | CTCTGGTTCTACATTG | 38 | 4371 |
| 1209262 | N/A | N/A | 2906 | 2921 | TGTTAACCACTCTGAT | 106 | 4372 |
| 1209288 | N/A | N/A | 2986 | 3001 | TAAGTCTTCAGTCCCA | 33 | 4373 |
| 1209313 | N/A | N/A | 3042 | 3057 | TCAGATAGCTGGAGTA | 82 | 4374 |
| 1209339 | N/A | N/A | 3414 | 3429 | GACCCTCAAAAAGGTC | 76 | 4375 |
| 1209352 | N/A | N/A | 3464 | 3479 | TACTCAACTGCTCAGG | 47 | 4376 |
| 1209365 | N/A | N/A | 3494 | 3509 | GGACAACACACTCTCT | 73 | 4377 |
| 1209378 | N/A | N/A | 3611 | 3626 | CGTAGTCTTACCAGGG | 27 | 4378 |
| 1209391 | N/A | N/A | 3678 | 3693 | GCAGAGTTCCTTGGAC | 22 | 4379 |
| 1209404 | N/A | N/A | 3713 | 3728 | GCCCACCCTGCCCTAT | 83 | 4380 |
| 1209417 | N/A | N/A | 3891 | 3906 | TACCAGGAGAGTAATG | 34 | 4381 |
| 1209430 | N/A | N/A | 3955 | 3970 | AAAGGGTATTGTGGAG | 19 | 4382 |
| 1209443 | N/A | N/A | 4020 | 4035 | CAAGCTTGGTTTACCC | 48 | 4383 |
| 1209456 | N/A | N/A | 4053 | 4068 | TACTTGCCTTGTGACC | 42 | 4384 |
| 1209469 | N/A | N/A | 4075 | 4090 | GGGCCAAGGCCCTTCT | 51 | 4385 |
| 1209482 | N/A | N/A | 4299 | 4314 | GTAGGCCCAGGGTTGC | 33 | 4386 |
| 1209495 | N/A | N/A | 4340 | 4355 | TAGGACCATGCCAAGT | 39 | 4387 |
| 1209508 | N/A | N/A | 4530 | 4545 | CCGTTCCCAACCATCT | 60 | 4388 |
| 1209521 | N/A | N/A | 4638 | 4653 | GGAACGCAGTGAGCCA | 73 | 4389 |
| 1209534 | N/A | N/A | 4814 | 4829 | CTTCCTGGCAAGCCCG | 45 | 4390 |
| 1209547 | N/A | N/A | 5161 | 5176 | GTTGTCCGGGTTCCTG | 39 | 4391 |
| 1209560 | N/A | N/A | 5439 | 5454 | CCGCGGCCGGCTGGCC | 42 | 4392 |
| 1209573 | N/A | N/A | 5756 | 5771 | GGAGACGGAGGAGCCG | 71 | 4393 |
| 1209586 | N/A | N/A | 5885 | 5900 | AGCCCCTGCTCCCGA | 50 | 4394 |
| 1209599 | N/A | N/A | 6126 | 6141 | GGGCCCAAGCTCTCT | 30 | 4395 |
| 1209612 | N/A | N/A | 6372 | 6387 | CTTCCGCCTAACCCAG | 36 | 4396 |

TABLE 68-continued

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209625 | N/A | N/A | 6456 | 6471 | GATTCACCTACACATT | 40 | 4397 |
| 1209638 | N/A | N/A | 6490 | 6505 | AGCAGTGAATCCCAGG | 35 | 4398 |
| 1209651 | N/A | N/A | 6569 | 6584 | GGCCTTTGCAGCCCGG | 58 | 4399 |
| 1209664 | N/A | N/A | 6636 | 6651 | CCACCCATCCAGAGTC | 73 | 4400 |
| 1209677 | N/A | N/A | 6730 | 6745 | GTGCCATTAATTCAAT | 61 | 4401 |
| 1209690 | N/A | N/A | 6804 | 6819 | GGACAAAGCTGCTCCA | 75 | 4402 |
| 1209703 | N/A | N/A | 6868 | 6883 | CGCCCCTGCGAACACA | 27 | 4403 |
| 1209716 | N/A | N/A | 7068 | 7083 | CTGAGATTTGTGCCTG | 25† | 4404 |

TABLE 69

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 98 | 2426 |
| 1129531 | 2009 | 2024 | 7397 | 7412 | GAGTTCCTGCGCCATC | 13 | 3837 |
| 1129948 | N/A | N/A | 4840 | 4855 | ATCTGCTTTCCGCACT | 71 | 3630 |
| 1194290 | N/A | N/A | 4841 | 4856 | CATCTGCTTTCCGCAC | 44 | 4405 |
| 1208272 | N/A | N/A | 117 | 132 | ACAATCCTGGTTCCCA | 40 | 4406 |
| 1208307 | N/A | N/A | 177 | 192 | GGTCATGAGCAGAGGC | 58 | 4407 |
| 1208338 | N/A | N/A | 217 | 232 | TCACCTTTCCACATAG | 59 | 4408 |
| 1208375 | N/A | N/A | 301 | 316 | ATCTCCCCCAGAAATG | 40 | 4409 |
| 1208403 | N/A | N/A | 343 | 358 | CCCAAACCCTTTCTAC | 86 | 4410 |
| 1208436 | N/A | N/A | 421 | 436 | GTCATAGCCTGCCACC | 72 | 4411 |
| 1208468 | N/A | N/A | 468 | 483 | AAGGTGGAATCTACAA | 47 | 4412 |
| 1208498 | N/A | N/A | 560 | 575 | ATCCCCACCCAAGGGT | 53 | 4413 |
| 1208524 | N/A | N/A | 618 | 633 | AGCACCAGGTAGGCAC | 49 | 4414 |
| 1208555 | N/A | N/A | 648 | 663 | ATCACTCTAGTGCCCA | 111 | 4415 |
| 1208581 | N/A | N/A | 696 | 711 | CACTTAGACACAGCCC | 83 | 4416 |
| 1208594 | N/A | N/A | 834 | 849 | AATGATGCCCATGAGA | 40 | 4417 |
| 1208607 | N/A | N/A | 868 | 883 | TGCCCATTGAAGGCCC | 60 | 4418 |
| 1208620 | N/A | N/A | 906 | 921 | GGCATTCAGATGCCAG | 108 | 4419 |
| 1208633 | N/A | N/A | 937 | 952 | CAGCTCATAAGTGATA | 55 | 4420 |
| 1208646 | N/A | N/A | 1006 | 1021 | TTATCAACCTGGTTTC | 57 | 4421 |
| 1208659 | N/A | N/A | 1025 | 1040 | AACCCTAAGAGGTTTA | 40 | 4422 |

TABLE 69-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208672 | N/A | N/A | 1073 | 1088 | TGCACCAGGTGATGGG | 53 | 4423 |
| 1208685 | N/A | N/A | 1135 | 1150 | CAGGTACCCTTCATCT | 51 | 4424 |
| 1208698 | N/A | N/A | 1202 | 1217 | TAATTTAGTGTCTGGA | 89 | 4425 |
| 1208711 | N/A | N/A | 1547 | 1562 | CATCTGGTTCACAGGC | 53 | 4426 |
| 1208724 | N/A | N/A | 1580 | 1595 | ACCCCACCAAGTCAGG | 106 | 4427 |
| 1208748 | N/A | N/A | 1625 | 1640 | CAGGGTTGGAATGTGC | 88 | 4428 |
| 1208775 | N/A | N/A | 1698 | 1713 | CACCAAGTTTGGGTAA | 93 | 4429 |
| 1208802 | N/A | N/A | 1763 | 1778 | ATGCAGATGGGATGGA | 41 | 4430 |
| 1208825 | N/A | N/A | 2081 | 2096 | GGACCTTTAAGATGCA | 44 | 4431 |
| 1208852 | N/A | N/A | 2117 | 2132 | CAGAACTAGGACAGTA | 90 | 4432 |
| 1208881 | N/A | N/A | 2134 | 2149 | CTTGCCAAGGACCAAA | 84 | 4433 |
| 1208905 | N/A | N/A | 2172 | 2187 | ATAAGCTTTTGCCACT | 66 | 4434 |
| 1208930 | N/A | N/A | 2207 | 2222 | ATGCTGAGCAGTGTCT | 30 | 4435 |
| 1208956 | N/A | N/A | 2277 | 2292 | CGAATAATGAGAATTG | 73 | 4436 |
| 1208984 | N/A | N/A | 2328 | 2343 | TACTGTTTGCTAGTTC | 81 | 4437 |
| 1209009 | N/A | N/A | 2378 | 2393 | ATGCTGTTGGTTGATG | 39 | 4438 |
| 1209035 | N/A | N/A | 2451 | 2466 | AGCATTGATGAATCAG | 117 | 4439 |
| 1209058 | N/A | N/A | 2473 | 2488 | TGTGCTATAGTGCCAT | 111 | 4440 |
| 1209085 | N/A | N/A | 2522 | 2537 | AGAAGGCTACCTTAGG | 79 | 4441 |
| 1209111 | N/A | N/A | 2580 | 2595 | GGCTTTTGGAAATGGC | 62 | 4442 |
| 1209137 | N/A | N/A | 2698 | 2713 | TAAGGTTCAACAAGGC | 44 | 4443 |
| 1209166 | N/A | N/A | 2717 | 2732 | AAATTTGCACATTCCC | 86 | 4444 |
| 1209192 | N/A | N/A | 2778 | 2793 | CTCCCAAGTCAATACT | 105 | 4445 |
| 1209215 | N/A | N/A | 2810 | 2825 | GAATGTGCCTACTTGC | 42 | 4446 |
| 1209241 | N/A | N/A | 2851 | 2866 | ATAGTACAGTTGATCC | 40 | 4447 |
| 1209265 | N/A | N/A | 2908 | 2923 | ACTGTTAACCACTCTG | 57 | 4448 |
| 1209289 | N/A | N/A | 2988 | 3003 | GGTAAGTCTTCAGTCC | 46 | 4449 |
| 1209316 | N/A | N/A | 3043 | 3058 | GTCAGATAGCTGGAGT | 94 | 4450 |
| 1209340 | N/A | N/A | 3415 | 3430 | AGACCCTCAAAAAGGT | 40 | 4451 |
| 1209353 | N/A | N/A | 3465 | 3480 | GTACTCAACTGCTCAG | 57 | 4452 |
| 1209366 | N/A | N/A | 3496 | 3511 | AGGGACAACACACTCT | 35 | 4453 |
| 1209379 | N/A | N/A | 3625 | 3640 | CTCCAACTCCTCTGCG | 61 | 4454 |
| 1209392 | N/A | N/A | 3681 | 3696 | CAAGCAGAGTTCCTTG | 62 | 4455 |
| 1209405 | N/A | N/A | 3745 | 3760 | GACAAGGCTTCCCTGC | 106 | 4456 |
| 1209418 | N/A | N/A | 3892 | 3907 | ATACCAGGAGAGTAAT | 51 | 4457 |

TABLE 69-continued

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209431 | N/A | N/A | 3959 | 3974 | TTCCAAAGGGTATTGT | 41 | 4458 |
| 1209444 | N/A | N/A | 4021 | 4036 | CCAAGCTTGGTTTACC | 90 | 4459 |
| 1209457 | N/A | N/A | 4054 | 4069 | CTACTTGCCTTGTGAC | 42 | 4460 |
| 1209470 | N/A | N/A | 4126 | 4141 | GAGAGATGGACATGGT | 44 | 4461 |
| 1209483 | N/A | N/A | 4301 | 4316 | CTGTAGGCCCAGGGTT | 44 | 4462 |
| 1209496 | N/A | N/A | 4341 | 4356 | CTAGGACCATGCCAAG | 84 | 4463 |
| 1209509 | N/A | N/A | 4531 | 4546 | CCCGTTCCCAACCATC | 114 | 4464 |
| 1209522 | N/A | N/A | 4640 | 4655 | AGGGAACGCAGTGAGC | 74 | 4465 |
| 1209535 | N/A | N/A | 4833 | 4848 | TTCCGCACTCTCCCTC | 81 | 4466 |
| 1209548 | N/A | N/A | 5162 | 5177 | CGTTGTCCGGGTTCCT | 11 | 4467 |
| 1209561 | N/A | N/A | 5441 | 5456 | GCCCGCGGCCGGCTGG | 39 | 4468 |
| 1209574 | N/A | N/A | 5757 | 5772 | GGGAGACGGAGGAGCC | 76 | 4469 |
| 1209587 | N/A | N/A | 5886 | 5901 | AAGCCCCTGCTCCCG | 99 | 4470 |
| 1209600 | N/A | N/A | 6173 | 6188 | GCAACAGAGCTAACCC | 52 | 4471 |
| 1209613 | N/A | N/A | 6374 | 6389 | TTCTTCCGCCTAACCC | 31 | 4472 |
| 1209626 | N/A | N/A | 6460 | 6475 | CTGGGATTCACCTACA | 58 | 4473 |
| 1209639 | N/A | N/A | 6491 | 6506 | CAGCAGTGAATCCCAG | 66 | 4474 |
| 1209652 | N/A | N/A | 6574 | 6589 | TAGTTGGCCTTTGCAG | 33 | 4475 |
| 1209665 | N/A | N/A | 6637 | 6652 | ACCACCCATCCAGAGT | 54 | 4476 |
| 1209678 | N/A | N/A | 6736 | 6751 | GAGGAGGTGCCATTAA | 37 | 4477 |
| 1209691 | N/A | N/A | 6805 | 6820 | TGGACAAAGCTGCTCC | 57 | 4478 |
| 1209704 | N/A | N/A | 6869 | 6884 | CCGCCCTGCGAACAC | 48 | 4479 |
| 1209717 | N/A | N/A | 7069 | 7084 | CCTGAGATTTGTGCCT | 88† | 4480 |

TABLE 70

Reduction of FXII RNA by 3-10-3 cEt gapmers with uniform
PS internucleoside linkages (Huh7, electroporation,
2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 99 | 2426 |
| 1129531 | 2009 | 2024 | 7397 | 7412 | GAGTTCCTGCGCCATC | 11 | 3837 |
| 1129948 | N/A | N/A | 4840 | 4855 | ATCTGCTTTCCGCACT | 43 | 3630 |
| 1194291 | N/A | N/A | 4842 | 4857 | TCATCTGCTTTCCGCA | 55 | 4481 |
| 1208276 | N/A | N/A | 118 | 133 | GACAATCCTGGTTCCC | 81 | 4482 |
| 1208310 | N/A | N/A | 182 | 197 | CCACAGGTCATGAGCA | 44 | 4483 |

TABLE 70-continued

Reduction of FXII RNA by 3-10-3 cEt gapmers with uniform
PS internucleoside linkages (Huh7, electroporation,
2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208342 | N/A | N/A | 231 | 246 | CTTCCGGGCTGGCCTC | 104 | 4484 |
| 1208376 | N/A | N/A | 309 | 324 | TAAGGCCCATCTCCCC | 117 | 4485 |
| 1208407 | N/A | N/A | 349 | 364 | CCAAGACCCAAACCCT | 60 | 4486 |
| 1208438 | N/A | N/A | 424 | 439 | TAAGTCATAGCCTGCC | 71 | 4487 |
| 1208469 | N/A | N/A | 471 | 486 | CCCAAGGTGGAATCTA | 92 | 4488 |
| 1208500 | N/A | N/A | 570 | 585 | CACCATACACATCCCC | 44 | 4489 |
| 1208525 | N/A | N/A | 620 | 635 | CTAGCACCAGGTAGGC | 52 | 4490 |
| 1208559 | N/A | N/A | 650 | 665 | CGATCACTCTAGTGCC | 69 | 4491 |
| 1208582 | N/A | N/A | 698 | 713 | GGCACTTAGACACAGC | 61 | 4492 |
| 1208595 | N/A | N/A | 835 | 850 | GAATGATGCCCATGAG | 65 | 4493 |
| 1208608 | N/A | N/A | 869 | 884 | TTGCCCATTGAAGGCC | 61 | 4494 |
| 1208621 | N/A | N/A | 907 | 922 | AGGCATTCAGATGCCA | 43 | 4495 |
| 1208634 | N/A | N/A | 951 | 966 | CGCCCAGAGTCACCCA | 58 | 4496 |
| 1208647 | N/A | N/A | 1007 | 1022 | GTTATCAACCTGGTTT | 76 | 4497 |
| 1208660 | N/A | N/A | 1026 | 1041 | CAACCCTAAGAGGTTT | 83 | 4498 |
| 1208673 | N/A | N/A | 1074 | 1089 | ATGCACCAGGTGATGG | 48 | 4499 |
| 1208686 | N/A | N/A | 1140 | 1155 | AATGGCAGGTACCCTT | 64 | 4500 |
| 1208699 | N/A | N/A | 1205 | 1220 | AGGTAATTTAGTGTCT | 96 | 4501 |
| 1208712 | N/A | N/A | 1550 | 1565 | GTCCATCTGGTTCACA | 69 | 4502 |
| 1208725 | N/A | N/A | 1581 | 1596 | AACCCCACCAAGTCAG | 55 | 4503 |
| 1208749 | N/A | N/A | 1629 | 1644 | AGTCCAGGGTTGGAAT | 45 | 4504 |
| 1208777 | N/A | N/A | 1700 | 1715 | GGCACCAAGTTTGGGT | 72 | 4505 |
| 1208803 | N/A | N/A | 1766 | 1781 | AAGATGCAGATGGGAT | 99 | 4506 |
| 1208828 | N/A | N/A | 2083 | 2098 | ATGGACCTTTAAGATG | 58 | 4507 |
| 1208855 | N/A | N/A | 2118 | 2133 | CCAGAACTAGGACAGT | 70 | 4508 |
| 1208882 | N/A | N/A | 2135 | 2150 | ACTTGCCAAGGACCAA | 40 | 4509 |
| 1208906 | N/A | N/A | 2173 | 2188 | AATAAGCTTTTGCCAC | 69 | 4510 |
| 1208932 | N/A | N/A | 2208 | 2223 | AATGCTGAGCAGTGTC | 96 | 4511 |
| 1208959 | N/A | N/A | 2278 | 2293 | GCGAATAATGAGAATT | 50 | 4512 |
| 1208985 | N/A | N/A | 2329 | 2344 | ATACTGTTTGCTAGTT | 81 | 4513 |
| 1209012 | N/A | N/A | 2379 | 2394 | TATGCTGTTGGTTGAT | 54 | 4514 |
| 1209036 | N/A | N/A | 2453 | 2468 | TTAGCATTGATGAATC | 50 | 4515 |
| 1209061 | N/A | N/A | 2482 | 2497 | ATTCAGGTGTGTGCTA | 47 | 4516 |
| 1209088 | N/A | N/A | 2528 | 2543 | AGCACAAGAAGGCTAC | 57 | 4517 |
| 1209112 | N/A | N/A | 2587 | 2602 | GGGATTTGGCTTTTGG | 76 | 4518 |

TABLE 70-continued

Reduction of FXII RNA by 3-10-3 cEt gapmers with uniform
PS internucleoside linkages (Huh7, electroporation,
2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209140 | N/A | N/A | 2699 | 2714 | TTAAGGTTCAACAAGG | 64 | 4519 |
| 1209169 | N/A | N/A | 2723 | 2738 | AGTGAAAAATTTGCAC | 70 | 4520 |
| 1209195 | N/A | N/A | 2779 | 2794 | ACTCCCAAGTCAATAC | 88 | 4521 |
| 1209216 | N/A | N/A | 2811 | 2826 | AGAATGTGCCTACTTG | 37 | 4522 |
| 1209243 | N/A | N/A | 2853 | 2868 | TAATAGTACAGTTGAT | 46 | 4523 |
| 1209266 | N/A | N/A | 2909 | 2924 | CACTGTTAACCACTCT | 84 | 4524 |
| 1209292 | N/A | N/A | 2990 | 3005 | TGGGTAAGTCTTCAGT | 62 | 4525 |
| 1209317 | N/A | N/A | 3044 | 3059 | AGTCAGATAGCTGGAG | 94 | 4526 |
| 1209341 | N/A | N/A | 3416 | 3431 | CAGACCCTCAAAAAGG | 64 | 4527 |
| 1209354 | N/A | N/A | 3467 | 3482 | CTGTACTCAACTGCTC | 47 | 4528 |
| 1209367 | N/A | N/A | 3497 | 3512 | CAGGGACAACACACTC | 61 | 4529 |
| 1209380 | N/A | N/A | 3648 | 3663 | GGTACATGTCTCCCAG | 42 | 4530 |
| 1209393 | N/A | N/A | 3682 | 3697 | CCAAGCAGAGTTCCTT | 74 | 4531 |
| 1209406 | N/A | N/A | 3758 | 3773 | ACCTGTAGAAAGAGAC | 41 | 4532 |
| 1209419 | N/A | N/A | 3893 | 3908 | GATACCAGGAGAGTAA | 70 | 4533 |
| 1209432 | N/A | N/A | 3960 | 3975 | CTTCCAAAGGGTATTG | 79 | 4534 |
| 1209445 | N/A | N/A | 4022 | 4037 | TCCAAGCTTGGTTTAC | 99 | 4535 |
| 1209458 | N/A | N/A | 4055 | 4070 | CCTACTTGCCTTGTGA | 67 | 4536 |
| 1209471 | N/A | N/A | 4130 | 4145 | GTCTGAGAGATGGACA | 54 | 4537 |
| 1209484 | N/A | N/A | 4305 | 4320 | TATTCTGTAGGCCCAG | 38 | 4538 |
| 1209497 | N/A | N/A | 4342 | 4357 | TCTAGGACCATGCCAA | 69 | 4539 |
| 1209510 | N/A | N/A | 4533 | 4548 | GGCCCGTTCCCAACCA | 45 | 4540 |
| 1209523 | N/A | N/A | 4641 | 4656 | GAGGGAACGCAGTGAG | 120 | 4541 |
| 1209536 | N/A | N/A | 4834 | 4849 | TTTCCGCACTCTCCCT | 78 | 4542 |
| 1209549 | N/A | N/A | 5382 | 5397 | CCCCCCACTTCCTAAC | 51 | 4543 |
| 1209562 | N/A | N/A | 5442 | 5457 | AGCCCGCGGCCGGCTG | 82 | 4544 |
| 1209575 | N/A | N/A | 5761 | 5776 | CGCTGGGAGACGGAGG | 31 | 4545 |
| 1209588 | N/A | N/A | 5913 | 5928 | TCAGACCTGGCCACAA | 45 | 4546 |
| 1209601 | N/A | N/A | 6326 | 6341 | CCTAGCAGTTGTGCCT | 70 | 4547 |
| 1209614 | N/A | N/A | 6404 | 6419 | GGCACCCGGAACGATA | 53 | 4548 |
| 1209627 | N/A | N/A | 6461 | 6476 | CCTGGGATTCACCTAC | 51 | 4549 |
| 1209640 | N/A | N/A | 6494 | 6509 | TCCCAGCAGTGAATCC | 49 | 4550 |
| 1209653 | N/A | N/A | 6575 | 6590 | CTAGTTGGCCTTTGCA | 52 | 4551 |
| 1209666 | N/A | N/A | 6638 | 6653 | CACCACCCATCCAGAG | 47 | 4552 |
| 1209679 | N/A | N/A | 6758 | 6773 | CTCTCGCAGCAAGCCC | 52 | 4553 |
| 1209692 | N/A | N/A | 6806 | 6821 | ATGGACAAAGCTGCTC | 29 | 4554 |

TABLE 70-continued

Reduction of FXII RNA by 3-10-3 cEt gapmers with uniform
PS internucleoside linkages (Huh7, electroporation,
2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209705 | N/A | N/A | 6872 | 6887 | CCTCCGCCCCTGCGAA | 60 | 4555 |
| 1209718 | N/A | N/A | 7070 | 7085 | ACCTGAGATTTGTGCC | 65† | 4556 |

TABLE 71

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 35 | 2426 |
| 1129531 | 2009 | 2024 | 7397 | 7412 | GAGTTCCTGCGCCATC | 14 | 3837 |
| 1129948 | N/A | N/A | 4840 | 4855 | ATCTGCTTTCCGCACT | 31 | 3630 |
| 1194292 | N/A | N/A | 4843 | 4858 | CTCATCTGCTTTCCGC | 65 | 4557 |
| 1208277 | N/A | N/A | 121 | 136 | TGGGACAATCCTGGTT | 92 | 4558 |
| 1208312 | N/A | N/A | 183 | 198 | CCCACAGGTCATGAGC | 63 | 4559 |
| 1208347 | N/A | N/A | 233 | 248 | GCCTTCCGGGCTGGCC | 57 | 4560 |
| 1208378 | N/A | N/A | 310 | 325 | TTAAGGCCCATCTCCC | 111 | 4561 |
| 1208408 | N/A | N/A | 358 | 373 | GATTTCTTCCCAAGAC | 49 | 4562 |
| 1208439 | N/A | N/A | 430 | 445 | TGACTATAAGTCATAG | 43 | 4563 |
| 1208473 | N/A | N/A | 472 | 487 | TCCCAAGGTGGAATCT | 75 | 4564 |
| 1208502 | N/A | N/A | 572 | 587 | TGCACCATACACATCC | 59 | 4565 |
| 1208529 | N/A | N/A | 621 | 636 | CCTAGCACCAGGTAGG | 40 | 4566 |
| 1208562 | N/A | N/A | 651 | 666 | ACGATCACTCTAGTGC | 78 | 4567 |
| 1208583 | N/A | N/A | 717 | 732 | GCTCCGAGCCAGGCTC | 81 | 4568 |
| 1208596 | N/A | N/A | 836 | 851 | TGAATGATGCCCATGA | 41 | 4569 |
| 1208609 | N/A | N/A | 872 | 887 | TCCTTGCCCATTGAAG | 72 | 4570 |
| 1208622 | N/A | N/A | 909 | 924 | AGAGGCATTCAGATGC | 109 | 4571 |
| 1208635 | N/A | N/A | 952 | 967 | TCGCCCAGAGTCACCC | 55 | 4572 |
| 1208648 | N/A | N/A | 1008 | 1023 | TGTTATCAACCTGGTT | 42 | 4573 |
| 1208661 | N/A | N/A | 1036 | 1051 | CCCTTCTCAACAACCC | 76 | 4574 |
| 1208674 | N/A | N/A | 1076 | 1091 | CCATGCACCAGGTGAT | 52 | 4575 |
| 1208687 | N/A | N/A | 1141 | 1156 | AAATGGCAGGTACCCT | 103 | 4576 |
| 1208700 | N/A | N/A | 1209 | 1224 | ATGTAGGTAATTTAGT | 76 | 4577 |
| 1208713 | N/A | N/A | 1552 | 1567 | AGGTCCATCTGGTTCA | 84 | 4578 |
| 1208726 | N/A | N/A | 1582 | 1597 | CAACCCCACCAAGTCA | 45 | 4579 |

TABLE 71-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208752 | N/A | N/A | 1630 | 1645 | GAGTCCAGGGTTGGAA | 26 | 4580 |
| 1208779 | N/A | N/A | 1703 | 1718 | TAGGGCACCAAGTTTG | 27 | 4581 |
| 1208805 | N/A | N/A | 1913 | 1928 | GAAGTTGTGTGCCTGT | 64 | 4582 |
| 1208829 | N/A | N/A | 2085 | 2100 | AGATGGACCTTTAAGA | 34 | 4583 |
| 1208856 | N/A | N/A | 2119 | 2134 | ACCAGAACTAGGACAG | 57 | 4584 |
| 1208884 | N/A | N/A | 2136 | 2151 | CACTTGCCAAGGACCA | 47 | 4585 |
| 1208909 | N/A | N/A | 2174 | 2189 | CAATAAGCTTTTGCCA | 78 | 4586 |
| 1208933 | N/A | N/A | 2214 | 2229 | CCATGAAATGCTGAGC | 29 | 4587 |
| 1208960 | N/A | N/A | 2286 | 2301 | TAACCATCGCGAATAA | 52 | 4588 |
| 1208988 | N/A | N/A | 2331 | 2346 | TAATACTGTTTGCTAG | 48 | 4589 |
| 1209013 | N/A | N/A | 2384 | 2399 | GATTATATGCTGTTGG | 82 | 4590 |
| 1209039 | N/A | N/A | 2454 | 2469 | CTTAGCATTGATGAAT | 51 | 4591 |
| 1209064 | N/A | N/A | 2484 | 2499 | TGATTCAGGTGTGTGC | 75 | 4592 |
| 1209089 | N/A | N/A | 2537 | 2552 | TAGTTCCTAAGCACAA | 32 | 4593 |
| 1209115 | N/A | N/A | 2614 | 2629 | CGTTTTTCACACTTTG | 40 | 4594 |
| 1209142 | N/A | N/A | 2701 | 2716 | AGTTAAGGTTCAACAA | 55 | 4595 |
| 1209170 | N/A | N/A | 2725 | 2740 | GCAGTGAAAAATTTGC | 62 | 4596 |
| 1209196 | N/A | N/A | 2780 | 2795 | AACTCCCAAGTCAATA | 30 | 4597 |
| 1209219 | N/A | N/A | 2812 | 2827 | GAGAATGTGCCTACTT | 40 | 4598 |
| 1209244 | N/A | N/A | 2864 | 2879 | AACGGCAGTAATAATA | 69 | 4599 |
| 1209269 | N/A | N/A | 2914 | 2929 | GAAGTCACTGTTAACC | 65 | 4600 |
| 1209293 | N/A | N/A | 2993 | 3008 | CCTTGGGTAAGTCTTC | 86 | 4601 |
| 1209320 | N/A | N/A | 3050 | 3065 | TTCAGGAGTCAGATAG | 87 | 4602 |
| 1209342 | N/A | N/A | 3419 | 3434 | GGACAGACCCTCAAAA | 54 | 4603 |
| 1209355 | N/A | N/A | 3468 | 3483 | CCTGTACTCAACTGCT | 36 | 4604 |
| 1209368 | N/A | N/A | 3498 | 3513 | GCAGGGACAACACACT | 53 | 4605 |
| 1209381 | N/A | N/A | 3650 | 3665 | AGGGTACATGTCTCCC | 93 | 4606 |
| 1209394 | N/A | N/A | 3684 | 3699 | CTCCAAGCAGAGTTCC | 56 | 4607 |
| 1209407 | N/A | N/A | 3760 | 3775 | ACACCTGTAGAAAGAG | 58 | 4608 |
| 1209420 | N/A | N/A | 3894 | 3909 | TGATACCAGGAGAGTA | 61 | 4609 |
| 1209433 | N/A | N/A | 3961 | 3976 | ACTTCCAAAGGGTATT | 26 | 4610 |
| 1209446 | N/A | N/A | 4023 | 4038 | TTCCAAGCTTGGTTTA | 48 | 4611 |
| 1209459 | N/A | N/A | 4056 | 4071 | ACCTACTTGCCTTGTG | 31 | 4612 |
| 1209472 | N/A | N/A | 4131 | 4146 | GGTCTGAGAGATGGAC | 41 | 4613 |
| 1209485 | N/A | N/A | 4307 | 4322 | CCTATTCTGTAGGCCC | 71 | 4614 |
| 1209498 | N/A | N/A | 4346 | 4361 | AGAGTCTAGGACCATG | 50 | 4615 |

TABLE 71-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209511 | N/A | N/A | 4577 | 4592 | ACCACCCGGCCTCCTG | 71 | 4616 |
| 1209524 | N/A | N/A | 4642 | 4657 | GGAGGGAACGCAGTGA | 113 | 4617 |
| 1209537 | N/A | N/A | 4909 | 4924 | TTGCCTTGGTGTCTGA | 40 | 4618 |
| 1209550 | N/A | N/A | 5383 | 5398 | CCCCCCCACTTCCTAA | 68 | 4619 |
| 1209563 | N/A | N/A | 5444 | 5459 | AGAGCCCGCGGCCGGC | 79 | 4620 |
| 1209576 | N/A | N/A | 5767 | 5782 | AAGCTGCGCTGGGAGA | 43 | 4621 |
| 1209589 | N/A | N/A | 5918 | 5933 | CGCTCTCAGACCTGGC | 79 | 4622 |
| 1209602 | N/A | N/A | 6336 | 6351 | TACCCCTGCCCCTAGC | 51 | 4623 |
| 1209615 | N/A | N/A | 6411 | 6426 | TTCTGTAGGCACCCGG | 49 | 4624 |
| 1209628 | N/A | N/A | 6465 | 6480 | TCTACCTGGGATTCAC | 84 | 4625 |
| 1209641 | N/A | N/A | 6495 | 6510 | ATCCCAGCAGTGAATC | 111 | 4626 |
| 1209654 | N/A | N/A | 6601 | 6616 | CTAGCCCGGAGCGCGG | 66 | 4627 |
| 1209667 | N/A | N/A | 6660 | 6675 | GCGGAAACAGAAACCC | 49 | 4628 |
| 1209680 | N/A | N/A | 6764 | 6779 | CTTCCTCTCTCGCAGC | 60 | 4629 |
| 1209693 | N/A | N/A | 6807 | 6822 | GATGGACAAAGCTGCT | 87 | 4630 |
| 1209706 | N/A | N/A | 6875 | 6890 | ATTCCTCCGCCCCTGC | 76 | 4631 |
| 1209719 | N/A | N/A | 7071 | 7086 | GACCTGAGATTTGTGC | 98† | 4632 |

TABLE 72

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 20 | 2426 |
| 1129531 | 2009 | 2024 | 7397 | 7412 | GAGTTCCTGCGCCATC | 8 | 3837 |
| 1129948 | N/A | N/A | 4840 | 4855 | ATCTGCTTTCCGCACT | 21 | 3630 |
| 1129949 | N/A | N/A | 4844 | 4859 | TCTCATCTGCTTTCCG | 27 | 3706 |
| 1208281 | N/A | N/A | 122 | 137 | CTGGGACAATCCTGGT | 104 | 4633 |
| 1208314 | N/A | N/A | 184 | 199 | ACCCACAGGTCATGAG | 28 | 4634 |
| 1208349 | N/A | N/A | 234 | 249 | GGCCTTCCGGGCTGGC | 59 | 4635 |
| 1208379 | N/A | N/A | 311 | 326 | CTTAAGGCCCATCTCC | 37 | 4636 |
| 1208412 | N/A | N/A | 398 | 413 | TGCTAGTCTGCAGCTT | 35 | 4637 |
| 1208443 | N/A | N/A | 431 | 446 | CTGACTATAAGTCATA | 47 | 4638 |
| 1208476 | N/A | N/A | 517 | 532 | CCGACTGTGTGCTCTT | 13 | 4639 |

TABLE 72-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208504 | N/A | N/A | 573 | 588 | CTGCACCATACACATC | 27 | 4640 |
| 1208530 | N/A | N/A | 622 | 637 | ACCTAGCACCAGGTAG | 85 | 4641 |
| 1208564 | N/A | N/A | 656 | 671 | AGCTCACGATCACTCT | 86 | 4642 |
| 1208584 | N/A | N/A | 718 | 733 | TGCTCCGAGCCAGGCT | 45 | 4643 |
| 1208597 | N/A | N/A | 837 | 852 | ATGAATGATGCCCATG | 35 | 4644 |
| 1208610 | N/A | N/A | 878 | 893 | GATCCTTCCTTGCCCA | 27 | 4645 |
| 1208623 | N/A | N/A | 913 | 928 | CTTCAGAGGCATTCAG | 65 | 4646 |
| 1208636 | N/A | N/A | 954 | 969 | CCTCGCCCAGAGTCAC | 109 | 4647 |
| 1208649 | N/A | N/A | 1011 | 1026 | TACTGTTATCAACCTG | 40 | 4648 |
| 1208662 | N/A | N/A | 1046 | 1061 | ACATGGGTTTCCCTTC | 52 | 4649 |
| 1208675 | N/A | N/A | 1078 | 1093 | TTCCATGCACCAGGTG | 34 | 4650 |
| 1208688 | N/A | N/A | 1142 | 1157 | GAAATGGCAGGTACCC | 47 | 4651 |
| 1208701 | N/A | N/A | 1210 | 1225 | CATGTAGGTAATTTAG | 21 | 4652 |
| 1208714 | N/A | N/A | 1554 | 1569 | TAAGGTCCATCTGGTT | 92 | 4653 |
| 1208729 | N/A | N/A | 1584 | 1599 | CTCAACCCCACCAAGT | 79 | 4654 |
| 1208753 | N/A | N/A | 1667 | 1682 | AAACTTTTGGGTGTGG | 35 | 4655 |
| 1208782 | N/A | N/A | 1705 | 1720 | GATAGGGCACCAAGTT | 85 | 4656 |
| 1208806 | N/A | N/A | 1915 | 1930 | ATGAAGTTGTGTGCCT | 48 | 4657 |
| 1208832 | N/A | N/A | 2086 | 2101 | GAGATGGACCTTTAAG | 38 | 4658 |
| 1208859 | N/A | N/A | 2122 | 2137 | CAAACCAGAACTAGGA | 58 | 4659 |
| 1208887 | N/A | N/A | 2142 | 2157 | AAAGTGCACTTGCCAA | 29 | 4660 |
| 1208910 | N/A | N/A | 2175 | 2190 | TCAATAAGCTTTTGCC | 31 | 4661 |
| 1208936 | N/A | N/A | 2215 | 2230 | GCCATGAAATGCTGAG | 24 | 4662 |
| 1208963 | N/A | N/A | 2294 | 2309 | ATAGAACATAACCATC | 35 | 4663 |
| 1208989 | N/A | N/A | 2333 | 2348 | CCTAATACTGTTTGCT | 21 | 4664 |
| 1209016 | N/A | N/A | 2385 | 2400 | AGATTATATGCTGTTG | 23 | 4665 |
| 1209040 | N/A | N/A | 2455 | 2470 | GCTTAGCATTGATGAA | 51 | 4666 |
| 1209065 | N/A | N/A | 2486 | 2501 | CTTGATTCAGGTGTGT | 31 | 4667 |
| 1209092 | N/A | N/A | 2538 | 2553 | GTAGTTCCTAAGCACA | 48 | 4668 |
| 1209118 | N/A | N/A | 2630 | 2645 | AGTCTACTTAGTGCAA | 39 | 4669 |
| 1209144 | N/A | N/A | 2702 | 2717 | CAGTTAAGGTTCAACA | 26 | 4670 |
| 1209173 | N/A | N/A | 2744 | 2759 | ATTTGTGGGCATGCAC | 57 | 4671 |
| 1209199 | N/A | N/A | 2781 | 2796 | TAACTCCCAAGTCAAT | 49 | 4672 |
| 1209220 | N/A | N/A | 2813 | 2828 | TGAGAATGTGCCTACT | 24 | 4673 |
| 1209246 | N/A | N/A | 2865 | 2880 | AAACGGCAGTAATAAT | 59 | 4674 |
| 1209270 | N/A | N/A | 2917 | 2932 | GTTGAAGTCACTGTTA | 23 | 4675 |

TABLE 72-continued

Reduction of FXII RNA by 3-10-3 cEt gapmers with
uniform PS internucleoside linkages (Huh7,
electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209296 | N/A | N/A | 3013 | 3028 | ACAACCTGCTAGCTGT | 73 | 4676 |
| 1209321 | N/A | N/A | 3051 | 3066 | GTTCAGGAGTCAGATA | 57 | 4677 |
| 1209343 | N/A | N/A | 3421 | 3436 | AAGGACAGACCCTCAA | 60 | 4678 |
| 1209356 | N/A | N/A | 3470 | 3485 | CCCCTGTACTCAACTG | 64 | 4679 |
| 1209369 | N/A | N/A | 3499 | 3514 | TGCAGGGACAACACAC | 82 | 4680 |
| 1209382 | N/A | N/A | 3651 | 3666 | CAGGGTACATGTCTCC | 39 | 4681 |
| 1209395 | N/A | N/A | 3686 | 3701 | CTCTCCAAGCAGAGTT | 74 | 4682 |
| 1209408 | N/A | N/A | 3762 | 3777 | GCACACCTGTAGAAAG | 54 | 4683 |
| 1209421 | N/A | N/A | 3896 | 3911 | GGTGATACCAGGAGAG | 56 | 4684 |
| 1209434 | N/A | N/A | 3962 | 3977 | GACTTCCAAAGGGTAT | 57 | 4685 |
| 1209447 | N/A | N/A | 4025 | 4040 | GTTTCCAAGCTTGGTT | 55 | 4686 |
| 1209460 | N/A | N/A | 4057 | 4072 | AACCTACTTGCCTTGT | 28 | 4687 |
| 1209473 | N/A | N/A | 4242 | 4257 | CACCTTTCTGGCAGTG | 56 | 4688 |
| 1209486 | N/A | N/A | 4317 | 4332 | TATCCAGCAACCTATT | 45 | 4689 |
| 1209499 | N/A | N/A | 4351 | 4366 | TCAGGAGAGTCTAGGA | 42 | 4690 |
| 1209512 | N/A | N/A | 4579 | 4594 | ACACCACCCGGCCTCC | 30 | 4691 |
| 1209525 | N/A | N/A | 4657 | 4672 | GTGCGGCAGGCTTGGG | 27 | 4692 |
| 1209538 | N/A | N/A | 5077 | 5092 | CCCACGCGGCGCACCG | 57 | 4693 |
| 1209551 | N/A | N/A | 5404 | 5419 | GCCCTCTCGGCTCCTC | 33 | 4694 |
| 1209564 | N/A | N/A | 5445 | 5460 | GAGAGCCCGCGGCCGG | 60 | 4695 |
| 1209577 | N/A | N/A | 5771 | 5786 | GTGGAAGCTGCGCTGG | 30 | 4696 |
| 1209590 | N/A | N/A | 5919 | 5934 | GCGCTCTCAGACCTGG | 111 | 4697 |
| 1209603 | N/A | N/A | 6352 | 6367 | CAAAGGTCTCCTCCCC | 54 | 4698 |
| 1209616 | N/A | N/A | 6414 | 6429 | CCATTCTGTAGGCACC | 25 | 4699 |
| 1209629 | N/A | N/A | 6468 | 6483 | GATTCTACCTGGGATT | 70 | 4700 |
| 1209642 | N/A | N/A | 6496 | 6511 | GATCCCAGCAGTGAAT | 74 | 4701 |
| 1209655 | N/A | N/A | 6607 | 6622 | CCCACACTAGCCCGGA | 80 | 4702 |
| 1209668 | N/A | N/A | 6661 | 6676 | AGCGGAAACAGAAACC | 83 | 4703 |
| 1209681 | N/A | N/A | 6766 | 6781 | CCCTTCCTCTCTCGCA | 67 | 4704 |
| 1209694 | N/A | N/A | 6808 | 6823 | CGATGGACAAAGCTGC | 40 | 4705 |
| 1209707 | N/A | N/A | 7014 | 7029 | ACCTGGCACGCATCGG | 10† | 4706 |
| 1209720 | N/A | N/A | 7073 | 7088 | TGGACCTGAGATTTGT | 44† | 4707 |

TABLE 73

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 42 | 2426 |
| 1129531 | 2009 | 2024 | 7397 | 7412 | GAGTTCCTGCGCCATC | 12 | 3837 |
| 1129948 | N/A | N/A | 4840 | 4855 | ATCTGCTTTCCGCACT | 25 | 3630 |
| 1194293 | N/A | N/A | 4845 | 4860 | CTCTCATCTGCTTTCC | 46 | 4708 |
| 1208282 | N/A | N/A | 124 | 139 | TCCTGGGACAATCCTG | 94 | 4709 |
| 1208317 | N/A | N/A | 185 | 200 | GACCCACAGGTCATGA | 41 | 4710 |
| 1208351 | N/A | N/A | 265 | 280 | ACCCAGTCTGGTTGTC | 54 | 4711 |
| 1208382 | N/A | N/A | 312 | 327 | TCTTAAGGCCCATCTC | 78 | 4712 |
| 1208413 | N/A | N/A | 399 | 414 | TTGCTAGTCTGCAGCT | 22 | 4713 |
| 1208444 | N/A | N/A | 432 | 447 | ACTGACTATAAGTCAT | 79 | 4714 |
| 1208478 | N/A | N/A | 518 | 533 | ACCGACTGTGTGCTCT | 26 | 4715 |
| 1208506 | N/A | N/A | 576 | 591 | ACACTGCACCATACAC | 18 | 4716 |
| 1208534 | N/A | N/A | 625 | 640 | AAGACCTAGCACCAGG | 25 | 4717 |
| 1208566 | N/A | N/A | 657 | 672 | CAGCTCACGATCACTC | 40 | 4718 |
| 1208585 | N/A | N/A | 721 | 736 | ACCTGCTCCGAGCCAG | 79 | 4719 |
| 1208598 | N/A | N/A | 838 | 853 | CATGAATGATGCCCAT | 36 | 4720 |
| 1208611 | N/A | N/A | 881 | 896 | CTTGATCCTTCCTTGC | 39 | 4721 |
| 1208624 | N/A | N/A | 914 | 929 | GCTTCAGAGGCATTCA | 45 | 4722 |
| 1208637 | N/A | N/A | 961 | 976 | TCAAATCCCTCGCCCA | 63 | 4723 |
| 1208650 | N/A | N/A | 1012 | 1027 | TTACTGTTATCAACCT | 34 | 4724 |
| 1208663 | N/A | N/A | 1048 | 1063 | TCACATGGGTTTCCCT | 30 | 4725 |
| 1208676 | N/A | N/A | 1080 | 1095 | ATTTCCATGCACCAGG | 105 | 4726 |
| 1208689 | N/A | N/A | 1143 | 1158 | GGAAATGGCAGGTACC | 26 | 4727 |
| 1208702 | N/A | N/A | 1211 | 1226 | GCATGTAGGTAATTTA | 44 | 4728 |
| 1208715 | N/A | N/A | 1563 | 1578 | CCACCAGGGTAAGGTC | 30 | 4729 |
| 1208730 | N/A | N/A | 1585 | 1600 | ACTCAACCCCACCAAG | 143 | 4730 |
| 1208756 | N/A | N/A | 1669 | 1684 | AGAAACTTTTGGGTGT | 55 | 4731 |
| 1208784 | N/A | N/A | 1706 | 1721 | GGATAGGGCACCAAGT | 110 | 4732 |
| 1208808 | N/A | N/A | 1918 | 1933 | AGCATGAAGTTGTGTG | 68 | 4733 |
| 1208833 | N/A | N/A | 2087 | 2102 | TGAGATGGACCTTTAA | 63 | 4734 |
| 1208860 | N/A | N/A | 2123 | 2138 | CCAAACCAGAACTAGG | 26 | 4735 |
| 1208888 | N/A | N/A | 2144 | 2159 | GCAAAGTGCACTTGCC | 79 | 4736 |
| 1208913 | N/A | N/A | 2177 | 2192 | GCTCAATAAGCTTTTG | 29 | 4737 |
| 1208937 | N/A | N/A | 2216 | 2231 | TGCCATGAAATGCTGA | 32 | 4738 |
| 1208964 | N/A | N/A | 2316 | 2331 | GTTCAATGTTCACTGT | 31 | 4739 |
| 1208992 | N/A | N/A | 2334 | 2349 | ACCTAATACTGTTTGC | 59 | 4740 |

TABLE 73-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209017 | N/A | N/A | 2386 | 2401 | CAGATTATATGCTGTT | 18 | 4741 |
| 1209043 | N/A | N/A | 2456 | 2471 | AGCTTAGCATTGATGA | 38 | 4742 |
| 1209068 | N/A | N/A | 2488 | 2503 | CACTTGATTCAGGTGT | 66 | 4743 |
| 1209093 | N/A | N/A | 2539 | 2554 | TGTAGTTCCTAAGCAC | 35 | 4744 |
| 1209119 | N/A | N/A | 2633 | 2648 | CTCAGTCTACTTAGTG | 16 | 4745 |
| 1209147 | N/A | N/A | 2704 | 2719 | CCCAGTTAAGGTTCAA | 40 | 4746 |
| 1209174 | N/A | N/A | 2745 | 2760 | CATTTGTGGGCATGCA | 41 | 4747 |
| 1209200 | N/A | N/A | 2782 | 2797 | GTAACTCCCAAGTCAA | 64 | 4748 |
| 1209247 | N/A | N/A | 2868 | 2883 | GTAAAACGGCAGTAAT | 56 | 4749 |
| 1209273 | N/A | N/A | 2924 | 2939 | GTTGAATGTTGAAGTC | 53 | 4750 |
| 1209297 | N/A | N/A | 3014 | 3029 | CACAACCTGCTAGCTG | 36 | 4751 |
| 1209324 | N/A | N/A | 3059 | 3074 | AAACTTGGGTTCAGGA | 43 | 4752 |
| 1209344 | N/A | N/A | 3422 | 3437 | AAAGGACAGACCCTCA | 55 | 4753 |
| 1209357 | N/A | N/A | 3471 | 3486 | TCCCCTGTACTCAACT | 123 | 4754 |
| 1209370 | N/A | N/A | 3501 | 3516 | ACTGCAGGGACAACAC | 26 | 4755 |
| 1209383 | N/A | N/A | 3654 | 3669 | AGGCAGGGTACATGTC | 55 | 4756 |
| 1209396 | N/A | N/A | 3700 | 3715 | TATCACAGTCCCCTCT | 45 | 4757 |
| 1209409 | N/A | N/A | 3836 | 3851 | GTGTAGCACCTTTCAC | 58 | 4758 |
| 1209422 | N/A | N/A | 3898 | 3913 | CTGGTGATACCAGGAG | 17 | 4759 |
| 1209435 | N/A | N/A | 3975 | 3990 | AACTCTCCCTCTGGAC | 41 | 4760 |
| 1209448 | N/A | N/A | 4026 | 4041 | AGTTTCCAAGCTTGGT | 26 | 4761 |
| 1209461 | N/A | N/A | 4063 | 4078 | TTCTTGAACCTACTTG | 96 | 4762 |
| 1209474 | N/A | N/A | 4243 | 4258 | TCACCTTTCTGGCAGT | 33 | 4763 |
| 1209487 | N/A | N/A | 4319 | 4334 | AGTATCCAGCAACCTA | 42 | 4764 |
| 1209500 | N/A | N/A | 4352 | 4367 | CTCAGGAGAGTCTAGG | 79 | 4765 |
| 1209513 | N/A | N/A | 4605 | 4620 | CCCCCCAGAGAGCTCT | 40 | 4766 |
| 1209526 | N/A | N/A | 4660 | 4675 | TTGGTGCGGCAGGCTT | 26 | 4767 |
| 1209539 | N/A | N/A | 5079 | 5094 | GCCCCACGCGGCGCAC | 46 | 4768 |
| 1209552 | N/A | N/A | 5405 | 5420 | CGCCCTCTCGGCTCCT | 52 | 4769 |
| 1209565 | N/A | N/A | 5454 | 5469 | CTGAGGACGGAGAGCC | 19 | 4770 |
| 1209578 | N/A | N/A | 5802 | 5817 | GGAGAAGGTAGGGCAC | 101 | 4771 |
| 1209591 | N/A | N/A | 6090 | 6105 | CCCACGCACCCAGGTC | 57 | 4772 |
| 1209604 | N/A | N/A | 6353 | 6368 | TCAAAGGTCTCCTCCC | 100 | 4773 |
| 1209617 | N/A | N/A | 6416 | 6431 | ACCCATTCTGTAGGCA | 73 | 4774 |
| 1209630 | N/A | N/A | 6469 | 6484 | GGATTCTACCTGGGAT | 33 | 4775 |

TABLE 73-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209643 | N/A | N/A | 6516 | 6531 | GTATCCCCAGGAGATT | 59 | 4776 |
| 1209656 | N/A | N/A | 6609 | 6624 | CTCCCACACTAGCCCG | 91 | 4777 |
| 1209669 | N/A | N/A | 6662 | 6677 | GAGCGGAAACAGAAAC | 75 | 4778 |
| 1209682 | N/A | N/A | 6777 | 6792 | ACCCACTCATGCCCTT | 76 | 4779 |
| 1209695 | N/A | N/A | 6820 | 6835 | TTGCCGCCCGGACGAT | 31 | 4780 |
| 1209708 | N/A | N/A | 7023 | 7038 | TAAGAGCTCACCTGGC | 57[†] | 4781 |
| 1209721 | N/A | N/A | 7079 | 7094 | GCGCTGTGGACCTGAG | 37[†] | 4782 |

TABLE 74

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 29 | 2426 |
| 1129531 | 2009 | 2024 | 7397 | 7412 | GAGTTCCTGCGCCATC | 18 | 3837 |
| 1129948 | N/A | N/A | 4840 | 4855 | ATCTGCTTTCCGCACT | 54 | 3630 |
| 1194294 | N/A | N/A | 4846 | 4861 | CCTCTCATCTGCTTTC | 27 | 4783 |
| 1208286 | N/A | N/A | 125 | 140 | ATCCTGGGACAATCCT | 50 | 4784 |
| 1208319 | N/A | N/A | 188 | 203 | CTGGACCCACAGGTCA | 42 | 4785 |
| 1208354 | N/A | N/A | 266 | 281 | CACCCAGTCTGGTTGT | 49 | 4786 |
| 1208383 | N/A | N/A | 313 | 328 | TTCTTAAGGCCCATCT | 79 | 4787 |
| 1208417 | N/A | N/A | 400 | 415 | GTTGCTAGTCTGCAGC | 58 | 4788 |
| 1208448 | N/A | N/A | 433 | 448 | AACTGACTATAAGTCA | 25 | 4789 |
| 1208480 | N/A | N/A | 519 | 534 | TACCGACTGTGTGCTC | 49 | 4790 |
| 1208508 | N/A | N/A | 578 | 593 | ACACACTGCACCATAC | 22 | 4791 |
| 1208535 | N/A | N/A | 627 | 642 | ATAAGACCTAGCACCA | 40 | 4792 |
| 1208568 | N/A | N/A | 658 | 673 | ACAGCTCACGATCACT | 30 | 4793 |
| 1208586 | N/A | N/A | 724 | 739 | AGCACCTGCTCCGAGC | 81 | 4794 |
| 1208599 | N/A | N/A | 839 | 854 | GCATGAATGATGCCCA | 55 | 4795 |
| 1208612 | N/A | N/A | 885 | 900 | AGCTCTTGATCCTTCC | 18 | 4796 |
| 1208625 | N/A | N/A | 915 | 930 | GGCTTCAGAGGCATTC | 57 | 4797 |
| 1208638 | N/A | N/A | 962 | 977 | CTCAAATCCCTCGCCC | 27 | 4798 |
| 1208651 | N/A | N/A | 1013 | 1028 | TTTACTGTTATCAACC | 22 | 4799 |
| 1208664 | N/A | N/A | 1049 | 1064 | CTCACATGGGTTTCCC | 52 | 4800 |
| 1208677 | N/A | N/A | 1122 | 1137 | TCTAAAAGGTAGTTTC | 27 | 4801 |

TABLE 74-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208690 | N/A | N/A | 1144 | 1159 | GGGAAATGGCAGGTAC | 30 | 4802 |
| 1208703 | N/A | N/A | 1212 | 1227 | GGCATGTAGGTAATTT | 44 | 4803 |
| 1208716 | N/A | N/A | 1564 | 1579 | CCCACCAGGGTAAGGT | 147 | 4804 |
| 1208731 | N/A | N/A | 1589 | 1604 | AGAGACTCAACCCCAC | 50 | 4805 |
| 1208757 | N/A | N/A | 1670 | 1685 | GAGAAACTTTTGGGTG | 19 | 4806 |
| 1208786 | N/A | N/A | 1714 | 1729 | TTAGGCAAGGATAGGG | 79 | 4807 |
| 1208809 | N/A | N/A | 1919 | 1934 | GAGCATGAAGTTGTGT | 73 | 4808 |
| 1208836 | N/A | N/A | 2088 | 2103 | CTGAGATGGACCTTTA | 26 | 4809 |
| 1208863 | N/A | N/A | 2124 | 2139 | ACCAAACCAGAACTAG | 24 | 4810 |
| 1208891 | N/A | N/A | 2147 | 2162 | AAGGCAAAGTGCACTT | 42 | 4811 |
| 1208914 | N/A | N/A | 2179 | 2194 | CTGCTCAATAAGCTTT | 96 | 4812 |
| 1208940 | N/A | N/A | 2219 | 2234 | TAATGCCATGAAATGC | 58 | 4813 |
| 1208967 | N/A | N/A | 2318 | 2333 | TAGTTCAATGTTCACT | 27 | 4814 |
| 1208993 | N/A | N/A | 2335 | 2350 | AACCTAATACTGTTTG | 30 | 4815 |
| 1209020 | N/A | N/A | 2387 | 2402 | CCAGATTATATGCTGT | 40 | 4816 |
| 1209044 | N/A | N/A | 2458 | 2473 | TCAGCTTAGCATTGAT | 52 | 4817 |
| 1209069 | N/A | N/A | 2491 | 2506 | AGACACTTGATTCAGG | 21 | 4818 |
| 1209096 | N/A | N/A | 2542 | 2557 | CTGTGTAGTTCCTAAG | 28 | 4819 |
| 1209122 | N/A | N/A | 2639 | 2654 | GTCCTTCTCAGTCTAC | 32 | 4820 |
| 1209148 | N/A | N/A | 2705 | 2720 | TCCCAGTTAAGGTTCA | 22 | 4821 |
| 1209176 | N/A | N/A | 2747 | 2762 | GCCATTTGTGGGCATG | 24 | 4822 |
| 1209203 | N/A | N/A | 2783 | 2798 | TGTAACTCCCAAGTCA | 80 | 4823 |
| 1209224 | N/A | N/A | 2815 | 2830 | ATTGAGAATGTGCCTA | 39 | 4824 |
| 1209249 | N/A | N/A | 2869 | 2884 | TGTAAAACGGCAGTAA | 27 | 4825 |
| 1209274 | N/A | N/A | 2954 | 2969 | TTGCCACAAAGTAGGC | 45 | 4826 |
| 1209299 | N/A | N/A | 3015 | 3030 | CCACAACCTGCTAGCT | 57 | 4827 |
| 1209325 | N/A | N/A | 3060 | 3075 | AAAACTTGGGTTCAGG | 60 | 4828 |
| 1209345 | N/A | N/A | 3423 | 3438 | AAAAGGACAGACCCTC | 72 | 4829 |
| 1209358 | N/A | N/A | 3472 | 3487 | TTCCCCTGTACTCAAC | 53 | 4830 |
| 1209371 | N/A | N/A | 3502 | 3517 | AACTGCAGGGACAACA | 140 | 4831 |
| 1209384 | N/A | N/A | 3655 | 3670 | CAGGCAGGGTACATGT | 27 | 4832 |
| 1209397 | N/A | N/A | 3701 | 3716 | CTATCACAGTCCCCTC | 39 | 4833 |
| 1209410 | N/A | N/A | 3872 | 3887 | CGGGAGGAGAGAGCCC | 37 | 4834 |
| 1209423 | N/A | N/A | 3918 | 3933 | GAATCCCAGGTGTGTG | 74 | 4835 |
| 1209436 | N/A | N/A | 3994 | 4009 | TGGGACCACTCCTTCC | 48 | 4836 |

TABLE 74-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209449 | N/A | N/A | 4027 | 4042 | AAGTTTCCAAGCTTGG | 24 | 4837 |
| 1209462 | N/A | N/A | 4064 | 4079 | CTTCTTGAACCTACTT | 38 | 4838 |
| 1209475 | N/A | N/A | 4265 | 4280 | CGCCCAGGTCCTCCAC | 59 | 4839 |
| 1209488 | N/A | N/A | 4327 | 4342 | AGTCTCCGAGTATCCA | 112 | 4840 |
| 1209501 | N/A | N/A | 4353 | 4368 | TCTCAGGAGAGTCTAG | 56 | 4841 |
| 1209514 | N/A | N/A | 4606 | 4621 | CCCCCCCAGAGAGCTC | 20 | 4842 |
| 1209527 | N/A | N/A | 4765 | 4780 | GACCCTCACTCACCCA | 72 | 4843 |
| 1209540 | N/A | N/A | 5081 | 5096 | CAGCCCCACGCGGCGC | 76 | 4844 |
| 1209553 | N/A | N/A | 5406 | 5421 | GCGCCCTCTCGGCTCC | 107 | 4845 |
| 1209566 | N/A | N/A | 5455 | 5470 | GCTGAGGACGGAGAGC | 41 | 4846 |
| 1209579 | N/A | N/A | 5845 | 5860 | CTCCCCGGGAGCTCCG | 68 | 4847 |
| 1209592 | N/A | N/A | 6091 | 6106 | CCCCACGCACCCAGGT | 47 | 4848 |
| 1209605 | N/A | N/A | 6354 | 6369 | ATCAAAGGTCTCCTCC | 30 | 4849 |
| 1209618 | N/A | N/A | 6421 | 6436 | GCGCCACCCATTCTGT | 35 | 4850 |
| 1209631 | N/A | N/A | 6472 | 6487 | CTGGGATTCTACCTGG | 30 | 4851 |
| 1209644 | N/A | N/A | 6526 | 6541 | GATTCTCCCTGTATCC | 69 | 4852 |
| 1209657 | N/A | N/A | 6616 | 6631 | AACCTGGCTCCCACAC | 40 | 4853 |
| 1209670 | N/A | N/A | 6663 | 6678 | GGAGCGGAAACAGAAA | 105 | 4854 |
| 1209683 | N/A | N/A | 6778 | 6793 | AACCCACTCATGCCCT | 108 | 4855 |
| 1209696 | N/A | N/A | 6824 | 6839 | ACGCTTGCCGCCCGGA | 32 | 4856 |
| 1209709 | N/A | N/A | 7024 | 7039 | CTAAGAGCTCACCTGG | 82† | 4857 |
| 1209722 | N/A | N/A | 7092 | 7107 | AACACGCAGCTCAGCG | 63† | 4858 |

TABLE 75

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1128802 | 218 | 233 | 3569 | 3584 | TACATTTGTGGTACAG | 94 | 2426 |
| 1129531 | 2009 | 2024 | 7397 | 7412 | GAGTTCCTGCGCCATC | 12 | 3837 |
| 1129948 | N/A | N/A | 4840 | 4855 | ATCTGCTTTCCGCACT | 45 | 3630 |
| 1194295 | N/A | N/A | 4847 | 4862 | CCCTCTCATCTGCTTT | 46 | 4859 |
| 1208287 | N/A | N/A | 129 | 144 | AACAATCCTGGGACAA | 49 | 4860 |
| 1208322 | N/A | N/A | 194 | 209 | AGTCACCTGGACCCAC | 33 | 4861 |
| 1208356 | N/A | N/A | 267 | 282 | CCACCCAGTCTGGTTG | 76 | 4862 |

TABLE 75-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1208387 | N/A | N/A | 314 | 329 | CTTCTTAAGGCCCATC | 52 | 4863 |
| 1208418 | N/A | N/A | 402 | 417 | CTGTTGCTAGTCTGCA | 72 | 4864 |
| 1208449 | N/A | N/A | 438 | 453 | CAGGGAACTGACTATA | 42 | 4865 |
| 1208483 | N/A | N/A | 525 | 540 | GCCACTTACCGACTGT | 50 | 4866 |
| 1208509 | N/A | N/A | 585 | 600 | AGACTGCACACACTGC | 80 | 4867 |
| 1208539 | N/A | N/A | 628 | 643 | CATAAGACCTAGCACC | 54 | 4868 |
| 1208570 | N/A | N/A | 661 | 676 | CACACAGCTCACGATC | 61 | 4869 |
| 1208587 | N/A | N/A | 733 | 748 | CATATCTCAAGCACCT | 40 | 4870 |
| 1208600 | N/A | N/A | 840 | 855 | GGCATGAATGATGCCC | 56 | 4871 |
| 1208613 | N/A | N/A | 886 | 901 | AAGCTCTTGATCCTTC | 102 | 4872 |
| 1208626 | N/A | N/A | 925 | 940 | GATAAAGCTGGGCTTC | 71 | 4873 |
| 1208639 | N/A | N/A | 968 | 983 | GGAGAACTCAAATCCC | 65 | 4874 |
| 1208652 | N/A | N/A | 1014 | 1029 | GTTTACTGTTATCAAC | 79 | 4875 |
| 1208665 | N/A | N/A | 1052 | 1067 | TACCTCACATGGGTTT | 43 | 4876 |
| 1208678 | N/A | N/A | 1124 | 1139 | CATCTAAAAGGTAGTT | 64 | 4877 |
| 1208691 | N/A | N/A | 1164 | 1179 | ATGGCAGAGCTTGAGG | 50 | 4878 |
| 1208704 | N/A | N/A | 1213 | 1228 | TGGCATGTAGGTAATT | 54 | 4879 |
| 1208717 | N/A | N/A | 1565 | 1580 | GCCCACCAGGGTAAGG | 46 | 4880 |
| 1208734 | N/A | N/A | 1595 | 1610 | ATGCTTAGAGACTCAA | 61 | 4881 |
| 1208760 | N/A | N/A | 1671 | 1686 | GGAGAAACTTTTGGGT | 42 | 4882 |
| 1208788 | N/A | N/A | 1715 | 1730 | ATTAGGCAAGGATAGG | 41 | 4883 |
| 1208812 | N/A | N/A | 1920 | 1935 | TGAGCATGAAGTTGTG | 108 | 4884 |
| 1208839 | N/A | N/A | 2091 | 2106 | GATCTGAGATGGACCT | 63 | 4885 |
| 1208865 | N/A | N/A | 2125 | 2140 | GACCAAACCAGAACTA | 69 | 4886 |
| 1208892 | N/A | N/A | 2148 | 2163 | CAAGGCAAAGTGCACT | 65 | 4887 |
| 1208917 | N/A | N/A | 2181 | 2196 | ACCTGCTCAATAAGCT | 58 | 4888 |
| 1208943 | N/A | N/A | 2226 | 2241 | CATGAGATAATGCCAT | 80 | 4889 |
| 1208968 | N/A | N/A | 2319 | 2334 | CTAGTTCAATGTTCAC | 62 | 4890 |
| 1208996 | N/A | N/A | 2336 | 2351 | GAACCTAATACTGTTT | 83 | 4891 |
| 1209021 | N/A | N/A | 2388 | 2403 | ACCAGATTATATGCTG | 43 | 4892 |
| 1209047 | N/A | N/A | 2460 | 2475 | CATCAGCTTAGCATTG | 36 | 4893 |
| 1209072 | N/A | N/A | 2492 | 2507 | TAGACACTTGATTCAG | 33 | 4894 |
| 1209097 | N/A | N/A | 2544 | 2559 | AGCTGTGTAGTTCCTA | 82 | 4895 |
| 1209123 | N/A | N/A | 2646 | 2661 | AATGAGTGTCCTTCTC | 135 | 4896 |
| 1209151 | N/A | N/A | 2706 | 2721 | TTCCCAGTTAAGGTTC | 75 | 4897 |

TABLE 75-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209177 | N/A | N/A | 2748 | 2763 | GGCCATTTGTGGGCAT | 63 | 4898 |
| 1209204 | N/A | N/A | 2784 | 2799 | TTGTAACTCCCAAGTC | 55 | 4899 |
| 1209227 | N/A | N/A | 2816 | 2831 | CATTGAGAATGTGCCT | 37 | 4900 |
| 1209250 | N/A | N/A | 2870 | 2885 | CTGTAAAACGGCAGTA | 45 | 4901 |
| 1209276 | N/A | N/A | 2956 | 2971 | ACTTGCCACAAAGTAG | 76 | 4902 |
| 1209300 | N/A | N/A | 3017 | 3032 | CTCCACAACCTGCTAG | 32 | 4903 |
| 1209328 | N/A | N/A | 3370 | 3385 | AAAAGTTGGGTTCAGG | 43 | 4904 |
| 1209346 | N/A | N/A | 3425 | 3440 | GGAAAAGGACAGACCC | 35 | 4905 |
| 1209359 | N/A | N/A | 3473 | 3488 | CTTCCCCTGTACTCAA | 72 | 4906 |
| 1209372 | N/A | N/A | 3503 | 3518 | GAACTGCAGGGACAAC | 62 | 4907 |
| 1209385 | N/A | N/A | 3656 | 3671 | ACAGGCAGGGTACATG | 43 | 4908 |
| 1209398 | N/A | N/A | 3702 | 3717 | CCTATCACAGTCCCCT | 51 | 4909 |
| 1209411 | N/A | N/A | 3878 | 3893 | ATGAGGCGGGAGGAGA | 37 | 4910 |
| 1209424 | N/A | N/A | 3919 | 3934 | AGAATCCCAGGTGTGT | 50 | 4911 |
| 1209437 | N/A | N/A | 3997 | 4012 | AAATGGGACCACTCCT | 114 | 4912 |
| 1209450 | N/A | N/A | 4028 | 4043 | CAAGTTTCCAAGCTTG | 90 | 4913 |
| 1209463 | N/A | N/A | 4065 | 4080 | CCTTCTTGAACCTACT | 65 | 4914 |
| 1209476 | N/A | N/A | 4266 | 4281 | CCGCCCAGGTCCTCCA | 60 | 4915 |
| 1209489 | N/A | N/A | 4329 | 4344 | CAAGTCTCCGAGTATC | 71 | 4916 |
| 1209502 | N/A | N/A | 4354 | 4369 | GTCTCAGGAGAGTCTA | 43 | 4917 |
| 1209515 | N/A | N/A | 4608 | 4623 | GACCCCCCCAGAGAGC | 107 | 4918 |
| 1209528 | N/A | N/A | 4773 | 4788 | TTGCCCCAGACCCTCA | 70 | 4919 |
| 1209541 | N/A | N/A | 5118 | 5133 | CGCCGGGAGCCCGGAG | 80 | 4920 |
| 1209554 | N/A | N/A | 5427 | 5442 | GGCCGGAATCTAGCTC | 41 | 4921 |
| 1209567 | N/A | N/A | 5714 | 5729 | CGGGTACTCGCCGGTC | 58 | 4922 |
| 1209580 | N/A | N/A | 5847 | 5862 | TCCTCCCCGGGAGCTC | 64 | 4923 |
| 1209593 | N/A | N/A | 6094 | 6109 | CGCCCCACGCACCCA | 92 | 4924 |
| 1209606 | N/A | N/A | 6356 | 6371 | TGATCAAAGGTCTCCT | 31 | 4925 |
| 1209619 | N/A | N/A | 6435 | 6450 | AACCCATCAGGTCAGC | 43 | 4926 |
| 1209632 | N/A | N/A | 6473 | 6488 | CCTGGGATTCTACCTG | 29 | 4927 |
| 1209645 | N/A | N/A | 6528 | 6543 | TCGATTCTCCCTGTAT | 28 | 4928 |
| 1209658 | N/A | N/A | 6617 | 6632 | GAACCTGGCTCCCACA | 55 | 4929 |
| 1209671 | N/A | N/A | 6679 | 6694 | CAGGATTTGAATGGGC | 31 | 4930 |
| 1209684 | N/A | N/A | 6779 | 6794 | AAACCCACTCATGCCC | 39 | 4931 |
| 1209697 | N/A | N/A | 6837 | 6852 | ACCCCATCTGACAACG | 65 | 4932 |

TABLE 75-continued

Reduction of FXII RNA by 3-10-3 cEt gapmers with uniform PS internucleoside linkages (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | FXII (% UTC) | SEQ ID NO |
|---|---|---|---|---|---|---|---|
| 1209710 | N/A | N/A | 7025 | 7040 | GCTAAGAGCTCACCTG | 86† | 4933 |
| 1209723 | N/A | N/A | 7108 | 7123 | ATCACCCTGGGTCGGA | 68† | 4934 |

TABLE 76

Reduction of FXII RNA by 3-10-3 cEt gapmers with uniform PS internucleoside linkages (Huh7, electroporation, 3000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1128718 | 3437 | 3452 | 13 | 28 | CTGCCTATCCAGGAGT | 69 | 4935 |
| 1128719 | 3439 | 3454 | 15 | 30 | AGCTGCCTATCCAGGA | 33 | 4936 |
| 1128720 | 3449 | 3464 | 25 | 40 | CCGTTGGTCCAGCTGC | 22 | 4937 |
| 1128721 | 3450 | 3465 | 26 | 41 | TCCGTTGGTCCAGCTG | 49 | 4938 |
| 1128726 | 3459 | 3474 | 35 | 50 | TGGCATCCGTCCGTTG | 60 | 4939 |
| 1128727 | 3460 | 3475 | 36 | 51 | ATGGCATCCGTCCGTT | 60 | 4940 |
| 1128728 | 3463 | 3478 | 39 | 54 | CTCATGGCATCCGTCC | 66 | 4941 |
| 1128729 | 3464 | 3479 | 40 | 55 | CCTCATGGCATCCGTC | 85 | 4942 |
| 1128730 | 3465 | 3480 | 41 | 56 | CCCTCATGGCATCCGT | 72 | 4943 |
| 1128731 | 3468 | 3483 | 44 | 59 | GAGCCCTCATGGCATC | 60 | 4944 |

TABLE 77

Reduction of FXII RNA by 3-10-3 cEt gapmers with uniform PS internucleoside linkages (Huh7, electroporation, 3000 nM modified oligonucleotide)

| Compound Number | SEQ ID NO: 3 Start Site | SEQ ID NO: 3 Stop Site | SEQ ID NO: 4 Start Site | SEQ ID NO: 4 Stop Site | Sequence (5' to 3') | FXII (% UTC) | SEQ ID NO |
|---|---|---|---|---|---|---|---|
| 1128724 | 3455 | 3470 | 31 | 46 | ATCCGTCCGTTGGTCC | 42 | 4945 |
| 1128725 | 3457 | 3472 | 33 | 48 | GCATCCGTCCGTTGGT | 59 | 4946 |

Example 4: Effects of Modified Oligonucleotides with Mixed Sugar Modifications and Mixed Backbones on Human FXII RNA In Vitro, Single Dose Modified oligonucleotides complementary to an FXII nucleic acid were synthesized and tested for their effect on FXII RNA levels in vitro. The modified oligonucleotides were tested in a series of experiments using similar culture conditions. The results for each separate experiment are presented in separate tables below.

The chemistry notation column in the tables below specifies the specific chemistry notation for modified oligonucleotides; wherein subscript 'd' represents a 2'-β-D-deoxyribosyl sugar moiety, subscript 'e' represents a 2'-MOE sugar moiety, subscript 'y' represents a 2-O-methyl sugar moiety, subscript 'k' represents a cEt modified sugar moiety, subscript 's' represents a phosphorothioate internucleoside linkage, subscript 'o' represents a phosphodiester internucleoside linkage, and superscript 'm' before the cytosine residue ($^m$C) represents a 5-methyl cytosine.

"Start site" indicates the 5'-most nucleoside of the target sequence to which the modified oligonucleotide is complementary. "Stop site" indicates the 3'-most nucleoside of the target sequence to which the modified oligonucleotide is complementary. As shown in the tables below, the modified oligonucleotides are 100% complementary to one or more of human FXII target sequences including the human FXII mRNA sequence designated herein as SEQ ID NO: 1 (ENSEMBL ID ENST00000253496.3 from ENSEMBL version 99: January 2020), the human FXII genomic sequence, designated herein as SEQ ID NO: 2 (ENSEMBL ID ENSG00000131187.9 from ENSEML version 99: January 2020, human reference assembly version GRCh38.p13 located on the reverse strand of chromosome 5 from positions 177,402,140 to 177,409,576), the human FXII genomic sequence, designated herein as SEQ ID No. 3 (the complement of GENBANK Accession No. NC_000005.10 truncated from truncated from nucleotides 177399001 to 177413000), and the human FXII mRNA sequence designated herein as SEQ ID No: 4 (GENBANK Accession No. NM_0005053), 'N/A' indicates that the modified oligonucleotide is not complementary to that particular target sequence with 100% complementarity.

Cultured Huh7 cells, at a density of 20,000 cells per well, were transfected using electroporation with either 2000 nM or 4000 nM modified oligonucleotide. After a treatment period of approximately 24 hours, RNA was isolated from the cells and FXII RNA levels were measured by quantitative real-time RTPCR. Human primer probe set RTS40528 (described herein above) was used to measure RNA levels. FXII RNA levels were normalized to total RNA content, as measured by RIBOGREEN®. Reduction of FXII RNA is presented in the tables below as percent FXII RNA relative to the amount in untreated control cells (% UTC). The symbol "†" indicates that the modified oligonucleotide is complementary to the target transcript within the amplicon region of the primer probe set. In such instances, additional assays using alternative primer probes must be performed to accurately assess the potency and efficacy of such modified oligonucleotides.

TABLE 78

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence with Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}C_{ds}T_{ds}G_{ds}{}^mC_{ds}G_{ds}{}^mC_{ds}{}^mC_{ds}A_{ks}T_{ks}{}^mC_k$ | 44 | 3837 |
| 1206480 | 1782 | 1797 | 7170 | 7185 | $A_{ks}T_{ks}G_{ks}{}^mC_{ds}{}^mC_{ds}T_{ds}T_{ds}G_{ds}{}^mC_{ds}A_{ds}G_{ds}G_{ds}G_{ds}T_{ks}G_{ks}A_k$ | 60 | 4947 |
| 1206486 | 1915 | 1930 | 7303 | 7318 | $T_{ks}{}^mC_{ks}A_{ks}{}^mC_{ds}{}^mC_{ds}A_{ds}A_{ds}G_{ds}G_{ds}A_{ds}G_{ds}G_{ds}G_{ds}A_{ks}A_{ks}A_k$ | 59 | 4948 |
| 1206491 | 1934 | 1949 | 7322 | 7337 | ${}^mC_{ks}{}^mC_{ks}A_{ks}{}^mC_{ds}T_{ds}{}^mC_{ds}T_{ds}{}^mC_{ds}T_{ds}{}^mC_{ds}A_{ds}{}^mC_{ds}T_{ds}G_{ks}{}^mC_{ks}G_k$ | 64 | 4949 |
| 1206495 | 141 | 156 | 508 | 523 | $T_{ks}G_{ks}{}^mC_{ks}T_{ds}{}^mC_{ds}T_{ds}T_{ds}{}^mC_{ds}A_{ds}G_{ds}{}^mC_{ds}T_{ds}T_{ds}T_{ks}G_{ks}T_k$ | 64 | 4950 |
| 1206901 | 144 | 159 | 511 | 526 | $G_{ks}T_{es}G_{ks}T_{ds}G_{ds}{}^mC_{ds}T_{ds}{}^mC_{ds}T_{ds}T_{ds}{}^mC_{ds}T_{ds}G_{es}{}^mC_{es}T_{ks}C_k$ | 81 | 4951 |
| 1206909 | 152 | 167 | N/A | N/A | $G_{ks}A_{es}A_{ks}{}^mC_{ds}G_{ds}A_{ds}{}^mC_{ds}T_{ds}G_{ds}T_{ds}G_{ds}T_{ds}G_{es}{}^mC_{es}T_{ks}{}^mC_k$ | 53 | 3647 |
| 1206917 | 209 | 224 | 3560 | 3575 | $G_{ks}G_{es}T_{ks}A_{ds}{}^mC_{ds}A_{ds}G_{ds}{}^mC_{ds}T_{ds}G_{ds}{}^mC_{ds}{}^mC_{ds}G_{es}G_{es}T_{ks}G_k$ | 42 | 4952 |
| 1206925 | 217 | 232 | 3568 | 3583 | $A_{ks}{}^mC_{es}A_{ks}T_{ds}T_{ds}T_dG_{ds}T_dG_{ds}G_{ds}T_{ds}A_{ds}{}^mC_{es}A_{es}G_{ks}{}^mC_k$ | 64 | 3114 |
| 1206933 | 1777 | 1792 | 7165 | 7180 | $T_{ks}T_{es}G_{ks}{}^mC_{ds}A_{ds}G_{ds}G_{ds}G_{ds}T_{ds}G_{ds}A_{ds}G_{ds}{}^mC_{es}{}^mC_{es}G_{ks}G_k$ | 62 | 3375 |
| 1206941 | 1785 | 1800 | 7173 | 7188 | $A_{ks}T_{es}G_{ks}A_{ds}T_{ds}G_{ds}{}^mC_d{}^mC_{ds}T_{ds}T_{ds}G_{ds}{}^mC_{ds}A_{es}G_{es}G_{ks}G_k$ | 57 | 3603 |
| 1206949 | 1793 | 1808 | 7181 | 7196 | ${}^mC_{ks}{}^mC_{es}{}^mC_{ks}A_{ds}G_{ds}{}^mC_{ds}T_{ds}G_{ds}A_{ds}T_{ds}G_{ds}A_{ds}T_{es}G_{es}{}^mC_{ks}{}^mC_k$ | 64 | 4953 |
| 1206957 | 1899 | 1914 | 7287 | 7302 | $G_{ks}A_{es}T_{ks}G_{ds}A_{ds}G_{ds}T_{ds}{}^mC_{ds}{}^mC_{ds}{}^mC_{ds}T_{ds}G_{ds}A_{es}G_{es}{}^mC_{ks}A_k$ | 47 | 2537 |
| 1206965 | 1914 | 1929 | 7302 | 7317 | ${}^mC_{ks}A_{es}{}^mC_{ks}{}^mC_{ds}A_{ds}A_{ds}G_{ds}G_{ds}A_{ds}G_{ds}G_{ds}G_{ds}A_{es}A_{es}A_{ks}G_k$ | 60 | 4954 |

TABLE 78-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence with Chemistry notation (5' to 3') | FXII (% UTC) | SEQ ID NO |
|---|---|---|---|---|---|---|---|
| 1206973 | 1922 | 1937 | 7310 | 7325 | $T_{ks}G_{es}{}^mC_{ks}G_{ds}G_{ds}A_{ds}A_{ds}T_{ds}{}^mC_{ds}A_{ds}{}^mC_{ds}{}^mC_{ds}A_{es}A_{es}G_{ks}G_k$ | 62 | 3455 |
| 1206981 | 1930 | 1945 | 7318 | 7333 | $T_{ks}{}^mC_{es}T_{ks}{}^mC_{ds}T_{ds}{}^mC_{ds}A_{ds}{}^mC_{ds}T_{ds}G_{ds}{}^mC_{ds}G_{ds}G_{es}A_{es}A_{ks}T_k$ | 50 | 4955 |
| 1206989 | 2000 | 2015 | 7388 | 7403 | ${}^mC_{ks}G_{es}{}^mC_{ks}{}^mC_{ds}A_{ds}T_{ds}{}^mC_{ds}{}^mC_{ds}T_{ds}G_{ds}G_{ds}{}^mC_{ds}G_{es}{}^mC_{es}G_{ks}G_k$ | 91 | 3228 |
| 1206997 | 2008 | 2023 | 7396 | 7411 | $A_{ks}G_{es}T_{ks}T_{ds}{}^mC_{ds}{}^mC_{ds}T_{ds}G_{ds}{}^mC_{ds}G_{ds}{}^mC_{ds}{}^mC_{ds}A_{es}T_{es}{}^mC_{ks}{}^mC_k$ | 38 | 3761 |
| 1207005 | 2017 | 2032 | 7405 | 7420 | $A_{ks}{}^mC_{es}T_{ks}T_{ds}T_{ds}A_{ds}T_{ds}T_{ds}G_{ds}A_{ds}G_{ds}T_{ds}T_{es}{}^mC_{es}{}^mC_{ks}T_k$ | 41 | 2848 |
| 1207013 | 2031 | 2046 | 7419 | 7434 | $A_{ks}G_{es}{}^mC_{ks}A_{ds}T_{ds}T_{ds}T_{ds}T_{ds}{}^mC_{ds}A_{ds}A_{ds}A_{ds}G_{es}{}^mC_{es}A_{ks}{}^mC_k$ | 106 | 3458 |
| 1207032 | 147 | 162 | 514 | 529 | $A_{ks}{}^mC_{ks}T_{ds}G_{ds}T_{ds}G_{ds}T_{ds}G_{ds}{}^mC_{ds}T_{ds}{}^mC_{ds}T_{es}T_{es}{}^mC_{es}A_{ks}G_k$ | 51 | 3267 |
| 1207040 | 155 | 170 | N/A | N/A | $T_{ks}G_{ks}A_{ds}G_{ds}A_{ds}A_{ds}{}^mC_{ds}G_{ds}A_{ds}{}^mC_{ds}T_{ds}G_{es}T_{es}G_{es}T_{ks}G_k$ | 71 | 3875 |
| 1207048 | 212 | 227 | 3563 | 3578 | $T_{kS}G_{kS}T_{ds}G_{ds}G_{ds}T_{ds}A_{ds}{}^mC_{ds}A_{ds}G_{ds}{}^mC_{ds}T_{es}G_{es}{}^mC_{es}{}^mC_{ks}C_k$ | 63 | 2734 |
| 1207056 | 220 | 235 | 3571 | 3586 | $G_{ks}G_{ks}T_{ds}A_{ds}{}^mC_{ds}A_{ds}T_{ds}T_{ds}T_{ds}G_{ds}T_{ds}G_{es}G_{es}T_{es}A_{ks}{}^mC_k$ | 66 | 3269 |
| 1207064 | 1780 | 1795 | 7168 | 7183 | $G_{ks}{}^mC_{ks}{}^mC_{ds}T_{ds}T_{dsds}{}^mC_{ds}A_{dsdsds}G_{ds}T_{es}G_{es}A_eG_{ks}{}^mC_k$ | 58 | 3451 |
| 1207085 | 1788 | 1803 | 7176 | 7191 | ${}^mC_{ks}T_{ks}G_{ds}A_{ds}T_{ds}G_{ds}A_{ds}T_{ds}G_{ds}{}^mC_{ds}{}^mC_{ds}T_{es}T_{es}G_{es}{}^mC_{ks}A_k$ | 61 | 3679 |
| 1207093 | 1894 | 1909 | 7282 | 7297 | ${}^mC_{ks}A_{ks}{}^mC_{ds}T_{ds}G_{ds}{}^mC_{ds}G_{ds}G_{ds}A_{ds}A_{ds}A_{ds}A_{es}T_{es}{}^mC_{es}A_{ks}G_k$ | 56 | 3682 |
| 1207101 | 1902 | 1917 | 7290 | 7305 | $A_{ks}A_{ks}A_{ds}G_{ds}A_{ds}T_{ds}G_{ds}A_{ds}G_{ds}T_{ds}{}^mC_{ds}{}^mC_{es}{}^mC_{es}T_{es}G_{ks}A_k$ | 48 | 2768 |
| 1207109 | 1917 | 1932 | 7305 | 7320 | $A_{ks}A_{ks}T_{ds}{}^mC_{ds}A_{ds}{}^mC_{ds}{}^mC_{ds}A_{ds}A_{ds}G_{ds}G_{ds}A_{es}G_{es}G_{es}G_{ks}A_k$ | 42 | 4956 |
| 1207117 | 1925 | 1940 | 7313 | 7328 | ${}^mC_{ks}A_{kS}{}^mC_{ds}T_{ds}G_{ds}{}^mC_{ds}G_{ds}G_{ds}G_{ds}A_{ds}A_{ds}T_{ds}{}^mC_{es}A_{es}{}^mC_{es}{}^mC_{ks}A_k$ | 56 | 3683 |
| 1207133 | 1933 | 1948 | 7321 | 7336 | ${}^mC_{ks}A_{ks}{}^mC_{ds}T_{ds}{}^mC_{ds}T_{ds}{}^mC_{ds}T_{ds}{}^mC_{ds}A_{ds}{}^mC_{ds}T_{es}G_{es}{}^mC_{es}G_{ks}G_k$ | 33 | 4957 |
| 1207146 | 2003 | 2018 | 7391 | 7406 | ${}^mC_{ks}T_{ks}G_{ds}{}^mC_{ds}G_{ds}{}^mC_{ds}{}^mC_{ds}A_{ds}T_{ds}{}^mC_{ds}{}^mC_{ds}T_{es}G_{es}G_{es}{}^mC_{ks}G_k$ | 76 | 3381 |
| 1207154 | 2011 | 2026 | 7399 | 7414 | $T_{ks}T_{kS}G_{ds}A_{ds}G_{ds}T_{ds}T_{ds}{}^mC_{ds}{}^mC_{ds}T_{ds}G_{ds}{}^mC_{es}G_{es}{}^mC_{es}{}^mC_{ks}A_k$ | 48 | 2463 |
| 1207162 | 2020 | 2035 | 7408 | 7423 | $A_{ks}G_{ks}{}^mC_{ds}A_{ds}{}^mC_{ds}T_{ds}T_{ds}T_{ds}A_{ds}T_{ds}T_{ds}G_{es}A_{es}G_{es}T_{ks}T_k$ | 55 | 3076 |
| 1207170 | 142 | 157 | 509 | 524 | $g_{ks}T_{ks}G_{ds}{}^mC_{ds}T_{ds}{}^mC_{ds}T_{ds}T_{ds}{}^mC_{ds}A_{ds}G_{ds}{}^mC_{es}T_{ks}T_{es}T_{ks}G_e$ | 47 | 4958 |
| 1207178 | 150 | 165 | N/A | N/A | $A_{ks}{}^mC_{ks}G_{ds}A_{ds}{}^mC_{ds}T_{ds}G_{ds}T_{ds}G_{ds}T_{ds}G_{ds}{}^mC_{es}T_{ks}{}^mC_{es}T_{ks}T_e$ | 50 | 3495 |
| 1207186 | 158 | 173 | N/A | N/A | ${}^mC_{ks}A_{ks}G_{ds}T_{dS}G_{ds}A_{ds}G_{ds}A_{ds}A_{ds}{}^mC_{ds}G_{ds}A_{es}{}^mC_{ks}T_{es}G_{ks}T_e$ | 78 | 2579 |

TABLE 78-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence with Chemistry notation (5' to 3') | FXII (% UTC) | SEQ ID NO |
|---|---|---|---|---|---|---|---|
| 1207194 | 215 | 230 | 3566 | 3581 | $A_{ks}T_{ks}T_{ds}T_{d}G_{ds}T_{ds}G_{ds}G_{ds}T_{ds}A_{ds}C_{ds}A_{es}G_{ks}{}^mC_{es}T_{ks}G_e$ | 70 | 2963 |
| 1207202 | 223 | 238 | 3574 | 3589 | $G_{ks}T_{ks}G_{ds}G_{ds}G_{ds}T_{ds}A_{ds}{}^mC_{ds}A_{ds}T_{ds}T_{ds}T_{es}G_{ks}T_{es}G_{ks}G_e$ | 36 | 3497 |
| 1207210 | 1783 | 1798 | 7171 | 7186 | $G_{ks}A_{ks}T_{ds}G_{ds}{}^mC_{ds}{}^mC_{ds}T_{ds}T_{ds}G_{ds}{}^mC_{ds}A_{ds}G_{es}G_{ks}G_{es}T_{ks}G_e$ | 39 | 4959 |
| 1207218 | 1791 | 1806 | 7179 | 7194 | ${}^mC_{ks}A_{ks}G_{ds}{}^mC_{ds}T_{ds}G_{ds}A_{ds}T_{ds}G_{ds}A_{ds}T_{ds}G_{es}{}^mC_{ks}{}^mC_{es}T_{ks}T_e$ | 89 | 4960 |
| 1207226 | 1897 | 1912 | 7285 | 7300 | $T_{ks}G_{ks}A_{ds}G_{ds}T_{ds}{}^mC_{ds}{}^mC_{ds}{}^mC_{ds}T_{ds}G_{ds}A_{ds}G_{es}{}^mC_{ks}A_{es}A_{ks}T_e$ | 65 | 3910 |
| 1207234 | 1905 | 1920 | 7293 | 7308 | $G_{ks}G_{ks}G_{ds}A_{ds}A_{ds}A_{ds}G_{ds}A_{ds}T_{ds}G_{ds}A_{ds}G_{es}T_{ks}{}^mC_{es}{}^mC_{ks}{}^mC_e$ | 68 | 2997 |
| 1207242 | 1920 | 1935 | 7308 | 7323 | ${}^mC_{ks}G_{ks}G_{ds}A_{ds}A_{ds}T_{ds}{}^mC_{ds}A_{ds}{}^mC_{ds}{}^mC_{ds}A_{ds}A_{es}G_{ks}G_{es}A_{ks}G_e$ | 26 | 3303 |
| 1207250 | 1928 | 1943 | 7316 | 7331 | $T_{ks}{}^mC_{ks}T_{ds}{}^mC_{ds}A_{ds}{}^mC_{ds}T_{ds}G_{ds}{}^mC_{ds}G_{ds}G_{ds}A_{es}A_{ks}T_{es}{}^mC_{ks}A_e$ | 31 | 3911 |
| 1207258 | 1936 | 1951 | 7324 | 7339 | $A_{ks}G_{ks}{}^mC_{ds}{}^mC_{ds}A_{ds}{}^mC_{ds}T_{ds}{}^mC_{ds}T_{ds}{}^mC_{ds}T_{ds}{}^mC_{es}A_{ks}{}^mC_{es}T_{ks}G_e$ | 29 | 4961 |
| 1207266 | 2006 | 2021 | 7394 | 7409 | $T_{ks}T_{ks}{}^mC_{ds}{}^mC_{ds}T_{ds}G_{ds}{}^mC_{ds}G_{ds}{}^mC_{ds}{}^mC_{ds}A_{ds}T_{es}{}^mC_{ks}{}^mC_{es}T_{ks}G_e$ | 70 | 3609 |
| 1207274 | 2014 | 2029 | 7402 | 7417 | $T_{ks}T_{ks}A_{ds}T_{d}T_{d}G_{ds}A_{ds}G_{ds}T_{ds}T_{ds}{}^mC_{ds}{}^mC_{es}T_{ks}G_{es}{}^mC_{ks}G_e$ | 54 | 2694 |
| 1207282 | 2023 | 2038 | 7411 | 7426 | ${}^mC_{ks}A_{ks}A_{ds}A_{ds}G_{ds}{}^mC_{ds}A_{ds}{}^mC_{ds}T_{ds}T_{ds}T_{ds}A_{es}T_{ks}T_{es}G_{ks}A_e$ | 68 | 3306 |
| 1207290 | 145 | 160 | 512 | 527 | $T_{ks}G_{ks}T_{ds}G_{ds}T_{ds}G_{ds}{}^mC_{ds}T_{ds}{}^mC_{ds}T_{ds}T_{ds}{}^mC_{ks}A_{es}G_{ks}{}^mC_{es}T_k$ | 74 | 3112 |
| 1207298 | 153 | 168 | N/A | N/A | $A_{ks}G_{ks}A_{ds}A_{ds}{}^mC_{ds}G_{ds}A_{ds}{}^mC_{ds}T_{ds}G_{ds}T_{ds}G_{ks}T_{es}G_{ks}{}^mC_{es}T_k$ | 52 | 3723 |
| 1207306 | 210 | 225 | 3561 | 3576 | $T_{ks}G_{ks}G_{ds}T_{ds}A_{ds}{}^mC_{ds}A_{ds}G_{ds}{}^mC_{ds}T_{ds}G_{ds}{}^mC_{ks}{}^mC_{es}G_{ks}G_{es}T_k$ | 91 | 2657 |
| 1207314 | 218 | 233 | 3569 | 3584 | $T_{ks}A_{ks}{}^mC_{ds}A_{ds}T_{ds}T_{ds}T_{ds}G_{ds}T_{ds}G_{ds}G_{ds}T_{ks}A_{es}{}^mC_{ks}A_{es}G_k$ | 66 | 2426 |
| 1207322 | 1778 | 1793 | 7166 | 7181 | ${}^mC_{ks}T_{ks}T_{ds}G_{ds}{}^mC_{ds}A_{ds}G_{ds}G_{ds}G_{ds}T_{ds}G_{ds}A_{ks}G_{es}{}^mC_{ks}{}^mC_{es}G_k$ | 59 | 4962 |
| 1207330 | 1786 | 1801 | 7174 | 7189 | $G_{ks}A_{ks}T_{ds}G_{ds}A_{ds}T_{d}G_{ds}{}^mC_{ds}{}^mC_{ds}T_{ds}T_{ds}G_{ks}{}^mC_{es}A_{ks}G_{es}G_k$ | 53 | 4963 |
| 1207338 | 1892 | 1907 | 7280 | 7295 | ${}^mC_{ks}{}^mC_{ks}{}^mC_{ds}T_{ds}G_{ds}A_{ds}G_{ds}{}^mC_{ds}A_{ds}A_{ds}T_{ds}{}^mC_{ks}A_{es}G_{ks}G_{es}A_k$ | 74 | 3530 |
| 1207346 | 1900 | 1915 | 7288 | 7303 | $A_{ks}G_{ks}A_{ds}T_{ds}G_{ds}G_{ds}A_{d}G_{ds}T_{ds}{}^mC_{ds}{}^mC_{ds}{}^mC_{ds}T_{ks}G_{es}A_{ks}G_{es}{}^mC_k$ | 76 | 2614 |
| 1207354 | 1915 | 1930 | 7303 | 7318 | $T_{ks}{}^mC_{ks}A_{ds}{}^mC_{ds}{}^mC_{ds}A_{ds}A_{ds}G_{ds}G_{ds}A_{ds}G_{ds}G_{ks}G_{es}A_{ks}A_{es}A_k$ | 44 | 4948 |
| 1207362 | 1923 | 1938 | 7311 | 7326 | ${}^mC_{ks}T_{ks}G_{ds}{}^mC_{ds}G_{ds}G_{ds}A_{ds}A_{ds}T_{ds}{}^mC_{ds}A_{ds}{}^mC_{ks}{}^mC_{es}A_{ks}A_{es}G_k$ | 46 | 3531 |
| 1207370 | 1931 | 1946 | 7319 | 7334 | ${}^mC_{ks}T_{ks}{}^mC_{ds}T_{ds}{}^mC_{ds}T_{ds}{}^mC_{ds}A_{ds}{}^mC_{ds}T_{ds}G_{ds}{}^mC_{ks}G_{es}G_{ks}A_{es}A_k$ | 41 | 2461 |

TABLE 78-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence with Chemistry notation (5' to 3') | FXII (% UTC) | SEQ ID NO |
|---|---|---|---|---|---|---|---|
| 1207378 | 2001 | 2016 | 7389 | 7404 | $G_{ks}{}^mC_{ds}G_{ds}{}^mC_{ds}{}^mC_{ds}A_{ds}T_{ds}{}^mC_{ds}{}^mC_{ds}T_{ds}G_{ds}G_{ks}{}^mC_{es}G_{ks}{}^mC_{es}G_{k}$ | 80 | 4964 |
| 1207386 | 2009 | 2024 | 7397 | 7412 | $G_{ks}A_{ks}G_{ds}T_{ds}T_{ds}{}^mC_{ds}{}^mC_{ds}T_{ds}G_{ds}{}^mC_{ds}G_{ds}{}^mC_{ks}{}^mC_{es}A_{ks}T_{es}{}^mC_{k}$ | 71 | 3837 |
| 1207394 | 2018 | 2033 | 7406 | 7421 | ${}^mC_{ks}A_{ks}{}^mC_{ds}T_{ds}T_{ds}T_{ds}A_{ds}T_{ds}T_{ds}G_{ds}A_{ds}G_{ks}T_{es}T_{ks}{}^mC_{es}{}^mC_{k}$ | 47 | 2924 |
| 1207402 | 2033 | 2048 | 7421 | 7436 | $T_{ks}{}^mC_{ks}A_{ds}G_{ds}{}^mC_{ds}A_{ds}T_{ds}T_{ds}T_{ds}{}^mC_{ds}A_{ks}A_{es}A_{ks}G_{es}{}^mC_{k}$ | 32 | 3534 |
| 1207410 | 148 | 163 | 515 | 530 | $G_{ks}A_{ks}{}^mC_{ks}T_{ds}G_{ds}T_{ds}G_{ds}T_{ds}G_{ds}{}^mC_{ds}T_{ds}{}^mC_{ds}T_{ks}T_{ks}{}^mC_{ks}A_{e}$ | 64 | 3343 |
| 1207418 | 156 | 171 | N/A | N/A | $G_{ks}T_{ks}G_{ks}A_{ds}G_{ds}A_{ds}A_{ds}{}^mC_{ds}G_{ds}A_{ds}{}^mC_{ds}T_{ds}G_{ks}T_{ks}G_{ks}T_{e}$ | 88 | 2424 |
| 1207426 | 213 | 228 | 3564 | 3579 | $T_{ks}T_{ks}G_{ks}T_{ds}G_{ds}G_{ds}T_{ds}A_{ds}{}^mC_{ds}A_{ds}G_{ds}{}^mC_{ds}T_{ks}G_{ks}{}^mC_{ks}{}^mC_{e}$ | 54 | 2.811 |
| 1207434 | 221 | 236 | 3572 | 3587 | $G_{ks}G_{ks}G_{ks}T_{ds}A_{ds}{}^mC_{ds}A_{ds}T_{ds}T_{ds}T_{ds}G_{ds}T_{ds}G_{ks}G_{ks}T_{ks}A_{e}$ | 63 | 3345 |
| 1207442 | 1781 | 1796 | 7169 | 7184 | $T_{ksks}{}^mC_{ks}{}^mC_{ds}T_{ds}T_{ds}{}^mC_{dsds}{}^mC_{ds}A_{ds}G_{ds}G_{ds}G_{ds}T_{ks}G_{ks}A_{ks}G_{e}$ | 70 | 3527 |
| 1207450 | 1789 | 1804 | 7177 | 7192 | $G_{ks}{}^mC_{ks}T_{ks}G_{ds}A_{ds}T_{ds}G_{ds}A_{ds}A_{ds}T_{ds}G_{ds}{}^mC_{ds}{}^mC_{ds}T_{ks}T_{ks}G_{ks}{}^mC_{e}$ | 67 | 3755 |
| 1207458 | 1895 | 1910 | 7283 | 7298 | $A_{ks}G_{ks}T_{ks}{}^mC_{ds}{}^mC_{ds}{}^mC_{ds}T_{ds}G_{ds}A_{ds}G_{ds}{}^mC_{ds}A_{ds}T_{ks}{}^mC_{ks}A_{e}$ | 51 | 3758 |
| 1207466 | 1903 | 1918 | 7291 | 7306 | $G_{ks}A_{ks}A_{ks}A_{ds}G_{ds}A_{ds}T_{ds}G_{ds}A_{ds}G_{ds}T_{ds}{}^mC_{ds}{}^mC_{ks}{}^mC_{ks}T_{ks}G_{e}$ | 36 | 2845 |
| 1207474 | 1918 | 1933 | 7306 | 7321 | $G_{ks}A_{ks}A_{ks}T_{ds}{}^mC_{ds}A_{ds}{}^mC_{ds}{}^mC_{ds}A_{ds}A_{ds}G_{ds}G_{ds}A_{ks}G_{ks}G_{ks}G_{e}$ | 36 | 4965 |
| 1207482 | 1926 | 1941 | 7314 | 7329 | $T_{ks}{}^mC_{ks}A_{ks}{}^mC_{ds}T_{ds}G_{ds}{}^mC_{ds}G_{ds}G_{ds}G_{ds}A_{ds}A_{ds}T_{ds}{}^mC_{ks}A_{ks}{}^mC_{k}{}^mC_{e}$ | 50 | 3759 |
| 1207490 | 1934 | 1949 | 7322 | 7337 | ${}^mC_{ks}{}^mC_{ks}A_{ks}{}^mC_{ds}T_{ds}{}^mC_{ds}T_{ds}{}^mC_{ds}T_{ds}{}^mC_{ds}A_{ds}{}^mC_{ds}T_{ks}G_{ks}G_{ks}{}^mC_{e}$ | 38 | 4949 |
| 1207498 | 2004 | 2019 | 7392 | 7407 | ${}^mC_{ks}{}^mC_{ks}T_{ks}G_{ds}{}^mC_{ds}G_{ds}{}^mC_{ds}{}^mC_{ds}A_{ds}T_{ds}{}^mC_{ds}{}^mC_{ds}T_{ks}G_{ks}G_{ks}{}^mC_{e}$ | 54 | 3457 |
| 1207506 | 2012 | 2027 | 7400 | 7415 | $A_{ks}T_{ks}T_{ks}G_{ds}A_{ds}G_{ds}T_{ds}T_{ds}{}^mC_{ds}{}^mC_{ds}T_{ds}G_{ds}{}^mC_{ks}G_{ks}{}^mC_{ks}{}^mC_{e}$ | 66 | 2540 |
| 1207514 | 2021 | 2036 | 7409 | 7424 | $A_{ks}A_{ks}G_{ks}{}^mC_{ds}A_{ds}{}^mC_{ds}T_{ds}T_{ds}T_{ds}A_{ds}T_{ds}T_{ds}G_{ks}A_{ks}G_{ks}T_{e}$ | 42 | 3147 |

TABLE 79

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ds}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_{k}$ | 21 | 3837 |

TABLE 79-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206475 | 142 | 157 | 509 | 524 | $G_{ks}T_{ks}G_{ks}{}^mC_{ds}T_{ds}{}^mC_{ds}T_{ds}T_{ds}{}^mC_{ds}A_{ds}G_{ds}{}^mC_{ds}T_{ds}T_{ks}T_{ks}G_k$ | 32 | 4958 |
| 1206487 | 1916 | 1931 | 7304 | 7319 | $A_{ks}T_{ks}{}^mC_{ks}A_{ds}{}^mC_{ds}{}^mC_{ds}A_{ds}A_{ds}G_{ds}G_{ds}A_{ds}G_{ds}G_{ds}G_{ks}A_{ks}A_k$ | 33 | 4966 |
| 1206492 | 1935 | 1950 | 7323 | 7338 | $G_{ks}{}^mC_{ks}{}^mC_{ks}A_{ds}{}^mC_{ds}T_{ds}{}^mC_{ds}T_{ds}{}^mC_{ds}T_{ds}{}^mC_{ds}A_{ds}{}^mC_{ds}T_{ks}G_{ks}{}^mC_k$ | 5 | 4967 |
| 1206500 | 1783 | 1798 | 7171 | 7186 | $G_{ks}A_{ks}T_{ks}G_{ds}{}^mC_{ds}T_{ds}T_{ds}G_{ds}{}^mC_{ds}A_{ds}G_{ds}G_{ds}G_{ks}T_{ks}G_k$ | 22 | 4959 |
| 1206902 | 145 | 160 | 512 | 527 | $T_{ks}G_{es}T_{ks}G_{ds}T_{ds}{}^mC_{ds}T_{ds}{}^mC_{ds}T_{ds}T_{ds}C_{ds}A_{es}G_{es}{}^mC_{ks}T_k$ | 33 | 3112 |
| 1206910 | 153 | 168 | N/A | N/A | $A_{ks}G_{es}A_{ks}A_{ds}C_{ds}G_{ds}A_{ds}C_{ds}T_{ds}G_{ds}T_{ds}G_{ds}T_{es}G_{es}{}^mC_{ks}T_k$ | 39 | 3723 |
| 1206918 | 210 | 225 | 3561 | 3576 | $T_{ks}G_{es}G_{ks}T_{ds}A_{ds}{}^mC_{ds}A_{ds}G_{ds}{}^mC_{ds}T_{ds}G_{ds}{}^mC_{ds}{}^mC_{es}G_{es}G_{ks}T_k$ | 45 | 2657 |
| 1206926 | 218 | 233 | 3569 | 3584 | $T_{ks}A_{es}{}^mC_{ks}A_{ds}T_{ds}T_{ds}G_{ds}T_{ds}G_{ds}G_{ds}T_{ds}A_{es}{}^mC_{es}A_{ks}G_k$ | 17 | 2426 |
| 1206934 | 1778 | 1793 | 7166 | 7181 | ${}^mC_{ks}T_{es}T_{ks}G_{ds}{}^mC_{ds}A_{ds}G_{ds}G_{ds}G_{ds}T_{ds}G_{ds}A_{ds}G_{es}{}^mC_{es}{}^mC_{ks}G_k$ | 31 | 4962 |
| 1206942 | 1786 | 1801 | 7174 | 7189 | $G_{ks}A_{es}T_{ks}G_{ds}A_{ds}G_{ds}{}^mC_{ds}{}^mC_{ds}T_{ds}T_{ds}G_{ds}{}^mC_{es}A_{ks}G_{ks}G_k$ | 24 | 4963 |
| 1206950 | 1892 | 1907 | 7280 | 7295 | ${}^mC_{ks}{}^mC_{es}{}^mC_{ks}T_{ds}G_{ds}A_{ds}G_{ds}{}^mC_{ds}A_{ds}A_{ds}T_{ds}C_{ds}A_{es}G_{es}{}^mC_{ks}A_k$ | 47 | 3530 |
| 1206958 | 1900 | 1915 | 7288 | 7303 | $A_{ks}G_{es}A_{ks}T_{ds}G_{ds}A_{ds}G_{ds}T_{ds}C_{ds}C_{ds}C_{ds}T_{ds}G_{es}A_{es}G_{ks}{}^mC_k$ | 24 | 2614 |
| 1206966 | 1915 | 1930 | 7303 | 7318 | $T_{ks}{}^mC_{es}A_{ks}{}^mC_{ds}{}^mC_{ds}A_{ds}A_{ds}G_{ds}G_{ds}G_{ds}A_{ds}G_{ds}G_{ds}G_{es}A_{es}A_{ks}A_k$ | 24 | 4948 |
| 1206974 | 1923 | 1938 | 7311 | 7326 | ${}^mC_{ks}T_{es}G_{ks}{}^mC_{ds}G_{ds}G_{ds}G_{ds}A_{ds}A_{ds}T_{ds}{}^mC_{ds}A_{ds}{}^mC_{ds}{}^mC_{es}A_{es}A_{ks}G_k$ | 15 | 3531 |
| 1206982 | 1931 | 1946 | 7319 | 7334 | $C_{ks}T_{es}C_{ks}T_{ds}C_{ds}T_{ds}C_{ds}C_{ds}A_{ds}C_{ds}T_{ds}G_{ds}{}^mC_{ds}G_{es}G_{es}A_{ks}A_k$ | 17 | 2461 |
| 1206990 | 2001 | 2016 | 7389 | 7404 | $G_{ks}{}^mC_{es}G_{ks}{}^mC_{ds}{}^mC_{ds}A_{ds}T_{ds}{}^mC_{ds}{}^mC_{ds}T_{ds}G_{ds}G_{ds}{}^mC_{es}G_{es}{}^mC_{ks}G_k$ | 73 | 4964 |
| 1206998 | 2009 | 2024 | 7397 | 7412 | $G_{ks}A_{es}G_{ks}T_{ds}T_{ds}{}^mC_{ds}{}^mC_{ds}T_{ds}G_{ds}{}^mC_{ds}G_{ds}{}^mC_{ds}{}^mC_{es}A_{es}T_{ks}{}^mC_k$ | 21 | 3837 |
| 1207006 | 2018 | 2033 | 7406 | 7421 | $C_{ks}A_{es}C_{ks}T_{ds}T_{ds}T_{ds}A_{ds}T_{ds}T_{ds}G_{ds}A_{ds}G_{ds}T_{es}T_{es}{}^mC_{ks}{}^mC_k$ | 20 | 2924 |
| 1207014 | 2033 | 2048 | 7421 | 7436 | $T_{ks}{}^mC_{es}A_{ks}G_{ds}{}^mC_{ds}A_{ds}T_{ds}T_{ds}T_{ds}{}^mC_{ds}A_{ds}A_{es}A_{es}G_{ks}C_k$ | 44 | 3534 |
| 1207033 | 148 | 163 | 515 | 530 | $G_{ks}A_{ks}C_{ds}T_{ds}G_{ds}T_{ds}G_{ds}T_{ds}G_{ds}C_{ds}T_{ds}C_{es}T_{es}T_{es}C_{ks}A_k$ | 11 | 3343 |
| 1207041 | 156 | 171 | N/A | N/A | $G_{ks}T_{ks}G_{ds}A_{ds}G_{ds}A_{ds}A_{ds}{}^mC_{ds}G_{ds}A_{ds}{}^mC_{ds}T_{es}G_{es}T_{es}G_{ks}T_k$ | 48 | 2424 |
| 1207049 | 213 | 228 | 3564 | 3579 | $T_{ks}T_{ks}G_{ds}T_{ds}G_{ds}G_{ds}T_{ds}A_{ds}{}^mC_{ds}A_{ds}G_{ds}{}^mC_{es}T_{es}G_{es}{}^mC_{ks}{}^mC_k$ | 25 | 2811 |
| 1207057 | 221 | 236 | 3572 | 3587 | $G_{ks}G_{ks}G_{ds}T_{ds}A_{ds}{}^mC_{ds}A_{ds}T_{ds}T_{ds}T_{ds}G_{ds}T_{es}G_{es}G_{es}T_{ks}A_k$ | 47 | 3345 |

TABLE 79-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207071 | 1781 | 1796 | 7169 | 7184 | $T_{ks}G_{ks}{}^mC_{ds}{}^mC_{ds}T_{ds}T_{ds}G_{ds}{}^mC_{ds}A_{ds}G_{ds}G_{ds}G_{es}T_{es}G_{es}A_{ks}G_k$ | 35 | 3527 |
| 1207086 | 1789 | 1804 | 7177 | 7192 | $G_{ks}{}^mC_{ks}T_{ds}G_{ds}A_{ds}T_{ds}G_{ds}A_{ds}T_{ds}G_{ds}{}^mC_{ds}C_{es}T_{es}T_{es}G_{ks}C_k$ | 24 | 3755 |
| 1207094 | 1895 | 1910 | 7283 | 7298 | $A_{ks}G_{ks}T_{ds}{}^mC_{ds}{}^mC_{ds}{}^mC_{ds}T_{ds}G_{ds}A_{ds}G_{ds}{}^mC_{ds}A_{es}A_{es}T_{es}T_{ks}A_k$ | 36 | 3758 |
| 1207102 | 1903 | 1918 | 7291 | 7306 | $G_{ks}A_{ks}A_{ds}A_{ds}G_{ds}A_{ds}T_{ds}G_{ds}G_{ds}A_{ds}G_{ds}T_{ds}C_{es}{}^mC_{es}{}^mC_{es}T_{ks}G_k$ | 28 | 2845 |
| 1207110 | 1918 | 1933 | 7306 | 7321 | $G_{ks}A_{ks}A_{ds}T_{ds}C_{ds}A_{ds}C_{ds}C_{ds}A_{ds}A_{ds}G_{ds}G_{es}A_{es}G_{ks}G_k$ | 24 | 4965 |
| 1207118 | 1926 | 1941 | 7314 | 7329 | $T_{ks}{}^mC_{ks}A_{ds}{}^mC_{ds}T_{ds}G_{ds}{}^mC_{ds}G_{ds}G_{ds}A_{ds}A_{ds}T_{es}{}^mC_{es}A_{es}{}^mC_{ks}{}^mC_k$ | 12 | 3759 |
| 1207135 | 1934 | 1949 | 7322 | 7337 | ${}^mC_{ks}{}^m{}_{ks}A_{ds}C_{ds}A_{ds}C_{ds}A_{ds}C_{ds}A_{ds}A_{ds}{}^mC_{es}T_{es}G_{es}{}^mC_{ks}G_k$ | 16 | 4949 |
| 1207155 | 2012 | 2027 | 7400 | 7415 | ${}^mC_{ks}{}^mC_{ks}A_{ds}{}^mC_{ds}T_{ds}G_{ds}{}^mC_{ds}A_{ds}T_{ds}C_{ds}C_{es}T_{es}G_{es}{}^mC_{ks}C_k$ | 33 | 2540 |
| 1207163 | 2021 | 2036 | 7409 | 7424 | $A_{ks}T_{ks}T_{ds}G_{ds}A_{ds}G_{ds}T_{ds}T_{ds}C_{ds}{}^mC_{ds}T_{ds}G_{es}{}^mC_{es}G_{es}{}^mC_{ks}{}^mC_k$ | 22 | 3147 |
| 1207171 | 143 | 158 | 510 | 525 | $A_{ks}A_{ks}G_{ds}C_{ds}A_{ds}C_{ds}T_{ds}T_{ds}T_{ds}A_{ds}T_{ds}T_{es}G_{es}A_{es}G_{ks}T_k$ | 49 | 3037 |
| 1207179 | 151 | 166 | N/A | N/A | $T_{ks}G_{ks}T_{ds}G_{ds}{}^mC_{ds}T_{ds}{}^mC_{ds}T_{ds}T_{ds}{}^mC_{ds}A_{ds}G_{es}{}^mC_{ks}T_{es}T_{ks}T_e$ | 43 | 3571 |
| 1207187 | 208 | 223 | 3559 | 3574 | $A_{ks}A_{ks}C_{ds}G_{ds}A_{ds}C_{ds}T_{ds}G_{ds}T_{ds}G_{ds}T_{ds}G_{es}{}^mC_{ks}T_{es}{}^mC_{ks}T_e$ | 45 | 4968 |
| 1207195 | 216 | 231 | 3567 | 3582 | $G_{ks}T_{ks}A_{ds}{}^mC_{ds}A_{ds}G_{ds}{}^mC_{ds}T_{ds}G_{ds}{}^mC_{ds}{}^mC_{ds}G_{es}G_{ks}T_{es}G_{ks}G_e$ | 26 | 3039 |
| 1207203 | 1776 | 1791 | 7164 | 7179 | ${}^mC_{ks}A_{ks}T_{ds}T_{ds}T_{ds}G_{ds}T_{ds}G_{ds}G_{ds}T_{ds}A_{ds}C_{es}A_{ks}G_{es}C_{ks}T_e$ | 68 | 3299 |
| 1207211 | 1784 | 1799 | 7172 | 7187 | $T_{ks}G_{ks}C_{ds}A_{ds}G_{ds}G_{ds}G_{ds}G_{ds}T_{ds}G_{ds}A_{ds}G_{ds}{}^mC_{es}{}^mC_{ks}G_{es}G_{ks}{}^mC_e$ | 46 | 4969 |
| 1207219 | 1792 | 1807 | 7180 | 7195 | $T_{ks}G_{ks}A_{ds}T_{ds}G_{ds}{}^mC_{ds}{}^mC_{ds}T_{ds}T_{ds}G_{ds}{}^mC_{ds}A_{es}G_{ks}G_{es}G_{ks}T_e$ | 39 | 4970 |
| 1207227 | 1898 | 1913 | 7286 | 7301 | ${}^mC_{ks}{}^mC_{ks}A_{ds}G_{ds}{}^mC_{ds}T_{ds}G_{ds}G_{ds}A_{ds}T_{ds}G_{ds}A_{ds}T_{es}G_{ks}{}^mC_{es}{}^mC_{ks}T_e$ | 31 | 2460 |
| 1207235 | 1906 | 1921 | 7294 | 7309 | $A_{ks}T_{ks}G_{ds}A_{ds}G_{ds}T_{ds}C_{ds}C_{ds}C_{ds}T_{ds}G_{ds}A_{es}G_{es}{}^mC_{es}A_{ks}A_e$ | 46 | 3073 |
| 1207243 | 1921 | 1936 | 7309 | 7324 | $A_{ks}G_{ks}G_{ds}G_{ds}A_{ds}A_{ds}A_{ds}G_{ds}A_{ds}T_{ds}G_{ds}A_{es}G_{ks}T_{es}{}^mC_{ks}{}^mC_e$ | 26 | 3379 |
| 1207251 | 1929 | 1944 | 7317 | 7332 | $G_{ks}{}^mC_{ks}G_{ds}G_{ds}A_{ds}A_{ds}T_{ds}{}^mC_{ds}A_{ds}{}^mC_{ds}C_{ds}A_{es}A_{ks}G_{es}G_{ks}A_e$ | 11 | 4971 |
| 1207259 | 1937 | 1952 | 7325 | 7340 | ${}^mC_{ks}T_{ks}{}^mC_{ds}T_{ds}{}^mC_{ds}A_{ds}A_{ds}{}^mC_{ds}T_{ds}G_{ds}{}^mC_{ds}G_{ds}G_{es}A_{ks}A_{es}T_{ks}{}^mC_e$ | 20 | 4972 |
| 1207267 | 2007 | 2022 | 7395 | 7410 | ${}^mC_{ks}A_{ks}G_{ds}{}^mC_{ds}{}^mC_{ds}A_{ds}{}^mC_{ds}T_{ds}{}^mC_{ds}T_{ds}C_{ds}T_{es}{}^mC_{ks}A_{es}{}^mC_{ks}T_e$ | 32 | 3685 |
| 1207275 | 2016 | 2031 | 7404 | 7419 | $G_{ks}T_{ks}T_{ds}{}^mC_{ds}{}^mC_{ds}T_{ds}G_{ds}{}^mC_{ds}G_{ds}{}^mC_{ds}{}^mC_{ds}A_{es}T_{ks}{}^mC_{es}{}^mC_{ks}T_e$ | 10 | 2771 |

TABLE 79-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207283 | 2024 | 2039 | 7412 | 7427 | $C_{ks}T_{ks}T_{ds}T_{ds}A_{ds}T_{ds}T_{ds}G_{ds}A_{ds}G_{ds}T_{ds}T_{es}{}^mC_{ks}{}^mC_{es}T_{ks}G_e$ | 24 | 3382 |
| 1207291 | 146 | 161 | 513 | 528 | $T_{ks}{}^mC_{ks}A_{ds}A_{ds}A_{ds}G_{ds}{}^mC_{ds}A_{ds}{}^mC_{ds}T_{ds}T_{ds}T_{es}A_{ks}T_{es}T_{ks}G_e$ | 29 | 3190 |
| 1207299 | 154 | 169 | N/A | N/A | ${}^mC_{ks}T_{ks}G_{ds}T_{ds}G_{ds}T_{ds}G_{ds}{}^mC_{ds}T_{ds}{}^mC_{ds}T_{ds}T_{ks}{}^mC_{es}A_{ks}G_{es}{}^mC_k$ | 56 | 3799 |
| 1207307 | 211 | 226 | 3562 | 3577 | $G_{ks}A_{ks}G_{ds}A_{ds}A_{ds}{}^mC_{ds}G_{ds}A_{ds}{}^mC_{ds}T_{ds}G_{ds}T_{ks}G_{es}T_{ks}G_{es}{}^{mm}C_k$ | 36 | 4973 |
| 1207315 | 219 | 234 | 3570 | 3585 | $G_{ks}T_{ks}G_{ds}G_{ds}T_{ds}A_{ds}{}^mC_{ds}A_{ds}G_{ds}{}^mC_{ds}T_{ds}G_{ks}C_{es}C_{ks}G_{es}G_k$ | 88 | 3192 |
| 1207323 | 1779 | 1794 | 7167 | 7182 | $G_{ks}T_{ks}A_{ds}{}^mC_{ds}A_{ds}T_{ds}T_{ds}T_{ds}G_{ds}T_{ds}G_{ds}G_{ks}T_{es}A_{ks}{}^mC_{es}A_k$ | 41 | 4974 |
| 1207331 | 1787 | 1802 | 7175 | 7190 | ${}^mC_{ks}{}^mC_{ks}T_{ds}T_{ds}G_{ds}{}^mC_{ds}A_{ds}G_{ds}G_{ds}G_{ds}T_{ds}G_{ks}A_{es}G_{ks}{}^mC_{es}{}^mC_k$ | 35 | 4975 |
| 1207339 | 1893 | 1908 | 7281 | 7296 | $T_{ks}{}^mC_{ks}{}^mC_{ds}{}^mC_{ds}T_{ds}G_{ds}A_{ds}A_{ds}G_{ds}{}^mC_{ds}A_{ds}A_{ds}T_{ks}{}^mC_{es}A_{ks}G_{es}G_k$ | 44 | 3606 |
| 1207347 | 1901 | 1916 | 7289 | 7304 | $A_{ks}A_{ks}G_{ds}A_{ds}T_{ds}G_{ds}A_{ds}A_{ds}G_{ds}T_{ds}{}^mC_{ds}{}^mC_{ds}{}^mC_{ks}T_{es}G_{ks}A_{es}G_k$ | 37 | 2691 |
| 1207355 | 1916 | 1931 | 7304 | 7319 | $A_{ks}T_{ks}{}^mC_{ds}A_{ds}{}^mC_{ds}{}^mC_{ds}A_{ds}A_{ds}G_{ds}G_{ds}A_{ds}G_{ks}G_{es}G_{ks}A_{es}A_k$ | 41 | 4966 |
| 1207363 | 1924 | 1939 | 7312 | 7327 | $A_{ks}{}^mC_{ks}T_{ds}G_{ds}{}^mC_{ds}G_{ds}G_{ds}G_{ds}A_{ds}A_{ds}T_{ds}{}^mC_{ds}A_{ks}{}^mC_{es}{}^mC_{ks}A_{es}A_k$ | 22 | 3607 |
| 1207371 | 1932 | 1947 | 7320 | 7335 | $A_{ks}{}^mC_{ks}T_{ds}{}^mC_{ds}T_{ds}{}^mC_{ds}T_{ds}{}^mC_{ds}A_{ds}{}^mC_{ds}T_{ds}G_{ks}{}^mC_{es}G_{ks}G_{es}A_k$ | 22 | 4976 |
| 1207379 | 2002 | 2017 | 7390 | 7405 | $T_{ks}G_{ks}{}^mC_{ds}G_{ds}{}^mC_{ds}{}^mC_{ds}A_{ds}A_{ds}A_{ds}{}^mC_{ds}C_{ds}T_{ds}G_{ks}G_{es}{}^mC_{ks}G_{es}{}^mC_k$ | 96 | 3305 |
| 1207387 | 2010 | 2025 | 7398 | 7413 | $T_{ks}G_{ks}A_{ds}G_{ds}T_{ds}T_{ds}{}^mC_{ds}{}^mC_{ds}T_{ds}G_{ds}{}^mC_{ds}G_{ks}T_{es}T_{ks}A_{es}T_k$ | 24 | 3913 |
| 1207395 | 2019 | 2034 | 7407 | 7422 | $G_{ks}{}^mC_{ks}A_{ds}{}^mC_{ds}T_{ds}T_{ds}T_{ds}A_{ds}T_{ds}G_{ds}A_{ks}G_{es}T_{ks}T_{es}{}^mC_k$ | 26 | 3000 |
| 1207403 | 141 | 156 | 508 | 523 | $T_{ks}G_{ks}C_{ks}T_{ds}{}^mC_{ds}T_{ds}T_{ds}{}^mC_{ds}A_{ds}G_{ds}{}^mC_{ds}T_{ds}T_{ks}T_{ks}G_{ks}T_e$ | 38 | 4950 |
| 1207411 | 149 | 164 | 516 | 531 | ${}^mC_{ks}G_{ks}A_{ks}{}^mC_{ds}T_{ds}G_{ds}T_{ds}G_{ds}T_{ds}G_{ds}{}^mC_{ds}T_{ds}{}^mC_{ks}T_{ks}T_{ks}{}^mC_e$ | 24 | 3419 |
| 1207419 | 157 | 172 | N/A | N/A | $A_{ks}G_{ks}T_{ks}G_{ds}A_{ds}G_{ds}A_{ds}A_{ds}A_{ds}{}^mC_{ds}G_{ds}A_{ds}{}^mC_{ds}T_{ks}G_{ks}T_{ks}G_e$ | 25 | 2502 |
| 1207427 | 214 | 229 | 3565 | 3580 | $T_{ks}T_{ks}T_{ks}G_{ds}T_{ds}G_{ds}G_{ds}T_{ds}A_{ds}{}^mC_{ds}A_{ds}G_{ds}T_{ks}T_{ks}GTC_e$ | 31 | 2887 |
| 1207435 | 222 | 237 | 3573 | 3588 | $T_{ks}G_{ks}G_{ks}G_{ds}T_{ds}G_{ds}{}^mC_{ds}A_{ds}T_{ds}T_{ds}T_{ds}G_{ds}T_{ks}G_{ks}G_{ks}T_e$ | 53 | 3421 |
| 1207443 | 1782 | 1797 | 7170 | 7185 | $A_{ks}T_{ks}G_{ks}{}^mC_{ds}{}^mC_{ds}T_{ds}T_{ds}G_{ds}{}^mC_{ds}A_{ds}G_{ds}G_{ds}G_{ks}T_{ks}G_{ks}A_e$ | 46 | 4947 |
| 1207451 | 1790 | 1805 | 7178 | 7193 | $A_{ks}G_{ks}{}^mC_{ks}T_{ds}G_{ds}A_{ds}T_{ds}G_{ds}A_{ds}A_{ds}T_{ds}G_{ds}{}^mC_{ds}T_{ks}T_{ks}T_{ks}G_e$ | 49 | 3831 |
| 1207459 | 1896 | 1911 | 7284 | 7299 | $G_{ks}A_{ks}G_{ks}T_{ds}{}^mC_{ds}{}^mC_{ds}{}^mC_{ds}T_{ds}G_{ds}A_{ds}G_{ds}{}^mC_{ds}A_{ks}A_{ks}T_{ks}{}^mC_e$ | 33 | 3834 |

TABLE 79-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207467 | 1904 | 1919 | 7292 | 7307 | $G_{ks}G_{ks}A_{ks}A_{ds}A_{ds}G_{ds}A_{ds}T_{ds}G_{ds}A_{ds}G_{ds}T_{ds}{}^mC_{ks}{}^mC_{ks}{}^mC_{ks}T_e$ | 38 | 2921 |
| 1207475 | 1919 | 1934 | 7307 | 7322 | $G_{ks}G_{ks}A_{ks}A_{ds}T_{ds}{}^mC_{ds}A_{ds}{}^mC_{ds}{}^mC_{ds}A_{ds}A_{ds}G_{ds}G_{ks}A_{ks}G_{ks}G_e$ | 16 | 3226 |
| 1207483 | 1927 | 1942 | 7315 | 7330 | ${}^mC_{ks}T_{ks}{}^mC_{ks}A_{ds}{}^mC_{ds}T_{ds}G_{ds}{}^mC_{ds}G_{ds}G_{ds}A_{ds}A_{ds}T_{ks}{}^mC_{ks}A_{ks}{}^mC_e$ | 22 | 3835 |
| 1207491 | 1935 | 1950 | 7323 | 7338 | $G_{ks}{}^mC_{ks}{}^mC_{ks}A_{ds}{}^mC_{ds}T_{ds}{}^mC_{ds}T_{ds}{}^mC_{ds}T_{ds}{}^mC_{ds}A_{ds}{}^mC_{ks}T_{ks}G_{ks}{}^mC_e$ | 22 | 4967 |
| 1207499 | 2005 | 2020 | 7393 | 7408 | $T_{ks}{}^mC_{ks}{}^mC_{ks}T_{ds}G_{ds}{}^mC_{ds}G_{ds}{}^mC_{ds}{}^mC_{ds}A_{ds}T_{ds}{}^mC_{ds}{}^mC_{ks}T_{ks}G_{ks}G_e$ | 21 | 3533 |
| 1207507 | 2013 | 2028 | 7401 | 7416 | $T_{ks}A_{ks}T_{ks}T_{ds}G_{ds}A_{ds}G_{ds}T_{ds}T_{ds}{}^mC_{ds}{}^mC_{ds}T_{ds}G_{ks}{}^mC_{ks}G_{ks}{}^mC_e$ | 26 | 2617 |
| 1207515 | 2022 | 2037 | 7410 | 7425 | $A_{ks}A_{ks}A_{ks}G_{ds}{}^mC_{ds}A_{ds}{}^mC_{ds}T_{ds}T_{ds}T_{ds}A_{ds}T_{ds}T_{ks}G_{ks}A_{ks}G_e$ | 21 | 3229 |

TABLE 80

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 19 | 3837 |
| 1206476 | 144 | 159 | 511 | 526 | $G_{ks}T_{ks}G_{ks}T_{ds}G_{ds}{}^mC_{ds}T_{ds}{}^mC_{ds}T_{ds}T_{ds}{}^mC_{ds}A_{ds}G_{ds}C_{ks}T_{ks}T_k$ | 24 | 4951 |
| 1206481 | 1784 | 1799 | 7172 | 7187 | $T_{ks}G_{ks}A_{ks}T_{ds}G_{ds}C_{ds}C_{ds}T_{ds}T_{ds}G_{ds}C_{ds}A_{ds}G_{ds}G_{ks}G_{ks}T_k$ | 42 | 4969 |
| 1206505 | 1917 | 1932 | 7305 | 7320 | $A_{ks}A_{ks}T_{ks}{}^mC_{ds}A_{ds}{}^mC_{ds}{}^mC_{ds}A_{ds}A_{ds}G_{ds}G_{ds}A_{ds}G_{ds}G_{ks}G_{ks}A_k$ | 27 | 4956 |
| 1206508 | 1936 | 1951 | 7324 | 7339 | $A_{ks}G_{ks}{}^mC_{ks}{}^mC_{ds}A_{ds}{}^mC_{ds}T_{ds}{}^mC_{ds}T_{ds}{}^mC_{ds}T_{ds}{}^mC_{ds}A_{ds}{}^mC_{ks}T_{ks}G_k$ | 9 | 4961 |
| 1206903 | 146 | 161 | 513 | 528 | ${}^mC_{ks}T_{es}G_{ks}T_{ds}G_{ds}{}^mC_{ds}T_{ds}{}^mC_{ds}T_{ds}T_{ds}{}^mC_{ds}T_{es}A_{es}G_{ks}{}^mC_k$ | 14 | 3190 |
| 1206911 | 154 | 169 | N/A | N/A | $G_{ks}A_{es}G_{ks}A_{ds}A_{ds}{}^mC_{ds}G_{ds}G_{ds}A_{ds}{}^mC_{ds}T_{ds}G_{ds}T_{ds}G_{es}T_{es}G_{ks}{}^mC_k$ | 29 | 3799 |
| 1206919 | 211 | 226 | 3562 | 3577 | $G_{ks}T_{es}G_{ks}G_{ds}T_{ds}A_{ds}{}^mC_{ds}A_{ds}G_{ds}{}^mC_{ds}T_{ds}G_{ds}C_{es}C_{es}G_{ks}G_k$ | 24 | 4973 |
| 1206927 | 219 | 234 | 3570 | 3585 | $G_{ks}T_{es}A_{ks}{}^mC_{ds}A_{ds}T_{ds}T_{ds}T_{ds}G_{ds}T_{ds}G_{ds}G_{ds}T_{es}A_{es}{}^mC_{ks}A_k$ | 27 | 3192 |
| 1206935 | 1779 | 1794 | 7167 | 7182 | ${}^mC_{ks}{}^mC_{es}T_{ks}T_{ds}G_{ds}{}^mC_{ds}A_{ds}G_{ds}G_{ds}G_{ds}T_{ds}G_{ds}A_{es}G_{es}{}^mC_{ks}{}^mC_k$ | 51 | 4974 |
| 1206943 | 1787 | 1802 | 7175 | 7190 | $T_{ks}G_{es}A_{ks}T_{ds}G_{ds}A_{ds}T_{ds}G_{ds}{}^mC_{ds}{}^mC_{ds}T_{ds}T_{ds}G_{es}C_{es}A_{ks}G_k$ | 36 | 4975 |

TABLE 80-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206951 | 1893 | 1908 | 7281 | 7296 | $T_{ks}C_{es}{}^mC_{ks}C_{ds}T_{ds}G_{ds}A_{ds}A_{ds}G_{ds}C_{ds}A_{ds}A_{ds}T_{ds}{}^mC_{es}A_{es}G_{ks}G_k$ | 46 | 3606 |
| 1206959 | 1901 | 1916 | 7289 | 7304 | $A_{ks}A_{es}G_{ks}A_{ds}T_{ds}G_{ds}A_{ds}G_{ds}T_{ds}{}^mC_{ds}{}^mC_{ds}{}^mC_{ds}T_{es}G_{es}A_{ks}G_k$ | 34 | 2691 |
| 1206967 | 1916 | 1931 | 7304 | 7319 | $A_{ks}T_{es}{}^mC_{ks}A_{ds}{}^mC_{ds}{}^mC_{ds}A_{ds}A_{ds}G_{ds}G_{ds}A_{ds}G_{ds}G_{es}G_{es}A_{ks}A_k$ | 14 | 4966 |
| 1206975 | 1924 | 1939 | 7312 | 7327 | $A_{ks}{}^mC_{es}T_{ks}G_{ds}{}^mC_{ds}G_{ds}G_{ds}A_{ds}A_{ds}T_{ds}{}^mC_{ds}A_{ds}{}^mC_{es}{}^mC_{es}A_{ks}A_k$ | 13 | 3607 |
| 1206983 | 1932 | 1947 | 7320 | 7335 | $A_{ks}{}^mC_{es}T_{ks}{}^mC_{ds}T_{ds}{}^mC_{ds}T_{ds}{}^mC_{ds}A_{ds}C_{ds}T_{ds}G_{ds}C_{es}G_{es}G_{ks}A_k$ | 9 | 4976 |
| 1206991 | 2002 | 2017 | 7390 | 7405 | $T_{ks}G_{es}{}^mC_{ks}G_{ds}{}^mC_{ds}{}^mC_{ds}A_{ds}T_{ds}{}^mC_{ds}{}^mC_{ds}T_{ds}G_{ds}G_{es}C_{es}G_{ks}C_k$ | 64 | 3305 |
| 1206999 | 2010 | 2025 | 7398 | 7413 | $T_{ks}G_{es}A_{ks}G_{ds}T_{ds}{}^mC_{ds}{}^mC_{ds}T_{ds}G_{ds}{}^mC_{ds}G_{ds}{}^mC_{es}{}^mC_{es}A_{ks}T_k$ | 12 | 3913 |
| 1207007 | 2019 | 2034 | 7407 | 7422 | $G_{ks}{}^mC_{es}A_{ks}{}^mC_{ds}T_{ds}T_{ds}T_{ds}A_{ds}T_{ds}T_{ds}G_{ds}A_{ds}G_{es}T_{ks}{}^mC_k$ | 7 | 3000 |
| 1207026 | 141 | 156 | 508 | 523 | $T_{ks}G_{ks}C_{ds}T_{ds}C_{ds}T_{ds}T_{ds}C_{ds}A_{ds}G_{ds}C_{ds}T_{es}T_{es}T_{es}G_{ks}T_k$ | 49 | 4950 |
| 1207034 | 149 | 164 | 516 | 531 | ${}^mC_{ks}G_{ks}A_{ds}{}^mC_{ds}T_{ds}G_{ds}T_{ds}G_{ds}T_{ds}G_{ds}{}^mC_{ds}T_{es}{}^mC_{es}T_{ks}{}^mC_k$ | 36 | 3419 |
| 1207042 | 157 | 172 | N/A | N/A | $A_{ks}G_{ks}T_{ds}G_{ds}A_{ds}G_{ds}A_{ds}A_{ds}{}^mC_{ds}G_{ds}A_{ds}{}^mC_{es}T_{es}G_{es}T_{ks}G_k$ | 42 | 2502 |
| 1207050 | 214 | 229 | 3565 | 3580 | $T_{ks}T_{ks}T_{ds}G_{ds}T_{ds}G_{ds}G_{ds}T_{ds}A_{ds}{}^mC_{ds}A_{ds}G_{es}{}^mC_{es}T_{es}G_{ks}{}^mC_k$ | 43 | 2887 |
| 1207058 | 222 | 237 | 3573 | 3588 | $T_{ks}G_{ks}G_{ds}G_{ds}T_{ds}A_{ds}A_{ds}{}^mC_{ds}A_{ds}T_{ds}T_{ds}T_{ds}G_{es}T_{es}G_{es}G_{ks}T_k$ | 25 | 3421 |
| 1207078 | 1782 | 1797 | 7170 | 7185 | $A_{ks}T_{ks}G_{ds}{}^mC_{ds}{}^mC_{ds}T_{ds}T_{ds}G_{ds}{}^mC_{ds}A_{ds}G_{ds}G_{es}G_{es}T_{es}G_{ks}A_k$ | 52 | 4947 |
| 1207087 | 1790 | 1805 | 7178 | 7193 | $A_{ks}G_{ks}C_{ds}T_{ds}G_{ds}A_{ds}T_{ds}G_{ds}A_{ds}T_{ds}G_{ds}{}^mC_{es}{}^mC_{es}$ | 42 | 3831 |
| 1207095 | 1896 | 1911 | 7284 | 7299 | $G_{ks}A_{ks}G_{ds}T_{ds}{}^mC_{ds}{}^mC_{ds}{}^mC_{ds}T_{ds}G_{ds}A_{ds}G_{ds}{}^mC_{es}A_{es}A_{es}T_{ks}{}^mC_k$ | 25 | 3834 |
| 1207103 | 1904 | 1919 | 7292 | 7307 | $G_{ks}G_{ks}A_{ds}A_{ds}A_{ds}G_{ds}A_{ds}T_{ds}G_{ds}A_{ds}G_{ds}T_{es}{}^mC_{es}{}^mC_{es}{}^mC_{ks}T_k$ | 31 | 2921 |
| 1207111 | 1919 | 1934 | 7307 | 7322 | $G_{ks}G_{ks}A_{ds}A_{ds}T_{ds}C_{ds}C_{ds}C_{ds}A_{ds}A_{ds}G_{es}G_{es}A_{es}G_{ks}G_k$ | 9 | 3226 |
| 1207120 | 1927 | 1942 | 7315 | 7330 | ${}^mC_{ks}T_{ks}{}^mC_{ds}A_{ds}{}^mC_{ds}T_{ds}G_{ds}{}^mC_{ds}G_{ds}G_{ds}A_{ds}A_{es}T_{es}C_{es}A_{ks}C_k$ | 10 | 3835 |
| 1207137 | 1935 | 1950 | 7323 | 7338 | $G_{ks}{}^mC_{ks}{}^mC_{ds}A_{ds}{}^mC_{ds}T_{ds}{}^mC_{ds}T_{ds}{}^mC_{ds}T_{ds}{}^mC_{ds}T_{ds}C_{ds}A_{es}C_{es}T_{es}G_{ks}C_k$ | 19 | 4967 |
| 1207148 | 2005 | 2020 | 7393 | 7408 | $T_{ks}{}^mC_{ks}{}^mC_{ds}T_{ds}G_{ds}{}^mC_{ds}G_{ds}{}^mC_{ds}{}^mC_{ds}A_{ds}T_{ds}{}^mC_{es}{}^mC_{es}T_{es}G_{ks}G_k$ | 13 | 3533 |
| 1207156 | 2013 | 2028 | 7401 | 7416 | $T_{ks}A_{ks}T_{ds}G_{ds}A_{ds}G_{ds}T_{ds}T_{ds}{}^mC_{ds}{}^mC_{ds}T_{es}G_{es}{}^mC_{es}G_{ks}{}^mC_k$ | 9 | 2617 |
| 1207164 | 2022 | 2037 | 7410 | 7425 | $A_{ks}A_{ks}A_{ds}G_{ds}C_{ds}A_{ds}C_{ds}T_{ds}T_{ds}T_{ds}A_{ds}T_{es}T_{es}G_{es}A_{ks}G_k$ | 5 | 3229 |

TABLE 80-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207172 | 144 | 159 | 511 | 526 | $G_{ks}T_{ks}G_{ds}T_{ds}G_{ds}{}^mC_{ds}T_{ds}{}^mC_{ds}T_{ds}T_{ds}{}^mC_{ds}A_{es}G_{ks}{}^mC_{es}T_{ks}T_e$ | 14 | 4951 |
| 1207180 | 152 | 167 | N/A | N/A | $G_{ks}A_{ks}A_{ds}{}^mC_{ds}G_{ds}A_{ds}{}^mC_{ds}T_{ds}G_{ds}G_{ds}T_{es}G_{ks}{}^mC_{es}T_{ks}{}^mC_e$ | 32 | 3647 |
| 1207188 | 209 | 224 | 3560 | 3575 | $G_{ks}G_{ks}T_{ds}A_{ds}{}^mC_{ds}A_{ds}G_{ds}{}^mC_{ds}T_{ds}G_{ds}{}^mC_{ds}{}^mC_{es}G_{ks}G_{es}T_{ks}G_e$ | 23 | 4952 |
| 1207196 | 217 | 232 | 3568 | 3583 | $A_{ks}C_{ks}A_{ds}T_{ds}T_{ds}T_{ds}G_{ds}T_{ds}G_{ds}G_{ds}T_{ds}A_{es}{}^mC_{ks}A_{es}G_{ks}{}^mC_e$ | 13 | 3114 |
| 1207204 | 1777 | 1792 | 7165 | 7180 | $T_{ks}T_{ks}G_{ds}{}^mC_{ds}A_{ds}G_{ds}G_{ds}G_{ds}T_{ds}G_{ds}A_{ds}G_{es}C_{ks}C_{es}G_{ks}G_e$ | 50 | 3375 |
| 1207212 | 1785 | 1800 | 7173 | 7188 | $A_{ks}T_{ks}G_{ds}A_{ds}T_{ds}G_{ds}G_{ds}C_{ds}C_{ds}T_{ds}T_{ds}G_{ds}C_{es}A_{ks}G_{es}G_{ks}G_e$ | 25 | 3603 |
| 1207220 | 1793 | 1808 | 7181 | 7196 | $C_{ks}C_{ks}C_{ds}A_{ds}G_{ds}{}^mC_{ds}T_{ds}G_{ds}A_{ds}T_{ds}G_{ds}A_{es}T_{ks}G_{es}{}^mC_{ks}{}^mC_e$ | 26 | 4953 |
| 1207228 | 1899 | 1914 | 7287 | 7302 | $G_{ks}A_{ks}T_{ds}G_{ds}A_{ds}G_{ds}T_{ds}{}^mC_{ds}{}^mC_{ds}{}^mC_{ds}T_{ds}G_{es}A_{ks}G_{es}{}^mC_{ks}A_e$ | 6 | 2537 |
| 1207236 | 1914 | 1929 | 7302 | 7317 | ${}^mC_{ks}A_{ks}{}^mC_{ds}{}^mC_{ds}A_{ds}A_{ds}A_{ds}G_{ds}G_{ds}A_{ds}G_{ds}G_{es}A_{ks}A_{es}A_{ks}G_e$ | 12 | 4954 |
| 1207244 | 1922 | 1937 | 7310 | 7325 | $T_{ks}G_{ks}{}^mC_{ds}G_{ds}G_{ds}A_{ds}A_{ds}T_{ds}{}^mC_{ds}A_{ds}{}^mC_{ds}{}^mC_{es}A_{ks}A_{es}G_{ks}G_e$ | 17 | 3455 |
| 1207252 | 1930 | 1945 | 7318 | 7333 | $T_{ks}{}^mC_{ks}T_{ds}{}^mC_{ds}T_{ds}{}^mC_{ds}A_{ds}{}^mC_{ds}T_{ds}G_{ds}{}^mC_{ds}G_{es}{}^mC_{ks}A_{es}A_{ks}T_e$ | 16 | 4955 |
| 1207260 | 2000 | 2015 | 7388 | 7403 | ${}^mC_{ks}G_{ks}{}^mC_{ds}{}^mC_{ds}A_{ds}T_{ds}{}^mC_{ds}{}^mC_{ds}T_{ds}G_{ds}G_{ds}{}^mC_{es}G_{ks}{}^mC_{es}G_{ks}G_e$ | 77 | 3228 |
| 1207268 | 2008 | 2023 | 7396 | 7411 | $A_{ks}G_{ks}T_{ds}T_{ds}{}^mC_{ds}{}^mC_{ds}T_{ds}G_{ds}{}^mC_{ds}G_{ds}{}^mC_{ds}{}^mC_{es}A_{ks}T_{es}{}^mC_{ks}{}^mC_e$ | 18 | 3761 |
| 1207276 | 2017 | 2032 | 7405 | 7420 | $A_{ks}C_{ks}T_{ds}T_{ds}T_{ds}A_{ds}T_{ds}G_{ds}G_{ds}A_{ds}G_{ds}T_{es}T_{ks}{}^mC_{es}{}^mC_{ks}T_e$ | 8 | 2848 |
| 1207284 | 2031 | 2046 | 7419 | 7434 | $A_{ks}G_{ks}{}^mC_{ds}A_{ds}T_{ds}T_{ds}T_{ds}T_{ds}{}^mC_{ds}A_{ds}A_{ds}A_{es}G_{ks}{}^mC_{es}A_{ks}{}^mC_e$ | 20 | 3458 |
| 1207292 | 147 | 162 | 514 | 529 | $A_{ks}{}^mC_{ks}T_{ds}G_{ds}T_{ds}G_{ds}T_{ds}G_{ds}{}^mC_{ds}T_{ds}{}^mC_{ds}T_{ks}T_{es}{}^mC_{ks}A_{es}G_k$ | 36 | 3267 |
| 1207300 | 155 | 170 | N/A | N/A | $T_{ks}G_{ks}A_{ds}G_{ds}A_{ds}A_{ds}{}^mC_{ds}G_{ds}A_{ds}{}^mC_{ds}T_{ds}G_{es}T_{ks}G_{es}T_{es}G_k$ | 25 | 3875 |
| 1207308 | 212 | 227 | 3563 | 3578 | $T_{ks}G_{ks}T_{ds}G_{ds}G_{ds}T_{ds}A_{ds}C_{ds}A_{ds}G_{ds}C_{ds}T_{ks}G_{es}{}^mC_{ks}{}^mC_{es}G_k$ | 18 | 2734 |
| 1207316 | 220 | 235 | 3571 | 3586 | $G_{ks}G_{ks}T_{ds}A_{ds}C_{ds}A_{ds}T_{ds}T_{ds}T_{ds}G_{ds}T_{ds}G_{ks}G_{es}T_{ks}A_{es}{}^mC_k$ | 49 | 3269 |
| 1207324 | 1780 | 1795 | 7168 | 7183 | $G_{ks}{}^mC_{ks}{}^mC_{ds}T_{ds}T_{ds}G_{ds}{}^mC_{ds}A_{ds}G_{ds}G_{ds}G_{ds}T_{ks}G_{es}A_{ks}G_{es}{}^mC_k$ | 47 | 3451 |
| 1207332 | 1788 | 1803 | 7176 | 7191 | $C_{ks}T_{ks}G_{ds}A_{ds}T_{ds}G_{ds}A_{ds}T_{ds}G_{ds}G_{ds}C_{ds}C_{ds}T_{ks}T_{es}G_{ks}{}^mC_{es}A_k$ | 29 | 3679 |
| 1207340 | 1894 | 1909 | 7282 | 7297 | $G_{ks}T_{ks}{}^mC_{ds}{}^mC_{ds}{}^mC_{ds}T_{ds}G_{ds}A_{ds}G_{ds}{}^mC_{ds}A_{ds}A_{ks}T_{es}{}^mC_{ks}A_{es}G_k$ | 57 | 3682 |
| 1207348 | 1902 | 1917 | 7290 | 7305 | $A_{ks}A_{ks}A_{ds}G_{ds}A_{ds}T_{ds}G_{ds}A_{ds}G_{ds}T_{ds}C_{ds}C_{ks}C_{es}T_{ks}G_{es}A_k$ | 32 | 2768 |

TABLE 80-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207356 | 1917 | 1932 | 7305 | 7320 | $A_{ks}A_{ks}T_{ds}{}^mC_{ds}A_{ds}{}^mC_{ds}{}^mC_{ds}A_{ds}A_{ds}G_{ds}G_{ds}A_{ks}G_{es}G_{ks}G_{es}A_k$ | 57 | 4956 |
| 1207364 | 1925 | 1940 | 7313 | 7328 | ${}^mC_{ks}A_{ks}{}^mC_{ds}T_{ds}G_{ds}{}^mC_{ds}G_{ds}G_{ds}A_{ds}A_{ds}T_{ds}{}^mC_{ks}A_{es}{}^mC_{ks}{}^mC_{es}A_k$ | 14 | 3683 |
| 1207372 | 1933 | 1948 | 7321 | 7336 | $C_{ks}A_{ks}C_{ds}T_{ds}C_{ds}T_{ds}C_{ds}T_{ds}C_{ds}A_{ds}{}^mC_{ds}T_{ks}G_{es}{}^mC_{ks}G_{es}G_k$ | 20 | 4957 |
| 1207380 | 2003 | 2018 | 7391 | 7406 | $C_{ks}T_{ks}G_{ds}C_{ds}G_{ds}{}^mC_{ds}C_{ds}A_{ds}T_{ds}C_{ds}{}^mC_{ds}T_{ks}G_{es}G_{ks}{}^mC_{es}G_k$ | 50 | 3381 |
| 1207388 | 2011 | 2026 | 7399 | 7414 | $T_{ks}T_{ks}G_{ds}A_{ds}G_{ds}T_{ds}T_{ds}{}^mC_{ds}{}^mC_{ds}T_{ds}G_{ds}{}^mC_{ks}G_{es}{}^mC_{ks}{}^mC_{es}A_k$ | 27 | 2463 |
| 1207396 | 2020 | 2035 | 7408 | 7423 | $A_{ks}G_{ks}{}^mC_{ds}A_{ds}{}^mC_{ds}T_{ds}T_{ds}T_{ds}A_{ds}T_{ds}T_{ds}G_{ks}A_{es}G_{ks}T_{es}T_k$ | 17 | 3076 |
| 1207404 | 142 | 157 | 509 | 524 | $G_{ks}T_{ks}G_{ks}{}^mC_{ds}T_{ds}{}^mC_{ds}T_{ds}T_{ds}{}^mC_{ds}A_{ds}G_{ds}{}^mC_{ds}T_{ks}T_{ks}T_{ks}G_e$ | 33 | 4958 |
| 1207412 | 150 | 165 | N/A | N/A | $A_{ks}{}^mC_{ks}G_{ks}A_{ds}{}^mC_{ds}T_{ds}G_{ds}T_{ds}G_{ds}T_{ds}G_{ds}G_{ds}C_{ds}T_{ks}C_{ks}T_{ks}T_e$ | 24 | 3495 |
| 1207420 | 158 | 173 | N/A | N/A | $C_{ks}A_{ks}G_{ks}T_{ds}G_{ds}A_{ds}G_{ds}A_{ds}A_{ds}C_{ds}G_{ds}A_{ds}C_{ks}T_{fes}G_{ks}T_e$ | 20 | 2579 |
| 1207428 | 215 | 230 | 3566 | 3581 | $A_{ks}T_{ks}T_{ks}T_{ds}G_{ds}T_{ds}G_{ds}G_{ds}T_{ds}A_{ds}C_{ds}A_{ds}G_{ks}{}^mC_{ks}T_{ks}G_e$ | 27 | 2963 |
| 1207436 | 223 | 238 | 3574 | 3589 | $G_{ks}T_{ks}G_{ks}G_{ds}G_{ds}T_{ds}A_{ds}{}^mC_{ds}A_{ds}T_{ds}T_{ds}T_{ds}G_{ks}T_{ks}G_{ks}G_e$ | 25 | 3497 |
| 1207444 | 1783 | 1798 | 7171 | 7186 | $G_{ks}A_{ks}T_{ks}G_{ds}C_{ds}C_{ds}T_{ds}T_{ds}G_{ds}C_{ds}A_{ds}G_{ds}G_{ks}G_{ks}T_{ks}G_e$ | 43 | 4959 |
| 1207452 | 1791 | 1806 | 7179 | 7194 | ${}^mC_{ks}A_{ks}G_{ks}{}^mC_{ds}T_{ds}G_{ds}A_{ds}T_{ds}G_{ds}G_{ds}A_{ds}T_{ds}G_{ds}{}^mC_{ks}{}^mC_{ks}T_{ks}T_e$ | 24 | 4960 |
| 1207460 | 1897 | 1912 | 7285 | 7300 | $T_{ks}G_{ks}A_{ks}G_{ds}T_{ds}{}^mC_{ds}{}^mC_{ds}{}^mC_{ds}T_{ds}G_{ds}A_{ds}G_{ds}C_{ks}A_{ks}A_{ks}T_e$ | 36 | 3910 |
| 1207468 | 1905 | 1920 | 7293 | 7308 | $G_{ks}G_{ks}G_{ks}A_{ds}A_{ds}A_{ds}G_{ds}A_{ds}T_{ds}G_{ds}A_{ds}G_{ds}T_{ks}{}^mC_{ks}{}^mC_{ks}{}^mC_e$ | 54 | 2997 |
| 1207476 | 1920 | 1935 | 7308 | 7323 | ${}^mC_{ks}G_{ks}G_{ks}A_{ds}A_{ds}T_{ds}{}^mC_{ds}A_{ds}{}^mC_{ds}{}^mC_{ds}A_{ds}A_{ds}G_{ks}G_{ks}A_{ks}G_e$ | 22 | 3303 |
| 1207484 | 1928 | 1943 | 7316 | 7331 | $T_{ks}C_{ks}T_{ks}{}^mC_{ds}A_{ds}C_{ds}T_{ds}G_{ds}C_{ds}G_{ds}G_{ds}A_{ds}A_{ks}T_{ks}C_{ks}A_e$ | 9 | 3911 |
| 1207492 | 1936 | 1951 | 7324 | 7339 | $A_{ks}G_{ks}{}^mC_{ks}{}^mC_{ds}A_{ds}{}^mC_{ds}T_{ds}{}^mC_{ds}T_{ds}{}^mC_{ds}T_{ds}{}^mC_{ds}A_{ks}{}^mC_{ks}T_{ks}G_e$ | 40 | 4961 |
| 1207500 | 2006 | 2021 | 7394 | 7409 | $T_{ks}T_{ks}{}^mC_{ks}{}^mC_{ds}T_{ds}G_{ds}{}^mC_{ds}G_{ds}G_{ds}{}^mC_{ds}{}^mC_{ds}A_{ds}T_{es}{}^mC_{ks}T_{ks}G_e$ | 33 | 3609 |
| 1207508 | 2014 | 2029 | 7402 | 7417 | $T_{ks}T_{ks}A_{ks}T_{ds}T_{ds}G_{ds}A_{ds}G_{ds}T_{ds}T_{ds}{}^mC_{ds}{}^mC_{ds}T_{ks}G_{ks}{}^mC_{ks}G_e$ | 17 | 2694 |
| 1207516 | 2023 | 2038 | 7411 | 7426 | ${}^mC_{ks}A_{ks}A_{ks}A_{ds}G_{ds}{}^mC_{ds}A_{ds}{}^mC_{ds}T_{ds}T_{ds}T_{ds}A_{ds}T_{ks}T_{ks}G_{ks}A_e$ | 5 | 3306 |

TABLE 81

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 13 | 3837 |
| 1206496 | 208 | 223 | 3559 | 3574 | $G_{ks}T_{ks}A_{ks}{}^mC_{ds}A_{ds}G_{ds}{}^mC_{ds}T_{ds}G_{ds}{}^mC_{ds}{}^mC_{ds}G_{ds}G_{ds}T_{ks}G_{ks}G_k$ | 27 | 4968 |
| 1206501 | 1786 | 1801 | 7174 | 7189 | $G_{ks}A_{ks}T_{ks}G_{ds}A_{ds}G_{ds}{}^mC_{ds}{}^mC_{ds}T_{ds}T_{ds}G_{ds}{}^mC_{ds}A_{ks}G_{ks}G_k$ | 48 | 4963 |
| 1206506 | 1918 | 1933 | 7306 | 7321 | $G_{ks}A_{ks}A_{ks}T_{ds}{}^mC_{ds}A_{ds}{}^mC_{ds}{}^mC_{ds}A_{ds}A_{ds}G_{ds}G_{ds}A_{ds}G_{ks}G_{ks}G_k$ | 10 | 4965 |
| 1206509 | 1937 | 1952 | 7325 | 7340 | ${}^mC_{ks}A_{ks}G_{ks}{}^mC_{ds}{}^mC_{ds}A_{ds}{}^mC_{ds}T_{ds}{}^mC_{ds}T_{ds}{}^mC_{ds}T_{ds}{}^mC_{ds}A_{ks}{}^mC_{ks}T_k$ | 6 | 4972 |
| 1206904 | 147 | 162 | 514 | 529 | $A_{ks}{}^mC_{es}T_{ks}G_{ds}T_{ds}G_{ds}T_{ds}G_{ds}{}^mC_{ds}T_{ds}{}^mC_{ds}T_{ds}T_{es}{}^mC_{es}A_{ks}G_k$ | 23 | 3267 |
| 1206912 | 155 | 170 | N/A | N/A | $T_{ks}G_{es}A_{ks}G_{ds}A_{ds}A_{ds}{}^mC_{ds}G_{ds}A_{ds}{}^mC_{ds}T_{ds}G_{ds}T_{es}G_{es}T_{ks}G_k$ | 23 | 3875 |
| 1206920 | 212 | 227 | 3563 | 3578 | $T_{ks}G_{es}T_{ks}G_{ds}T_{ds}G_{ds}{}^mC_{ds}A_{ds}A_{ds}G_{ds}{}^mC_{ds}T_{ds}G_{es}{}^mC_{es}{}^mC_{ks}G_k$ | 13 | 2734 |
| 1206928 | 220 | 235 | 3571 | 3586 | $G_{ks}G_{es}T_{ks}A_{ds}{}^mC_{ds}A_{ds}T_{ds}T_{ds}T_{ds}G_{ds}T_{ds}G_{ds}G_{es}T_{es}A_{ks}{}^mC_k$ | 45 | 3269 |
| 1206936 | 1780 | 1795 | 7168 | 7183 | $G_{ks}{}^mC_{es}{}^mC_{ks}T_{ds}T_{ds}G_{ds}{}^mC_{ds}A_{ds}G_{ds}G_{ds}G_{ds}T_{ds}G_{es}A_{Es}G_{ks}{}^mC_k$ | 48 | 3451 |
| 1206944 | 1788 | 1803 | 7176 | 7191 | ${}^mC_{ks}T_{es}G_{ks}A_{ds}T_{ds}G_{ds}A_{ds}T_{ds}G_{ds}{}^mC_{ds}{}^mC_{ds}T_{ds}T_{es}G_{es}{}^mC_{ks}A_k$ | 46 | 3679 |
| 1206952 | 1894 | 1909 | 7282 | 7297 | $G_{ks}T_{es}{}^mC_{ks}{}^mC_{ks}{}^mC_{ds}T_{ds}G_{ds}A_{ds}G_{ds}{}^mC_{ds}A_{ds}A_{ds}T_{es}{}^mC_{es}A_{ks}G_k$ | 19 | 3682 |
| 1206960 | 1902 | 1917 | 7290 | 7305 | $A_{ks}A_{es}A_{ks}G_{ds}A_{ds}T_{ds}G_{ds}A_{ds}A_{ds}G_{ds}T_{ds}{}^mC_{ds}{}^mC_{ds}{}^mC_{es}T_{es}G_{ks}A_k$ | 17 | 2768 |
| 1206968 | 1917 | 1932 | 7305 | 7320 | $A_{ks}A_{es}T_{ks}{}^mC_{ds}A_{ds}{}^mC_{ds}{}^mC_{ds}A_{ds}A_{ds}G_{ds}G_{ds}A_{ds}G_{es}G_{es}G_{ks}A_k$ | 41 | 4956 |
| 1206976 | 1925 | 1940 | 7313 | 7328 | ${}^mC_{ks}A_{es}{}^mC_{ks}T_{ds}G_{ds}{}^mC_{ds}G_{ds}G_{ds}A_{ds}A_{ds}T_{ds}{}^mC_{ds}A_{es}{}^mC_{es}{}^mC_{ks}A_k$ | 29 | 3683 |
| 1206984 | 1933 | 1948 | 7321 | 7336 | ${}^mC_{ks}A_{es}{}^mC_{ks}T_{ds}{}^mC_{ds}T_{ds}{}^mC_{ds}T_{ds}{}^mC_{ds}A_{ds}{}^mC_{ds}T_{ds}G_{es}{}^mC_{es}G_{ks}G_k$ | N.D | 4957 |
| 1206992 | 2003 | 2018 | 7391 | 7406 | ${}^mC_{ks}T_{es}G_{ks}{}^mC_{ds}G_{ds}{}^mC_{ds}{}^mC_{ds}A_{ds}T_{ds}{}^mC_{ds}{}^mC_{ds}T_{ds}G_{es}G_{es}{}^mC_{ks}G_k$ | 77 | 3381 |
| 1207000 | 2011 | 2026 | 7399 | 7414 | $T_{ks}T_{es}G_{ks}A_{ds}G_{ds}T_{ds}T_{ds}{}^mC_{ds}{}^mC_{ds}T_{ds}G_{ds}{}^mC_{ds}G_{es}{}^mC_{es}{}^mC_{ks}A_k$ | 11 | 2463 |
| 1207008 | 2020 | 2035 | 7408 | 7423 | $A_{ks}G_{es}{}^mC_{ks}A_{ds}{}^mC_{ds}T_{ds}T_{ds}T_{ds}A_{ds}T_{ds}T_{ds}G_{ds}A_{es}G_{es}T_{ks}T_k$ | 5 | 3076 |
| 1207027 | 142 | 157 | 509 | 524 | $G_{ks}T_{ks}G_{ds}{}^mC_{ds}T_{ds}{}^mC_{ds}T_{ds}T_{ds}{}^mC_{ds}A_{ds}G_{ds}{}^mC_{es}T_{es}T_{es}T_{ks}G_k$ | 40 | 4958 |
| 1207035 | 150 | 165 | N/A | N/A | $A_{ks}{}^mC_{ks}G_{ds}A_{ds}{}^mC_{ds}T_{ds}G_{ds}T_{ds}G_{ds}T_{ds}G_{ds}{}^mC_{es}T_{es}{}^mC_{es}T_{ks}T_k$ | 35 | 3495 |
| 1207043 | 158 | 173 | N/A | N/A | ${}^mC_{ks}A_{ks}G_{ds}T_{ds}G_{ds}A_{ds}A_{ds}G_{ds}A_{ds}{}^mC_{ds}G_{ds}A_{es}{}^mC_{es}T_{es}G_{ks}T_k$ | 36 | 2579 |
| 1207051 | 215 | 230 | 3566 | 3581 | $A_{ks}T_{ks}T_{ds}T_{ds}G_{ds}T_{ds}G_{ds}G_{ds}T_{ds}A_{ds}{}^mC_{ds}A_{es}G_{es}{}^mC_{es}T_{ks}G_k$ | 43 | 2963 |
| 1207059 | 223 | 238 | 3574 | 3589 | $G_{ks}T_{ks}G_{ds}G_{ds}G_{ds}T_{ds}A_{ds}{}^mC_{ds}A_{ds}T_{ds}T_{ds}T_{es}G_{es}T_{es}G_{ks}G_k$ | 25 | 3497 |

TABLE 81-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207079 | 1783 | 1798 | 7171 | 7186 | $G_{ks}A_{ks}T_{ds}G_{ds}{}^mC_{ds}{}^mC_{ds}T_{ds}T_{ds}G_{ds}{}^mC_{ds}A_{ds}G_{es}G_{es}G_{es}T_{ks}G_k$ | 37 | 4959 |
| 1207088 | 1791 | 1806 | 7179 | 7194 | ${}^mC_{ks}A_{ks}G_{ds}{}^mC_{ds}T_{ds}G_{ds}A_{ds}T_{ds}G_{ds}A_{ds}T_{ds}G_{es}{}^mC_{es}{}^mC_{es}T_{ks}T_k$ | 40 | 4960 |
| 1207096 | 1897 | 1912 | 7285 | 7300 | $T_{ks}G_{ks}A_{ds}G_{ds}T_{ds}{}^mC_{ds}{}^mC_{ds}{}^mC_{ds}T_{ds}G_{ds}A_{ds}G_{es}{}^mC_{es}A_{es}A_{ks}T_k$ | 27 | 3910 |
| 1207104 | 1905 | 1920 | 7293 | 7308 | $G_{ks}G_{ks}G_{ds}A_{ds}A_{ds}A_{ds}G_{ds}A_{ds}T_{ds}G_{ds}A_{ds}G_{es}T_{es}{}^mC_{es}{}^mC_{ks}{}^mC_k$ | 31 | 2997 |
| 1207112 | 1920 | 1935 | 7308 | 7323 | ${}^mC_{ks}G_{ds}G_{ds}A_{ds}A_{ds}T_{ds}{}^mC_{ds}A_{ds}{}^mC_{ds}{}^mC_{ds}A_{ds}A_{es}G_{es}G_{es}A_{ks}G_k$ | 19 | 3303 |
| 1207123 | 1928 | 1943 | 7316 | 7331 | $T_{ks}{}^mC_{ks}T_{ds}{}^mC_{ds}A_{ds}{}^mC_{ds}T_{ds}G_{ds}{}^mC_{ds}G_{ds}G_{ds}A_{es}A_{es}T_{es}{}^mC_{ks}A_k$ | 7 | 3911 |
| 1207139 | 1936 | 1951 | 7324 | 7339 | $A_{ks}G_{ks}{}^mC_{ds}{}^mC_{ds}A_{ds}{}^mC_{ds}T_{ds}{}^mC_{ds}T_{ds}{}^mC_{ds}T_{ds}{}^mC_{es}A_{es}{}^mC_{es}T_{ks}G_k$ | 7 | 4961 |
| 1207149 | 2006 | 2021 | 7394 | 7409 | $T_{ks}T_{ks}{}^mC_{ds}{}^mC_{ds}T_{ds}G_{ds}{}^mC_{ds}G_{ds}{}^mC_{ds}{}^mC_{ds}A_{ds}T_{Es}{}^mC_{es}{}^mC_{es}T_{ks}G_k$ | 13 | 3609 |
| 1207157 | 2014 | 2029 | 7402 | 7417 | $T_{ks}T_{ks}A_{ds}T_{ds}T_{ds}G_{ds}A_{ds}G_{ds}T_{ds}T_{ds}{}^mC_{ds}{}^mC_{es}T_{es}G_{es}{}^mC_{ks}G_k$ | 15 | 2694 |
| 1207165 | 2023 | 2038 | 7411 | 7426 | ${}^mC_{ks}A_{ks}A_{ds}A_{ds}G_{ds}{}^mC_{ds}A_{ds}{}^mC_{ds}T_{ds}T_{ds}T_{ds}A_{es}T_{es}G_{ks}A_k$ | 18 | 3306 |
| 1207173 | 145 | 160 | 512 | 527 | $T_{ks}G_{ks}T_{ds}G_{ds}T_{ds}G_{ds}{}^mC_{ds}T_{ds}{}^mC_{ds}T_{ds}T_{ds}{}^mC_{es}A_{ks}G_{es}{}^mC_{ks}T_e$ | 12 | 3112 |
| 1207181 | 153 | 168 | N/A | N/A | $A_{ks}G_{ks}A_{ds}A_{ds}{}^mC_{ds}G_{ds}A_{ds}{}^mC_{ds}T_{ds}G_{ds}T_{ds}G_{es}T_{ks}G_{es}{}^mC_{ks}T_e$ | 53 | 3723 |
| 1207189 | 210 | 225 | 3561 | 3576 | $T_{ks}G_{ks}G_{ds}T_{ds}A_{ds}{}^mC_{ds}A_{ds}G_{ds}{}^mC_{ds}T_{ds}G_{ds}{}^mC_{es}{}^mC_{ks}G_{es}G_{ks}T_e$ | 30 | 2657 |
| 1207197 | 218 | 233 | 3569 | 3584 | $T_{ks}A_{ks}{}^mC_{ds}A_{ds}T_{ds}T_{ds}T_{ds}G_{ds}T_{ds}G_{ds}G_{ds}T_{es}A_{ks}{}^mC_{es}A_{ks}G_e$ | 14 | 2426 |
| 1207205 | 1778 | 1793 | 7166 | 7181 | ${}^mC_{ks}T_{ks}T_{ds}G_{ds}{}^mC_{ds}A_{ds}G_{ds}G_{ds}G_{ds}T_{ds}G_{ds}A_{es}G_{ks}{}^mC_{es}{}^mC_{ks}G_e$ | 48 | 4962 |
| 1207213 | 1786 | 1801 | 7174 | 7189 | $G_{ks}A_{ks}T_{ds}G_{ds}A_{ds}T_{ds}G_{ds}{}^mC_{ds}{}^mC_{ds}T_{ds}T_{ds}G_{es}{}^mC_{ks}A_{es}G_{ks}G_e$ | 16 | 4963 |
| 1207221 | 1892 | 1907 | 7280 | 7295 | ${}^mC_{ks}{}^mC_{ks}{}^mC_{ds}T_{ds}G_{ds}A_{ds}G_{ds}{}^mC_{ds}A_{ds}A_{ds}T_{ds}{}^mC_{es}A_{ks}G_{es}G_{ks}A_e$ | 53 | 3530 |
| 1207229 | 1900 | 1915 | 7288 | 7303 | $A_{ks}G_{ks}A_{ds}T_{ds}G_{ds}A_{ds}G_{ds}T_{ds}{}^mC_{ds}{}^mC_{ds}{}^mC_{ds}T_{es}G_{ks}A_{es}G_{ks}{}^mC_e$ | 14 | 2614 |
| 1207237 | 1915 | 1930 | 7303 | 7318 | $T_{ks}{}^mC_{ks}A_{ds}{}^mC_{ds}{}^mC_{ds}A_{ds}A_{ds}G_{ds}G_{ds}A_{ds}G_{ds}G_{es}G_{ks}A_{es}A_{ks}A_e$ | 30 | 4948 |
| 1207245 | 1923 | 1938 | 7311 | 7326 | ${}^mC_{ks}T_{ks}G_{ds}{}^mC_{ds}G_{ds}G_{ds}A_{ds}A_{ds}T_{ds}{}^mC_{ds}A_{ds}{}^mC_{es}{}^mC_{ks}A_{es}A_{ks}G_e$ | 11 | 3531 |
| 1207253 | 1931 | 1946 | 7319 | 7334 | ${}^mC_{ks}T_{ks}{}^mC_{ds}T_{ds}{}^mC_{ds}T_{ds}{}^mC_{ds}A_{ds}{}^mC_{ds}T_{ds}G_{ds}{}^mC_{es}G_{ks}G_{es}A_{ks}A_e$ | 9 | 2461 |
| 1207261 | 2001 | 2016 | 7389 | 7404 | $G_{ks}{}^mC_{ks}G_{ds}{}^mC_{ds}{}^mC_{ds}A_{ds}T_{ds}{}^mC_{ds}{}^mC_{ds}T_{ds}G_{ds}{}^mC_{es}{}^mC_{ks}G_{es}{}^mC_{ks}G_e$ | 56 | 4964 |
| 1207269 | 2009 | 2024 | 7397 | 7412 | $G_{ks}A_{ks}G_{ds}T_{ds}T_{ds}{}^mC_{ds}{}^mC_{ds}T_{ds}G_{ds}{}^mC_{ds}G_{ds}{}^mC_{es}{}^mC_{es}A_{es}T_{ks}{}^mC_e$ | 11 | 3837 |
| 1207277 | 2018 | 2033 | 7406 | 7421 | ${}^mC_{ks}A_{ks}{}^mC_{ds}T_{ds}T_{ds}T_{ds}A_{ds}T_{ds}G_{ds}A_{ds}G_{es}T_{ks}T_{es}{}^mC_{ks}{}^mC_e$ | 6 | 2924 |

TABLE 81-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207285 | 2033 | 2048 | 7421 | 7436 | $T_{ks}{}^mC_{ks}A_{ds}G_{ds}{}^mC_{ds}A_{ds}T_{ds}T_{ds}T_{ds}T_{ds}{}^mC_{ds}A_{es}A_{ks}A_{es}G^mC_e$ | 36 | 3534 |
| 1207293 | 148 | 163 | 515 | 530 | $G_{ks}A_{ks}{}^mC_{ds}T_{ds}G_{ds}T_{ds}G_{ds}T_{ds}G_{ds}{}^mC_{ds}T_{ds}{}^mC_{ks}T_{es}T_{ks}{}^mC_{es}A_k$ | 12 | 3343 |
| 1207301 | 156 | 171 | N/A | N/A | $G_{ks}T_{ks}G_{ds}A_{ds}G_{ds}A_{ds}A_{ds}{}^mC_{ds}G_{ds}A_{ds}{}^mC_{ds}T_{ks}G_{es}T_{ks}G_{es}T_k$ | 29 | 2424 |
| 1207309 | 213 | 228 | 3564 | 3579 | $T_{ks}T_{ks}G_{ds}T_{ds}G_{ds}G_{ds}T_{ds}A_{ds}{}^mC_{ds}A_{ds}G_{ds}{}^mC_{ks}T_{es}G_{ks}{}^mC_{es}{}^mC_k$ | 21 | 2811 |
| 1207317 | 221 | 236 | 3572 | 3587 | $G_{ks}G_{ks}G_{ds}T_{ds}A_{ds}{}^mC_{ds}A_{ds}T_{ds}T_{ds}T_{ds}G_{ds}T_{ks}G_{es}G_{ks}T_{es}A_k$ | 46 | 3345 |
| 1207325 | 1781 | 1796 | 7169 | 7184 | $T_{ks}G_{ks}{}^mC_{ds}{}^mC_{ds}T_{ds}T_{ds}G_{ds}{}^mC_{ds}A_{ds}G_{ds}G_{ds}G_{ks}T_{es}G_{ks}A_{es}G_k$ | 28 | 3527 |
| 1207333 | 1789 | 1804 | 7177 | 7192 | $G_{ks}{}^mC_{ks}T_{ds}G_{ds}A_{ds}T_{ds}G_{ds}A_{ds}T_{ds}G_{ds}{}^mC_{ds}{}^mC_{ks}T_{es}T_{ks}G_{es}{}^mC_k$ | 26 | 3755 |
| 1207341 | 1895 | 1910 | 7283 | 7298 | $A_{ks}G_{ks}T_{ds}{}^mC_{ds}{}^mC_{ds}{}^mC_{ds}T_{ds}G_{ds}A_{ds}G_{ds}{}^mC_{ds}A_{es}T_{ks}{}^mC_{es}A_k$ | 27 | 3758 |
| 1207349 | 1903 | 1918 | 7291 | 7306 | $G_{ks}A_{ks}A_{ds}A_{ds}G_{ds}A_{ds}T_{ds}G_{ds}A_{ds}G_{ds}T_{ds}{}^mC_{ks}{}^mC_{es}{}^mC_{ks}T_{es}G_k$ | 29 | 2845 |
| 1207357 | 1918 | 1933 | 7306 | 7321 | $G_{ks}A_{ks}A_{ds}T_{ds}{}^mC_{ds}A_{ds}{}^mC_{ds}{}^mC_{ds}A_{ds}A_{ds}G_{ds}G_{ks}A_{es}G_{ks}G_{es}G_k$ | 35 | 4965 |
| 1207365 | 1926 | 1941 | 7314 | 7329 | $T_{ks}{}^mC_{ks}A_{ds}{}^mC_{ds}T_{ds}G_{ds}{}^mC_{ds}G_{ds}G_{ds}A_{ds}A_{ds}T_{ks}{}^mC_{es}A_{ks}{}^mC_{es}{}^mC_k$ | 10 | 3759 |
| 1207373 | 1934 | 1949 | 7322 | 7337 | ${}^mC_{ks}{}^mC_{ks}A_{ds}{}^mC_{ds}T_{ds}{}^mC_{ds}T_{ds}{}^mC_{ds}T_{ds}{}^mC_{ds}A_{ds}{}^mC_{ks}T_{es}G_{ks}{}^mC_{es}G_k$ | 23 | 4949 |
| 1207381 | 2004 | 2019 | 7392 | 7407 | ${}^mC_{ks}{}^mC_{ks}T_{ds}G_{ds}{}^mC_{ds}G_{ds}G_{ds}{}^mC_{ds}{}^mC_{ds}A_{ds}T_{ds}{}^mC_{ks}T_{es}G_{ks}G_{es}{}^mC_k$ | 9 | 3457 |
| 1207389 | 2012 | 2027 | 7400 | 7415 | $A_{ks}T_{ks}T_{ds}G_{ds}A_{ds}G_{ds}T_{ds}T_{ds}{}^mC_{ds}{}^mC_{ds}T_{ds}G_{ks}{}^mC_{es}G_{ks}{}^mC_{es}{}^mC_k$ | 44 | 2540 |
| 1207397 | 2021 | 2036 | 7409 | 7424 | $A_{ks}A_{ks}G_{ds}{}^mC_{ds}A_{ds}{}^mC_{ds}T_{ds}T_{ds}T_{ds}A_{ds}T_{ds}T_{ks}G_{es}A_{ks}G_{es}T_k$ | 22 | 3147 |
| 1207405 | 143 | 158 | 510 | 525 | $T_{ks}G_{ks}T_{ks}G_{ds}{}^mC_{ds}T_{ds}{}^mC_{ds}T_{ds}T_{ds}{}^mC_{ds}A_{ds}G_{ds}{}^mC_{ks}T_{ks}T_{ks}T_e$ | 29 | 3037 |
| 1207413 | 151 | 166 | N/A | N/A | $A_{ks}A_{ks}{}^mC_{ks}G_{ds}A_{ds}{}^mC_{ds}T_{ds}G_{ds}T_{ds}G_{ds}T_{ds}G_{ds}{}^mC_{ks}T_{ks}{}^mC_{ks}T_e$ | 24 | 3571 |
| 1207421 | 208 | 223 | 3559 | 3574 | $G_{ks}T_{ks}A_{ks}{}^mC_{ds}A_{ds}G_{ds}{}^mC_{ds}T_{ds}G_{ds}{}^mC_{ds}{}^mC_{ds}G_{ds}G_{ks}T_{ks}G_{ks}G_e$ | 25 | 4968 |
| 1207429 | 216 | 231 | 3567 | 3582 | ${}^mC_{ks}A_{ks}T_{ks}T_{ds}T_{ds}G_{ds}T_{ds}G_{ds}G_{ds}T_{ds}A_{ds}{}^mC_{ds}A_{ks}G_{ks}{}^mC_{ks}T_e$ | 14 | 3039 |
| 1207437 | 1776 | 1791 | 7164 | 7179 | $T_{ks}G_{ks}{}^mC_{ds}A_{ds}G_{ds}G_{ds}T_{ds}G_{ds}G_{ds}A_{ds}G_{ds}{}^mC_{ds}{}^mC_{ks}G_{ks}G_{ks}{}^mC_e$ | 37 | 3299 |
| 1207445 | 1784 | 1799 | 7172 | 7187 | $T_{ks}G_{ks}A_{ks}T_{ds}G_{ds}{}^mC_{ds}{}^mC_{ds}T_{ds}T_{ds}G_{ds}{}^mC_{ds}A_{ds}G_{ks}G_{ks}G_{ks}T_e$ | 36 | 4969 |
| 1207453 | 1792 | 1807 | 7180 | 7195 | ${}^mC_{ks}{}^mC_{ks}A_{ks}G_{ds}{}^mC_{ds}T_{ds}G_{ds}G_{ds}A_{ds}T_{ds}G_{ds}A_{ds}T_{ks}G_{ks}{}^mC_{ks}T_e$ | 28 | 4970 |
| 1207461 | 1898 | 1913 | 7286 | 7301 | $A_{ks}T_{ks}G_{ks}A_{ds}G_{ds}T_{ds}{}^mC_{ds}{}^mC_{ds}{}^mC_{ds}T_{ds}G_{ds}A_{ds}G_{ks}{}^mC_{ks}A_{ks}A_e$ | 21 | 2460 |
| 1207469 | 1906 | 1921 | 7294 | 7309 | $A_{ks}G_{ks}G_{ks}G_{ds}A_{ds}A_{ds}A_{ds}G_{ds}A_{ds}T_{ds}G_{ds}A_{ds}G_{ks}T_{ks}{}^mC_{ks}{}^mC_e$ | 15 | 3073 |

TABLE 81-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207477 | 1921 | 1936 | 7309 | 7324 | $G_{ks}{}^mC_{ks}G_{ks}G_{ds}A_{ds}A_{ds}T_{ds}{}^mC_{ds}A_{ds}{}^mC_{ds}{}^mC_{ds}A_{ds}A_{ks}G_{ks}G_{ks}A_e$ | 15 | 3379 |
| 1207485 | 1929 | 1944 | 7317 | 7332 | ${}^mC_{ks}T_{ks}{}^mC_{ks}T_{ds}{}^mC_{ds}A_{ds}{}^mC_{ds}T_{ds}G_{ds}{}^mC_{ds}G_{ds}G_{ds}A_{ks}A_{ks}T_{ks}{}^mC_e$ | 12 | 4971 |
| 1207493 | 1937 | 1952 | 7325 | 7340 | ${}^mC_{ks}A_{ks}G_{ks}{}^mC_{ds}{}^mC_{ds}A_{ds}{}^mC_{ds}T_{ds}{}^mC_{ds}T_{ds}{}^mC_{ds}T_{ds}{}^mC_{ks}A_{ks}{}^mC_{ks}T_e$ | 14 | 4972 |
| 1207501 | 2007 | 2022 | 7395 | 7410 | $G_{ks}T_{ks}T_{ks}{}^mC_{ds}{}^mC_{ds}T_{ds}G_{ds}{}^mC_{ds}G_{ds}{}^mC_{ds}{}^mC_{ds}A_{ds}T_{ks}{}^mC_{ks}{}^mC_{ks}T_e$ | 21 | 3685 |
| 1207509 | 2016 | 2031 | 7404 | 7419 | ${}^mC_{ks}T_{ks}T_{ks}T_{ds}A_{ds}T_{ds}T_{ds}G_{ds}A_{ds}G_{ds}T_{ds}T_{ds}{}^mC_{ks}{}^mC_{ks}T_{ks}G_e$ | 8 | 2771 |
| 1207517 | 2024 | 2039 | 7412 | 7427 | $T_{ks}{}^mC_{ks}A_{ks}A_{ds}A_{ds}G_{ds}{}^mC_{ds}A_{ds}{}^mC_{ds}T_{ds}T_{ds}T_{ds}A_{ks}T_{ks}T_{ks}G_e$ | 11 | 3382 |

TABLE 82

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 12 | 3837 |
| 1206479 | 209 | 224 | 3560 | 3575 | $G_{ks}G_{ks}T_{ks}A_{ds}{}^mC_{ds}A_{ds}G_{ds}{}^mC_{ds}T_{ds}G_{ds}{}^mC_{ds}G_{ds}G_{ks}T_{ks}G_k$ | 20 | 4952 |
| 1206502 | 1787 | 1802 | 7175 | 7190 | $T_{ks}G_{ks}A_{ks}T_{ds}G_{ds}A_{ds}T_{ds}G_{ds}{}^mC_{ds}{}^mC_{ds}T_{ds}T_{ds}G_{ds}{}^mC_{ks}A_{ks}G_k$ | 27 | 4975 |
| 1206507 | 1929 | 1944 | 7317 | 7332 | ${}^mC_{ks}T_{ks}{}^mC_{ks}T_{ds}{}^mC_{ds}A_{ds}{}^mC_{ds}T_{ds}G_{ds}{}^mC_{ds}G_{ds}G_{ds}A_{ks}A_{ks}T_{ks}{}^mC_k$ | 11 | 4971 |
| 1206897 | 2001 | 2016 | 7389 | 7404 | $G_{ks}{}^mC_{ks}G_{ks}{}^mC_{ds}A_{ds}T_{ds}{}^mC_{ds}{}^mC_{ds}T_{ds}G_{ds}G_{ds}{}^mC_{ds}G_{ks}{}^mC_{ks}G_k$ | 41 | 4964 |
| 1206905 | 148 | 163 | 515 | 530 | $G_{ks}A_{es}{}^mC_{ks}T_{ds}G_{ds}T_{ds}G_{ds}T_{ds}G_{ds}{}^mC_{ds}T_{ds}{}^mC_{ds}T_{es}T_{es}{}^mC_{ks}A_k$ | 10 | 3343 |
| 1206913 | 156 | 171 | N/A | N/A | $G_{ks}T_{es}G_{ks}A_{ds}G_{ds}A_{ds}A_{ds}{}^mC_{ds}G_{ds}A_{ds}{}^mC_{ds}T_{ds}T_{es}T_{es}G_{ks}T_k$ | 21 | 2424 |
| 1206921 | 213 | 228 | 3564 | 3579 | $T_{ks}T_{es}G_{ks}T_{ds}G_{ds}G_{ds}T_{ds}A_{ds}{}^mC_{ds}A_{ds}G_{ds}{}^mC_{ds}T_{es}G_{es}{}^mC_{ks}{}^mC_k$ | 21 | 2811 |
| 1206929 | 221 | 236 | 3572 | 3587 | $G_{ks}G_{es}G_{ks}T_{ds}A_{ds}{}^mC_{ds}A_{ds}A_{ds}T_{ds}T_{ds}G_{ds}T_{ds}G_{es}G_{es}T_{ks}A_k$ | 22 | 3345 |
| 1206937 | 1781 | 1796 | 7169 | 7184 | $T_{ks}G_{es}{}^mC_{ks}{}^mC_{ds}T_{ds}T_{ds}G_{ds}{}^mC_{ds}A_{ds}G_{ds}G_{ds}G_{ds}T_{es}G_{es}A_{ks}G_k$ | 58 | 3527 |
| 1206945 | 1789 | 1804 | 7177 | 7192 | $G_{ks}{}^mC_{es}T_{ks}G_{ds}A_{ds}T_{ds}G_{ds}A_{ds}T_{ds}G_{ds}{}^mC_{ds}{}^mC_{ds}T_{es}T_{es}G_{ks}{}^mC_k$ | 23 | 3755 |
| 1206953 | 1895 | 1910 | 7283 | 7298 | $A_{ks}G_{es}T_{ks}{}^mC_{ds}{}^mC_{ds}{}^mC_{ds}T_{ds}G_{ds}G_{ds}A_{ds}G_{ds}{}^mC_{ds}A_{es}A_{es}T_{es}{}^mC_{ks}A_k$ | 8 | 3758 |
| 1206961 | 1903 | 1918 | 7291 | 7306 | $G_{ks}A_{es}A_{ks}A_{ds}G_{ds}A_{ds}T_{ds}G_{ds}G_{ds}A_{ds}G_{ds}T_{ds}{}^mC_{ds}{}^mC_{es}{}^mC_{es}T_{ks}G_k$ | 17 | 2845 |
| 1206969 | 1918 | 1933 | 7306 | 7321 | $G_{ks}A_{es}A_{ks}T_{ds}{}^mC_{ds}A_{ds}{}^mC_{ds}{}^mC_{ds}A_{ds}A_{ds}G_{ds}G_{ds}A_{es}G_{es}{}^mC_{ks}G_k$ | 18 | 4965 |

TABLE 82-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206977 | 1926 | 1941 | 7314 | 7329 | $T_{ks}C_{es}A_{ks}C_{ds}T_{ds}G_{ds}C_{ds}G_{ds}G_{ds}A_{ds}A_{ds}T_{ds}{}^mC_{es}A_{es}{}^mC_{ks}{}^mC_k$ | 12 | 3759 |
| 1206985 | 1934 | 1949 | 7322 | 7337 | ${}^mC_{ks}{}^mC_{es}A_{ks}{}^mC_{ds}T_{ds}{}^mC_{ds}T_{ds}{}^mC_{ds}T_{ds}{}^mC_{ds}A_{ds}{}^mC_{ds}T_{es}G_{es}{}^mC_{ks}G_k$ | 13 | 4949 |
| 1206993 | 2004 | 2019 | 7392 | 7407 | ${}^mC_{ks}{}^mC_{es}T_{ks}G_{ds}{}^mC_{ds}G_{ds}{}^mC_{ds}{}^mC_{ds}A_{ds}T_{ds}{}^mC_{ds}{}^mC_{ds}T_{es}G_{es}G_{ks}{}^mC_k$ | 7 | 3457 |
| 1207001 | 2012 | 2027 | 7400 | 7415 | $A_{ks}T_{es}T_{ks}G_{ds}A_{ds}G_{ds}T_{ds}T_{ds}{}^mC_{ds}{}^mC_{ds}T_{ds}G_{ds}T_{es}G_{es}T_{ks}T_k$ | 28 | 2540 |
| 1207009 | 2021 | 2036 | 7409 | 7424 | $A_{ks}A_{es}G_{ks}{}^mC_{ds}A_{ds}{}^mC_{ds}T_{ds}T_{ds}A_{ds}T_{ds}T_{ds}G_{es}A_{es}G_{ks}T_k$ | N.D | 3147 |
| 1207028 | 143 | 158 | 510 | 525 | $T_{ks}G_{ks}T_{ds}G_{ds}{}^mC_{ds}T_{ds}{}^mC_{ds}T_{ds}T_{ds}{}^mC_{ds}A_{ds}G_{es}{}^mC_{es}T_{es}T_{ks}T_k$ | 72 | 3037 |
| 1207036 | 151 | 166 | N/A | N/A | $A_{ks}A_{ks}{}^mC_{ds}G_{ds}A_{ds}{}^mC_{ds}T_{ds}G_{ds}T_{ds}G_{ds}T_{ds}G_{es}{}^mC_{es}T_{es}{}^mC_{ks}T_k$ | 19 | 3571 |
| 1207044 | 208 | 223 | 3559 | 3574 | $G_{ks}T_{ks}A_{ds}{}^mC_{ds}A_{ds}G_{ds}{}^mC_{ds}T_{ds}G_{ds}{}^mC_{ds}{}^mC_{ds}G_{es}G_{es}T_{es}G_{ks}G_k$ | 58 | 4968 |
| 1207052 | 216 | 231 | 3567 | 3582 | ${}^mC_{ks}A_{ks}T_{ds}T_{ds}T_{ds}G_{ds}T_{ds}G_{ds}G_{ds}G_{ds}T_{ds}A_{ds}C_{es}A_{es}G_{es}{}^mC_{ks}T_k$ | 24 | 3039 |
| 1207060 | 1776 | 1791 | 7164 | 7179 | $T_{ks}G_{ks}{}^mC_{ds}A_{ds}G_{ds}G_{ds}G_{ds}T_{ds}G_{ds}A_{ds}G_{ds}{}^mC_{es}{}^mC_{es}G_{es}G_{ks}{}^mC_k$ | 26 | 3299 |
| 1207081 | 1784 | 1799 | 7172 | 7187 | $T_{ks}G_{ks}A_{ds}T_{ds}G_{ds}{}^mC_{ds}{}^mC_{ds}T_{ds}T_{ds}G_{ds}{}^mC_{ds}A_{es}G_{es}G_{es}G_{ks}T_k$ | 39 | 4969 |
| 1207089 | 1792 | 1807 | 7180 | 7195 | ${}^mC_{ks}{}^mC_{ks}A_{ds}G_{ds}{}^mC_{ds}T_{ds}G_{ds}G_{ds}A_{ds}T_{ds}G_{ds}A_{ds}T_{es}G_{es}{}^mC_{ks}T_k$ | 45 | 4970 |
| 1207097 | 1898 | 1913 | 7286 | 7301 | $A_{ks}T_{es}G_{ds}A_{ds}G_{ds}T_{ds}{}^mC_{ds}{}^mC_{ds}{}^mC_{ds}T_{ds}G_{ds}A_{es}{}^mC_{es}A_{ks}A_k$ | 14 | 2460 |
| 1207105 | 1906 | 1921 | 7294 | 7309 | $A_{ks}G_{ks}G_{ds}G_{ds}A_{ds}A_{ds}A_{ds}G_{ds}A_{ds}T_{ds}G_{ds}A_{es}G_{es}T_{es}{}^mC_{ks}{}^mC_k$ | 25 | 3073 |
| 1207113 | 1921 | 1936 | 7309 | 7324 | $G_{ks}{}^mC_{ks}G_{ds}G_{ds}A_{ds}A_{ds}A_{ds}T_{ds}{}^mC_{ds}A_{ds}{}^mC_{ds}{}^mC_{ds}A_{es}G_{es}G_{ks}A_k$ | 8 | 3379 |
| 1207125 | 1929 | 1944 | 7317 | 7332 | ${}^mC_{ks}T_{ks}{}^mC_{ds}T_{ds}{}^mC_{ds}A_{ds}{}^mC_{ds}T_{ds}G_{ds}{}^mC_{ds}G_{ds}G_{es}A_{es}A_{es}T_{ks}{}^mC_k$ | 9 | 4971 |
| 1207141 | 1937 | 1952 | 7325 | 7340 | ${}^mC_{ks}A_{ks}G_{ds}{}^mC_{ds}{}^mC_{ds}A_{ds}{}^mC_{ds}T_{ds}{}^mC_{ds}T_{ds}{}^mC_{ds}T_{es}{}^mC_{es}A_{es}{}^mC_{ks}T_k$ | 28 | 4972 |
| 1207150 | 2007 | 2022 | 7395 | 7410 | $G_{ks}T_{ks}T_{ds}{}^mC_{ds}{}^mC_{ds}T_{ds}G_{ds}{}^mC_{ds}G_{ds}{}^mC_{ds}{}^mC_{ds}A_{es}T_{es}{}^mC_{es}{}^mC_{ks}T_k$ | 21 | 3685 |
| 1207158 | 2016 | 2031 | 7404 | 7419 | $C_{ks}T_{ks}T_{ds}T_{ds}A_{ds}T_{ds}T_{ds}G_{ds}A_{ds}G_{ds}T_{ds}T_{es}{}^mC_{es}{}^mC_{es}T_{ks}G_k$ | 27 | 2771 |
| 1207166 | 2024 | 2039 | 7412 | 7427 | $T_{ks}{}^mC_{ks}A_{ds}A_{ds}A_{ds}G_{ds}{}^mC_{ds}A_{ds}{}^mC_{ds}T_{ds}T_{ds}A_{es}T_{es}T_{ks}G_k$ | 22 | 3382 |
| 1207174 | 146 | 161 | 513 | 528 | ${}^mC_{ks}T_{ks}G_{ds}T_{ds}G_{ds}T_{ds}G_{ds}{}^mC_{ds}T_{ds}{}^mC_{ds}T_{ds}T_{es}{}^mC_{ks}A_{es}G_{ks}{}^mC_e$ | 28 | 3190 |
| 1207182 | 154 | 169 | N/A | N/A | $G_{ks}A_{ks}G_{ds}A_{ds}A_{ds}{}^mC_{ds}G_{ds}A_{ds}{}^mC_{ds}T_{ds}G_{ds}T_{es}G_{ks}T_{es}G_{ks}{}^mC_e$ | 16 | 3799 |
| 1207190 | 211 | 226 | 3562 | 3577 | $G_{ks}T_{ks}G_{ds}G_{ds}T_{ds}A_{ds}{}^mC_{ds}A_{ds}G_{ds}{}^mC_{ds}T_{ds}G_{es}{}^mC_{ks}{}^mC_{es}G_{ks}G_e$ | 5 | 4973 |
| 1207198 | 219 | 234 | 3570 | 3585 | $G_{ks}T_{ks}A_{ds}{}^mC_{ds}A_{ds}T_{ds}T_{ds}T_{ds}G_{ds}T_{ds}G_{ds}G_{es}T_{ks}A_{es}{}^mC_{ks}A_e$ | 48 | 3192 |

TABLE 82-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207206 | 1779 | 1794 | 7167 | 7182 | $^mC_{ks}{}^mC_{ks}T_{ds}T_{ds}G_{ds}{}^mC_{ds}A_{ds}G_{ds}G_{ds}G_{ds}T_{ds}G_{es}A_{ks}G_{es}{}^mC_{ks}{}^mC_e$ | 36 | 4974 |
| 1207214 | 1787 | 1802 | 7175 | 7190 | $T_{ks}G_{ks}A_{ds}T_{ds}G_{ds}A_{ds}T_{ds}G_{ds}{}^mC_{ds}{}^mC_{ds}T_{ds}T_{es}G_{ks}{}^mC_{es}A_{ks}G_e$ | 26 | 4975 |
| 1207222 | 1893 | 1908 | 7281 | 7296 | $T_{ks}{}^mC_{ks}{}^mC_{ds}{}^mC_{ds}T_{ds}G_{ds}A_{ds}G_{ds}{}^mC_{ds}A_{ds}A_{ds}T_{es}{}^mC_{ks}A_{es}G_{ks}G_e$ | 35 | 3606 |
| 1207230 | 1901 | 1916 | 7289 | 7304 | $A_{ks}A_{ks}G_{ds}A_{ds}T_{ds}G_{ds}A_{ds}G_{ds}T_{ds}{}^mC_{ds}{}^mC_{ds}{}^mC_{es}T_{ks}G_{es}A_{ks}G_e$ | 7 | 2691 |
| 1207238 | 1916 | 1931 | 7304 | 7319 | $A_{ks}T_{ks}{}^mC_{ds}A_{ds}{}^mC_{ds}{}^mC_{ds}A_{ds}A_{ds}G_{ds}G_{ds}A_{ds}G_{es}G_{ks}G_{es}A_{ks}A_e$ | 32 | 4966 |
| 1207246 | 1924 | 1939 | 7312 | 7327 | $A_{ks}{}^mC_{ks}T_{ds}G_{ds}{}^mC_{ds}G_{ds}G_{ds}A_{ds}A_{ds}T_{ds}{}^mC_{ds}A_{es}{}^mC_{ks}{}^mC_{es}A_{ks}A_e$ | 17 | 3607 |
| 1207254 | 1932 | 1947 | 7320 | 7335 | $A_{ks}{}^mC_{ks}T_{ds}{}^mC_{ds}T_{ds}{}^mC_{ds}T_{ds}{}^mC_{ds}A_{ds}{}^mC_{ds}T_{ds}G_{es}{}^mC_{ks}G_{es}G_{ks}A_e$ | 18 | 4976 |
| 1207262 | 2002 | 2017 | 7390 | 7405 | $T_{ks}G_{ks}{}^mC_{ds}G_{ds}{}^mC_{ds}{}^mC_{ds}A_{ds}T_{ds}{}^mC_{ds}{}^mC_{ds}T_{ds}G_{es}G_{ks}{}^mC_{es}G_{ks}{}^mC_e$ | 37 | 3305 |
| 1207270 | 2010 | 2025 | 7398 | 7413 | $T_{ks}G_{ks}A_{ds}G_{ds}T_{ds}T_{ds}{}^mC_{ds}{}^mC_{ds}T_{ds}G_{ds}{}^mC_{ds}G_{es}{}^mC_{ks}T_{es}A_{ks}T_e$ | 21 | 3913 |
| 1207278 | 2019 | 2034 | 7407 | 7422 | $G_{ks}{}^mC_{ks}A_{ds}{}^mC_{ds}T_{ds}T_{ds}T_{ds}A_{ds}T_{ds}T_{ds}G_{ds}A_{es}G_{ks}T_{es}T_{ks}{}^mC_e$ | 7 | 3000 |
| 1207286 | 141 | 156 | 508 | 523 | $T_{ks}G_{ks}{}^mC_{ds}T_{ds}{}^mC_{ds}T_{ds}T_{ds}{}^mC_{ds}A_{ds}G_{ds}{}^mC_{ds}T_{es}T_{ks}G_{es}T_k$ | 27 | 4950 |
| 1207294 | 149 | 164 | 516 | 531 | $^mC_{ks}G_{ks}A_{ds}{}^mC_{ds}T_{ds}G_{ds}T_{ds}G_{ds}T_{ds}G_{ds}{}^mC_{ds}T_{ks}{}^mC_{es}T_{es}{}^mC_k$ | 21 | 3419 |
| 1207302 | 157 | 172 | N/A | N/A | $A_{ks}G_{ks}T_{ds}G_{ds}A_{ds}G_{ds}A_{ds}A_{ds}{}^mC_{ds}G_{ds}A_{ds}{}^mC_{ks}T_{es}G_{ks}T_{es}G_k$ | 38 | 2502 |
| 1207310 | 214 | 229 | 3565 | 3580 | $T_{ks}T_{ks}T_{ds}G_{ds}T_{ds}G_{ds}G_{ds}G_{ds}T_{ds}A_{ds}{}^mC_{ds}A_{ds}G_{ks}{}^mC_{es}T_{ks}G_{es}{}^mC_k$ | 26 | 2887 |
| 1207318 | 222 | 237 | 3573 | 3588 | $T_{ks}G_{ks}G_{ds}G_{ds}G_{ds}T_{ds}A_{ds}{}^mC_{ds}A_{ds}T_{ds}T_{ds}T_{ds}G_{ks}T_{es}G_{ks}G_{es}T_k$ | 30 | 3421 |
| 1207326 | 1782 | 1797 | 7170 | 7185 | $A_{ks}T_{ks}G_{ds}{}^mC_{ds}{}^mC_{ds}T_{ds}T_{ds}G_{ds}{}^mC_{ds}A_{ds}G_{ds}G_{ks}G_{es}T_{ks}G_{es}A_k$ | 34 | 4947 |
| 1207334 | 1790 | 1805 | 7178 | 7193 | $A_{ks}G_{ks}{}^mC_{ds}T_{ds}G_{ds}A_{ds}T_{ds}G_{ds}A_{ds}T_{ds}G_{ds}{}^mC_{ks}{}^mC_{es}T_{ks}T_{es}G_k$ | 32 | 3831 |
| 1207342 | 1896 | 1911 | 7284 | 7299 | $G_{ks}A_{ks}G_{ds}T_{ds}{}^mC_{ds}{}^mC_{ds}{}^mC_{ds}T_{ds}G_{ds}A_{ds}G_{ds}T_{es}A_{ks}A_{es}T_{es}T_k$ | 33 | 3834 |
| 1207350 | 1904 | 1919 | 7292 | 7307 | $G_{ks}G_{ks}A_{ds}A_{ds}A_{ds}G_{ds}A_{ds}T_{ds}G_{ds}A_{ds}G_{ds}T_{ks}{}^mC_{es}{}^mC_{ks}{}^mC_{es}T_k$ | 54 | 2921 |
| 1207358 | 1919 | 1934 | 7307 | 7322 | $G_{ks}G_{ks}A_{ds}A_{ds}T_{ds}{}^mC_{ds}A_{ds}{}^mC_{ds}{}^mC_{ds}A_{ds}A_{ds}G_{ks}G_{es}A_{ks}G_{es}G_k$ | 8 | 3226 |
| 1207366 | 1927 | 1942 | 7315 | 7330 | $^mC_{ks}T_{ks}{}^mC_{ds}A_{ds}{}^mC_{ds}T_{ds}G_{ds}{}^mC_{ds}G_{ds}G_{ds}A_{ds}A_{ks}T_{es}{}^mC_{ks}A_{es}{}^mC_k$ | 13 | 3835 |
| 1207374 | 1935 | 1950 | 7323 | 7338 | $G_{ks}{}^mC_{ks}{}^mC_{ds}A_{ds}A_{ds}{}^mC_{ds}T_{ds}{}^mC_{ds}T_{ds}{}^mC_{ds}T_{ds}{}^mC_{ds}A_{ks}{}^mC_{es}T_{ks}G_{es}{}^mC_k$ | 31 | 4967 |
| 1207382 | 2005 | 2020 | 7393 | 7408 | $T_{ks}{}^mC_{ks}{}^mC_{ds}T_{ds}G_{ds}G_{ds}{}^mC_{ds}G_{ds}{}^mC_{ds}{}^mC_{ds}A_{ds}T_{ds}{}^mC_{ks}{}^mC_{es}T_{ks}{}^mC_{es}G_k$ | 27 | 3533 |
| 1207390 | 2013 | 2028 | 7401 | 7416 | $T_{ks}A_{ks}T_{ds}T_{ds}G_{ds}A_{ds}G_{ds}T_{ds}T_{ds}{}^mC_{ds}{}^mC_{ds}T_{ks}G_{es}{}^mC_{ks}G_{es}{}^mC_k$ | 38 | 2617 |

TABLE 82-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207398 | 2022 | 2037 | 7410 | 7425 | $A_{ks}A_{ks}A_{ds}G_{ds}{}^mC_{ds}A_{ds}{}^mC_{ds}T_{ds}T_{ds}A_{ds}T_{ks}T_{es}G_{ks}A_{es}G_k$ | 24 | 3229 |
| 1207406 | 144 | 159 | 511 | 526 | $G_{ks}T_{ks}G_{ks}T_{ds}G_{ds}C_{ds}T_{ds}C_{ds}T_{ds}C_{ds}A_{ds}G_{ks}C_{ks}T_{ks}T_e$ | 6 | 4951 |
| 1207414 | 152 | 167 | N/A | N/A | $G_{ks}A_{ks}A_{ks}{}^mC_{ds}G_{ds}A_{ds}C_{ds}T_{ds}G_{ds}T_{ds}G_{ds}T_{ds}G_{ks}{}^mC_{ks}T_{ks}{}^mC_e$ | 19 | 3647 |
| 1207422 | 209 | 224 | 3560 | 3575 | $G_{ks}G_{ks}T_{ks}A_{ds}{}^mC_{ds}A_{ds}G_{ds}{}^mC_{ds}T_{ds}G_{ds}{}^mC_{ds}{}^mC_{ds}G_{ks}G_{ks}T_{ks}G_e$ | 44 | 4952 |
| 1207430 | 217 | 232 | 3568 | 3583 | $A_{ks}C_{ks}A_{ks}T_{ds}T_{ds}T_{ds}G_{ds}T_{ds}G_{ds}G_{ds}T_{ds}A_{ds}{}^mC_{ks}A_{ks}G_{ks}{}^mC_e$ | 12 | 3114 |
| 1207438 | 1777 | 1792 | 7165 | 7180 | $T_{ks}T_{ks}G_{ks}{}^mC_{ds}A_{ds}G_{ds}G_{ds}G_{ds}T_{ds}G_{ds}A_{ds}G_{ds}T_{ks}T_{ks}G_{ks}G_e$ | 40 | 3375 |
| 1207446 | 1785 | 1800 | 7173 | 7188 | $A_{ks}T_{ks}G_{ks}A_{ds}T_{ds}G_{ds}{}^mC_{ds}{}^mC_{ds}T_{ds}T_{ds}G_{ds}T_{ds}A_{ks}G_{ks}G_{ks}G_e$ | 16 | 3603 |
| 1207454 | 1793 | 1808 | 7181 | 7196 | ${}^mC_{ks}{}^mC_{ks}{}^mC_{ks}A_{ds}G_{ds}{}^mC_{ds}T_{ds}G_{ds}A_{ds}T_{ds}G_{ds}A_{ds}T_{ks}G_{ks}{}^mC_{ks}{}^mC_e$ | 11 | 4953 |
| 1207462 | 1899 | 1914 | 7287 | 7302 | $G_{ks}A_{ks}T_{ks}G_{ds}A_{ds}G_{ds}T_{ds}{}^mC_{ds}{}^mC_{ds}{}^mC_{ds}T_{ds}G_{ds}A_{ks}G_{ks}{}^mC_{ks}A_e$ | 15 | 2537 |
| 1207470 | 1914 | 1929 | 7302 | 7317 | $C_{ks}A_{ks}C_{ks}C_{ds}A_{ds}A_{ds}G_{ds}G_{ds}A_{ds}G_{ds}G_{ds}G_{ds}A_{ks}A_{ks}A_{ks}G_e$ | 40 | 4954 |
| 1207478 | 1922 | 1937 | 7310 | 7325 | $T_{ks}G_{ks}{}^mC_{ks}G_{ds}G_{ds}A_{ds}A_{ds}T_{ds}{}^mC_{ds}A_{ds}{}^mC_{ds}C_{ds}A_{ks}A_{ks}G_{ks}G_e$ | 16 | 3455 |
| 1207486 | 1930 | 1945 | 7318 | 7333 | $T_{ks}{}^mC_{ks}T_{ks}{}^mC_{ds}T_{ds}{}^mC_{ds}A_{ds}{}^mC_{ds}T_{ds}{}^mG_{ds}C_{ds}G_{ds}G_{ks}A_{ks}A_{ks}T_e$ | 22 | 4955 |
| 1207494 | 2000 | 2015 | 7388 | 7403 | ${}^mC_{ks}G_{ks}{}^mC_{ks}{}^mC_{ds}A_{ds}T_{ds}{}^mC_{ds}{}^mC_{ds}T_{ds}G_{ds}G_{ds}{}^mC_{ds}G_{ks}T_{ks}G_{ks}G_e$ | 39 | 3228 |
| 1207502 | 2008 | 2023 | 7396 | 7411 | $A_{ks}G_{ks}T_{ks}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_{ks}{}^mC_e$ | 22 | 3761 |
| 1207518 | 2031 | 2046 | 7419 | 7434 | $A_{ks}G_{ks}{}^mC_{ks}A_{ds}T_{ds}T_{ds}T_{ds}T_{ds}{}^mC_{ds}AA_{dsds}A_{ds}G_{ks}{}^mC_{ks}A_{ks}{}^mC_e$ | 13 | 3458 |

TABLE 83

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}C_{ds}C_{ds}A_{ks}T_{ks}C_k$ | 8 | 3837 |
| 1206488 | 1930 | 1945 | 7318 | 7333 | $T_{ks}{}^mC_{ks}T_{ks}{}^mC_{ds}T_{ds}{}^mC_{ds}A_{ds}{}^mC_{ds}T_{d s}G_{ds}{}^mC_{ds}G_{ds}G_{ds}A_{ks}A_{ks}T_k$ | 10 | 4955 |
| 1206497 | 211 | 226 | 3562 | 3577 | $G_{ks}T_{ks}G_{ks}G_{ds}T_{ds}A_{ds}{}^mC_{ds}A_{ds}G_{ds}{}^mC_{ds}T_{ds}G_{ds}{}^mC_{ds}{}^mC_{ks}G_{ks}G_k$ | 7 | 4973 |
| 1206503 | 1792 | 1807 | 7180 | 7195 | ${}^mC_{ks}{}^mC_{ks}A_{ks}G_{ds}{}^mC_{ds}T_{ds}G_{ds}A_{ds}T_{ds}G_{ds}A_{ds}T_{ds}G_{ds}C_{ks}C_{ks}T_k$ | 35 | 4970 |

TABLE 83-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206898 | 141 | 156 | 508 | 523 | $T_{ks}G_{es}C_{ks}T_{ds}C_{ds}T_{ds}T_{ds}C_{ds}A_{ds}G_{ds}{}^mC_{ds}T_{ds}T_{es}T_{es}G_{ks}T_k$ | 18 | 4950 |
| 1206906 | 149 | 164 | 516 | 531 | ${}^mC_{ks}G_{es}A_{ks}{}^mC_{ds}T_{ds}G_{ds}T_{ds}G_{ds}T_{ds}G_{ds}{}^mC_{ds}T_{ds}{}^mC_{es}T_{es}G_{ks}T_k$ | 5 | 3419 |
| 1206914 | 157 | 172 | N/A | N/A | $A_{ks}G_{es}T_{ks}G_{ds}A_{ds}G_{ds}A_{ds}A_{ds}C_{ds}G_{ds}A_{ds}{}^mC_{ds}T_{es}G_{es}T_{ks}G_k$ | 14 | 2502 |
| 1206922 | 214 | 229 | 3565 | 3580 | $T_{ks}T_{es}T_{ks}G_{ds}T_{ds}G_{ds}G_{ds}T_{ds}A_{ds}{}^mC_{ds}A_{ds}G_{ds}{}^mC_{es}T_{es}G_{ks}{}^mC_k$ | 22 | 2887 |
| 1206930 | 222 | 237 | 3573 | 3588 | $T_{ks}G_{es}G_{ks}G_{ds}T_{ds}A_{ds}{}^mC_{ds}A_{ds}T_{ds}T_{ds}T_{ds}G_{ds}T_{es}G_{es}G_{ks}T_k$ | 11 | 3421 |
| 1206938 | 1782 | 1797 | 7170 | 7185 | $A_{ks}T_{es}G_{ks}{}^mC_{ds}{}^mC_{ds}T_{ds}T_{ds}G_{ds}{}^mC_{ds}A_{ds}G_{ds}G_{es}T_{es}G_{ks}A_k$ | 27 | 4947 |
| 1206946 | 1790 | 1805 | 7178 | 7193 | $A_{ks}G_{es}{}^mC_{ks}T_{ds}G_{ds}A_{ds}T_{ds}G_{ds}A_{ds}T_{ds}G_{ds}{}^mC_{ds}{}^mC_{es}T_{es}T_{ks}G_k$ | 32 | 3831 |
| 1206954 | 1896 | 1911 | 7284 | 7299 | $G_{ks}A_{es}G_{ks}T_{ds}{}^mC_{ds}{}^mC_{ds}{}^mC_{ds}T_{ds}G_{ds}A_{ds}G_{ds}{}^mC_{ds}A_{es}A_{es}T_{ks}{}^mC_k$ | 16 | 3834 |
| 1206962 | 1904 | 1919 | 7292 | 7307 | $G_{ks}G_{es}A_{ks}A_{ds}A_{ds}G_{ds}A_{ds}T_{ds}G_{ds}A_{ds}G_{ds}T_{ds}{}^mC_{es}{}^mC_{es}{}^mC_{ks}T_k$ | 16 | 2921 |
| 1206970 | 1919 | 1934 | 7307 | 7322 | $G_{ks}G_{es}A_{ks}A_{ds}T_{ds}C_{ds}A_{ds}C_{ds}C_{ds}A_{ds}A_{ds}G_{ds}G_{es}A_{es}G_{ks}G_k$ | 7 | 3226 |
| 1206978 | 1927 | 1942 | 7315 | 7330 | ${}^mC_{ks}T_{es}{}^mC_{ks}A_{ds}{}^mC_{ds}T_{ds}G_{ds}G_{ds}{}^mC_{ds}G_{ds}G_{ds}A_{ds}A_{ds}T_{es}{}^mC_{es}A_{ks}{}^mC_k$ | 7 | 3835 |
| 1206986 | 1935 | 1950 | 7323 | 7338 | $G_{ks}{}^mC_{es}{}^mC_{ks}A_{ds}{}^mC_{ds}T_{ds}{}^mC_{ds}T_{ds}{}^mC_{ds}T_{ds}{}^mC_{ds}{}^mC_{ds}A_{ds}{}^mC_{es}T_{es}G_{ks}{}^mC_k$ | 8 | 4967 |
| 1206994 | 2005 | 2020 | 7393 | 7408 | $T_{ks}{}^mC_{es}{}^mC_{ks}T_{ds}G_{ds}{}^mC_{ds}G_{ds}{}^mC_{ds}{}^mC_{ds}A_{ds}T_{ds}C_{ds}C_{es}T_{es}G_{ks}G_k$ | 10 | 3533 |
| 1207002 | 2013 | 2028 | 7401 | 7416 | $T_{ks}A_{es}T_{ks}T_{ds}G_{ds}A_{ds}G_{ds}T_{ds}T_{ds}{}^mC_{ds}{}^mC_{ds}T_{ds}G_{es}{}^mC_{es}G_{ks}{}^mC_k$ | 19 | 2617 |
| 1207010 | 2022 | 2037 | 7410 | 7425 | $A_{ks}A_{es}A_{ks}G_{ds}{}^mC_{ds}A_{ds}{}^mC_{ds}T_{ds}T_{ds}T_{ds}A_{ds}T_{ds}T_{es}G_{es}A_{ks}G_k$ | 3 | 3229 |
| 1207029 | 144 | 159 | 511 | 526 | $G_{ks}T_{es}G_{ds}T_{ds}G_{ds}G_{ds}{}^mC_{ds}T_{ds}T_{ds}{}^mC_{ds}T_{ds}T_{ds}{}^mC_{ds}A_{es}G_{es}{}^mC_{es}T_{ks}T_k$ | 11 | 4951 |
| 1207037 | 152 | 167 | N/A | N/A | $G_{ks}A_{ks}A_{ds}{}^mC_{ds}G_{ds}A_{ds}{}^mC_{ds}T_{ds}G_{ds}T_{ds}G_{ds}T_{es}G_{es}{}^mC_{es}T_{ks}{}^mC_k$ | 14 | 3647 |
| 1207045 | 209 | 224 | 3560 | 3575 | $G_{ks}G_{ks}T_{ds}A_{ds}{}^mC_{ds}A_{ds}G_{ds}{}^mC_{ds}T_{ds}G_{ds}{}^mC_{ds}T_{es}G_{es}G_{es}T_{ks}G_k$ | 5 | 4952 |
| 1207053 | 217 | 232 | 3568 | 3583 | $A_{ks}C_{ks}A_{ds}T_{ds}T_{ds}T_{ds}G_{ds}T_{ds}G_{ds}G_{ds}T_{ds}A_{es}{}^mC_{es}A_{es}G_{ks}{}^mC_k$ | 12 | 3114 |
| 1207061 | 1777 | 1792 | 7165 | 7180 | $T_{ks}T_{ks}G_{ds}{}^mC_{ds}A_{ds}G_{ds}G_{ds}G_{ds}T_{ds}G_{ds}A_{ds}G_{es}{}^mC_{es}{}^mC_{es}G_{ks}G_k$ | 20 | 3375 |
| 1207082 | 1785 | 1800 | 7173 | 7188 | $A_{ks}T_{ks}G_{ds}A_{ds}T_{ds}G_{ds}{}^mC_{ds}T_{ds}{}^mC_{ds}T_{ds}T_{ds}G_{ds}C_{es}A_{es}G_{es}G_{ks}G_k$ | 15 | 3603 |
| 1207090 | 1793 | 1808 | 7181 | 7196 | ${}^mC_{ks}{}^mC_{ks}{}^mC_{ds}A_{ds}G_{ds}{}^mC_{ds}T_{ds}G_{ds}A_{ds}T_{ds}G_{ds}A_{es}T_{es}G_{es}{}^mC_{ks}{}^mC_k$ | 52 | 4953 |
| 1207098 | 1899 | 1914 | 7287 | 7302 | $G_{ks}A_{ks}T_{ds}G_{ds}A_{ds}G_{ds}T_{ds}{}^mC_{ds}{}^mC_{ds}{}^mC_{ds}T_{ds}G_{es}A_{es}G_{es}{}^mC_{ks}A_k$ | 12 | 2537 |
| 1207106 | 1914 | 1929 | 7302 | 7317 | ${}^mC_{ks}A_{ks}{}^mC_{ds}{}^mC_{ds}A_{ds}A_{ds}G_{ds}G_{ds}A_{ds}G_{ds}G_{ds}G_{es}A_{es}A_{es}A_{ks}G_k$ | 13 | 4954 |

TABLE 83-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207114 | 1922 | 1937 | 7310 | 7325 | $T_{ks}G_{ks}C_{ds}G_{ds}G_{ds}A_{ds}A_{ds}T_{ds}C_{ds}A_{ds}{}^mC_{ds}{}^mC_{es}A_{es}A_{es}G_{ks}G_k$ | 11 | 3455 |
| 1207127 | 1930 | 1945 | 7318 | 7333 | $T_{ks}{}^mC_{ks}T_{ds}{}^mC_{ds}{}^mC_{ds}A_{ds}{}^mC_{ds}T_{ds}G_{ds}{}^mC_{ds}G_{es}G_{es}A_{es}A_{ks}T_k$ | 12 | 4955 |
| 1207142 | 2000 | 2015 | 7388 | 7403 | ${}^mC_{ks}G_{ks}{}^mC_{ds}{}^mC_{ds}A_{ds}T_{ds}{}^mC_{ds}{}^mC_{ds}T_{ds}G_{ds}G_{ds}{}^mC_{es}G_{es}{}^mC_{es}G_{ks}G_k$ | 24 | 3228 |
| 1207151 | 2008 | 2023 | 7396 | 7411 | $A_{ks}G_{ks}T_{ds}T_{ds}{}^mC_{ds}{}^mC_{ds}T_{ds}G_{ds}{}^mC_{ds}G_{ds}{}^mC_{ds}{}^mC_{es}A_{es}T_{es}{}^mC_{ks}{}^mC_k$ | 19 | 3761 |
| 1207159 | 2017 | 2032 | 7405 | 7420 | $A_{ks}{}^mC_{ks}T_{ds}T_{ds}T_{ds}A_{ds}T_{ds}T_{ds}G_{ds}A_{ds}G_{ds}T_{es}T_{es}C_{es}C_{ks}T_k$ | 4 | 2848 |
| 1207167 | 2031 | 2046 | 7419 | 7434 | $A_{ks}G_{ks}C_{ds}A_{ds}T_{ds}T_{ds}T_{ds}T_{ds}C_{ds}A_{ds}A_{ds}A_{es}G_{es}C_{es}A_{ks}C_k$ | 20 | 3458 |
| 1207175 | 147 | 162 | 514 | 529 | $A_{ks}{}^mC_{ks}T_{ds}G_{ds}T_{ds}G_{ds}T_{ds}G_{ds}{}^mC_{ds}T_{ds}{}^mC_{ds}T_{es}T_{ks}{}^mC_{es}A_{ks}G_e$ | 13 | 3267 |
| 1207183 | 155 | 170 | N/A | N/A | $T_{ks}G_{ks}A_{ds}G_{ds}A_{ds}A_{ds}C_{ds}G_{ds}A_{ds}C_{ds}T_{ds}G_{es}T_{ks}G_{es}T_{ks}G_e$ | 26 | 3875 |
| 1207191 | 212 | 227 | 3563 | 3578 | $T_{ks}G_{ks}T_{ds}G_{ds}G_{ds}T_{ds}A_{ds}C_{ds}A_{ds}G_{ds}C_{ds}T_{es}G_{ks}{}^mC_{es}{}^mC_{ks}G_e$ | 11 | 2734 |
| 1207199 | 220 | 235 | 3571 | 3586 | $G_{ks}G_{ks}T_{ds}A_{ds}{}^mC_{ds}A_{ds}T_{ds}T_{ds}T_{ds}G_{ds}T_{ds}G_{es}G_{ks}T_{es}A_{ks}{}^mC_e$ | 14 | 3269 |
| 1207207 | 1780 | 1795 | 7168 | 7183 | $G_{ks}{}^mC_{ks}{}^mC_{ds}T_{ds}T_{ds}G_{ds}{}^mC_{ds}A_{ds}G_{ds}G_{ds}G_{ds}T_{es}G_{ks}A_{es}G_{ks}C_e$ | 22 | 3451 |
| 1207215 | 1788 | 1803 | 7176 | 7191 | ${}^mC_{ks}T_{ks}G_{ds}A_{ds}T_{ds}G_{ds}A_{ds}T_{ds}G_{ds}{}^mC_{ds}{}^mC_{ds}T_{es}T_{ks}G_{es}{}^mC_{ks}A_e$ | 12 | 3679 |
| 1207223 | 1894 | 1909 | 7282 | 7297 | $G_{ks}T_{ks}{}^mC_{ds}{}^mC_{ds}{}^mC_{ds}T_{ds}G_{ds}A_{ds}A_{ds}G_{ds}{}^mC_{ds}A_{es}T_{ks}{}^mC_{es}A_{ks}G_e$ | 27 | 3682 |
| 1207231 | 1902 | 1917 | 7290 | 7305 | $A_{ks}A_{ks}A_{ds}G_{ds}A_{ds}T_{ds}G_{ds}A_{ds}G_{ds}T_{ds}C_{ds}{}^mC_{es}{}^mC_{ks}T_{es}G_{ks}A_e$ | 19 | 2768 |
| 1207239 | 1917 | 1932 | 7305 | 7320 | $A_{ks}A_{ks}T_{ds}C_{ds}A_{ds}C_{ds}C_{ds}A_{ds}A_{ds}G_{ds}G_{ds}A_{es}G_{ks}G_{es}G_{ks}A_e$ | 14 | 4956 |
| 1207247 | 1925 | 1940 | 7313 | 7328 | ${}^mC_{ks}A_{ks}{}^mC_{ds}T_{ds}G_{ds}{}^mC_{ds}G_{ds}G_{ds}A_{ds}A_{ds}T_{ds}{}^mC_{es}A_{ks}{}^mC_{es}{}^mC_{ks}A_e$ | 11 | 3683 |
| 1207255 | 1933 | 1948 | 7321 | 7336 | ${}^mC_{ks}A_{ks}{}^mC_{ds}T_{ds}{}^mC_{ds}T_{ds}{}^mC_{ds}T_{ds}{}^mC_{ds}A_{ds}{}^mC_{ds}T_{es}G_{ks}{}^mC_{es}G_{ks}G_e$ | N.D. | 4957 |
| 1207263 | 2003 | 2018 | 7391 | 7406 | ${}^mC_{ks}T_{ks}G_{ds}{}^mC_{ds}G_{ds}{}^mC_{ds}{}^mC_{ds}A_{ds}T_{ds}{}^mC_{ds}{}^mC_{ds}T_{es}G_{ks}G_{es}{}^mC_{ks}G_e$ | 30 | 3381 |
| 1207271 | 2011 | 2026 | 7399 | 7414 | $T_{ks}T_{ks}G_{ds}A_{ds}G_{ds}T_{ds}T_{ds}C_{ds}C_{ds}T_{ds}G_{ds}{}^mC_{es}G_{ks}{}^mC_{es}{}^mC_{ks}A_e$ | 9 | 2463 |
| 1207279 | 2020 | 2035 | 7408 | 7423 | $A_{ks}G_{ks}{}^mC_{ds}A_{ds}{}^mC_{ds}T_{ds}T_{ds}T_{ds}A_{ds}T_{ds}T_{ds}G_{es}A_{ks}G_{es}T_{ks}T_e$ | 6 | 3076 |
| 1207287 | 142 | 157 | 509 | 524 | $G_{ks}T_{ks}G_{ds}{}^mC_{ds}T_{ds}{}^mC_{ds}T_{ds}T_{ds}{}^mC_{ds}A_{ds}G_{ds}{}^mC_{ks}T_{es}T_{ks}T_{es}G_k$ | 15 | 4958 |
| 1207295 | 150 | 165 | N/A | N/A | $A_{ks}{}^mC_{ks}G_{ds}A_{ds}{}^mC_{ds}T_{ds}G_{ds}T_{ds}G_{ds}T_{ds}G_{ds}{}^mC_{ks}T_{es}{}^mC_{ks}T_{es}T_k$ | 13 | 3495 |
| 1207303 | 158 | 173 | N/A | N/A | ${}^mC_{ks}A_{ks}G_{ds}T_{ds}G_{ds}A_{ds}G_{ds}A_{ds}A_{ds}{}^mC_{ds}G_{ds}A_{ks}{}^mC_{es}T_{ks}G_{es}T_k$ | 31 | 2579 |
| 1207311 | 215 | 230 | 3566 | 3581 | $A_{ks}T_{ks}T_{ds}T_{ds}G_{ds}T_{ds}G_{ds}G_{ds}T_{ds}A_{ds}{}^mC_{ds}A_{ks}G_{es}{}^mC_{ks}T_{es}G_k$ | 30 | 2963 |

TABLE 83-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207319 | 223 | 238 | 3574 | 3589 | $G_{ks}T_{ks}G_{ds}G_{ds}G_{ds}T_{ds}A_{ds}C_{ds}A_{ds}T_{ds}T_{ds}T_{ks}G_{es}T_{ks}G_{es}G_{k}$ | 19 | 3497 |
| 1207327 | 1783 | 1798 | 7171 | 7186 | $G_{ks}A_{ks}T_{ds}G_{ds}{}^mC_{ds}{}^mC_{ds}T_{ds}T_{ds}G_{ds}{}^mC_{ds}A_{ds}G_{ks}G_{es}G_{ks}T_{es}G_{k}$ | 66 | 4959 |
| 1207335 | 1791 | 1806 | 7179 | 7194 | ${}^mC_{ks}A_{ks}G_{ds}{}^mC_{ds}T_{ds}G_{ds}A_{ds}T_{ds}G_{ds}A_{ds}T_{ds}G_{ks}C_{es}C_{ks}T_{es}T_{k}$ | 24 | 4960 |
| 1207343 | 1897 | 1912 | 7285 | 7300 | $T_{ks}G_{ks}A_{ds}G_{ds}T_{ds}C_{ds}C_{ds}C_{ds}T_{ds}G_{ds}A_{ds}G_{ks}{}^mC_{es}A_{ks}A_{es}T_{k}$ | 20 | 3910 |
| 1207351 | 1905 | 1920 | 7293 | 7308 | $G_{ks}G_{ks}G_{ds}A_{ds}A_{ds}A_{ds}G_{ds}A_{ds}T_{ds}G_{ds}A_{ds}G_{ks}T_{es}{}^mC_{ks}{}^mC_{es}{}^mC_{k}$ | 10 | 2997 |
| 1207359 | 1920 | 1935 | 7308 | 7323 | ${}^mC_{ks}G_{ks}G_{ds}A_{ds}A_{ds}T_{ds}{}^mC_{ds}A_{ds}{}^mC_{ds}{}^mC_{ds}A_{ds}A_{ks}G_{es}G_{ks}A_{es}G_{k}$ | 18 | 3303 |
| 1207367 | 1928 | 1943 | 7316 | 7331 | $T_{ks}{}^mC_{ks}T_{ds}{}^mC_{ds}A_{ds}{}^mC_{ds}T_{ds}G_{ds}{}^mC_{ds}G_{ds}G_{ds}A_{ks}A_{es}T_{ks}C_{es}A_{k}$ | 4 | 3911 |
| 1207375 | 1936 | 1951 | 7324 | 7339 | $A_{ks}G_{ks}{}^mC_{ds}{}^mC_{ds}A_{ds}{}^mC_{ds}T_{ds}{}^mC_{ds}T_{ds}{}^mC_{ds}T_{ds}{}^mC_{ks}A_{es}{}^mC_{ks}T_{es}G_{k}$ | 10 | 4961 |
| 1207383 | 2006 | 2021 | 7394 | 7409 | $T_{ks}T_{ks}T_{ds}C_{ds}T_{ds}G_{ds}C_{ds}G_{ds}C_{ds}C_{ds}A_{ds}T_{ks}C_{es}C_{ks}T_{es}G_{k}$ | 20 | 3609 |
| 1207391 | 2014 | 2029 | 7402 | 7417 | $T_{ks}T_{ks}A_{ds}T_{ds}G_{ds}A_{ds}G_{ds}T_{ds}T_{ds}C_{ds}{}^mC_{ks}T_{es}G_{ks}{}^mC_{es}G_{k}$ | 28 | 2694 |
| 1207399 | 2023 | 2038 | 7411 | 7426 | ${}^mC_{ks}A_{ks}A_{ds}A_{ds}G_{ds}{}^mC_{ds}A_{ds}{}^mC_{ds}T_{ds}T_{ds}T_{ds}A_{ks}T_{es}T_{ks}G_{es}A_{k}$ | 13 | 3306 |
| 1207407 | 145 | 160 | 512 | 527 | $T_{ks}G_{ks}T_{ks}G_{ds}T_{ds}G_{ds}C_{ds}T_{ds}C_{ds}T_{ds}T_{ds}T_{ds}A_{ks}G_{ks}{}^mC_{ks}T_{e}$ | 6 | 3112 |
| 1207415 | 153 | 168 | N/A | N/A | $A_{ks}G_{ks}A_{ks}A_{ds}{}^mC_{ds}G_{ds}A_{ds}{}^mC_{ds}T_{ds}G_{ds}T_{ds}G_{ds}T_{ks}G_{ks}{}^mC_{ks}T_{e}$ | 19 | 3723 |
| 1207423 | 210 | 225 | 3561 | 3576 | $T_{ks}G_{ks}G_{ks}T_{ds}A_{ds}{}^mC_{ds}A_{ds}G_{ds}{}^mC_{ds}T_{ds}G_{ds}{}^mC_{ds}{}^mC_{ks}G_{ks}G_{ks}T_{e}$ | 23 | 2657 |
| 1207431 | 218 | 233 | 3569 | 3584 | $T_{ks}A_{ks}{}^mC_{ks}A_{ds}T_{ds}T_{ds}T_{ds}G_{ds}T_{ds}G_{ds}G_{ds}T_{ds}A_{ks}{}^mC_{ks}A_{ks}G_{e}$ | 18 | 2426 |
| 1207439 | 1778 | 1793 | 7166 | 7181 | ${}^mC_{ks}T_{ks}T_{ks}G_{ds}{}^mC_{ds}A_{ds}G_{ds}G_{ds}G_{ds}T_{ds}G_{ds}A_{ds}G_{ks}{}^mC_{ks}{}^mC_{ks}G_{e}$ | 26 | 4962 |
| 1207447 | 1786 | 1801 | 7174 | 7189 | $G_{ks}A_{ks}T_{ks}G_{ds}A_{ds}T_{ds}G_{ds}{}^mC_{ds}{}^mC_{ds}T_{ds}T_{ds}G_{ds}{}^mC_{ks}A_{ks}G_{ks}G_{e}$ | 7 | 4963 |
| 1207455 | 1892 | 1907 | 7280 | 7295 | ${}^mC_{ks}{}^mC_{ks}{}^mC_{ks}T_{ds}G_{ds}A_{ds}G_{ds}{}^mC_{ds}A_{ds}A_{ds}T_{ds}{}^mC_{ds}A_{ks}G_{ks}G_{ks}A_{e}$ | 18 | 3530 |
| 1207463 | 1900 | 1915 | 7288 | 7303 | $A_{ks}G_{ks}A_{ks}T_{ds}G_{ds}A_{ds}G_{ds}T_{ds}{}^mC_{ds}{}^mC_{ds}{}^mC_{ds}T_{ds}G_{ks}A_{ks}G_{ks}{}^mC_{e}$ | 14 | 2614 |
| 1207471 | 1915 | 1930 | 7303 | 7318 | $T_{ks}{}^mC_{ks}A_{ks}{}^mC_{ds}{}^mC_{ds}A_{ds}A_{ds}G_{ds}G_{ds}A_{ds}G_{ds}G_{ds}G_{ks}A_{ks}A_{ks}A_{e}$ | 24 | 4948 |
| 1207479 | 1923 | 1938 | 7311 | 7326 | ${}^mC_{ks}T_{ks}G_{ks}{}^mC_{ds}G_{ds}G_{ds}A_{ds}T_{ds}{}^mC_{ds}A_{ds}{}^mC_{ds}{}^mC_{ks}A_{ks}A_{ks}G_{e}$ | 11 | 3531 |
| 1207487 | 1931 | 1946 | 7319 | 7334 | ${}^mC_{ks}T_{ks}{}^mC_{ks}T_{ds}{}^mC_{ds}T_{ds}{}^mC_{ds}A_{ds}{}^mC_{ds}T_{ds}G_{ds}{}^mC_{ds}G_{ks}G_{ks}A_{ks}A_{e}$ | 6 | 2461 |
| 1207495 | 2001 | 2016 | 7389 | 7404 | $G_{ks}{}^mC_{ks}G_{ks}{}^mC_{ds}{}^mC_{ds}A_{ds}T_{ds}{}^mC_{ds}{}^mC_{ds}T_{ds}G_{ds}G_{ds}{}^mC_{ks}G_{ks}{}^mC_{ks}G_{e}$ | 116 | 4964 |
| 1207503 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ks}A_{ks}T_{ks}{}^mC_{e}$ | 9 | 3837 |

TABLE 83-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207511 | 2018 | 2033 | 7406 | 7421 | $^mC_{ks}A_{ks}{}^mC_{ks}T_{ds}T_{ds}T_{ds}A_{ds}T_{ds}T_{ds}G_{ds}A_{ds}G_{ds}T_{ks}T_{ks}{}^mC_{ks}{}^mC_e$ | 11 | 2924 |
| 1207519 | 2033 | 2048 | 7421 | 7436 | $T_{ks}{}^mC_{ks}A_{ks}G_{ds}{}^mC_{ds}A_{ds}T_{ds}T_{ds}T_{ds}{}^mC_{ds}A_{ds}A_{ks}A_{ks}G_{ks}{}^mC_e$ | 20 | 3534 |

TABLE 84

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129491 | 1927 | 1942 | 7315 | 7330 | $^mC_{ks}T_{ks}{}^mC_{ks}A_{ds}{}^mC_{ds}T_{ds}G_{ds}{}^mC_{ds}G_{ds}G_{ds}A_{ds}A_{ds}T_{ds}{}^mC_{ks}A_{ks}{}^mC_k$ | 14 | 3835 |
| 1129531 | 2009 | 2024 | 7397 | 7412 | $G_{ks}A_{ks}G_{ds}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 7 | 3837 |
| 1206489 | 1932 | 1947 | 7320 | 7335 | $A_{ks}{}^mC_{ks}T_{ks}{}^mC_{ds}T_{ds}{}^mC_{ds}T_{ds}{}^mC_{ds}A_{ds}{}^mC_{ds}T_{ds}G_{ds}{}^mC_{ds}G_{ks}G_{ks}A_k$ | 5 | 4976 |
| 1206498 | 1778 | 1793 | 7166 | 7181 | $^mC_{ks}T_{ks}T_{ks}G_{ds}{}^mC_{ds}A_{ds}G_{ds}G_{ds}G_{ds}T_{ds}G_{ds}A_{ds}G_{ds}{}^mC_{ks}{}^mC_{ks}G_k$ | 24 | 4962 |
| 1206504 | 1793 | 1808 | 7181 | 7196 | $^mC_{ks}{}^mC_{ks}{}^mC_{ks}A_{ds}G_{ds}{}^mC_{ds}T_{ds}G_{ds}A_{ds}T_{ds}G_{ds}A_{ds}T_{ds}G_{ks}{}^mC_{ks}{}^mC_k$ | 29 | 4953 |
| 1206899 | 142 | 157 | 509 | 524 | $G_{ks}T_{es}G_{ks}{}^mC_{ds}T_{ds}{}^mC_{ds}T_{ds}T_{ds}{}^mC_{ds}A_{ds}G_{ds}{}^mC_{ds}T_{es}T_{es}T_{ks}G_k$ | 8 | 4958 |
| 1206907 | 150 | 165 | N/A | N/A | $A_{ks}{}^mC_{es}G_{ks}A_{ds}{}^mC_{ds}T_{ds}G_{ds}T_{ds}G_{ds}T_{ds}G_{ds}{}^mC_{ds}T_{es}{}^mC_{es}T_{ks}T_k$ | 20 | 3495 |
| 1206915 | 158 | 173 | N/A | N/A | $^mC_{ks}A_{es}G_{ks}T_{ds}G_{ds}A_{ds}G_{ds}A_{ds}A_{ds}{}^mC_{ds}G_{ds}A_{ds}{}^mC_{es}T_{es}G_{ks}T_k$ | 25 | 2579 |
| 1206923 | 215 | 230 | 3566 | 3581 | $A_{ks}T_{es}T_{ks}T_{ds}G_{ds}T_{ds}G_{ds}G_{ds}T_{ds}A_{ds}{}^mC_{ds}A_{ds}{}^mC_{es}{}^mC_{es}T_{ks}G_k$ | 23 | 2963 |
| 1206931 | 223 | 238 | 3574 | 3589 | $G_{ks}T_{es}G_{ks}G_{ds}G_{ds}T_{ds}A_{ds}{}^mC_{ds}A_{ds}T_{ds}T_{ds}T_{ds}G_{es}T_{es}G_{ks}G_k$ | 23 | 3497 |
| 1206939 | 1783 | 1798 | 7171 | 7186 | $G_{ks}A_{es}T_{ks}G_{ds}{}^mC_{ds}{}^mC_{ds}T_{ds}T_{ds}G_{ds}{}^mC_{ds}A_{ds}G_{ds}G_{es}G_{es}T_{ks}G_k$ | 32 | 4959 |
| 1206947 | 1791 | 1806 | 7179 | 7194 | $^mC_{ks}A_{es}G_{ks}{}^mC_{ds}T_{ds}G_{ds}A_{ds}T_{ds}G_{ds}A_{ds}T_{ds}G_{ds}{}^mC_{es}{}^mC_{es}T_{ks}T_k$ | 41 | 4960 |
| 1206955 | 1897 | 1912 | 7285 | 7300 | $T_{ks}G_{es}A_{ks}G_{ds}T_{ds}{}^mC_{ds}{}^mC_{ds}{}^mC_{ds}T_{ds}G_{ds}A_{ds}G_{ds}{}^mC_{es}A_{es}A_{ks}T_k$ | 25 | 3910 |
| 1206963 | 1905 | 1920 | 7293 | 7308 | $G_{ks}G_{es}G_{ks}A_{ds}A_{ds}A_{ds}G_{ds}T_{ds}T_{ds}G_{ds}A_{ds}G_{ds}T_{es}{}^mC_{es}{}^mC_{ks}{}^mC_k$ | 43 | 2997 |
| 1206971 | 1920 | 1935 | 7308 | 7323 | $^mC_{ks}G_{es}G_{ks}A_{ds}A_{ds}T_{ds}{}^mC_{ds}A_{ds}{}^mC_{ds}{}^mC_{ds}A_{ds}A_{ds}G_{es}G_{es}A_{ks}G_k$ | 7 | 3303 |
| 1206979 | 1928 | 1943 | 7316 | 7331 | $T_{ks}{}^mC_{es}T_{ks}{}^mC_{ds}A_{ds}{}^mC_{ds}T_{ds}G_{ds}{}^mC_{ds}G_{ds}G_{ds}A_{ds}A_{es}T_{es}{}^mC_{ks}A_k$ | 15 | 3911 |
| 1206987 | 1936 | 1951 | 7324 | 7339 | $A_{ks}G_{es}{}^mC_{ks}{}^mC_{ds}A_{ds}{}^mC_{ds}T_{ds}{}^mC_{ds}T_{ds}{}^mC_{ds}T_{ds}{}^mC_{ds}A_{es}{}^mC_{es}T_{ks}G_k$ | 8 | 4961 |

TABLE 84-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206995 | 2006 | 2021 | 7394 | 7409 | $T_{ks}T_{es}{}^mC_{ks}{}^mC_{ds}T_{ds}G_{ds}{}^mC_{ds}G_{ds}{}^mC_{ds}{}^mC_{ds}A_{ds}T_{ds}{}^mC_{es}{}^mC_{es}T_{ks}G_k$ | 30 | 3609 |
| 1207003 | 2014 | 2029 | 7402 | 7417 | $T_{ks}T_{es}A_{ks}T_{ds}T_{ds}G_{ds}A_{ds}G_{ds}T_{ds}T_{ds}{}^mC_{ds}{}^mC_{ds}T_{es}G_{es}{}^mC_{ks}G_k$ | 16 | 2694 |
| 1207011 | 2023 | 2038 | 7411 | 7426 | ${}^mC_{ks}A_{es}A_{ks}A_{ds}G_{ds}{}^mC_{ds}A_{ds}{}^mC_{ds}T_{ds}T_{ds}T_{ds}A_{ds}T_{es}T_{es}G_{ks}A_k$ | 25 | 3306 |
| 1207030 | 145 | 160 | 512 | 527 | $T_{ks}G_{ks}T_{ds}G_{ds}T_{ds}G_{ds}{}^mC_{ds}T_{ds}{}^mC_{ds}T_{ds}T_{ds}{}^mC_{es}A_{es}G_{es}{}^mC_{ks}T_k$ | 7 | 3112 |
| 1207038 | 153 | 168 | N/A | N/A | $A_{ks}G_{ks}A_{ds}A_{ds}{}^mC_{ds}G_{ds}A_{ds}{}^mC_{ds}T_{ds}G_{ds}T_{ds}G_{es}T_{es}G_{es}{}^mC_{ks}T_k$ | 15 | 3723 |
| 1207046 | 210 | 225 | 3561 | 3576 | $T_{ks}G_{ks}G_{ds}T_{ds}A_{ds}{}^mC_{ds}A_{ds}G_{ds}{}^mC_{ds}T_{ds}G_{ds}{}^mC_{es}{}^mC_{es}G_{es}G_{ks}T_k$ | 18 | 2657 |
| 1207054 | 218 | 233 | 3569 | 3584 | $T_{ks}A_{ks}{}^mC_{ds}A_{ds}T_{ds}T_{ds}T_{ds}G_{ds}T_{ds}G_{ds}G_{ds}T_{es}A_{es}{}^mC_{es}A_{ks}G_k$ | 27 | 2426 |
| 1207062 | 1778 | 1793 | 7166 | 7181 | ${}^mC_{ks}T_{ks}T_{ds}G_{ds}{}^mC_{ds}A_{ds}G_{ds}G_{ds}T_{ds}G_{ds}A_{es}G_{es}{}^mC_{es}{}^mC_{ks}G_k$ | 31 | 4962 |
| 1207083 | 1786 | 1801 | 7174 | 7189 | $G_{ks}A_{ks}T_{ds}G_{ds}A_{ds}T_{ds}G_{ds}{}^mC_{ds}{}^mC_{ds}T_{ds}T_{ds}G_{es}{}^mC_{es}A_{es}G_{ks}G_k$ | 18 | 4963 |
| 1207091 | 1892 | 1907 | 7280 | 7295 | ${}^mC_{ks}{}^mC_{ks}{}^mC_{ds}T_{ds}G_{ds}A_{ds}G_{ds}{}^mC_{ds}A_{ds}A_{ds}T_{ds}{}^mC_{es}A_{es}G_{es}G_{ks}A_k$ | 48 | 3530 |
| 1207099 | 1900 | 1915 | 7288 | 7303 | $A_{ks}G_{ks}A_{ds}T_{ds}G_{ds}A_{ds}G_{ds}T_{ds}{}^mC_{ds}{}^mC_{ds}{}^mC_{ds}T_{es}G_{es}A_{es}G_{ks}{}^mC_k$ | 18 | 2614 |
| 1207107 | 1915 | 1930 | 7303 | 7318 | $T_{ks}{}^mC_{es}A_{ds}{}^mC_{ds}{}^mC_{ds}A_{ds}A_{ds}G_{ds}G_{ds}A_{ds}G_{ds}G_{es}A_{es}A_{ks}A_k$ | 20 | 4948 |
| 1207115 | 1923 | 1938 | 7311 | 7326 | ${}^mC_{ks}T_{ds}G_{ds}{}^mC_{ds}G_{ds}G_{ds}A_{ds}A_{ds}T_{ds}{}^mC_{ds}A_{ds}{}^mC_{es}{}^mC_{es}A_{es}A_{ks}G_k$ | 10 | 3531 |
| 1207129 | 1931 | 1946 | 7319 | 7334 | ${}^mC_{ks}T_{ks}{}^mC_{ds}T_{ds}{}^mC_{ds}T_{ds}{}^mC_{ds}A_{ds}{}^mC_{ds}T_{ds}G_{ds}{}^mC_{es}G_{es}G_{es}A_{ks}A_k$ | 8 | 2461 |
| 1207144 | 2001 | 2016 | 7389 | 7404 | $G_{ks}{}^mC_{ks}G_{ds}{}^mC_{ds}{}^mC_{ds}A_{ds}T_{ds}{}^mC_{ds}{}^mC_{ds}T_{ds}G_{ds}G_{es}{}^mC_{es}G_{es}{}^mC_{ks}G_k$ | 74 | 4964 |
| 1207152 | 2009 | 2024 | 7397 | 7412 | $G_{ks}A_{ks}G_{ds}T_{ds}T_{ds}{}^mC_{ds}{}^mC_{ds}T_{ds}G_{ds}{}^mC_{ds}G_{ds}{}^mC_{es}{}^mC_{es}A_{es}T_{ks}{}^mC_k$ | 16 | 3837 |
| 1207160 | 2018 | 2033 | 7406 | 7421 | ${}^mC_{ks}A_{ks}{}^mC_{ds}T_{ds}T_{ds}T_{ds}T_{ds}A_{ds}T_{ds}T_{ds}G_{ds}A_{es}G_{es}T_{es}{}^mC_{ks}{}^mC_k$ | 8 | 2924 |
| 1207168 | 2033 | 2048 | 7421 | 7436 | $T_{ks}{}^mC_{ks}A_{ds}G_{ds}{}^mC_{ds}A_{ds}T_{ds}T_{ds}T_{ds}T_{ds}{}^mC_{ds}A_{es}A_{es}A_{es}G_{ks}{}^mC_k$ | 29 | 3534 |
| 1207176 | 148 | 163 | 515 | 530 | $G_{ks}A_{ks}{}^mC_{ds}T_{ds}G_{ds}T_{ds}G_{ds}T_{ds}G_{ds}{}^mC_{ds}T_{ds}{}^mC_{es}T_{ks}T_{es}{}^mC_{ks}A_e$ | 16 | 3343 |
| 1207184 | 156 | 171 | N/A | N/A | $G_{ks}T_{ds}A_{ds}G_{ds}G_{ds}A_{ds}A_{ds}{}^mC_{ds}G_{ds}A_{ds}{}^mC_{ds}T_{es}G_{ks}T_{es}G_{ks}T_e$ | 18 | 2424 |
| 1207192 | 213 | 228 | 3564 | 3579 | $T_{ks}T_{ks}G_{ds}T_{ds}G_{ds}G_{ds}G_{ds}T_{ds}A_{ds}G_{ds}A_{ds}G_{ds}{}^mC_{es}G_{es}{}^mC_{ks}{}^mC_e$ | 25 | 2811 |
| 1207200 | 221 | 236 | 3572 | 3587 | $G_{ks}G_{ks}G_{ds}T_{ds}A_{ds}{}^mC_{ds}A_{ds}T_{ds}T_{ds}T_{ds}G_{ds}T_{es}G_{ks}G_{es}T_{ks}A_e$ | 51 | 3345 |
| 1207208 | 1781 | 1796 | 7169 | 7184 | $T_{ks}G_{ks}{}^mC_{ds}{}^mC_{ds}T_{ds}T_{ds}G_{ds}{}^mC_{ds}A_{ds}G_{ds}G_{ds}G_{ds}T_{es}G_{es}A_{ks}G_e$ | 45 | 3527 |
| 1207216 | 1789 | 1804 | 7177 | 7192 | $G_{ks}{}^mC_{ks}T_{ds}G_{ds}A_{ds}T_{ds}G_{ds}A_{ds}T_{ds}G_{ds}{}^mC_{ds}{}^mC_{es}T_{ks}T_{es}G_{ks}{}^mC_e$ | 17 | 3755 |

TABLE 84-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207224 | 1895 | 1910 | 7283 | 7298 | $A_{ks}G_{ks}T_{ds}C_{ds}C_{ds}C_{ds}T_{ds}G_{ds}A_{ds}G_{ds}C_{ds}A_{es}A_{ks}T_{es}{}^mC_{ks}A_e$ | 18 | 3758 |
| 1207232 | 1903 | 1918 | 7291 | 7306 | $G_{ks}A_{ks}A_{ds}A_{ds}G_{ds}A_{ds}T_{ds}G_{ds}A_{ds}G_{ds}T_{ds}C_{es}{}^mC_{ks}{}^mC_{es}T_{ks}G_e$ | 13 | 2845 |
| 1207240 | 1918 | 1933 | 7306 | 7321 | $G_{ks}A_{ks}A_{ds}T_{ds}C_{ds}A_{ds}C_{ds}C_{ds}A_{ds}A_{ds}G_{ds}G_{es}A_{ks}G_{es}G_{ks}G_e$ | 18 | 4965 |
| 1207248 | 1926 | 1941 | 7314 | 7329 | $T_{ks}C_{ks}A_{ds}C_{ds}T_{ds}G_{ds}C_{ds}G_{ds}G_{ds}A_{ds}A_{ds}T_{es}{}^mC_{ks}A_{es}{}^mC_{ks}{}^mC_e$ | 6 | 3759 |
| 1207256 | 1934 | 1949 | 7322 | 7337 | ${}^mC_{ks}{}^mC_{ks}A_{ds}{}^mC_{ds}T_{ds}{}^mC_{ds}T_{ds}{}^mC_{ds}T_{ds}{}^mC_{ds}A_{ds}{}^mC_{es}T_{ks}G_{es}{}^mC_{ks}G_e$ | 19 | 4949 |
| 1207264 | 2004 | 2019 | 7392 | 7407 | ${}^mC_{ks}{}^mC_{ks}T_{ds}G_{ds}{}^mC_{ds}G_{ds}{}^mC_{ds}{}^mC_{ds}A_{ds}T_{ds}{}^mC_{ds}{}^mC_{es}T_{ks}G_{es}G_{ks}C_e$ | 18 | 3457 |
| 1207272 | 2012 | 2027 | 7400 | 7415 | $A_{ks}T_{ks}T_{ds}G_{ds}A_{ds}G_{ds}T_{ds}T_{ds}C_{ds}{}^mC_{ds}T_{ds}G_{es}{}^mC_{ks}G_{es}{}^mC_{ks}{}^mC_e$ | 22 | 2540 |
| 1207280 | 2021 | 2036 | 7409 | 7424 | $A_{ks}A_{ks}G_{ds}C_{ds}A_{ds}C_{ds}T_{ds}T_{ds}T_{ds}A_{ds}T_{ds}T_{es}G_{ks}A_{es}G_{ks}T_e$ | 9 | 3147 |
| 1207288 | 143 | 158 | 510 | 525 | $T_{ks}G_{ks}T_{ds}G_{ds}C_{ds}T_{ds}C_{ds}T_{ds}T_{ds}C_{ds}A_{ds}G_{ks}{}^mC_{es}T_{ks}T_{es}T_k$ | 12 | 3037 |
| 1207296 | 151 | 166 | N/A | N/A | $A_{ks}A_{ks}C_{ds}G_{ds}A_{ds}C_{ds}T_{ds}G_{ds}T_{ds}G_{ds}T_{ds}G_{ks}{}^mC_{es}T_{ks}{}^mC_{es}T_k$ | 33 | 3571 |
| 1207304 | 208 | 223 | 3559 | 3574 | $G_{ks}T_{ks}A_{ds}{}^mC_{ds}A_{ds}A_{ds}G_{ds}{}^mC_{ds}T_{ds}G_{ds}{}^mC_{ds}{}^mC_{ds}G_{ks}G_{es}T_{ks}G_{es}G_k$ | 21 | 4968 |
| 1207312 | 216 | 231 | 3567 | 3582 | ${}^mC_{ks}A_{ks}T_{ds}T_{ds}T_{ds}G_{ds}T_{ds}G_{ds}G_{ds}T_{ds}A_{ds}{}^mC_{ks}A_{es}G_{ks}{}^mC_{es}T_k$ | 6 | 3039 |
| 1207320 | 1776 | 1791 | 7164 | 7179 | $T_{ks}G_{ks}{}^mC_{ds}A_{ds}G_{ds}G_{ds}G_{ds}T_{ds}G_{ds}A_{ds}G_{ds}{}^mC_{ks}{}^mC_{es}G_{ks}G_{es}{}^mC_k$ | 58 | 3299 |
| 1207328 | 1784 | 1799 | 7172 | 7187 | $T_{ks}G_{ks}A_{ds}T_{ds}G_{ds}{}^mC_{ds}{}^mC_{ds}T_{ds}T_{ds}G_{ds}{}^mC_{ds}A_{ks}G_{es}G_{ks}G_{es}T_k$ | 42 | 4969 |
| 1207336 | 1792 | 1807 | 7180 | 7195 | $C_{ks}C_{ks}A_{ds}G_{ds}C_{ds}T_{ds}G_{ds}A_{ds}T_{ds}G_{ds}A_{ds}T_{ks}G_{es}C_{ks}C_{es}T_k$ | 25 | 4970 |
| 1207344 | 1898 | 1913 | 7286 | 7301 | $A_{ks}T_{ks}G_{ds}A_{ds}G_{ds}T_{ds}C_{ds}C_{ds}C_{ds}T_{ds}G_{ds}A_{ks}G_{es}{}^mC_{ks}A_{es}A_k$ | 30 | 2460 |
| 1207352 | 1906 | 1921 | 7294 | 7309 | $A_{ks}G_{ks}G_{ds}G_{ds}A_{ds}A_{ds}A_{ds}G_{ds}A_{ds}T_{ds}G_{ds}A_{ks}G_{es}T_{ks}{}^mC_{es}{}^mC_k$ | 18 | 3073 |
| 1207360 | 1921 | 1936 | 7309 | 7324 | $G_{ks}{}^mC_{ks}G_{ds}G_{ds}A_{ds}A_{ds}T_{ds}{}^mC_{ds}A_{ds}{}^mC_{ds}{}^mC_{ds}A_{ks}A_{es}G_{ks}G_{es}A_k$ | 6 | 3379 |
| 1207368 | 1929 | 1944 | 7317 | 7332 | ${}^mC_{ks}T_{ks}{}^mC_{ds}T_{ds}{}^mC_{ds}A_{ds}{}^mC_{ds}T_{ds}G_{ds}{}^mC_{ds}G_{ds}G_{ks}A_{es}A_{ks}T_{es}{}^mC_k$ | 16 | 4971 |
| 1207376 | 1937 | 1952 | 7325 | 7340 | ${}^mC_{ks}A_{ks}G_{ds}{}^mC_{ds}{}^mC_{ds}A_{ds}{}^mC_{ds}T_{ds}{}^mC_{ds}T_{ds}C_{ds}T_{ks}{}^mC_{es}A_{ks}{}^mC_{es}T_k$ | 11 | 4972 |
| 1207384 | 2007 | 2022 | 7395 | 7410 | $G_{ks}T_{ks}T_{ds}{}^mC_{ds}{}^mC_{ds}T_{ds}G_{ds}{}^mC_{ds}G_{ds}{}^mC_{ds}{}^mC_{ds}A_{ks}T_{es}{}^mC_{ks}{}^mC_{es}T_k$ | 15 | 3685 |
| 1207392 | 2016 | 2031 | 7404 | 7419 | $C_{ks}T_{ks}T_{ds}T_{ds}A_{ds}T_{ds}T_{ds}G_{ds}A_{ds}G_{ds}T_{ds}T_{ks}{}^mC_{es}{}^mC_{es}T_{es}G_k$ | 11 | 2771 |
| 1207400 | 2024 | 2039 | 7412 | 7427 | $T_{ks}C_{ks}A_{ds}A_{ds}A_{ds}G_{ds}C_{ds}A_{ds}C_{ds}T_{ds}T_{ds}T_{ks}A_{es}T_{ks}T_{es}G_k$ | 21 | 3382 |

TABLE 84-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207408 | 146 | 161 | 513 | 528 | $^mC_{ks}T_{ks}G_{ks}T_{ds}G_{ds}T_{ds}G_{ds}{}^mC_{ds}T_{ds}{}^mC_{ds}T_{ds}T_{ds}{}^mC_{ks}A_{ks}G_{ks}{}^mC_e$ | 20 | 3190 |
| 1207416 | 154 | 169 | N/A | N/A | $G_{ks}A_{ks}G_{ks}A_{ds}A_{ds}{}^mC_{ds}G_{ds}A_{ds}{}^mC_{ds}T_{ds}G_{ds}T_{ds}G_{ks}T_{ks}G_{ks}{}^mC_e$ | 24 | 3799 |
| 1207424 | 211 | 226 | 3562 | 3577 | $G_{ks}T_{ks}G_{ks}G_{ds}T_{ds}A_{ds}{}^mC_{ds}A_{ds}G_{ds}{}^mC_{ds}T_{ds}G_{ds}C_{ds}C_{ks}G_{ks}G_e$ | 41 | 4973 |
| 1207432 | 219 | 234 | 3570 | 3585 | $G_{ks}T_{ks}A_{ks}C_{ds}A_{ds}T_{ds}T_{ds}G_{ds}T_{ds}G_{ds}G_{ds}T_{ks}A_{ks}{}^mC_{ks}A_e$ | 50 | 3192 |
| 1207440 | 1779 | 1794 | 7167 | 7182 | $^mC_{ks}{}^mC_{ks}T_{ks}T_{ds}G_{ds}{}^mC_{ds}A_{ds}G_{ds}G_{ds}G_{ds}T_{ds}G_{ds}A_{ks}G_{ks}{}^mC_{ks}{}^mC_e$ | 34 | 4974 |
| 1207448 | 1787 | 1802 | 7175 | 7190 | $T_{ks}G_{ks}A_{ks}T_{ds}G_{ds}A_{ds}T_{ds}G_{ds}{}^mC_{ds}{}^mC_{ds}T_{ds}T_{ds}G_{ks}{}^mC_{ks}A_{ks}G_e$ | 25 | 4975 |
| 1207456 | 1893 | 1908 | 7281 | 7296 | $T_{ks}C_{ks}C_{ks}C_{ds}T_{ds}G_{ds}A_{ds}G_{ds}C_{ds}A_{ds}A_{ds}T_{ds}C_{ks}A_{ks}G_{ks}G_e$ | 21 | 3606 |
| 1207464 | 1901 | 1916 | 7289 | 7304 | $A_{ks}A_{ks}G_{ks}A_{ds}T_{ds}G_{ds}A_{ds}G_{ds}T_{ds}{}^mC_{ds}{}^mC_{ds}C_{ds}T_{ks}G_{ks}A_{ks}G_e$ | 22 | 2691 |
| 1207472 | 1916 | 1931 | 7304 | 7319 | $A_{ks}T_{ks}{}^mC_{ks}A_{ds}{}^mC_{ds}{}^mC_{ds}A_{ds}A_{ds}G_{ds}G_{ds}A_{ds}G_{ds}G_{ks}G_{ks}A_{ks}A_e$ | 10 | 4966 |
| 1207480 | 1924 | 1939 | 7312 | 7327 | $A_{ks}C_{ks}T_{ks}G_{ds}C_{ds}G_{ds}G_{ds}A_{ds}A_{ds}T_{ds}C_{ds}A_{ds}{}^mC_{ks}{}^mC_{ks}A_{ks}A_e$ | 2 | 3607 |
| 1207488 | 1932 | 1947 | 7320 | 7335 | $A_{ks}{}^mC_{ks}T_{ks}{}^mC_{ds}T_{ds}{}^mC_{ds}T_{ds}C_{ds}A_{ds}C_{ds}T_{ds}G_{ds}{}^mC_{ks}G_{ks}G_{ks}A_e$ | 6 | 4976 |
| 1207496 | 2002 | 2017 | 7390 | 7405 | $T_{ks}G_{ks}C_{ks}G_{ds}C_{ds}C_{ds}A_{ds}T_{ds}{}^mC_{ds}{}^mC_{ds}T_{ds}G_{ds}G_{ks}{}^mC_{ks}G_{ks}{}^mC_e$ | 73 | 3305 |
| 1207504 | 2010 | 2025 | 7398 | 7413 | $T_{ks}G_{ks}A_{ks}G_{ds}T_{ds}T_{ds}C_{ds}C_{ds}T_{ds}G_{ds}C_{ds}G_{ds}{}^mC_{ks}{}^mC_{ks}A_{ks}T_e$ | 5 | 3913 |
| 1207512 | 2019 | 2034 | 7407 | 7422 | $G_{ks}{}^mC_{ks}A_{ks}{}^mC_{ds}T_{ds}T_{ds}T_{ds}A_{ds}T_{ds}G_{ds}A_{ds}G_{ks}T_{ks}T_{ks}{}^mC_e$ | 3 | 3000 |

TABLE 85

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 15 | 3837 |
| 1129532 | 2010 | 2025 | 7398 | 7413 | $T_{ks}G_{ks}A_{ks}G_{ds}T_{ds}T_{ds}{}^mC_{ds}{}^mC_{ds}T_{ds}G_{ds}{}^mC_{ds}G_{ds}C_{ds}C_{ks}A_{ks}T_k$ | 7 | 3913 |
| 1206485 | 1914 | 1929 | 7302 | 7317 | $^mC_{ks}A_{ks}{}^mC_{ks}{}^mC_{ds}A_{ds}A_{ds}G_{ds}G_{ds}A_{ds}G_{ds}G_{ds}G_{ds}A_{ks}A_{ks}G_k$ | 27 | 4954 |
| 1206490 | 1933 | 1948 | 7321 | 7336 | $^mC_{ks}A_{ks}{}^mC_{ks}T_{ds}{}^mC_{ds}T_{ds}{}^mC_{ds}T_{ds}{}^mC_{ds}A_{ds}{}^mC_{ds}T_{ds}G_{ds}{}^mC_{ks}G_{ks}G_k$ | 6 | 4957 |
| 1206499 | 1779 | 1794 | 7167 | 7182 | $^mC_{ks}{}^mC_{ks}T_{ks}T_{ds}G_{ds}{}^mC_{ds}A_{ds}G_{ds}G_{ds}G_{ds}T_{ds}G_{ds}A_{ks}G_{ks}{}^mC_{ks}{}^mC_k$ | 36 | 4974 |

TABLE 85-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1206900 | 143 | 158 | 510 | 525 | $T_{ks}G_{es}T_{ks}G_{ds}C_{ds}T_{ds}C_{ds}T_{ds}T_{ds}C_{ds}A_{ds}G_{ds}C_{es}T_{es}T_{ks}T_k$ | 24 | 3037 |
| 1206908 | 151 | 166 | N/A | N/A | $A_{ks}A_{es}{}^mC_{ks}G_{ds}A_{ds}{}^mC_{ds}T_{ds}G_{ds}T_{ds}G_{ds}T_{ds}{}^mC_{es}T_{es}{}^mC_{ks}T_k$ | 12 | 3571 |
| 1206916 | 208 | 223 | 3559 | 3574 | $G_{ks}T_{es}A_{ks}{}^mC_{ds}A_{ds}G_{ds}{}^mC_{ds}T_{ds}G_{ds}{}^mC_{ds}{}^mC_{ds}G_{ds}G_{es}T_{es}G_{ks}G_k$ | 32 | 4968 |
| 1206924 | 216 | 231 | 3567 | 3582 | $T_{ks}A_{es}T_{ks}T_{ds}T_{ds}G_{ds}T_{ds}G_{ds}G_{ds}T_{ds}A_{ds}{}^mC_{ds}A_{es}G_{es}{}^mC_{ks}T_k$ | 26 | 3039 |
| 1206932 | 1776 | 1791 | 7164 | 7179 | $T_{ks}G_{es}{}^mC_{ks}A_{ds}G_{ds}G_{ds}T_{ds}G_{ds}A_{ds}G_{ds}{}^mC_{ds}{}^mC_{es}G_{es}G_{ks}{}^mC_k$ | 40 | 3299 |
| 1206940 | 1784 | 1799 | 7172 | 7187 | $T_{ks}G_{es}A_{ks}T_{ds}G_{ds}{}^mC_{ds}{}^mC_{ds}T_{ds}T_{ds}G_{ds}{}^mC_{ds}A_{ds}G_{es}G_{es}G_{ks}T_k$ | 25 | 4969 |
| 1206948 | 1792 | 1807 | 7180 | 7195 | ${}^mC_{ks}{}^mC_{es}A_{ks}G_{ds}{}^mC_{ds}T_{ds}G_{ds}A_{ds}T_{ds}G_{ds}A_{ds}T_{ds}G_{es}{}^mC_{es}{}^mC_{ks}T_k$ | 24 | 4970 |
| 1206956 | 1898 | 1913 | 7286 | 7301 | $A_{ks}T_{es}G_{ks}A_{ds}G_{ds}T_{ds}{}^mC_{ds}{}^mC_{ds}T_{ds}G_{ds}A_{ds}G_{es}{}^mC_{es}A_{ks}A_k$ | 16 | 2460 |
| 1206964 | 1906 | 1921 | 7294 | 7309 | $A_{ks}G_{es}G_{ks}G_{ds}A_{ds}A_{ds}A_{ds}G_{ds}A_{ds}T_{ds}G_{ds}A_{ds}G_{es}T_{es}{}^mC_{ks}{}^mC_k$ | 21 | 3073 |
| 1206972 | 1921 | 1936 | 7309 | 7324 | $G_{ks}{}^mC_{es}G_{ks}G_{ds}A_{ds}A_{ds}T_{ds}{}^mC_{ds}A_{ds}{}^mC_{ds}{}^mC_{ds}A_{ds}A_{es}G_{es}G_{ks}A_k$ | 15 | 3379 |
| 1206980 | 1929 | 1944 | 7317 | 7332 | ${}^mC_{ks}T_{es}{}^mC_{ks}T_{ds}{}^mC_{ds}A_{ds}A_{ds}{}^mC_{ds}T_{ds}G_{ds}{}^mC_{ds}G_{ds}G_{ds}A_{es}A_{es}T_{ks}{}^mC_k$ | 8 | 4971 |
| 1206988 | 1937 | 1952 | 7325 | 7340 | ${}^mC_{ks}A_{es}G_{ks}{}^mC_{ds}{}^mC_{ds}A_{ds}{}^mC_{ds}T_{ds}T_{ds}{}^mC_{ds}T_{ds}{}^mC_{ds}T_{ds}{}^mC_{es}A_{es}{}^mC_{ks}T_k$ | 15 | 4972 |
| 1206996 | 2007 | 2022 | 7395 | 7410 | $G_{ks}T_{es}T_{ks}{}^mC_{ds}{}^mC_{ds}T_{ds}G_{ds}{}^mC_{ds}G_{ds}{}^mC_{ds}{}^mC_{ds}A_{ds}T_{es}{}^mC_{es}{}^mC_{ks}T_k$ | 10 | 3685 |
| 1207004 | 2016 | 2031 | 7404 | 7419 | ${}^mC_{ks}T_{es}T_{ks}T_{ds}A_{ds}T_{ds}G_{ds}A_{ds}A_{ds}G_{ds}T_{ds}T_{ds}{}^mC_{es}{}^mC_{es}T_{ks}G_k$ | 7 | 2771 |
| 1207012 | 2024 | 2039 | 7412 | 7427 | $T_{ks}{}^mC_{es}A_{ks}A_{ds}A_{ds}G_{ds}{}^mC_{ds}A_{ds}{}^mC_{ds}T_{ds}T_{ds}T_{ds}A_{es}T_{es}G_{ks}G_k$ | 14 | 3382 |
| 1207031 | 146 | 161 | 513 | 528 | ${}^mC_{ks}T_{ks}G_{ds}T_{ds}G_{ds}T_{ds}G_{ds}{}^mC_{ds}T_{ds}{}^mC_{ds}T_{ds}T_{es}{}^mC_{es}A_{es}G_{ks}{}^mC_k$ | 24 | 3190 |
| 1207039 | 154 | 169 | N/A | N/A | $G_{ks}A_{ds}G_{ds}A_{ds}A_{ds}{}^mC_{ds}G_{ds}A_{ds}{}^mC_{ds}T_{ds}G_{ds}T_{es}G_{es}T_{es}G_{ks}{}^mC_k$ | 14 | 3799 |
| 1207047 | 211 | 226 | 3562 | 3577 | $G_{ks}T_{ks}G_{ds}G_{ds}T_{ds}A_{ds}{}^mC_{ds}A_{ds}G_{ds}{}^mC_{ds}T_{ds}G_{es}{}^mC_{es}{}^mC_{es}G_{ks}G_k$ | 18 | 4973 |
| 1207055 | 219 | 234 | 3570 | 3585 | $G_{ks}T_{ks}A_{ds}{}^mC_{ds}A_{ds}T_{ds}T_{ds}T_{ds}G_{ds}T_{ds}G_{ds}G_{es}T_{es}A_{es}{}^mC_{ks}A_k$ | 65 | 3192 |
| 1207063 | 1779 | 1794 | 7167 | 7182 | ${}^mC_{ks}{}^mC_{ks}T_{ds}G_{ds}{}^mC_{ds}A_{ds}G_{ds}G_{ds}G_{ds}T_{ds}G_{es}A_{es}G_{es}{}^mC_{ks}{}^mC_k$ | 32 | 4974 |
| 1207084 | 1787 | 1802 | 7175 | 7190 | $T_{ks}G_{ks}A_{ds}T_{ds}G_{ds}A_{ds}T_{ds}G_{ds}{}^mC_{ds}{}^mC_{ds}T_{ds}T_{es}G_{es}{}^mC_{es}A_{ks}G_k$ | 15 | 4975 |
| 1207092 | 1893 | 1908 | 7281 | 7296 | $T_{ks}{}^mC_{ks}{}^mC_{ds}{}^mC_{ds}T_{ds}G_{ds}A_{ds}G_{ds}{}^mC_{ds}A_{ds}A_{ds}T_{es}{}^mC_{es}A_{es}G_{ks}G_k$ | 29 | 3606 |
| 1207100 | 1901 | 1916 | 7289 | 7304 | $A_{ks}A_{ks}G_{ds}A_{ds}T_{ds}G_{ds}A_{ds}G_{ds}T_{ds}{}^mC_{ds}{}^mC_{ds}{}^mC_{es}T_{es}G_{es}A_{ks}G_k$ | 16 | 2691 |

TABLE 85-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207108 | 1916 | 1931 | 7304 | 7319 | $A_{ks}T_{ks}{}^mC_{ds}A_{ds}{}^mC_{ds}{}^mC_{ds}A_{ds}A_{ds}G_{ds}G_{ds}A_{ds}G_{es}G_{es}G_{es}A_{ks}A_k$ | 9 | 4966 |
| 1207116 | 1924 | 1939 | 7312 | 7327 | $A_{ks}{}^mC_{ks}T_{ds}G_{ds}{}^mC_{ds}G_{ds}G_{ds}A_{ds}A_{ds}T_{ds}{}^mC_{ds}A_{Es}{}^mC_{es}{}^mC_{es}{}^mC_{es}A_{ks}A_k$ | 10 | 3607 |
| 1207131 | 1932 | 1947 | 7320 | 7335 | $A_{ks}{}^mC_{ks}T_{ds}{}^mC_{ds}T_{ds}{}^mC_{ds}T_{ds}{}^mC_{ds}A_{ds}{}^mC_{ds}T_{ds}G_{es}{}^mC_{es}G_{es}G_{ks}A_k$ | 6 | 4976 |
| 1207145 | 2002 | 2017 | 7390 | 7405 | $T_{ks}G_{ks}{}^mC_{ds}G_{ds}{}^mC_{ds}{}^mC_{ds}A_{ds}T_{ds}{}^mC_{ds}{}^mC_{ds}T_{ds}G_{es}G_{es}{}^mC_{es}G_{ks}{}^mC_k$ | 46 | 3305 |
| 1207153 | 2010 | 2025 | 7398 | 7413 | $T_{ks}G_{ks}A_{ds}G_{ds}T_{ds}T_{ds}{}^mC_{ds}{}^mC_{ds}T_{ds}G_{ds}{}^mC_{ds}G_{es}C_{es}C_{es}A_{ks}T_k$ | 13 | 3913 |
| 1207161 | 2019 | 2034 | 7407 | 7422 | $G_{ks}{}^mC_{ks}A_{ds}{}^mC_{ds}T_{ds}T_{ds}T_{ds}A_{ds}T_{ds}T_{ds}G_{ds}A_{es}G_{es}T_{es}T_{ks}{}^mC_k$ | 17 | 3000 |
| 1207169 | 141 | 156 | 508 | 523 | $T_{ks}G_{ks}{}^mC_{ds}T_{ds}{}^mC_{ds}T_{ds}T_{ds}{}^mC_{ds}A_{ds}G_{ds}{}^mC_{ds}T_{es}T_{ks}T_{es}G_{ks}T_e$ | 33 | 4950 |
| 1207177 | 149 | 164 | 516 | 531 | ${}^mC_{ks}G_{ks}A_{ds}{}^mC_{ds}T_{ds}G_{ds}T_{ds}G_{ds}T_{ds}G_{ds}{}^mC_{ds}T_{es}{}^mC_{ks}T_{es}T_{ks}{}^mC_e$ | 17 | 3419 |
| 1207185 | 157 | 172 | N/A | N/A | $A_{ks}G_{ks}T_{ds}G_{ds}A_{ds}G_{ds}A_{ds}A_{ds}{}^mC_{ds}G_{ds}A_{ds}{}^mC_{es}T_{ks}G_{es}T_{ks}G_e$ | 15 | 2502 |
| 1207193 | 214 | 229 | 3565 | 3580 | $T_{ks}T_{ks}T_{ds}G_{ds}T_{ds}G_{ds}G_{ds}T_{ds}A_{ds}C_{ds}A_{ds}G_{es}{}^mC_{ks}T_{es}G_{ks}{}^mC_e$ | 17 | 2887 |
| 1207201 | 222 | 237 | 3573 | 3588 | $T_{ks}G_{ks}G_{ds}G_{ks}T_{ds}A_{ds}C_{ds}A_{ds}T_{ds}T_{ds}T_{ds}G_{es}T_{ks}G_{es}G_{ks}T_e$ | 25 | 3421 |
| 1207209 | 1782 | 1797 | 7170 | 7185 | $A_{ks}T_{ks}G_{ds}{}^mC_{ds}{}^mC_{ds}T_{ds}T_{ds}G_{ds}{}^mC_{ds}A_{ds}G_{ds}G_{es}G_{ks}T_{es}G_{ks}A_e$ | 26 | 4947 |
| 1207217 | 1790 | 1805 | 7178 | 7193 | $A_{ks}G_{ks}{}^mC_{ds}T_{ds}G_{ds}A_{ds}T_{ds}G_{ds}G_{ds}A_{ds}T_{ds}G_{ds}{}^mC_{es}{}^mC_{ks}T_{es}T_{ks}G_e$ | 22 | 3831 |
| 1207225 | 1896 | 1911 | 7284 | 7299 | $G_{ks}A_{ks}G_{ds}T_{ds}{}^mC_{ds}{}^mC_{ds}{}^mC_{ds}T_{ds}G_{ds}A_{ds}G_{ds}C_{es}A_{ks}A_{es}T_{ks}C_e$ | 7 | 3834 |
| 1207233 | 1904 | 1919 | 7292 | 7307 | $G_{ks}G_{ks}A_{ds}A_{ds}A_{ds}G_{ds}A_{ds}T_{ds}G_{ds}A_{ds}G_{ds}T_{es}C_{ks}C_{es}C_{ks}T_e$ | 31 | 2921 |
| 1207241 | 1919 | 1934 | 7307 | 7322 | $G_{ks}A_{ks}A_{ds}A_{ds}T_{ds}C_{ds}A_{ds}{}^mC_{ds}C_{ds}A_{ds}A_{ds}G_{es}G_{ks}A_{es}G_{ks}G_e$ | 21 | 3226 |
| 1207249 | 1927 | 1942 | 7315 | 7330 | ${}^mC_{ks}T_{ks}{}^mC_{ds}A_{ds}{}^mC_{ds}T_{ds}G_{ds}{}^mC_{ds}G_{ds}G_{ds}A_{ds}A_{es}T_{ks}{}^mC_{es}A_{ks}{}^mC_e$ | 12 | 3835 |
| 1207257 | 1935 | 1950 | 7323 | 7338 | $G_{ks}{}^mC_{ks}{}^mC_{ds}A_{ds}{}^mC_{ds}A_{ds}{}^mC_{ds}T_{ds}{}^mC_{ds}T_{ds}{}^mC_{ds}A_{es}{}^mC_{es}{}^mC_{ks}T_{es}G_{ks}{}^mC_e$ | 25 | 4967 |
| 1207265 | 2005 | 2020 | 7393 | 7408 | $T_{ks}C_{ks}C_{ds}T_{ds}G_{ds}G_{ds}G_{ds}C_{ds}C_{ds}A_{ds}T_{ds}{}^mC_{es}{}^mC_{ks}T_{es}G_{ks}G_e$ | 24 | 3533 |
| 1207273 | 2013 | 2028 | 7401 | 7416 | $T_{ks}A_{ks}T_{ds}T_{ds}G_{ds}A_{ds}G_{ds}T_{ds}T_{ds}{}^mC_{ds}{}^mC_{ds}T_{es}G_{ks}{}^mC_{es}G_{ks}{}^mC_e$ | 21 | 2617 |
| 1207281 | 2022 | 2037 | 7410 | 7425 | $A_{ks}A_{ks}A_{ds}G_{ds}{}^mC_{ds}A_{ds}{}^mC_{ds}T_{ds}T_{ds}T_{ds}A_{ds}T_{es}T_{ks}G_{es}A_{ks}G_e$ | 21 | 3229 |
| 1207289 | 144 | 159 | 511 | 526 | $G_{ks}T_{ks}G_{ds}T_{ds}G_{ds}{}^mC_{ds}T_{ds}{}^mC_{ds}T_{ds}T_{ds}{}^mC_{ds}A_{ks}G_{es}{}^mC_{ks}T_{es}T_k$ | 20 | 4951 |
| 1207297 | 152 | 167 | N/A | N/A | $G_{ks}A_{ks}A_{ds}{}^mC_{ds}G_{ds}A_{ds}{}^mC_{ds}T_{ds}G_{ds}T_{ds}G_{ds}T_{ks}G_{es}{}^mC_{ks}T_{es}{}^mC_k$ | 23 | 3647 |

TABLE 85-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207305 | 209 | 224 | 3560 | 3575 | $G_{ks}G_{ks}T_{ds}A_{ds}{}^mC_{ds}A_{ds}G_{ds}C_{ds}T_{ds}G_{ds}C_{ds}{}^mC_{ks}G_{es}G_{ks}T_{es}G_k$ | 23 | 4952 |
| 1207313 | 217 | 232 | 3568 | 3583 | $A_{ks}C_{ks}A_{ds}T_{ds}T_{ds}G_{ds}T_{ds}G_{ds}G_{ds}T_{ds}A_{ks}{}^mC_{es}A_{ks}G_{es}{}^mC_k$ | 12 | 3114 |
| 1207321 | 1777 | 1792 | 7165 | 7180 | $T_{ks}T_{ks}G_{ds}{}^mC_{ds}A_{ds}G_{ds}G_{ds}G_{ds}T_{ds}G_{ds}A_{ds}G_{ks}{}^mC_{es}{}^mC_{ks}G_{es}G_k$ | 36 | 3375 |
| 1207329 | 1785 | 1800 | 7173 | 7188 | $A_{ks}T_{ks}G_{ds}A_{ds}T_{ds}G_{ds}C_{ds}C_{ds}T_{ds}T_{ds}G_{ds}{}^mC_{ks}A_{es}G_{ks}G_{es}G_k$ | 21 | 3603 |
| 1207337 | 1793 | 1808 | 7181 | 7196 | ${}^mC_{ks}{}^mC_{ks}{}^mC_{ds}A_{ds}G_{ds}{}^mC_{ds}T_{ds}G_{ds}G_{ds}A_{ds}T_{ds}G_{ds}A_{ks}T_{es}G_{ks}{}^mC_{es}{}^mC_k$ | 53 | 4953 |
| 1207345 | 1899 | 1914 | 7287 | 7302 | $G_{ks}A_{ks}T_{ds}G_{ds}A_{ds}G_{ds}T_{ds}{}^mC_{ds}{}^mC_{ds}{}^mC_{ds}T_{ds}G_{ks}A_{es}G_{ks}C_{es}A_k$ | 12 | 2537 |
| 1207353 | 1914 | 1929 | 7302 | 7317 | ${}^mC_{ks}A_{ks}{}^mC_{ds}{}^mC_{ds}A_{ds}A_{ds}G_{ds}G_{ds}A_{ds}G_{ds}G_{ds}G_{ks}A_{es}A_{ks}A_{es}G_k$ | 22 | 4954 |
| 1207361 | 1922 | 1937 | 7310 | 7325 | $T_{ks}G_{ks}{}^mC_{ds}G_{ds}G_{ds}G_{ds}A_{ds}A_{ds}T_{ds}{}^mC_{ds}A_{ds}{}^mC_{ds}{}^mC_{ks}A_{es}A_{ks}G_{es}G_k$ | 11 | 3455 |
| 1207369 | 1930 | 1945 | 7318 | 7333 | $T_{ks}C_{ks}T_{ds}C_{ds}T_{ds}C_{ds}A_{ds}A_{ds}C_{ds}T_{ds}G_{ds}{}^mC_{ds}G_{ks}G_{es}A_{ks}A_{es}T_k$ | 13 | 4955 |
| 1207377 | 2000 | 2015 | 7388 | 7403 | ${}^mC_{ks}G_{ks}{}^mC_{ds}{}^mC_{ds}A_{ds}A_{ds}{}^mC_{ds}{}^mC_{ds}T_{ds}G_{ds}G_{ds}{}^mC_{ks}G_{es}{}^mC_{ks}G_{es}G_k$ | 42 | 3228 |
| 1207385 | 2008 | 2023 | 7396 | 7411 | $A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ks}A_{es}T_{ks}{}^mC_{es}{}^mC_k$ | 14 | 3761 |
| 1207393 | 2017 | 2032 | 7405 | 7420 | $A_{ks}{}^mC_{ds}T_{ds}T_{ds}T_{ds}A_{ds}T_{ds}G_{ds}A_{ds}G_{ds}T_{ks}T_{es}{}^mC_{ks}C_{es}T_k$ | 7 | 2848 |
| 1207401 | 2031 | 2046 | 7419 | 7434 | $A_{ks}G_{ks}C_{ds}A_{ds}T_{ds}T_{ds}T_{ds}T_{ds}{}^mC_{ds}A_{ds}A_{ds}A_{ks}G_{es}{}^mC_{ks}A_{es}{}^mC_k$ | 10 | 3458 |
| 1207409 | 147 | 162 | 514 | 529 | $A_{ks}{}^mC_{ks}T_{ks}G_{ds}T_{ds}G_{ds}T_{ds}G_{ds}{}^mC_{ds}T_{ds}{}^mC_{ds}T_{ks}{}^mC_{ks}A_{ks}G_e$ | 21 | 3267 |
| 1207417 | 155 | 170 | N/A | N/A | $T_{ks}G_{ks}A_{ks}G_{ds}A_{ds}A_{ds}{}^mC_{ds}G_{ds}G_{ds}A_{ds}{}^mC_{ds}T_{ds}G_{ks}T_{ks}G_{ks}T_{ks}G_e$ | 35 | 3875 |
| 1207425 | 212 | 227 | 3563 | 3578 | $T_{ks}G_{ks}T_{ks}G_{ds}G_{ds}T_{ds}A_{ds}{}^mC_{ds}A_{ds}G_{ds}{}^mC_{ds}T_{ds}G_{ks}{}^mC_{ks}G_{ks}C_e$ | 30 | 2734 |
| 1207433 | 220 | 235 | 3571 | 3586 | $G_{ks}G_{ks}T_{ks}A_{ds}{}^mC_{ds}A_{ds}G_{ds}T_{ds}T_{ds}G_{ds}T_{ds}G_{ds}G_{ks}T_{ks}A_{ks}{}^mC_e$ | 23 | 3269 |
| 1207441 | 1780 | 1795 | 7168 | 7183 | $G_{ks}{}^mC_{ks}{}^mC_{ks}T_{ds}T_{ds}G_{ds}{}^mC_{ds}A_{ds}G_{ds}G_{ds}G_{ds}T_{ds}G_{ks}A_{ks}G_{ks}{}^mC_e$ | 26 | 3451 |
| 1207449 | 1788 | 1803 | 7176 | 7191 | ${}^mC_{ks}T_{ks}G_{ks}A_{ds}T_{ds}G_{ds}A_{ds}T_{ds}G_{ds}{}^mC_{ds}{}^mC_{ds}T_{ds}T_{ks}G_{ks}{}^mC_{ks}A_e$ | 25 | 3679 |
| 1207457 | 1894 | 1909 | 7282 | 7297 | $G_{ks}T_{ks}{}^mC_{ks}{}^mC_{ds}T_{ds}G_{ds}A_{ds}G_{ds}{}^mC_{ds}A_{ds}A_{ds}T_{ks}{}^mC_{ks}A_{ks}G_e$ | 25 | 3682 |
| 1207465 | 1902 | 1917 | 7290 | 7305 | $A_{ks}A_{ks}A_{ks}G_{ds}A_{ds}T_{ds}G_{ds}A_{ds}G_{ds}T_{ds}C_{ds}{}^mC_{ds}{}^mC_{ks}T_{ks}G_{ks}A_e$ | 13 | 2768 |
| 1207473 | 1917 | 1932 | 7305 | 7320 | $A_{ks}A_{ks}T_{ks}C_{ds}C_{ds}C_{ds}A_{ds}A_{ds}G_{ds}G_{ds}A_{ds}G_{ks}G_{ks}G_{ks}A_e$ | 23 | 4956 |
| 1207481 | 1925 | 1940 | 7313 | 7328 | ${}^mC_{ks}A_{ks}{}^mC_{ks}T_{ds}G_{ds}{}^mC_{ds}G_{ds}G_{ds}G_{ds}A_{ds}A_{ds}T_{ds}{}^mC_{ds}A_{ks}{}^mC_{ks}{}^mC_{ks}A_e$ | 4 | 3683 |

TABLE 85-continued

Reduction of FXII RNA (Huh7, electroporation, 4000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (% UTC) | SEQ ID NO |
|---|---|---|---|---|---|---|---|
| 1207489 | 1933 | 1948 | 7321 | 7336 | $^{m}C_{ks}A_{ks}{}^{m}C_{ks}T_{ds}{}^{m}C_{ds}T_{ds}{}^{m}C_{ds}T_{ds}{}^{m}C_{ds}A_{ds}{}^{m}C_{ds}T_{ds}G_{ks}{}^{m}C_{ks}G_{ks}G_{e}$ | 12 | 4957 |
| 1207497 | 2003 | 2018 | 7391 | 7406 | $^{m}C_{ks}T_{ks}G_{ks}{}^{m}C_{ds}G_{ds}{}^{m}C_{ds}{}^{m}C_{ds}A_{ds}T_{ds}{}^{m}C_{ds}{}^{m}C_{ds}T_{ds}G_{ks}G_{ks}{}^{m}C_{ks}G_{e}$ | 45 | 3381 |
| 1207505 | 2011 | 2026 | 7399 | 7414 | $T_{ks}T_{ks}G_{ks}A_{ds}G_{ds}T_{ds}T_{ds}{}^{m}C_{ds}{}^{m}C_{ds}T_{ds}G_{ds}{}^{m}C_{ds}G_{ks}{}^{m}C_{ks}{}^{m}C_{ks}A_{e}$ | 7 | 2463 |
| 1207513 | 2020 | 2035 | 7408 | 7423 | $A_{ks}G_{ks}C_{ks}A_{ds}{}^{m}C_{ds}T_{ds}T_{ds}T_{ds}A_{ds}T_{ds}T_{ds}G_{ds}A_{ks}G_{ks}T_{ks}T_{e}$ | 4 | 3076 |

TABLE 86

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1128769 | 153 | 168 | N/A | N/A | $A_{ks}G_{ks}A_{ks}A_{ds}{}^{m}C_{ds}G_{ds}A_{ds}{}^{m}C_{ds}T_{ds}G_{ds}T_{ds}G_{ds}T_{ds}G_{ks}{}^{m}C_{ks}T_{k}$ | 19 | 3723 |
| 1128802 | 218 | 233 | 3569 | 3584 | $T_{ks}A_{ks}{}^{m}C_{ks}A_{ds}T_{ds}T_{ds}T_{ds}G_{ds}T_{ds}G_{ds}G_{ds}T_{ds}A_{ds}{}^{m}C_{ks}A_{ks}G_{k}$ | 108 | 2426 |
| 1128870 | 470 | 485 | 4415 | 4430 | $T_{ks}G_{ks}T_{ks}G_{ds}G_{ds}A_{ds}A_{ds}A_{ds}A_{ds}A_{ds}{}^{m}C_{ds}{}^{m}C_{ds}G_{ds}G_{ks}A_{ks}G_{k}$ | 31 | 3728 |
| 1129485 | 1921 | 1936 | 7309 | 7324 | $G_{ks}{}^{m}C_{ks}G_{ks}G_{ds}A_{ds}A_{ds}T_{ds}{}^{m}C_{ds}A_{ds}{}^{m}C_{ds}{}^{m}C_{ds}A_{ds}A_{ds}G_{ks}G_{ks}A_{k}$ | 20 | 3379 |
| 1129491 | 1927 | 1942 | 7315 | 7330 | $^{m}C_{ks}T_{ks}{}^{m}C_{ks}A_{ds}{}^{m}C_{ds}T_{ds}G_{ds}{}^{m}C_{ds}G_{ds}G_{ds}A_{ds}A_{ds}T_{ds}{}^{m}C_{ks}A_{ks}{}^{m}C_{k}$ | 17 | 3835 |
| 1129492 | 1928 | 1943 | 7316 | 7331 | $T_{ks}{}^{m}C_{ks}T_{ks}{}^{m}C_{ds}A_{ds}{}^{m}C_{ds}T_{ds}G_{ds}{}^{m}C_{ds}G_{ds}G_{ds}A_{ds}A_{ds}T_{ks}{}^{m}C_{ks}A_{k}$ | 7 | 3911 |
| 1129531 | 2009 | 2024 | 7397 | 7412 | $G_{ks}A_{ks}G_{ks}T_{ds}T_{ds}{}^{m}C_{ds}{}^{m}C_{ds}T_{ds}G_{ds}{}^{m}C_{ds}G_{ds}{}^{m}C_{ds}{}^{m}C_{ds}A_{ks}T_{ks}{}^{m}C_{k}$ | 17 | 3837 |
| 1129532 | 2010 | 2025 | 7398 | 7413 | $T_{ks}G_{ks}A_{ks}G_{ds}T_{ds}T_{ds}{}^{m}C_{ds}{}^{m}C_{ds}T_{ds}G_{ds}{}^{m}C_{ds}G_{ds}{}^{m}C_{ds}{}^{m}C_{ks}A_{ks}T_{k}$ | 6 | 3913 |
| 1129538 | 2017 | 2032 | 7405 | 7420 | $A_{ks}{}^{m}C_{ks}T_{ks}T_{ds}T_{ds}A_{ds}T_{ds}T_{ds}G_{ds}A_{ds}G_{ds}T_{ds}T_{ds}{}^{m}C_{ks}{}^{m}C_{ks}T_{k}$ | 7 | 2848 |
| 1129540 | 2019 | 2034 | 7407 | 7422 | $G_{ks}{}^{m}C_{ks}A_{ks}{}^{m}C_{ds}T_{ds}T_{ds}T_{ds}A_{ds}T_{ds}T_{ds}G_{ds}A_{ds}G_{ds}T_{ks}T_{ks}{}^{m}C_{k}$ | 3 | 3000 |
| 1129579 | N/A | N/A | 208 | 223 | $^{m}C_{ks}A_{ks}{}^{m}C_{ks}A_{ds}T_{ds}A_{ds}G_{ds}G_{ds}{}^{m}C_{ds}{}^{m}C_{ds}T_{ds}{}^{m}C_{ds}{}^{m}C_{ds}T_{ks}A_{ks}G_{k}$ | 55 | 2926 |
| 1129714 | N/A | N/A | 1558 | 1573 | $A_{ks}G_{ks}G_{ks}G_{ds}T_{ds}A_{ds}A_{ds}G_{ds}G_{ds}T_{ds}{}^{m}C_{ds}{}^{m}C_{ds}A_{ds}T_{ks}{}^{m}C_{ks}T_{k}$ | 63 | 2549 |
| 1129740 | N/A | N/A | 1758 | 1773 | $G_{ks}A_{ks}T_{ks}G_{ds}G_{ds}G_{ds}A_{ds}T_{ds}G_{ds}G_{ds}A_{ds}{}^{m}C_{ds}G_{ds}G_{ks}A_{ks}{}^{m}C_{k}$ | 69 | 3010 |
| 1129760 | N/A | N/A | 2284 | 2299 | $A_{ks}{}^{m}C_{ks}{}^{m}C_{ks}A_{ds}T_{ds}{}^{m}C_{ds}G_{ds}{}^{m}C_{ds}G_{ds}A_{ds}A_{ds}T_{ds}A_{ds}A_{ks}T_{ks}G_{k}$ | 44 | 3011 |
| 1129773 | N/A | N/A | 2450 | 2465 | $G_{ks}{}^{m}C_{ks}A_{ks}T_{ds}T_{ds}G_{ds}A_{ds}T_{ds}G_{ds}A_{ds}A_{ds}T_{ds}{}^{m}C_{ds}A_{ks}G_{ks}{}^{m}C_{k}$ | 28 | 2475 |

TABLE 86-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1129779 | N/A | N/A | 2470 | 2485 | $G_{ks}{}^mC_{ks}T_{ks}A_{ds}T_{ds}A_{ds}G_{ds}T_{ds}G_{ds}{}^mC_{ds}{}^mC_{ds}A_{ds}T_{ds}{}^mC_{ks}A_{ks}G_k$ | 27 | 2936 |
| 1129802 | N/A | N/A | 2654 | 2669 | $T_{ks}{}^mC_{ks}{}^mC_{ks}T_{ds}A_{ds}T_{ds}T_{ds}G_{ds}A_{ds}A_{ds}T_{ds}G_{ds}A_{ds}G_{ks}T_{ks}G_k$ | 33 | 3160 |
| 1129948 | N/A | N/A | 4840 | 4855 | $A_{ks}T_{ks}{}^mC_{ks}T_{ds}G_{ds}{}^mC_{ds}T_{ds}T_{ds}T_{ds}{}^mC_{ds}{}^mC_{ds}G_{ds}{}^mC_{ds}A_{ks}{}^mC_{ks}T_k$ | 51 | 3630 |
| 1129949 | N/A | N/A | 4844 | 4859 | $T_{ks}{}^mC_{ks}T_{ks}{}^mC_{ds}A_{ds}T_{ds}{}^mC_{ds}T_{ds}G_{ds}{}^mC_{ds}T_{ds}T_{ds}T_{ds}{}^mC_{ks}{}^mC_{ks}G_k$ | 24 | 3706 |
| 1130060 | N/A | N/A | 6178 | 6193 | $A_{ks}A_{ks}G_{ks}G_{ds}{}^mC_{ds}G_{ds}{}^mC_{ds}A_{ds}A_{ds}{}^mC_{ds}A_{ds}G_{ds}A_{ds}G_{ks}{}^mC_{ks}T_k$ | 22 | 3026 |
| 1130240 | N/A | N/A | 7098 | 7113 | $G_{ks}T_{ks}{}^mC_{ks}G_{ds}G_{ds}A_{ds}A_{ds}A_{ds}{}^mC_{ds}A_{ds}{}^mC_{ds}G_{ds}{}^mC_{ds}A_{ks}G_{ks}{}^mC_k$ | 47† | 3035 |
| 1213035 | 141 | 156 | 508 | 523 | $T_{ks}G_{ks}{}^mC_{ks}T_{ds}C_{ys}T_{ds}T_{ds}{}^mC_{ds}A_{ds}Gd_{ds}{}^mC_{ds}T_{ds}T_{ds}T_{ks}G_{ks}T_k$ | 40 | 4950 |
| 1213036 | 142 | 157 | 509 | 524 | $G_{ks}T_{ks}G_{ks}{}^mC_{ds}U_{ys}{}^mC_{ds}T_{ds}T_{ds}{}^mC_{ds}A_{ds}G_{ds}{}^mC_{ds}T_{ds}T_{ks}T_{ks}G_k$ | 28 | 4977 |
| 1213037 | 143 | 158 | 510 | 525 | $T_{ks}G_{ks}T_{ks}G_{ds}C_{ys}T_{ds}{}^mC_{ds}T_{ds}T_{ds}{}^mC_{ds}A_{ds}G_{ds}{}^mC_{ds}T_{ks}T_{ks}T_k$ | 46 | 3037 |
| 1213038 | 144 | 159 | 511 | 526 | $G_{ks}T_{ks}G_{ks}T_{ds}G_{ys}{}^mC_{ds}T_{ds}{}^mC_{ds}T_{ds}T_{ds}{}^mC_{ds}A_{ds}G_{ds}{}^mC_{ks}T_{ks}T_k$ | 33 | 4951 |
| 1213039 | 145 | 160 | 512 | 527 | $T_{ks}G_{ks}T_{ks}G_{ds}U_{ys}G_{ds}{}^mC_{ds}T_{ds}{}^mC_{ds}T_{ds}T_{ds}{}^mC_{ds}A_{ds}G_{ks}{}^mC_{ks}T_k$ | 91 | 4978 |
| 1213040 | 146 | 161 | 513 | 528 | ${}^mC_{ks}T_{ks}G_{ks}T_{ds}G_{ys}T_{ds}G_{ds}{}^mC_{ds}T_{ds}{}^mC_{ds}T_{ds}T_{ds}{}^mC_{ds}A_{ks}G_{ks}{}^mC_k$ | 35 | 3190 |
| 1213041 | 147 | 162 | 514 | 529 | $A_{ks}{}^mC_{ks}T_{ks}G_{ds}U_{ys}G_{ds}T_{ds}G_{ds}{}^mC_{ds}T_{ds}{}^mC_{ds}T_{ds}T_{ds}{}^mC_{ks}A_{ks}G_k$ | 27 | 4979 |
| 1213042 | 148 | 163 | 515 | 530 | $G_{ks}A_{ks}{}^mC_{ks}T_{ds}G_{ys}T_{ds}G_{ds}T_{ds}G_{ds}{}^mC_{ds}T_{ds}{}^mC_{ds}T_{ds}T_{ks}{}^mC_{ks}A_k$ | 50 | 3343 |
| 1213043 | 149 | 164 | 516 | 531 | ${}^mC_{ks}G_{ks}A_{ks}{}^mC_{ds}U_{ys}G_{ds}T_{ds}G_{ds}T_{ds}G_{ds}{}^mC_{ds}T_{ds}{}^mC_{ds}T_{ks}T_{ks}{}^mC_k$ | 65 | 4980 |
| 1213044 | 150 | 165 | N/A | N/A | $A_{ks}{}^mC_{ks}G_{ks}A_{ds}C_{ys}T_{ds}G_{ds}T_{ds}G_{ds}T_{ds}G_{ds}{}^mC_{ds}T_{ds}{}^mC_{ks}T_{ks}T_k$ | 52 | 3495 |
| 1213045 | 151 | 166 | N/A | N/A | $A_{ks}A_{ks}{}^mC_{ks}G_{ds}A_{ys}{}^mC_{ds}T_{ds}G_{ds}T_{ds}G_{ds}T_{ds}G_{ds}{}^mC_{ds}T_{ks}{}^mC_{ks}T_k$ | 47 | 3571 |
| 1213046 | 152 | 167 | N/A | N/A | $G_{ks}A_{ks}A_{ks}{}^mC_{ds}G_{ys}A_{ds}{}^mC_{ds}T_{ds}G_{ds}T_{ds}G_{ds}T_{ds}G_{ds}{}^mC_{ks}T_{ks}{}^mC_k$ | 77 | 3647 |
| 1213047 | 153 | 168 | N/A | N/A | $A_{ks}G_{ks}A_{ks}A_{ds}C_{ys}G_{ds}A_{ds}{}^mC_{ds}T_{ds}G_{ds}T_{ds}G_{ds}T_{ds}G_{ks}{}^mC_{ks}T_k$ | 42 | 3723 |
| 1213048 | 154 | 169 | N/A | N/A | $G_{ks}A_{ks}G_{ks}A_{ds}A_{ys}{}^mC_{ds}G_{ds}A_{ds}{}^mC_{ds}T_{ds}G_{ds}T_{ds}G_{ds}T_{ks}G_{ks}{}^mC_k$ | 61 | 3799 |
| 1213049 | 155 | 170 | N/A | N/A | $T_{ks}G_{ks}A_{ks}G_{ds}A_{ys}A_{ds}{}^mC_{ds}G_{ds}A_{ds}{}^mC_{ds}T_{ds}G_{ds}T_{ds}G_{ks}T_{ks}G_k$ | 42 | 3875 |
| 1213050 | 156 | 171 | N/A | N/A | $G_{ks}T_{ks}G_{ks}A_{ds}G_{ys}A_{ds}A_{ds}{}^mC_{ds}G_{ds}A_{ds}{}^mC_{ds}T_{ds}G_{ds}T_{ks}G_{ks}T_k$ | 35 | 2424 |
| 1213051 | 157 | 172 | N/A | N/A | $A_{ks}G_{ks}T_{ks}G_{ds}A_{ys}G_{ds}A_{ds}A_{ds}{}^mC_{ds}G_{ds}A_{ds}{}^mC_{ds}T_{ds}G_{ks}T_{ks}G_k$ | 69 | 2502 |

TABLE 86-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213052 | 158 | 173 | N/A | N/A | $^mC_{ks}A_{ks}G_{ks}T_{ds}G_{ys}A_{ds}G_{ds}A_{ds}A_{ds}{}^mC_{ds}$ $G_{ds}A_{ds}{}^mC_{ks}T_{ks}G_{k}T_{k}$ | 54 | 2579 |
| 1213053 | 208 | 223 | 3559 | 3574 | $G_{ks}T_{ks}A_{ks}{}^mC_{ds}A_{ys}G_{ds}{}^mC_{ds}T_{ds}G_{ds}{}^mC_{ds}{}^m$ $C_{ds}G_{ds}G_{ds}T_{ks}G_{ks}G_{k}$ | 33 | 4968 |
| 1213054 | 209 | 224 | 3560 | 3575 | $G_{ks}G_{ks}T_{ks}A_{ds}{}^mC_{ys}A_{ds}G_{ds}{}^mC_{ds}T_{ds}G_{ds}{}^m$ $C_{ds}{}^mC_{ds}G_{ds}G_{ks}T_{ks}G_{k}$ | 33 | 4952 |
| 1213055 | 210 | 225 | 3561 | 3576 | $T_{ks}G_{ks}G_{ks}T_{ds}A_{ys}{}^mC_{ds}A_{ds}G_{ds}{}^mC_{ds}T_{ds}G_{ds}$ $^mC_{ds}{}^mC_{ds}G_{ks}G_{ks}T_{k}$ | 26 | 2657 |
| 1213056 | 211 | 226 | 3562 | 3577 | $G_{ks}T_{ks}G_{ks}G_{ds}U_{ys}A_{ds}{}^mC_{ds}A_{ds}G_{ds}{}^mC_{ds}$ $T_{ds}G_{ds}{}^mC_{ds}{}^mC_{ks}G_{ks}G_{k}$ | 34 | 4981 |
| 1213057 | 212 | 227 | 3563 | 3578 | $T_{ks}G_{ks}T_{ks}G_{ds}G_{ys}T_{ds}A_{ds}{}^mC_{ds}A_{ds}G_{ds}{}^mC_{ds}$ $T_{ds}G_{ds}{}^mC_{ks}{}^mC_{ks}G_{k}$ | 78 | 2734 |
| 1213058 | 213 | 228 | 3564 | 3579 | $T_{ks}T_{ks}G_{ks}T_{ds}G_{ys}G_{ds}T_{ds}A_{ds}{}^mC_{ds}A_{ds}G_{ds}$ $^mC_{ds}T_{ds}G_{ks}{}^mC_{ks}{}^mC_{k}$ | 29 | 2811 |
| 1213059 | 214 | 229 | 3565 | 3580 | $T_{ks}T_{ks}T_{ks}G_{ds}U_{ys}G_{ds}G_{ds}T_{ds}A_{ds}{}^mC_{ds}A_{ds}$ $G_{ds}{}^mC_{ds}T_{ks}G_{ks}{}^mC_{k}$ | 44 | 4982 |
| 1213060 | 215 | 230 | 3566 | 3581 | $A_{ks}T_{ks}T_{ks}T_{ds}G_{ys}T_{ds}G_{ds}G_{ds}T_{ds}A_{ds}{}^mC_{ds}$ $A_{ds}G_{ds}{}^mC_{ks}T_{ks}G_{k}$ | 44 | 2963 |
| 1213061 | 216 | 231 | 3567 | 3582 | $^mC_{ks}A_{ks}T_{ks}T_{ds}U_{ys}G_{ds}T_{ds}G_{ds}G_{ds}T_{ds}A_{ds}$ $^mC_{ds}A_{ds}G_{ks}{}^mC_{ks}T_{k}$ | 36 | 4983 |
| 1213062 | 217 | 232 | 3568 | 3583 | $A_{ks}{}^mC_{ks}A_{ks}T_{ds}U_{ys}T_{ds}G_{ds}T_{ds}G_{ds}G_{ds}T_{ds}$ $A_{ds}{}^mC_{ds}A_{ks}G_{ks}{}^mC_{k}$ | 75 | 4984 |
| 1213063 | 218 | 233 | 3569 | 3584 | $T_{ks}A_{ks}{}^mC_{ks}A_{ds}U_{ys}T_{ds}T_{ds}G_{ds}T_{ds}G_{ds}G_{ds}$ $T_{ds}A_{ds}{}^mC_{ks}A_{ks}G_{k}$ | 55 | 4985 |
| 1213064 | 219 | 234 | 3570 | 3585 | $G_{ks}T_{ks}A_{ks}{}^mC_{ds}A_{ys}T_{ds}T_{ds}T_{ds}G_{ds}T_{ds}G_{ds}$ $G_{ds}T_{ds}A_{ks}{}^mC_{ks}A_{k}$ | 38 | 3192 |
| 1213065 | 220 | 235 | 3571 | 3586 | $G_{ks}G_{ks}T_{ks}A_{ds}{}^mC_{ys}A_{ds}T_{ds}T_{ds}T_{ds}G_{ds}T_{ds}$ $G_{ds}G_{ds}T_{ks}A_{ks}{}^mC_{k}$ | 54 | 3269 |
| 1213066 | 221 | 236 | 3572 | 3587 | $G_{ks}G_{ks}G_{ks}T_{ds}A_{ys}{}^mC_{ds}A_{ds}T_{ds}T_{ds}T_{ds}G_{ds}$ $T_{ds}G_{ds}G_{ks}T_{ks}A_{k}$ | 24 | 3345 |
| 1213067 | 222 | 237 | 3573 | 3588 | $T_{ks}G_{ks}G_{ks}G_{ds}U_{ys}A_{ds}{}^mC_{ds}A_{ds}T_{ds}T_{ds}T_{ds}$ $G_{ds}T_{ds}G_{ks}G_{ks}T_{k}$ | 31 | 4986 |
| 1213068 | 223 | 238 | 3574 | 3589 | $G_{ks}T_{ks}G_{ks}G_{ds}G_{ys}T_{ds}A_{ds}{}^mC_{ds}A_{ds}T_{ds}T_{ds}$ $T_{ds}G_{ds}T_{ks}G_{ks}G_{k}$ | 63 | 3497 |
| 1213069 | 1776 | 1791 | 7164 | 7179 | $T_{ks}G_{ks}{}^mC_{ks}A_{ds}G_{ys}G_{ds}G_{ds}T_{ds}G_{ds}A_{ds}G_{ds}$ $^mC_{ds}{}^mC_{ds}G_{ks}G_{ks}{}^mC_{k}$ | 26 | 3299 |
| 1213070 | 1777 | 1792 | 7165 | 7180 | $T_{ks}T_{ks}G_{ks}{}^mC_{ds}A_{ys}G_{ds}G_{ds}G_{ds}T_{ds}G_{ds}A_{ds}$ $G_{ds}{}^mC_{ds}{}^mC_{ks}G_{ks}G_{k}$ | 38 | 3375 |
| 1213071 | 1778 | 1793 | 7166 | 7181 | $^mC_{ks}T_{ks}T_{ks}G_{ds}{}^mC_{ys}A_{ds}G_{ds}G_{ds}G_{ds}T_{ds}G_{ds}$ $A_{ds}G_{ds}{}^mC_{ks}{}^mC_{ks}G_{k}$ | 24 | 4962 |
| 1213072 | 1779 | 1794 | 7167 | 7182 | $^mC_{ks}{}^mC_{ks}T_{ks}T_{ds}G_{ys}{}^mC_{ds}A_{ds}G_{ds}G_{ds}G_{ds}$ $T_{ds}G_{ds}A_{ds}G_{ks}{}^mC_{ks}{}^mC_{k}$ | 41 | 4974 |
| 1213073 | 1780 | 1795 | 7168 | 7183 | $G_{ks}{}^mC_{ks}{}^mC_{ks}T_{ds}U_{ys}G_{ds}{}^mC_{ds}A_{ds}G_{ds}G_{ds}$ $G_{ds}T_{ds}G_{ds}A_{ks}G_{ks}{}^mC_{k}$ | 25 | 4987 |
| 1213074 | 1781 | 1796 | 7169 | 7184 | $T_{ks}G_{ks}{}^mC_{ks}{}^mC_{ds}U_{ys}T_{ds}G_{ds}{}^mC_{ds}A_{ds}G_{ds}$ $G_{ds}G_{ds}T_{ds}G_{ks}A_{ks}G_{k}$ | 16 | 4988 |

TABLE 86-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213075 | 1782 | 1797 | 7170 | 7185 | $A_{ks}T_{ks}G_{ks}{}^mC_{ds}C_{ys}T_{ds}T_{ds}G_{ds}{}^mC_{ds}A_{ds}G_{ds}G_{ds}G_{ds}T_{ks}G_{ks}A_k$ | 26 | 4947 |
| 1213076 | 1783 | 1798 | 7171 | 7186 | $G_{ks}A_{ks}T_{ks}G_{ds}C_{ys}{}^mC_{ds}T_{ds}T_{ds}G_{ds}{}^mC_{ds}A_{ds}G_{ds}G_{ds}G_{ks}T_{ks}G_k$ | 23 | 4959 |
| 1213077 | 1784 | 1799 | 7172 | 7187 | $A_{ks}G_{ks}A_{ks}A_{ds}G_{ys}{}^mC_{ds}{}^mC_{ds}T_{ds}T_{ds}G_{ds}{}^mC_{ds}A_{ds}G_{ds}G_{ks}G_{ks}T_k$ | 17 | 4969 |
| 1213078 | 1785 | 1800 | 7173 | 7188 | $A_{ks}T_kG_{ks}A_{ds}U_{ys}G_{ds}{}^mC_{ds}{}^mC_{ds}T_{ds}T_{ds}G_{ds}{}^mC_{ds}A_{ds}G_{ks}G_{ks}G_k$ | 25 | 4989 |
| 1213079 | 1786 | 1801 | 7174 | 7189 | $G_{ks}A_{ks}T_{ks}G_{ds}A_{ys}T_{ds}{}^mC_{ds}{}^mC_{ds}T_{ds}T_{ds}G_{ds}{}^mC_{ds}A_{ks}G_{ks}G_k$ | 24 | 4963 |
| 1213080 | 1787 | 1802 | 7175 | 7190 | $T_{ks}G_{ks}A_{ks}T_{ds}G_{ys}A_{ds}T_{ds}G_{ds}{}^mC_{ds}{}^mC_{ds}T_{ds}Td_sG_{ds}{}^mC_{ks}A_{ks}G_k$ | 34 | 4975 |
| 1213081 | 1788 | 1803 | 7176 | 7191 | ${}^mC_{ks}T_{ks}G_{ks}A_{ds}U_{ys}G_{ds}A_{ds}T_{ds}G_{ds}{}^mC_{ds}{}^mC_{ds}T_{ds}T_{ds}G_{ks}{}^mC_{ks}A_k$ | 19 | 4990 |
| 1213082 | 1789 | 1804 | 7177 | 7192 | $G_{ks}{}^mC_{ks}T_{ks}G_{ds}A_{ys}T_{ds}G_{ds}A_{ds}T_{ds}G_{ds}{}^mC_{ds}{}^mC_{ds}T_{ds}T_{ks}G_{ks}{}^mC_k$ | 50 | 3755 |
| 1213083 | 1790 | 1805 | 7178 | 7193 | $A_{ks}G_{ks}{}^mC_{ks}T_{ds}G_{ys}A_{ds}T_{ds}G_{ds}A_{ds}T_{ds}G_{ds}{}^mC_{ds}{}^mC_{ds}T_{ks}T_{ks}G_k$ | 59 | 3831 |
| 1213084 | 1791 | 1806 | 7179 | 7194 | ${}^mC_{ks}A_{ks}G_{ks}{}^mC_{ds}U_{ys}G_{ds}A_{ds}T_{ds}G_{ds}A_{ds}T_{ds}G_{ds}{}^mC_{ds}{}^mC_{ks}T_{ks}T_k$ | 35 | 4991 |
| 1213085 | 1792 | 1807 | 7180 | 7195 | ${}^mC_{ks}{}^mC_{ks}A_{ks}G_{ds}C_{ys}T_{ds}G_{ds}A_{ds}T_{ds}G_{ds}A_{ds}T_{ds}G_{ds}{}^mC_{ks}{}^mC_{ks}T_k$ | 31 | 4970 |
| 1213086 | 1793 | 1808 | 7181 | 7196 | ${}^mC_{ks}{}^mC_{ks}{}^mC_{ks}A_{ds}G_{ys}{}^mC_{ds}T_{ds}G_{ds}A_{ds}T_{ds}G_{ds}A_{ds}T_{ds}G_{ks}{}^mC_{ks}{}^mC_k$ | 39 | 4953 |
| 1213087 | 1892 | 1907 | 7280 | 7295 | ${}^mC_{ks}{}^mC_{ks}{}^mC_{ks}T_{ds}G_{ys}A_{ds}G_{ds}{}^mC_{ds}A_{ds}A_{ds}T_{ds}{}^mC_{ds}A_{ds}G_{ks}G_{ks}A_k$ | 27 | 3530 |
| 1213088 | 1893 | 1908 | 7281 | 7296 | $T_{ks}{}^mC_{ks}{}^mC_{ks}{}^mC_{ds}U_{ys}G_{ds}A_{ds}G_{ds}{}^mC_{ds}A_{ds}A_{ds}T_{ds}{}^mC_{ds}A_{ks}G_{ks}G_k$ | 43 | 4992 |
| 1213089 | 1894 | 1909 | 7282 | 7297 | $G_{ks}T_{ks}{}^mC_{ks}{}^mC_{ds}C_{ys}T_{ds}G_{ds}A_{ds}G_{ds}{}^mC_{ds}A_{ds}A_{ds}T_{ds}{}^mC_{ks}A_{ks}G_k$ | 22 | 3682 |
| 1213090 | 1895 | 1910 | 7283 | 7298 | $A_{ks}G_{ks}T_{ks}{}^mC_{ds}C_{ys}{}^mC_{ds}T_{ds}G_{ds}A_{ds}G_{ds}{}^mC_{ds}A_{ds}A_{ds}T_{ks}{}^mC_{ks}A_k$ | 29 | 3758 |
| 1213091 | 1896 | 1911 | 7284 | 7299 | $G_{ks}A_{ks}G_{ks}T_{ds}C_{ys}{}^mC_{ds}{}^mC_{ds}T_{ds}G_{ds}A_{ds}G_{ds}{}^mC_{ds}A_{ds}A_{ks}T_{ks}{}^mC_k$ | 33 | 3834 |
| 1213092 | 1897 | 1912 | 7285 | 7300 | $T_{ks}G_{ks}A_{ks}G_{ds}U_{ys}{}^mC_{ds}{}^mC_{ds}{}^mC_{ds}T_{ds}G_{ds}A_{ds}G_{ds}{}^mC_{ds}A_{ks}A_{ks}T_k$ | 38 | 4993 |

TABLE 87

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1128769 | 153 | 168 | N/A | N/A | $A_{ks}G_{ks}A_{ks}A_{ds}{}^mC_{ds}G_{ds}A_{ds}{}^mC_{ds}T_{ds}G_{ds}T_{ds}G_{ds}T_{ds}G_{ks}{}^mC_{ks}T_k$ | 63 | 3723 |

TABLE 87-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1128802 | 218 | 233 | 3569 | 3584 | $T_{ks}A_{ks}{}^mC_{ks}A_{ds}T_{ds}T_{ds}T_{ds}G_{ds}T_{ds}G_{ds}G_{ds}T_{ds}A_{ds}{}^mC_{ks}A_{ks}G_k$ | 90 | 2426 |
| 1128870 | 470 | 485 | 4415 | 4430 | $T_{ks}G_{ks}T_{ks}G_{ds}G_{ds}A_{ds}A_{ds}A_{ds}A_{ds}{}^mC_{ds}{}^mC_{ds}G_{ds}G_{ks}A_{ks}G_k$ | 44 | 3728 |
| 1129409 | 1788 | 1803 | 7176 | 7191 | ${}^mC_{ks}T_{ks}G_{ks}A_{ds}T_{ds}G_{ds}A_{ds}T_{ds}G_{ds}{}^mC_{ds}{}^mC_{ds}T_{ds}T_{ds}G_{ks}{}^mC_{ks}A_k$ | 7 | 3679 |
| 1129486 | 1922 | 1937 | 7310 | 7325 | $T_{ks}G_{ks}{}^mC_{ks}G_{ds}G_{ds}A_{ds}A_{ds}T_{ds}{}^mC_{ds}A_{ds}{}^mC_{ds}{}^mC_{ds}A_{ds}A_{ks}G_{ks}G_k$ | 11 | 3455 |
| 1129489 | 1925 | 1940 | 7313 | 7328 | ${}^mC_{ks}A_{ks}{}^mC_{ks}T_{ds}G_{ds}{}^mC_{ds}G_{ds}G_{ds}A_{ds}A_{ds}T_{ds}{}^mC_{ds}A_{ds}{}^mC_{ks}{}^mC_{ks}A_k$ | 21 | 3683 |
| 1129491 | 1927 | 1942 | 7315 | 7330 | ${}^mC_{ks}T_{ks}{}^mC_{ks}A_{ds}C_{ds}T_{ds}G_{ds}{}^mC_{ds}G_{ds}G_{ds}A_{ds}A_{ds}T_{ds}{}^mC_{ks}A_{ks}{}^mC_k$ | 54 | 3835 |
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 9 | 3837 |
| 1129532 | 2010 | 2025 | 7398 | 7413 | $T_{ks}G_{ks}A_{ks}G_{ds}T_{ds}T_{ds}{}^mC_{ds}{}^mC_{ds}T_{ds}G_{ds}{}^mC_{ds}G_{ds}{}^mC_{ds}{}^mC_{ks}A_{ks}T_k$ | 16 | 3913 |
| 1129540 | 2019 | 2034 | 7407 | 7422 | $G_{ks}{}^mC_{ks}A_{ks}{}^mC_{ds}T_{ds}T_{ds}A_{ds}T_{ds}T_{ds}G_{ds}A_{ds}G_{ds}T_{ks}T_{ks}{}^mC_k$ | 19 | 3000 |
| 1129572 | N/A | N/A | 186 | 201 | $G_{ks}G_{ks}A_{ks}{}^mC_{ds}{}^mC_{ds}{}^mC_{ds}A_{ds}{}^mC_{ds}A_{ds}G_{ds}G_{ds}T_{ds}{}^mC_{ds}A_{ks}T_{ks}G_k$ | 47 | 3915 |
| 1129857 | N/A | N/A | 3881 | 3896 | $G_{ks}T_{ks}A_{ks}A_{ds}T_{ds}G_{ds}G_{ds}G_{ds}G_{ds}C_{ds}G_{ds}G_{ds}G_{ds}A_{ks}G_{ks}G_k$ | 48 | 2787 |
| 1129938 | N/A | N/A | 4635 | 4650 | $A_{ks}{}^mC_{ks}G_{ks}{}^mC_{ds}A_{ds}G_{ds}T_{ds}G_{ds}A_{ds}G_{ds}{}^mC_{ds}{}^mC_{ds}A_{ds}{}^mC_{ks}{}^mC_{ks}{}^mC_k$ | 62 | 2868 |
| 1129948 | N/A | N/A | 4840 | 4855 | $A_{ks}T_{ks}{}^mC_{ks}T_{ds}G_{ds}{}^mC_{ds}T_{ds}T_{ds}T_{ds}{}^mC_{ds}{}^mC_{ds}G_{ds}{}^mC_{ds}A_{ks}{}^mC_{ks}T_k$ | 34 | 3630 |
| 1129949 | N/A | N/A | 4844 | 4859 | $T_{ks}{}^mC_{ks}T_{ks}{}^mC_{ds}A_{ds}A_{ds}{}^mC_{ds}T_{ds}G_{ds}{}^mC_{ds}T_{ds}T_{ds}T_{ds}{}^mC_{ks}{}^mC_{ks}G_k$ | 41 | 3706 |
| 1130010 | N/A | N/A | 5752 | 5767 | $A_{ks}{}^mC_{ks}G_{ks}G_{ds}A_{ds}G_{ds}G_{ds}G_{ds}A_{ds}G_{ds}{}^mC_{ds}{}^mC_{ds}G_{ds}{}^mC_{ks}G_{ks}{}^mC_k$ | 29 | 3785 |
| 1130142 | N/A | N/A | 6579 | 6594 | ${}^mC_{ks}G_{ks}T_{ks}{}^mC_{ds}{}^mC_{ds}T_{ds}A_{ds}G_{ds}T_{ds}T_{ds}G_{ds}G_{ds}{}^mC_{ds}{}^mC_{ks}T_{ks}T_k$ | 32 | 3177 |
| 1130215 | N/A | N/A | 7015 | 7030 | $C_{ks}A_{ks}{}^mC_{ks}{}^mC_{ds}T_{ds}G_{ds}G_{ds}{}^mC_{ds}A_{ds}{}^mC_{ds}G_{ds}{}^mC_{ds}A_{ds}T_{ks}{}^mC_{ks}G_k$ | 41† | 2651 |
| 1130251 | N/A | N/A | 7111 | 7126 | $G_{ks}G_{ks}A_{ks}A_{ds}T_{ds}{}^mC_{ds}A_{ds}{}^mC_{ds}{}^mC_{ds}{}^mC_{ds}T_{ds}G_{ds}G_{ds}G_{ks}T_{ks}{}^mC_k$ | 30† | 3873 |
| 1130252 | N/A | N/A | 7112 | 7127 | ${}^mC_{ks}G_{ks}G_{ks}A_{ds}A_{ds}T_{ds}{}^mC_{ds}A_{ds}{}^mC_{ds}{}^mC_{ds}{}^mC_{ds}T_{ds}G_{ds}G_{ks}G_{ks}T_k$ | 15† | 3949 |
| 1213093 | 1898 | 1913 | 7286 | 7301 | $A_{ks}T_{ks}G_{ks}A_{ds}G_{ys}T_{ds}{}^mC_{ds}{}^mC_{ds}{}^mC_{ds}T_{ds}G_{ds}A_{ds}G_{ds}{}^mC_{ks}A_{ks}A_k$ | 42 | 2460 |
| 1213094 | 1899 | 1914 | 7287 | 7302 | $G_{ks}A_{ks}T_{ks}G_{ds}A_{ys}G_{ds}T_{ds}{}^mC_{ds}{}^mC_{ds}{}^mC_{ds}T_{ds}G_{ds}A_{ds}G_{ks}{}^mC_{ks}A_k$ | 18 | 2537 |
| 1213095 | 1900 | 1915 | 7288 | 7303 | $A_{ks}G_{ks}A_{ks}T_{ds}G_{ys}A_{ds}G_{ds}T_{ds}{}^mC_{ds}{}^mC_{ds}{}^mC_{ds}T_{ds}G_{ds}A_{ks}G_{ks}{}^mC_k$ | 13 | 2614 |
| 1213096 | 1901 | 1916 | 7289 | 7304 | $A_{ks}A_{ks}G_{ks}A_{ds}U_{ys}G_{ds}A_{ds}G_{ds}T_{ds}{}^mC_{ds}{}^mC_{ds}{}^mC_{ds}T_{ds}G_{ks}A_{ks}G_k$ | 28 | 4994 |

TABLE 87-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213097 | 1902 | 1917 | 7290 | 7305 | $A_{ks}A_{ks}A_{ks}G_{ds}A_{ys}T_{ds}G_{ds}A_{ds}G_{ds}T_{ds}{}^{m}C_{ds}{}^{m}C_{ds}{}^{m}C_{ds}T_{ks}G_{ks}A_{k}$ | 19 | 2768 |
| 1213098 | 1903 | 1918 | 7291 | 7306 | $G_{ks}A_{ks}A_{ks}A_{ds}G_{ys}A_{ds}T_{ds}G_{ds}A_{ds}G_{ds}T_{ds}{}^{m}C_{ds}{}^{m}C_{ds}{}^{m}C_{ks}T_{ks}G_{k}$ | 36 | 2845 |
| 1213099 | 1904 | 1919 | 7292 | 7307 | $G_{ks}G_{ks}A_{ks}A_{ds}A_{ys}G_{ds}A_{ds}T_{ds}G_{ds}A_{ds}G_{ds}T_{ds}{}^{m}C_{ds}{}^{m}C_{ks}{}^{m}C_{ks}T_{k}$ | 25 | 2921 |
| 1213100 | 1905 | 1920 | 7293 | 7308 | $G_{ks}G_{ks}G_{ks}A_{ds}A_{ys}A_{ds}G_{ds}A_{ds}T_{ds}G_{ds}A_{ds}G_{ds}T_{ds}{}^{m}C_{ks}{}^{m}C_{ks}{}^{m}C_{k}$ | 26 | 2997 |
| 1213101 | 1906 | 1921 | 7294 | 7309 | $A_{ks}G_{ks}G_{ks}G_{ds}A_{ys}A_{ds}A_{ds}G_{ds}A_{ds}T_{ds}G_{ds}A_{ds}G_{ds}T_{ks}{}^{m}C_{ks}{}^{m}C_{k}$ | 24 | 3073 |
| 1213102 | 1914 | 1929 | 7302 | 7317 | ${}^{m}C_{ks}A_{ks}{}^{m}C_{ks}{}^{m}C_{ds}A_{ys}A_{ds}G_{ds}G_{ds}A_{ds}G_{ds}G_{ds}G_{ds}A_{ds}A_{ks}A_{ks}G_{k}$ | 34 | 4954 |
| 1213103 | 1915 | 1930 | 7303 | 7318 | $T_{ks}{}^{m}C_{ks}A_{ks}{}^{m}C_{ds}C_{ys}A_{ds}A_{ds}G_{ds}G_{ds}A_{ds}G_{ds}G_{ds}G_{ds}A_{ks}A_{ks}A_{k}$ | 41 | 4948 |
| 1213104 | 1916 | 1931 | 7304 | 7319 | $A_{ks}T_{ks}{}^{m}C_{ks}A_{ds}C_{ys}{}^{m}C_{ds}A_{ds}A_{ds}G_{ds}G_{ds}A_{ds}G_{ds}G_{ds}G_{ks}A_{ks}A_{k}$ | 41 | 4966 |
| 1213105 | 1917 | 1932 | 7305 | 7320 | $A_{ks}A_{ks}T_{ks}{}^{m}C_{ds}A_{ys}{}^{m}C_{ds}{}^{m}C_{ds}A_{ds}A_{ds}G_{ds}G_{ds}A_{ds}G_{ds}G_{ks}G_{ks}A_{k}$ | 21 | 4956 |
| 1213106 | 1918 | 1933 | 7306 | 7321 | $G_{ks}A_{ks}A_{ks}T_{ds}C_{ys}A_{ds}{}^{m}C_{ds}{}^{m}C_{ds}A_{ds}A_{ds}G_{ds}G_{ds}A_{ds}G_{ks}G_{ks}G_{k}$ | 23 | 4965 |
| 1213107 | 1919 | 1934 | 7307 | 7322 | $G_{ks}G_{ks}A_{ks}A_{ds}U_{ys}{}^{m}C_{ds}A_{ds}{}^{m}C_{ds}{}^{m}C_{ds}A_{ds}A_{ds}G_{ds}G_{ds}A_{ks}G_{ks}G_{k}$ | 18 | 4995 |
| 1213108 | 1920 | 1935 | 7308 | 7323 | ${}^{m}C_{ks}G_{ks}G_{ks}A_{ds}A_{ys}T_{ds}{}^{m}C_{ds}A_{ds}{}^{m}C_{ds}{}^{m}C_{ds}A_{ds}A_{ds}G_{ds}G_{ks}A_{ks}G_{k}$ | 28 | 3303 |
| 1213109 | 1921 | 1936 | 7309 | 7324 | $G_{ks}{}^{m}C_{ks}G_{ks}G_{ds}A_{ys}A_{ds}T_{ds}{}^{m}C_{ds}A_{ds}{}^{m}C_{ds}{}^{m}C_{ds}A_{ds}A_{ds}G_{ks}G_{ks}A_{k}$ | 37 | 3379 |
| 1213110 | 1922 | 1937 | 7310 | 7325 | $T_{ks}G_{ks}{}^{m}C_{ks}G_{ds}G_{ys}A_{ds}A_{ds}T_{ds}{}^{m}C_{ds}A_{ds}{}^{m}C_{ds}{}^{m}C_{ds}A_{ds}A_{ks}G_{ks}G_{k}$ | 20 | 3455 |
| 1213111 | 1923 | 1938 | 7311 | 7326 | ${}^{m}C_{ks}T_{ks}G_{ks}{}^{m}C_{ds}G_{ys}G_{ds}A_{ds}A_{ds}T_{ds}C_{ds}A_{ds}{}^{m}C_{ds}{}^{m}C_{ds}A_{ks}A_{ks}G_{k}$ | 12 | 3531 |
| 1213112 | 1924 | 1939 | 7312 | 7327 | $A_{ks}{}^{m}C_{ks}T_{ks}G_{ds}C_{ys}G_{ds}G_{ds}A_{ds}A_{ds}T_{ds}{}^{m}C_{ds}A_{ds}{}^{m}C_{ds}{}^{m}C_{ks}A_{ks}A_{k}$ | 20 | 3607 |
| 1213113 | 1925 | 1940 | 7313 | 7328 | ${}^{m}C_{ks}A_{ks}{}^{m}C_{ks}T_{ds}G_{ys}{}^{m}C_{ds}G_{ds}G_{ds}A_{ds}A_{ds}T_{ds}{}^{m}C_{ds}A_{ds}{}^{m}C_{ks}{}^{m}C_{ks}A_{k}$ | 29 | 3683 |
| 1213114 | 1926 | 1941 | 7314 | 7329 | $T_{ks}{}^{m}C_{ks}A_{ks}{}^{m}C_{ds}U_{ys}G_{ds}{}^{m}C_{ds}G_{ds}G_{ds}A_{ds}A_{ds}T_{ds}{}^{m}C_{ds}A_{ks}{}^{m}C_{ks}{}^{m}C_{k}$ | 30 | 4996 |
| 1213115 | 1927 | 1942 | 7315 | 7330 | ${}^{m}C_{ks}T_{ks}{}^{m}C_{ks}A_{ds}C_{ys}T_{ds}G_{ds}{}^{m}C_{ds}G_{ds}G_{ds}A_{ds}A_{ds}T_{ds}{}^{m}C_{ks}A_{ks}{}^{m}C_{k}$ | 18 | 3835 |
| 1213116 | 1928 | 1943 | 7316 | 7331 | $T_{ks}{}^{m}C_{ks}T_{ks}{}^{m}C_{ds}A_{ys}{}^{m}C_{ds}T_{ds}G_{ds}{}^{m}C_{ds}G_{ds}G_{ds}A_{ds}A_{ds}T_{ks}{}^{m}C_{ks}A_{k}$ | 28 | 3911 |
| 1213117 | 1929 | 1944 | 7317 | 7332 | ${}^{m}C_{ks}T_{ks}{}^{m}C_{ks}T_{ds}C_{ys}A_{ds}{}^{m}C_{ds}T_{ds}G_{ds}{}^{m}C_{ds}G_{ds}G_{ds}A_{ds}A_{ks}T_{ks}{}^{m}C_{k}$ | 26 | 4971 |
| 1213118 | 1930 | 1945 | 7318 | 7333 | $T_{ks}{}^{m}C_{ks}T_{ks}{}^{m}C_{ds}U_{ys}{}^{m}C_{ds}A_{ds}{}^{m}C_{ds}T_{ds}G_{ds}{}^{m}C_{ds}G_{ds}G_{ds}A_{ks}A_{ks}T_{k}$ | 19 | 4997 |
| 1213119 | 1931 | 1946 | 7319 | 7334 | ${}^{m}C_{ks}T_{ks}{}^{m}C_{ks}T_{ds}C_{ys}T_{ds}{}^{m}C_{ds}A_{ds}{}^{m}C_{ds}T_{ds}G_{ds}{}^{m}C_{ds}G_{ds}G_{ks}A_{ks}A_{k}$ | 52 | 2461 |

TABLE 87-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213120 | 1932 | 1947 | 7320 | 7335 | $A_{ks}{}^mC_{ks}T_{ks}{}^mC_{ds}U_{ys}{}^mC_{ds}T_{ds}{}^mC_{ds}A_{ds}{}^mC_{ds}T_{ds}G_{ds}{}^mC_{ds}G_{ks}G_{ks}A_k$ | 10 | 4998 |
| 1213121 | 1933 | 1948 | 7321 | 7336 | ${}^mC_{ks}A_{ks}{}^mC_{ks}T_{ds}C_{ys}T_{ds}{}^mC_{ds}T_{ds}{}^mC_{ds}A_{ds}{}^mC_{ds}T_{ds}G_{ds}{}^mC_{ks}G_{ks}G_k$ | 34 | 4957 |
| 1213122 | 1934 | 1949 | 7322 | 7337 | ${}^mC_{ks}{}^mC_{ks}A_{ks}{}^mC_{ds}U_{ys}{}^mC_{ds}T_{ds}{}^mC_{ds}T_{ds}{}^mC_{ds}A_{ds}{}^mC_{ds}T_{ds}G_{ks}{}^mC_{ks}G_k$ | 19 | 4999 |
| 1213123 | 1935 | 1950 | 7323 | 7338 | $G_{ks}{}^mC_{ks}{}^mC_{ks}A_{ds}C_{ys}T_{ds}{}^mC_{ds}T_{ds}{}^mC_{ds}T_{ds}{}^mC_{ds}A_{ds}{}^mC_{ds}A_{ks}G_{ks}{}^mC_k$ | 33 | 4967 |
| 1213124 | 1936 | 1951 | 7324 | 7339 | $A_{ks}G_{ks}{}^mC_{ks}{}^mC_{ds}A_{ys}{}^mC_{ds}T_{ds}{}^mC_{ds}T_{ds}{}^mC_{ds}T_{ds}{}^mC_{ds}A_{ds}{}^mC_{ks}T_{ks}G_k$ | 14 | 4961 |
| 1213125 | 1937 | 1952 | 7325 | 7340 | ${}^mC_{ks}A_{ks}G_{ks}{}^mC_{ds}C_{ys}A_{ds}{}^mC_{ds}T_{ds}{}^mC_{ds}T_{ds}{}^mC_{ds}T_{ds}{}^mC_{ds}A_{ds}{}^mC_{ks}T_k$ | 42 | 4972 |
| 1213126 | 2000 | 2015 | 7388 | 7403 | ${}^mC_{ks}G_{ks}{}^mC_{ks}{}^mC_{ds}A_{ys}T_{ds}{}^mC_{ds}{}^mC_{ds}T_{ds}G_{ds}G_{ds}{}^mC_{ds}G_{ds}{}^mC_{ks}G_{ks}G_k$ | 53 | 3228 |
| 1213127 | 2001 | 2016 | 7389 | 7404 | $G_{ks}{}^mC_{ks}G_{ks}{}^mC_{ds}C_{ys}A_{ds}T_{ds}{}^mC_{ds}{}^mC_{ds}T_{ds}G_{ds}G_{ds}{}^mC_{ds}G_{ks}{}^mC_{ks}G_k$ | 34 | 4964 |
| 1213128 | 2002 | 2017 | 7390 | 7405 | $T_{ks}G_{ks}{}^mC_{ks}G_{ds}C_{ys}{}^mC_{ds}A_{ds}T_{ds}{}^mC_{ds}{}^mC_{ds}T_{ds}G_{ds}G_{ds}{}^mC_{ks}G_{ks}{}^mC_k$ | 61 | 3305 |
| 1213129 | 2003 | 2018 | 7391 | 7406 | ${}^mC_{ks}T_{ks}G_{ks}{}^mC_{ds}G_{ys}{}^mC_{ds}{}^mC_{ds}A_{ds}T_{ds}{}^mC_{ds}{}^mC_{ds}T_{ds}G_{ds}G_{ks}{}^mC_{ks}G_k$ | 114 | 3381 |
| 1213130 | 2004 | 2019 | 7392 | 7407 | ${}^mC_{ks}{}^mC_{ks}T_{ks}G_{ds}C_{ys}G_{ds}{}^mC_{ds}{}^mC_{ds}A_{ds}T_{ds}{}^mC_{ds}{}^mC_{ds}T_{ds}G_{ks}G_{ks}{}^mC_k$ | 24 | 3457 |
| 1213131 | 2005 | 2020 | 7393 | 7408 | $T_{ks}{}^mC_{ks}{}^mC_{ks}T_{ds}G_{ys}{}^mC_{ds}G_{ds}{}^mC_{ds}{}^mC_{ds}A_{ds}T_{ds}{}^mC_{ds}{}^mC_{ds}T_{ks}G_{ks}G_k$ | 35 | 3533 |
| 1213132 | 2006 | 2021 | 7394 | 7409 | $T_{ks}T_{ks}{}^mC_{ks}{}^mC_{ds}C_{ys}G_{ds}{}^mC_{ds}G_{ds}{}^mC_{ds}{}^mC_{ds}A_{ds}T_{ds}{}^mC_{ds}{}^mC_{ks}T_{ks}G_k$ | 29 | 5000 |
| 1213133 | 2007 | 2022 | 7395 | 7410 | $G_{ks}T_{ks}T_{ks}{}^mC_{ds}C_{ys}T_{ds}G_{ds}{}^mC_{ds}G_{ds}{}^mC_{ds}{}^mC_{ds}A_{ds}T_{ds}{}^mC_{ks}{}^mC_{ks}T_k$ | 33 | 3685 |
| 1213134 | 2008 | 2023 | 7396 | 7411 | $A_{ks}G_{ks}T_{ks}T_{ds}C_{ys}{}^mC_{ds}T_{ds}G_{ds}{}^mC_{ds}G_{ds}{}^mC_{ds}{}^mC_{ds}A_{ds}T_{ks}{}^mC_{ks}{}^mC_k$ | 33 | 3761 |
| 1213135 | 2009 | 2024 | 7397 | 7412 | $G_{ks}A_kGG_{ks}T_{ds}U_{ys}{}^mC_{ds}{}^mC_{ds}T_{ds}G_{ds}{}^mC_{ds}G_{ds}{}^mC_{ds}{}^mC_{ds}A_{ks}T_{ks}{}^mC_k$ | 9 | 5001 |
| 1213136 | 2010 | 2025 | 7398 | 7413 | $T_{ks}G_{ks}A_{ks}G_{ds}U_{ys}T_{ds}{}^mC_{ds}{}^mC_{ds}T_{ds}G_{ds}{}^mC_{ds}G_{ds}{}^mC_{ds}{}^mC_{ks}A_{ks}T_k$ | 20 | 5002 |
| 1213137 | 2011 | 2026 | 7399 | 7414 | $T_{ks}T_{ks}G_{ks}A_{ds}G_{ys}T_{ds}T_{ds}{}^mC_{ds}{}^mC_{ds}T_{ds}G_{ds}{}^mC_{ds}G_{ds}{}^mC_{ks}{}^mC_{ks}A_k$ | 17 | 2463 |
| 1213138 | 2012 | 2027 | 7400 | 7415 | $A_{ks}T_{ks}T_{ks}G_{ds}A_{ys}G_{ds}T_{ds}T_{ds}{}^mC_{ds}{}^mC_{ds}T_{ds}G_{ds}{}^mC_{ds}G_{ks}{}^mC_{ks}{}^mC_k$ | 17 | 2540 |
| 1213139 | 2013 | 2028 | 7401 | 7416 | $T_{ks}A_{ks}T_{ks}T_{ds}G_{ys}A_{ds}G_{ds}T_{ds}T_{ds}{}^mC_{ds}{}^mC_{ds}T_{ds}G_{ds}{}^mC_{ks}G_{ks}{}^mC_k$ | 26 | 2617 |
| 1213140 | 2014 | 2029 | 7402 | 7417 | $T_{ks}T_{ks}A_{ks}T_{ds}U_{ys}G_{ds}A_{ds}G_{ds}T_{ds}T_{ds}{}^mC_{ds}{}^mC_{ds}T_{ds}G_{ks}{}^mC_{ks}G_k$ | 25 | 5003 |
| 1213141 | 2016 | 2031 | 7404 | 7419 | ${}^mC_{ks}T_{ks}T_{ks}T_{ds}A_{ys}T_{ds}T_{ds}G_{ds}A_{ds}G_{ds}T_{ds}T_{ds}{}^mC_{ds}{}^mC_{ks}T_{ks}G_k$ | 22 | 2771 |
| 1213142 | 2017 | 2032 | 7405 | 7420 | $A_{ks}{}^mC_{ks}T_{ks}T_{ds}U_{ys}A_{ds}T_{ds}T_{ds}G_{ds}A_{ds}G_{ds}T_{ds}T_{ds}{}^mC_{ks}{}^mC_{ks}T_k$ | 30 | 5004 |

TABLE 87-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213143 | 2018 | 2033 | 7406 | 7421 | $^mC_{ks}A_{ks}{}^mC_{ks}T_{ds}U_{ys}T_{ds}A_{ds}T_{ds}T_{ds}G_{ds}A_{ds}G_{ds}T_{ds}T_{ks}{}^mC_{ks}{}^mC_k$ | 25 | 5005 |
| 1213144 | 2019 | 2034 | 7407 | 7422 | $G_{ks}{}^mC_{ks}A_{ks}{}^mC_{ds}U_{ys}T_{ds}A_{ds}T_{ds}T_{ds}G_{ds}A_{ds}G_{ds}T_{ks}T_{ks}{}^mC_k$ | 10 | 5006 |
| 1213145 | 2020 | 2035 | 7408 | 7423 | $A_{ks}G_{ks}{}^mC_{ks}A_{ds}C_{ys}T_{ds}T_{ds}T_{ds}A_{ds}T_{ds}T_{ds}G_{ds}A_{ds}G_{ks}T_{ks}T_k$ | 20 | 3076 |
| 1213146 | 2021 | 2036 | 7409 | 7424 | $A_{ks}A_{ks}G_{ks}{}^mC_{ds}A_{ys}{}^mC_{ds}T_{ds}T_{ds}T_{ds}A_{ds}T_{ds}T_{ds}G_{ds}A_{ks}G_{ks}T_k$ | 11 | 3147 |
| 1213147 | 2022 | 2037 | 7410 | 7425 | $A_{ks}A_{ks}A_{ks}G_{ds}C_{ys}A_{ds}{}^mC_{ds}T_{ds}T_{ds}T_{ds}A_{ds}T_{ds}T_{ds}G_{ks}A_{ks}G_k$ | 15 | 3229 |
| 1213148 | 2023 | 2038 | 7411 | 7426 | $^mC_{ks}A_{ks}A_{ks}A_{ds}G_{ys}{}^mC_{ds}A_{ds}{}^mC_{ds}T_{ds}T_{ds}T_{ds}A_{ds}T_{ds}T_{ks}G_{ks}A_k$ | 34 | 3306 |
| 1213149 | 2024 | 2039 | 7412 | 7427 | $T_{ks}{}^mC_{ks}A_{ks}A_{ds}A_{ys}G_{ds}{}^mC_{ds}A_{ds}{}^mC_{ds}T_{ds}T_{ds}T_{ds}A_{ds}T_{ks}T_{ks}G_k$ | 35 | 3382 |
| 1213150 | 2031 | 2046 | 7419 | 7434 | $A_{ks}G_{ks}{}^mC_{ks}A_{ds}U_{ys}T_{ds}T_{ds}T_{ds}{}^mC_{ds}A_{ds}A_{ds}A_{ds}G_{ds}{}^mC_{ks}A_{ks}{}^mC_k$ | 41 | 5007 |
| 1213151 | 2033 | 2048 | 7421 | 7436 | $T_{ks}{}^mC_{ks}A_{ks}G_{ds}C_{ys}A_{ds}T_{ds}T_{ds}T_{ds}T_{ds}{}^mC_{ds}A_{ds}A_{ds}A_{ks}G_{ks}{}^mC_k$ | 23 | 3534 |

TABLE 88

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Chemistry notation (5' to 3') | FXII (%UTC) | SEQ ID NO |
|---|---|---|---|---|---|---|---|
| 1128769 | 153 | 168 | N/A | N/A | $A_{ks}G_{ks}A_{ks}A_{ds}{}^mC_{ds}G_{ds}A_{ds}C_{ds}T_{ds}G_{ds}T_{ds}G_{ds}T_{ds}G_{ks}{}^mC_{ks}T_k$ | 41 | 3723 |
| 1128802 | 218 | 233 | 3569 | 3584 | $T_{ks}A_{ks}{}^mC_{ks}A_{ds}T_{ds}T_{ds}T_{ds}G_{ds}T_{ds}G_{ds}G_{ds}T_{ds}A_{ds}{}^mC_{ks}A_{ks}G_k$ | N/A | 2426 |
| 1128870 | 470 | 485 | 4415 | 4430 | $T_{ks}G_{ks}T_{ks}G_{ds}G_{ds}A_{ds}A_{ds}A_{ds}A_{ds}A_{ds}{}^mC_{ds}{}^mC_{ds}G_{ds}G_{ks}A_{ks}G_k$ | 31 | 3728 |
| 1129491 | 1927 | 1942 | 7315 | 7330 | $^mC_{ks}T_{ks}{}^mC_{ks}A_{ds}{}^mC_{ds}T_{ds}G_{ds}{}^mC_{ds}G_{ds}G_{ds}A_{ds}A_{ds}T_{ds}{}^mC_{ks}A_{ks}{}^mC_k$ | 16 | 3835 |
| 1129510 | 1984 | 1999 | 7372 | 7387 | $A_{ks}G_{ks}{}^mC_{ks}T_{ds}G_{ds}G_{ds}{}^mC_{ds}{}^mC_{ds}G_{ds}G_{ds}{}^mC_{ds}A_{ds}{}^mC_{ds}T_{ds}G_{ks}G_{ks}G_k$ | 29 | 3760 |
| 1129530 | 2008 | 2023 | 7396 | 7411 | $A_{ks}G_{ks}T_{ks}T_{ds}{}^mC_{ds}{}^mC_{ds}T_{ds}G_{ds}G_{ds}{}^mC_{ds}G_{ds}{}^mC_{ds}{}^mC_{ds}A_{ds}T_{ks}{}^mC_{ks}{}^mC_k$ | 80 | 3761 |
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}G_{ds}{}^mC_{ds}G_{ds}{}^mC_{ds}{}^mC_{ds}A_{ks}T_{ks}{}^mC_k$ | 29 | 3837 |
| 1129532 | 2010 | 2025 | 7398 | 7413 | $T_{ks}G_{ks}A_{ks}G_{ds}T_{ds}T_{ds}{}^mC_{ds}{}^mC_{ds}T_{ds}G_{ds}{}^mC_{ds}G_{ds}{}^mC_{ds}{}^mC_{ks}A_{ks}T_k$ | 19 | 3913 |
| 1129540 | 2019 | 2034 | 7407 | 7422 | $G_{ks}{}^mC_{ks}A_{ks}{}^mC_{ds}T_{ds}T_{ds}T_{ds}A_{ds}T_{ds}T_{ds}G_{ds}A_{ds}G_{ds}T_{ks}T_{ks}{}^mC_k$ | 48 | 3000 |
| 1129683 | N/A | N/A | 1003 | 1018 | $T_{ks}{}^mC_{ks}A_{ks}A_{ds}{}^mC_{ds}{}^mC_{ds}T_{ds}G_{ds}G_{ds}T_{ds}T_{ds}T_{ds}{}^mC_{ds}A_{ks}{}^mC_{ks}A_k$ | 64 | 3236 |

TABLE 88-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Chemistry notation (5' to 3') | FXII (%UTC) | SEQ ID NO |
|---|---|---|---|---|---|---|---|
| 1129703 | N/A | N/A | 1139 | 1154 | $A_{ks}T_{ks}G_{ks}Ga_{ds}{}^mC_{ds}A_{ds}G_{ds}G_{ds}T_{ds}A_{ds}{}^mC_{ds}{}^mC_{ds}{}^mC_{ds}T_{ks}T_{ks}C_k$ | 32 | 3237 |
| 1129715 | N/A | N/A | 1559 | 1574 | $C_{ks}A_{ks}G_{ks}G_{ds}G_{ds}T_{ds}A_{ds}A_{ds}G_{ds}G_{ds}T_{ds}{}^mC_{ds}{}^mC_{ds}A_{ks}T_{ks}C_k$ | 52 | 2626 |
| 1129783 | N/A | N/A | 2494 | 2509 | $G_{ks}T_{ks}T_{ks}A_{ds}G_{ds}A_{ds}{}^mC_{ds}A_{ds}{}^mC_{ds}T_{ds}T_{ds}G_{ds}A_{ds}T_{ks}T_{ks}{}^mC_k$ | 104 | 3241 |
| 1129796 | N/A | N/A | 2628 | 2643 | $T_{ks}{}^mC_{ks}T_{ks}A_{ds}{}^mC_{ds}T_{ds}T_{ds}A_{ds}G_{ds}T_{ds}G_{ds}{}^mC_{ds}A_{ds}A_{ks}{}^mC_{ks}G_k$ | 57 | 2707 |
| 1129877 | N/A | N/A | 4035 | 4050 | $G_{ks}{}^mC_{ks}T_{ks}A_{ds}C_{ds}T_{ds}{}^mC_{ds}{}^mC_{ds}A_{ds}A_{ds}C_{ds}T_{ds}T_{ks}T_{ks}{}^mC_{ks}{}^mC_k$ | 66 | 2788 |
| 1129916 | N/A | N/A | 4363 | 4378 | $G_{ks}G_{ks}G_{ks}A_{ds}T_{ds}A_{ds}G_{ds}T_{ds}G_{ds}G_{ds}G_{ds}T_{ds}{}^mC_{ds}T_{ds}{}^mC_{ks}A_{ks}G_k$ | 103 | 2713 |
| 1129938 | N/A | N/A | 4635 | 4650 | $A_{ks}{}^mC_{ks}G_{ks}{}^mC_{ds}A_{ds}G_{ds}T_{ds}G_{ds}A_{ds}G_{ds}{}^mC_{ds}{}^mC_{ds}A_{ds}{}^mC_{ks}{}^mC_{ks}{}^mC_k$ | 52 | 2868 |
| 1129943 | N/A | N/A | 4808 | 4823 | $G_{ks}G_{ks}{}^mC_{ks}A_{ds}A_{ds}G_{ds}{}^mC_{ds}{}^mC_{ds}{}^mC_{ds}G_{ds}T_{ds}{}^mC_{ds}{}^mC_{ds}{}^mC_{ks}A_{ks}{}^mC_k$ | 63 | 3249 |
| 1129948 | N/A | N/A | 4840 | 4855 | $A_{ks}T_{ks}{}^mC_{ks}T_{ds}G_{ds}{}^mC_{ds}T_{ds}T_{ds}T_{ds}{}^mC_{ds}{}^mC_{ds}G_{ds}{}^mC_{ds}A_{ks}{}^mC_{ks}T_k$ | 108 | 3630 |
| 1129949 | N/A | N/A | 4844 | 4859 | $T_{ks}{}^mC_{ks}T_{ks}{}^mC_{ds}A_{ds}G_{ds}{}^mC_{ds}T_{ds}G_{ds}{}^mC_{ds}T_{ds}T_{ds}T_{ds}{}^mC_{ks}{}^mC_{ks}G_k$ | 81 | 3706 |
| 1213152 | 141 | 156 | 508 | 523 | $T_{ks}G_{ks}{}^mC_{ks}T_{ds}{}^mC_{ds}U_{ys}T_{ds}{}^mC_{ds}A_{ds}G_{ds}{}^mC_{ds}T_{ds}T_{ds}T_{ks}G_{ks}T_k$ | 72 | 5008 |
| 1213153 | 142 | 157 | 509 | 524 | $G_{ks}T_{ks}G_{ks}{}^mC_{ds}T_{ds}C_{ys}T_{ds}T_{ds}{}^mC_{ds}A_{ds}G_{ds}C_{ds}T_{ds}T_{ks}T_{ks}G_k$ | 29 | 4958 |
| 1213154 | 143 | 158 | 510 | 525 | $T_{ks}G_{ks}T_{ks}G_{ds}{}^mC_{ds}U_{ys}{}^mC_{ds}T_{ds}T_{ds}{}^mC_{ds}A_{ds}G_{ds}{}^mC_{ds}T_{ks}T_{ks}T_k$ | 75 | 5009 |
| 1213155 | 144 | 159 | 511 | 526 | $G_{ks}T_{ks}G_{ks}T_{ds}G_{ds}C_{ys}T_{ds}{}^mC_{ds}T_{ds}T_{ds}{}^mC_{ds}A_{ds}G_{ds}{}^mC_{ks}T_{ks}T_k$ | 70 | 4951 |
| 1213156 | 145 | 160 | 512 | 527 | $T_{ks}G_{ks}T_{ks}G_{ds}T_{ds}G_{ys}{}^mC_{ds}T_{ds}{}^mC_{ds}T_{ds}T_{ds}{}^mC_{ds}A_{ds}G_{ks}{}^mC_{ks}T_k$ | 35 | 3112 |
| 1213157 | 146 | 161 | 513 | 528 | ${}^mC_{ks}T_{ks}G_{ks}T_{ds}G_{ds}U_{ys}G_{ds}{}^mC_{ds}T_{ds}{}^mC_{ds}T_{ds}T_{ds}{}^mC_{ds}A_{ks}G_{ks}{}^mC_k$ | 60 | 5010 |
| 1213158 | 147 | 162 | 514 | 529 | $A_{ks}{}^mC_{ks}T_{ks}G_{ds}T_{ds}G_{ys}T_{ds}G_{ds}{}^mC_{ds}T_{ds}{}^mC_{ds}T_{ds}T_{ds}{}^mC_{ks}A_{ks}G_k$ | 56 | 3267 |
| 1213160 | 149 | 164 | 516 | 531 | ${}^mC_{ks}G_{ks}A_{ks}{}^mC_{ds}T_{ds}G_{ys}T_{ds}G_{ds}T_{ds}G_{ds}{}^mC_{ds}T_{ds}{}^mC_{ds}T_{ks}T_{ks}{}^mC_k$ | 61 | 3419 |
| 1213161 | 150 | 165 | N/A | N/A | $A_{ks}{}^mC_{ks}G_{ks}A_{ds}{}^mC_{ds}U_{ys}G_{ds}T_{ds}G_{ds}T_{ds}G_{ds}{}^mC_{ds}T_{ds}{}^mC_{ks}T_{ks}T_k$ | 36 | 5011 |
| 1213162 | 151 | 166 | N/A | N/A | $A_{ks}A_{ks}{}^mC_{ks}G_{ds}A_{ds}C_{ys}T_{ds}G_{ds}T_{ds}G_{ds}T_{ds}G_{ds}{}^mC_{ds}T_{ks}{}^mC_{ks}T_k$ | 97 | 3571 |
| 1213163 | 152 | 167 | N/A | N/A | $G_{ks}A_{ks}A_{ks}{}^mC_{ds}G_{ds}A_{ys}{}^mC_{ds}T_{ds}G_{ds}T_{ds}G_{ds}T_{ds}G_{ds}{}^mC_{ks}T_{ks}{}^mC_k$ | 50 | 3647 |
| 1213164 | 153 | 168 | N/A | N/A | $A_{ks}G_{ks}A_{ks}A_{ds}{}^mC_{ds}G_{ys}A_{ds}{}^mC_{ds}T_{ds}G_{ds}T_{ds}G_{ds}T_{ds}G_{ks}{}^mC_{ks}T_k$ | 99 | 3723 |
| 1213165 | 154 | 169 | N/A | N/A | $G_{ks}A_{ks}G_{ks}A_{ds}A_{ds}C_{ys}G_{ds}A_{ds}{}^mC_{ds}T_{ds}G_{ds}T_{ds}G_{ds}T_{ks}G_{ks}{}^mC_k$ | 132 | 3799 |

TABLE 88-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Chemistry notation (5' to 3') | FXII (%UTC) | SEQ ID NO |
|---|---|---|---|---|---|---|---|
| 1213166 | 155 | 170 | N/A | N/A | $T_{ks}G_{ks}A_{ks}G_{ds}A_{ds}A_{ys}{}^mC_{ds}G_{ds}A_{ds}{}^mC_{ds}T_{ds}G_{ds}T_{ds}T_{ks}G_{ks}G_{k}$ | 70 | 3875 |
| 1213167 | 156 | 171 | N/A | N/A | $G_{ks}T_{ks}G_{ks}A_{ds}G_{ds}A_{ys}A_{ds}{}^mC_{ds}G_{ds}A_{ds}{}^mC_{ds}T_{ds}G_{ds}T_{ks}G_{ks}T_{k}$ | 45 | 2424 |
| 1213168 | 157 | 172 | N/A | N/A | $A_{ks}G_{ks}T_{ks}G_{ds}A_{ds}G_{ys}A_{ds}A_{ds}{}^mC_{ds}G_{ds}A_{ds}{}^mC_{ds}T_{ds}G_{ks}T_{ks}G_{k}$ | 112 | 2502 |
| 1213169 | 158 | 173 | N/A | N/A | ${}^mC_{ks}A_{ks}G_{ks}T_{ds}G_{ds}A_{ys}G_{ds}A_{ds}A_{ds}{}^mC_{ds}G_{ds}A_{ds}{}^mC_{ds}T_{ks}G_{ks}T_{k}$ | 73 | 2579 |
| 1213170 | 208 | 223 | 3559 | 3574 | $G_{ks}T_{ks}A_{ks}{}^mC_{ds}A_{ds}G_{ys}{}^mC_{ds}T_{ds}G_{ds}{}^mC_{ds}{}^mC_{ds}G_{ds}G_{ds}T_{ks}G_{ks}G_{k}$ | 47 | 4968 |
| 1213171 | 209 | 224 | 3560 | 3575 | $G_{ks}G_{ks}T_{ks}A_{ds}{}^mC_{ds}A_{ys}G_{ds}{}^mC_{ds}T_{ds}G_{ds}{}^mC_{ds}{}^mC_{ds}G_{ds}G_{ds}T_{ks}G_{k}$ | 22 | 4952 |
| 1213173 | 211 | 226 | 3562 | 3577 | $G_{ks}T_{ks}G_{ks}G_{ds}T_{ds}A_{ys}{}^mC_{ds}A_{ds}G_{ds}{}^mC_{ds}T_{ds}G_{ds}{}^mC_{ds}{}^mC_{ks}G_{ks}G_{k}$ | 112 | 4973 |
| 1213174 | 212 | 227 | 3563 | 3578 | $T_{ks}G_{ks}T_{ks}G_{ds}G_{ds}U_{ys}A_{ds}{}^mC_{ds}A_{ds}G_{ds}{}^mC_{ds}T_{ds}G_{ds}{}^mC_{ks}G_{k}$ | 72 | 5012 |
| 1213175 | 213 | 228 | 3564 | 3579 | $T_{ks}T_{ks}G_{ks}T_{ds}G_{ds}G_{ys}T_{ds}A_{ds}{}^mC_{ds}A_{ds}G_{ds}{}^mC_{ds}T_{ds}G_{ks}{}^mC_{ks}{}^mC_{k}$ | 46 | 2811 |
| 1213176 | 214 | 229 | 3565 | 3580 | $T_{ks}T_{ks}T_{ks}G_{ds}T_{ds}G_{ys}G_{ds}T_{ds}A_{ds}{}^mC_{ds}A_{ds}G_{ds}{}^mC_{ds}T_{ks}G_{ks}{}^mC_{k}$ | 62 | 2887 |
| 1213177 | 215 | 230 | 3566 | 3581 | $A_{ks}T_{ks}T_{ks}T_{ds}G_{ds}U_{ys}G_{ds}G_{ds}T_{ds}A_{ds}{}^mC_{ds}A_{ds}G_{ds}{}^mC_{ks}T_{ks}G_{k}$ | 45 | 5013 |
| 1213178 | 216 | 231 | 3567 | 3582 | ${}^mC_{ks}A_{ks}T_{ks}T_{ds}T_{ds}G_{ys}T_{ds}G_{ds}G_{ds}T_{ds}A_{ds}{}^mC_{ds}A_{ds}G_{ds}{}^mC_{ks}T_{k}$ | 33 | 3039 |
| 1213179 | 217 | 232 | 3568 | 3583 | $A_{ks}{}^mC_{ks}A_{ks}T_{ds}T_{ds}U_{ys}G_{ds}T_{ds}G_{ds}G_{ds}T_{ds}A_{ds}{}^mC_{ds}A_{k}G_{ks}{}^mC_{k}$ | 49 | 5014 |
| 1213180 | 218 | 233 | 3569 | 3584 | $T_{ks}A_{ks}{}^mC_{ks}A_{ds}T_{ds}U_{ys}T_{ds}G_{ds}T_{ds}G_{ds}G_{ds}T_{ds}A_{ds}{}^mC_{ks}A_{ks}G_{k}$ | 26 | 5015 |
| 1213181 | 219 | 234 | 3570 | 3585 | $G_{ks}T_{ks}A_{ks}{}^mC_{ds}A_{ds}U_{ys}T_{ds}T_{ds}G_{ds}T_{ds}G_{ds}G_{ds}T_{ds}A_{ks}{}^mC_{ks}A_{k}$ | 50 | 5016 |
| 1213182 | 220 | 235 | 3571 | 3586 | $G_{ks}G_{ks}T_{ks}A_{ds}{}^mC_{ds}A_{ys}T_{ds}T_{ds}T_{ds}G_{ds}T_{ds}G_{ds}G_{ds}T_{ks}A_{ks}{}^mC_{k}$ | 46 | 3269 |
| 1213183 | 221 | 236 | 3572 | 3587 | $G_{ks}G_{ks}G_{ks}T_{ds}A_{ds}C_{ys}A_{ds}T_{ds}T_{ds}T_{ds}G_{ds}T_{ds}G_{ds}G_{ks}T_{ks}A_{k}$ | 117 | 3345 |
| 1213184 | 222 | 237 | 3573 | 3588 | $T_{ks}G_{ks}G_{ks}G_{ds}T_{ds}A_{ys}{}^mC_{ds}A_{ds}T_{ds}T_{ds}T_{ds}G_{ds}T_{ds}G_{ks}G_{ks}T_{k}$ | N/A | 3421 |
| 1213185 | 223 | 238 | 3574 | 3589 | $G_{ks}T_{ks}G_{ks}G_{ds}G_{ds}U_{ys}A_{ds}{}^mC_{ds}A_{ds}T_{ds}T_{ds}T_{ds}G_{ds}T_{ks}G_{ks}G_{k}$ | 63 | 5017 |
| 1213186 | 1776 | 1791 | 7164 | 7179 | $T_{ks}G_{ks}{}^mC_{ds}A_{ds}G_{ds}G_{ys}G_{ds}T_{ds}G_{ds}A_{ds}G_{ds}{}^mC_{ds}{}^mC_{ds}G_{ks}G_{ks}{}^mC_{k}$ | 149 | 3299 |
| 1213187 | 1777 | 1792 | 7165 | 7180 | $T_{ks}T_{ks}G_{ks}{}^mC_{ds}A_{ds}G_{ys}G_{ds}G_{ds}T_{ds}G_{ds}A_{ds}G_{ds}{}^mC_{ds}{}^mC_{ks}G_{ks}G_{k}$ | 98 | 3375 |
| 1213188 | 1778 | 1793 | 7166 | 7181 | ${}^mC_{ks}T_{ks}T_{ks}G_{ds}{}^mC_{ds}A_{ys}G_{ds}G_{ds}G_{ds}T_{ds}G_{ds}A_{ds}G_{ds}{}^mC_{ks}{}^mC_{ks}G_{k}$ | 71 | 4962 |
| 1213189 | 1779 | 1794 | 7167 | 7182 | ${}^mC_{ks}{}^mC_{ks}T_{ks}T_{ds}G_{ds}C_{ys}A_{ds}G_{ds}G_{ds}G_{ds}T_{ds}G_{ds}A_{ds}G_{ks}{}^mC_{ks}{}^mC_{k}$ | 40 | 4974 |

TABLE 88-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Chemistry notation (5' to 3') | FXII (%UTC) | SEQ ID NO |
|---|---|---|---|---|---|---|---|
| 1213190 | 1780 | 1795 | 7168 | 7183 | $G_{ks}{}^mC_{ks}{}^mC_{ks}T_{ds}T_{ds}G_{ys}{}^mC_{ds}A_{ds}G_{ds}G_{ds}G_{ds}T_{ds}G_{ds}A_{ks}G_{ks}{}^mC_k$ | 53 | 3451 |
| 1213192 | 1782 | 1797 | 7170 | 7185 | $A_{ks}T_{ks}G_{ks}{}^mC_{ds}{}^mC_{ds}U_{ys}T_{ds}G_{ds}{}^mC_{ds}A_{ds}G_{ds}G_{ds}G_{ds}T_{ks}G_{ks}A_k$ | 107 | 5018 |
| 1213193 | 1783 | 1798 | 7171 | 7186 | $G_{ks}A_{ks}T_{ks}G_{ds}{}^mC_{ds}C_{ys}T_{ds}G_{ds}{}^mC_{ds}A_{ds}G_{ds}G_{ds}G_{ks}T_{ks}G_k$ | 54 | 4959 |
| 1213194 | 1784 | 1799 | 7172 | 7187 | $T_{ks}G_{ks}A_{ks}T_{ds}G_{ds}C_{ys}{}^mC_{ds}T_{ds}T_{ds}G_{ds}{}^mC_{ds}A_{ds}G_{ds}G_{ks}G_{ks}T_k$ | 28 | 4969 |
| 1213195 | 1785 | 1800 | 7173 | 7188 | $A_{ks}T_{ks}G_{ks}A_{ds}T_{ds}G_{ys}{}^mC_{ds}{}^mC_{ds}T_{ds}T_{ds}G_{ds}{}^mC_{ds}A_{ds}G_{ks}G_{ks}G_k$ | 53 | 3603 |
| 1213196 | 1786 | 1801 | 7174 | 7189 | $G_{ks}A_{ks}T_{ks}G_{ds}A_{ds}U_{ys}G_{ds}{}^mC_{ds}{}^mC_{ds}T_{ds}T_{ds}G_{ds}{}^mC_{ds}A_{ks}G_{ks}G_k$ | 73 | 5019 |
| 1213197 | 1787 | 1802 | 7175 | 7190 | $T_{ks}G_{ks}A_{ks}T_{ds}G_{ds}A_{ys}T_{ds}G_{ds}{}^mC_{ds}{}^mC_{ds}T_{ds}T_{ds}G_{ds}{}^mC_{ks}A_{ks}G_k$ | 43 | 4975 |
| 1213198 | 1788 | 1803 | 7176 | 7191 | ${}^mC_{ks}T_{ks}G_{ks}A_{ds}T_{ds}G_{ys}A_{ds}T_{ds}G_{ds}{}^mC_{ds}{}^mC_{ds}T_{ds}T_{ds}G_{ks}{}^mC_{ks}A_k$ | 65 | 3679 |
| 1213199 | 1789 | 1804 | 7177 | 7192 | $G_{ks}{}^mC_{ks}T_{ks}G_{ds}A_{ds}U_{ys}G_{ds}A_{ds}T_{ds}G_{ds}{}^mC_{ds}{}^mC_{ds}T_{ds}T_{ks}G_{ks}{}^mC_k$ | 80 | 5020 |
| 1213200 | 1790 | 1805 | 7178 | 7193 | $A_{ks}G_{ks}{}^mC_{ks}T_{ds}G_{ds}A_{ys}T_{ds}G_{ds}A_{ds}T_{ds}G_{ds}{}^mC_{ds}{}^mC_{ds}T_{ks}T_{ks}G_k$ | 49 | 3831 |
| 1213201 | 1791 | 1806 | 7179 | 7194 | ${}^mC_{ks}A_{ks}G_{ks}{}^mC_{ds}T_{ds}G_{ys}A_{ds}T_{ds}G_{ds}A_{ds}T_{ds}G_{ds}{}^mC_{ds}{}^mC_{ks}T_{ks}T_k$ | 83 | 4960 |
| 1213202 | 1792 | 1807 | 7180 | 7195 | ${}^mC_{ks}{}^mC_{ks}A_{ks}G_{ds}{}^mC_{ds}U_{ys}G_{ds}A_{ds}T_{ds}G_{ds}A_{ds}T_{ds}G_{ds}{}^mC_{ks}{}^mC_{ks}T_k$ | 44 | 5021 |
| 1213203 | 1793 | 1808 | 7181 | 7196 | ${}^mC_{ks}{}^mC_{ks}{}^mC_{ks}A_{ds}G_{ds}C_{ys}T_{ds}G_{ds}A_{ds}T_{ds}G_{ds}A_{ds}T_{ds}G_{ks}{}^mC_{ks}{}^mC_k$ | 42 | 4953 |
| 1213204 | 1892 | 1907 | 7280 | 7295 | ${}^mC_{ks}{}^mC_{ks}{}^mC_{ks}T_{ds}G_{ds}A_{ys}G_{ds}{}^mC_{ds}A_{ds}A_{ds}T_{ds}{}^mC_{ds}A_{ds}G_{ks}G_{ks}A_k$ | 53 | 3530 |
| 1213205 | 1893 | 1908 | 7281 | 7296 | $T_{ks}{}^mC_{ks}{}^mC_{ks}{}^mC_{ds}T_{ds}G_{ys}A_{ds}G_{ds}{}^mC_{ds}A_{ds}A_{ds}T_{ds}{}^mC_{ds}A_{ks}G_{ks}G_k$ | 104 | 3606 |
| 1213206 | 1894 | 1909 | 7282 | 7297 | $G_{ks}T_{ks}{}^mC_{ks}{}^mC_{ds}{}^mC_{ds}U_{ys}G_{ds}A_{ds}G_{ds}{}^mC_{ds}A_{ds}A_{ds}T_{ds}{}^mC_{ks}A_{ks}G_k$ | 45 | 5022 |
| 1213207 | 1895 | 1910 | 7283 | 7298 | $A_{ks}G_{ks}T_{ks}{}^mC_{ds}{}^mC_{ds}C_{ys}T_{ds}G_{ds}A_{ds}G_{ds}{}^mC_{ds}A_{ds}A_{ds}T_{ks}{}^mC_{ks}A_k$ | 36 | 3758 |
| 1213208 | 1896 | 1911 | 7284 | 7299 | $G_{ks}A_{ks}G_{ks}T_{ds}{}^mC_{ds}C_{ys}{}^mC_{ds}T_{ds}G_{ds}A_{ds}G_{ds}{}^mC_{ds}A_{ds}A_{ks}T_{ks}{}^mC_k$ | 62 | 3834 |
| 1213209 | 1897 | 1912 | 7285 | 7300 | $T_{ks}G_{ks}A_{ks}G_{ds}T_{ds}C_{ys}{}^mC_{ds}{}^mC_{ds}T_{ds}G_{ds}A_{ds}G_{ds}{}^mC_{ds}A_{ks}A_{ks}T_k$ | 46 | 3910 |

TABLE 89

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1128769 | 153 | 168 | N/A | N/A | $A_{ks}G_{ks}A_{ks}A_{ds}{}^mC_{ds}G_{ds}A_{ds}{}^mC_{ds}T_{ds}G_{ds}T_{ds}$ $G_{ds}T_{ds}G_{ks}{}^mC_{ks}T_k$ | 84 | 3723 |
| 1128796 | 212 | 227 | 3563 | 3578 | $T_{ks}G_{ks}T_{ks}G_{ds}G_{ds}T_{ds}A_{ds}{}^mC_{ds}A_{ds}A_{ds}G_{ds}{}^mC_{ds}$ $T_{ds}G_{ds}{}^mC_{ks}{}^mC_{ks}G_k$ | 103 | 2734 |
| 1128802 | 218 | 233 | 3569 | 3584 | $T_{ks}A_{ks}{}^mC_{ks}A_{ds}T_{ds}T_{ds}T_{ds}G_{ds}T_{ds}G_{ds}G_{ds}$ $T_{ds}A_{ds}{}^mC_{ks}A_{ks}G_k$ | 97 | 2426 |
| 1128870 | 470 | 485 | 4415 | 4430 | $T_{ks}G_{ks}T_{ks}G_{ds}G_{ds}A_{ds}A_{ds}A_{ds}A_{ds}A_{ds}{}^mC_{ds}$ $^mC_{ds}G_{ds}G_{ks}A_{ks}G_k$ | 60 | 3728 |
| 1129221 | 1357 | 1372 | 6017 | 6032 | $^mC_{ks}G_{ks}T_{ks}{}^mC_{ds}T_{ds}G_{ds}G_{ds}{}^mC_{ds}A_{ds}{}^mC_{ds}$ $G_{ds}G_{ds}{}^mC_{ds}T_{ks}{}^mC_{ks}A_k$ | 19 | 3060 |
| 1129407 | 1781 | 1796 | 7169 | 7184 | $T_{ks}G_{ks}{}^mC_{ks}{}^mC_{ds}T_{ds}T_{ds}G_{ds}{}^mC_{ds}A_{ds}G_{ds}$ $G_{ds}G_{ds}T_{ds}G_{ks}A_{ks}G_k$ | 12 | 3527 |
| 1129472 | 1897 | 1912 | 7285 | 7300 | $T_{ks}G_{ks}A_{ks}G_{ds}T_{ds}{}^mC_{ds}{}^mC_{ds}{}^mC_{ds}T_{ds}G_{ds}$ $A_{ds}G_{ds}{}^mC_{ds}A_{ks}A_{ks}T_k$ | 18 | 3910 |
| 1129488 | 1924 | 1939 | 7312 | 7327 | $A_{ks}{}^mC_{ks}T_{ks}G_{ds}{}^mC_{ds}G_{ds}G_{ds}A_{ds}A_{ds}T_{ds}{}^m$ $C_{ds}A_{ds}{}^mC_{ds}{}^mC_{ks}A_{ks}A_k$ | 5 | 3607 |
| 1129491 | 1927 | 1942 | 7315 | 7330 | $^mC_{ks}T_{ks}{}^mC_{ks}A_{ds}C_{ds}T_{ds}G_{ds}{}^mC_{ds}G_{ds}G_{ds}$ $A_{ds}A_{ds}T_{ds}{}^mC_{ks}A_{ks}{}^mC_k$ | 15 | 3835 |
| 1129531 | 2009 | 2024 | 7397 | 7412 | $G_{ks}A_{ks}G_{ks}T_{ds}T_{ds}{}^mC_{ds}{}^mC_{ds}T_{ds}G_{ds}{}^mC_{ds}$ $G_{ds}{}^mC_{ds}A_{ds}T_{ks}T_{ks}{}^mC_k$ | 12 | 3837 |
| 1129532 | 2010 | 2025 | 7398 | 7413 | $T_{ks}G_{ks}A_{ks}G_{ds}T_{ds}T_{ds}{}^mC_{ds}{}^mC_{ds}T_{ds}G_{ds}{}^m$ $C_{ds}G_{ds}{}^mC_{ds}{}^mC_{ks}A_{ks}T_k$ | 11 | 3913 |
| 1129533 | 2011 | 2026 | 7399 | 7414 | $T_{ks}T_{ks}G_{ks}A_{ds}G_{ds}T_{ds}T_{ds}{}^mC_{ds}{}^mC_{ds}T_{ds}G_{ds}$ $^mC_{ds}G_{ds}{}^mC_{ks}{}^mC_{ks}A_k$ | 8 | 2463 |
| 1129540 | 2019 | 2034 | 7407 | 7422 | $G_{ks}{}^mC_{ks}A_{ks}{}^mC_{ds}T_{ds}T_{ds}T_{ds}A_{ds}T_{ds}T_{ds}G_{ds}$ $A_{ds}G_{ds}T_{ks}T_{ks}{}^mC_k$ | 4 | 3000 |
| 1129542 | 2021 | 2036 | 7409 | 7424 | $A_{ks}A_{ks}G_{ks}{}^mC_{ds}A_{ds}{}^mC_{ds}T_{ds}T_{ds}T_{ds}A_{ds}T_{ds}$ $T_{ds}G_{ds}A_{ks}G_{ks}T_k$ | 17 | 3147 |
| 1129565 | N/A | N/A | 144 | 159 | $A_{ks}T_{ks}A_{ks}G_{ds}{}^mC_{ds}G_{ds}A_{ds}{}^mC_{ds}{}^mC_{ds}{}^mC_{ds}$ $^mC_{ds}{}^mC_{ds}{}^mC_{ds}A_{ks}G_{ks}A_k$ | 82 | 3383 |
| 1129744 | N/A | N/A | 2082 | 2097 | $T_{ks}G_{ks}G_{ks}A_{ds}{}^mC_{ds}{}^mC_{ds}T_{ds}T_{ds}T_{ds}A_{ds}A_{ds}$ $G_{ds}A_{ds}T_{ks}G_{ks}{}^mC_k$ | 75 | 3316 |
| 1129864 | N/A | N/A | 3897 | 3912 | $T_{ks}G_{ks}G_{ks}T_{ds}G_{ds}A_{ds}A_{ds}T_{ds}A_{ds}{}^mC_{ds}A_{ds}$ $G_{ds}G_{ds}A_{ks}G_{ks}A_k$ | 74 | 3322 |
| 1129946 | N/A | N/A | 4812 | 4827 | $T_{ks}{}^mC_{ks}{}^mC_{ks}T_{ds}G_{ds}G_{ds}{}^mC_{ds}A_{ds}A_{ds}G_{ds}{}^m$ $C_{ds}{}^mC_{ds}{}^mC_{ds}G_{ks}T_{ks}{}^mC_k$ | 119 | 3478 |
| 1129948 | N/A | N/A | 4840 | 4855 | $A_{ks}T_{ks}{}^mC_{ks}T_{ds}G_{ds}{}^mC_{ds}T_{ds}T_{ds}T_{ds}{}^mC_{ds}{}^m$ $C_{ds}G_{ds}{}^mC_{ds}A_{ks}{}^mC_{ks}T_k$ | 77 | 3630 |
| 1129949 | N/A | N/A | 4844 | 4859 | $T_{ks}{}^mC_{ks}T_{ks}{}^mC_{ds}A_{ds}T_{ds}{}^mC_{ds}T_{ds}G_{ds}{}^mC_{ds}$ $T_{ds}T_{ds}T_{ds}{}^mC_{ks}{}^mC_{ks}G_k$ | 84 | 3706 |
| 1213210 | 1898 | 1913 | 7286 | 7301 | $A_{ks}T_{ks}G_{ks}A_{ds}G_{ds}U_{ys}{}^mC_{ds}{}^mC_{ds}{}^mC_{ds}T_{ds}$ $G_{ds}A_{ds}G_{ds}{}^mC_{ks}A_{ks}A_k$ | 40 | 5023 |
| 1213211 | 1899 | 1914 | 7287 | 7302 | $G_{ks}A_{ks}T_{ks}G_{ds}A_{ds}G_{ys}T_{ds}{}^mC_{ds}{}^mC_{ds}{}^mC_{ds}$ $T_{ds}G_{ds}A_{ds}G_{ks}{}^mC_{ks}A_k$ | 27 | 2537 |
| 1213212 | 1900 | 1915 | 7288 | 7303 | $A_{ks}G_{ks}A_{ks}T_{ds}G_{ds}A_{ys}G_{ds}T_{ds}{}^mC_{ds}{}^mC_{ds}{}^m$ $C_{ds}T_{ds}G_{ds}A_{ks}G_{ks}{}^mC_k$ | 24 | 2614 |
| 1213213 | 1901 | 1916 | 7289 | 7304 | $A_{ks}A_{ks}G_{ks}A_{ds}T_{ds}G_{ys}A_{ds}G_{ds}T_{ds}{}^mC_{ds}{}^m$ $C_{ds}{}^mC_{ds}T_{ds}G_{ks}A_{ks}G_k$ | 19 | 2691 |

TABLE 89-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213214 | 1902 | 1917 | 7290 | 7305 | $A_{ks}A_{ks}A_{ks}G_{ds}A_{ds}U_{ys}G_{ds}A_{ds}G_{ds}T_{ds}{}^mC_{ds}{}^mC_{ds}{}^mC_{ds}T_{ks}G_{ks}A_k$ | 31 | 5024 |
| 1213215 | 1903 | 1918 | 7291 | 7306 | $G_{ks}A_{ks}A_{ks}A_{ds}G_{ds}A_{ys}T_{ds}G_{ds}A_{ds}G_{ds}T_{ds}{}^mC_{ds}{}^mC_{ds}{}^mC_{ks}T_{ks}G_k$ | 23 | 2845 |
| 1213216 | 1904 | 1919 | 7292 | 7307 | $G_{ks}G_{ks}A_{ks}A_{ds}A_{ds}G_{ys}A_{ds}T_{ds}G_{ds}A_{ds}G_{ds}T_{ds}{}^mC_{ds}{}^mC_{ks}{}^mC_{ks}T_k$ | 39 | 2921 |
| 1213217 | 1905 | 1920 | 7293 | 7308 | $G_{ks}G_{ks}G_{ks}A_{ds}A_{ds}A_{ys}G_{ds}A_{ds}T_{ds}G_{ds}A_{ds}G_{ds}T_{ds}{}^mC_{ks}{}^mC_{ks}{}^mC_k$ | 55 | 2997 |
| 1213218 | 1906 | 1921 | 7294 | 7309 | $A_{ks}G_{ks}G_{ks}G_{ds}A_{ds}A_{ys}A_{ds}G_{ds}A_{ds}T_{ds}G_{ds}A_{ds}G_{ds}T_{ks}{}^mC_{ks}{}^mC_k$ | 18 | 3073 |
| 1213219 | 1914 | 1929 | 7302 | 7317 | ${}^mC_{ks}A_{ks}{}^mC_{ks}{}^mC_{ds}A_{ds}A_{ys}G_{ds}G_{ds}A_{ds}G_{ds}G_{ds}G_{ds}A_{ds}A_{ks}A_{ks}G_k$ | 31 | 4954 |
| 1213220 | 1915 | 1930 | 7303 | 7318 | $T_{ks}{}^mC_{ks}A_{ks}{}^mC_{ds}{}^mC_{ds}A_{ys}G_{ds}G_{ds}A_{ds}G_{ds}G_{ds}G_{ds}A_{ds}A_{ks}A_{ks}A_k$ | 9 | 4948 |
| 1213221 | 1916 | 1931 | 7304 | 7319 | $A_{ks}T_{ks}{}^mC_{ks}A_{ds}{}^mC_{ds}C_{ys}A_{ds}G_{ds}G_{ds}A_{ds}G_{ds}G_{ds}G_{ks}A_{ks}A_k$ | 31 | 4966 |
| 1213222 | 1917 | 1932 | 7305 | 7320 | $A_{ks}A_{ks}T_{ks}{}^mC_{ds}A_{ds}C_{ys}{}^mC_{ds}A_{ds}G_{ds}G_{ds}A_{ds}G_{ds}G_{ks}G_{ks}A_k$ | 44 | 4956 |
| 1213223 | 1918 | 1933 | 7306 | 7321 | $G_{ks}A_{ks}A_{ks}T_{ds}{}^mC_{ds}A_{ys}{}^mC_{ds}Ca_{ds}{}^mC_{ds}A_{ds}A_{ds}G_{ds}G_{ds}A_{ds}G_{ks}G_{ks}G_k$ | 28 | 4965 |
| 1213224 | 1919 | 1934 | 7307 | 7322 | $G_{ks}G_{ks}A_{ks}A_{ds}T_{ds}C_{ys}A_{ds}{}^mC_{ds}{}^mC_{ds}A_{ds}A_{ds}G_{ds}G_{ds}A_{ks}G_{ks}G_k$ | 21 | 3226 |
| 1213225 | 1920 | 1935 | 7308 | 7323 | ${}^mC_{ks}G_{ks}G_{ks}A_{ds}A_{ds}U_{ys}{}^mC_{ds}A_{ds}{}^mC_{ds}{}^mC_{ds}A_{ds}A_{ds}G_{ds}G_{ks}A_{ks}G_k$ | 33 | 5025 |
| 1213226 | 1921 | 1936 | 7309 | 7324 | $G_{ks}{}^mC_{ks}G_{ks}G_{ds}A_{ds}A_{ys}T_{ds}{}^mC_{ds}A_{ds}{}^mC_{ds}{}^mC_{ds}A_{ds}A_{ds}G_{ks}G_{ks}A_k$ | 21 | 3379 |
| 1213227 | 1922 | 1937 | 7310 | 7325 | $T_{ks}G_{ks}{}^mC_{ks}G_{ds}G_{ds}A_{ys}A_{ds}T_{ds}{}^mC_{ds}A_{ds}{}^mC_{ds}{}^mC_{ds}A_{ds}A_{ks}G_{ks}G_k$ | 8 | 3455 |
| 1213228 | 1923 | 1938 | 7311 | 7326 | ${}^mC_{ks}T_{ks}G_{ks}{}^mC_{ds}G_{ds}G_{ys}A_{ds}A_{ds}T_{ds}{}^mC_{ds}A_{ds}{}^mC_{ds}{}^mC_{ds}A_{ks}A_{ks}G_k$ | 17 | 3531 |
| 1213229 | 1924 | 1939 | 7312 | 7327 | $A_{ks}{}^mC_{ks}T_{ks}G_{ds}{}^mC_{ds}G_{ys}G_{ds}A_{ds}A_{ds}T_{ds}{}^mC_{ds}A_{ds}{}^mC_{ds}{}^mC_{ks}A_{ks}A_k$ | 12 | 3607 |
| 1213230 | 1925 | 1940 | 7313 | 7328 | ${}^mC_{ks}A_{ks}{}^mC_{ks}T_{ds}G_{ds}C_{ys}G_{ds}G_{ds}A_{ds}A_{ds}T_{ds}{}^mC_{ds}A_{ds}{}^mC_{ks}{}^mC_{ks}A_k$ | 22 | 3683 |
| 1213231 | 1926 | 1941 | 7314 | 7329 | $T_{ks}{}^mC_{ks}A_{ks}{}^mC_{ds}T_{ds}G_{ys}{}^mC_{ds}G_{ds}G_{ds}A_{ds}A_{ds}T_{ds}{}^mC_{ds}A_{ks}{}^mC_{ks}{}^mC_k$ | 23 | 3759 |
| 1213232 | 1927 | 1942 | 7315 | 7330 | ${}^mC_{ks}T_{ks}{}^mC_{ks}A_{ds}{}^mC_{ds}U_{ys}G_{ds}{}^mC_{ds}G_{ds}G_{ds}A_{ds}A_{ds}T_{ds}{}^mC_{ks}A_{ks}{}^mC_k$ | 11 | 5026 |
| 1213233 | 1928 | 1943 | 7316 | 7331 | $T_{ks}{}^mC_{ks}T_{ks}{}^mC_{ds}A_{ds}C_{ys}T_{ds}G_{ds}{}^mC_{ds}G_{ds}G_{ds}A_{ds}A_{ds}T_{ks}{}^mC_{ks}A_k$ | 16 | 3911 |
| 1213234 | 1929 | 1944 | 7317 | 7332 | ${}^mC_{ks}T_{ks}{}^mC_{ks}T_{ds}{}^mC_{ds}A_{ys}{}^mC_{ds}T_{ds}G_{ds}{}^mC_{ds}G_{ds}G_{ds}A_{ds}A_{ks}T_{ks}{}^mC_k$ | 11 | 4971 |
| 1213235 | 1930 | 1945 | 7318 | 7333 | $T_{ks}{}^mC_{ks}T_{ks}{}^mC_{ds}T_{ds}C_{ys}A_{ds}{}^mC_{ds}T_{ds}G_{ds}{}^mC_{ds}G_{ds}G_{ds}A_{ks}A_{ks}T_k$ | 11 | 4955 |
| 1213236 | 1931 | 1946 | 7319 | 7334 | ${}^mC_{ks}T_{ks}{}^mC_{ks}T_{ds}{}^mC_{ds}U_{ys}{}^mC_{ds}A_{ds}{}^mC_{ds}T_{ds}G_{ds}{}^mC_{ds}G_{ds}G_{ks}A_{ks}A_k$ | 34 | 5027 |

TABLE 89-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213237 | 1932 | 1947 | 7320 | 7335 | $A_{ks}{}^mC_{ks}T_{ks}{}^mC_{ds}T_{ds}C_{ys}T_{ds}{}^mC_{ds}A_{ds}{}^mC_{ds}T_{ds}G_{ds}{}^mC_{ds}G_{ks}G_{ks}A_k$ | 20 | 4976 |
| 1213238 | 1933 | 1948 | 7321 | 7336 | ${}^mC_{ks}A_{ks}{}^mC_{ks}T_{ds}{}^mC_{ds}U_{ys}{}^mC_{ds}T_{ds}{}^mC_{ds}A_{ds}{}^mC_{ds}T_{ds}G_{ds}{}^mC_{ks}G_{ks}G_k$ | 26 | 5028 |
| 1213239 | 1934 | 1949 | 7322 | 7337 | ${}^mC_{ks}{}^mC_{ks}A_{ks}{}^mC_{ds}T_{ds}C_{ys}T_{ds}{}^mC_{ds}T_{ds}{}^mC_{ds}A_{ds}{}^mC_{ds}T_{ds}G_{ds}{}^mC_{ks}G_k$ | 18 | 4949 |
| 1213240 | 1935 | 1950 | 7323 | 7338 | $G_{ks}{}^mC_{ks}{}^mC_{ks}A_{ds}{}^mC_{ds}U_{ys}{}^mC_{ds}T_{ds}{}^mC_{ds}T_{ds}{}^mC_{ds}A_{ds}{}^mC_{ds}T_{ks}G_{ks}{}^mC_k$ | 32 | 5029 |
| 1213241 | 1936 | 1951 | 7324 | 7339 | $A_{ks}G_{ks}{}^mC_{ks}{}^mC_{ds}A_{ds}C_{ys}T_{ds}{}^mC_{ds}T_{ds}{}^mC_{ds}T_{ds}{}^mC_{ds}A_{ds}{}^mC_{ks}T_{ks}G_k$ | 28 | 4961 |
| 1213242 | 1937 | 1952 | 7325 | 7340 | ${}^mC_{ks}A_{ks}G_{ks}{}^mC_{ds}{}^mC_{ds}A_{ys}{}^mC_{ds}T_{ds}{}^mC_{ds}T_{ds}{}^mC_{ds}T_{ds}{}^mC_{ds}A_{ks}{}^mC_{ks}T_k$ | 55 | 4972 |
| 1213243 | 2000 | 2015 | 7388 | 7403 | ${}^mC_{ks}G_{ks}{}^mC_{ks}{}^mC_{ds}A_{ds}U_{ys}{}^mC_{ds}{}^mC_{ds}T_{ds}G_{ds}G_{ds}{}^mC_{ds}G_{ds}{}^mC_{ks}G_{ks}G_k$ | 92 | 5030 |
| 1213244 | 2001 | 2016 | 7389 | 7404 | $G_{ks}{}^mC_{ks}G_{ks}{}^mC_{ds}{}^mC_{ds}A_{ys}T_{ds}{}^mC_{ds}{}^mC_{ds}T_{ds}G_{ds}G_{ds}{}^mC_{ds}G_{ks}{}^mC_{ks}G_k$ | 92 | 4964 |
| 1213245 | 2002 | 2017 | 7390 | 7405 | $T_{ks}G_{ks}{}^mC_{ks}G_{ds}{}^mC_{ds}C_{ys}A_{ds}T_{ds}{}^mC_{ds}{}^mC_{ds}T_{ds}G_{ds}G_{ds}{}^mC_{ks}G_{ks}{}^mC_k$ | 71 | 3305 |
| 1213246 | 2003 | 2018 | 7391 | 7406 | ${}^mC_{ks}T_{ks}G_{ks}{}^mC_{ds}G_{ds}C_{ys}{}^mC_{ds}A_{ds}T_{ds}{}^mC_{ds}{}^mC_{ds}T_{ds}G_{ds}G_{ks}{}^mC_{ks}G_k$ | 54 | 3381 |
| 1213247 | 2004 | 2019 | 7392 | 7407 | ${}^mC_{ks}{}^mC_{ks}T_{ks}G_{ds}{}^mC_{ds}G_{ys}{}^mC_{ds}{}^mC_{ds}A_{ds}T_{ds}{}^mC_{ds}{}^mC_{ds}T_{ds}G_{ks}G_{ks}{}^mC_k$ | 54 | 3457 |
| 1213248 | 2005 | 2020 | 7393 | 7408 | $T_{ks}{}^mC_{ks}{}^mC_{ks}T_{ds}G_{ds}C_{ys}G_{ds}{}^mC_{ds}{}^mC_{ds}A_{ds}T_{ds}{}^mC_{ds}{}^mC_{ds}T_{ks}G_{ks}G_k$ | 21 | 3533 |
| 1213249 | 2006 | 2021 | 7394 | 7409 | $T_{ks}T_{ks}{}^mC_{ks}{}^mC_{ds}T_{ds}G_{ys}{}^mC_{ds}G_{ds}{}^mC_{ds}{}^mC_{ds}A_{ds}T_{ds}{}^mC_{ds}{}^mC_{ks}T_{ks}G_k$ | 64 | 3609 |
| 1213250 | 2007 | 2022 | 7395 | 7410 | $G_{ks}T_{ks}T_{ks}{}^mC_{ds}{}^mC_{ds}U_{ys}G_{ds}{}^mC_{ds}G_{ds}{}^mC_{ds}{}^mC_{ds}A_{ds}T_{ds}{}^mC_{ks}{}^mC_{ks}T_k$ | 30 | 5031 |
| 1213251 | 2008 | 2023 | 7396 | 7411 | $A_{ks}G_{ks}T_{ks}T_{ds}{}^mC_{ds}C_{ys}T_{ds}G_{ds}{}^mC_{ds}G_{ds}{}^mC_{ds}{}^mC_{ds}A_{ds}T_{ks}{}^mC_{ks}{}^mC_k$ | 21 | 3761 |
| 1213252 | 2009 | 2024 | 7397 | 7412 | $G_{ks}A_{ks}G_{ks}T_{ds}T_{ds}C_{ys}{}^mC_{ds}T_{ds}G_{ds}{}^mC_{ds}G_{ds}{}^mC_{ds}{}^mC_{ds}A_{ks}T_{ks}{}^mC_k$ | 24 | 3837 |
| 1213253 | 2010 | 2025 | 7398 | 7413 | $T_{ks}G_{ks}A_{ks}G_{ds}T_{ds}U_{ys}{}^mC_{ds}{}^mC_{ds}T_{ds}G_{ds}{}^mC_{ds}G_{ds}{}^mC_{ds}{}^mC_{ks}A_{ks}T_k$ | 17 | 5032 |
| 1213254 | 2011 | 2026 | 7399 | 7414 | $T_{ks}T_{ks}G_{ks}A_{ds}G_{ds}U_{ys}T_{ds}{}^mC_{ds}{}^mC_{ds}T_{ds}G_{ds}{}^mC_{ds}G_{ds}{}^mC_{ks}{}^mC_{ks}A_k$ | 30 | 5033 |
| 1213255 | 2012 | 2027 | 7400 | 7415 | $A_{ks}T_{ks}T_{ks}G_{ds}A_{ds}G_{ys}T_{ds}T_{ds}{}^mC_{ds}{}^mC_{ds}T_{ds}G_{ds}{}^mC_{ds}G_{ks}{}^mC_{ks}{}^mC_k$ | 20 | 2540 |
| 1213256 | 2013 | 2028 | 7401 | 7416 | $T_{ks}A_{ks}T_{ks}T_{ds}G_{ds}A_{ys}G_{ds}T_{ds}T_{ds}{}^mC_{ds}{}^mC_{ds}T_{ds}G_{ds}{}^mC_{ks}G_{ks}{}^mC_k$ | 26 | 2617 |
| 1213257 | 2014 | 2029 | 7402 | 7417 | $T_{ks}T_{ks}A_{ks}T_{ds}T_{ds}G_{ys}A_{ds}G_{ds}T_{ds}T_{ds}{}^mC_{ds}{}^mC_{ds}T_{ds}G_{ks}{}^mC_{ks}G_k$ | 21 | 2694 |
| 1213258 | 2016 | 2031 | 7404 | 7419 | ${}^mC_{ks}T_{ks}T_{ks}T_{ds}A_{ds}U_{ys}T_{ds}G_{ds}A_{ds}G_{ds}T_{ds}T_{ds}{}^mC_{ds}{}^mC_{ks}T_{ks}G_k$ | 19 | 5034 |
| 1213259 | 2017 | 2032 | 7405 | 7420 | $A_{ks}{}^mC_{ks}T_{ks}T_{ds}T_{ds}A_{ys}T_{ds}T_{ds}G_{ds}A_{ds}G_{ds}T_{ds}T_{ds}{}^mC_{ks}{}^mC_{ks}T_k$ | 2 | 2848 |

TABLE 89-continued

Reduction of FXII RNA (Huh7, electroporation, 2000 nM modified oligonucleotide)

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | FXII (%UTC) | SEQ ID NO |
|---|---|---|---|---|---|---|---|
| 1213260 | 2018 | 2033 | 7406 | 7421 | $^mC_{ks}A_{ks}{}^mC_{ks}T_{ds}T_{ds}U_{ys}A_{ds}T_{ds}T_{ds}G_{ds}A_{ds}G_{ds}T_{ds}T_{ks}{}^mC_{ks}{}^mC_k$ | 2 | 5035 |
| 1213261 | 2019 | 2034 | 7407 | 7422 | $G_{ks}{}^mC_{ks}A_{ks}{}^mC_{ds}T_{ds}U_{ys}T_{ds}A_{ds}T_{ds}T_{ds}G_{ds}A_{ds}G_{ds}T_{ks}T_{ks}{}^mC_k$ | 12 | 5036 |
| 1213262 | 2020 | 2035 | 7408 | 7423 | $A_{ks}G_{ks}{}^mC_{ks}A_{ds}{}^mC_{ds}U_{ys}T_{ds}T_{ds}A_{ds}T_{ds}T_{ds}G_{ds}A_{ds}G_{ks}T_{ks}T_k$ | 4 | 5037 |
| 1213263 | 2021 | 2036 | 7409 | 7424 | $A_{ks}A_{ks}G_{ks}{}^mC_{ds}A_{ds}C_{ys}T_{ds}T_{ds}T_{ds}A_{ds}T_{ds}T_{ds}G_{ds}A_{ks}G_{ks}T_k$ | 19 | 3147 |
| 1213264 | 2022 | 2037 | 7410 | 7425 | $A_{ks}A_{ks}A_{ks}G_{ds}{}^mC_{ds}A_{ys}{}^mC_{ds}T_{ds}T_{ds}T_{ds}A_{ds}T_{ds}T_{ds}G_{ks}A_{ks}G_k$ | 11 | 3229 |
| 1213265 | 2023 | 2038 | 7411 | 7426 | $^mC_{ks}A_{ks}A_{ks}A_{ds}G_{ds}C_{ys}A_{ds}{}^mC_{ds}T_{ds}T_{ds}T_{ds}A_{ds}T_{ks}T_{ks}G_{ks}A_k$ | 19 | 3306 |
| 1213266 | 2024 | 2039 | 7412 | 7427 | $T_{ks}{}^mC_{ks}A_{ks}A_{ds}A_{ds}G_{ys}{}^mC_{ds}A_{ds}{}^mC_{ds}T_{ds}T_{ds}T_{ds}A_{ds}T_{ks}T_{ks}G_k$ | 54 | 3382 |
| 1213267 | 2031 | 2046 | 7419 | 7434 | $A_{ks}G_{ks}{}^mC_{ks}A_{ds}T_{ds}U_{ys}T_{ds}T_{ds}{}^mC_{ds}A_{ds}A_{ds}A_{ds}G_{ds}{}^mC_{ks}A_{ks}{}^mC_k$ | 23 | 5038 |
| 1213268 | 2033 | 2048 | 7421 | 7436 | $T_{ks}{}^mC_{ks}A_{ks}G_{ds}{}^mC_{ds}A_{ys}T_{ds}T_{ds}T_{ds}T_{ds}{}^mC_{ds}A_{ds}A_{ds}A_{ks}G_{ks}C_k$ | 20 | 3534 |

Example 5: Dose-Dependent Reduction of Human FXII RNA by Modified Oligonucleotides In Vitro Certain modified oligonucleotides described in the studies above exhibiting significant in vitro inhibition of FXII RNA were selected and tested at various doses in HepG2 cells.

The modified oligonucleotides were tested in a series of experiments using the same culture conditions. The results for each experiment are presented in separate tables shown below. Cultured HepG2 cells at a density of 10,000 cells per well were transfected using lipofectin with modified oligonucleotides diluted to different concentrations as specified in the tables below. After a treatment period of approximately 24 hours, FXII RNA levels were measured as previously described using the Human FXII primer-probe set RTS2976_MGB (forward sequence CCGG-GAGCACACCGTTT, designated herein as SEQ ID NO: 11; reverse sequence GGAATCACCAAGGAGGGAAAG, designated herein as SEQ ID NO: 12; probe sequence CTGAT-TGCTCAGGGACT, designated herein as SEQ ID NO: 13). FXII RNA levels were normalized to total RNA, as measured by RIBOGREEN®. Reduction of FXII RNA is presented in the tables below as percent FXII RNA relative to the amount in untreated control cells (% UTC).

The half maximal inhibitory concentration ($IC_{50}$) of each modified oligonucleotide was calculated using a linear regression on a log/linear plot of the data in excel and is also presented in the tables below.

TABLE 90

Dose-dependent reduction of human FXII RNA by modified oligonucleotides

| Compound Number | FXII (% UTC) | | | | | 150 nM | IC50 (µM) |
|---|---|---|---|---|---|---|---|
| | 5 nM | 9 nM | 19 nM | 38 nM | 75 nM | | |
| 413627 | 74 | 57 | 45 | 30 | 22 | 18 | 0.02 |
| 413631 | 77 | 66 | 46 | 36 | 27 | 11 | 0.02 |
| 413632 | 80 | 64 | 53 | 42 | 27 | 21 | 0.02 |
| 413636 | 87 | 71 | 58 | 44 | 28 | 21 | 0.03 |
| 413637 | 85 | 66 | 56 | 36 | 24 | 15 | 0.02 |
| 413642 | 72 | 57 | 42 | 32 | 17 | 11 | 0.01 |
| 413643 | 75 | 50 | 37 | 25 | 18 | 13 | 0.01 |
| 413644 | 81 | 77 | 54 | 39 | 29 | 18 | 0.03 |
| 413645 | 80 | 69 | 51 | 35 | 28 | 21 | 0.02 |
| 413652 | 77 | 62 | 46 | 32 | 21 | 12 | 0.02 |

Example 6: Dose-Dependent Reduction of Human FXII RNA by Modified Oligonucleotides In Vitro Certain modified oligonucleotides described in the studies above exhibiting significant in vitro inhibition of FXII RNA were selected and tested at various doses in Huh7 cells.

The modified oligonucleotides were tested in a series of experiments using the same culture conditions. The results for each experiment are presented in separate tables shown below. Cultured Huh7 cells at a density of 5,000 cells per well were transfected using oligofectamine with modified oligonucleotides diluted to different concentrations as specified in the tables below. After a treatment period of approximately 24 hours, FXII RNA levels were measured as previously described using the Human FXII primer-probe set RTS2992. FXII RNA levels were normalized to total RNA, as measured by RIBOGREEN®. Reduction of FXII RNA is presented in the tables below as percent FXII RNA relative to the amount in untreated control cells (% UTC).

The half maximal inhibitory concentration (IC$_{50}$) of each modified oligonucleotide was calculated using a linear regression on a log/linear plot of the data in excel and is also presented in the tables below. The symbol "†" indicates that the modified oligonucleotide is complementary to the target transcript within the amplicon region of the primer probe set. In such instances, additional assays using alternative primer probes must be performed to accurately assess the potency and efficacy of such modified oligonucleotides.

TABLE 91

Dose-dependent reduction of human FXII RNA by modified oligonucleotides

| Compound Number | FXII (% UTC) | | | | | IC$_{50}$ μM |
|---|---|---|---|---|---|---|
| | 14 nM | 28 nM | 55 nM | 110 nM | 220 nM | |
| 462145 | 87 | 68 | 48 | 37 | 20 | 0.06 |
| 462147 | 80 | 66 | 43 | 34 | 28 | 0.056 |
| 462176 | 95 | 79 | 67 | 56 | 31 | 0.113 |
| 462183 | 76 | 64 | 52 | 39 | 24 | 0.058 |
| 462189 | 56 | 60 | 37 | 25 | 22 | 0.028 |
| 462190 | 72 | 67 | 52 | 34 | 26 | 0.056 |
| 462192 | 53 | 44 | 32 | 15 | 22 | 0.015 |
| 462193 | 86 | 75 | 48 | 43 | 27 | 0.072 |
| 462195 | 50 | 42 | 35 | 19 | 23 | 0.013 |
| 462196 | 53 | 31 | 36 | 17 | 19 | 0.012 |
| 462197 | 46 | 40 | 31 | 17 | 15 | <14 nM |
| 462198 | 42 | 34 | 32 | 27 | 19 | <14 nM |

TABLE 92

Dose-dependent reduction of human FXII RNA by modified oligonucleotides

| Compound Number | FXII (% UTC) | | | | | IC$_{50}$ μM |
|---|---|---|---|---|---|---|
| | 14 nM | 28 nM | 55 nM | 110 nM | 220 nM | |
| 462072 | 80 | 55 | 40 | 26 | 12 | 0.041 |
| 462073 | 81 | 47 | 30 | 22 | 23 | 0.035 |
| 462098 | 89 | 89 | 57 | 38 | 19 | 0.075 |
| 462107 | 90 | 88 | 54 | 58 | 32 | 0.109 |
| 462131 | 69 | 61 | 68 | 42 | 34 | 0.08 |
| 462188 | 95 | 84 | 52 | 46 | 41 | 0.106 |
| 462194 | 73 | 63 | 50 | 40 | 49 | 0.087 |
| 462199 | 50 | 46 | 44 | 28 | 31 | 0.016 |
| 462064† | 73 | 62 | 32 | 16 | 13 | N/A |
| 462065† | 66 | 48 | 41 | 13 | 4 | N/A |
| 462068† | 56 | 52 | 29 | 15 | 8 | N/A |
| 462069† | 81 | 57 | 53 | 21 | 10 | N/A |

Example 7: Dose-Dependent Reduction of Human FXII RNA by Modified Oligonucleotides In Vitro Certain modified oligonucleotides described in the studies above exhibiting significant in vitro inhibition of FXII RNA were selected and tested at various doses in Huh7 cells.

The modified oligonucleotides were tested in a series of experiments using the same culture conditions. The results for each experiment are presented in separate tables shown below. Cultured Huh7 cells at a density of 20,000 cells per well were transfected using electroporation with modified oligonucleotides diluted to different concentrations as specified in the tables below. After a treatment period of approximately 24 hours, FXII RNA levels were measured as previously described using the Human FXII primer-probe set RTS40528. FXII RNA levels were normalized to total RNA, as measured by RIBOGREEN®. Reduction of FXII RNA is presented in the tables below as percent FXII RNA relative to the amount in untreated control cells (% UTC).

The half maximal inhibitory concentration (IC$_{50}$) of each modified oligonucleotide was calculated using a linear regression on a log/linear plot of the data in excel and is also presented in the tables below.

TABLE 93

Dose-dependent reduction of human FXII RNA by modified oligonucleotides

| Compound Number | FXII (% UTC) | | | | IC$_{50}$ μM |
|---|---|---|---|---|---|
| | 47 nM | 188 nM | 750 nM | 3000 nM | |
| 1128754 | 94 | 82 | 66 | 37 | 1.6 |
| 1128802 | 81 | 54 | 38 | 16 | 0.3 |
| 1128835 | 92 | 83 | 57 | 37 | 1.3 |
| 1128873 | 91 | 75 | 63 | 42 | 1.8 |
| 1128874 | 93 | 67 | 41 | 17 | 0.5 |
| 1128875 | 93 | 76 | 60 | 36 | 1.3 |
| 1129015 | 93 | 71 | 44 | 30 | 0.7 |
| 1129094 | 81 | 66 | 42 | 24 | 0.5 |
| 1129114 | 92 | 64 | 50 | 23 | 0.6 |
| 1129294 | 86 | 55 | 55 | 30 | 0.6 |
| 1129473 | 84 | 63 | 37 | 22 | 0.4 |
| 1129475 | 76 | 50 | 28 | 15 | 0.2 |
| 1129476 | 70 | 44 | 40 | 22 | 0.2 |
| 1129493 | 81 | 48 | 23 | 11 | 0.2 |
| 1129494 | 87 | 85 | 45 | 26 | 0.7 |
| 1129533 | 65 | 54 | 21 | 21 | 0.2 |
| 1129534 | 77 | 46 | 36 | 17 | 0.2 |
| 1129535 | 80 | 64 | 32 | 25 | 0.4 |
| 1129536 | 85 | 47 | 30 | 25 | 0.3 |

TABLE 94

Dose-dependent reduction of human FXII RNA by modified oligonucleotides

| Compound Number | FXII (% UTC) | | | | IC$_{50}$ μM |
|---|---|---|---|---|---|
| | 47 nM | 188 nM | 750 nM | 3000 nM | |
| 1128795 | 84 | 63 | 38 | 28 | 0.5 |
| 1128796 | 66 | 50 | 21 | 12 | 0.2 |
| 1128797 | 86 | 71 | 37 | 24 | 0.5 |
| 1128802 | 86 | 62 | 37 | 15 | 0.4 |
| 1128836 | 80 | 67 | 44 | 30 | 0.6 |
| 1128878 | 85 | 74 | 50 | 27 | 0.7 |
| 1128958 | 92 | 94 | 74 | 42 | >3.0 |
| 1129058 | 94 | 54 | 45 | 28 | 0.5 |
| 1129136 | 77 | 68 | 62 | 32 | 1.0 |
| 1129477 | 96 | 56 | 39 | 26 | 0.5 |
| 1129478 | 98 | 65 | 37 | 22 | 0.5 |
| 1129496 | 88 | 76 | 70 | 45 | 2.8 |
| 1129497 | 100 | 75 | 43 | 17 | 0.6 |
| 1129498 | 80 | 69 | 43 | 32 | 0.6 |
| 1129499 | 77 | 65 | 31 | 26 | 0.4 |
| 1129516 | 82 | 43 | 38 | 32 | 0.3 |
| 1129537 | 69 | 57 | 21 | 16 | 0.2 |
| 1129538 | 55 | 38 | 18 | 11 | 0.1 |
| 1129539 | 45 | 22 | 14 | 7 | <0.04 |

TABLE 95

Dose-dependent reduction of human FXII RNA by modified oligonucleotides

| Compound Number | FXII (% UTC) 47 nM | 188 nM | 750 nM | 3000 nM | IC$_{50}$ µM |
|---|---|---|---|---|---|
| 1128738 | 88 | 72 | 56 | 32 | 0.9 |
| 1128799 | 92 | 68 | 58 | 22 | 0.7 |
| 1128802 | 104 | 73 | 40 | 23 | 0.6 |
| 1128879 | 81 | 76 | 33 | 23 | 0.5 |
| 1128880 | 97 | 72 | 39 | 25 | 0.6 |
| 1128980 | 112 | 85 | 62 | 42 | 1.7 |
| 1129000 | 118 | 97 | 65 | 38 | 1.7 |
| 1129020 | 106 | 92 | 52 | 35 | 1.2 |
| 1129039 | 84 | 63 | 45 | 24 | 0.5 |
| 1129119 | 108 | 77 | 65 | 35 | 1.3 |
| 1129139 | 78 | 58 | 44 | 19 | 0.4 |
| 1129180 | 97 | 88 | 40 | 34 | 0.9 |
| 1129420 | 88 | 69 | 47 | 33 | 0.8 |
| 1129460 | 86 | 60 | 39 | 24 | 0.4 |
| 1129479 | 98 | 58 | 36 | 17 | 0.4 |
| 1129481 | 79 | 63 | 42 | 31 | 0.5 |
| 1129500 | 82 | 64 | 44 | 18 | 0.4 |
| 1129540 | 48 | 28 | 19 | 11 | <0.04 |
| 1129541 | 64 | 36 | 17 | 10 | 0.1 |

TABLE 96

Dose-dependent reduction of human FXII RNA by modified

| Compound Number | FXII (% UTC) 47 nM | 188 nM | 750 nM | 3000 nM | IC$_{50}$ µM |
|---|---|---|---|---|---|
| 1128762 | 73 | 63 | 37 | 21 | 0.3 |
| 1128801 | 99 | 56 | 35 | 18 | 0.4 |
| 1128802 | 97 | 65 | 37 | 14 | 0.4 |
| 1128821 | 78 | 55 | 57 | 21 | 0.5 |
| 1128841 | 106 | 91 | 73 | 36 | 1.9 |
| 1128881 | 80 | 66 | 42 | 27 | 0.5 |
| 1129022 | 122 | 100 | 80 | 46 | 2.9 |
| 1129043 | 112 | 98 | 57 | 31 | 1.2 |
| 1129142 | 98 | 79 | 48 | 20 | 0.7 |
| 1129221 | 63 | 49 | 28 | 14 | 0.1 |
| 1129423 | 99 | 72 | 36 | 29 | 0.6 |
| 1129441 | 78 | 45 | 27 | 12 | 0.2 |
| 1129462 | 95 | 70 | 64 | 25 | 0.9 |
| 1129482 | 84 | 63 | 70 | 29 | 1.0 |
| 1129483 | 69 | 33 | 14 | 8 | 0.1 |
| 1129501 | 95 | 66 | 35 | 14 | 0.4 |
| 1129502 | 93 | 73 | 49 | 19 | 0.6 |
| 1129542 | 66 | 34 | 24 | 12 | 0.1 |
| 1129543 | 89 | 44 | 30 | 17 | 0.3 |

TABLE 97

Dose-dependent reduction of human FXII RNA by modified oligonucleotides

| Compound Number | FXII (% UTC) 47 nM | 188 nM | 750 nM | 3000 nM | IC$_{50}$ µM |
|---|---|---|---|---|---|
| 1128763 | 80 | 57 | 37 | 22 | 0.3 |
| 1128764 | 73 | 42 | 26 | 12 | 0.2 |
| 1128802 | 68 | 58 | 32 | 19 | 0.2 |
| 1129044 | 88 | 69 | 43 | 26 | 0.6 |
| 1129065 | 85 | 60 | 36 | 15 | 0.4 |
| 1129084 | 87 | 70 | 47 | 23 | 0.6 |
| 1129104 | 103 | 87 | 54 | 40 | 1.4 |
| 1129143 | 81 | 65 | 40 | 24 | 0.4 |
| 1129144 | 98 | 68 | 45 | 30 | 0.7 |
| 1129424 | 95 | 59 | 39 | 24 | 0.5 |
| 1129445 | 83 | 54 | 40 | 20 | 0.4 |
| 1129484 | 61 | 40 | 22 | 15 | 0.1 |
| 1129485 | 55 | 39 | 21 | 10 | 0.1 |
| 1129486 | 57 | 38 | 21 | 9 | 0.1 |
| 1129503 | 114 | 110 | 86 | 43 | >3.0 |
| 1129504 | 100 | 71 | 43 | 26 | 0.7 |
| 1129544 | 82 | 46 | 33 | 18 | 0.3 |
| 1129545 | 70 | 54 | 32 | 15 | 0.2 |
| 1129864 | 89 | 66 | 53 | 31 | 0.8 |

TABLE 98

Dose-dependent reduction of human FXII RNA by modified oligonucleotides

| Compound Number | FXII (% UTC) 47 nM | 188 nM | 750 nM | 3000 nM | IC$_{50}$ µM |
|---|---|---|---|---|---|
| 1128747 | 99 | 95 | 60 | 38 | 1.6 |
| 1128765 | 76 | 48 | 29 | 11 | 0.2 |
| 1128766 | 49 | 52 | 36 | 17 | 0.1 |
| 1128768 | 65 | 53 | 34 | 25 | 0.2 |
| 1128802 | 83 | 55 | 41 | 15 | 0.3 |
| 1128808 | 98 | 85 | 67 | 31 | 1.4 |
| 1128848 | 79 | 59 | 47 | 18 | 0.4 |
| 1129227 | 81 | 60 | 39 | 31 | 0.5 |
| 1129287 | 72 | 72 | 34 | 18 | 0.3 |
| 1129407 | 59 | 51 | 44 | 27 | 0.2 |
| 1129408 | 61 | 58 | 40 | 25 | 0.2 |
| 1129426 | 81 | 68 | 46 | 19 | 0.5 |
| 1129466 | 84 | 55 | 48 | 29 | 0.5 |
| 1129487 | 71 | 56 | 23 | 35 | 0.3 |
| 1129488 | 59 | 49 | 26 | 11 | 0.1 |
| 1129489 | 58 | 42 | 16 | 15 | 0.1 |
| 1129526 | 96 | 79 | 64 | 33 | 1.3 |
| 1129527 | 69 | 58 | 31 | 19 | 0.2 |
| 1129948 | 84 | 65 | 45 | 27 | 0.5 |

TABLE 99

Dose-dependent reduction of human FXII RNA by modified oligonucleotides

| Compound Number | FXII (% UTC) 47 nM | 188 nM | 750 nM | 3000 nM | IC$_{50}$ µM |
|---|---|---|---|---|---|
| 1128769 | 49 | 37 | 24 | 19 | <0.04 |
| 1128802 | 67 | 49 | 25 | 12 | 0.2 |
| 1128810 | 75 | 77 | 43 | 29 | 0.6 |
| 1128830 | 117 | 72 | 33 | 29 | 0.7 |
| 1128870 | 49 | 36 | 38 | 18 | <0.04 |
| 1129051 | 88 | 71 | 52 | 33 | 0.9 |
| 1129092 | 86 | 66 | 43 | 27 | 0.6 |
| 1129211 | 76 | 54 | 57 | 19 | 0.4 |
| 1129409 | 60 | 32 | 34 | 13 | 0.1 |
| 1129472 | 70 | 35 | 42 | 18 | 0.2 |
| 1129490 | 58 | 29 | 13 | 6 | 0.1 |
| 1129491 | 52 | 31 | 22 | 7 | <0.04 |
| 1129492 | 62 | 26 | 10 | 9 | 0.1 |
| 1129510 | 55 | 42 | 42 | 14 | 0.1 |
| 1129529 | 73 | 50 | 44 | 21 | 0.3 |

TABLE 99-continued

Dose-dependent reduction of human FXII RNA by modified oligonucleotides

| Compound Number | FXII (% UTC) 47 nM | 188 nM | 750 nM | 3000 nM | IC$_{50}$ µM |
|---|---|---|---|---|---|
| 1129530 | 66 | 34 | 24 | 9 | 0.1 |
| 1129531 | 48 | 42 | 32 | 10 | <0.04 |
| 1129532 | 55 | 27 | 13 | 8 | <0.04 |
| 1129949 | 84 | 98 | 56 | 42 | 2.0 |

TABLE 100

Dose-dependent reduction of human FXII RNA by modified oligonucleotides

| Compound Number | FXII (% UTC) 78 nM | 313 nM | 1250 nM | 5000 nM | IC$_{50}$ µM |
|---|---|---|---|---|---|
| 1130826 | 88 | 63 | 43 | 14 | 0.7 |
| 1130828 | 73 | 56 | 37 | 23 | 0.5 |
| 1130871 | 65 | 28 | 19 | 18 | 0.1 |
| 1130883 | 94 | 57 | 44 | 21 | 0.8 |
| 1131023 | 89 | 64 | 42 | 22 | 0.8 |
| 1131024 | 92 | 68 | 43 | 31 | 1.1 |
| 1131247 | 107 | 105 | 54 | 34 | 2.3 |
| 1131416 | 81 | 67 | 39 | 23 | 0.7 |
| 1131640 | 97 | 64 | 45 | 20 | 0.9 |
| 1131695 | 78 | 54 | 33 | 21 | 0.5 |
| 1131696 | 100 | 45 | 34 | 14 | 0.6 |
| 1131697 | 70 | 46 | 31 | 7 | 0.3 |
| 1131724 | 96 | 60 | 36 | 37 | 1.0 |
| 1131725 | 83 | 64 | 45 | 17 | 0.7 |
| 1131751 | 88 | 54 | 34 | 15 | 0.5 |
| 1131752 | 75 | 49 | 40 | 21 | 0.5 |
| 1131753 | 61 | 38 | 20 | 8 | 0.1 |
| 1131891 | 80 | 46 | 37 | 13 | 0.4 |
| 1131892 | 77 | 84 | 61 | 33 | 2.1 |

TABLE 101

Dose-dependent reduction of human FXII RNA by modified oligonucleotides

| Compound Number | FXII (% UTC) 78 nM | 313 nM | 1250 nM | 5000 nM | IC$_{50}$ µM |
|---|---|---|---|---|---|
| 1130829 | 78 | 62 | 28 | 18 | 0.5 |
| 1130830 | 92 | 49 | 26 | 25 | 0.6 |
| 1130871 | 75 | 53 | 27 | 15 | 0.4 |
| 1130914 | 100 | 86 | 73 | 43 | 4.2 |
| 1130970 | 88 | 84 | 63 | 39 | 3.0 |
| 1130997 | 87 | 73 | 57 | 24 | 1.2 |
| 1130998 | 92 | 76 | 61 | 45 | 3.4 |
| 1131025 | 71 | 76 | 42 | 20 | 0.7 |
| 1131053 | 84 | 85 | 55 | 32 | 1.8 |
| 1131473 | 90 | 74 | 35 | 19 | 0.8 |
| 1131474 | 94 | 77 | 55 | 36 | 1.9 |
| 1131641 | 82 | 69 | 43 | 23 | 0.8 |
| 1131671 | 61 | 49 | 35 | 21 | 0.3 |
| 1131698 | 88 | 87 | 48 | 14 | 1.0 |
| 1131699 | 73 | 43 | 24 | 11 | 0.3 |
| 1131754 | 48 | 22 | 14 | 7 | <0.1 |
| 1131755 | 61 | 41 | 18 | 5 | 0.2 |
| 1132453 | 96 | 74 | 55 | 23 | 1.2 |
| 1132537 | 88 | 65 | 46 | 22 | 0.9 |

TABLE 102

Dose-dependent reduction of human FXII RNA by modified oligonucleotides

| Compound Number | FXII (% UTC) 78 nM | 313 nM | 1250 nM | 5000 nM | IC$_{50}$ µM |
|---|---|---|---|---|---|
| 1130831 | 68 | 50 | 20 | 11 | 0.3 |
| 1130832 | 77 | 55 | 35 | 21 | 0.5 |
| 1130858 | 80 | 88 | 55 | 35 | 2.0 |
| 1130871 | 72 | 37 | 24 | 16 | 0.2 |
| 1130973 | 85 | 61 | 45 | 22 | 0.8 |
| 1131084 | 85 | 95 | 49 | 27 | 1.5 |
| 1131198 | 85 | 68 | 38 | 24 | 0.8 |
| 1131223 | 91 | 53 | 41 | 16 | 0.6 |
| 1131309 | 87 | 64 | 34 | 42 | 1.1 |
| 1131310 | 86 | 62 | 51 | 28 | 1.1 |
| 1131700 | 67 | 45 | 29 | 9 | 0.2 |
| 1131701 | 55 | 48 | 26 | 5 | 0.2 |
| 1131702 | 96 | 42 | 16 | 9 | 0.4 |
| 1131730 | 93 | 64 | 38 | 32 | 1.0 |
| 1131756 | 39 | 13 | 13 | 5 | 0.1 |
| 1131757 | 54 | 27 | 14 | 10 | 0.1 |
| 1131758 | 73 | 58 | 25 | 9 | 0.4 |
| 1132455 | 88 | 74 | 59 | 33 | 1.8 |
| 1132651 | 76 | 76 | 55 | 38 | 2.0 |

TABLE 103

Dose-dependent reduction of human FXII RNA by modified oligonucleotides

| Compound Number | FXII (% UTC) 78 nM | 313 nM | 1250 nM | 5000 nM | IC$_{50}$ µM |
|---|---|---|---|---|---|
| 1130871 | 65 | 52 | 30 | 22 | 0.3 |
| 1130894 | 72 | 66 | 50 | 38 | 1.3 |
| 1131006 | 100 | 92 | 68 | 47 | 4.8 |
| 1131146 | 84 | 91 | 56 | 37 | 2.4 |
| 1131199 | 76 | 75 | 54 | 22 | 1.0 |
| 1131255 | 83 | 65 | 53 | 19 | 0.9 |
| 1131314 | 77 | 71 | 61 | 34 | 1.9 |
| 1131337 | 70 | 81 | 57 | 36 | 2.1 |
| 1131423 | 74 | 64 | 40 | 21 | 0.6 |
| 1131426 | 98 | 87 | 81 | 44 | >5.0 |
| 1131481 | 91 | 66 | 43 | 28 | 1.0 |
| 1131593 | 66 | 51 | 37 | 26 | 0.4 |
| 1131673 | 93 | 63 | 45 | 35 | 1.2 |
| 1131704 | 96 | 45 | 39 | 19 | 0.6 |
| 1131706 | 93 | 80 | 62 | 40 | 2.7 |
| 1131759 | 62 | 67 | 40 | 23 | 0.5 |
| 1131760 | 87 | 71 | 55 | 40 | 2.0 |
| 1131761 | 89 | 75 | 60 | 29 | 1.6 |
| 1132797 | 100 | 75 | 77 | 54 | >5.0 |

TABLE 104

Dose-dependent reduction of human FXII RNA by modified oligonucleotides

| Compound Number | FXII (% UTC) 78 nM | 313 nM | 1250 nM | 5000 nM | IC$_{50}$ µM |
|---|---|---|---|---|---|
| 1130839 | 141 | 86 | 58 | 32 | 2.0 |
| 1130871 | 57 | 34 | 22 | 9 | 0.1 |
| 1130920 | 89 | 83 | 76 | 23 | 2.1 |
| 1130952 | 94 | 71 | 49 | 29 | 1.3 |
| 1130979 | 81 | 84 | 68 | 34 | 2.7 |
| 1131007 | 104 | 73 | 61 | 43 | 2.6 |
| 1131120 | 108 | 68 | 44 | 42 | 1.6 |

TABLE 104-continued

Dose-dependent reduction of human FXII RNA by modified oligonucleotides

| Compound Number | 78 nM | 313 nM | 1250 nM | 5000 nM | IC$_{50}$ μM |
|---|---|---|---|---|---|
| 1131204 | 71 | 50 | 27 | 26 | 0.4 |
| 1131340 | 92 | 78 | 63 | 27 | 1.7 |
| 1131344 | 88 | 69 | 44 | 35 | 1.2 |
| 1131368 | 87 | 79 | 63 | 41 | 3.0 |
| 1131424 | 74 | 79 | 47 | 33 | 1.3 |
| 1131428 | 99 | 64 | 47 | 21 | 0.9 |
| 1131480 | 82 | 60 | 57 | 17 | 0.8 |
| 1131484 | 85 | 67 | 46 | 24 | 0.9 |
| 1131595 | 67 | 48 | 35 | 23 | 0.3 |
| 1131736 | 79 | 78 | 40 | 14 | 0.7 |
| 1131763 | 49 | 38 | 22 | 15 | <0.1 |
| 1131764 | 59 | 44 | 25 | 15 | 0.2 |

TABLE 105

Dose-dependent reduction of human FXII RNA by modified oligonucleotides

| Compound Number | 78 nM | 313 nM | 1250 nM | 5000 nM | IC$_{50}$ μM |
|---|---|---|---|---|---|
| 1130840 | 76 | 69 | 46 | 27 | 0.9 |
| 1130868 | 54 | 49 | 33 | 13 | 0.2 |
| 1130870 | 76 | 57 | 48 | 18 | 0.6 |
| 1130871 | 72 | 41 | 29 | 18 | 0.3 |
| 1130925 | 70 | 60 | 31 | 19 | 0.4 |
| 1130981 | 86 | 62 | 42 | 23 | 0.8 |
| 1130983 | 88 | 62 | 43 | 29 | 0.9 |
| 1131009 | 92 | 91 | 50 | 35 | 1.9 |
| 1131036 | 83 | 72 | 59 | 32 | 1.7 |
| 1131095 | 74 | 59 | 31 | 34 | 0.6 |
| 1131375 | 91 | 89 | 67 | 46 | 4.9 |
| 1131429 | 75 | 61 | 45 | 24 | 0.7 |
| 1131624 | 72 | 56 | 49 | 22 | 0.6 |
| 1131625 | 61 | 72 | 43 | 22 | 0.6 |
| 1131627 | 91 | 58 | 42 | 20 | 0.7 |
| 1131711 | 94 | 100 | 53 | 30 | 1.9 |
| 1131737 | 79 | 62 | 42 | 19 | 0.6 |
| 1131739 | 94 | 80 | 58 | 31 | 1.8 |
| 1131767 | 82 | 50 | 42 | 34 | 0.8 |

TABLE 106

Dose-dependent reduction of human FXII RNA by modified oligonucleotides

| Compound Number | 78 nM | 313 nM | 1250 nM | 5000 nM | IC$_{50}$ μM |
|---|---|---|---|---|---|
| 1130871 | 59 | 39 | 23 | 11 | 0.1 |
| 1130872 | 77 | 59 | 31 | 38 | 0.7 |
| 1130900 | 57 | 50 | 51 | 23 | 0.3 |
| 1130928 | 76 | 53 | 57 | 55 | >5.0 |
| 1131013 | 75 | 58 | 25 | 16 | 0.4 |
| 1131040 | 61 | 57 | 43 | 23 | 0.4 |
| 1131096 | 82 | 70 | 39 | 35 | 1.1 |
| 1131208 | 102 | 80 | 57 | 33 | 1.9 |
| 1131347 | 86 | 67 | 63 | 31 | 1.7 |
| 1131348 | 74 | 67 | 42 | 29 | 0.8 |
| 1131432 | 61 | 45 | 34 | 22 | 0.2 |
| 1131433 | 91 | 63 | 28 | 20 | 0.6 |
| 1131599 | 70 | 61 | 37 | 23 | 0.5 |
| 1131601 | 88 | 58 | 49 | 34 | 1.1 |
| 1131630 | 93 | 54 | 42 | 20 | 0.7 |
| 1131712 | 73 | 54 | 32 | 22 | 0.4 |
| 1131713 | 101 | 66 | 33 | 27 | 0.9 |
| 1132188 | 89 | 75 | 69 | 41 | 3.4 |
| 1132271 | 80 | 76 | 68 | 48 | >5.0 |

TABLE 107

Dose-dependent reduction of human FXII RNA by modified oligonucleotides

| Compound Number | 78 nM | 313 nM | 1250 nM | 5000 nM | IC$_{50}$ μM |
|---|---|---|---|---|---|
| 1130763 | 91 | 71 | 50 | 44 | 2.1 |
| 1130846 | 64 | 56 | 42 | 37 | 0.6 |
| 1130871 | 63 | 41 | 19 | 16 | 0.2 |
| 1130874 | 69 | 74 | 40 | 24 | 0.7 |
| 1130903 | 119 | 90 | 65 | 35 | 2.4 |
| 1130987 | 66 | 39 | 27 | 17 | 0.2 |
| 1131015 | 80 | 84 | 65 | 33 | 2.4 |
| 1131126 | 66 | 77 | 51 | 28 | 1.1 |
| 1131155 | 87 | 79 | 61 | 31 | 1.9 |
| 1131350 | 79 | 66 | 46 | 30 | 1.0 |
| 1131434 | 83 | 56 | 40 | 23 | 0.6 |
| 1131462 | 73 | 73 | 56 | 34 | 1.6 |
| 1131463 | 98 | 104 | 77 | 45 | >5.0 |
| 1131686 | 71 | 53 | 48 | 29 | 0.7 |
| 1131687 | 78 | 60 | 42 | 29 | 0.8 |
| 1131688 | 74 | 57 | 34 | 23 | 0.5 |
| 1131716 | 100 | 58 | 43 | 23 | 0.9 |
| 1131744 | 78 | 67 | 32 | 58 | 2.2 |
| 1132387 | 104 | 96 | 77 | 51 | >5.0 |

TABLE 108

Dose-dependent reduction of human FXII RNA by modified oligonucleotides

| Compound Number | 78 nM | 313 nM | 1250 nM | 5000 nM | IC$_{50}$ μM |
|---|---|---|---|---|---|
| 1130871 | 69.8 | 45.8 | 26.5 | 23.1 | 0.3 |
| 1130988 | 76.2 | 74.4 | 49.9 | 24.9 | 1.0 |
| 1131018 | 92.2 | 62.8 | 43.5 | 20.2 | 0.8 |
| 1131019 | 90.5 | 78.4 | 36.3 | 20.4 | 0.9 |
| 1131100 | 90.3 | 69.0 | 47.3 | 29.5 | 1.2 |
| 1131242 | 85.1 | 59.3 | 45.8 | 19.2 | 0.7 |
| 1131243 | 84.3 | 70.1 | 49.8 | 23.1 | 1.0 |
| 1131409 | 85.6 | 82.4 | 46.3 | 26.1 | 1.2 |
| 1131411 | 95.8 | 87.5 | 48.1 | 39.4 | 2.0 |
| 1131605 | 77.7 | 80.7 | 44.5 | 25.8 | 1.0 |
| 1131635 | 80.9 | 50.2 | 44.3 | 28.5 | 0.7 |
| 1131663 | 80.0 | 74.7 | 44.0 | 17.3 | 0.8 |
| 1131689 | 92.7 | 72.3 | 64.7 | 27.1 | 1.6 |
| 1131691 | 76.5 | 55.0 | 35.1 | 16.4 | 0.5 |
| 1131717 | 85.2 | 58.3 | 39.3 | 23.6 | 0.7 |
| 1131718 | 94.4 | 63.5 | 47.4 | 33.6 | 1.2 |
| 1131745 | 73.3 | 49.4 | 32.1 | 25.7 | 0.4 |
| 1131746 | 81.7 | 54.2 | 39.0 | 15.6 | 0.5 |
| 1131747 | 69.9 | 48.1 | 33.6 | 18.1 | 0.3 |

TABLE 109

Dose-dependent reduction of human FXII RNA by modified oligonucleotides

| Compound Number | FXII (% UTC) 78 nM | 313 nM | 1250 nM | 5000 nM | $IC_{50}$ µM |
|---|---|---|---|---|---|
| 1130824 | 86 | 73 | 56 | 29 | 1.4 |
| 1130825 | 111 | 78 | 49 | 42 | 2.0 |
| 1130871 | 76 | 39 | 26 | 17 | 0.3 |
| 1130908 | 76 | 65 | 51 | 28 | 1.0 |
| 1130938 | 97 | 77 | 57 | 19 | 1.2 |
| 1131020 | 79 | 62 | 47 | 15 | 0.6 |
| 1131021 | 77 | 72 | 51 | 27 | 1.1 |
| 1131216 | 78 | 87 | 56 | 55 | >5.0 |
| 1131357 | 90 | 84 | 64 | 38 | 2.8 |
| 1131608 | 100 | 70 | 51 | 30 | 1.4 |
| 1131692 | 70 | 63 | 33 | 22 | 0.5 |
| 1131693 | 63 | 41 | 29 | 18 | 0.2 |
| 1131694 | 79 | 57 | 21 | 16 | 0.4 |
| 1131720 | 92 | 63 | 72 | 27 | 1.7 |
| 1131721 | 92 | 85 | 67 | 40 | 3.3 |
| 1131722 | 106 | 95 | 56 | 40 | 2.6 |
| 1131748 | 75 | 57 | 53 | 20 | 0.7 |
| 1131749 | 90 | 66 | 47 | 25 | 1.0 |
| 1132505 | 85 | 78 | 50 | 36 | 1.7 |

TABLE 110

Dose-dependent reduction of human FXII RNA by modified oligonucleotides

| Compound Number | FXII (% UTC) 78 nM | 313 nM | 1250 nM | 5000 nM | $IC_{50}$ µM |
|---|---|---|---|---|---|
| 413643 | 71 | 57 | 28 | 26 | 0.4 |
| 462073 | 94 | 68 | 30 | 23 | 0.8 |
| 462192 | 64 | 50 | 41 | 16 | 0.3 |
| 626671 | 101 | 98 | 74 | 45 | >5.0 |
| 1124324 | 97 | 87 | 102 | 52 | >5.0 |
| 1124408 | 103 | 74 | 50 | 22 | 1.2 |
| 1124489 | 86 | 84 | 75 | 56 | >5.0 |
| 1124490 | 98 | 83 | 58 | 44 | 3.0 |
| 1124620 | 91 | 74 | 55 | 33 | 1.6 |
| 1124621 | 93 | 74 | 45 | 21 | 1.0 |
| 1124677 | 112 | 83 | 66 | 48 | 3.8 |
| 1124813 | 102 | 86 | 55 | 39 | 2.3 |
| 1124996 | 93 | 62 | 49 | 32 | 1.2 |
| 1125047 | 72 | 63 | 59 | 24 | 1.0 |
| 1125074 | 92 | 70 | 56 | 39 | 2.0 |
| 1125075 | 100 | 94 | 58 | 51 | >5.0 |
| 1125101 | 120 | 108 | 50 | 43 | 2.7 |
| 1125102 | 105 | 61 | 57 | 45 | 2.3 |
| 1125570 | 115 | 113 | 115 | 81 | >5.0 |

TABLE 111

Dose-dependent reduction of human FXII RNA by modified oligonucleotides

| Compound Number | FXII (% UTC) 78 nM | 313 nM | 1250 nM | 5000 nM | $IC_{50}$ µM |
|---|---|---|---|---|---|
| 413644 | 129 | 90 | 69 | 36 | 2.6 |
| 462073 | 117 | 78 | 46 | 36 | 1.6 |
| 1124222 | 490 | 74 | 81 | 51 | >5.0 |
| 1124223 | 93 | 84 | 66 | 51 | >5.0 |
| 1124328 | 129 | 93 | 82 | 42 | 4.0 |
| 1124384 | 80 | 101 | 79 | 59 | >5.0 |
| 1124491 | 76 | 78 | 52 | 35 | 1.6 |
| 1124598 | 100 | 87 | 91 | 51 | >5.0 |
| 1124842 | 105 | 93 | 65 | 56 | >5.0 |
| 1124998 | 122 | 77 | 67 | 41 | 2.7 |
| 1125023 | 96 | 91 | 53 | 36 | 2.1 |
| 1125049 | 105 | 91 | 56 | 43 | 2.7 |
| 1125050 | 100 | 78 | 67 | 29 | 1.9 |
| 1125051 | 80 | 58 | 39 | 19 | 0.6 |
| 1125076 | 103 | 96 | 83 | 51 | >5.0 |
| 1125077 | 106 | 99 | 74 | 42 | 4.4 |
| 1125078 | 94 | 92 | 87 | 40 | >5.0 |
| 1125103 | 99 | 116 | 65 | 37 | 3.5 |
| 1125104 | 115 | 94 | 49 | 55 | 3.5 |

TABLE 112

Dose-dependent reduction of human FXII RNA by modified oligonucleotides

| Compound Number | FXII (% UTC) 63 nM | 250 nM | 1000 nM | 4000 nM | $IC_{50}$ µM |
|---|---|---|---|---|---|
| 1129531 | 78 | 53 | 26 | 11 | 0.3 |
| 1206486 | 82 | 65 | 51 | 31 | 0.9 |
| 1206977 | 92 | 69 | 50 | 23 | 0.8 |
| 1206981 | 79 | 66 | 45 | 25 | 0.7 |
| 1207005 | 67 | 41 | 17 | 13 | 0.2 |
| 1207007 | 51 | 31 | 15 | 6 | <0.1 |
| 1207009 | 90 | 65 | 38 | 26 | 0.7 |
| 1207111 | 87 | 56 | 44 | 22 | 0.6 |
| 1207113 | 92 | 73 | 45 | 26 | 0.9 |
| 1207133 | 72 | 48 | 29 | 18 | 0.3 |
| 1207164 | 77 | 76 | 52 | 36 | 1.3 |
| 1207228 | 87 | 65 | 53 | 37 | 1.2 |
| 1207230 | 106 | 77 | 63 | 60 | >4.0 |
| 1207244 | 91 | 57 | 46 | 24 | 0.7 |
| 1207276 | 63 | 39 | 11 | 11 | 0.1 |
| 1207362 | 75 | 71 | 48 | 20 | 0.6 |
| 1207366 | 94 | 53 | 38 | 24 | 0.6 |
| 1207370 | 68 | 55 | 39 | 21 | 0.3 |
| 1207394 | 61 | 39 | 22 | 11 | 0.1 |

TABLE 113

Dose-dependent reduction of human FXII RNA by modified oligonucleotides

| Compound Number | FXII (% UTC) 63 nM | 250 nM | 1000 nM | 4000 nM | $IC_{50}$ µM |
|---|---|---|---|---|---|
| 1129531 | 92 | 47 | 28 | 14 | 0.4 |
| 1206487 | 82 | 68 | 54 | 29 | 1 |
| 1206497 | 99 | 70 | 58 | 31 | 1.3 |
| 1206970 | 77 | 54 | 35 | 12 | 0.4 |
| 1206978 | 93 | 63 | 35 | 15 | 0.5 |
| 1206986 | 91 | 71 | 52 | 36 | 1.3 |
| 1207010 | 76 | 51 | 17 | 7 | 0.2 |
| 1207106 | 84 | 65 | 49 | 19 | 0.7 |
| 1207125 | 91 | 52 | 28 | 8 | 0.4 |
| 1207159 | 71 | 36 | 14 | 6 | 0.2 |
| 1207190 | 78 | 61 | 59 | 31 | 1 |
| 1207247 | 101 | 70 | 28 | 16 | 0.6 |
| 1207254 | 71 | 49 | 29 | 18 | 0.3 |
| 1207255 | 71 | 49 | 28 | 21 | 0.3 |

TABLE 113-continued

Dose-dependent reduction of human FXII RNA by modified oligonucleotides

| Compound Number | FXII (% UTC) | | | | IC$_{50}$ µM |
|---|---|---|---|---|---|
| | 63 nM | 250 nM | 1000 nM | 4000 nM | |
| 1207271 | 113 | 80 | 55 | 29 | 1.3 |
| 1207278 | 46 | 36 | 11 | 4 | <0.1 |
| 1207279 | 66 | 38 | 23 | 10 | 0.2 |
| 1207358 | 78 | 61 | 43 | 17 | 0.5 |
| 1207367 | 79 | 48 | 30 | 9 | 0.3 |

TABLE 114

Dose-dependent reduction of human FXII RNA by modified oligonucleotides

| Compound Number | FXII (% UTC) | | | | IC$_{50}$ µM |
|---|---|---|---|---|---|
| | 63 nM | 250 nM | 1000 nM | 4000 nM | |
| 1129531 | 57 | 40 | 17 | 7 | 0.1 |
| 1206490 | 72 | 42 | 35 | 24 | 0.3 |
| 1206492 | 73 | 60 | 46 | 22 | 0.5 |
| 1206980 | 68 | 51 | 34 | 13 | 0.3 |
| 1206996 | 76 | 54 | 30 | 20 | 0.4 |
| 1207004 | 66 | 57 | 41 | 30 | 0.4 |
| 1207006 | 47 | 19 | 10 | 7 | <0.1 |
| 1207118 | 73 | 53 | 31 | 14 | 0.3 |
| 1213120 | 60 | 45 | 24 | 15 | 0.1 |
| 1213135 | 70 | 53 | 31 | 23 | 0.3 |
| 1213144 | 42 | 20 | 25 | 6 | <0.1 |
| 1213220 | 58 | 53 | 41 | 33 | 0.3 |
| 1213227 | 78 | 72 | 40 | 27 | 0.7 |
| 1213234 | 80 | 64 | 44 | 25 | 0.6 |
| 1213235 | 66 | 59 | 30 | 18 | 0.3 |
| 1213259 | 52 | 29 | 16 | 9 | <0.1 |
| 1213260 | 51 | 35 | 13 | 13 | <0.1 |
| 1213262 | 56 | 27 | 18 | 9 | <0.1 |
| 1213264 | 77 | 46 | 18 | 9 | 0.2 |

TABLE 115

Dose-dependent reduction of human FXII RNA by modified oligonucleotides

| Compound Number | FXII (% UTC) | | | | IC$_{50}$ µM |
|---|---|---|---|---|---|
| | 63 nM | 250 nM | 1000 nM | 4000 nM | |
| 1129531 | 77 | 44 | 20 | 20 | 0.2 |
| 1206489 | 83 | 53 | 35 | 21 | 0.4 |
| 1206509 | 97 | 89 | 72 | 33 | 2.3 |
| 1206971 | 84 | 65 | 38 | 22 | 0.6 |
| 1206972 | 69 | 70 | 49 | 21 | 0.6 |
| 1206984 | 64 | 51 | 37 | 25 | 0.3 |
| 1206987 | 70 | 82 | 64 | 47 | >4.0 |
| 1207008 | 58 | 37 | 18 | 14 | 0.1 |
| 1207123 | 96 | 73 | 59 | 26 | 1.1 |
| 1207131 | 79 | 57 | 45 | 27 | 0.6 |
| 1207139 | 86 | 66 | 54 | 24 | 0.9 |
| 1207160 | 53 | 27 | 13 | 11 | <0.1 |
| 1207161 | 53 | 31 | 16 | 13 | <0.1 |
| 1207248 | 83 | 58 | 43 | 31 | 0.7 |
| 1207277 | 42 | 28 | 12 | 6 | <0.1 |
| 1207312 | 85 | 75 | 39 | 23 | 0.7 |
| 1207360 | 80 | 48 | 39 | 22 | 0.4 |
| 1207381 | 79 | 85 | 61 | 46 | 3.6 |
| 1207393 | 58 | 38 | 17 | 7 | 0.1 |

TABLE 116

Dose-dependent reduction of human FXII RNA by modified oligonucleotides

| Compound Number | FXII (% UTC) | | | | IC$_{50}$ µM |
|---|---|---|---|---|---|
| | 63 nM | 250 nM | 1000 nM | 4000 nM | |
| 1128802 | 88 | 57 | 36 | 17 | 0.5 |
| 1129531 | 68 | 44 | 30 | 14 | 0.2 |
| 1208476 | 71 | 62 | 35 | 23 | 0.4 |
| 1208506 | 80 | 80 | 77 | 67 | >4.0 |
| 1208689 | 84 | 76 | 66 | 76 | >4.0 |
| 1208937 | 92 | 85 | 83 | 69 | >4.0 |
| 1209017 | 80 | 73 | 72 | 59 | >4.0 |
| 1209119 | 80 | 66 | 72 | 59 | >4.0 |
| 1209422 | 94 | 90 | 54 | 61 | >4.0 |
| 1209543 | 91 | 94 | 83 | 76 | >4.0 |
| 1209545 | 88 | 82 | 71 | 70 | >4.0 |
| 1209565 | 98 | 95 | 70 | 78 | >4.0 |
| 1209576 | 82 | 83 | 68 | 60 | >4.0 |
| 1209607 | 93 | 88 | 74 | 85 | >4.0 |
| 1209615 | 97 | 83 | 68 | 71 | >4.0 |
| 1209616 | 82 | 76 | 70 | 60 | >4.0 |
| 1209630 | 92 | 86 | 83 | 71 | >4.0 |
| 1209659 | 91 | 98 | 67 | 57 | >4.0 |
| 1209674 | 99 | 81 | 81 | 70 | >4.0 |

TABLE 117

Dose-dependent reduction of human FXII RNA by modified oligonucleotides

| Compound Number | FXII (% UTC) | | | | IC$_{50}$ µM |
|---|---|---|---|---|---|
| | 63 nM | 250 nM | 1000 nM | 4000 nM | |
| 1128802 | 82 | 55 | 38 | 16 | 0.4 |
| 1129531 | 77 | 38 | 29 | 9 | 0.2 |
| 1208612 | 83 | 79 | 63 | 58 | >4.0 |
| 1208757 | 84 | 76 | 74 | 69 | >4.0 |
| 1208977 | 76 | 75 | 76 | 43 | >4.0 |
| 1209134 | 81 | 78 | 75 | 72 | >4.0 |
| 1209238 | 76 | 73 | 68 | 71 | >4.0 |
| 1209391 | 91 | 100 | 89 | 78 | >4.0 |
| 1209430 | 84 | 77 | 73 | 54 | >4.0 |
| 1209455 | 77 | 74 | 71 | 71 | >4.0 |
| 1209514 | 76 | 77 | 70 | 73 | >4.0 |
| 1209547 | 89 | 78 | 58 | 35 | 1.6 |
| 1209548 | 81 | 74 | 59 | 35 | 1.5 |
| 1209605 | 103 | 100 | 78 | 80 | >4.0 |
| 1209624 | 89 | 90 | 75 | 70 | >4.0 |
| 1209645 | 105 | 85 | 79 | 62 | >4.0 |
| 1209670 | 115 | 96 | 82 | 85 | >4.0 |
| 1209688 | 78 | 75 | 80 | 76 | >4.0 |
| 1209692 | 88 | 97 | 89 | 71 | >4.0 |

Example 8: Design of Oligomeric Compounds Complementary to a Human FXII Nucleic Acid Oligomeric compounds were designed as indicated in the tables below. Modified oligonucleotides described in the Examples above (parent compounds) were further modified by either adding a THA-C6-GalNAc3 conjugate (designated as [THA-GalNAc] in the table below) at the 5' end of the modified oligonucleotide, or by adding a 3'-THA-C6-GalNAc hydroxyproline PO conjugate (designated as 3'-HPPO-GalNAc in the tables below), at the 3'-end of the modified oligonucleotide. THA-GalNAc is represented by the structure below wherein the phosphate group is attached to the 5'-oxygen atom of the 5' nucleoside:

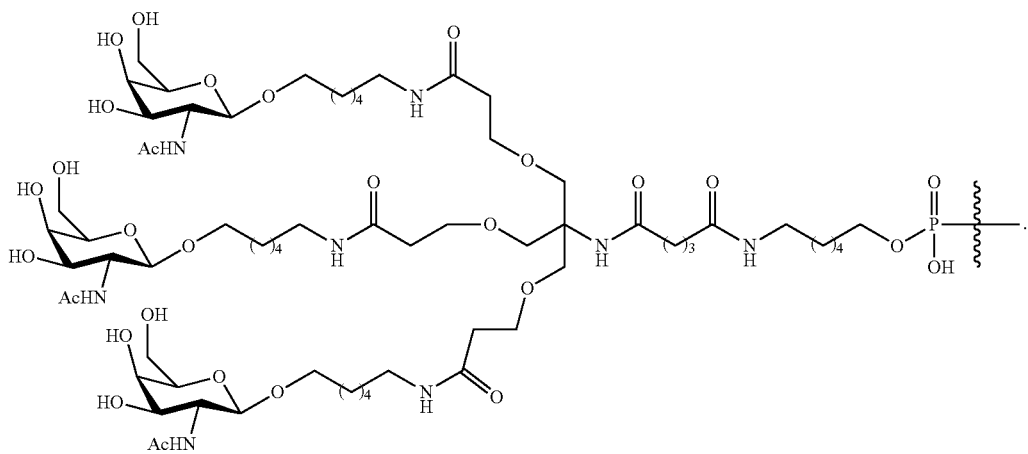

3'-HPPO-GalNAc is represented by the structure below wherein the phosphate group is attached to the 3'-oxygen atom of the 3' nucleoside:

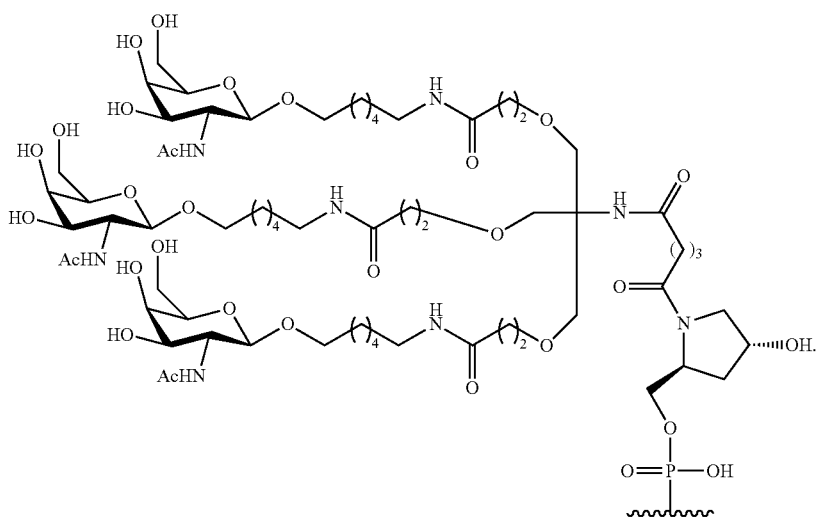

The chemistry notation column in the tables below specifies the specific chemistry notation for modified oligonucleotides; wherein subscript 'd' represents a 2'-β-D-deoxyribosyl sugar moiety, subscript 'e' represents a 2'-MOE sugar moiety, subscript 'y' represents a 2'-O-methyl sugar moiety, subscript 'k' represents a cEt modified sugar moiety, subscript 's' represents a phosphorothioate internucleoside linkage, subscript 'o' represents a phosphodiester internucleoside linkage, and superscript 'm' before the cytosine residue ($^{m}C$) represents a 5-methyl cytosine.

TABLE 118

Design of GalNAc conjugated modified oligonucleotides complementary to human FXII

| Compound No. | Parent Compound No. | Sequence and Chemistry notation (5' to 3') | SEQ ID No. |
|---|---|---|---|
| 1194343 | 1128769 | THA-GalNAc-$_{o}A_{ks}G_{ks}A_{ks}A_{ds}{}^{m}C_{ds}G_{ds}A_{ds}{}^{m}C_{ds}T_{ds}G_{ds}T_{ds}G_{ds}T_{ds}G_{ks}{}^{m}C_{ks}T_{k}$ | 3723 |
| 1194345 | 1128801 | THA-GalNAc-$_{o}A_{ks}{}^{m}C_{ks}A_{ks}T_{ds}T_{ds}T_{ds}G_{ds}T_{ds}G_{ds}G_{ds}T_{ds}A_{ds}{}^{m}C_{ds}A_{ks}G_{ks}{}^{m}C_{k}$ | 3114 |
| 1194346 | 1128802 | THA-GalNAc-$_{o}T_{ks}A_{ks}{}^{m}C_{ks}A_{ds}T_{ds}T_{ds}T_{ds}G_{ds}T_{ds}G_{ds}G_{ds}T_{ds}A_{ds}{}^{m}C_{ks}A_{ks}G_{k}$ | 2426 |
| 1194347 | 1128870 | THA-GalNAc-$_{o}T_{ks}G_{ks}T_{ks}G_{ds}G_{ds}A_{ds}A_{ds}A_{ds}A_{ds}A_{ds}{}^{m}C_{ds}{}^{m}C_{ds}G_{ds}G_{ks}A_{ks}G_{k}$ | 3728 |
| 1194348 | 1129221 | THA-GalNAc-$_{o}{}^{m}C_{ks}G_{ks}T_{ks}{}^{m}C_{ds}T_{ds}G_{ds}G_{ds}{}^{m}C_{ds}A_{ds}{}^{m}C_{ds}G_{ds}G_{ds}{}^{m}C_{ds}T_{ks}{}^{m}C_{ks}A_{k}$ | 3060 |

TABLE 118-continued

Design of GalNAc conjugated modified oligonucleotides complementary to human FXII

| Compound No. | Parent Compound No. | Sequence and Chemistry notation (5' to 3') | SEQ ID No. |
|---|---|---|---|
| 1194349 | 1129287 | THA-GalNAc-$_o{}^mC_{ks}G_{ks}T_{ks}A_{ds}A_{ds}G_{ds}G_{ds}{}^mC_{ds}G_{ds}A_{ds}{}^mC_{ds}A_{ds}G_{ds}G_{ks}A_{ks}G_k$ | 3521 |
| 1194350 | 1129407 | THA-GalNAc-$_oT_{ks}G_{ks}{}^mC_{ks}{}^mC_{ds}T_{ds}T_{ds}G_{ds}{}^mC_{ds}A_{ds}G_{ds}G_{ds}T_{ds}G_{ks}A_{ks}G_k$ | 3527 |
| 1194357 | 1129485 | THA-GalNAc-$_oG_{ks}{}^mC_{ks}G_{ks}G_{ds}A_{ds}A_{ds}T_{ds}{}^mC_{ds}A_{ds}{}^mC_{ds}{}^mC_{ds}A_{ds}A_{ds}G_{ks}G_{ks}A_k$ | 3379 |
| 1194358 | 1129486 | THA-GalNAc-$_oT_{ks}G_{ks}{}^mC_{ks}G_{ds}G_{ds}A_{ds}A_{ds}T_{ds}{}^mC_{ds}A_{ds}{}^mC_{ds}{}^mC_{ds}A_{ds}A_{ks}G_{ks}G_k$ | 3455 |
| 1194359 | 1129487 | THA-GalNAc-$_o{}^mC_{ks}T_{ks}G_{ks}{}^mC_{ds}G_{ds}G_{ds}A_{ds}A_{ds}T_{ds}{}^mC_{ds}A_{ds}{}^mC_{ds}{}^mC_{ds}A_{ks}A_{ks}G_k$ | 3531 |
| 1194360 | 1129488 | THA-GalNAc-$_oA_{ks}{}^mC_{ks}T_{ks}G_{ds}{}^mC_{ds}G_{ds}G_{ds}A_{ds}A_{ds}T_{ds}{}^mC_{ds}A_{ds}{}^mC_{ds}{}^mC_{ks}A_{ks}A_k$ | 3607 |
| 1194361 | 1129489 | THA-GalNAc-$_o{}^mC_{ks}A_{ks}{}^mC_{ks}T_{ds}G_{ds}{}^mC_{ds}G_{ds}G_{ds}A_{ds}A_{ds}T_{ds}{}^mC_{ds}A_{ds}{}^mC_{ks}{}^mC_{ks}A_k$ | 3683 |
| 1194363 | 1129492 | THA-GalNAc-$_oT_{ks}{}^mC_{ks}T_{ks}{}^mC_{ds}A_{ds}{}^mC_{ds}T_{ds}G_{ds}{}^mC_{ds}G_{ds}G_{ds}A_{ds}A_{ds}T_{ks}{}^mC_{ks}A_k$ | 3911 |
| 1194370 | 1129534 | THA-GalNAc-$_oA_{ks}T_{ks}T_{ks}G_{ds}A_{ds}G_{ds}T_{ds}T_{ds}{}^mC_{ds}{}^mC_{ds}T_{ds}G_{ds}{}^mC_{ds}G_{ks}{}^mC_{ks}{}^mC_k$ | 2540 |
| 1194371 | 1129538 | THA-GalNAc-$_oA_{ks}{}^mC_{ks}T_{ks}T_{ds}T_{ds}A_{ds}T_{ds}T_{ds}G_{ds}A_{ds}G_{ds}T_{ds}T_{ds}{}^mC_{ks}{}^mC_{ks}T_k$ | 2848 |
| 1194372 | 1129540 | THA-GalNAc-$_oG_{ks}{}^mC_{ks}A_{ks}{}^mC_{ds}T_{ds}T_{ds}T_{ds}A_{ds}T_{ds}T_{ds}G_{ds}A_{ds}G_{ds}T_{ks}T_{ks}{}^mC_k$ | 3000 |
| 1194373 | 1129542 | THA-GalNAc-$_oA_{ks}A_{ks}G_{ks}{}^mC_{ds}A_{ds}{}^mC_{ds}T_{ds}T_{ds}T_{ds}A_{ds}T_{ds}T_{ds}G_{ds}A_{ks}G_{ks}T_k$ | 3147 |
| 1194374 | 1129543 | THA-GalNAc-$_oA_{ks}A_{ks}A_{ks}G_{ds}{}^mC_{ds}A_{ds}{}^mC_{ds}T_{ds}T_{ds}T_{ds}A_{ds}T_{ds}T_{ds}G_{ks}A_{ks}G_k$ | 3229 |
| 1194375 | 1129544 | THA-GalNAc-$_o{}^mC_{ks}A_{ks}A_{ks}A_{ds}G_{ds}{}^mC_{ds}A_{ds}{}^mC_{ds}T_{ds}T_{ds}T_{ds}A_{ds}T_{ds}T_{ks}G_{ks}A_k$ | 3306 |
| 1194376 | 1129545 | THA-GalNAc-$_oT_{ks}{}^mC_{ks}A_{ks}A_{ds}A_{ds}G_{ds}{}^mC_{ds}A_{ds}{}^mC_{ds}T_{ds}T_{ds}T_{ds}A_{ds}T_{ks}T_{ks}G_k$ | 3382 |
| 1194377 | 1129947 | THA-GalNAc-$_oT_{ks}G_{ks}{}^mC_{ks}T_{ds}T_{ds}T_{ds}{}^mC_{ds}{}^mC_{ds}G_{ds}{}^mC_{ds}A_{ds}{}^mC_{ds}T_{ds}{}^mC_{ks}T_{ks}{}^mC_k$ | 3554 |
| 1194378 | 1130831 | THA-GalNAc-$_oG_{es}A_{eo}A_{eo}{}^mC_{eo}G_{eo}A_{ds}{}^mC_{ds}T_{ds}G_{ds}T_{ds}G_{ds}T_{ds}G_{ds}{}^mC_{ds}T_{ds}{}^mC_{eo}T_{eo}T_{es}{}^mC_{es}A_e$ | 997 |
| 1194379 | 1130868 | THA-GalNAc-$_oA_{es}{}^mC_{eo}A_{eo}T_{eo}T_{eo}T_{ds}G_{ds}T_{ds}G_{ds}G_{ds}T_{ds}A_{ds}{}^mC_{ds}A_{ds}G_{ds}{}^mC_{eo}T_{eo}G_{es}{}^mC_{es}{}^mC_e$ | 1756 |
| 1194380 | 1130871 | THA-GalNAc-$_oG_{es}G_{eo}T_{eo}A_{eo}{}^mC_{eo}A_{ds}T_{ds}T_{ds}T_{ds}G_{ds}T_{ds}G_{ds}G_{ds}T_{ds}A_{ds}{}^mC_{eo}A_{eo}G_{es}{}^mC_{es}T_e$ | 183 |
| 1194381 | 1130900 | THA-GalNAc-$_oA_{es}T_{eo}{}^mC_{eo}G_{eo}{}^mC_{eo}T_{ds}G_{ds}G_{ds}T_{ds}{}^mC_{ds}{}^mC_{ds}T_{ds}G_{ds}A_{ds}T_{ds}{}^mC_{eo}A_{eo}A_{es}A_{es}G_e$ | 1906 |
| 1194382 | 1130925 | THA-GalNAc-$_oG_{es}G_{eo}T_{eo}{}^mC_{eo}T_{eo}T_{ds}T_{ds}{}^mC_{ds}A_{ds}{}^mC_{ds}T_{ds}T_{ds}T_{ds}{}^mC_{ds}T_{ds}T_{eo}G_{eo}G_{es}G_{es}{}^mC_e$ | 1758 |
| 1194383 | 1130987 | THA-GalNAc-$_oG_{es}G_{eo}{}^mC_{eo}T_{eo}{}^mC_{eo}A_{ds}A_{ds}A_{ds}G_{ds}{}^mC_{ds}A_{ds}{}^mC_{ds}T_{ds}T_{ds}{}^mC_{ds}T_{eo}{}^mC_{eo}T_{es}T_{es}T_e$ | 2135 |
| 1194384 | 1131013 | THA-GalNAc-$_oA_{es}{}^mC_{eo}{}^mC_{eo}A_{eo}T_{eo}A_{ds}T_{ds}{}^mC_{ds}T_{ds}{}^mC_{ds}A_{ds}T_{ds}T_{ds}{}^mC_{ds}T_{ds}T_{eo}G_{eo}T_{es}G_{es}G_e$ | 1984 |
| 1194385 | 1131040 | THA-GalNAc-$_oA_{es}{}^mC_{eo}{}^mC_{eo}{}^mC_{eo}T_{eo}T_{ds}G_{ds}{}^mC_{ds}A_{ds}{}^mC_{ds}T_{ds}G_{ds}G_{ds}{}^mC_{ds}A_{ds}T_{eo}{}^mC_{eo}T_{es}G_{es}G_e$ | 1911 |
| 1194387 | 1131204 | THA-GalNAc-$_oA_{es}G_{eo}T_{eo}T_{eo}{}^mC_{eo}T_{ds}G_{ds}{}^mC_{ds}G_{ds}{}^mC_{ds}T_{ds}T_{ds}G_{ds}{}^mC_{ds}T_{ds}{}^mC_{eo}G_{eo}G_{es}{}^mC_{es}A_e$ | 1618 |
| 1194388 | 1131432 | THA-GalNAc-$_oG_{es}G_{eo}T_{eo}A_{eo}G_{eo}G_{ds}A_{ds}G_{ds}{}^mC_{ds}G_{ds}{}^mC_{ds}A_{ds}{}^mC_{ds}G_{ds}G_{ds}{}^mC_{eo}{}^mC_{eo}A_{es}A_{es}{}^mC_e$ | 1925 |
| 1194389 | 1131593 | THA-GalNAc-$_oT_{es}G_{eo}A_{eo}T_{eo}G_{eo}{}^mC_{ds}{}^mC_{ds}T_{ds}T_{ds}G_{ds}{}^mC_{ds}A_{ds}G_{ds}G_{ds}G_{ds}T_{eo}G_{eo}A_{es}G_{es}{}^mC_e$ | 1326 |
| 1194390 | 1131595 | THA-GalNAc-$_oG_{es}A_{eo}T_{eo}G_{eo}A_{eo}T_{ds}G_{ds}{}^mC_{ds}{}^mC_{ds}T_{ds}T_{ds}G_{ds}{}^mC_{ds}A_{ds}G_{ds}G_{eo}G_{eo}T_{es}G_{es}A_e$ | 1556 |
| 1194391 | 1131671 | THA-GalNAc-$_oG_{es}{}^mC_{eo}A_{eo}A_{eo}T_{eo}{}^mC_{ds}A_{ds}G_{ds}G_{ds}A_{ds}A_{ds}A_{ds}{}^mC_{ds}G_{ds}G_{ds}T_{eo}G_{eo}T_{es}G_{es}{}^mC_e$ | 950 |
| 1194392 | 1131693 | THA-GalNAc-$_oT_{es}G_{eo}{}^mC_{eo}G_{eo}G_{eo}A_{ds}A_{ds}T_{ds}{}^mC_{ds}A_{ds}{}^mC_{ds}{}^mC_{ds}A_{ds}A_{ds}G_{ds}G_{eo}A_{eo}G_{es}G_{es}G_e$ | 496 |

TABLE 118-continued

Design of GalNAc conjugated modified oligonucleotides complementary to human FXII

| Compound No. | Parent Compound No. | Sequence and Chemistry notation (5' to 3') | SEQ ID No. |
|---|---|---|---|
| 1194393 | 1131694 | THA-GalNAc-$_o{}^mC_{es}T_{eo}G_{eo}{}^mC_{eo}G_{eo}G_{ds}A_{ds}A_{ds}T_{ds}{}^mC_{ds}A_{ds}{}^mC_{ds}{}^mC_{ds}A_{ds}A_{ds}G_{eo}G_{eo}A_{es}G_{es}G_e$ | 571 |
| 1194394 | 1131697 | THA-GalNAc-$_o{}^mC_{es}T_{eo}{}^mC_{eo}A_{eo}{}^mC_{eo}T_{ds}G_{ds}{}^mC_{ds}G_{ds}G_{ds}A_{ds}A_{ds}T_{ds}{}^mC_{ds}A_{ds}{}^mC_{eo}{}^mC_{eo}A_{es}A_{es}G_e$ | 802 |
| 1194395 | 1131699 | THA-GalNAc-$_oT_{es}{}^mC_{eo}T_{eo}{}^mC_{eo}T_{eo}{}^mC_{ds}A_{ds}{}^mC_{ds}T_{ds}G_{ds}{}^mC_{ds}G_{ds}G_{ds}A_{ds}A_{ds}T_{eo}{}^mC_{eo}A_{es}{}^mC_{es}{}^mC_e$ | 951 |
| 1194396 | 1131700 | THA-GalNAc-$_o{}^mC_{es}T_{eo}{}^mC_{eo}T_{eo}{}^mC_{eo}T_{ds}{}^mC_{ds}A_{ds}{}^mC_{ds}T_{ds}G_{ds}{}^mC_{ds}G_{ds}G_{ds}A_{ds}A_{eo}T_{eo}{}^mC_{es}A_{es}{}^mC_e$ | 1028 |
| 1194397 | 1131701 | THA-GalNAc-$_oA_{es}{}^mC_{eo}T_{eo}{}^mC_{eo}T_{eo}{}^mC_{ds}T_{ds}{}^mC_{ds}A_{ds}{}^mC_{ds}T_{ds}G_{ds}{}^mC_{ds}G_{ds}G_{ds}A_{eo}A_{eo}T_{es}{}^mC_{es}A_e$ | 1179 |
| 1194398 | 1131702 | THA-GalNAc-$_o{}^mC_{es}{}^mC_{eo}A_{eo}{}^mC_{eo}T_{eo}{}^mC_{ds}T_{ds}{}^mC_{ds}T_{ds}{}^mC_{ds}A_{ds}{}^mC_{ds}T_{ds}G_{ds}{}^mC_{ds}G_{eo}G_{eo}A_{es}A_{es}T_e$ | 1103 |
| 1194399 | 1131712 | THA-GalNAc-$_o{}^mC_{es}T_{eo}T_{eo}{}^mC_{eo}{}^mC_{eo}A_{ds}T_{ds}G_{ds}{}^mC_{ds}{}^mC_{ds}{}^mC_{ds}{}^mC_{ds}A_{ds}G_{ds}{}^mC_{ds}{}^mC_{eo}A_{eo}{}^mC_{es}T_{es}{}^mC_e$ | 1935 |
| 1194400 | 1131745 | THA-GalNAc-$_oA_{es}G_{eo}T_{eo}T_{eo}{}^mC_{eo}{}^mC_{ds}T_{ds}G_{ds}{}^mC_{ds}G_{ds}{}^mC_{ds}{}^mC_{ds}A_{ds}T_{ds}{}^mC_{ds}{}^mC_{eo}T_{eo}G_{es}G_{es}{}^mC_e$ | 2309 |
| 1194401 | 1131747 | THA-GalNAc-$_oT_{es}G_{eo}A_{eo}G_{eo}T_{eo}T_{ds}{}^mC_{ds}{}^mC_{ds}T_{ds}G_{ds}{}^mC_{ds}G_{ds}{}^mC_{ds}{}^mC_{ds}A_{ds}T_{eo}{}^mC_{eo}{}^mC_{es}T_{es}G_e$ | 347 |
| 1194402 | 1131753 | THA-GalNAc-$_o{}^mC_{es}A_{eo}{}^mC_{eo}T_{eo}T_{eo}T_{ds}A_{ds}T_{ds}T_{ds}G_{ds}A_{ds}G_{ds}T_{ds}T_{ds}{}^mC_{ds}{}^mC_{eo}T_{eo}G_{es}{}^mC_{es}G_e$ | 163 |
| 1194403 | 1131754 | THA-GalNAc-$_oG_{es}{}^mC_{eo}A_{eo}{}^mC_{eo}T_{eo}T_{ds}T_{ds}A_{ds}T_{ds}T_{ds}G_{ds}A_{ds}G_{ds}T_{ds}T_{ds}{}^mC_{eo}{}^mC_{eo}T_{es}G_{es}{}^mC_e$ | 164 |
| 1194404 | 1131755 | THA-GalNAc-$_oA_{es}G_{eo}{}^mC_{eo}A_{eo}{}^mC_{eo}T_{ds}T_{ds}T_{ds}A_{ds}T_{ds}T_{ds}G_{ds}A_{ds}G_{ds}T_{ds}T_{eo}{}^mC_{eo}{}^mC_{es}T_{es}G_e$ | 953 |
| 1194405 | 1131756 | THA-GalNAc-$_oA_{es}A_{eo}G_{eo}{}^mC_{eo}A_{eo}{}^mC_{ds}T_{ds}T_{ds}T_{ds}A_{ds}T_{ds}T_{ds}G_{ds}A_{ds}G_{ds}T_{eo}T_{eo}{}^mC_{es}{}^mC_{es}T_e$ | 1030 |
| 1194406 | 1131757 | THA-GalNAc-$_oA_{es}A_{eo}A_{eo}G_{eo}{}^mC_{eo}A_{ds}{}^mC_{ds}T_{ds}T_{ds}T_{ds}A_{ds}T_{ds}T_{ds}G_{ds}A_{ds}G_{eo}T_{eo}T_{es}{}^mC_{es}{}^mC_e$ | 165 |
| 1194407 | 1131758 | THA-GalNAc-$_o{}^mC_{es}A_{eo}A_{eo}A_{eo}G_{eo}{}^mC_{ds}A_{ds}{}^mC_{ds}T_{ds}T_{ds}T_{ds}A_{ds}T_{ds}T_{ds}G_{ds}A_{eo}G_{eo}T_{es}T_{es}{}^mC_e$ | 1105 |
| 1194408 | 1131763 | THA-GalNAc-$_oG_{es}{}^mC_{eo}A_{eo}T_{eo}T_{eo}T_{ds}T_{ds}{}^mC_{ds}A_{ds}A_{ds}A_{ds}G_{ds}{}^mC_{ds}A_{ds}{}^mC_{ds}T_{eo}T_{eo}T_{es}A_{es}T_e$ | 1562 |
| 1194409 | 1131764 | THA-GalNAc-$_oA_{es}G_{eo}{}^mC_{eo}A_{eo}T_{eo}T_{ds}T_{ds}T_{ds}{}^mC_{ds}A_{ds}A_{ds}A_{ds}G_{ds}{}^mC_{ds}A_{ds}{}^mC_{eo}T_{eo}T_{es}T_{es}A_e$ | 97 |
| 1194410 | 1131891 | THA-GalNAc-$_o{}^mC_{es}{}^mC_{eo}G_{eo}A_{eo}{}^mC_{eo}T_{ds}G_{ds}T_{ds}G_{ds}T_{ds}G_{ds}{}^mC_{ds}T_{ds}{}^mC_{ds}T_{ds}T_{eo}{}^mC_{eo}A_{es}G_{es}{}^mC_e$ | 659 |
| 1194411 | 1132187 | THA-GalNAc-$_oG_{es}T_{eo}T_{eo}T_{eo}G_{eo}{}^mC_{ds}T_{ds}A_{ds}G_{ds}T_{ds}T_{ds}{}^mC_{ds}A_{ds}A_{ds}T_{ds}G_{eo}T_{eo}T_{es}{}^mC_{es}A_e$ | 1876 |
| 1194412 | 1132188 | THA-GalNAc-$_oA_{es}{}^mC_{eo}T_{eo}G_{eo}T_{eo}T_{ds}G_{ds}{}^mC_{ds}T_{ds}A_{ds}G_{ds}T_{ds}T_{ds}{}^mC_{ds}A_{eo}A_{eo}T_{es}G_{es}T_e$ | 1951 |
| 1194413 | 1132189 | THA-GalNAc-$_oA_{es}A_{eo}T_{eo}A_{eo}{}^mC_{eo}T_{ds}G_{ds}T_{ds}T_{ds}G_{ds}{}^mC_{ds}T_{ds}A_{ds}G_{ds}T_{eo}T_{eo}{}^mC_{es}A_{es}A_e$ | 2025 |
| 1194415 | 1132270 | THA-GalNAc-$_oa_{es}T_{eo}T_{eo}{}^mC_{eo}{}^mC_{eo}{}^mC_{ds}A_{ds}G_{ds}T_{ds}T_{ds}A_{ds}A_{ds}G_{ds}G_{ds}T_{o}{}^mC_{eo}A_{es}A_{es}{}^mC_e$ | 1730 |
| 1194416 | 1132271 | THA-GalNAc-$_o{}^mC_{es}A_{eo}{}^mC_{eo}A_{eo}A_{eo}T_{ds}{}^mC_{ds}{}^mC_{ds}{}^mC_{ds}A_{ds}G_{ds}T_{ds}T_{ds}A_{ds}A_{ds}G_{eo}G_{eo}T_{es}T_{es}{}^mC_e$ | 1879 |
| 1194417 | 1132272 | THA-GalNAc-$_oT_{es}T_{eo}G_{eo}{}^mC_{eo}A_{eo}{}^mC_{ds}A_{ds}T_{ds}T_{ds}{}^mC_{ds}{}^mC_{ds}{}^mC_{ds}A_{ds}G_{ds}T_{ds}T_{eo}A_{eo}A_{es}G_{es}G_e$ | 1954 |

TABLE 118-continued

Design of GalNAc conjugated modified oligonucleotides complementary to human FXII

| Compound No. | Parent Compound No. | Sequence and Chemistry notation (5' to 3') | SEQ ID No. |
|---|---|---|---|
| 1194419 | 1132504 | THA-GalNAc-$_o$G$_{es}$T$_{eo}$T$_{eo}$Te$^m$C$_{eo}$$^m$C$_{ds}$A$_{ds}$A$_{ds}$G$_{ds}$$^m$C$_{ds}$T$_{ds}$T$_{ds}$G$_{ds}$G$_{ds}$T$_{ds}$T$_{eo}$T$_{eo}$A$_{es}$$^m$C$_{es}$$^m$C$_e$ | 449 |
| 1194420 | 1132505 | THA-GalNAc-$_o$$^m$C$_{es}$A$_{eo}$A$_{eo}$G$_{eo}$T$_{eo}$T$_{ds}$T$_{ds}$$^m$C$_{ds}$$^m$C$_{ds}$A$_{ds}$A$_{ds}$G$_{ds}$$^m$C$_{ds}$T$_{ds}$T$_{ds}$G$_{eo}$G$_{eo}$T$_{es}$T$_{es}$T$_e$ | 525 |
| 1194421 | 1132506 | THA-GalNAc-$_o$$^m$C$_{es}$T$_{eo}$$^m$C$_{eo}$C$_{eo}$A$_{eo}$A$_{ds}$G$_{ds}$T$_{ds}$T$_{ds}$T$_{ds}$$^m$C$_{ds}$$^m$C$_{ds}$A$_{ds}$A$_{ds}$G$_{ds}$$^m$C$_{eo}$T$_{eo}$T$_{es}$G$_{es}$G$_e$ | 600 |
| 1194423 | 1132650 | THA-GalNAc-$_o$T$_{es}$T$_{eo}$G$_{eo}$$^m$C$_{eo}$$^m$C$_{eo}$T$_{ds}$T$_{ds}$G$_{ds}$G$_{ds}$T$_{ds}$G$_{ds}$T$_{ds}$$^m$C$_{ds}$T$_{ds}$G$_{ds}$A$_{eo}$G$_{eo}$G$_{es}$A$_{es}$G$_e$ | 910 |
| 1194424 | 1132651 | THA-GalNAc-$_o$A$_{es}$G$_{eo}$$^m$C$_{eo}$T$_{eo}$T$_{eo}$G$_{ds}$$^m$C$_{ds}$$^m$C$_{ds}$T$_{ds}$T$_{ds}$G$_{ds}$G$_{ds}$T$_{ds}$G$_{ds}$T$_{ds}$$^m$C$_{eo}$T$_{eo}$G$_{es}$A$_{es}$G$_e$ | 985 |
| 1194425 | 1132652 | THA-GalNAc-$_o$A$_{es}$G$_{eo}$$^m$C$_{eo}$A$_{eo}$G$_{eo}$$^m$C$_{ds}$T$_{ds}$T$_{ds}$G$_{ds}$$^m$C$_{ds}$$^m$C$_{ds}$T$_{ds}$T$_{ds}$G$_{ds}$G$_{ds}$T$_{eo}$G$_{eo}$T$_{es}$$^m$C$_{es}$T$_e$ | 1062 |
| 1194426 | 1132796 | THA-GalNAc-$_o$G$_{es}$A$_{eo}$A$_{eo}$$^m$C$_{eo}$$^m$C$_{eo}$A$_{ds}$A$_{ds}$G$_{ds}$A$_{ds}$G$_{ds}$$^m$C$_{ds}$A$_{ds}$A$_{ds}$G$_{ds}$T$_{ds}$T$_{eo}$$^m$C$_{eo}$G$_{es}$A$_{es}$T$_e$ | 1523 |
| 1194427 | 1132797 | THA-GalNAc-$_o$A$_{es}$G$_{eo}$G$_{eo}$G$_{eo}$A$_{eods}$$^m$C$_{ds}$$^m$C$_{ds}$A$_{ds}$A$_{ds}$G$_{ds}$A$_{ds}$G$_{ds}$$^m$C$_{ds}$A$_{ds}$A$_{eo}$G$_{eo}$T$_{es}$T$_{es}$$^m$C$_e$ | 1369 |
| 1194429 | 1194286 | THA-GalNAc-$_o$$^m$C$_{ks}$T$_{ks}$T$_{ks}$T$_{ds}$$^m$C$_{ds}$$^m$C$_{ds}$G$_{ds}$$^m$C$_{ds}$A$_{ds}$$^m$C$_{ds}$T$_{ds}$$^m$C$_{ds}$T$_{ds}$$^m$C$_{ks}$$^m$C$_{ks}$$^m$C$_k$ | 4026 |
| 1194430 | 1194287 | THA-GalNAc-$_o$G$_{ks}$$^m$C$_{ks}$T$_{ks}$T$_{ds}$T$_{ds}$$^m$Cd$^m$C$_{ds}$G$_{ds}$$^m$C$_{ds}$A$_{ds}$$^m$C$_{ds}$T$_{ds}$$^m$C$_{ds}$T$_{ks}$$^m$C$_{ks}$$^m$C$_k$ | 4102 |
| 1194483 | 1129948 | A$_{ks}$T$_{ks}$$^m$C$_{ks}$T$_{ds}$G$_{ds}$$^m$C$_{ds}$T$_{ds}$T$_{ds}$T$_{ds}$$^m$C$_{ds}$$^m$C$_{ds}$G$_{ds}$$^m$C$_{ds}$A$_{ks}$$^m$C$_{ks}$T$_k$-3'-HPPO-GalNAc | 3630 |
| 1194484 | 1129949 | T$_{ks}$$^m$C$_{ks}$T$_{ks}$$^m$C$_{ds}$A$_{ds}$T$_{ds}$$^m$C$_{ds}$T$_{ds}$G$_{ds}$$^m$C$_{ds}$T$_{ds}$T$_{ds}$T$_{ds}$$^m$C$_{ks}$$^m$C$_{ks}$G$_k$-3'-HPPO-GalNAc | 3706 |
| 1194486 | 1128769 | A$_{ks}$G$_{ks}$A$_{ks}$A$_{ds}$$^m$C$_{ds}$G$_{ds}$A$_{ds}$$^m$C$_{ds}$T$_{ds}$G$_{ds}$T$_{ds}$G$_{ds}$T$_{ds}$G$_{ks}$$^m$C$_{ks}$T$_k$-3'-HPPO-GalNAc | 3723 |
| 1194487 | 1128796 | T$_{ks}$G$_{ks}$T$_{ks}$G$_{ds}$G$_{ds}$T$_{ds}$A$_{ds}$$^m$C$_{ds}$A$_{ds}$G$_{ds}$$^m$C$_{ds}$T$_{ds}$G$_{ds}$$^m$C$_{ks}$$^m$C$_{ks}$G$_k$-3'-HPPO-GalNAc | 2734 |
| 1194488 | 1128801 | A$_{ks}$$^m$C$_{ks}$A$_{ks}$T$_{ds}$T$_{ds}$T$_{ds}$G$_{ds}$T$_{ds}$G$_{ds}$G$_{ds}$T$_{ds}$A$_{ds}$$^m$C$_{ds}$A$_{ks}$G$_{ks}$$^m$C$_k$-3'-HPPO-GalNAc | 3114 |
| 1194489 | 1128802 | T$_{ks}$A$_{ks}$$^m$C$_{ks}$A$_{ds}$T$_{ds}$T$_{ds}$T$_{ds}$G$_{ds}$T$_{ds}$G$_{ds}$G$_{ds}$T$_{ds}$A$_{ds}$$^m$C$_{ks}$A$_{ks}$G$_k$-3'-HPPO-GalNAc | 2426 |
| 1194490 | 1128870 | T$_{ks}$G$_{ks}$T$_{ks}$G$_{ds}$G$_{ds}$A$_{ds}$A$_{ds}$A$_{ds}$A$_{ds}$A$_{ds}$$^m$C$_{ds}$$^m$C$_{ds}$G$_{ds}$G$_{ks}$A$_{ks}$G$_k$-3'-HPPO-GalNAc | 3728 |
| 1194491 | 1129221 | $^m$C$_{ks}$G$_{ks}$T$_{ks}$$^m$C$_{ds}$T$_{ds}$G$_{ds}$G$_{ds}$$^m$C$_{ds}$A$_{ds}$$^m$C$_{ds}$G$_{ds}$G$_{ds}$$^m$C$_{ds}$T$_{ks}$$^m$C$_{ks}$A$_k$-3'-HPPO-GalNAc | 3060 |
| 1194492 | 1129287 | $^m$C$_{ks}$G$_{ks}$T$_{ks}$A$_{ds}$A$_{ds}$G$_{ds}$G$_{ds}$$^m$C$_{ds}$G$_{ds}$A$_{ds}$$^m$C$_{ds}$A$_{ds}$G$_{ds}$G$_{ks}$A$_{ks}$G$_k$-3'-HPPO-GalNAc | 3521 |
| 1194493 | 1129407 | T$_{ks}$G$_{ks}$$^m$C$_{ks}$$^m$C$_{ds}$T$_{ds}$T$_{ds}$G$_{ds}$$^m$C$_{ds}$A$_{ds}$G$_{ds}$G$_{ds}$T$_{ds}$G$_{ks}$A$_{ks}$G$_k$-3'-HPPO-GalNAc | 3527 |
| 1194494 | 1129408 | A$_{ks}$T$_{ks}$G$_{ks}$A$_{ds}$T$_{ds}$G$_{ds}$$^m$C$_{ds}$$^m$C$_{ds}$T$_{ds}$T$_{ds}$G$_{ds}$$^m$C$_{ds}$A$_{ds}$G$_{ks}$G$_{ks}$G$_k$-3'-HPPO-GalNAc | 3603 |
| 1194495 | 1129409 | $^m$C$_{ks}$T$_{ks}$G$_{ks}$A$_{ds}$T$_{ds}$G$_{ds}$A$_{ds}$T$_{ds}$G$_{ds}$$^m$C$_{ds}$$^m$C$_{ds}$T$_{ds}$T$_{ds}$G$_{ks}$$^m$C$_{ks}$A$_k$-3'-HPPO-GalNAc | 3679 |
| 1194496 | 1129441 | A$_{ks}$G$_{ks}$T$_{ks}$A$_{ds}$G$_{ds}$G$_{ds}$$^m$C$_{ds}$$^m$C$_{ds}$A$_{ds}$$^m$C$_{ds}$A$_{ds}$T$_{ds}$$^m$C$_{ds}$G$_{ks}$G$_{ks}$T$_k$-3'-HPPO-GalNAc | 3071 |
| 1194497 | 1129472 | T$_{ks}$G$_{ks}$A$_{ks}$G$_{ds}$T$_{ds}$$^m$C$_{ds}$$^m$C$_{ds}$$^m$C$_{ds}$T$_{ds}$G$_{ds}$A$_{ds}$G$_{ds}$$^m$C$_{ds}$A$_{ks}$A$_{ks}$T$_k$-3'-HPPO-GalNAc | 3910 |
| 1194498 | 1129476 | A$_{ks}$A$_{ks}$G$_{ks}$A$_{ds}$T$_{ds}$G$_{ds}$A$_{ds}$G$_{ds}$T$_{ds}$$^m$C$_{ds}$$^m$C$_{ds}$$^m$C$_{ds}$T$_{ds}$G$_{ks}$A$_{ks}$G$_k$-3'-HPPO-GalNAc | 2691 |
| 1194499 | 1129483 | G$_{ks}$G$_{ks}$A$_{ks}$A$_{ds}$T$_{ds}$$^m$C$_{ds}$A$_{ds}$$^m$C$_{ds}$$^m$C$_{ds}$A$_{ds}$A$_{ds}$G$_{ds}$A$_{ds}$G$_{ks}$G$_{ks}$G$_k$-3'-HPPO-GalNAc | 3226 |
| 1194500 | 1129485 | G$_{ks}$$^m$C$_{ks}$G$_{ks}$G$_{ds}$A$_{ds}$A$_{ds}$T$_{ds}$$^m$C$_{ds}$A$_{ds}$$^m$C$_{ds}$$^m$C$_{ds}$A$_{ds}$A$_{ds}$G$_{ks}$G$_{ks}$A$_k$-3'-HPPO-GalNAc | 3379 |
| 1194501 | 1129486 | T$_{ks}$G$_{ks}$$^m$C$_{ks}$G$_{ds}$G$_{ds}$A$_{ds}$A$_{ds}$T$_{ds}$$^m$C$_{ds}$A$_{ds}$$^m$C$_{ds}$$^m$C$_{ds}$A$_{ds}$A$_{ks}$G$_{ks}$G$_k$-3'-HPPO-GalNAc | 3455 |
| 1194502 | 1129487 | $^m$C$_{ks}$T$_{ks}$G$_{ks}$$^m$C$_{ds}$G$_{ds}$G$_{ds}$A$_{ds}$A$_{ds}$T$_{ds}$$^m$C$_{ds}$A$_{ds}$$^m$C$_{ds}$$^m$C$_{ds}$A$_{ks}$A$_{ks}$G$_k$-3'-HPPO-GalNAc | 3531 |
| 1194503 | 1129488 | A$_{ks}$$^m$C$_{ks}$T$_{ks}$G$_{ds}$$^m$C$_{ds}$G$_{ds}$G$_{ds}$A$_{ds}$A$_{ds}$T$_{ds}$$^m$C$_{ds}$A$_{ds}$$^m$C$_{ds}$$^m$C$_{ks}$A$_{ks}$A$_k$-3'-HPPO-GalNAc | 3607 |
| 1194504 | 1129489 | $^m$C$_{ks}$A$_{ks}$$^m$C$_{ks}$T$_{ds}$G$_{ds}$$^m$C$_{ds}$G$_{ds}$G$_{ds}$A$_{ds}$A$_{ds}$T$_{ds}$$^m$C$_{ds}$A$_{ds}$$^m$C$_{ks}$$^m$C$_{ks}$A$_k$-3'-HPPO-GalNAc | 3683 |
| 1194505 | 1129491 | $^m$C$_{ks}$T$_{ks}$$^m$CsA$_{ds}$$^m$C$_{ds}$T$_{ds}$G$_{ds}$$^m$C$_{ds}$G$_{ds}$G$_{ds}$A$_{ds}$A$_{ds}$T$_{ds}$$^m$C$_{ks}$A$_{ks}$$^m$C$_k$-3'-HPPO-GalNAc | 3835 |
| 1194506 | 1129492 | T$_{ks}$$^m$C$_{ks}$T$_{ks}$$^m$C$_{ds}$A$_{ds}$$^m$C$_{ds}$T$_{ds}$G$_{ds}$$^m$C$_{ds}$G$_{ds}$G$_{ds}$A$_{ds}$A$_{ds}$T$_{ks}$$^m$C$_{ks}$A$_k$-3'-HPPO-GalNAc | 3911 |

TABLE 118-continued

Design of GalNAc conjugated modified oligonucleotides complementary to human FXII

| Compound No. | Parent Compound No. | Sequence and Chemistry notation (5' to 3') | SEQ ID No. |
|---|---|---|---|
| 1194507 | 1129510 | $A_{ks}G_{ks}{}^mC_{ks}T_{ds}G_{ds}G_{ds}{}^mC_{ds}{}^mC_{ds}G_{ds}{}^mC_{ds}A_{ds}{}^mC_{ds}T_{ds}G_{ks}G_{ks}G_{k}$-3'-HPPO-GalNAc | 3760 |
| 1194508 | 1129527 | $T_{ks}{}^mC_{ks}{}^mC_{ks}T_{ds}G_{ds}{}^mC_{ds}G_{ds}{}^mC_{ds}{}^mC_{ds}A_{ds}T_{ds}{}^mC_{ds}{}^mC_{ds}T_{ks}G_{ks}G_{k}$-3'-HPPO-GalNAc | 3533 |
| 1194509 | 1129530 | $A_{ks}G_{ks}T_{ks}T_{ds}{}^mC_{ds}{}^mC_{ds}T_{ds}G_{ds}{}^mC_{ds}G_{ds}{}^mC_{ds}{}^mC_{ds}A_{ds}T_{ks}{}^mC_{ks}{}^mC_{k}$-3'-HPPO-GalNAc | 3761 |
| 1194510 | 1129531 | $G_{ks}A_{ks}G_{ks}T_{ds}T_{ds}{}^mC_{ds}{}^mC_{ds}T_{ds}G_{ds}{}^mC_{ds}G_{ds}{}^mC_{ds}{}^mC_{ds}A_{ks}T_{ks}{}^mC_{k}$-3'-HPPO-GalNAc | 3837 |
| 1194512 | 1129533 | $T_{ks}T_{ks}G_{ks}A_{ds}G_{ds}T_{ds}T_{ds}{}^mC_{ds}{}^mC_{ds}T_{ds}G_{ds}{}^mC_{ds}G_{ds}{}^mC_{ks}{}^mC_{ks}A_{k}$-3'-HPPO-GalNAc | 2463 |
| 1194513 | 1129534 | $A_{ks}T_{ks}T_{ks}G_{ds}A_{ds}G_{ds}T_{ds}T_{ds}{}^mC_{ds}{}^mC_{ds}T_{ds}G_{ds}{}^mC_{ds}G_{ks}{}^mC_{ks}{}^mC_{k}$-3'-HPPO-GalNAc | 2540 |
| 1194514 | 1129538 | $A_{ks}{}^mC_{ks}T_{ks}T_{ds}T_{ds}A_{ds}T_{ds}T_{ds}G_{ds}A_{ds}G_{ds}T_{ds}T_{ds}{}^mG_{ks}{}^mC_{ks}T_{k}$-3'-HPPO-GalNAc | 2848 |
| 1194515 | 1129540 | $G_{ks}{}^mC_{ks}A_{ks}{}^mC_{ds}T_{ds}T_{ds}T_{ds}A_{ds}T_{ds}T_{ds}G_{ds}A_{ds}G_{ds}T_{ks}T_{ks}{}^mC_{k}$-3'-HPPO-GalNAc | 3000 |
| 1194516 | 1129542 | $A_{ks}A_{ks}G_{ks}{}^mC_{ds}A_{ds}{}^mC_{ds}T_{ds}T_{ds}T_{ds}A_{ds}T_{ds}T_{ds}G_{ds}A_{ks}G_{ks}T_{k}$-3'-HPPO-GalNAc | 3147 |
| 1194517 | 1129543 | $A_{ks}A_{ks}A_{ks}G_{ds}{}^mC_{ds}A_{ds}{}^mC_{ds}T_{ds}T_{ds}T_{ds}A_{ds}T_{ds}T_{ds}G_{ks}A_{ks}G_{k}$-3'-HPPO-GalNAc | 3229 |
| 1194518 | 1129544 | ${}^mC_{ks}A_{ks}A_{ks}A_{ds}G_{ds}{}^mC_{ds}A_{ds}{}^mC_{ds}T_{ds}T_{ds}T_{ds}A_{ds}T_{ds}T_{ks}G_{ks}A_{k}$-3'-HPPO-GalNAc | 3306 |
| 1194519 | 1129545 | $T_{ks}{}^mC_{ks}A_{ks}A_{ds}A_{ds}G_{ds}{}^mC_{ds}A_{ds}{}^mC_{ds}T_{ds}T_{ds}T_{ds}A_{ds}T_{ks}T_{ks}G_{k}$-3'-HPPO-GalNAc | 3382 |
| 1194520 | 1129947 | $T_{ks}G_{ks}{}^mC_{ks}T_{ds}T_{ds}T_{ds}T_{ds}{}^mC_{ds}{}^mC_{ds}G_{ds}{}^mC_{ds}A_{ds}{}^mC_{ds}T_{ks}{}^mC_{ks}{}^mC_{k}$-3'-HPPO-GalNAc | 3554 |
| 1194572 | 1194286 | ${}^mC_{ks}T_{ks}T_{ks}T_{ds}{}^mC_{ds}{}^mC_{ds}G_{ds}{}^mC_{ds}A_{ds}{}^mC_{ds}T_{ds}{}^mC_{ds}T_{ds}{}^mC_{ks}{}^mC_{ks}{}^mC_{k}$-3'-HPPO-GalNAc | 4026 |
| 1194573 | 1194287 | $G_{ks}{}^mC_{ks}T_{ks}T_{ds}T_{ds}{}^mC_{ds}{}^mC_{ds}G_{ds}{}^mC_{ds}A_{ds}{}^mC_{ds}T_{ds}{}^mC_{ds}T_{ks}{}^mC_{ks}{}^mC_{k}$-3'-HPPO-GalNAc | 4102 |
| 1194574 | 1194288 | ${}^mC_{ks}T_{ks}G_{ks}{}^mC_{ds}T_{ds}T_{ds}T_{ds}{}^mC_{ds}{}^mC_{ds}G_{ds}{}^mC_{ds}A_{ds}{}^mC_{ds}T_{ks}{}^mC_{ks}T_{k}$-3'-HPPO-GalNAc | 4253 |
| 1194575 | 1194289 | $T_{ks}{}^mC_{ks}T_{ks}G_{ds}{}^mC_{ds}T_{ds}T_{ds}T_{ds}{}^mC_{ds}{}^mC_{ds}G_{ds}{}^mC_{ds}A_{ds}{}^mC_{ks}T_{ks}{}^mC_{k}$-3'-HPPO-GalNAc | 4329 |
| 1194576 | 1194290 | ${}^mC_{ks}A_{ks}T_{ks}{}^mC_{ds}T_{ds}G_{ds}{}^mC_{ds}T_{ds}T_{ds}T_{ds}{}^mC_{ds}{}^mC_{ds}G_{ds}{}^mC_{ks}A_{ks}{}^mC_{k}$-3'-HPPO-GalNAc | 4405 |
| 1194578 | 1194292 | ${}^mC_{ks}T_{ks}{}^mC_{ks}A_{ds}T_{ds}{}^mC_{ds}T_{ds}G_{ds}{}^mC_{ds}T_{ds}T_{ds}T_{ds}{}^mC_{ds}{}^mC_{ks}G_{ks}{}^mC_{k}$-3'-HPPO-GalNAc | 4557 |
| 1194579 | 1194293 | ${}^mC_{ks}T_{ks}{}^mC_{ks}T_{ds}{}^mC_{ds}A_{ds}T_{ds}{}^mC_{ds}T_{ds}G_{ds}{}^mC_{ds}T_{ds}T_{ks}{}^mC_{ks}{}^mC_{k}$-3'-HPPO-GalNAc | 4708 |
| 1194580 | 1194294 | ${}^mC_{ks}{}^mC_{ks}T_{ks}{}^mC_{ds}T_{ds}{}^mC_{ds}A_{ds}T_{ds}{}^mC_{ds}T_{ds}G_{ds}{}^mC_{ds}T_{ds}T_{ks}T_{ks}{}^mC_{k}$-3'-HPPO-GalNAc | 4783 |
| 1194581 | 1194295 | ${}^mC_{ks}{}^mC_{ks}{}^mC_{ks}T_{ds}{}^mC_{ds}T_{ds}{}^mC_{ds}A_{ds}T_{ds}{}^mC_{ds}T_{ds}G_{ds}{}^mC_{ds}T_{ks}T_{ks}T_{k}$-3'-HPPO-GalNAc | 4859 |
| 1194582 | 1194296 | $T_{ks}{}^mC_{ks}{}^mC_{ks}{}^mC_{ds}T_{ds}{}^mC_{ds}T_{ds}{}^mC_{ds}A_{ds}T_{ds}{}^mC_{ds}T_{ds}G_{ds}{}^mC_{ks}T_{ks}T_{k}$-3'-HPPO-GalNAc | 3950 |
| 1194583 | 1194297 | ${}^mC_{ks}T_{ks}{}^mC_{ks}{}^mC_{ds}{}^mC_{ds}T_{ds}{}^mC_{ds}T_{ds}{}^mC_{ds}A_{ds}T_{ds}{}^mC_{ds}T_{ds}G_{ks}{}^mC_{ks}T_{k}$-3'-HPPO-GalNAc | 4027 |
| 1270699 | 1207006 | THA-GalNAc-${}_o{}^mC_kA_{es}{}^mC_{ks}T_{ds}T_{ds}T_{ds}A_{ds}T_{ds}T_{ds}G_{ds}A_{ds}G_{ds}T_{es}T_{es}{}^mC_{ks}{}^mC_{k}$ | 2924 |
| 1270700 | 1207007 | THA-GalNAc-${}_oG_{ks}{}^mC_{es}A_{ks}{}^mC_{ds}T_{ds}T_{ds}T_{ds}A_{ds}T_{ds}T_{ds}G_{ds}A_{ds}G_{es}T_{es}T_{ks}{}^mC_{k}$ | 3000 |
| 1270701 | 1207160 | THA-GalNAc-${}_o{}^mC_{ks}A_{ks}{}^mC_{ds}T_{ds}T_{ds}T_{ds}A_{ds}T_{ds}T_{ds}G_{ds}A_{ds}G_{es}T_{es}T_{es}{}^mC_{ks}{}^mC_{k}$ | 2924 |
| 1270702 | 1207161 | THA-GalNAc-${}_oG_{ks}{}^mC_{ks}A_{ds}{}^mC_{ds}T_{ds}T_{ds}T_{ds}A_{ds}T_{ds}T_{ds}G_{ds}A_{es}G_{es}T_{es}T_{ks}{}^mC_{k}$ | 3000 |
| 1270703 | 1207277 | THA-GalNAc-${}_o{}^mC_{ks}A_{ks}{}^mC_{ds}T_{ds}T_{ds}T_{ds}A_{ds}T_{ds}T_{ds}G_{ds}A_{ds}G_{es}T_{ks}T_{es}{}^mC_{ks}{}^mC_{e}$ | 2924 |
| 1270705 | 1213144 | THA-GalNAc-${}_oG_{ks}{}^mC_{ks}A_{ks}{}^mC_{ds}UyT_{ds}T_{ds}A_{ds}T_{ds}T_{ds}G_{ds}A_{ds}G_{ds}T_{ks}T_{ks}{}^mC_{k}$ | 5006 |
| 1270707 | 1213260 | THA-GalNAc-${}_o{}^mC_{ks}A_{ks}{}^mC_{ks}T_{ds}T_{ds}UysA_{ds}T_{ds}T_{ds}G_{ds}A_{ds}G_{ds}T_{ds}T_{ks}{}^mC_{ks}{}^mC_{k}$ | 5035 |
| 1270710 | 1207393 | THA-GalNAc-${}_oA_{ks}{}^mC_{ks}T_{ds}T_{ds}T_{ds}A_{ds}T_{ds}T_{ds}G_{ds}A_{ds}G_{ds}T_{ks}T_{es}{}^mC_{ks}{}^mC_{es}T_{k}$ | 2848 |
| 1270712 | 1207394 | THA-GalNAc-${}_o{}^mC_{ks}A_{ks}{}^mC_{ds}T_{ds}T_{ds}T_{ds}A_{ds}T_{ds}T_{ds}G_{ds}A_{ds}G_{ks}T_{es}T_{ks}{}^mC_{es}{}^mC_{k}$ | 2924 |
| 1270714 | 1207279 | THA-GalNAc-${}_oA_{ks}G_{ks}{}^mC_{ds}A_{ds}{}^mC_{ds}T_{ds}T_{ds}T_{ds}A_{ds}T_{ds}T_{ds}G_{es}A_{ks}G_{es}T_{ks}Te$ | 3076 |
| 1270715 | 1207159 | THA-GalNAc-${}_oA_{ks}{}^mC_{ks}T_{ds}T_{ds}T_{ds}A_{ds}T_{ds}T_{ds}G_{ds}A_{ds}G_{ds}T_{es}T_{es}{}^mC_{es}{}^mC_{ks}T_{k}$ | 2848 |
| 1270716 | 1207005 | THA-GalNAc-${}_oA_{ks}{}^mC_{es}T_{ks}T_{ds}T_{ds}A_{ds}T_{ds}T_{ds}G_{ds}A_{ds}G_{ds}T_{ds}T_{es}{}^mC_{es}{}^mC_{ks}T_{k}$ | 2848 |

Example 9: Design of Oligomeric Compounds Complementary to a Human FXII Nucleic Acid Modified oligonucleotides were designed as indicated in the tables below. The chemistry notation column in the tables below specifies the specific chemistry notation for modified oligonucleotides; wherein subscript 'd' represents a 2'-β-D-deoxyribosyl sugar moiety, subscript 'e' represents a 2'-MOE sugar moiety, subscript 'y' represents a 2'-O-methyl sugar moiety, subscript 'k' represents a cET modified sugar moiety, subscript 's' represents a phosphorothioate internucleoside linkage, subscript 'o' represents a phosphodiester internucleoside linkage, and superscript 'm' before the cytosine residue ($^m$C) represents a 5-methyl cytosine.

"Start site" indicates the 5'-most nucleoside of the target sequence to which the modified oligonucleotide is complementary. "Stop site" indicates the 3'-most nucleoside of the target sequence to which the modified oligonucleotide is complementary. As shown in the tables below, the modified oligonucleotides are complementary to either the human FXII mRNA, designated herein as SEQ ID NO: 1 (described herein above) or to the human FXII genomic sequence, designated herein as SEQ ID NO: 2 (described herein above) or to both. 'N/A' indicates that the modified oligonucleotide is not complementary to that particular target sequence with 100% complementarity.

TABLE 119

5-10-5 2'O-methyl modified oligonucleotides complementary to human FXII

| Compound Number | SEQ ID NO: 1 Start Site | SEQ ID NO: 1 Stop Site | SEQ ID NO: 2 Start Site | SEQ ID NO: 2 Stop Site | Sequence and Chemistry notation (5' to 3') | SEQ ID No. |
|---|---|---|---|---|---|---|
| 1213034 | 2014 | 2033 | 7402 | 7421 | $C_{ys}A_{ys}C_{ys}U_{ys}U_{ys}T_{ds}A_{ds}T_{ds}T_{ds}G_{ds}A_{ds}G_{ds}T_{ds}T_{ds}{}^mC_{ds}C_{ys}U_{ys}G_{ys}C_{ys}G_y$ | 5039 |
| 1358035 | 1936 | 1955 | 7324 | 7343 | $C_{ys}C_{ys}C_{ys}C_{ys}A_{ys}G_{ds}{}^mC_{ds}{}^mC_{ds}A_{ds}{}^mC_{ds}T_{ds}{}^mC_{ds}T_{ds}{}^mC_{ds}T_{ds}C_{ys}A_{ys}C_{ys}U_{ys}G_y$ | 5040 |
| 1213030 | 1924 | 1943 | 7312 | 7331 | $U_{ys}C_{ys}U_{ys}C_{ys}A_{ys}{}^mC_{ds}T_{ds}G_{ds}{}^mC_{ds}G_{ds}G_{ds}A_{ds}A_{ds}T_{ds}{}^mC_{ds}A_{ys}C_{ys}C_{ys}A_{ys}A_y$ | 5041 |
| 1213029 | 1914 | 1933 | 7302 | 7321 | $G_{ys}A_{ys}A_{ys}U_{ys}C_{ys}A_{ds}{}^mC_{ds}{}^mC_{ds}A_{ds}A_{ds}G_{ds}G_{ds}A_{ds}G_{ds}G_{ys}A_{ys}A_{ys}A_{ys}G_y$ | 5042 |

Example 10: Tolerability of Modified Oligonucleotides Targeting Human FXII in CD-1 Mice CD-1 mice are a multipurpose mouse model frequently utilized for safety and efficacy testing. The mice were treated with modified oligonucleotides selected from studies described above and evaluated for changes in the levels of various plasma chemistry markers.

Study 1

Groups of four 7-to-8-week-old male CD-1 mice were injected subcutaneously once a week for six weeks (for a total of 6 treatments) with 80 mg/kg of modified oligonucleotides. One group of four male CD-1 mice was injected with saline. Mice were euthanized 72 hours following the final administration.

To evaluate the effect of modified oligonucleotides on liver and kidney function, plasma levels of aspartate aminotransferase (AST), alanine aminotransferase (ALT), total bilirubin (TBIL), blood urea nitrogen (BUN), creatinine (CRT) and albumin were measured using an automated clinical chemistry analyzer (Hitachi Olympus AU400c, Melville, NY). The results are presented in the table below. Modified oligonucleotides that caused changes in the levels of any of the liver or kidney function markers outside the expected range for modified oligonucleotides were excluded in further studies.

TABLE 120

Plasma chemistry markers in male CD-1 mice

| Compound No. | AST (IU/L) | ALT (IU/L) | TBIL (mg/dL) | BUN (mg/dL) | CRT (mg/dL) | Albumin (mg/dL) |
|---|---|---|---|---|---|---|
| saline | 51 | 33 | 0.27 | 25 | 0.05 | 2.82 |
| 1194378 | 603 | 1124 | 0.34 | 27 | 0.07 | 2.61 |
| 1194379 | 255 | 740 | 0.25 | 22 | 0.04 | 2.65 |
| 1194380 | 62 | 58 | 0.17 | 26 | 0.08 | 2.84 |
| 1194381 | 368 | 375 | 0.18 | 24 | 0.09 | 2.83 |
| 1194382 | 380 | 423 | 0.21 | 25 | 0.08 | 2.67 |
| 1194383 | 72 | 104 | 0.15 | 25 | 0.06 | 2.54 |
| 1194384 | 66 | 41 | 0.17 | 23 | 0.05 | 2.70 |
| 1194385 | 1287 | 1501 | 0.24 | 27 | 0.08 | 2.10 |
| 1194387 | 157 | 239 | 0.26 | 27 | 0.06 | 2.69 |
| 1194388 | 68 | 48 | 0.17 | 24 | 0.07 | 2.77 |
| 1194389 | 69 | 53 | 0.16 | 25 | 0.06 | 2.75 |
| 1194390 | 870 | 1395 | 0.22 | 26 | 0.08 | 2.84 |
| 1194391 | 49 | 40 | 0.17 | 23 | 0.07 | 2.81 |
| 1194392 | 62 | 56 | 0.16 | 27 | 0.07 | 2.75 |

TABLE 120-continued

Plasma chemistry markers in male CD-1 mice

| Compound No. | AST (IU/L) | ALT (IU/L) | TBIL (mg/dL) | BUN (mg/dL) | CRT (mg/dL) | Albumin (mg/dL) |
|---|---|---|---|---|---|---|
| 1194393 | 51 | 39 | 0.16 | 22 | 0.07 | 2.58 |
| 1194394 | 99 | 106 | 0.20 | 24 | 0.07 | 2.84 |
| 1194395 | 71 | 112 | 0.13 | 24 | 0.05 | 2.53 |
| 1194396 | 1614 | 1954 | 1.81 | 18 | 0.03 | 2.54 |
| 1194397 | 678 | 836 | 0.20 | 17 | 0.06 | 2.62 |
| 1194398 | 713 | 867 | 0.20 | 23 | 0.07 | 2.76 |
| 1194399 | 548 | 393 | 0.26 | 26 | 0.07 | 2.84 |
| 1194400 | 854 | 1165 | 0.66 | 22 | 0.07 | 2.78 |
| 1194401 | 457 | 1201 | 0.23 | 27 | 0.05 | 2.76 |

Body weights of CD-1 mice were measured at days 1 and 40, and the average body weight for each group is presented in the table below. Liver, kidney and spleen weights were measured at the end of the study and are presented in the table below. Modified oligonucleotides that caused any changes in organ weights outside the expected range for modified oligonucleotides were excluded from further studies.

TABLE 121

Body and organ weights (in grams)

| Compound No. | Body Weight (g) Day 1 | Body Weight (g) Day 40 | Liver (g) | Kidney (g) | Spleen (g) |
|---|---|---|---|---|---|
| saline | 31 | 36 | 2.0 | 0.6 | 0.1 |
| 1194378 | 32 | 39 | 2.6 | 0.6 | 0.1 |
| 1194379 | 32 | 38 | 2.7 | 0.6 | 0.1 |
| 1194380 | 32 | 38 | 2.6 | 0.6 | 0.1 |
| 1194381 | 32 | 40 | 2.8 | 0.6 | 0.1 |
| 1194382 | 32 | 38 | 2.5 | 0.6 | 0.1 |
| 1194383 | 31 | 36 | 2.2 | 0.5 | 0.1 |
| 1194384 | 32 | 40 | 2.2 | 0.6 | 0.1 |
| 1194385 | 31 | 39 | 3.0 | 0.6 | 0.1 |
| 1194387 | 30 | 37 | 2.2 | 0.5 | 0.3 |
| 1194388 | 31 | 38 | 2.5 | 0.6 | 0.2 |
| 1194389 | 30 | 37 | 2.3 | 0.6 | 0.1 |
| 1194390 | 32 | 38 | 3.2 | 0.6 | 0.1 |
| 1194391 | 30 | 37 | 2.4 | 0.6 | 0.1 |
| 1194392 | 32 | 38 | 2.2 | 0.6 | 0.1 |
| 1194393 | 31 | 38 | 2.0 | 0.6 | 0.1 |
| 1194394 | 31 | 37 | 2.1 | 0.6 | 0.1 |
| 1194395 | 32 | 37 | 2.4 | 0.6 | 0.1 |
| 1194396 | 31 | 35 | 2.0 | 0.6 | 0.1 |
| 1194397 | 32 | 40 | 2.8 | 0.6 | 0.1 |
| 1194398 | 32 | 38 | 3.0 | 0.6 | 0.2 |
| 1194399 | 32 | 38 | 2.9 | 0.6 | 0.2 |
| 1194400 | 31 | 38 | 3.2 | 0.6 | 0.1 |
| 1194401 | 33 | 41 | 2.6 | 0.6 | 0.2 |

Study 2

Groups of four 7-to-8-week-old male CD-1 mice were injected subcutaneously once a week for six weeks (for a total of 6 treatments) with 80 mg/kg of modified oligonucleotides. One group of four male CD-1 mice was injected with saline. Mice were euthanized 72 hours following the final administration.

To evaluate the effect of modified oligonucleotides on liver and kidney function, plasma levels of aspartate aminotransferase (AST), alanine aminotransferase (ALT), total bilirubin (TBIL), blood urea nitrogen (BUN), creatinine (CRT) and albumin were measured using an automated clinical chemistry analyzer (Hitachi Olympus AU400c, Melville, NY). The results are presented in the table below. Modified oligonucleotides that caused changes in the levels of any of the liver or kidney function markers outside the expected range for modified oligonucleotides were excluded in further studies.

TABLE 122

Plasma chemistry markers in male CD-1 mice

| Compound No. | AST (IU/L) | ALT (IU/L) | TBIL (mg/dL) | BUN (mg/dL) | CRT (mg/dL) | Albumin (mg/dL) |
|---|---|---|---|---|---|---|
| saline | 70 | 68 | 0.16 | 22 | 0.09 | 2.84 |
| 1194402 | 66 | 66 | 0.17 | 24 | 0.09 | 2.73 |
| 1194403 | 67 | 64 | 0.15 | 26 | 0.09 | 2.64 |
| 1194404 | 77 | 82 | 0.17 | 25 | 0.10 | 2.91 |
| 1194405 | 100 | 155 | 0.14 | 25 | 0.07 | 2.53 |
| 1194406 | 95 | 84 | 0.15 | 25 | 0.07 | 2.60 |
| 1194407 | 94 | 69 | 0.11 | 19 | 0.07 | 2.56 |
| 1194408 | 111 | 137 | 0.15 | 26 | 0.06 | 2.54 |
| 1194409 | 134 | 102 | 0.16 | 25 | 0.06 | 2.69 |
| 1194410 | 344 | 385 | 0.18 | 28 | 0.08 | 2.53 |
| 1194411 | 321 | 242 | 0.15 | 22 | 0.08 | 2.53 |
| 1194412 | 227 | 333 | 0.17 | 25 | 0.06 | 2.49 |
| 1194413 | 110 | 61 | 0.16 | 24 | 0.10 | 2.79 |
| 1194415 | 143 | 132 | 0.13 | 25 | 0.08 | 2.39 |
| 1194416 | 73 | 107 | 0.11 | 21 | 0.06 | 2.43 |
| 1194417 | 488 | 672 | 0.24 | 23 | 0.05 | 2.43 |
| 1194419 | 72 | 60 | 0.14 | 28 | 0.08 | 2.64 |
| 1194420 | 104 | 86 | 0.15 | 26 | 0.09 | 2.72 |
| 1194421 | 548 | 502 | 0.26 | 26 | 0.12 | 2.99 |
| 1194423 | 255 | 443 | 0.11 | 25 | 0.04 | 1.54 |
| 1194424 | 325 | 423 | 0.14 | 26 | 0.09 | 2.48 |
| 1194425 | 447 | 490 | 0.18 | 25 | 0.10 | 2.95 |
| 1194426 | 320 | 298 | 0.21 | 26 | 0.10 | 2.80 |
| 1194427 | 147 | 194 | 0.18 | 22 | 0.08 | 2.75 |

Body weights of CD-1 mice were measured at days 1 and 39, and the average body weight for each group is presented in the table below. Liver, kidney and spleen weights were measured at the end of the study and are presented in the table below. Modified oligonucleotides that caused any changes in organ weights outside the expected range for modified oligonucleotides were excluded from further studies.

TABLE 123

Body and organ weights (in grams)

| Compound No. | Body Weight (g) Day 1 | Body Weight (g) Day 39 | Liver (g) | Kidney (g) | Spleen (g) |
|---|---|---|---|---|---|
| Saline | 33 | 38 | 2.0 | 0.6 | 0.1 |
| 1194402 | 35 | 41 | 2.3 | 0.6 | 0.1 |
| 1194403 | 32 | 37 | 2.2 | 0.5 | 0.1 |
| 1194404 | 33 | 39 | 2.4 | 0.6 | 0.2 |
| 1194405 | 35 | 41 | 2.7 | 0.6 | 0.1 |
| 1194406 | 34 | 43 | 2.7 | 0.7 | 0.1 |
| 1194407 | 32 | 38 | 2.1 | 0.6 | 0.1 |
| 1194408 | 33 | 39 | 2.6 | 0.7 | 0.2 |
| 1194409 | 32 | 39 | 2.7 | 0.6 | 0.1 |
| 1194410 | 35 | 41 | 2.9 | 0.6 | 0.2 |
| 1194411 | 35 | 41 | 2.9 | 0.6 | 0.1 |
| 1194412 | 32 | 38 | 2.7 | 0.6 | 0.2 |
| 1194413 | 32 | 39 | 2.3 | 0.6 | 0.1 |
| 1194415 | 33 | 37 | 2.2 | 0.6 | 0.2 |
| 1194416 | 34 | 39 | 2.3 | 0.6 | 0.1 |
| 1194417 | 35 | 41 | 2.3 | 0.6 | 0.2 |
| 1194419 | 33 | 37 | 2.1 | 0.5 | 0.1 |
| 1194420 | 33 | 38 | 2.2 | 0.6 | 0.1 |
| 1194421 | 37 | 42 | 2.7 | 0.6 | 0.1 |
| 1194423 | 33 | 39 | 2.7 | 0.6 | 0.2 |
| 1194424 | 33 | 41 | 2.8 | 0.6 | 0.2 |
| 1194425 | 37 | 41 | 2.0 | 0.6 | 0.1 |
| 1194426 | 35 | 41 | 2.7 | 0.6 | 0.2 |
| 1194427 | 34 | 41 | 2.9 | 0.6 | 0.1 |

Study 3

Groups of two 8-to-10-week-old male CD-1 mice were injected subcutaneously once (for a total of 1 treatment) with 50 mg/kg of modified oligonucleotides. One group of two male CD-1 mice was injected with saline. Mice were euthanized 4 days following administration.

To evaluate the effect of modified oligonucleotides on liver and kidney function, plasma levels of aspartate aminotransferase (AST), alanine aminotransferase (ALT), total bilirubin (TBIL), blood urea nitrogen (BUN), creatinine (CRT) and albumin were measured using an automated clinical chemistry analyzer (Hitachi Olympus AU400c, Melville, NY). The results are presented in the table below.

Assays include two animals in a group, except where the symbol "‡" indicates that only 1 animal was used for a specific assay. Modified oligonucleotides that caused changes in the levels of any of the liver or kidney function markers outside the expected range for modified oligonucleotides were excluded in further studies.

TABLE 124

Plasma chemistry markers in male CD-1 mice

| Compound No. | AST (IU/L) | ALT (IU/L) | TBIL (mg/dL) | BUN (mg/dL) | CRT (mg/dL) | Albumin (mg/dL) |
|---|---|---|---|---|---|---|
| saline | 81 | 63 | 0.13 | 18 | 0.12 | 2.5 |
| 1194483 | 1073 | 1351 | 0.78 | 19 | 0.13 | 2.58 |
| 1194484 | 5261 | 6171 | 4.19 | 15 | 0.13 | 2.46 |
| 1194486 | 112 | 115 | 0.17 | 19 | 0.14 | 2.85 |
| 1194487‡ | 2747 | 3998 | 5.21 | 16 | 0.2 | 2.91 |
| 1194488 | 68 | 46 | 0.14 | 25 | 0.14 | 2.92 |
| 1194489 | 43 | 38 | 0.16 | 23 | 0.13 | 2.48 |
| 1194490 | 61 | 62 | 0.13 | 21 | 0.13 | 2.74 |
| 1194491 | 59 | 77 | 0.16 | 21 | 0.16 | 2.85 |
| 1194492 | 47 | 26 | 0.13 | 23 | 0.14 | 2.59 |
| 1194493 | 114 | 141 | 0.15 | 21 | 0.15 | 2.77 |
| 1194494‡ | 2255 | 3189 | 3.49 | 25 | 0.09 | 2.25 |
| 1194495 | 3848 | 3311 | 1.48 | 19 | 0.15 | 2.56 |
| 1194496 | 839 | 3491 | 2.8 | 21 | 0.14 | 2.37 |
| 1194497 | 3145 | 3724 | 0.77 | 20 | 0.17 | 2.53 |
| 1194498 | 229 | 251 | 0.17 | 15 | 0.12 | 2.14 |
| 1194499 | 519 | 464 | 0.93 | 26 | 0.18 | 2.85 |
| 1194500 | 58 | 52 | 0.16 | 21 | 0.12 | 2.61 |
| 1194501 | 60 | 30 | 0.13 | 21 | 0.14 | 2.69 |
| 1194502 | 45 | 30 | 0.15 | 21 | 0.14 | 2.61 |
| 1194503 | 57 | 38 | 0.14 | 19 | 0.14 | 2.68 |
| 1194504 | 47 | 53 | 0.15 | 20 | 0.13 | 2.63 |
| 1194505‡ | 109 | 183 | 0.15 | 23 | 0.16 | 3.06 |
| 1194506 | 63 | 96 | 0.14 | 25 | 0.13 | 2.86 |
| 1194507 | 124 | 198 | 0.16 | 22 | 0.14 | 2.41 |
| 1194508 | 1291 | 797 | 0.3 | 17 | 0.14 | 2.81 |
| 1194509 | 6147 | 5321 | 3.17 | 18 | 0.18 | 2.99 |
| 1194510 | 322 | 505 | 0.21 | 19 | 0.15 | 2.83 |
| 1194512‡ | 2308 | 5902 | 1.98 | 18 | 0.09 | 2.52 |
| 1194513 | 87 | 112 | 0.21 | 20 | 0.14 | 2.42 |
| 1194514 | 60 | 63 | 0.13 | 19 | 0.14 | 2.52 |
| 1194515 | 90 | 116 | 0.14 | 23 | 0.13 | 2.52 |
| 1194516 | 54 | 47 | 0.15 | 21 | 0.16 | 2.62 |
| 1194517 | 102 | 102 | 0.14 | 17 | 0.16 | 2.54 |
| 1194518 | 78 | 83 | 0.15 | 22 | 0.13 | 2.62 |
| 1194519 | 43 | 32 | 0.19 | 19 | 0.12 | 2.66 |
| 1194520 | 84 | 61 | 0.12 | 20 | 0.15 | 2.56 |
| 1194572 | 148 | 153 | 0.14 | 22 | 0.11 | 2.54 |
| 1194573 | 71 | 50 | 0.16 | 18 | 0.14 | 2.6 |
| 1194574‡ | 324 | 428 | 0.11 | 25 | 0.13 | 2.77 |
| 1194575‡ | 6483 | 7128 | 6.54 | 27 | 0.14 | 2.39 |
| 1194576 | 2701 | 1943 | 6.15 | 30 | 0.32 | 2.44 |
| 1194578 | N/A | 1182‡ | 5.22 | 85 | 0.69 | 2.63 |
| 1194579 | 4055 | 6429 | 4.34 | 25 | 0.18 | 2.83 |
| 1194580‡ | 3302 | 4048 | 6.96 | 24 | 0.2 | 2.51 |
| 1194581 | 6176 | 6185 | 5.21 | 22 | 0.21 | 3.23 |
| 1194582 | 1160‡ | 16‡ | 3.86 | 32 | 0.32 | 3.31 |
| 1194583‡ | N/A | N/A | 5.19 | 27 | 0.19 | 3.44 |

Study 4

Groups of four 7-to-8-week-old male CD-1 mice were injected subcutaneously once per week for 6 weeks (for a total of 6 treatments) with 40 mg/kg of modified oligonucleotides. One group of four male CD-1 mice was injected with saline. Mice were euthanized 2 days following final administration.

To evaluate the effect of modified oligonucleotides on liver and kidney function, plasma levels of aspartate aminotransferase (AST), alanine aminotransferase (ALT), total bilirubin (TBIL), blood urea nitrogen (BUN), creatinine (CRT) and albumin were measured using an automated clinical chemistry analyzer (Hitachi Olympus AU400c, Melville, NY). The results are presented in the table below.

Assays include four animals in a group, except where the symbol "‡" indicates that 3 animals or less was used for a specific assay. Modified oligonucleotides that caused changes in the levels of any of the liver or kidney function markers outside the expected range for modified oligonucleotides were excluded in further studies.

TABLE 125

Plasma chemistry markers in male CD-1 mice

| Compound No. | AST (IU/L) | ALT (IU/L) | TBIL (mg/dL) | BUN (mg/dL) | CRT (mg/dL) | Albumin (mg/dL) |
|---|---|---|---|---|---|---|
| saline | 74 | 57 | 0.24 | 20 | 0.11 | 3.07 |
| 1194343 | 767 | 1036 | 0.41 | 16 | 0.10 | 2.87 |
| 1194345 | 165 | 163 | 0.20 | 23 | 0.12 | 2.75 |
| 1194346 | 826 | 955 | 0.25 | 25 | 0.16 | 3.06 |
| 1194347 | 965 | 1210 | 0.22 | 23 | 0.12 | 3.01 |
| 1194348 | 1886 | 3635 | 0.55 | 24 | 0.15 | 3.15 |
| 1194349 | 140 | 209 | 0.19 | 22 | 0.12 | 2.75 |
| 1194350 | 1342 | 1861 | 0.24 | 23 | 0.13 | 2.72 |
| 1194357 | 66 | 46 | 0.13 | 25 | 0.14 | 2.61 |
| 1194358 | 54 | 59 | 0.16 | 24 | 0.15 | 2.99 |
| 1194359 | 132 | 202 | 0.16 | 22 | 0.11 | 2.66 |
| 1194360 | 119 | 263 | 0.15 | 19 | 0.08 | 2.57 |
| 1194361 | 596 | 740 | 0.21 | 27 | 0.09 | 2.83 |
| 1194363‡ | 441 | 604 | 0.19 | 22 | 0.11 | 3.08 |
| 1194370 | 502 | 572 | 0.16 | 21 | 0.09 | 2.74 |
| 1194371 | 58 | 53 | 0.18 | 22 | 0.09 | 2.85 |
| 1194372 | 510 | 646 | 0.27 | 21 | 0.09 | 2.88 |
| 1194373 | 677 | 963 | 0.24 | 20 | 0.08 | 2.87 |
| 1194374 | 1530 | 2506 | 0.20 | 23 | 0.09 | 2.99 |
| 1194375 | 544 | 815 | 0.18 | 19 | 0.09 | 2.81 |
| 1194376 | 251 | 490 | 0.16 | 19 | 0.06 | 2.54 |
| 1194377 | 438 | 704 | 0.18 | 23 | 0.09 | 2.75 |
| 1194429 | 1282 | 1188 | 0.36 | 21 | 0.06 | 2.80 |
| 1194430 | 558 | 820 | 0.18 | 20 | 0.11 | 2.87 |

Body weights of CD-1 mice were measured at days 1 and 35, and the average body weight for each group is presented in the table below. Liver, kidney and spleen weights were measured at the end of the study and are presented in the table below. Modified oligonucleotides that caused any changes in organ weights outside the expected range for modified oligonucleotides were excluded from further studies.

TABLE 126

Body and organ weights (in grams)

| Compound No. | Body Weight (g) Day 1 | Body Weight (g) Day 35 | Liver (g) | Kidney (g) | Spleen (g) |
|---|---|---|---|---|---|
| Saline | 31 | 39 | 2.0 | 0.6 | 0.1 |
| 1194343 | 31 | 37 | 2.3 | 0.5 | 0.1 |
| 1194345 | 33 | 40 | 2.6 | 0.5 | 0.1 |
| 1194346 | 30 | 36 | 2.8 | 0.5 | 0.1 |
| 1194347 | 34 | 39 | 3.1 | 0.6 | 0.2 |
| 1194348 | 33 | 37 | 3.2 | 0.5 | 0.1 |
| 1194349 | 32 | 38 | 2.6 | 0.5 | 0.1 |
| 1194350 | 32 | 39 | 3.3 | 0.6 | 0.2 |
| 1194357 | 31 | 36 | 2.2 | 0.5 | 0.2 |
| 1194358 | 33 | 39 | 2.6 | 0.5 | 0.1 |
| 1194359 | 31 | 36 | 2.3 | 0.5 | 0.1 |
| 1194360 | 31 | 36 | 2.3 | 0.5 | 0.2 |
| 1194361 | 33 | 37 | 2.7 | 0.5 | 0.1 |
| 1194363 | 31 | 35 | 3.4 | 0.5 | 0.2 |
| 1194370 | 32 | 36 | 2.1 | 0.5 | 0.2 |
| 1194371 | 32 | 38 | 2.1 | 0.5 | 0.1 |
| 1194372 | 31 | 36 | 2.3 | 0.5 | 0.1 |
| 1194373 | 32 | 36 | 2.3 | 0.5 | 0.1 |
| 1194374 | 32 | 38 | 3.1 | 0.6 | 0.2 |
| 1194375 | 31 | 37 | 2.9 | 0.5 | 0.2 |
| 1194376 | 31 | 37 | 2.3 | 0.5 | 0.1 |

TABLE 126-continued

Body and organ weights (in grams)

| Compound No. | Body Weight (g) Day 1 | Body Weight (g) Day 35 | Liver (g) | Kidney (g) | Spleen (g) |
|---|---|---|---|---|---|
| 1194377 | 33 | 39 | 2.8 | 0.5 | 0.2 |
| 1194429 | 31 | 36 | 2.7 | 0.5 | 0.3 |
| 1194430 | 32 | 36 | 2.5 | 0.4 | 0.1 |

Example 11: Tolerability of Modified Oligonucleotides Targeting Human FXII in Sprague-Dawley Rats Sprague-Dawley rats are a multipurpose model used for safety and efficacy evaluations. The rats were treated with Ionis modified oligonucleotides described in the Examples above and evaluated for changes in the levels of various plasma chemistry markers.

Study 1

Groups of 4 Sprague-Dawley rats each were weekly injected subcutaneously with 80 mg/kg of Ionis oligonucleotide for 6 weeks (total 6 doses). The rats were euthanized; and organs, urine and plasma were harvested for further analysis 3 days after the last dose.

Plasma Chemistry Markers

To evaluate the effect of Ionis oligonucleotides on hepatic function, plasma levels of transaminases were measured using an automated clinical chemistry analyzer (Hitachi Olympus AU400c, Melville, NY). Plasma levels of ALT (alanine transaminase) and AST (aspartate transaminase) were measured and the results are presented in the table below expressed in IU/L. Plasma levels of total bilirubin (TBIL), creatinine (CREA), albumin (ALB), and Blood Urea Nitrogen (BUN) were also measured using the same clinical chemistry analyzer and the results are also presented in the table below. Ionis modified oligonucleotides that caused changes in the levels of any markers of liver function outside the expected range for modified oligonucleotides were excluded in further studies. In some cases, where less than 4 samples were available in a group, the compounds are marked with the symbol "‡".

TABLE 127

Plasma chemistry markers in Sprague-Dawley rats

| Compound No. | AST (IU/L) | ALT (IU/L) | TBIL (mg/dL) | BUN (mg/dL) | CREA (mg/dL) | ALB (mg/dL) |
|---|---|---|---|---|---|---|
| Saline | 68 | 41 | 0.16 | 17 | 0.21 | 3.13 |
| 1194380 | 89 | 56 | 0.28 | 19 | 0.26 | 3.03 |
| 1194383 | 198 | 158 | 0.22 | 17 | 0.22 | 3.18 |
| 1194384‡ | 52 | 24 | 0.12 | 17 | 0.18 | 2.93 |
| 1194388 | 244 | 80 | 0.34 | 17 | 0.15 | 2.22 |
| 1194389 | 157 | 103 | 0.20 | 27 | 0.59 | 3.31 |
| 1194392 | 64 | 29 | 0.18 | 18 | 0.20 | 3.18 |
| 1194393 | 59 | 32 | 0.15 | 16 | 0.23 | 3.19 |
| 1194394 | 58 | 28 | 0.12 | 17 | 0.20 | 3.03 |
| 1194395 | 154 | 83 | 0.20 | 17 | 0.23 | 2.99 |
| 1194402 | 82 | 64 | 0.17 | 19 | 0.20 | 3.23 |
| 1194403 | 68 | 37 | 0.17 | 16 | 0.22 | 3.13 |

Blood obtained from rat groups at week 6 were sent to IDEXX BioResearch for measurement of blood cell counts. Counts taken include red blood cell (RBC) count, white blood cell (WBC) count, hemoglobin (HGB), hematocrit (HCT), Mean corpuscular volume (MCV), mean corpuscular hemoglobin (MCH), mean corpuscular hemoglobin concentration (MCHC), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 128

Blood Cell Count in Sprague-Dawley Rats

| Compound No. | WBC (/nL) | RBC (/pL) | HGB (g/dL) | HCT (%) | MCV (fL) | MCH (pg) | MCHC (%) | NEU (%) | LYM (%) | MON (%) | PLT (/nL) |
|---|---|---|---|---|---|---|---|---|---|---|---|
| Saline | 11 | 8 | 15 | 44 | 52 | 18 | 35 | 17 | 78 | 4 | 786 |
| 1194380 | 5 | 9 | 15 | 44 | 52 | 18 | 34 | 16 | 77 | 5 | 981 |
| 1194383 | 10 | 9 | 17 | 48 | 51 | 18 | 35 | 12 | 80 | 5 | 916 |
| 1194384 | 8 | 9 | 15 | 44 | 51 | 18 | 35 | 15 | 79 | 4 | 958 |
| 1194388 | 6 | 5 | 10 | 34 | 68 | 21 | 31 | 19 | 74 | 6 | 229 |
| 1194389 | 10 | 9 | 16 | 44 | 52 | 18 | 36 | 16 | 79 | 4 | 1080 |
| 1194392 | 7 | 8 | 15 | 44 | 53 | 18 | 35 | 13 | 83 | 3 | 792 |
| 1194393 | 7 | 9 | 16 | 46 | 53 | 18 | 35 | 19 | 74 | 5 | 714 |
| 1194394 | 5 | 8 | 14 | 41 | 54 | 18 | 34 | 8 | 88 | 2 | 513 |
| 1194395 | 10 | 9 | 15 | 42 | 49 | 17 | 35 | 13 | 80 | 5 | 792 |
| 1194402 | 8 | 9 | 16 | 45 | 50 | 17 | 35 | 9 | 86 | 3 | 800 |
| 1194403 | 6 | 9 | 15 | 44 | 51 | 18 | 35 | 17 | 78 | 4 | 939 |

To evaluate the effect of Ionis oligonucleotides on kidney function, urinary levels of micro total protein (MTP) and creatinine were measured using an automated clinical chemistry analyzer (Hitachi Olympus AU400c, Melville, NY). The ratios of MTP to creatinine (MTP/C ratio) are presented in the table below. Ionis oligonucleotides that caused changes in the levels of the ratio outside the expected range for modified oligonucleotides were excluded in further studies.

TABLE 129

MTP to creatinine ratio in Sprague-Dawley rats

| Compound No. | MTP/C Ratio |
|---|---|
| saline | 1.7 |
| 1194380 | 1.9 |
| 1194383 | 2.5 |
| 1194384 | 2.5 |
| 1194388 | 2.4 |
| 1194389 | 1.9 |
| 1194392 | 1.6 |
| 1194393 | 1.7 |
| 1194394 | 1.9 |
| 1194395 | 1.9 |
| 1194402 | 2.0 |
| 1194403 | 1.8 |

Body weights of rats were measured at days 1 and 38, and the average body weight for each group is presented in the table below. Liver, spleen and kidney weights were measured at the end of the study, and are presented in the table below. Ionis oligonucleotides that caused any changes in organ weights outside the expected range for modified oligonucleotides were excluded from further studies.

TABLE 130

Body and organ weights (g)

| Compound No. | Body Weight (g) Day 1 | Body Weight (g) Day 38 | Liver Weight (g) | Kidney Weight (g) | Spleen Weight (g) |
|---|---|---|---|---|---|
| Saline | 266 | 424 | 18 | 3.4 | 1.0 |
| 1194380 | 255 | 378 | 17 | 3.1 | 1.1 |
| 1194383 | 260 | 370 | 16 | 3.3 | 1.2 |
| 1194384 | 256 | 396 | 17 | 3.5 | 1.4 |
| 1194388 | 256 | 346 | 27 | 3.4 | 4.8 |
| 1194389 | 257 | 398 | 18 | 3.3 | 1.4 |
| 1194392 | 256 | 387 | 19 | 3.3 | 1.5 |
| 1194393 | 245 | 363 | 16 | 2.8 | 1.0 |
| 1194394 | 265 | 389 | 18 | 3.5 | 1.9 |
| 1194395 | 264 | 377 | 14 | 3.2 | 1.3 |
| 1194402 | 249 | 335 | 13 | 2.7 | 1.1 |
| 1194403 | 260 | 387 | 16 | 3.4 | 1.1 |

Study 2

Groups of 4 Sprague-Dawley rats each were weekly injected subcutaneously with 80 mg/kg of Ionis oligonucleotide for 6 weeks (total 6 doses). The rats were euthanized; and organs, urine and plasma were harvested for further analysis 3 days after the last dose.

Plasma Chemistry Markers

To evaluate the effect of Ionis oligonucleotides on hepatic function, plasma levels of transaminases were measured using an automated clinical chemistry analyzer (Hitachi Olympus AU400c, Melville, NY). Plasma levels of ALT (alanine transaminase) and AST (aspartate transaminase) were measured and the results are presented in the table below expressed in IU/L. Plasma levels of total bilirubin (TBIL), creatinine (CREA), albumin (ALB), and Blood Urea Nitrogen (BUN) were also measured using the same clinical chemistry analyzer and the results are also presented in the table below. Ionis modified oligonucleotides that caused changes in the levels of any markers of liver function outside the expected range for modified oligonucleotides were excluded in further studies. In some cases, where less than 4 samples were available in a group, the compounds are marked with the symbol "‡".

TABLE 131

Plasma chemistry markers in Sprague-Dawley rats

| Compound No. | AST (IU/L) | ALT (IU/L) | TBIL (mg/dL) | BUN (mg/dL) | CREA (mg/dL) | ALB (mg/dL) |
|---|---|---|---|---|---|---|
| Saline | 81 | 49 | 0.16 | 15 | 0.22 | 3.11 |
| 1194404 | 99 | 47.5 | 0.22 | 18.375 | 0.28 | 3.21 |
| 1194405 | 853 | 783 | 0.28 | 19 | 0.30 | 3.32 |
| 1194406 | 96 | 50 | 0.16 | 16 | 0.21 | 3.40 |
| 1194407 | 71 | 34 | 0.15 | 17 | 0.24 | 3.20 |
| 1194408 | 223 | 179 | 0.23 | 16 | 0.24 | 3.49‡ |
| 1194409 | 169 | 133 | 0.24 | 17 | 0.22 | 3.30 |
| 1194413‡ | 209 | 167 | 0.28 | 17 | 0.21 | 3.27 |
| 1194415 | 61 | 41 | 0.14 | 17 | 0.21 | 3.44 |
| 1194416‡ | 91 | 57 | 0.16 | 17 | 0.22 | 3.47 |
| 1194419 | 105 | 48 | 0.16 | 15 | 0.23 | 3.32 |
| 1194420 | 84 | 52 | 0.13 | 16 | 0.22 | 3.36 |
| 1194427 | 113 | 71 | 0.18 | 14 | 0.22 | 3.65‡ |

Blood obtained from rat groups at week 6 were sent to IDEXX BioResearch for measurement of blood cell counts. Counts taken include red blood cell (RBC) count, white blood cell (WBC) count, hemoglobin (HGB), hematocrit (HCT), Mean corpuscular volume (MCV) mean corpuscular hemoglobin (MCH), mean corpuscular hemoglobin concentration (MCHC), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 132

Blood Cell Count in Sprague-Dawley Rats

| Compound No. | WBC (/nL) | RBC (/pL) | HGB (g/dL) | HCT (%) | MCV (fL) | MCH (pg) | MCHC (%) | NEU (%) | LYM (%) | MON (%) | PLT (/nL) |
|---|---|---|---|---|---|---|---|---|---|---|---|
| Saline | 12 | 8 | 15 | 43 | 55 | 19 | 35 | 17 | 78 | 5 | 882 |
| 1194404 | 13 | 8 | 15 | 43 | 53 | 19 | 35 | 10 | 86 | 4 | 868 |
| 1194405 | 10 | 9 | 16 | 44 | 52 | 18 | 35 | 10 | 77 | 12 | 909 |
| 1194406 | 11 | 8 | 15 | 44 | 52 | 18 | 35 | 11 | 82 | 6 | 867 |
| 1194407 | 11 | 8 | 15 | 44 | 54 | 19 | 35 | 12 | 83 | 4 | 817 |
| 1194408 | 9 | 8 | 16 | 45 | 54 | 19 | 35 | 14 | 78 | 7 | 918 |
| 1194409 | 10 | 8 | 15 | 43 | 55 | 19 | 35 | 8 | 86 | 6 | 735 |
| 1194413‡ | 8 | 8 | 15 | 44 | 55 | 19 | 35 | 12 | 79 | 8 | 798 |
| 1194415 | 8 | 8 | 16 | 45 | 54 | 19 | 35 | 10 | 82 | 7 | 855 |
| 1194416 | 9 | 8 | 16 | 45 | 53 | 19 | 35 | 10 | 83 | 6 | 1093 |
| 1194419 | 5 | 8 | 15 | 42 | 54 | 19 | 35 | 11 | 81 | 8 | 813 |
| 1194420 | 8 | 9 | 16 | 45 | 53 | 19 | 35 | 13 | 80 | 5 | 835 |
| 1194427 | 12 | 8 | 16 | 47 | 56 | 19 | 35 | 13 | 80 | 6 | 1003 |

To evaluate the effect of Ionis oligonucleotides on kidney function, urinary levels of micro total protein (MTP) and creatinine were measured using an automated clinical chemistry analyzer (Hitachi Olympus AU400c, Melville, NY). The ratios of MTP to creatinine (MTP/C ratio) are presented in the table below. Ionis oligonucleotides that caused changes in the levels of the ratio outside the expected range for modified oligonucleotides were excluded in further studies.

TABLE 133

MTP to creatinine ratio in Sprague-Dawley rats

| Compound No. | MTP/C Ratio |
|---|---|
| saline | 0.8 |
| 1194404 | 1.1 |
| 1194405 | 1.6 |
| 1194406 | 1.5 |
| 1194407 | 1.8 |
| 1194408 | 1.9 |
| 1194409 | 1.5 |
| 1194413 | 1.4 |
| 1194415 | 2.0 |
| 1194416 | 1.4 |
| 1194419 | 2.0 |
| 1194420 | 2.3 |
| 1194427 | 2.6 |

Body weights of rats were measured at days 1 and 35, and the average body weight for each group is presented in the table below. Liver, spleen and kidney weights were measured at the end of the study, and are presented in the table below. Ionis oligonucleotides that caused any changes in organ weights outside the expected range for modified oligonucleotides were excluded from further studies.

TABLE 134

Body and organ weights (g)

| Compound No. | Body Weight (g) Day 1 | Body Weight (g) Day 35 | Liver Weight (g) | Kidney Weight (g) | Spleen Weight (g) |
|---|---|---|---|---|---|
| Saline | 219 | 433 | 17 | 3.8 | 4.4 |
| 1194404 | 213 | 391 | 15 | 3.3 | 5.5 |
| 1194405 | 210 | 357 | 16 | 3.3 | 4.4 |
| 1194406 | 218 | 388 | 16 | 3.6 | 4.7 |
| 1194407 | 227 | 410 | 17 | 3.9 | 5.0 |
| 1194408 | 222 | 390 | 15 | 3.6 | 4.8 |
| 1194409 | 216 | 376 | 16 | 3.7 | 5.3 |
| 1194413* | 207 | 399 | 17 | 4.0 | 4.2 |
| 1194415 | 220 | 382 | 15 | 3.5 | 3.9 |
| 1194416 | 218 | 369 | 13 | 3.3 | 4.7 |
| 1194419 | 218 | 388 | 16 | 3.2 | 3.6 |
| 1194420 | 219 | 392 | 16 | 3.6 | 4.6 |
| 1194427 | 204 | 375 | 15 | 3.2 | 4.0 |

Study 3

Groups of 4 Sprague-Dawley rats each were weekly injected subcutaneously with 40 mg/kg of Ionis oligonucleotide for 6 weeks (total 6 doses). A group of 4 rats were treated subcutaneously with 80 mg/kg of Compound No. 1194391. The rats were euthanized; and organs, urine and plasma were harvested for further analysis 2 days after the last dose.

Plasma Chemistry Markers

To evaluate the effect of Ionis oligonucleotides on hepatic function, plasma levels of transaminases were measured using an automated clinical chemistry analyzer (Hitachi Olympus AU400c, Melville, NY). Plasma levels of ALT (alanine transaminase) and AST (aspartate transaminase) were measured and the results are presented in the table below expressed in IU/L. Plasma levels of total bilirubin (TBIL), creatinine (CREA), albumin (ALB), and Blood Urea Nitrogen (BUN) were also measured using the same clinical chemistry analyzer and the results are also presented in the table below. Ionis modified oligonucleotides that caused changes in the levels of any markers of liver function outside the expected range for modified oligonucleotides were excluded in further studies.

TABLE 135

Plasma chemistry markers in Sprague-Dawley rats

| Compound No. | AST (IU/L) | ALT (IU/L) | TBIL (mg/dL) | BUN (mg/dL) | CREA (mg/dL) | ALB (mg/dL) |
|---|---|---|---|---|---|---|
| Saline | 65 | 52 | 0.16 | 15 | 0.23 | 3.31 |
| 1194345 | 122 | 52 | 0.15 | 19 | 0.25 | 2.81 |
| 1194349 | 59 | 38 | 0.16 | 16 | 0.27 | 3.54 |
| 1194357 | 78 | 50 | 0.16 | 16 | 0.28 | 3.67 |
| 1194358 | 82 | 51 | 0.18 | 16 | 0.29 | 3.88 |
| 1194359 | 70 | 41 | 0.15 | 15 | 0.28 | 3.65 |
| 1194360 | 269 | 92 | 0.35 | 20 | 0.27 | 2.66 |
| 1194371 | 125 | 85 | 0.20 | 17 | 0.25 | 2.74 |
| 1194377 | 1054 | 319 | 1.04 | 16 | 0.35 | 3.18 |
| 1194430 | 1195 | 379 | 1.04 | 16 | 0.26 | 3.39 |
| 1194391 | 83 | 65 | 0.17 | 15 | 0.21 | 3.39 |

Blood obtained from rat groups at week 6 were sent to IDEXX BioResearch for measurement of blood cell counts. Counts taken include red blood cell (RBC) count, white blood cell (WBC) count, hemoglobin (HGB), hematocrit (HCT), Mean corpuscular volume (MCV) mean corpuscular hemoglobin (MCH), mean corpuscular hemoglobin concentration (MCHC), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 136

Blood Cell Count in Sprague-Dawley Rats

| Compound No. | WBC (/nL) | RBC (/pL) | HGB (g/dL) | HCT (%) | MCV (fL) | MCH (pg) | MCHC (%) | NEU (%) | LYM (%) | MON (%) | PLT (/nL) |
|---|---|---|---|---|---|---|---|---|---|---|---|
| Saline | 9 | 8 | 16 | 47 | 58 | 19 | 34 | 16 | 81 | 2 | 749 |
| 1194345 | 12 | 7 | 14 | 42 | 61 | 20 | 33 | 9 | 87 | 3 | 687 |
| 1194349 | 10 | 8 | 15 | 45 | 55 | 19 | 34 | 21 | 75 | 3 | 921 |
| 1194357 | 9 | 8 | 16 | 47 | 57 | 19 | 34 | 10 | 86 | 3 | 814 |
| 1194358 | 11 | 9 | 16 | 47 | 55 | 19 | 34 | 13 | 82 | 4 | 1020 |
| 1194359 | 10 | 8 | 15 | 45 | 55 | 19 | 34 | 13 | 82 | 3 | 887 |
| 1194360 | 16 | 8 | 13 | 38 | 50 | 17 | 34 | 10 | 84 | 6 | 733 |

TABLE 136-continued

Blood Cell Count in Sprague-Dawley Rats

| Compound No. | WBC (/nL) | RBC (/pL) | HGB (g/dL) | HCT (%) | MCV (fL) | MCH (pg) | MCHC (%) | NEU (%) | LYM (%) | MON (%) | PLT (/nL) |
|---|---|---|---|---|---|---|---|---|---|---|---|
| 1194371 | 9 | 8 | 14 | 43 | 56 | 18 | 33 | 19 | 74 | 5 | 910 |
| 1194377 | 9 | 8 | 15 | 43 | 56 | 19 | 34 | 17 | 76 | 6 | 917 |
| 1194430 | 13 | 8 | 14 | 42 | 56 | 19 | 34 | 20 | 73 | 7 | 1241 |
| 1194391 | 8 | 8 | 16 | 46 | 58 | 20 | 34 | 22 | 74 | 3 | 803 |

To evaluate the effect of Ionis oligonucleotides on kidney function, urinary levels of micro total protein (MTP) and creatinine were measured using an automated clinical chemistry analyzer (Hitachi Olympus AU400c, Melville, NY). The ratios of MTP to creatinine (MTP/C ratio) are presented in the table below. Ionis oligonucleotides that caused changes in the levels of the ratio outside the expected range for modified oligonucleotides were excluded in further studies.

TABLE 137

MTP to creatinine ratio in Sprague-Dawley rats

| Compound No. | MTP/C Ratio |
|---|---|
| saline | 1.1 |
| 1194345 | 1.8 |
| 1194349 | 2.9 |
| 1194357 | 2.1 |
| 1194358 | 1.6 |
| 1194359 | 1.8 |
| 1194360 | 1.7 |
| 1194371 | 1.2 |
| 1194377 | 2.4 |
| 1194430 | 2.2 |
| 1194391 | 1.4 |

Body weights of rats were measured at days 1 and 38, and the average body weight for each group is presented in the table below. Liver, spleen and kidney weights were measured at the end of the study, and are presented in the table below. Ionis oligonucleotides that caused any changes in organ weights outside the expected range for modified oligonucleotides were excluded from further studies.

TABLE 138

Body and organ weights (g)

| Compound No. | Body Weight (g) Day 1 | Body Weight (g) Day 38 | Liver Weight (g) | Kidney Weight (g) | Spleen Weight (g) |
|---|---|---|---|---|---|
| Saline | 237 | 450 | 17 | 3.5 | 0.8 |
| 1194345 | 249 | 446 | 20 | 3.8 | 2.3 |
| 1194349 | 232 | 425 | 19 | 3.2 | 1.2 |
| 1194357 | 235 | 409 | 17 | 3.6 | 1.2 |
| 1194358 | 240 | 396 | 16 | 3.3 | 1.2 |
| 1194359 | 249 | 414 | 15 | 3.4 | 1.1 |
| 1194360 | 239 | 385 | 15 | 3.5 | 1.8 |
| 1194371 | 235 | 422 | 19 | 3.5 | 1.4 |
| 1194377 | 243 | 376 | 10 | 3.0 | 1.4 |
| 1194391 | 233 | 414 | 16 | 3.3 | 0.8 |
| 1194430 | 243 | 406 | 13 | 3.7 | 1.5 |

Study 4

Groups of 4 Sprague-Dawley rats each were weekly injected subcutaneously with 40 mg/kg of Ionis oligonucleotide for 6 weeks (total 6 doses). The rats were euthanized; and organs, urine and plasma were harvested for further analysis 3 days after the last dose.

Plasma Chemistry Markers

To evaluate the effect of Ionis oligonucleotides on hepatic function, plasma levels of transaminases were measured using an automated clinical chemistry analyzer (Hitachi Olympus AU400c, Melville, NY). Plasma levels of ALT (alanine transaminase) and AST (aspartate transaminase) were measured and the results are presented in the table below expressed in IU/L. Plasma levels of total bilirubin (TBIL), creatinine (CREA), albumin (ALB), and Blood Urea Nitrogen (BUN) were also measured using the same clinical chemistry analyzer and the results are also presented in the table below. Ionis modified oligonucleotides that caused changes in the levels of any markers of liver function outside the expected range for modified oligonucleotides were excluded in further studies.

TABLE 139

Plasma chemistry markers in Sprague-Dawley rats

| Compound No. | AST (IU/L) | ALT (IU/L) | TBIL (mg/dL) | BUN (mg/dL) | CREA (mg/dL) | ALB (mg/dL) |
|---|---|---|---|---|---|---|
| Saline | 61 | 43 | 0.1 | 16 | 0.3 | 3.4 |
| 1270699 | 86 | 63 | 0.2 | 17 | 0.3 | 3.7 |
| 1270700 | 195 | 157 | 0.3 | 17 | 0.4 | 3.6 |
| 1270701 | 83 | 47 | 0.2 | 15 | 0.3 | 3.6 |
| 1270703 | 113 | 61 | 0.2 | 25 | 0.4 | 3.5 |
| 1270705 | 254 | 246 | 0.2 | 17 | 0.3 | 3.5 |
| 1270707 | 213 | 196 | 0.2 | 18 | 0.3 | 3.6 |
| 1270710 | 130 | 61 | 0.1 | 17 | 0.3 | 3.5 |
| 1270712 | 119 | 80 | 0.2 | 17 | 0.3 | 3.6 |
| 1270714 | 112 | 70 | 0.2 | 22 | 0.3 | 3.3 |
| 1270715 | 337 | 198 | 0.3 | 19 | 0.3 | 3.5 |
| 1270716 | 195 | 92 | 0.2 | 15 | 0.3 | 3.6 |

Blood obtained from rat groups at week 6 were sent to IDEXX BioResearch for measurement of blood cell counts. Counts taken include red blood cell (RBC) count, white blood cell (WBC) count, hemoglobin (HGB), hematocrit (HCT), Mean corpuscular volume (MCV), mean corpuscular hemoglobin (MCH), mean corpuscular hemoglobin concentration (MCHC), and individual white blood cell counts, such as that of monocytes (MON), neutrophils (NEU), lymphocytes (LYM), and platelets (PLT). The results are presented in the tables below. Ionis oligonucleotides that caused changes in the blood cell count outside the expected range for modified oligonucleotides were excluded in further studies.

TABLE 140

Blood Cell Count in Sprague-Dawley Rats

| Compound No. | WBC (/nL) | RBC (/pL) | HGB (g/dL) | HCT (%) | MCV (fL) | MCH (pg) | MCHC (%) | NEU (%) | LYM (%) | MON (%) | PLT (/nL) |
|---|---|---|---|---|---|---|---|---|---|---|---|
| Saline | 6 | 9 | 16 | 47 | 54 | 18 | 33 | 15 | 78 | 6 | 804 |
| 1270699 | 7 | 9 | 15 | 45 | 52 | 18 | 34 | 11 | 82 | 6 | 717 |
| 1270700 | 11 | 9 | 15 | 44 | 51 | 18 | 35 | 10 | 83 | 6 | 813 |
| 1270701 | 8 | 9 | 15 | 44 | 51 | 18 | 34 | 13 | 80 | 6 | 814 |
| 1270703 | 9 | 8 | 14 | 43 | 54 | 18 | 33 | 19 | 73 | 6 | 757 |
| 1270705 | 9 | 9 | 15 | 45 | 51 | 18 | 34 | 15 | 76 | 8 | 799 |
| 1270707 | 10 | 9 | 16 | 45 | 52 | 18 | 35 | 10 | 81 | 6 | 939 |
| 1270710 | 13 | 8 | 13 | 39 | 49 | 17 | 34 | 12 | 81 | 6 | 778 |
| 1270712 | 7 | 8 | 14 | 42 | 51 | 17 | 34 | 21 | 69 | 8 | 780 |
| 1270714 | 9 | 9 | 16 | 44 | 50 | 18 | 36 | 19 | 72 | 8 | 754 |
| 1270715 | 13 | 8 | 14 | 42 | 51 | 17 | 34 | 11 | 83 | 5 | 865 |
| 1270716 | 8 | 8 | 14 | 42 | 51 | 17 | 34 | 11 | 80 | 8 | 738 |

To evaluate the effect of Ionis oligonucleotides on kidney function, urinary levels of micro total protein (MTP) and creatinine were measured using an automated clinical chemistry analyzer (Hitachi Olympus AU400c, Melville, NY). The ratios of MTP to creatinine (MTP/C ratio) are presented in the table below. Ionis oligonucleotides that caused changes in the levels of the ratio outside the expected range for modified oligonucleotides were excluded in further studies.

TABLE 141

MTP to creatinine ratio in Sprague-Dawley rats

| Compound No. | MTP/C Ratio |
|---|---|
| saline | 1.0 |
| 1270699 | 2.5 |
| 1270700 | 1.0 |
| 1270701 | 1.6 |
| 1270703 | 1.3 |
| 1270705 | 1.2 |
| 1270707 | 1.8 |
| 1270710 | 2.6 |
| 1270712 | 1.2 |
| 1270714 | 0.9 |
| 1270715 | 3.1 |
| 1270716 | 2.5 |

Body weights of rats were measured at days 1 and 35, and the average body weight for each group is presented in the table below. Liver, spleen and kidney weights were measured at the end of the study, and are presented in the table below. Ionis oligonucleotides that caused any changes in organ weights outside the expected range for modified oligonucleotides were excluded from further studies.

TABLE 142

Body and organ weights (g)

| Compound No. | Body Weight (g) Day 1 | Body Weight (g) Day 35 | Liver Weight (g) | Kidney Weight (g) | Spleen Weight (g) |
|---|---|---|---|---|---|
| Saline | 469 | 529 | 18 | 4.0 | 0.8 |
| 1270699 | 484 | 511 | 22 | 4.3 | 1.6 |
| 1270700 | 496 | 507 | 19 | 4.0 | 1.4 |
| 1270701 | 469 | 513 | 19 | 4.4 | 1.2 |
| 1270703 | 491 | 509 | 19 | 4.6 | 1.4 |
| 1270705 | 499 | 527 | 21 | 4.7 | 1.6 |
| 1270707 | 486 | 500 | 21 | 4.5 | 1.7 |
| 1270710 | 499 | 540 | 22 | 4.6 | 1.5 |
| 1270712 | 500 | 552 | 17 | 4.5 | 1.4 |
| 1270714 | 504 | 548 | 17 | 4.8 | 1.2 |
| 1270715 | 474 | 494 | 19 | 4.0 | 1.7 |
| 1270716 | 477 | 501 | 17 | 4.2 | 1.5 |

Example 12: Activity of Modified Oligonucleotides Complementary to Human FXII in Transgenic Mice, Single Dose A transgenic mouse model was developed in-house using the Fosmid NCBI Clone DB ID: ABC12-49040200E6. The clone was digested at AgeI and NdeI restriction sites to produce a region containing the entire ~23 kb portion of human F12 gene, including regions 12 kb upstream and 4 kb downstream of the F12 gene. The gene fragment was introduced into fertilized eggs from C57Bl/6 mice by pronuclear injection to produce FXII founder lines. Line 16459 was used in the experiments described herein. Human FXII RNA expression is found in the liver and circulating protein is found in plasma.

Study 1
Treatment

The transgenic mice were divided into groups of 2 female mice each for modified oligonucleotide treatment. Groups received subcutaneous injections of modified oligonucleotide at a dose of 2.5 mg/kg twice a week for two weeks (4 treatments). One group of two mice received subcutaneous injections of PBS twice a week for two weeks (4 treatments). The PBS-injected group served as the control group to which oligonucleotide-treated groups were compared.

RNA Analysis 48 hours after the last treatment, mice were sacrificed and RNA was extracted from liver for real-time RTPCR analysis of FXII RNA expression. Human FXII primer probe sets RTS2992 (described herein above) and RTS40528 (described herein above) were used to measure human FXII RNA levels. FXII RNA levels were normalized to total RNA content, as measured by RIBOGREEN®. Reduction of FXII RNA is presented in the tables below as percent FXII RNA relative to the amount in PBS control animals (% control).

TABLE 143

Reduction of human FXII RNA in transgenic mice

| Compound No. | FXII RNA (% control) in liver | |
|---|---|---|
| | RTS2992 | RTS40528 |
| PBS | 100 | 100 |
| 1194343 | 2 | 9 |
| 1194347 | 15 | 20 |

Protein Analysis

Human FXII protein levels in plasma were determined using an Abcam FXII ELISA kit (ab192144). Reduction of FXII protein is presented in the tables below as percent FXII protein relative to the amount in PBS control animals (% control).

TABLE 144

Reduction of human FXII protein in transgenic mice

| Compound No. | FXII protein (% control) in plasma |
|---|---|
| PBS | 100 |
| 1194343 | 0.3 |
| 1194347 | 17 |

Study 2
Treatment

The transgenic mice were divided into groups of 4 mice (2 male and 2 female) each for modified oligonucleotide treatment. Groups received subcutaneous injections of modified oligonucleotide at a dose of 1.5 mg/kg twice a week for two weeks (4 treatments). One group of four mice (2 male and 2 female) received subcutaneous injections of PBS twice a week for two weeks (4 treatments). The PBS-injected group served as the control group to which oligonucleotide-treated groups were compared.

RNA Analysis 48 hours after the last treatment, mice were sacrificed and RNA was extracted from liver for real-time RTPCR analysis of FXII RNA expression. Human FXII primer probe sets RTS2992 (described herein above) and RTS40528 (described herein above) were used to measure human FXII RNA levels. FXII RNA levels were normalized to total RNA content, as measured by RIBOGREEN®. Reduction of FXII RNA is presented in the tables below as percent FXII RNA relative to the amount in PBS treated animals (% control).

TABLE 145

Reduction of human FXII RNA in transgenic mice

| Compound No. | FXII RNA (% control) in liver | |
|---|---|---|
| | RTS2992 | RTS40528 |
| PBS | 100 | 100 |
| 1194380 | 32 | 36 |
| 1194383 | 52 | 58 |
| 1194384 | 32 | 35 |
| 1194389 | 54 | 76 |
| 1194391 | 45 | 57 |
| 1194392 | 48 | 68 |
| 1194393 | 37 | 40 |
| 1194394 | 31 | 41 |
| 1194395 | 21 | 35 |
| 1194402 | 22 | 27 |
| 1194403 | 12 | 10 |
| 1194404 | 17 | 17 |
| 1194406 | 31 | 40 |
| 1194407 | 56 | 76 |
| 1194408 | 21 | 23 |
| 1194409 | 22 | 20 |
| 1194413 | 82 | 80 |
| 1194415 | 83 | 111 |
| 1194416 | 81 | 96 |
| 1194419 | 45 | 54 |
| 1194420 | 61 | 53 |
| 1194427 | 90 | 71 |
| 1194345 | 14 | 12 |
| 1194349 | 10 | 9 |
| 1194357 | 3 | 3 |
| 1194358 | 3 | 2 |
| 1194359 | 6 | 4 |
| 1194360 | 5 | 4 |
| 1194371 | 5 | 6 |
| 1194377 | 12 | 12 |
| 1194430 | 21 | 22 |

Protein Analysis

Human FXII protein levels in plasma were determined using an Abcam FXII ELISA kit (ab192144). Reduction of FXII protein is presented in the tables below as percent FXII protein relative to the amount in PBS treated animals (% control).

TABLE 146

Reduction of human FXII protein in transgenic mice

| Compound No. | FXII protein (% control) in plasma |
|---|---|
| PBS | 100 |
| 1194380 | 23 |
| 1194383 | 41 |
| 1194384 | 24 |
| 1194389 | 56 |
| 1194391 | 36 |
| 1194392 | 38 |
| 1194393 | 27 |
| 1194394 | 20 |
| 1194395 | 12 |
| 1194402 | 14 |
| 1194403 | 4 |
| 1194404 | 9 |
| 1194406 | 23 |
| 1194407 | 42 |
| 1194408 | 16 |
| 1194409 | 15 |
| 1194413 | 61 |
| 1194415 | 80 |
| 1194416 | 72 |
| 1194419 | 42 |
| 1194420 | 61 |
| 1194427 | 87 |
| 1194345 | 11 |
| 1194349 | 3 |
| 1194357 | 1 |
| 1194358 | 0 |
| 1194359 | 1 |
| 1194360 | 2 |
| 1194371 | 1 |
| 1194377 | 9 |
| 1194430 | 20 |

Example 13: Activity of Modified Oligonucleotides Complementary to Human FXII in Transgenic Mice, Multiple Dose A transgenic mouse model was developed in-house using the Fosmid NCBI Clone DB ID: ABC12-49040200E6. The clone was digested at AgeI and NdeI restriction sites to produce a region containing the entire ~23 kb portion of human F12 gene, including regions 12 kb upstream and 4 kb downstream of the F12 gene. The gene fragment was introduced into fertilized eggs from C57Bl/6 mice by pronuclear injection to produce FXII founder lines. Line 16459 was used in the experiments described herein. Human FXII RNA expression is found in the liver and circulating protein is found in plasma.

Study 1

Treatment

The transgenic mice were divided into groups of 2 female mice each for modified oligonucleotide treatment. Groups received subcutaneous injections of modified oligonucleotide at doses indicated in the table below twice a week for two weeks (4 treatments). One group of two mice received subcutaneous injections of PBS twice a week for two weeks (4 treatments). The PBS-injected group served as the control group to which oligonucleotide-treated groups were compared.

RNA Analysis 48 hours after the last treatment, mice were sacrificed and RNA was extracted from liver for real-time RTPCR analysis of FXII RNA expression. Human FXII primer probe set RTS2992 (described herein above) was used to measure human FXII RNA levels. FXII RNA levels were normalized to total RNA content, as measured by RIBOGREEN®. Reduction of FXII RNA is presented in the tables below as percent FXII RNA relative to the amount in PBS treated animals (% control).

TABLE 147

Reduction of human FXII RNA in transgenic mice

| Compound No. | Concentration (mpk) | RTS2992 FXII RNA (% control) in liver | ED50 (mpk) |
|---|---|---|---|
| 1194347 | 0.32 | 75 | 1.292 |
|  | 0.8 | 59 |  |
|  | 2 | 50 |  |
|  | 5 | 14 |  |

Protein Analysis

Human FXII protein levels in plasma were determined using an Abcam FXII ELISA kit (ab192144). Reduction of FXII protein is presented in the tables below as percent FXII protein relative to the amount in PBS treated animals (% control).

TABLE 148

Reduction of human FXII protein in transgenic mice

| Compound No. | Concentration (mpk) | FXII protein (% control) in plasma | ED50 (mpk) |
|---|---|---|---|
| 1194347 | 0.32 | 78 | 1.073 |
|  | 0.8 | 64 |  |
|  | 2 | 31 |  |
|  | 5 | 11 |  |

Study 2

Treatment

The transgenic mice were divided into groups of four mice (2 male and 2 female) each for modified oligonucleotide treatment. Groups received subcutaneous injections of modified oligonucleotide at doses indicated in the table below twice a week for two weeks (4 treatments). One group of four mice (2 male and 2 female) received subcutaneous injections of PBS twice a week for two weeks (4 treatments). The PBS-injected group served as the control group to which oligonucleotide-treated groups were compared.

RNA Analysis 48 hours after the last treatment, mice were sacrificed and RNA was extracted from liver for real-time RTPCR analysis of FXII RNA expression. Human FXII primer probe set RTS2992 (described herein above) was used to measure human FXII RNA levels. FXII RNA levels were normalized to total RNA content, as measured by RIBOGREEN®. Reduction of FXII RNA is presented in the tables below as percent FXII RNA relative to the amount in PBS treated animals (% control).

TABLE 149

Reduction of human FXII RNA in transgenic mice

| Compound No. | Concentration (mpk) | FXII RNA (% control) in liver (RTS2992) | ED50 (mpk) |
|---|---|---|---|
| 1194357 | 0.08 | 60 | 0.07514 |
|  | 0.1 | 33 |  |
|  | 0.2 | 27 |  |
|  | 0.3 | 14 |  |
|  | 0.6 | 8 |  |
|  | 0.9 | 4 |  |
| 1194349 | 0.1 | 60 | 0.4603 |
|  | 0.3 | 61 |  |
|  | 0.9 | 25 |  |
| 1194358 | 0.1 | 47 | 0.08653 |
|  | 0.3 | 18 |  |
|  | 0.9 | 9 |  |
| 1194359 | 0.1 | 80 | 0.1997 |
|  | 0.3 | 36 |  |
|  | 0.9 | 9 |  |
| 1194371 | 0.1 | 114 | 0.2737 |
|  | 0.3 | 35 |  |
|  | 0.9 | 10 |  |
| 1194377 | 0.1 | 91 | 0.5223 |
|  | 0.3 | 70 |  |
|  | 0.9 | 28 |  |
| 1270699 | 0.1 | 79 | 0.1731 |
|  | 0.3 | 31 |  |
|  | 0.9 | 6 |  |
| 1270700 | 0.1 | 57 | 0.1211 |
|  | 0.3 | 21 |  |
|  | 0.9 | 4 |  |
| 1270701 | 0.1 | 38 | 0.1871 |
|  | 0.3 | 41 |  |
|  | 0.9 | 6 |  |
| 1270702 | 0.1 | 59 | 0.1816 |
|  | 0.3 | 22 |  |
|  | 0.9 | 6 |  |
| 1270703 | 0.08 | 76 | 0.2228 |
|  | 0.2 | 71 |  |
|  | 0.6 | 11 |  |
| 1270705 | 0.08 | 62 | 0.113 |
|  | 0.2 | 33 |  |
|  | 0.6 | 12 |  |
| 1270707 | 0.08 | 82 | 0.2085 |
|  | 0.2 | 57 |  |
|  | 0.6 | 14 |  |

TABLE 149-continued

Reduction of human FXII RNA in transgenic mice

| Compound No. | Concentration (mpk) | FXII RNA (% control) in liver (RTS2992) | ED50 (mpk) |
|---|---|---|---|
| 1270710 | 0.08 | 92 | 0.265 |
|  | 0.2 | 61 |  |
|  | 0.6 | 19 |  |
| 1270712 | 0.08 | 92 | 0.3297 |
|  | 0.2 | 63 |  |
|  | 0.6 | 14 |  |
| 1270714 | 0.08 | 57 | 0.3936 |
|  | 0.2 | 47 |  |
|  | 0.6 | 25 |  |
| 1270715 | 0.08 | 69 | 0.3242 |
|  | 0.2 | 57 |  |
|  | 0.6 | 20 |  |
| 1270716 | 0.08 | 58 | 0.3093 |
|  | 0.2 | 52 |  |
|  | 0.6 | 20 |  |

Protein Analysis

Human FXII protein levels in plasma were determined using an Abcam FXII ELISA kit (ab192144). Reduction of FXII protein is presented in the tables below as percent FXII protein relative to the amount in PBS treated animals (% control).

TABLE 150

Reduction of human FXII protein in transgenic mice

| Compound No. | Concentration (mpk) | FXII protein (% control) in plasma | ED50 (mpk) |
|---|---|---|---|
| 1194357 | 0.08 | 67 | 0.065 |
|  | 0.1 | 43 |  |
|  | 0.2 | 25 |  |
|  | 0.3 | 15 |  |
|  | 0.6 | 3 |  |
|  | 0.9 | 6 |  |
| 1194349 | 0.1 | 84 | 0.2799 |
|  | 0.3 | 48 |  |
|  | 0.9 | 13 |  |
| 1194358 | 0.1 | 52 | 0.09148 |
|  | 0.3 | 20 |  |
|  | 0.9 | 5 |  |
| 1194359 | 0.1 | 53 | 0.0959 |
|  | 0.3 | 22 |  |
|  | 0.9 | 3 |  |
| 1194371 | 0.1 | 65 | 0.1356 |
|  | 0.3 | 29 |  |
|  | 0.9 | 3 |  |
| 1194377 | 0.1 | 80 | 0.2882 |
|  | 0.3 | 50 |  |
|  | 0.9 | 16 |  |
| 1270699 | 0.1 | 62 | 0.1153 |
|  | 0.3 | 22 |  |
|  | 0.9 | 4 |  |
| 1270700 | 0.1 | 53 | 0.08752 |
|  | 0.3 | 17 |  |
|  | 0.9 | 1 |  |
| 1270701 | 0.1 | 42 | 0.08131 |
|  | 0.3 | 27 |  |
|  | 0.9 | 5 |  |
| 1270702 | 0.1 | 65 | 0.1331 |
|  | 0.3 | 27 |  |
|  | 0.9 | 4 |  |

TABLE 150-continued

Reduction of human FXII protein in transgenic mice

| Compound No. | Concentration (mpk) | FXII protein (% control) in plasma | ED50 (mpk) |
|---|---|---|---|
| 1270703 | 0.08 | 79 | 0.1572 |
|  | 0.2 | 41 |  |
|  | 0.6 | 7 |  |
| 1270705 | 0.08 | 66 | 0.1174 |
|  | 0.2 | 36 |  |
|  | 0.6 | 7 |  |
| 1270707 | 0.08 | 77 | 0.1668 |
|  | 0.2 | 46 |  |
|  | 0.6 | 8 |  |
| 1270710 | 0.08 | 86 | 0.2288 |
|  | 0.2 | 56 |  |
|  | 0.6 | 13 |  |
| 1270712 | 0.08 | 86 | 0.2467 |
|  | 0.2 | 58 |  |
|  | 0.6 | 16 |  |
| 1270714 | 0.08 | 93 | 0.3053 |
|  | 0.2 | 62 |  |
|  | 0.6 | 24 |  |
| 1270715 | 0.08 | 89 | 0.3739 |
|  | 0.2 | 62 |  |
|  | 0.6 | 37 |  |
| 1270716 | 0.08 | 89 | 0.3447 |
|  | 0.2 | 71 |  |
|  | 0.6 | 25 |  |

Study 3

Treatment

The transgenic mice were divided into groups of four mice (2 male and 2 female) each for modified oligonucleotide treatment. Groups received subcutaneous injections of modified oligonucleotide at doses indicated in the table below twice a week for two weeks (4 treatments). One group of four mice (2 male and 2 female) received subcutaneous injections of PBS twice a week for two weeks (4 treatments). The PBS-injected group served as the control group to which oligonucleotide-treated groups were compared.

RNA Analysis 72 hours after the last treatment, mice were sacrificed and RNA was extracted from liver for real-time RTPCR analysis of FXII RNA expression. Human FXII primer probe sets RTS2992 (described herein above) was used to measure human FXII RNA levels. FXII RNA levels were normalized to total RNA content, as measured by RIBOGREEN®. Reduction of FXII RNA is presented in the tables below as percent FXII RNA relative to the amount in PBS treated animals (% control).

TABLE 151

Reduction of human FXII RNA in transgenic mice

| Compound No. | Concentration (mpk) | RTS2992 FXII RNA (% control) in liver | ED50 (mpk) |
|---|---|---|---|
| 1194371 | 0.075 | 94 | 0.2457 |
|  | 0.15 | 57 |  |
|  | 0.3 | 47 |  |
|  | 0.6 | 22 |  |
|  | 1.2 | 10 |  |

Example 14: Effect of Modified Oligonucleotides on Human FXII mRNA In Vitro, Multiple Doses Modified oligonucleotides selected from the examples above were tested at various doses in Huh7 cells. Cultured Huh7 cells at a density of 20,000 cells per well were transfected by electroporation with various concentrations of modified oligonucleotide as specified in the table below. After a treatment period of approximately 24 hours, total RNA was isolated from the cells, and FXII mRNA levels were measured by quantitative real-time RTPCR. Human FXII primer probe set RTS40528 (described herein above) was used to measure RNA levels. FXII levels were adjusted according to total RNA content, as measured by RIBOGREEN®. Reduction of FXII RNA is presented in the tables below as percent FXII RNA relative to the amount in untreated control cells (% UTC). The half maximal inhibitory concentration ($IC_{50}$) of each modified oligonucleotide was calculated in GraphPad Prism using the log (inhibitor) vs. normalized response—variable slope method.

Four comparator compounds from WO 2017/120397 were added to the study. These include Compound Nos. 1213034, 1358035, 1213030 and 1213029 designated as A-145676, A-145669, A-145668, and A-145667 respectively in WO 2017/120397.

TABLE 152

Dose-dependent reduction of human FXII RNA by modified oligonucleotides

| Compound No. | FXII RNA (% UTC) | | | | | IC50 (µM) |
|---|---|---|---|---|---|---|
| | 10 µM | 2 µM | 0.4 µM | 0.08 µM | 0.016 µM | |
| 1129485 | 7 | 15 | 44 | 81 | 98 | 0.34 |
| 1129486 | 8 | 18 | 51 | 96 | 97 | 0.48 |
| 1207006 | 8 | 10 | 28 | 52 | 84 | 0.1 |
| 1207160 | 17 | 18 | 30 | 58 | 65 | 0.09 |
| 1207161 | 12 | 20 | 27 | 68 | 83 | 0.17 |
| 1207277 | 6 | 9 | 29 | 59 | 84 | 0.13 |
| 1207279 | 12 | 29 | 45 | 80 | 95 | 0.43 |
| 1207393 | 7 | 14 | 26 | 63 | 83 | 0.14 |
| 1213260 | 12 | 18 | 26 | 62 | 87 | 0.15 |
| 1213144 | 8 | 25 | 37 | 71 | 95 | 0.28 |
| Comparator Compounds | | | | | | |
| 1213030 | 43 | 84 | 132 | 132 | 94 | 8.15 |
| 1213034 | 69 | 116 | 139 | 127 | 92 | >10 |
| 1213029 | 63 | 123 | 146 | 130 | 98 | >10 |
| 1358035 | 43 | 93 | 127 | 121 | 104 | 8.59 |

SEQUENCE LISTING

The patent contains a lengthy sequence listing. A copy of the sequence listing is available in electronic form from the USPTO web site (https://seqdata.uspto.gov/?pageRequest=docDetail&DocID=US12018261B2). An electronic copy of the sequence listing will also be available from the USPTO upon request and payment of the fee set forth in 37 CFR 1.19(b)(3).

The invention claimed is:
1. An oligomeric compound according to the following chemical structure:

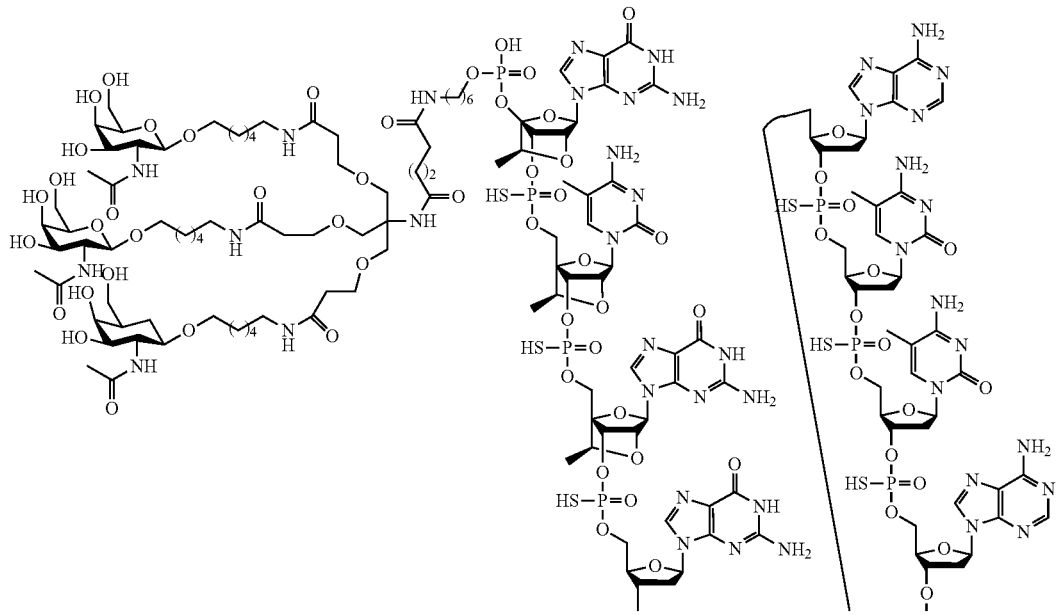

-continued
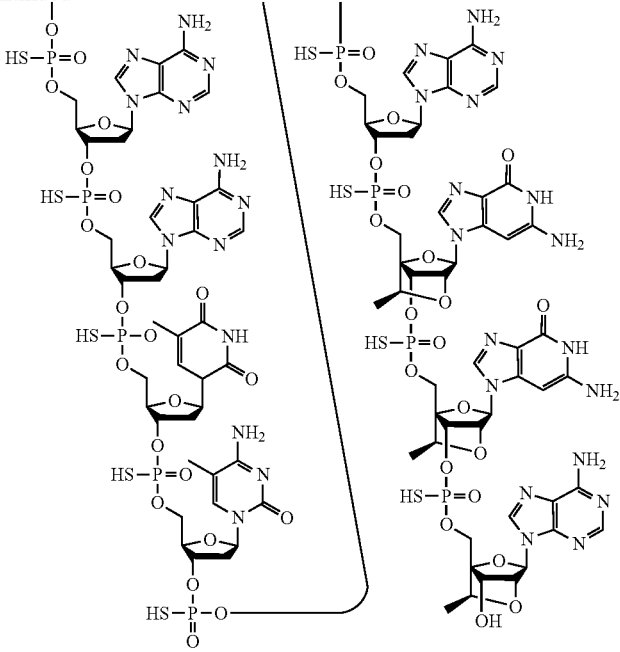
(SEQ ID NO: 3379), or a salt thereof.
2. The oligomeric compound of claim 1, which is the sodium salt or the potassium salt.

3. An oligomeric compound according to the following chemical structure:

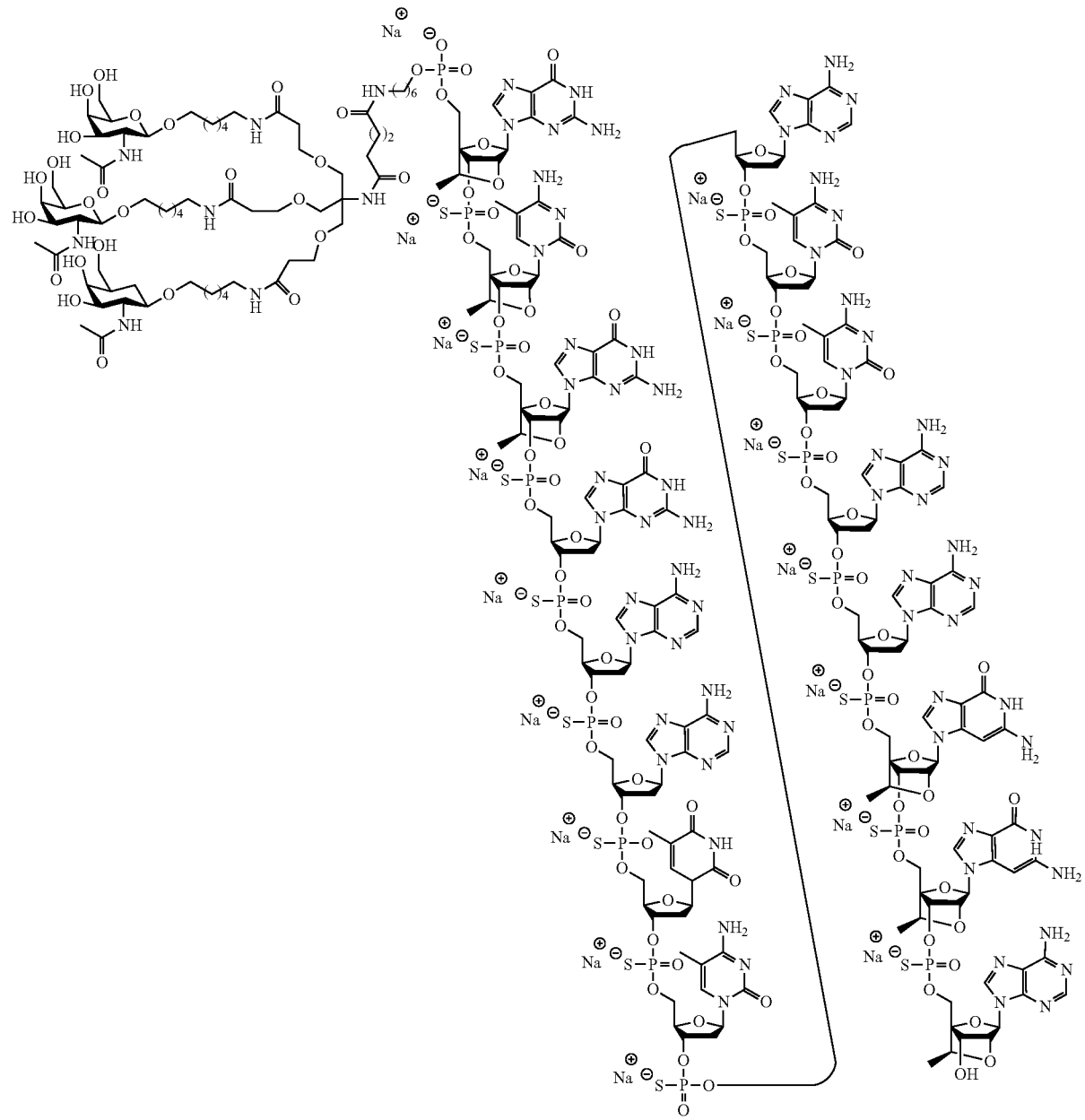

(SEQ ID NO: 3379).

4. An oligomeric compound comprising a modified oligonucleotide according to the following chemical notation: (THA-GalNAc₃)o Gks ᵐCks Gks Gds Ads Ads Tds ᵐCds Ads ᵐCds ᵐCds Ads Ads Gks Gks Ak (SEQ ID NO: 3379), wherein:

A=an adenine nucleobase,
mC=a 5-methyl cytosine nucleobase,
G=a guanine nucleobase,
T=a thymine nucleobase,
k=a cEt modified sugar moiety,
d=a 2'-β-D-deoxyribosyl sugar moiety,
o=a phosphodiester linkage, and
s=a phosphorothioate internucleoside linkage.

5. The oligomeric compound of claim 4, wherein THA-GalNAc₃ has the following chemical structure:

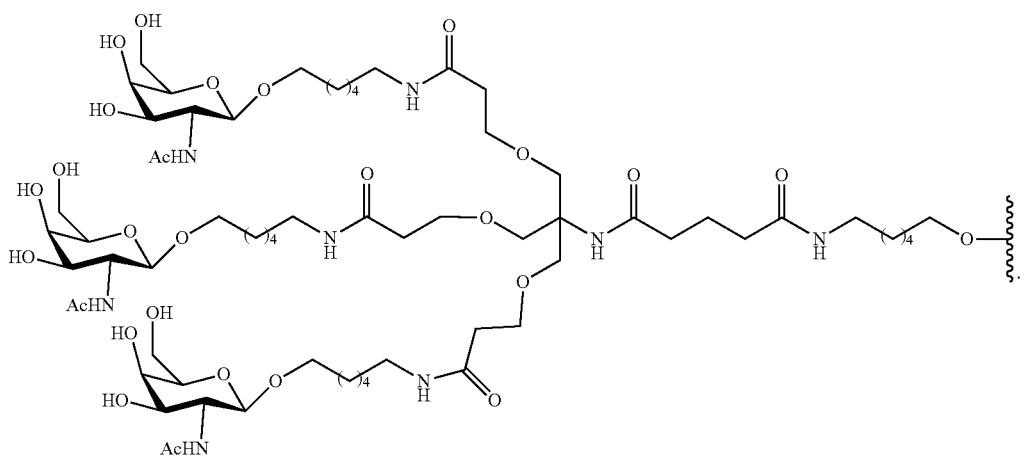

6. A population of oligomeric compounds of claim 1, wherein all of the phosphorothioate internucleoside linkages of the modified oligonucleotides are stereorandom.

7. A pharmaceutical composition comprising an oligomeric compound of claim 1 and a pharmaceutically acceptable diluent.

8. The pharmaceutical composition of claim 7, wherein the pharmaceutically acceptable diluent is phosphate-buffered saline (PBS) or water.

9. A population of oligomeric compounds of claim 2, wherein all of the phosphorothioate internucleoside linkages of the modified oligonucleotides are stereorandom.

10. A pharmaceutical composition comprising an oligomeric compound of claim 2 and a pharmaceutically acceptable diluent.

11. The pharmaceutical composition of claim 10, wherein the pharmaceutically acceptable diluent is phosphate-buffered saline (PBS) or water.

12. A population of oligomeric compounds of claim 3, wherein all of the phosphorothioate internucleoside linkages of the modified oligonucleotides are stereorandom.

13. A pharmaceutical composition comprising an oligomeric compound of claim 3 and a pharmaceutically acceptable diluent.

14. The pharmaceutical composition of claim 13, wherein the pharmaceutically acceptable diluent is phosphate-buffered saline (PBS) or water.

15. A population of oligomeric compounds of claim 4, wherein all of the phosphorothioate internucleoside linkages of the modified oligonucleotide are stereorandom.

16. A pharmaceutical composition comprising the oligomeric compound of claim 4 and a pharmaceutically acceptable diluent.

17. The pharmaceutical composition of claim 16, wherein the pharmaceutically acceptable diluent is phosphate-buffered saline (PBS) or water.

18. A method of reducing expression of FXII in a cell comprising contacting the cell with an oligomeric compound of claim 1.

19. The method of claim 18, wherein the contacting comprises administering the oligomeric compound of claim 1 to a subject.

20. The method of claim 19, wherein the subject is human.

21. A method of reducing expression of FXII in a cell comprising contacting the cell with an oligomeric compound of claim 2.

22. The method of claim 21, wherein the contacting comprises administering the oligomeric compound of claim 2 to a subject.

23. The method of claim 22, wherein the subject is human.

24. A method of reducing expression of FXII in a cell comprising contacting the cell with an oligomeric compound of claim 3.

25. The method of claim 24, wherein the contacting comprises administering the oligomeric compound of claim 3 to a subject.

26. The method of claim 25, wherein the subject is human.

27. A method of reducing expression of FXII in a cell comprising contacting the cell with an oligomeric compound of claim 4.

28. The method of claim 27, wherein the contacting comprises administering the oligomeric compound of claim 4 to a subject.

29. The method of claim 28, wherein the subject is human.

30. An oligomeric compound according to the following chemical structure:

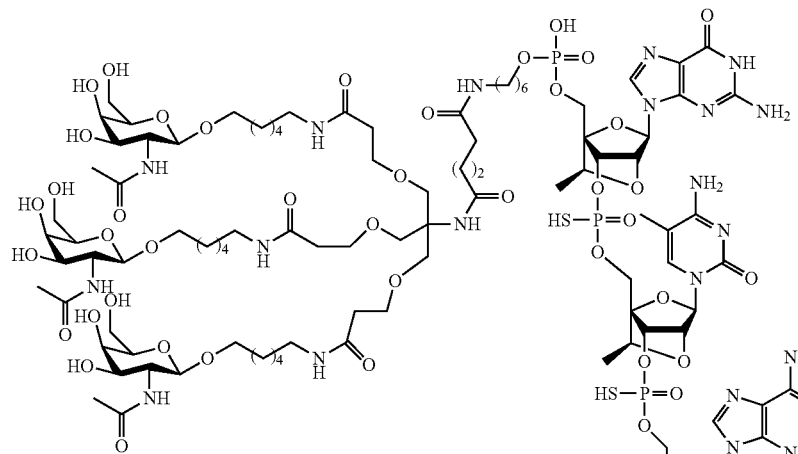
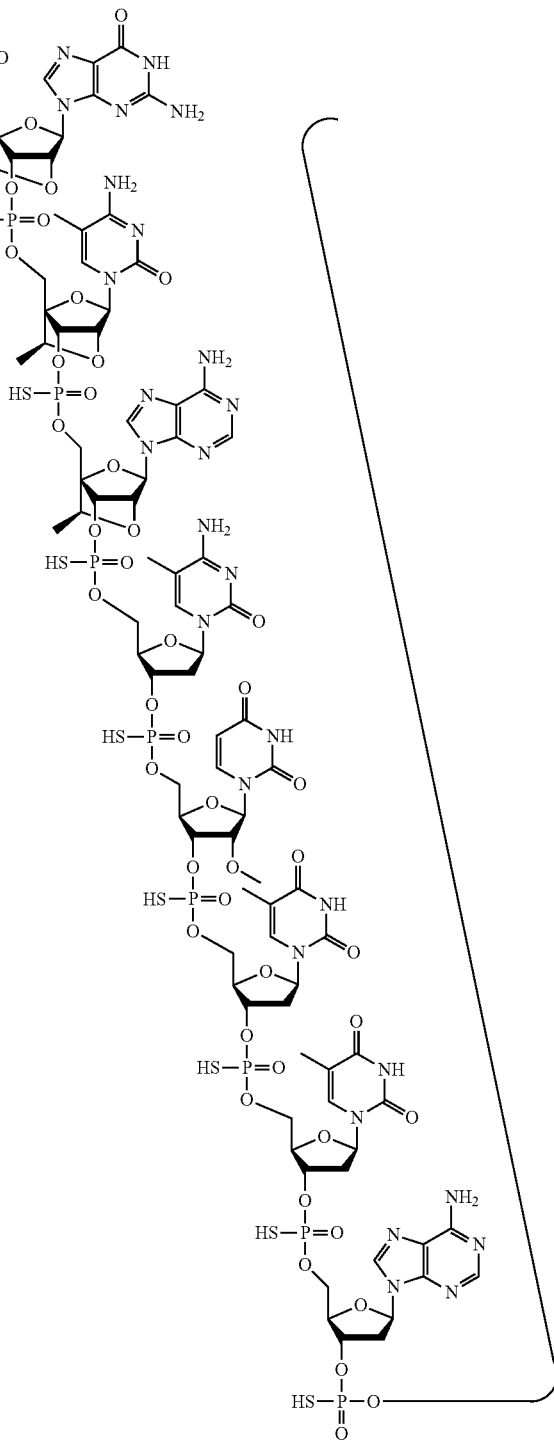

-continued
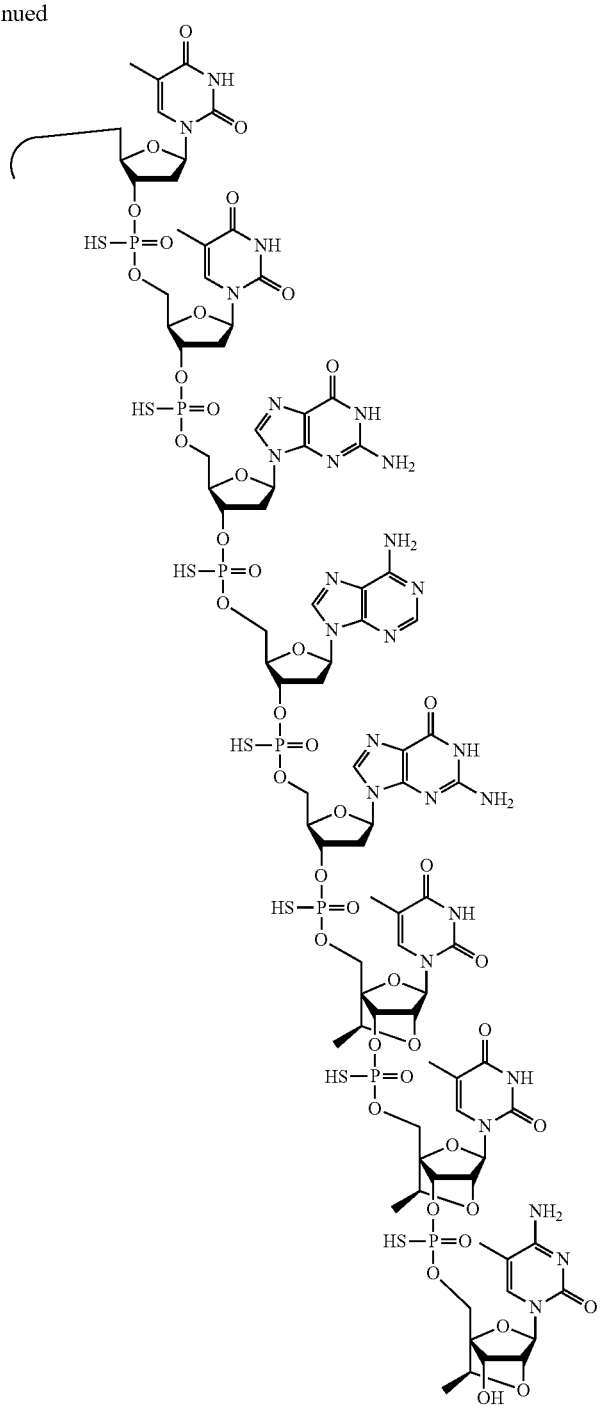
(SEQ ID NO: 5006), or a salt thereof.
31. The oligomeric compound of claim 30, which is the sodium salt or the potassium salt.

32. An oligomeric compound according to the following chemical structure:
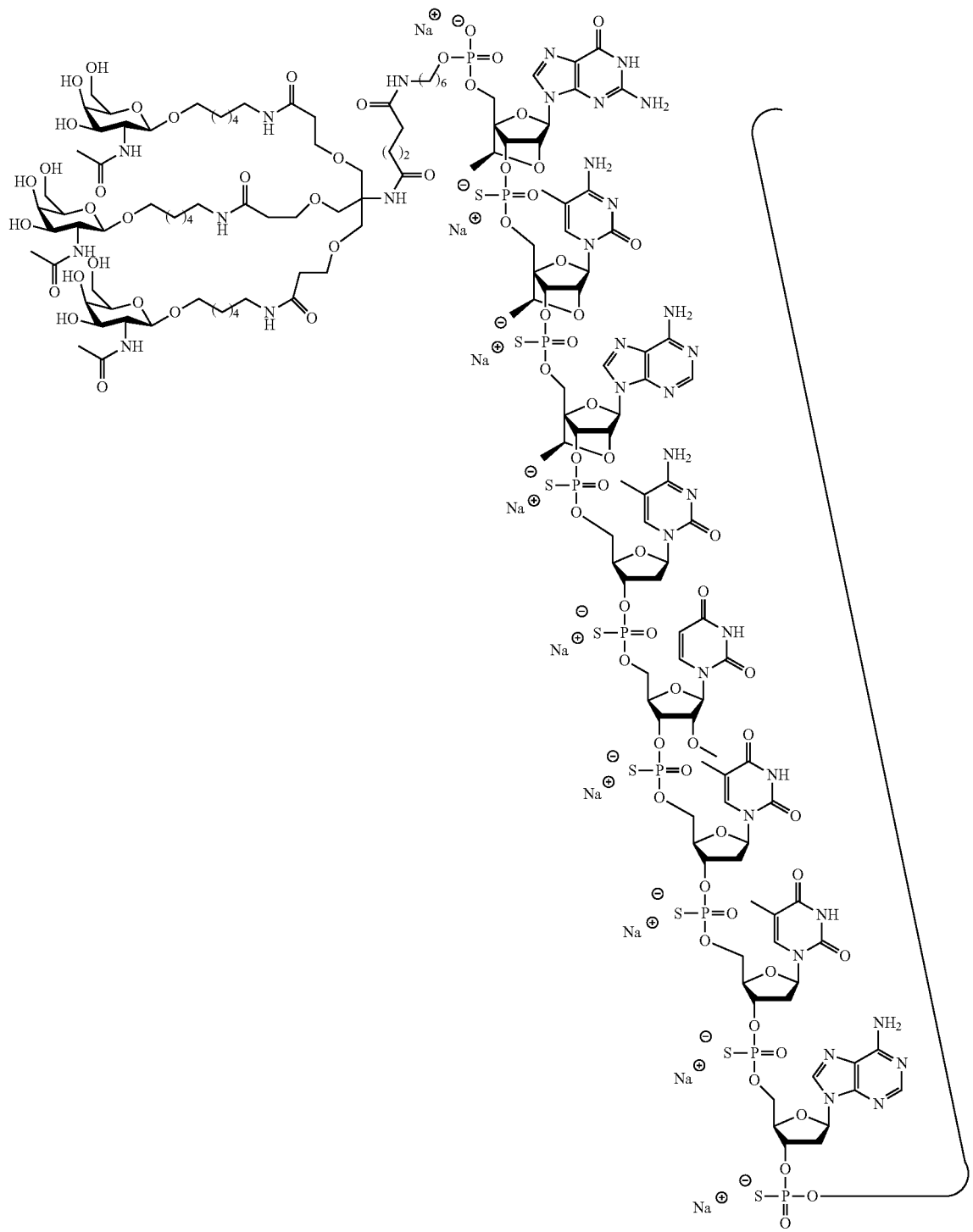

-continued

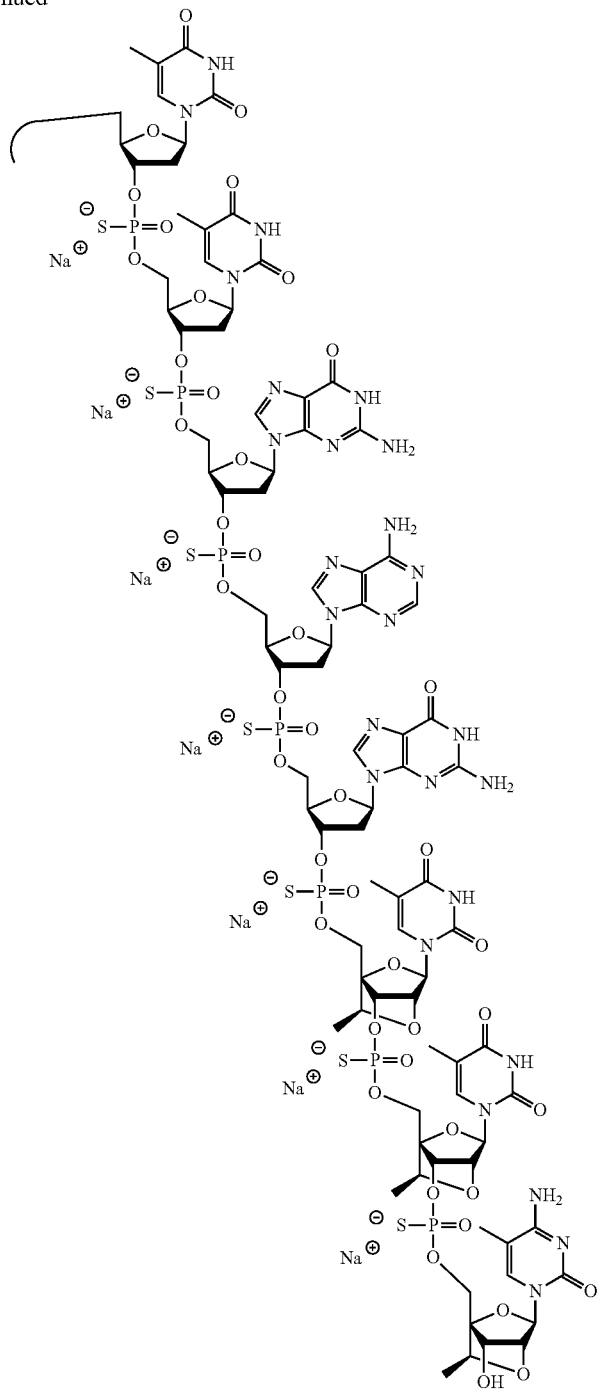

(SEQ ID NO: 5006).

33. An oligomeric compound comprising a modified oligonucleotide according to the following chemical notation: (THA-GalNAc₃)o Gks ᵐCks Aks ᵐCds Uys Tds Tds Ads Tds Tds Gds Ads Gds Tks Tks mCk (SEQ ID NO: 5006), wherein:
- A=an adenine nucleobase,
- mC=a 5-methyl cytosine nucleobase,
- G=a guanine nucleobase,
- T=a thymine nucleobase,
- U=a uracil nucleobase,
- k=a cEt modified sugar moiety,
- y=a 2'-O-methyl modified ribosyl sugar moiety,
- d=a 2'-β-D-deoxyribosyl sugar moiety,
- o=a phosphodiester linkage, and
- s=a phosphorothioate internucleoside linkage.

34. The oligomeric compound of claim 33, wherein THA-GalNAc₃ has the following chemical structure:

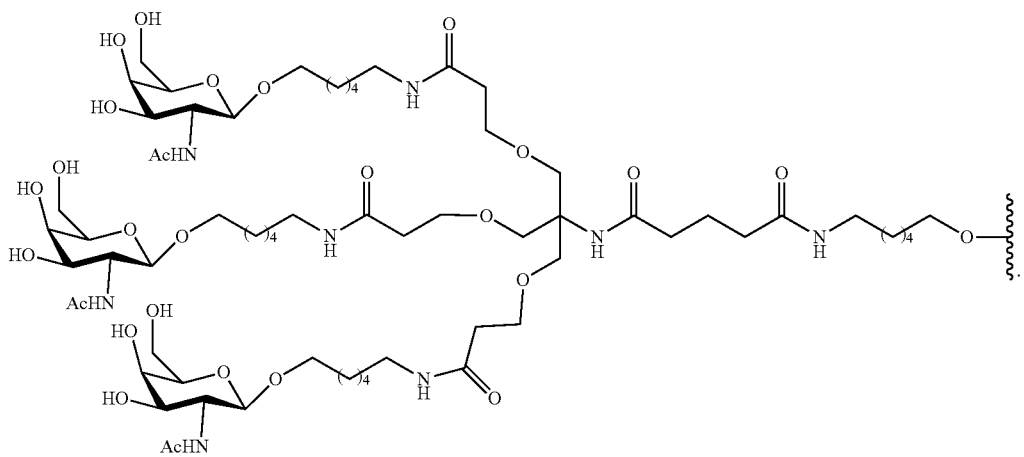

35. A population of oligomeric compounds of claim 30, wherein all of the phosphorothioate internucleoside linkages of the modified oligonucleotides are stereorandom.

36. A pharmaceutical composition comprising an oligomeric compound of claim 30 and a pharmaceutically acceptable diluent.

37. The pharmaceutical composition of claim 36, wherein the pharmaceutically acceptable diluent is phosphate-buffered saline (PBS) or water.

38. A population of oligomeric compounds of claim 31, wherein all of the phosphorothioate internucleoside linkages of the modified oligonucleotides are stereorandom.

39. A pharmaceutical composition comprising an oligomeric compound of claim 31 and a pharmaceutically acceptable diluent.

40. The pharmaceutical composition of claim 39, wherein the pharmaceutically acceptable diluent is phosphate-buffered saline (PBS) or water.

41. A population of oligomeric compounds of claim 32, wherein all of the phosphorothioate internucleoside linkages of the modified oligonucleotides are stereorandom.

42. A pharmaceutical composition comprising an oligomeric compound of claim 32 and a pharmaceutically acceptable diluent.

43. The pharmaceutical composition of claim 42, wherein the pharmaceutically acceptable diluent is phosphate-buffered saline (PBS) or water.

44. A population of oligomeric compounds of claim 33, wherein all of the phosphorothioate internucleoside linkages of the modified oligonucleotides are stereorandom.

45. A pharmaceutical composition comprising an oligomeric compound of claim 33 and a pharmaceutically acceptable diluent.

46. The pharmaceutical composition of claim 45, wherein the pharmaceutically acceptable diluent is phosphate-buffered saline (PBS) or water.

47. A method of reducing expression of FXII in a cell comprising contacting the cell with an oligomeric compound of claim 30.

48. The method of claim 47, wherein the contacting comprises administering the oligomeric compound of claim 30 to a subject.

49. The method of claim 48, wherein the subject is human.

50. A method of reducing expression of FXII in a cell comprising contacting the cell with an oligomeric compound of claim 31.

51. The method of claim 50, wherein the contacting comprises administering the oligomeric compound of claim 32 to a subject.

52. The method of claim 51, wherein the subject is human.

53. A method of reducing expression of FXII in a cell comprising contacting the cell with an oligomeric compound of claim 32.

54. The method of claim 53, wherein the contacting comprises administering the oligomeric compound of claim 32 to a subject.

55. The method of claim 54, wherein the subject is human.

56. A method of reducing expression of FXII in a cell comprising contacting the cell with an oligomeric compound of claim 33.

57. The method of claim 56, wherein the contacting comprises administering the oligomeric compound of claim 33 to a subject.

58. The method of claim 57, wherein the subject is human.

* * * * *